(12) United States Patent
Gesteira et al.

(10) Patent No.: US 11,542,534 B2
(45) Date of Patent: *Jan. 3, 2023

(54) METHODS FOR SYNTHESIZING ANTICOAGULANT POLYSACCHARIDES

(71) Applicant: OPTIMVIA, LLC, Batavia, OH (US)

(72) Inventors: Tarsis Ferreira Gesteira, Pearland, TX (US); Daniel H. Lajiness, Fairfield, OH (US)

(73) Assignee: OPTIMVIA, LLC, Batavia, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/376,354

(22) Filed: Jul. 15, 2021

(65) Prior Publication Data

US 2022/0010344 A1    Jan. 13, 2022

Related U.S. Application Data

(63) Continuation-in-part of application No. PCT/US2020/041404, filed on Jul. 9, 2020.

(60) Provisional application No. 63/033,687, filed on Jun. 2, 2020, provisional application No. 62/871,980, filed on Jul. 9, 2019.

(51) Int. Cl.

| | |
|---|---|
| *C12P 19/04* | (2006.01) |
| *A61K 31/727* | (2006.01) |
| *C12N 9/90* | (2006.01) |
| *C12P 19/26* | (2006.01) |
| *C12P 19/28* | (2006.01) |
| *C08B 37/00* | (2006.01) |
| *C08J 11/10* | (2006.01) |
| *C12N 9/10* | (2006.01) |

(52) U.S. Cl.
CPC ............ *C12P 19/04* (2013.01); *A61K 31/727* (2013.01); *C08B 37/0003* (2013.01); *C08B 37/0075* (2013.01); *C08J 11/105* (2013.01); *C12N 9/13* (2013.01); *C12N 9/90* (2013.01); *C08J 2305/10* (2013.01); *C12Y 208/02008* (2013.01); *C12Y 208/02023* (2013.01); *C12Y 501/03017* (2013.01)

(58) Field of Classification Search
CPC ......... C12P 19/04; A61K 31/727; C12N 9/13; C12N 9/90
See application file for complete search history.

(56) References Cited

U.S. PATENT DOCUMENTS

| | | |
|---|---|---|
| 3,766,167 A | 10/1973 | Lasker et al. |
| 3,936,351 A | 2/1976 | Bianchini |
| 4,281,108 A | 7/1981 | Fussi |
| 4,303,651 A | 12/1981 | Lindahl et al. |
| 4,351,938 A | 9/1982 | Barnett |
| 4,396,762 A | 8/1983 | Langer et al. |
| 4,401,758 A | 8/1983 | Lormeau et al. |
| 4,438,261 A | 3/1984 | Barnett |
| 4,440,926 A | 4/1984 | Mardiguian |
| 4,500,519 A | 2/1985 | Lormeau et al. |
| 4,554,101 A | 11/1985 | Hopp |
| 4,629,699 A | 12/1986 | Bianchini |
| 4,686,288 A | 8/1987 | Lormeau et al. |
| 4,692,435 A | 9/1987 | Lormeau et al. |
| 4,757,057 A | 7/1988 | Fussi et al. |
| 4,791,195 A | 12/1988 | Bianchini et al. |
| 4,804,652 A | 2/1989 | Lormeau et al. |
| 4,826,827 A | 5/1989 | Lormeau et al. |
| 4,981,955 A | 1/1991 | Lopez |
| 4,987,222 A | 1/1991 | De Ambrosi et al. |
| 4,990,502 A | 2/1991 | Lormeau et al. |
| 5,010,063 A | 4/1991 | Piani et al. |
| 5,019,649 A | 5/1991 | Lormeau et al. |
| 5,084,564 A | 1/1992 | Vila et al. |
| 5,106,734 A | 4/1992 | Nielsen |
| 5,164,377 A | 11/1992 | Van Dedem et al. |

(Continued)

FOREIGN PATENT DOCUMENTS

| | | |
|---|---|---|
| EP | 0014184 A2 | 8/1980 |
| EP | 0037319 A1 | 10/1981 |

(Continued)

OTHER PUBLICATIONS

FDA ("Questions and Answers about Changes to the USP Heparin Monograph", 2018, available at https://www.fda.gov/drugs/postmarket-drug-safety-information-patients-and-providers/question-and-answers-about-changes-usp-heparin-monograph, webcapture on Apr. 7, 2022), (Year: 2018).*

(Continued)

*Primary Examiner* — Robert J Yamasaki
*Assistant Examiner* — Charles Zoltan Constantine
(74) *Attorney, Agent, or Firm* — Daniel H. Lajiness; Daniel F. Nesbitt; Nesbitt IP LLC

(57) ABSTRACT

The present invention includes methods for preparing anticoagulant polysaccharides using several non-naturally occurring, engineered sulfotransferase enzymes that are designed to react with aryl sulfate compounds instead of the natural substrate, PAPS, to facilitate sulfo group transfer to polysaccharide sulfo group acceptors. Suitable aryl sulfate compounds include, but are not limited to, p-nitrophenyl sulfate or 4-nitrocatechol sulfate. Anticoagulant polysaccharides produced by methods of the present invention comprise N-, 3-O-, 6-O-sulfated glucosamine residues and 2-O sulfated hexuronic acid residues, have comparable anticoagulant activity compared to commercially-available anticoagulant polysaccharides, and can be utilized to form truncated anticoagulant polysaccharides having a reduced molecular weight.

27 Claims, 57 Drawing Sheets

Specification includes a Sequence Listing.

(56) References Cited

U.S. PATENT DOCUMENTS

| | | |
|---|---|---|
| 5,280,016 A | 1/1994 | Conrad et al. |
| 5,378,829 A | 1/1995 | Petitou et al. |
| 5,389,618 A | 2/1995 | Debrie |
| 5,541,095 A | 7/1996 | Hirschberg et al. |
| 5,599,801 A | 2/1997 | Branellec et al. |
| RE35,770 E | 4/1998 | Lormeau et al. |
| 5,817,487 A | 10/1998 | Kobayashi et al. |
| 5,834,282 A | 11/1998 | Habuchi et al. |
| 5,849,721 A | 12/1998 | Uzan |
| 5,919,673 A | 7/1999 | Wong et al. |
| 6,255,088 B1 | 7/2001 | Wong et al. |
| 6,569,998 B2 | 5/2003 | Cummings et al. |
| 6,844,329 B2 | 1/2005 | Duchaussoy et al. |
| 6,861,254 B1 | 3/2005 | Rosenberg et al. |
| RE38,743 E | 6/2005 | Debrie |
| 6,992,183 B2 | 1/2006 | Oreste et al. |
| 7,307,159 B2 | 12/2007 | Deangelis |
| 7,531,338 B2 | 5/2009 | Liu et al. |
| 7,655,445 B2 | 2/2010 | Rosenberg et al. |
| 7,687,479 B2 | 3/2010 | Sasisekharan et al. |
| 7,709,463 B2 | 5/2010 | Van Amsterdam |
| 7,741,091 B2 | 6/2010 | Deangelis et al. |
| 8,067,196 B2 | 11/2011 | Rosenberg et al. |
| 8,088,604 B2 | 1/2012 | Deangelis et al. |
| 8,450,297 B2 | 5/2013 | Rosenberg et al. |
| 8,580,290 B2 | 11/2013 | Deangelis |
| 8,609,632 B2 | 12/2013 | Shriver et al. |
| 8,771,995 B2 | 7/2014 | Liu et al. |
| 8,809,300 B2 | 8/2014 | Zhao et al. |
| 8,815,529 B2 | 8/2014 | Wu |
| 8,980,608 B2 | 3/2015 | Deangelis et al. |
| 9,629,914 B2 | 4/2017 | Deangelis |
| 9,951,149 B2 | 4/2018 | Liu et al. |
| 2004/0147469 A1 | 7/2004 | Grimpe et al. |
| 2005/0255562 A1 | 11/2005 | Rosenberg et al. |
| 2006/0154894 A1 | 7/2006 | Berry et al. |
| 2007/0020243 A1 | 1/2007 | Sengupta et al. |
| 2007/0287683 A1 | 12/2007 | Shriver et al. |
| 2008/0207895 A1 | 8/2008 | Rosenberg et al. |
| 2009/0035787 A1 | 2/2009 | Liu et al. |
| 2009/0197308 A1 | 8/2009 | Liu et al. |
| 2010/0048638 A1 | 2/2010 | Crawford et al. |
| 2011/0105418 A1 | 5/2011 | Nadji et al. |
| 2013/0296540 A1 | 11/2013 | Xu et al. |
| 2014/0349962 A1 | 11/2014 | Rosenberg et al. |
| 2016/0122446 A1 | 5/2016 | Liu et al. |
| 2017/0190803 A1 | 7/2017 | Deangelis |
| 2017/0226543 A1 | 8/2017 | Jendresen et al. |
| 2019/0225998 A1 | 7/2019 | Douaisi et al. |

FOREIGN PATENT DOCUMENTS

| | | |
|---|---|---|
| EP | 0040144 A1 | 11/1981 |
| EP | 0064452 A1 | 11/1982 |
| EP | 0101141 A2 | 2/1984 |
| EP | 0076279 B1 | 9/1986 |
| EP | 0244235 A2 | 11/1987 |
| EP | 0269981 A1 | 6/1988 |
| EP | 0287477 A2 | 10/1988 |
| EP | 0347588 A1 | 12/1989 |
| EP | 0380943 A1 | 8/1990 |
| EP | 0293539 B1 | 6/1994 |
| EP | 0623629 A1 | 11/1994 |
| EP | 3399044 | 11/2018 |
| FR | 2440376 A1 | 5/1980 |
| FR | 2453875 A1 | 11/1980 |
| FR | 2503714 A1 | 10/1982 |
| WO | 8103276 A1 | 11/1981 |
| WO | 2009059283 | 5/2009 |
| WO | 2009059284 | 5/2009 |
| WO | 2012116048 | 8/2012 |
| WO | 2017144671 | 8/2017 |
| WO | 2018048973 | 3/2018 |
| WO | 2018135027 | 7/2018 |
| WO | 2018165656 | 9/2018 |
| WO | 2019050051 | 3/2019 |

OTHER PUBLICATIONS

Gilbert, "The Reactions of Sulfur Trioxide, and of Its Adducts, With Organic Compounds", Nov. 6, 1961, Allied Chemical Corporation, p. 549-589 (41 pages).

Lloyd et al., "Preparation of [$^{35}$S] Sulphamate Derivatives for Studies on Heparin Degrading Enzymes of Mammalian Origin", 1971, Biochemical Pharmacology 20: p. 637-648 (12 pages).

Shively et al., "Formation of Anhydrosugars in the Chemical Depolymerization of Heparin", 1976, Biochemistry 15(18): p. 3932-3942 (11 pages).

Bienkowski et al., "Structural Characterization of the Oligosaccharides Formed by Depolymerization of Heparin with Nitrous Acid", Jan. 10, 1985, J. Biol. Chem. 260(1): p. 356-365 (10 pages).

Gallagher et al., "Molecular distinctions between heparan sulphate and heparin: Analysis of sulphation patterns indicates that heparan sulphate and heparin are separate families of N-sulphated polysaccharides", May 1985, Biochem J. 230: p. 665-674 (10 pages).

Ellis et al., "The relative molecular mass dependence of the antifactor Xa properties of heparin", 1986, Biochem. J. 238: p. 329-333 (5 pages).

Bradbrook et al., "ORG 10172: A low molecular weight heparinoid anticoagulant with a long half-life in man", 1987, Br. J. Clin. Pharmacol. 23: p. 667-675 (9 pages).

Meuleman, "Synopsis of the Anticoagulant and Antithrombotic Profile of the Low Molecular Weight Heparinoid Org 10172 in Experimental Models", 1989, Semin. Thromb. Hemost. 15(4): p. 370-372 (3 pages).

Linhardt et al., "Oligosaccharide Mapping of Low Molecular Weight Heparins: Structure and Activity Differences", 1990, J. Med. Chem. 33: p. 1639-1645 (7 pages).

Harding et al., "Molecular Weight Determination of Polysaccharides", 1991, Advances in Carbohydrate Analysis 1: p. 63-144 (82 pages).

Mulloy et al., "N.m.r. and molecular-modelling studies of the solution conformation of heparin", 1993, Biochem. J. 293: p. 849-858 (10 pages).

Division of Gastrointestinal & Coagulation Drug Products, "Consumer Safety Officer Review for: New Drug Application No. 20-164, Lovenox (enoxaparin) Injection, for Rhone-Poulenc Rorer", Jan. 14, 1993, Food & Drug Administration (377 pages).

Volpi, ""Fast moving" and "slow moving" heparins, dermatan sulfate, and chondroitin sulfate: qualitative and quantitative analysis by agarose-gel electrophoresis", Apr. 1993, Carbohydr. Res. 247: p. 263-278 (16 pages).

Pervin et al., "Separation of Glycosaminoglycan-Derived Oligosaccharides by Capillary Electrophoresis Using Reverse Polarity", 1994, Anal. Biochem. 221: p. 182-188 (7 pages).

Komatsu et al., "A P-loop-related Motif (GxxGxxK) Highly Conserved in Sulfotransferases is Required for Binding the Activated Sulfate Donor", Nov. 14, 1994, Biochem. Biophys. Res. Comm. 204(3): p. 1178-1185 (abstract only).

Marsolais et al., "Identification of Amino Acid Residues Critical for Catalysis and Cosubstrate Binding in the Flavonol 3-Sulfotransferase", Dec. 22, 1995, J. Biol. Chem. 270(51): p. 30458-30463 (6 pgs).

Nadkarni et al., "Preparation and biological activity of N-sulfonated chondroitin and dermatan sulfate derivatives", 1996, Carbohydr. Res. 290: p. 87-96 (10 pages).

Center for Drug Evaluation and Research, "Approval Package for: New Drug Application No. 020430, Danaproid Sodium Injection, for Organon, Inc.", Dec. 24, 1996, Food & Drug Administration (157 pages).

Desai et al, "Mechanism of Heparin Activation of Antithrombin", Mar. 27, 1998, J. Biol. Chem. 273(13): p. 7478-7487 (10 pages).

Herbert et al., "Biochemical and Pharmacological Properties of SANORG 34006, a Potent and Long-Acting Synthetic Pentasaccharide", Jun. 1, 1998, Blood 91(11): p. 4197-4205 (9 pages).

(56) References Cited

OTHER PUBLICATIONS

Sueyoshi et al., "A role of Lys614 in the sulfotransferase activity of human heparan sulfate N-deacetylase/N-sulfotransferase", Aug. 21, 1998, FEBS Letters 433: p. 211-214 (4 pages).
Uhlhorn-Dierks et al., "How Does Nature Cleave Sulfuric Acid Esters? A Novel Posttranslational Modification of Sulfatases", Oct. 2, 1998, Agnew. Chem. Int. Ed. 37(18): p. 2453-2455 (abstract only).
Linhardt et al., "Production and Chemical Processing of Low Molecular Weight Heparins", 1999, Seminars in Thrombosis and Hemostasis 25(3): p. 5-16 (12 pages).
Ahsan et al., "Isoamyl Nitrite Depolymerized Heparin as a Universal Calibrator for Heparins and Low Molecular Weight Heparins", 2000, Clin. Appl. Thrombosis/Hemostasis 6(3): p. 169-174 (6 pages).
Hagner-McWhirter et al., "Biosynthesis of heparin/heparan sulphate: mechanism of epimerization of glucuronyl C-5", 2000, Biochem J. 347: p. 69-75 (7 pages).
Center for Drug Evaluation and Research, "Chemistry Review for: New Drug Application No. 20-484, Tinzaparin Sodium Injection, for Dupont Pharmaceutical Company", Jul. 6, 2000, Food & Drug Administration (7 pages).
Kariya et al., "Preparation of completely 6-O-desulfated heparin and its ability to enhance activity of basic fibroblast growth factor", Aug. 25, 2000, J. Biol. Chem 275(34): p. 25949-25958 (10 pages).
Burkart et al., "Regeneration of PAPS for the enzymatic synthesis of sulfated oligosaccharides", Sep. 8, 2000, J Org Chem. 8;65(18): p. 5565-5574 (10 pages).
Hirsh et al., "Mechanism of Action and Pharmacology of Unfractionated Heparin", 2001, Arterioscler. Thromb. Vasc. Biol. 21: p. 1094-1096 (3 pages).
Rong et al., "Substrate Specificity of the Heparan Sulfate Hexuronic Acid 2-O-Sulfotransferase", 2001, Biochemistry 40: p. 5548-5555 (8 pages).
Yabe et al., "Portable sulphotransferase domain determines sequence specificity of heparan sulphate 3-O-sulphotransferases", 2001, Biochem J. 359: p. 235-241 (7 pages).
Li et al., "Characterization of the D-Glucuronyl C5-epimerase Involved in the Biosynthesis of Heparin and Heparan Sulfate", Mar. 26, 2001, J. Biol. Chem. 276(23): p. 20069-20077 (9 pages).
Negishi et al., "Structure and Function of Sulfotransferases", May 24, 2001, Arch. Biochem. Biophys. 390(2): p. 149-157 (9 pages).
Pinhal et al., "Enzyme interactions in heparan sulfate biosynthesis: Uronosyl 5-epimerase and 2-O-sulfotransferase interact in vivo", Nov. 6, 2001, PNAS 98(23): p. 12984-12989 (6 pages).
Zhang et al., "6-O-Sulfotransferase-1 Represents a Critical Enzyme in the Anticoagulant Heparan Sulfate Biosynthetic Pathway", Nov. 9, 2001, J. Biol. Chem. 276(45): p. 42311-42321 (11 pages).
Raman et al., "Identification of Structural Motifs and Amino Acids within the Structure of Human Heparan Sulfate 3-OSulfotransferase That Mediate Enzymatic Function", 2002, Biochem. Biophys. Res. Comm. 290: p. 1214-1219 (6 pages).
Mousa, "The Low Molecular Weight Heparin, Tinzaparin, in Thrombosis and Beyond", 2002, Cardiovasc. Drug Rev. 20(3): p. 199-216 (18 pages).
Pedersen et al., "Crystal Structure of the Human Estrogen Sulfotransferase-PAPS Complex", May 17, 2002, J. Biol. Chem. 277(20): p. 17928-17932 (5 pages).
Chapman et al., "Bemiparin—A Review of its Use in the Prevention of Venous Thromboembolism and Treatment of Deep Vein Thrombosis", 2003, Drugs 63(21): p. 2357-2377 (21 pages).
Jacobsen et al., "Low molecular weight heparin (dalteparin) for the treatment of venous thromboembolism in pregnancy", Feb. 2003, Br. J. Obstet. Gynaecol. 110: p. 139-144 (6 pages).
Bink et al., "Heparan Sulfate 6-O-Sulfotransferase is Essential for Muscle Development in Zebrafish", Aug. 15, 2003, J. Biol. Chem. 278(33): p. 31118-31127 (10 pages).
Kuberan et al., "Chemoenzymatic synthesis of classical and non-classical anticoagulant heparan sulfate polysaccharides", Dec. 26, 2003, J. Biol. Chem. 278(52): p. 52613-52621 (9 pages).

Fareed et al., "CME, Chapter 16: Low Molecular Weight Heparins: Basic and Applied Considerations", 2004, The Association of Physicians of India, p. 117-138 (22 pages).
Edavettal et al., "Crystal structure and mutational analysis of heparan sulfate 3-O-sulfotransferase isoform 1", Jun. 11, 2004, J. Biol. Chem. 24(11): p. 25789-25797 (9 pages).
Xu et al., "Characterization of heparan sulphate 3-O-sulphotransferase isoform 6 and its role in assisting the entry of herpes simplex virus type 1", Aug. 10, 2004, Biochem. J. 385: p. 451-459 (9 pages).
Li et al., "Structure of the antithrombin-thrombin-heparin ternary complex reveals the antithrombotic mechanism of heparin", Sep. 2004, Nature Struct. Mol. Biol. 11(9): p. 857-862 (6 pages).
Holmborn et al., "Heparan sulfate synthesized by mouse embryonic stem cells deficient in NDST1 and NDST2 is 6-O-sulfated but contains no N-sulfate groups", Oct. 8, 2004, J. Biol. Chem. 279(41): p. 42355-42358 (4 pages).
Ledin et al., "Heparan Sulfate Structure in Mice with Genetically Modified Heparan Sulfate Production", Oct. 8, 2004, J. Biol. Chem. 279(41): p. 42732-42741 (10 pages).
Sedita et al., "Differential Expression of Heparan Sulfate 6-OSulfotransferase Isoforms in the Mouse Embryo Suggests Distinctive Roles During Organogenesis", Oct. 21, 2004, Dev. Dynamics 231: p. 782-794 (13 pages).
Moon et al., "Structural Analysis of the Sulfotransferase (3-O-Sulfotransferase Isoform 3) Involved in the Biosynthesis of an Entry Receptor for Herpes Simplex Virus 1", Oct. 22, 2004, J Biol. Chem. 279(43): p. 45185-45193 (9 pages).
Rath et al., "Sulfotransferase structural biology and inhibitor discovery", Dec. 23, 2004, Drug Discovery Today 9(23): p. 1003-1011 (9 pages).
Whitelock et al., "Heparan Sulfate: A Complex Polymer Charged with Biological Activity", 2005, Chem. Rev. 105(7): p. 2745-2764 (20 pages).
Warkentin et al., "Heparin-Induced Thrombocytopenia", 5th ed., 2005, CRC Press, Boca Raton, FL (p. 191 only).
Chen et al., "Enzymatic Redesigning of Biologically Active Heparan Sulfate", Dec. 30, 2005, J. Biol. Chem. 280(52): p. 42817-42825 (9 pages).
Munoz et al., "Affinity, Kinetic, and Structural Study of the Interaction of 3-OSulfotransferase Isoform 1 with Heparan Sulfate", Apr. 25, 2006, Biochemistry 45(16): p. 5122-5128 (author manuscript, 16 pages).
Lauver et al., "Sulodexide: A Renewed Interest in This Glycosaminoglycan", Fall 2006, Cardiovasc. Drug Rev. 24(3-4): p. 214-226 (13 pages).
Bansode, "Medicine Update vol. 17", 2007, "Chapter 14—Low Molecular Weight Heparin Current Status", The Association of Physicians of India, p. 74-78 (5 pages).
Guerrini et al., "Low Molecular Weight Heparins: Structural Differentiation by Bidimensional Nuclear Magnetic Resonance Spectroscopy", Jul. 2007, Semin. Thromb. Haem. 33(5): p. 478-487 (10 pages).
Linhardt et al., "Enzymatic Synthesis of Glycosaminoglycan Heparin", Jul. 2007, Semin. Thromb. Hemost. 33(5): p. 453-465 (author manuscript, 24 pages).
Chen et al., "Using an Enzymatic Combinatorial Approach to Identify Novel Anticoagulant Heparan Sulfate Structures", Sep. 2007, Chem. Biol. 14(9): p. 986-993 (author manuscript, 18 pages).
Zhang et al., "Solution Structures of Chemoenzymatically Synthesized Heparin and Its Precursors", 2008, J. Am. Chem. Soc. 130: p. 12998-13007 (10 pages).
USP, "Revision Bulletin—Enoxaparin Sodium", 2008 (3 pages).
Xu et al., "Engineering Sulfotransferases to Modify Heparan Sulfate", Mar. 2008, Nat. Chem. Biol. 4(3): p. 200-202 (author manuscript, 8 pages).
Gray et al., "Heparin and low-molecular-weight heparin", May 2008, Thromb. Haemost. 99: p. 807-818 (12 pages).
Lawrence et al., "Evolutionary Differences in Glycosaminoglycan Fine Structure Detected by Quantitative Glycan Reductive Isotope Labeling", Nov. 28, 2008, J. Biol. Chem 283(48): p. 33674-33684 (11 pages).

(56) References Cited

OTHER PUBLICATIONS

Malojcic et al., "A structural and biochemical basis for PAPS-independent sulfuryl transfer by aryl sulfotransferase from uropathogenic *Escherichia coli*", Dec. 9, 2008, PNAS 105(49): p. 19217-19222 (6 pages).

USP, "Bemiparin Sodium", 2009, p. 1223 (1 page).

Peterson et al., "Design of biologically active heparan sulfate and heparin using an enzyme-based approach", Feb. 27, 2009, The Royal Society of Chemistry—Nat. Prod. Rev. 26: p. 610-627 (18 pages).

Veyrat-Follet et al., "The pharmacokinetics of idraparinux, a long-acting indirect factor Xa inhibitor: population pharmacokinetic analysis from Phase III clinical trials", Apr. 2009, J. Thromb. Haemost. 7: p. 559-565 (7 pages).

Rudd et al., "The potential for circular dichroism as an additional facile and sensitive method of monitoring low-molecular-weight heparins and heparinoids", May 11, 2009, Thromb. Haemost. 102: p. 874-878 (5 pages).

Viskov et al., "Description of the chemical and pharmacological characteristics of a new hemisynthetic ultra-low-molecular-weight heparin, AVE5026", Jul. 2009, J. Thromb. Haemost. 7: p. 1143-1151 (9 pages).

Bisio et al., "Structural features of low-molecular-weight heparins affecting their affinity to antithrombin", Sep. 15, 2009, Thromb. Haemost. 102: p. 865-873 (9 pages).

Camporese et al., "Update on the clinical use of the low-molecular-weight heparin, parnaparin", Sep. 24, 2009, Vascular Health and Risk Management 5: p. 819-831 (13 pages).

Sanchez-Ferrer, "Bemiparin—Physiological Profile", 2010, Drugs 70 Suppl. 2: p. 19-23 (5 pages).

"Dalteparin Sodium", 2010, European Pharmacopoeia 7.0: p. 1788-1789 (2 pages).

"Danaproid Sodium", 2010, European Pharmacopoeia 7.0: p. 1789-1792 (4 pages).

"Enoxaparin Sodium", 2010, European Pharmacopoeia 7.0: p. 1920-1921 (2 pages).

"Nadroparin Calcium", 2010, European Pharmacopoeia 7.0: p. 2543-2544 (2 pages).

"Parnaparin Sodium", 2010, European Pharmacopoeia 7.0: p. 2672 (1 page).

"Tinzaparin Sodium", 2010, European Pharmacopoeia 7.0: p. 3098 (1 page).

Kaysser et al., "A New Arylsulfate Sulfotransferase Involved in Liponucleoside Antibiotic Biosynthesis in Streptomycetes", Apr. 23, 2010, J. Biol. Chem. 285(17): p. 12864-12694 (11 pages).

Wang et al., "*E. coli* K5 fermentation and the Preparation of Heparosan, a Bioengineered Heparin Precursor", Dec. 15, 2010, Biotechnol Bioeng. 107(6): p. 964-973 (author manuscript, 19 pages).

Ly et al., "Analysis of *E. coli* K5 capsular polysaccharide Heparosan", Apr. 21, 2010, Anal. Bioanal. Chem. 399: p. 737-745 (9 pages).

Smeds et al., "Target selection of heparan sulfate hexuronic acid 2-O-sulfotransferase", Jun. 16, 2010, Glycobiology 20(10): p. 1274-1282 (9 pages).

Keire et al., "Characterization of currently marketed heparin products: key tests for quality assurance", Aug. 1, 2010, Anal. Bioanal. Chem. 399: p. 581-591 (11 pages).

Malojcic et al., "The PAPS-Independent Aryl Sulfotransferase and the Alternative Disulfide Bond Formation System in Pathogenic Bacteria", Aug. 31, 2010, Antioxidants & Redox Signaling 13(8): p. 1247-1259 (13 pages).

Guerrini, "Effects on Molecular Conformation and Anticoagulant Activities of 1,6-Anhydrosugars at the Reducing Terminal of Antithrombin-Binding Octasaccharides Isolated from Low-Molecular-Weight Heparin Enoxaparin", Oct. 2010, J. Med. Chem. 53: p. 8030-8040 (11 pages).

Lima et al., "Low molecular weight heparins: Structural differentiation by spectroscopic and multivariate approaches", Apr. 16, 2011, Carbohydr. Polym. 85: p. 903-909 (7 pages).

Sheng et al., "The dominating role of N-deacetylase/N-sulfotransferase 1 in forming domain structures in heparan sulfate", Jun. 3, 2011, J. Biol.Chem. 286(22): p. 19768-19776 (9 pages).

Wang et al., "Control of the heparosan N-deacetylation leads to an improved bioengineered heparin", Jul. 2011, Appl. Microbiol. Biotechnol. 91(1): p. 91-99 (author manuscript, 19 pages).

Xu et al., "Chemoenzymatic Synthesis of Homogeneous Ultralow Molecular Weight Heparins", Oct. 28, 2011, Science 334 (6055): p. 498-501 (4 pages).

Cosmi et al., "Old and new heparins", Dec. 2, 2011, Thromb. Res. 129: p. 388-391 (4 pages).

Higashi et al., "Photochemical Preparation of a Novel Low Molecular Weight Heparin", Feb. 1, 2012, Carbohydr. Polym. 67(2): p. 1737-1743 (author manuscript, 20 pages).

Linhardt et al., "Synthetic heparin", Feb. 8, 2012, Current Opinion in Pharmacology 12: p. 217-219 (3 pages).

Moon et al., "Dissecting the substrate recognition of 3-O-sulfotransferase for the biosynthesis of anticoagulant heparin", Apr. 3, 2012, PNAS 109(14): p. 5265-5270 (6 pages).

Pempe et al., "Substrate specificity of 6-O-endosulfatase (Sulf-2) and its implications in synthesizing anticoagulant heparan sulfate", Jun. 12, 2012, Glycobiology 22(10): p. 1353-1362 (10 pages).

Zhang et al., "Metabolic engineering of *Escherichia coli* BL21 for biosynthesis of heparosan, a bioengineered heparin precursor", Jul. 8, 2012, Metabolic Engineering 14: p. 521-527 (7 pages).

Kreuger et al., "Heparan Sulfate Biosynthesis: Regulation and Variability", Sep. 2012, J. Histochem. Cytochem. 60(12): p. 898-907 (10 pages).

Li et al., "Top-Down Approach for the Direct Characterization of Low Molecular Weight Heparins Using LC-FT-MS", Sep. 2012, ACS Anal. Chem. (accepted pre-print publication, 8 pages).

Cumpstey, "Chemical Modification of Polysaccharides", 2013, Hindawi Publishing Corporation—ISRN Organic Chemistry, Article ID 417672 (27 pages).

Lindahl et al., "Pathophysiology of heparan sulphate: many diseases, few drugs", 2013, J. Intern. Med. 273: 555-571 (17 pages).

Keire et al., "Characterization of currently marketed heparin products: composition analysis by 2D-NMR", 2013, Royal Soc. of Chemistry, Anal. Methods 5: p. 2984-2994 (11 pages).

Restaino et al., "High cell density cultivation of a recombinant *E. coli* strain expressing a key enzyme in bioengineered heparin production", Jan. 15, 2013, Appl. Microbiol. Biotechnol. 97: p. 3893-3900 (8 pages).

Ye et al., "Characterization of currently marketed heparin products: Key tests for LMWH quality assurance", Jul. 16, 2013, J. Pharm. Biomed. Anal. 85: p. 99-107 (9 pages).

Gesteira et al., "Insights into the N-sulfation mechanism: molecular dynamics simulations of the N-sulfotransferase domain of NDST1 and mutants", Aug. 5, 2013, PLoS One 8(8): e70880 (12 pages).

Garcia-Suarez et al., "Multiple alterations of heparan sulphate in cancer", May 2013, OA Cancer 1(1):1 (7 pages).

Fu et al., "Structural Characterization of Pharmaceutical Heparins Prepared from Different Animal Tissues", May 2013, J. Pharm. Sci. 102(5) (author manuscript, 19 pages).

Chen et al., "Tailor design and synthesis of heparan sulfate (HS) oligosaccharide analogs using sequential one-pot multienzyme (OPME) systems", Nov. 4, 2013, Angew. Chem. Int. Ed. Engl. 52(45): p. 11852-11856 (author manuscript, 12 pages).

Dejima et al., "Analysis of *Drosophila* Glucuronyl C5-Epimerase: Implications for Developmental Roles of Heparan Sulfate Sulfation Compensation and 2-O-Sulfated Glucuronic Acid", Nov. 29, 2013, J. Biol. Chem. 288(48): p. 34384-34393 (10 pages).

Coccheri et al., "Development and use of sulodexide in vascular diseases: implications for treatment", Dec. 24, 2013, Drug Des. Dev. Therapy 8: p. 49-65 (17 pages).

Taniguchi et al, "Handbook of Glycosyltransferases and Related Genes", $2^{nd}$ ed., 2014, Section X—Sulfotransferases, Chapters 86-103 (218 pages).

Zhang et al., "High cell density cultivation of a recombinant *Escherichia coli* strain expressing a 6-O-sulfotransferase for the production of bioengineered heparin", 2014, J. Appl. Microbiol. 118: p. 92-98 (7 pages).

(56) References Cited

OTHER PUBLICATIONS

Sterner et al., "Assays for determining heparan sulfate and heparin O-sulfotransferase activity and specificity", Jan. 2014, Anal Bioanal Chem. 406(2): p. 525-536 (author manuscript, 27 pages).

Ciccone et al., "Bemiparin, an effective and safe low molecular weight heparin: A review", Mar. 19, 2014, Vasc. Pharmacol. 62: p. 32-37 (6 pages).

Xu et al., "Homogeneous low-molecular-weight heparins with reversible anticoagulant activity", Apr. 2014, Nat. Chem. Biol. 10(4): p. 248-250 (author manuscript, 12 pages).

Driguez et al., "Synthetic oligosaccharides as active pharmaceutical ingredients: Lessons learned from the full synthesis of one heparin derivative on a large scale", Apr. 7, 2014, Royal Society of Chemistry, Nat. Prod. Rep. 31: p. 980-989 (10 pages).

Liu et al., "Molecular Mechanism of Substrate Specificity for Heparan Sulfate 2-O-Sulfotransferase", May 9, 2014, J. Biol. Chem. 289(19): p. 13407-13418 (15 pages).

Liu et al., "Chemoenzymatic synthesis of heparan sulfate and heparin", Jun. 2014, Royal Society of Chemistry, Nat. Prod. Rep., 31: p. 1676-1685 (10 pages).

Mulloy et al., "USP compendial methods for analysis of heparin: chromatographic determination of molecular weight distributions for heparin sodium", Jun. 24, 2014, Anal. Bioanal. Chem. 406: p. 4815-4823 (9 pages).

Santos et al., "Structural and functional analyses of bovine and porcine intestinal heparins confirm they are different drugs", Nov. 2014, Drug Discovery Today 19(11): p. 1801-1807 (7 pages).

Bhaskar et al., "Combinatorial one-pot chemoenzymatic synthesis of heparin", Nov. 7, 2014, Carbohydr. Polym. 122: p. 399-407 (9 pages).

Deangelis, "Heparosan, a promising 'naturally good' polymeric conjugating vehicle for delivery of injectable therapeutics", 2015, Expert Opin. Drug Deliv. 12(3): p. 349-352 (4 pages).

Joice et al., "Glycosaminoglycans: Chemistry and Biology—Chapter 2: Enzymatic Synthesis of Heparan Sulfate and Heparin", 2015, Springer Science + Business Media, p. 11-19 (9 pages).

Egan et al., "Measuring Anti-Factor Xa Activity to Monitor Low-Molecular-Weight Heparin in Obesity: A Critical Review", Jan. 2015, Can. J. Hosp. Pharm. 68(1): p. 33-47 (15 pages).

Pimpao et al., "Phenolic sulfates as new and highly abundant metabolites in human plasma after ingestion of a mixed berry fruit puree", Jan. 9, 2015, Br. J. Nutr. 113: p. 454-463 (10 pages).

Prechoux et al., "C5-Epimerase and 2-O-Sulfotransferase Associate in Vitro to Generate Contiguous Epimerized and 2-O-Sulfated Heparan Sulfate Domains", Jan. 16, 2015, ACS Chem. Biol. 10: p. 1064-1071 (8 pages).

Zhang et al., "High cell density cultivation of recombinant *Escherichia coli* strains expressing 2-O-sulfotransferase and C5-epimerase for the production of bioengineered heparin", Mar. 2015, Appl. Biochem. Biotechnol. 175(6): p. 2986-2995 (author manuscript, 13 pages).

Mourier et al., "Quantitative compositional analysis of heparin using exhaustive heparinase digestion and strong anion exchange chromatography", Mar. 2015, Anal. Chem. Res. 3: p. 46-53 (8 pages).

Bisio et al., "Determination of the Molecular Weight of Low-Molecular-Weight Heparins by Using High-Pressure Size Exclusion Chromatography on Line with a Triple Detector Array and Conventional Methods", Mar. 19, 2015, Molecules 20: p. 5085-5098 (14 pages).

Baik et al., "Optimization of bioprocess conditions improves production of a CHO cell-derived, bioengineered heparin", Jun. 3, 2015, Biotechnol. J. 10: p. 1067-1081 (15 pages).

Dou et al., "Role of Deacetylase Activity of N-Deacetylase/N-Sulfotransferase 1 in Forming N-Sulfated Domain in Heparan Sulfate", Jun. 24, 2015, J. Biol. Chem. 290(33): p. 20427-20437 (11 pages).

Sulfita et al., "Heparin and related polysaccharides: synthesis using recombinant enzymes and metabolic engineering", Jul. 29, 2015, Appl. Microbiol. Biotechnol. 99: p. 7465-7479 (15 pages).

Langereis et al., "A Multiplex Assay for the Diagnosis of Mucopolysaccharidoses and Mucolipidoses", Sep. 25, 2015, PLoS One 10(9): e0138622 (13 pages).

Keire et al., "Diversifying the Global Heparin Supply Chain: Reintroduction of Bovine Heparin in the United States?", Nov. 2, 2015, PharmTech, http://www.pharmtech.com/diversifying-global-heparin-supply-chain-reintroduction-bovine-heparin-united-states (7 pages).

Ange et al., "Analysis of Heparins Derived From Bovine Tissues and Comparison to Porcine Intestinal Heparins", 2016, Clin. Appl. Thrombosis/Hemostasis 22(6): p. 520-527 (8 pages).

Yates et al., "Recent innovations in the structural analysis of heparin", 2016, International Journal of Cardiology 212S1: p. S5-S9 (5 pages).

Vardanyan et al., "Synthesis of Best-Seller Drugs: Chapter 24—Antithrombotic Drugs (Anticoagulants, Antiplatelets, and Thrombolytics)", 2016, Elsevier B.V., p. 383-390 (4 pages).

Szajek et al., "The US regulatory and pharmacopeia response to the global heparin contamination crisis", Jun. 9, 2016, Nature Biotechnology 34(6): p. 625-630 (6 pages).

Mourier et al., "Analytical comparison of a US generic enoxaparin with the originator product: The focus on comparative assessment of antithrombin-binding components", Jul. 28, 2016, J. Pharm. Biomed. Anal. 129: p. 542-550 (9 pages).

Tovar et al., "Structural and haemostatic features of pharmaceutical heparins from different animal sources: challenges to define thresholds separating distinct drugs", Oct. 18, 2016, Nature Scientific Reports 6:35619 (12 pages).

Li et al., "Enzymatic Synthesis of Homogeneous Chondroitin Sulfate Oligosaccharides", 2017, Angew. Chem. Int. Ed. 56: p. 11784-11787 (4 pages).

Wang et al., "Sulfated Cyclocarya paliurus polysaccharides markedly attenuates inflammation and oxidative damage in lipopolysaccharide-treated macrophage cells and mice", Jan. 17, 2017, Nature Scientific Reports 7:40402 (12 pages).

Xu et al., "Structure Based Substrate Specificity Analysis of Heparan Sulfate 6-O-Sulfotransferases", Jan. 20, 2017, ACS Chem. Biol. 12(1): p. 73-82 (author manuscript, 18 pages).

Vaidyanathan et al., "Engineered heparins as new anticoagulant drugs", Mar. 2017, Bioengineering & Translational Medicine 2(1): p. 17-30 (accepted preprint version, 45 pages).

Gardini et al., "Characterization of Danaparoid Complex Extractive Drug by an Orthogonal Analytical Approach", Jul. 5, 2017, Molecules 22(7): 1116 (25 pages).

Bertini et al., "Molecular Weights of Bovine and Porcine Heparin Samples: Comparison of Chromatographic Methods and Results of a Collaborative Survey", Jul. 19, 2017, Molecules 22(1214) (10 pages).

Meneghetti et al., "Insights into the role of 3-O-sulfotransferase in heparan sulfate biosynthesis", Aug. 16, 2017, Org. Biomol. Chem. 15: p. 6792-6799 (author manuscript, 16 pages).

Stancanelli et al., "Recognition and Conformational Properties of an Alternative Antithrombin Binding Sequence Obtained by Chemoenzymatic Synthesis", 2018, ChemBioChem 19: p. 1178-1188 (11 pages).

Islam et al., "A robust protocol for directed aryl sulfotransferase evolution towards the carbohydrate building block GlcNAc", May 2018, Biotech. & Bioeng. 115(5): p. 1106-1115 (accepted preprint version, 34 pages).

Islam et al., "KnowVolution Campaign of an Aryl Sulfotransferase Increases Activity toward Cellobiose", 2018, Chem. Eur. J. 24: p. 17117-17124 (8 pages).

Sulfita, Matt, "Chemoenzymatic Synthesis of Heparan Sulfates, and Investigations of Their Role in Cell Signaling, Human Health and Disease", May 2018, Rensselaer Polytechnic Institute, Department of Biology (161 pages).

Cimini et al., "Microbial production and metabolic engineering of chondroitin and chondroitin sulfate", Oct. 4, 2018, Portland Press—Emerging Topics in Life Sciences (13 pages).

Taylor et al., "By-Products of Heparin Production Provide a Diverse Source of Heparin-like and Heparan Sulfate Glycosaminoglycans", Feb. 25, 2019, Nature Sci. Rep. 9: 2679 (12 pages).

(56) References Cited

OTHER PUBLICATIONS

Vessella et al., "Development of Semisynthetic, Regioselective Pathways for Accessing the Missing Sulfation Patterns of Chondroitin Sulfate", Jun. 24, 2019, Biomacromolecules 20: p. 3021-3030 (10 pages).
International Search Report and Written Opinion dated Apr. 20, 2020 in corresponding International Application No. PCT/US2020/013677 filed Jan. 15, 2020 (13 pages).
International Search Report and Written Opinion dated Nov. 4, 2020 in related International Application No. PCT/US2020/041404 filed Jul. 9, 2020 (12 pages).
International Preliminary Report on Patentability (Chapter I) dated Jun. 16, 2021 in corresponding International Application No. PCT/US2020/013677 filed Jan. 15, 2020 (8 pages).
U.S. Appl. No. 17/376,322, filed Jul. 15, 2021, Ferreira.
U.S. Appl. No. 17/376,332, filed Jul. 15, 2021, Ferreira.
U.S. Appl. No. 17/376,335, filed Jul. 15, 2021, Ferreira.
U.S. Appl. No. 17/376,341, filed Jul. 15, 2021, Ferreira.
Gesteira et al., "Structural basis of oligosaccharide processing by glycosaminoglycan sulfotransferases", Jun. 6, 2018, Glycobiology, 28(11): p. 885-897 (13 pages).
Non-final Office Action dated Jan. 27, 2022 in copending U.S. Appl. No. 17/376,322, filed Jul. 15, 2021 (17 pages).
Non-final Office action dated Feb. 7, 2022 in copending U.S. Appl. No. 17/376,332, filed Jul. 15, 2021 (19 pages).
Notice of Allowance dated Feb. 11, 2022 in copending U.S. Appl. No. 17/376,335, filed Jul. 15, 2021 (11 pages).
Notice of Allowance dated Mar. 4, 2022 in copending U.S. Appl. No. 17/376,335, filed Jul. 15, 2021 (11 pages).
Non-final Office action dated Mar. 24, 2022 in copending U.S. Appl. No. 17/376,341, filed Jul. 15, 2021 (9 pages).
Xu et al., Mutational Study of Heparan Sulfate 2-O-Sulfotransferase and Chondroitin Sulfate 2-O Sulfotransferase, The Journal of Biological Chemistry (2007), 282(11), 8356-8367 (12 pages).
Bethea et al., Redirecting the substrate specificity of heparan sulfate 2-O-sulfotransferase by structurally guided mutagenesis, PNAS, Dec. 2, 2008, vol. 105, No. 48, pp. 18724-18729 (6 pages).
Li et al., Using Engineered 2-O-Sulfotransferase to Determine the Activity of Heparan Sulfate C5-epimerase and Its Mutants, The Journal of Bio Chem, Apr. 9, 2010, vol. 285, No. 15, pp. 11106-11113 (8 pages).
Thieker et al, Downstream Products are Potent Inhibitors of the Heparan Sulfate 2-O-Sulfotransferase, Scientific Reports, 2018, 8:11832, pp. 1-13 (13 pages).
FDA ("Questions and Answers about Changes to the USP Heparin Monograph", 2018, available at https://www.fda.gov/drugs/postmarket-drug-safety-information-patients-and-providers/question-and-answers-about-changes-usp-heparin-monograph, webcapture on Apr. 7, 2022), 2018 (3 pages).

\* cited by examiner

Reaction

Transition State

Products

Reaction

Transition State

Products

Reaction

Transition State

Products

Reaction

Transition State

Products

METHODS FOR SYNTHESIZING ANTICOAGULANT POLYSACCHARIDES

CROSS-REFERENCE TO RELATED APPLICATIONS

The instant application is a continuation-in-part of International Application No. PCT/US2020/041404, filed Jul. 9, 2020, which claims the benefit of U.S. Provisional Application No. 62/871,980, filed on Jul. 9 2019, and 63/033,687, filed on Jun. 2, 2020, the disclosures of which are hereby incorporated by reference in their entireties.

FIELD OF THE INVENTION

The present invention relates to methods for synthesizing anticoagulant polysaccharides using engineered, non-natural sulfotransferase enzymes that are designed to react with aryl sulfate compounds as sulfo group donors.

REFERENCE TO SEQUENCE LISTING

The present application is being filed along with a sequence listing in electronic format. The sequence listing is provided as a file entitled "OPT-002X PCT_sequence_disclosure.txt" created on Jul. 9, 2020, and which is 175,283 bytes in size. The information in electronic format of the sequence listing is incorporated by reference in its entirety.

BACKGROUND OF THE INVENTION

Heparins and other anticoagulant polysaccharides are a class of compounds that are commonly prescribed as drugs in clinical settings to prevent blood clotting. Typically, these compounds are isolated and purified from the internal organs of animals, such as pigs and cows. However, because of recent disruptions in the worldwide supply due to potential contamination of heparin (over 200 people died as a result of contaminated compounds in 2007 in the United States alone) and geopolitical tensions with global suppliers, there has been a recent push to synthesize anticoagulant polysaccharides in vitro.

Within the animal, sulfated polysaccharides, including heparin, are synthesized by the catalytic transfer of sulfate functional groups, also called "sulfo groups", from a sulfo group donor to a polysaccharide, which acts as a sulfo group acceptor. Each sulfo group transfer is catalyzed by a sulfotransferase enzyme, and there are often multiple sulfotransfer reactions catalyzed by multiple sulfotransferase enzymes to ultimately arrive at each sulfated polysaccharide product. Sulfotransferases are nearly ubiquitous in nature, and they exist in nearly all types of organisms, including bacteria, yeast, and animals, including humans. Similarly, sulfotransferase enzymes play an integral role in the sulfation of a wide array of sulfo group acceptors, including many types of steroids, polysaccharides, proteins, xenobiotics, and other molecules.

There are several polysaccharides that can be utilized as sulfo group acceptors, including, for example, dermatan, keratan, heparosan, and chondroitin. In particular, heparosan comprises repeating disaccharide units of 1→4 glycosidically-linked, glucuronic acid and N-acetylated glucosamine ($[\beta(1,4)GlcA-\alpha(1,4)GlcNAc]_n$) residues, any of which can be further modified by one or more enzyme-catalyzed deacetylation, sulfation, or epimerization reactions. Sulfation of heparosan-based polysaccharides can be catalyzed by up to four sulfotransferase enzymes to form heparan sulfate (HS), and when performed in a particular order along with deacetylation of one or more glucosamine residues and epimerization of one or more glucuronic acid residues, can be utilized to form heparin.

there are only a couple of molecules that can be utilized by sulfotransferase enzymes as sulfo group donors. The nearly ubiquitous sulfo group donor, including for each of the four HS sulfotransferases, is 3'-phosphoadenosine 5'-phosphosulfate (PAPS). These in vivo systems have evolved to exclusively utilize PAPS because it has a short half-life and can readily be synthesized and metabolized, as needed, by the organism. However, that same short half-life renders PAPS to be unsuitable for most in vitro syntheses, particularly in large scale syntheses, that utilize sulfotransferases because it can readily decompose into adenosine 3',5'-diphosphate, which actively inhibits the sulfotransferases' biological activity.

Aryl sulfate compounds, such asp-nitrophenyl sulfate (PNS) and 4-methylumbelliferyl sulfate (MUS) have been identified as cheap, widely-available compounds that can be useful as sulfo donors with a very limited number of sulfotransferases to synthesize certain small molecule products (see Malojcic, G., et al. (2008) *Proc. Nat. Acad. Sci.* 105 (49):19217-19222 and Kaysser, L., et al., (2010) *J. Biol. Chem.* 285 (17):12684-12694, the disclosures of which are incorporated by reference in their entireties). Yet, only a small number of bacterial sulfotransferases have been shown to react with aryl sulfate compounds as sulfo group donors, and none of these react with polysaccharides, let alone heparosan-based polysaccharides, as sulfo group acceptors. As a result, when sulfotransferases are used in the in vitro synthesis of sulfated polysaccharides, PAPS must be included in the reaction mixture to effectively catalyze sulfo group transfer, and aryl sulfate compounds can only be used indirectly, to repopulate the system with PAPS (see U.S. Pat. No. 6,255,088, the disclosure of which is incorporated by reference in its entirety).

Consequently, there is a need to develop facile methods of synthesizing sulfated polysaccharides in vitro, particularly heparin, without utilizing PAPS as the sulfo group donor. In particular, the development of sulfotransferase enzymes that are capable of both reacting with aryl sulfate compounds as sulfo group donors and with heparosan-based polysaccharides as sulfo group acceptors would present a large step forward toward the development of large-scale syntheses of heparin in vitro.

SUMMARY OF THE INVENTION

The present invention provides methods for producing sulfated polysaccharides, particularly heparin and heparin derivatives, in vitro using non-naturally occurring sulfotransferase enzymes that have been engineered to catalyze the transfer of sulfo groups from aryl sulfate compounds as sulfo group donors to react with polysaccharides as sulfo group acceptors. According to the present invention, the polysaccharides can be heparosan-based polysaccharides that can be utilized to form heparin and other sulfated polysaccharides that possess anticoagulant activity. According to the present invention, heparin synthesized by the methods described herein can be prescribed and administered in a clinical setting to prevent blood clotting.

In an aspect of the present invention, a sulfated polysaccharide product can be synthesized enzymatically by a method comprising the steps of: (a) providing a polysaccharide; (b) providing an aryl sulfate compound; (c) providing an engineered sulfotransferase enzyme configured to recognize, bind, and react with the aryl sulfate compound as a sulfo group donor, and with the polysaccharide as a sulfo group acceptor; (d) forming a reaction mixture by combining the engineered sulfotransferase enzyme with the polysaccharide and the aryl sulfate compound; and (e) catalyzing the enzymatic transfer of a sulfo group from the aryl sulfate compound to the polysaccharide, using the engineered sulfotransferase enzyme, to form the sulfated polysaccharide product. According to the present invention, the polysaccharide can be a heparosan-based polysaccharide derived from heparosan, $[\beta(1,4)GlcA-\alpha(1,4)GlcNAc]_n$, in which GlcA is glucuronic acid and GlcNAc is N-acetyl glucosamine. Heparosan-based polysaccharides comprise repeating dimers of 1->4 glycosidically-linked hexuronic acid and glucosamine residues, wherein each hexuronic acid is either glucuronic acid (GlcA, above) or iduronic acid (IdoA), and each glucosamine residue can either be N-acetylated, N-sulfated, or N-unsubstituted. Heparosan-based polysaccharides in which at least one of the glucosamine residues is N-unsubstituted can also be called N-deacetylated heparosan. Further, in various embodiments, any of the GlcA or IdoA residues can be sulfated at the 2-O position, and/or any of the glucosamine residues can be sulfated at the N-, 6-O, or 3-O position, prior to reacting with an engineered sulfotransferase enzyme. Heparosan-based polysaccharides that contain at least one sulfate group in any of the above positions within a hexuronic acid or glucosamine residue can also be called heparan sulfate (HS).

According to the present invention, and useful in combination with any one or more of the above aspects and embodiments, a sulfated polysaccharide product formed in a first sulfotransfer reaction can be utilized as a sulfo group acceptor in a subsequent reaction with another sulfotransferase enzyme, which can either be performed in the same reaction mixture as the first sulfotransfer reaction, or in a separate reaction mixture after isolating the sulfated polysaccharide product and combining it with a sulfo group donor and a sulfotransferase enzyme. In various embodiments, a plurality of sulfotransfer reactions can be carried out, either sequentially or simultaneously, on a single heparosan-based polysaccharide, including at least two, at least three, or at least four sulfotransfer reactions. Each of the plurality of sulfotransfer reactions on a heparosan-based polysaccharide can be catalyzed by at least two, at least three, or up to four sulfotransferase enzymes. In various embodiments, at least one, and preferably all, of the sulfotransfer reactions are catalyzed by an engineered sulfotransferase enzyme which recognizes, binds, and reacts with the aryl sulfate compound as a sulfo group donor. In further embodiments, at least one, and preferably all, of the sulfotransfer reactions are carried out in reaction mixtures that contain only an aryl sulfate compound as a sulfate donor, and do not contain PAPS.

In another aspect of the invention, each engineered sulfotransferase enzyme comprises several amino acid mutations made within the active site of a corresponding natural sulfotransferase enzyme, in order to convert the enzyme's biological activity from reacting with PAPS as the sulfo group donor to reacting with an aryl sulfate compound as a sulfo group donor. However, in various embodiments, each engineered sulfotransferase enzyme retains the natural enzyme's biological activity with its particular sulfo acceptor polysaccharide. As a non-limiting example, a natural HS hexuronyl 2-O sulfotransferase (2OST), which has a biological activity in which the enzyme reacts with PAPS as a sulfo group donor and N-sulfated heparosan as a sulfo group acceptor, can be mutated in multiple amino acid positions to generate an engineered sulfotransferase enzyme that recognizes, binds, and reacts with an aryl sulfate compound as a sulfo group donor, but that still reacts with N-sulfated heparosan as a sulfo group acceptor. Such engineered aryl sulfate-dependent 2OST enzymes, and others, are described in further detail below.

In another aspect of the invention, an N-, 2-O-, 3-O-, 6-O-sulfated heparan sulfate (N,2,3,6-HS) product can be synthesized, the method comprising the following steps: (a) providing a starting polysaccharide reaction mixture comprising N-deacetylated heparosan; (b) combining the starting polysaccharide reaction mixture with a reaction mixture comprising a sulfo group donor and a first sulfotransferase enzyme selected from the group consisting of a glucosaminyl N-sulfotransferase enzyme (NST), a 2OST enzyme, and a glucosaminyl 6-O sulfotransferase (6OST) enzyme, to form a first sulfated polysaccharide; (c) combining the first sulfated polysaccharide with a reaction mixture comprising a sulfo group donor and a second sulfotransferase enzyme, wherein the second sulfotransferase enzyme is one of the two enzymes that were not selected in step (b), to form a second sulfated polysaccharide; (d) combining the second sulfated polysaccharide with a reaction mixture comprising a sulfo group donor and a third sulfotransferase enzyme, wherein the third sulfotransferase enzyme is the enzyme that was not selected in step (b) or step (c), to form a third sulfated polysaccharide; and (e) combining the third sulfated polysaccharide with a reaction mixture comprising a sulfo group donor and a glucosaminyl 3-O sulfotransferase (3OST) enzyme, to form the N,2,3,6-HS product; wherein (i) at least one of the sulfotransferase enzymes is an engineered sulfotransferase enzyme that is dependent on reacting with an aryl sulfate compound as a sulfo group donor to catalyze a sulfotransfer reaction, and (ii) in a reaction mixture comprising an engineered sulfotransferase enzyme, the reaction mixture comprises an aryl sulfate compound as a sulfo group donor. In various embodiments, the first sulfotransferase enzyme is an NST enzyme, the second sulfotransferase enzyme is a 2OST enzyme, and the third sulfotransferase enzyme is a 6OST enzyme.

In another aspect of the invention, methods to synthesize an N,2,3,6-HS product can comprise the following steps: (a) providing a starting polysaccharide reaction mixture comprising N-sulfated heparosan; (b) combining the starting polysaccharide reaction mixture with a reaction mixture comprising a sulfo group donor and a first sulfotransferase enzyme selected from the group consisting of a 2OST enzyme and a 6OST enzyme, to form a first sulfated polysaccharide product; (c) combining the first sulfated polysaccharide product with a reaction mixture comprising a sulfo group donor and a second sulfotransferase enzyme, wherein the second sulfotransferase enzyme is the enzyme that was not selected in step (b), to form a second sulfated polysaccharide product; and (d) combining the second sulfated polysaccharide product with a reaction mixture comprising a sulfo group donor and a 3OST enzyme, to form the N,2,3,6-HS product; wherein (i) at least one of the sulfotransferase enzymes is an engineered sulfotransferase enzyme that is dependent on reacting with an aryl sulfate compound as a sulfo group donor to catalyze a sulfotransfer reaction, and (ii) in a reaction mixture comprising an engineered sulfotransferase enzyme, the reaction mixture comprises an aryl sulfate compound as the sulfo group donor. In various embodiments, the first sulfotransferase enzyme is the 2OST enzyme, and the second sulfotransferase enzyme is the 6OST enzyme.

In various embodiments, the starting polysaccharide reaction mixture comprising N-sulfated heparosan can be provided by combining N-deacetylated heparosan, a sulfo group donor, and an NST enzyme into a reaction mixture. In various embodiments, the NST enzyme is an engineered sulfotransferase, which reacts with an aryl sulfate compound as a sulfo group donor in the absence of PAPS. In various embodiments, the N-sulfated heparosan can be provided by combining a natural glucosaminyl N-deacetylase/N-sulfotransferase (NDST) enzyme, PAPS, and heparosan.

In various embodiments, the step of providing the starting polysaccharide reaction mixture can comprise the chemical synthesis of N-sulfated heparosan, comprising the following sub-steps: (i) providing a precursor polysaccharide composition comprising heparosan; (ii) combining the precursor polysaccharide composition with a reaction mixture comprising a base, preferably lithium hydroxide or sodium hydroxide, for a time sufficient to N-deacetylate at least one of the N-acetylated glucosamine residues within the heparosan, forming an N-deacetylated heparosan composition; and (iii) combining the N-deacetylated heparosan composition with a reaction mixture comprising an N-sulfation agent, thereby forming the N-sulfated heparosan.

In various embodiments, the step of providing the precursor polysaccharide composition comprising heparosan can further comprise the sub-step of isolating heparosan from a bacterial or eukaryotic cell culture, preferably a bacterial cell culture, and more preferably a bacterial cell culture comprising bacteria selected from the group consisting of the K5 strain of *Escherichia coli* (*E. coli*) and the BL21 strain of *E. coli*. Heparosan can be isolated from *E. coli* as a polydisperse mixture of polysaccharides having a weight-average molecular weight of at least 10,000 Da, and up to at least 500,000 Da.

Treating heparosan with a base, such as lithium hydroxide or sodium hydroxide, removes acetyl groups from N-acetyl glucosamine residues, forming N-unsubstituted glucosamine residues that can subsequently be N-sulfated. In various embodiments, precursor polysaccharides can be treated with a base for a time sufficient to reduce the relative number of N-acetylated glucosamine residues to a desired level. The reaction time can be dependent on factors such as the average molecular weight of the heparosan within the precursor polysaccharide composition, the N-acetyl glucosamine content of the heparosan prior to reacting with the base, the desired N-acetyl content within the N-deacetylated heparosan composition, and the concentration and identity of the base itself. In various embodiments, the time sufficient to N-deacetylate the heparosan within the precursor polysaccharide composition can be the time sufficient to form an N-deacetylated heparosan composition in which less than 60%, down to less than 5%, preferably in the range of 12% to 18%, and more preferably 15%, of the glucosamine residues remain N-acetylated.

Additionally, treating the precursor polysaccharide composition with a base to reduce the number of N-acetylated glucosamine residues can also have the effect of depolymerizing the heparosan, causing the N-deacetylated heparosan composition to have a lower average molecular weight relative to the precursor polysaccharide composition. Accordingly, in various embodiments, the precursor polysaccharide composition can be treated with a base for a time sufficient to form an N-deacetylated heparosan composition having a desired average molecular weight. As with above, the reaction time can depend on several factors, including the average molecular weight of the heparosan within the precursor polysaccharide composition, and the desired average molecular weight of the polysaccharides within the N-deacetylated heparosan composition itself. In various embodiments, the time sufficient to N-deacetylate the heparosan within the precursor polysaccharide composition can be the time sufficient to form an N-deacetylated polysaccharide composition having a weight-average molecular weight in a range from 1,500 Da to 100,000 Da, for example, from at least 1,000 Da, up to 20,000 Da, or from at least 9,000 Da, and up to 12,500 Da.

In various embodiments, once the N-deacetylated heparosan is formed, the resulting N-unsubstituted glucosaminyl residues can then receive a sulfo group from an N-sulfation agent, such as, for example, an engineered or natural NST enzyme. In various embodiments, one or more of the N-unsubstituted glucosamine residues within N-deacetylated heparosan can be chemically N-sulfated. In various embodiments, chemical N-sulfation can either supplement or replace enzymatic N-sulfation catalyzed by an NST enzyme. A non-limiting example of a chemical N-sulfation agent can comprise a reaction mixture comprising a sulfur trioxide-containing compound or adduct, particularly a sulfur trioxide-trimethylamine adduct.

In various embodiments, by either chemical and/or enzymatic N-sulfation, at least about 10%, and up to at least about 95%, of the glucosaminyl residues within N-deacetylated heparosan are N-sulfated by the N-sulfation agent, prior to subsequently being sulfated at any of the 2-O, 3-O, or 6-O positions.

In various embodiments, during a synthesis of an N,2,3,6-HS product according to any of the methods described herein, the 3-O sulfation of the heparosan-based polysaccharide can be catalyzed after the 2-O sulfation step to form an N,2,3-HS product, followed by 6-O sulfation to form the N,2,3,6-HS product. Additionally, within any of the sulfotransfer reaction steps within methods described herein, reaction mixtures that do not comprise an engineered sulfotransferase enzyme can comprise PAPS and a natural HS sulfotransferase enzyme that possesses biological activity with PAPS as the sulfo group donor. In various embodiments, even if one or more of the NST enzyme, 2OST enzyme, and 6OST enzyme used to form an N,2,3,6-HS product is a natural sulfotransferase enzyme, the synthesis is completed using an engineered 3OST enzyme, using an aryl sulfate compound as a sulfo group donor in the absence of PAPS. In various embodiments, the sulfotransferase enzyme in all sulfotransfer steps in the synthesis of an N,2,3,6-HS product is an engineered sulfotransferase enzyme, in which the sulfo group donor in each step consists of one or more aryl sulfate compounds and the sulfotransferase reaction takes place in the absence of PAPS. In various embodiments, reaction mixtures for one or more of the sulfotransfer reactions can be combined into a single reaction vessel, or "pot." In other embodiments, each of the sulfotransfer reactions can be conducted sequentially, in separate reaction vessels.

In various embodiments, aryl sulfate compounds that can be utilized as sulfo donors are organosulfates that comprise a sulfo group covalently bound to an aromatic moiety, bound together by a sulfate ester linkage comprising a C—O bond. Non-limiting examples of aryl sulfate compounds that are suitable substrates with the engineered enzymes of the present invention include p-nitrophenyl sulfate (PNS), 4-methylumbelliferyl sulfate (MUS), 7-hydroxycoumarin sulfate, phenyl sulfate, 4-acetylphenyl sulfate, indoxyl sulfate, 1-naphthyl sulfate, 2-naphthyl sulfate (2NapS), and 4-nitrocatechol sulfate (NCS). In various embodiments, engineered enzymes utilized in accordance with any of the methods of the present invention can recognize, bind, and react with PNS. In some embodiments, PNS can be used as the aryl sulfate compound in every sulfotransfer reaction during the synthesis of the N,2,3,6-HS product. According to the present invention, engineered enzymes utilized in accordance with any of the methods of the present invention can recognize, bind, and react with NCS. In some embodiments, NCS can be used as the aryl sulfate compound in every sulfotransfer reaction during the synthesis of the N,2,3,6-HS product. According to the present invention, a single engineered enzyme utilized in accordance with any of the methods of the present invention can recognize, bind, and react with multiple aryl sulfate compounds.

In various embodiments, each of the engineered sulfotransferase enzymes utilized in the synthesis of an N,2,3,6-HS product according to any of the methods described herein can be selected to react with the same aryl sulfate compound as a sulfo group donor. In other embodiments, one or more of the engineered sulfotransferase enzymes can have a biological activity with different aryl sulfate compounds than other enzymes utilized in the same synthesis of an N,2,3,6-HS product. As a non-limiting example, an N,2,3,6-HS product can be synthesized using some engineered enzymes that react with NCS as a sulfo group donor, while other engineered enzymes within the same synthesis react with PNS as a sulfo group donor, and in syntheses in which multiple sulfotransfer reactions are carried out in a single reaction mixture, both PNS and NCS can be included within the reaction mixture.

In various embodiments, within any reaction mixture or composition comprising heparosan-based polysaccharides used as starting materials or formed as products while practicing any of the methods of the present invention, including but not limited to precursor polysaccharides, starting polysaccharides, sulfated polysaccharide products, and/or heparin, the polysaccharides can be present as a polydisperse mixture of varied chain lengths, molecular weights, N-acetylation, and/or N-, 2-O, 6-O, or 3-O sulfation. Alternatively, any of the polysaccharides described above can be present or provided as a homogeneous composition comprised of polysaccharides having identical chain lengths, molecular weights, N-acetylation, and/or N-, 2-O, 6-O, or 3-O sulfation.

In various embodiments, heparosan-based polysaccharides that can be used as sulfo group acceptors in any of the sulfotransfer reactions described herein can generally be any molecular weight greater than 1,000 Da, including greater than 1,000,000 Da. In various embodiments, compositions or mixtures comprising N-deacetylated heparosan polysaccharides can preferably have a weight-average molecular weight in the range of at least 2,000 Da and up to 20,000 Da, or at least 9,000 Da, and up to 12,500 Da. In various embodiments, sulfated polysaccharide products of any of the reactions described herein can comprise molecular weights associated with the addition of a single sulfo group (about 80 Da), and up to the addition of sulfo groups to all available N, 2-O, 3-O, and/or 6-O positions, based on the molecular weight of the polysaccharide used as the sulfo group acceptor.

In various embodiments, in any of the methods for synthesizing an N,2,3,6-HS product described herein, any reaction mixture comprising an engineered sulfotransferase enzyme and an aryl sulfate compound can further comprise one or more components for repopulating the aryl sulfate compound. In various embodiments, the one or more components for repopulating the aryl sulfate compound can comprise an aryl sulfate sulfotransferase (ASST) enzyme and a secondary aryl sulfate compound. According to the present invention, the engineered sulfotransferase enzyme has minimal or no activity with the secondary aryl sulfate compound as a sulfo group donor. The ASST enzyme from any bacteria can be utilized, and can either be isolated from the bacteria directly or generated recombinantly from an expression host in vitro. In various embodiments, the ASST enzyme can be a recombinant ASST from *E. coli* strain CFT073, comprising the amino acid sequence of SEQ ID NO: 55.

In one non-limiting example, a reaction mixture comprising an N,2,6-HS product, NCS, and an engineered 3OST enzyme comprising the amino acid sequence SEQ ID NO: 28 can further comprise an ASST enzyme and PNS, with which the engineered enzyme comprising the amino acid sequence SEQ ID NO: 28 is not active. Upon being formed as a product of the sulfotransfer reaction, 4-nitrocatechol can then act as a sulfo group acceptor for a reaction between PNS and the ASST enzyme, thereby re-synthesizing NCS for subsequent reactions with the engineered 3OST enzyme. Alternatively, the NCS utilized for the sulfotransfer reaction to form an N,2,3,6-HS product can be generated in situ by forming a reaction mixture comprising the engineered 3OST enzyme, 4-nitrocatechol, PNS, and an ASST enzyme.

In various embodiments, an engineered NST enzyme utilized in any of the methods described herein can comprise any amino acid sequence so long as the enzyme catalyzes the transfer of a sulfo group from an aryl sulfate compound to the amine functional group of an N-unsubstituted glucosamine residue of a heparosan-based polysaccharide, preferably N-deacetylated heparosan. In further embodiments, the engineered NST enzymes can be mutants of natural sulfotransferases that have HS NST activity, such as the NDST enzymes that are members of enzyme class (EC) 2.8.2.8. According to the present invention, an engineered NST or NDST enzyme can comprise several amino acid mutations relative to the N-sulfotransferase and/or N-deacetylase domain of a natural NDST enzyme, in order to engineer the active site to bind and react with an aryl sulfate compound as a sulfo group donor instead of PAPS.

Engineered NST enzymes utilized in accordance with any of the methods described herein can comprise an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40, each of which contains several amino acid mutations made relative to highly conserved regions within the N-sulfotransferase domain of natural NDST enzymes within EC 2.8.2.8. In various embodiments, engineered NST enzymes utilized in accordance with any of the methods described herein can also comprise an amino acid sequence having one or more amino residue differences or mutations from, and/or is a biological functional equivalent of, an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40. Non-limiting examples of such residue differences include amino acid insertions, deletions, substitutions, or any combination of such changes.

In various embodiments, any of the engineered NST enzymes described above can further include an N-deacetylase domain that is either identical or mutated relative to the N-deacetylase domain that is present in any of the natural NDST enzymes within EC 2.8.2.8. In various embodiments, any of the engineered NST enzymes can further include other domains or fusions with other proteins to facilitate solubility or secondary biochemical reactions.

In various embodiments, any natural NDST enzyme within EC 2.8.2.8 can be utilized to catalyze N-sulfation during the synthesis of HS products, particularly heparin products, in which engineered sulfotransferase enzymes are utilized to catalyze the 2-O, 6-O, and/or 3-O sulfation of the polysaccharide. A natural NST enzyme can either include both an N-deacetylase domain and an N-sulfotransferase domain, a single N-sulfotransferase domain, or a biologically-active fragment thereof. Reaction mixtures comprising a natural NST enzyme also comprise PAPS as a sulfo group donor.

Glucosamine residues within the heparosan-based polysaccharide that do not receive the sulfo group can be N-, 3-O, and/or 6-O sulfated, N-acetylated, or N-unsubstituted, and hexuronic acid residues can include GlcA or IdoA, either of which can be sulfated at the 2-O position. Preferably, and according to the present invention, the heparosan-based polysaccharide is N-deacetylated heparosan. In various embodiments, the 6-O group of an N-unsubstituted glucosamine residue can already be sulfated prior to the N-sulfation reaction.

One non-limiting example of a disaccharide unit within a heparosan-based polysaccharide that can react as a sulfo group acceptor with a natural or engineered NST enzyme can comprise the structure of Formula II, below:

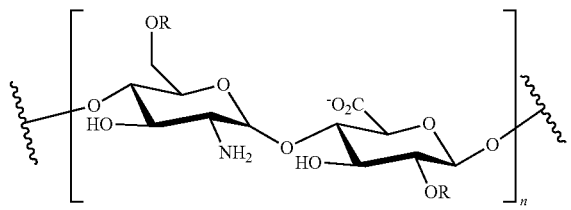

wherein n is an integer and R is selected from the group consisting of a hydrogen atom or a sulfo group. In various embodiments, both R groups within a disaccharide unit, and preferably all disaccharide units, can be hydrogen atoms. When the sulfo acceptor polysaccharide comprises the structure of Formula II, upon transfer of the sulfo group from an aryl sulfate compound, the sulfated polysaccharide product comprises the structure of Formula III, below:

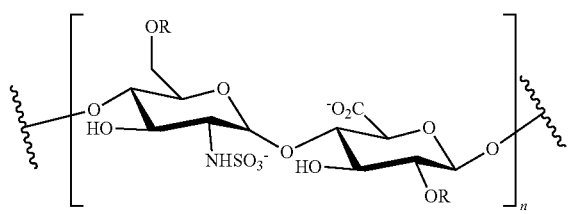

wherein n is an integer and R is selected from the group consisting of a hydrogen atom or a sulfo group. In various embodiments, both R groups within the disaccharide units are hydrogen atoms.

In various embodiments, an engineered 2OST enzyme utilized in any of the methods described herein can comprise any amino acid sequence so long as the enzyme catalyzes the transfer of a sulfo group from an aryl sulfate compound to the 2-O position of a hexuronic acid residue within a heparosan-based polysaccharide, particularly N-sulfated HS polysaccharides. In further embodiments, the engineered 2OST enzyme can be a mutant of any natural 2OST enzyme, particularly an enzyme that is a member of enzyme class EC 2.8.2.-. According to the present invention, an engineered 2OST enzyme can comprise several amino acid mutations relative to one or more of the natural 2OST enzymes, in order to engineer the active site to bind and react with an aryl sulfate compound as a sulfo group donor instead of PAPS.

As a non-limiting example, engineered 2OST enzymes utilized in accordance with any of the methods described herein can comprise an amino acid sequence selected from the group consisting of SEQ ID NO: 14, SEQ ID NO: 16, SEQ ID NO: 41, and SEQ ID NO: 42, each of which contains several amino acid mutations made relative to highly conserved regions within natural 2OST enzymes within EC 2.8.2.-. In various embodiments, engineered 2OST enzymes utilized in accordance with any of the methods described herein can also comprise an amino acid sequence having one or more amino residue differences or mutations from, and/or is a biological functional equivalent of, an amino acid sequence selected from the group consisting of SEQ ID NO: 14, SEQ ID NO: 16, SEQ ID NO: 41, and SEQ ID NO: 42. Non-limiting examples of such residue differences include amino acid insertions, deletions, substitutions, or any combination of such changes.

In various embodiments, any natural 2OST enzyme, or a biologically-active fragment thereof, can be utilized to catalyze 2-O sulfation during the synthesis of HS products, particularly N,2,3,6-HS products, in which engineered sulfotransferase enzymes are utilized to catalyze the N-, 6-O, and/or 3-O sulfation of the polysaccharide. Reaction mixtures comprising a natural 2OST enzyme also comprise PAPS as a sulfo group donor.

In various embodiments, a hexuronic acid residue that can receive a sulfo group from a natural or engineered 2OST enzyme can be either glucuronic acid or iduronic acid, and preferably iduronic acid, while other hexuronic acid residues within the polysaccharide can be glucuronic acid or iduronic acid, either of which can be 2-O sulfated. Both glucosamine residues adjacent to the hexuronic acid residue receiving the sulfo group can be, and preferably are, N-sulfated prior to reacting with the engineered or natural 2OST. Glucosamine residues that are not adjacent to the hexuronic acid residue receiving the sulfo group can optionally be N-, 3-O, and/or 6-O sulfated, N-acetylated, or N-unsubstituted. One non-limiting example of a portion of a heparosan-based polysaccharide that can react as a sulfo group acceptor with a natural or engineered 2OST enzyme can comprise the structure of Formula IV, below:

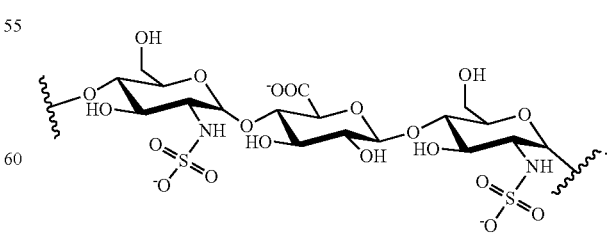

When the heparosan-based polysaccharide comprises the structure of Formula IV, the 2-O sulfated polysaccharide product comprises the structure of Formula VI, below:

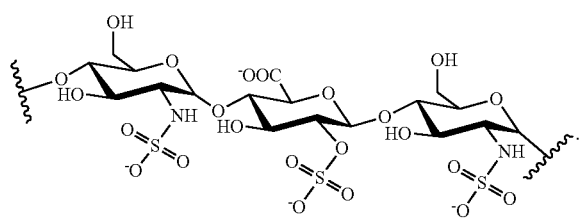

In another non-limiting example, when the hexuronic acid residue is iduronic acid, rather than glucuronic acid as illustrated in Formula IV, the heparosan-based polysaccharide comprises the structure of Formula V, below:

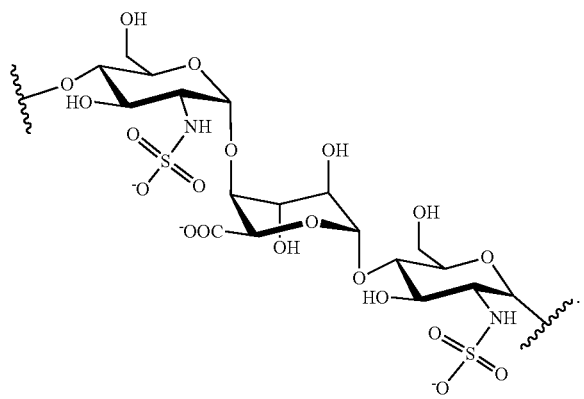

When the heparosan-based polysaccharide comprises the structure of Formula V, the 2-O sulfated polysaccharide product comprises the structure of Formula VII, below:

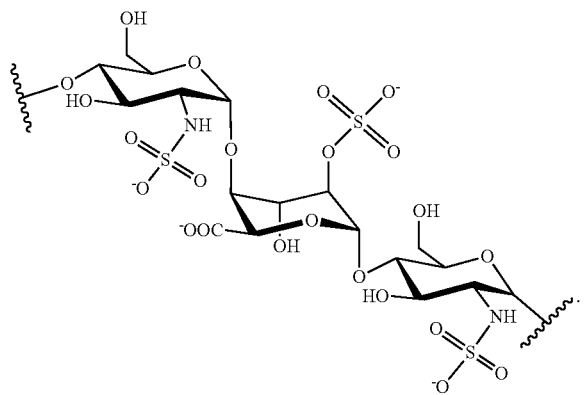

In various embodiments, an isolated or recombinant glucuronyl $C_5$-epimerase enzyme can be combined in a reaction mixture along with heparosan-based polysaccharides comprising the structure of Formula IV and/or Formula V. In some embodiments, the glucuronyl $C_5$-epimerase enzyme can comprise the amino acid sequence of SEQ ID NO: 29, preferably residues 34-617 of SEQ ID NO: 29.

In other embodiments, the glucuronyl $C_5$-epimerase enzyme can be any recombinant or natural glucuronyl $C_5$-epimerase enzyme. In some embodiments, a glucuronyl $C_5$-epimerase enzyme comprising any amino acid sequence, particularly the amino acid sequence of SEQ ID NO: 29 or residues 34-617 of SEQ ID NO: 29, can be included within a reaction mixture comprising N-sulfated heparosan and an engineered or natural 2OST, to form an N-sulfated, 2-O sulfated HS (N,2-HS) comprising one or more disaccharide units of 2-O sulfated iduronic acid and N-sulfo glucosamine.

In various embodiments, an engineered 6OST enzyme utilized in any of the methods described herein can comprise any amino acid sequence so long as the enzyme catalyzes the transfer of a sulfo group from an aryl sulfate compound to the 6-O position of a glucosamine residue within a heparosan-based polysaccharide, particularly N,2-HS polysaccharides comprising the structure of Formula VI and/or Formula VII. In further embodiments, the engineered 6OST enzymes can be a mutant of any natural 6OST enzyme, particularly a 6OST that is a member of enzyme class EC 2.8.2.-. According to the present invention, an engineered 6OST enzyme can comprise several amino acid mutations relative to one or more of the natural 6OST enzymes, in order to engineer the active site to bind and react with an aryl sulfate compound as a sulfo group donor instead of PAPS.

As non-limiting examples, engineered 6OST enzymes utilized in accordance with any of the methods described herein can comprise an amino acid sequence selected from the group consisting of SEQ ID NO: 18, SEQ ID NO: 20, SEQ ID NO: 22, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 59, SEQ ID NO: 60, and SEQ ID NO: 61, each of which contains several amino acid mutations made relative to highly conserved regions within natural 6OST enzymes within EC 2.8.2.-. In various embodiments, engineered 6OST enzymes utilized in accordance with any of the methods described herein can also comprise an amino acid sequence having one or more amino residue differences or mutations from, and/or is a biological functional equivalent of, an amino acid sequence selected from the group consisting of SEQ ID NO: 18, SEQ ID NO: 20, SEQ ID NO: 22, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 59, SEQ ID NO: 60, and SEQ ID NO: 61. Non-limiting examples of such residue differences include amino acid insertions, deletions, substitutions, or any combination of such changes. In various embodiments, the engineered 6OST enzyme comprises the amino acid sequence of SEQ ID NO: 20.

In various embodiments, any natural 6OST enzyme, or a biologically-active fragment thereof, can be utilized to catalyze 6-O sulfation during the synthesis of HS products, particularly N,2,3,6-HS products, in which engineered sulfotransferase enzymes are utilized to catalyze the N-, 2-O, and/or 3-O sulfation of the polysaccharide. According to the present invention, reaction mixtures comprising a natural 6OST enzyme also comprise PAPS as a sulfo group donor.

In various embodiments, a glucosamine residue that can receive a sulfo group from the 6OST enzyme can be N-unsubstituted, N-sulfated, and/or 3-O sulfated, prior to reacting with the enzyme. Any other glucosamine residue within the sulfo acceptor polysaccharide can be optionally be N-, 3-O, and/or 6-O sulfated, N-acetylated, or N-unsubstituted. Any of the hexuronic acid residues within the heparosan-based polysaccharide can either be iduronic acid or glucuronic acid, and can optionally be 2-O sulfated, prior to reacting with the 6OST enzyme. In various embodiments, the glucosamine residue receiving the sulfo group at the 6-O position is N-sulfated, and is adjacent to a 2-O sulfated iduronic acid residue, at either or both of the non-reducing and reducing ends of the glucosamine residue. One non-limiting example of a portion of a heparosan-based polysaccharide that can react with a natural or engineered 6OST enzyme can comprise the structure of Formula VIII, below:

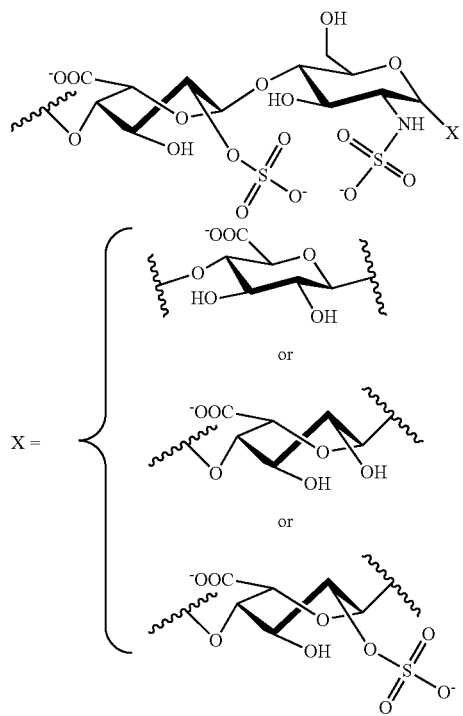

wherein X comprises any of the hexuronic acid residues depicted in Formula VIII, above.

When the heparosan-based polysaccharide comprises the structure of Formula VIII, the 6-O-sulfated polysaccharide product comprises the structure of Formula IX, below:

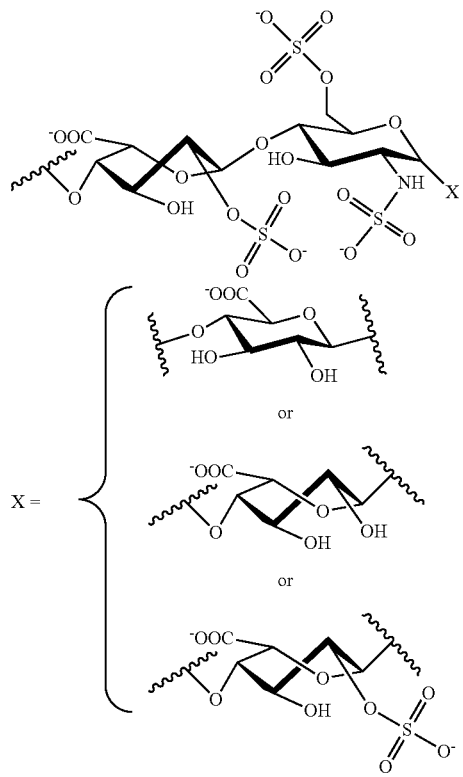

wherein X comprises any of the hexuronic acid residues depicted in Formula IX, above.

In various embodiments, an HS polysaccharide comprising the structure of Formula VIII can be an N,2-HS polysaccharide comprising no 6-O or 3-O sulfated glucosamine residues, which upon reacting with a 6OST, forms an N-sulfated, 2-O sulfated, 6-O sulfated HS (N,2,6-HS) product. In some embodiments, N,2-HS polysaccharides produced as products of a 2OST reaction can be isolated and purified prior to reacting with the 6OST in a separate reaction mixture, to ensure that 2-O sulfation occurs prior to 6-O sulfation. In other embodiments, 2-O sulfation of hexuronic acid residues and 6-0 sulfation of glucosamine residues can take place in the same reaction mixture.

In various embodiments, an engineered 3OST enzyme utilized in any of the methods described herein can comprise any amino acid sequence so long as the enzyme catalyzes the transfer of a sulfo group from an aryl sulfate compound to the 3-O position of a glucosamine residue within a heparosan-based polysaccharide, particularly N,2-HS, N,2,6-HS polysaccharides, and/or HS polysaccharides comprising the structure of Formula IX. In further embodiments, engineered 3OST enzymes can be a mutant of a natural 3OST enzyme, particularly a 3OST enzyme that is a member of enzyme class EC 2.8.2.23. According to the present invention, an engineered 3OST enzyme can comprise several amino acid mutations relative to one or more of the natural 3OST enzymes, in order to engineer the active site to bind and react with an aryl sulfate compound as a sulfo group donor instead of PAPS.

As non-limiting examples, engineered 3OST enzymes utilized in accordance with any of the methods described herein can comprise an amino acid sequence selected from the group consisting of SEQ ID NO: 24, SEQ ID NO: 26, SEQ ID NO: 28, SEQ ID NO: 51, SEQ ID NO: 52, SEQ ID NO: 53, SEQ ID NO: 54, SEQ ID NO: 56, SEQ ID NO: 57, and SEQ ID NO: 58, each of which contains several amino acid mutations made relative to highly conserved regions within natural 3OST enzymes within EC 2.8.2.23. In various embodiments, engineered 3OST enzymes utilized in accordance with any of the methods described herein can also comprise an amino acid sequence having one or more amino residue differences or mutations from, and/or is a biological functional equivalent of, an amino acid sequence selected from the group consisting of SEQ ID NO: 24, SEQ ID NO: 26, SEQ ID NO: 28, SEQ ID NO: 51, SEQ ID NO: 52, SEQ ID NO: 53, SEQ ID NO: 54, SEQ ID NO: 56, SEQ ID NO: 57, and SEQ ID NO: 58. Non-limiting examples of such residue differences include amino acid insertions, deletions, substitutions, or any combination of such changes. In various embodiments, the engineered 3OST enzyme comprises the amino acid sequence of SEQ ID NO: 28.

In various embodiments, any natural 3OST enzyme, or a biologically-active fragment thereof, can be utilized to catalyze 3-O sulfation during the synthesis of HS products, particularly N,2,3,6-HS products, in which engineered sulfotransferase enzymes are utilized to catalyze the N-, 2-O, and/or 6-O sulfation of the polysaccharide. In various embodiments, reaction mixtures comprising a natural 3OST enzyme also comprise PAPS. In various embodiments, an engineered 3OST enzyme is utilized to catalyze 3-O sulfation in the synthesis of an N,2,3,6-HS product, even if a natural HS sulfotransferase is utilized in one or more of the N-, 2-O, or 6-O sulfation steps.

In various embodiments, glucosamine residues within the HS polysaccharide that can receive a sulfo group at the 3-O position are N-sulfated, and can optionally comprise a 6-O sulfo group as well. Any other glucosamine residue within the sulfo acceptor polysaccharide can be optionally be N-, 3-O, and/or 6-O sulfated, N-acetylated, or N-unsubstituted. In various embodiments, one or more of the glucosamine residues within the HS polysaccharide, including the glucosamine residue being 3-O sulfated, can be both N-sulfated and 6-O sulfated. According to the present invention, the glucosamine residue being 3-O sulfated is adjacent to an unsulfated glucuronic acid residue at the non-reducing end and an iduronic acid residue, which can optionally be 2-O sulfated, at the reducing end. Any of the other hexuronic acid residues within the HS polysaccharide can optionally be iduronic acid or glucuronic acid, and can optionally be 2-O sulfated. One non-limiting example of a portion of an HS polysaccharide that can react as a sulfo group acceptor with a natural or engineered 3OST enzyme can comprise the structure of Formula X, below:

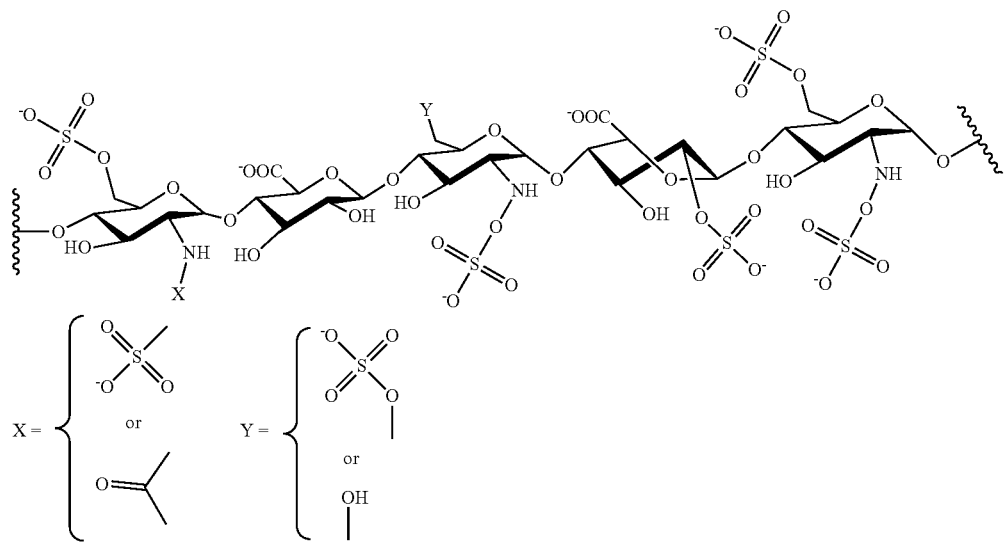

wherein X is either a sulfo group or an acetate group and Y is either a sulfo group or a hydroxyl group. According to the present invention, X can be a sulfo group and Y can be a sulfo group. When the HS polysaccharide comprises the structure of Formula X, the 3-O sulfated polysaccharide product comprises the structure of Formula I, below:

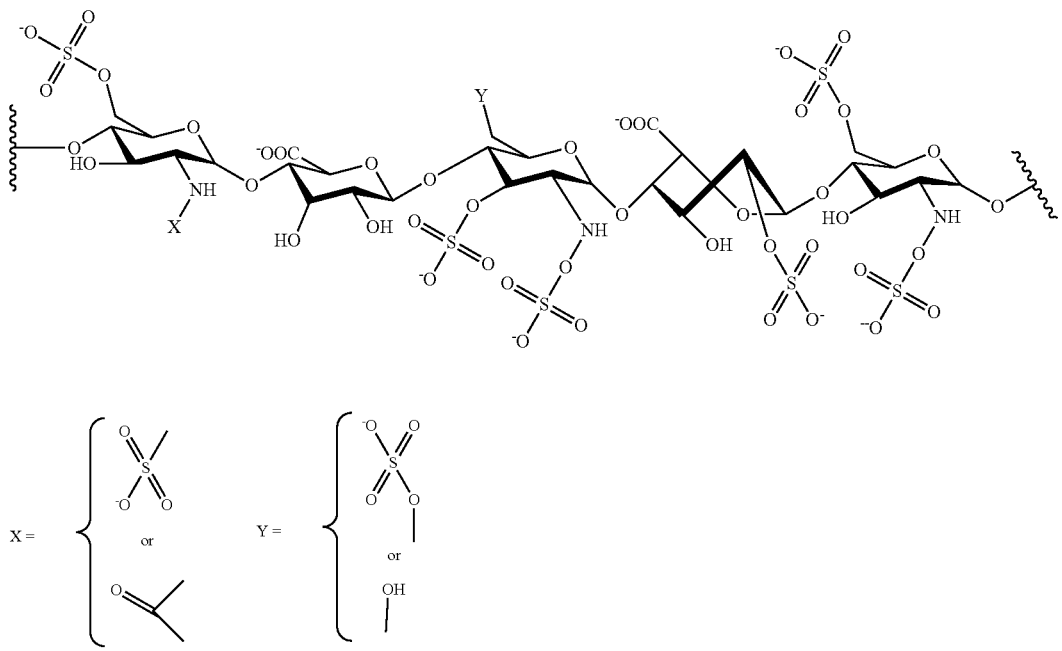

wherein X is either a sulfo group or an acetate group and Y is either a sulfo group or a hydroxyl group. In various embodiments, X can be a sulfo group and Y can be a sulfo group.

In various embodiments, HS products synthesized by any of the methods described herein can contain one, two, three, or four sulfo groups within each disaccharide unit, wherein each disaccharide unit comprises a hexuronic acid residue (GlcA or IdoA) and a glucosamine residue. In a non-limiting example, at least 45%, up to 90%, and preferably in the range of 65% to 80%, of the disaccharide units contain glucosamine residues that are both N-sulfated and 6-O sulfated. In various embodiments, at least 1%, up to at least 8%, and preferably in the range of 4% to 5%, of the glucosamine residues that are both N-sulfated and 6-O sulfated are also 3-O sulfated. In another non-limiting example, at least 1%, up to 30%, and preferably 3%, of the disaccharide units within the sulfated polysaccharide product comprise 2-O sulfated iduronic acid and N-sulfoglucosamine.

In various embodiments, N,2,3,6-HS polysaccharides produced by any of the methods of the present invention can have anticoagulant activity, including, but not limited to, the ability to bind and activate antithrombin. According to the present invention, and useful in combination with any one or more of the above aspects and embodiments, the synthesized N,2,3,6-HS product composition can comprise one or more polysaccharides having the pentasaccharide sequence of Formula I. In some embodiments, the N,2,3,6-HS product composition synthesized according to any of the methods of the present invention can have a substantially equivalent composition and/or anticoagulant activity relative to heparin extracted from animal sources, including but not limited to heparin extracted from porcine and bovine sources. In some embodiments, the N,2,3,6-HS product composition synthesized according to any of the methods of the present invention can have a substantially equivalent composition, physical properties, molecular weight profiles, anticoagulant activity, and/or purity relative to any of the heparin products described in the United States Pharmacopeia (USP), including but not limited to API heparin, Chemical Abstracts Service (CAS) reference standard numbers 9005-49-6 or 9041-08-1.

In some embodiments, the N,2,3,6-HS product composition synthesized according to any of the methods of the present invention can be engineered to have an identical composition, physical properties, molecular weight, and anticoagulant activity relative to API heparin, while also being substantially free, or completely free, of a sulfated polysaccharide impurity selected from the group consisting of dermatan sulfate, chondroitin sulfate, and keratan sulfate, including combinations thereof. Without being limited by a particular theory, it is believed that such product compositions can obviate the harmful side effects arising from the presence of dermatan sulfate and chondroitin sulfate found within animal-sourced heparins.

In various embodiments, antithrombin activation can be quantified as a function of its subsequent effect on the activity of Factor IIa and Factor Xa, in terms of International Units of activity per milligram (IU $mg^{-1}$). In various embodiments, N,2,3,6-HS product compositions made by methods of the present invention can have an anti-Factor IIa (anti-IIa) activity of at least about 1 IU $mg^{-1}$, and up to about 500 IU $mg^{-1}$, for example, at least 180 IU $mg^{-1}$. In various embodiments, N,2,3,6-HS product compositions synthesized by methods of the present invention can have an anti-Factor Xa (anti-Xa) activity of at least about 1 IU $mg^{-1}$, and up to about 500 IU $mg^{-1}$, for example, at least 180 IU $mg^{-1}$. In various embodiments, synthesized N,2,3,6-HS product compositions having an anti-Factor Xa and/or anti-Factor IIa activity greater than 180 IU $mg^{-1}$ can be diluted until an activity of 180 IU $mg^{-1}$ is reached. In various embodiments, the anticoagulant activity of N,2,3,6-HS product compositions synthesized by any of the methods of the present invention can be expressed as a ratio of anti-Xa activity to anti-IIa activity, ranging from at least 0.5:1, and up to at least 100:1, for example from 0.9:1 to 1.1:1.

In various embodiments, polysaccharides within N,2,3,6-HS product compositions produced by any of the methods above can have an average molecular weight of at least 1,500 Da, depending on the weight average molecular weight of polysaccharides utilized as sulfo group acceptors. In various embodiments, anticoagulant N,2,3,6-HS product mixtures can have a weight-average molecular weight in the range of 2,000 Da to 24,000 Da.

Generally, the average molecular weight of polysaccharides utilized as sulfo group acceptors, particularly the average molecular weight of N-deacetylated heparosan, can influence the average molecular weight of N,2,3,6-HS products produced by any of the methods described herein. In various embodiments, the reaction time for depolymerizing and N-deacetylating heparosan can be controlled to form N-deacetylated heparosan compositions of any desired weight-average molecular weight, such as, by non-limiting examples, at least 1,000 Da, at least 1,500 Da, at least 2,000 Da, at least 3,000 Da, at least 4,000 Da, at least 5,000 Da, at least 6,000 Da, at least 7,000 Da, at least 8,000 Da, at least 9,000 Da, at least 10,000 Da, at least 15,000 Da, or at least 20,000 Da.

In some embodiments, the reaction time for depolymerizing and N-deacetylating heparosan is controlled to form an N-deacetylated heparosan composition having a weight-average molecular weight of at least 9,000 Da, and up to 12,500 Da, such that the resulting N,2,3,6-HS product composition has a weight-average molecular weight of at least 15,000 Da, and up to 19,000 Da. In various embodiments, less than or equal to 20% of the polysaccharide chains within the N,2,3,6-HS product can have a molecular weight greater than 24,000 Da. In various embodiments, and useful in combination with any one or more of the above aspects and embodiments, the number of polysaccharide chains within the N,2,3,6-HS product having a molecular weight between 8,000 Da and 16,000 Da can be greater than the number of polysaccharide chains having a molecular weight between 16,000 Da and 24,000 Da.

In various embodiments, anticoagulant N,2,3,6-HS product compositions produced by any of the methods described herein can have a molecular weight profile such that: (a) the weight-average molecular weight of the anticoagulant N,2,3,6-HS product mixture is at least 15,000 Da, and up to 19,000 Da; (b) less than or equal to 20% of the polysaccharides within the anticoagulant N,2,3,6-HS product mixture has a molecular weight greater than 24,000 Da; and (c) the number of polysaccharide chains within the anticoagulant N,2,3,6-HS product mixture having a molecular weight between 8,000 Da and 16,000 Da is greater than the number of polysaccharide chains having a molecular weight between 16,000 Da and 24,000 Da. In various embodiments, anticoagulant N,2,3,6-HS product mixtures having the molecular weight profile described above can also have a ratio of anti-Xa activity to anti-IIa activity of at least 0.9:1, up to 1.1:1, and preferably 1:1. In various embodiments, anticoagulant N,2,3,6-HS product mixtures can be prepared as a salt, particularly, as a non-limiting example, a sodium salt.

In various embodiments, the anticoagulant N,2,3,6-HS product composition can be substantially equivalent to API heparin. In various embodiments, an anticoagulant N,2,3,6-HS product composition that is otherwise substantially equivalent to API heparin can be synthesized without containing any chondroitin sulfate or dermatan sulfate.

In various embodiments, engineered sulfotransferase enzymes having biological activity with aryl sulfate compounds as sulfo group donors can be expressed from a nucleic acid comprising a nucleotide sequence that encodes for any of the amino acid sequences described above. Non-limiting examples of such nucleotide sequences include SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, and SEQ ID NO: 27. Persons skilled in the art can determine appropriate nucleotide sequences that encode for polypeptides having the amino acid sequence of SEQ ID NOs: 33-54 and 56-61, based on the nucleotide sequences above.

In various embodiments, a nucleic acid comprising any nucleotide sequence encoding for any of the engineered sulfotransferase enzymes described above can be inserted into an expression vector that is engineered to be inserted into biological host cells configured to retain the expression vector and overexpress the desired enzyme. According to the present invention, the nucleic acid inserted into an expression vector can comprise a nucleotide sequence that encodes for any of the amino acid sequences described above. According to the present invention, the nucleic acid inserted into an expression vector can comprise any of the nucleotide sequences described above.

In various embodiments, the expression vector can optionally further comprise one or more nucleic acid sequences or genes encoding for proteins or host recognition sites that supplement the production of engineered sulfotransferase enzymes of the present invention. Non-limiting examples include promoter sequences, antibiotic resistance genes, and genes encoding for fusion proteins that assist in the folding and stability of the engineered sulfotransferase enzyme. In various embodiments, an expression vector can further comprise the malE gene from *Escherichia coli*, which encodes for maltose binding protein (MBP). For example, an expression vector can comprise the malE gene and any of the nucleotide sequences, SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, or SEQ ID NO: 27, or any nucleotide sequence that encodes for polypeptides having the amino acid sequence of SEQ ID NOs: 33-54 and 56-61. Protein expression from those vectors can generate engineered sulfotransferase enzymes that are fused with MBP.

Expression vectors are typically transformed into host cells from which the enzyme can be overexpressed and extracted. In various embodiments, host cells can be transformed with any of the expression vectors described above, non-limiting examples of which include expression vectors comprising a nucleic acid sequence set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, or any sequence that encodes for an enzyme having the amino acid sequence of SEQ ID NOs: 33-54 and 56-61. In various embodiments, the transformed host cells can be bacterial, yeast, insect, or mammalian cells. In various embodiments, the host cells can be bacterial cells. In various embodiments, the bacterial cells can be from a non-pathogenic strain of *Escherichia coli* (*E. coli*). In various embodiments, the host cells can be yeast cells.

In various embodiments, sulfotransferase reactions within any of the methods described above can be carried out by engineered enzymes comprising at least a functional fragment of any amino acid sequences described above. In various embodiments, the invention provides substantially pure protein purifications of engineered sulfotransferase enzymes comprising any of the amino acid sequences above, including functional fragments thereof.

In another aspect of the invention, once an HS product composition, particularly an anticoagulant N,2,3,6-HS product composition, is formed by any of the methods described above, it can be combined with a glycosaminoglycan (GAG) composition comprising at least one GAG selected from the group consisting of dermatan sulfate and chondroitin sulfate, to form an HS-GAG mixture. For example, an HS-GAG mixture can comprise at least 10%, and up to 90%, of an anticoagulant N,2,3,6-HS product composition synthesized by any of the methods of the present invention, with the remainder comprising dermatan sulfate and/or chondroitin sulfate. In some embodiments, dermatan sulfate and/or chondroitin sulfate are added to an anticoagulant N,2,3,6-HS product composition that does not otherwise contain dermatan sulfate or chondroitin sulfate. In some embodiments, the anticoagulant activity of the anticoagulant N,2,3,6-HS product composition can be maintained upon the formation of the HS-GAG mixture.

In various embodiments, the sulfate to carboxyl ratio can describe the average relative abundance of sulfo groups compared to the relative abundance of carboxyl groups within disaccharide units that comprise the anticoagulant N,2,3,6-HS product.

In one non-limiting example, an HS-GAG mixture can be formed to comprise N,2,3,6-HS products synthesized by any of the methods of the present invention, wherein: (a) dermatan sulfate comprises 20% of the polysaccharides within the HS-GAG mixture; (b) the weight-average molecular weight of the anticoagulant N,2,3,6-HS product within the HS-GAG mixture is in the range of 7,000 Da to 8,000 Da; and (c) the anticoagulant N,2,3,6-HS product composition comprises a sulfate to carboxyl group ratio in the range of 2.0:1 to 2.2:1. In a further embodiment, the HS-GAG mixture can comprise a substantially equivalent composition, weight-average molecular weight, and/or anticoagulant activity relative to sulodexide.

In another non-limiting example, an HS-GAG mixture can be formed to comprise N,2,3,6-HS products synthesized by any of the methods of the present invention, wherein: (a) dermatan sulfate comprises at least 10%, up to 15%, and preferably 12%, of the polysaccharides within the HS-GAG mixture; (b) chondroitin sulfate comprises at least 3%, up to 5%, and preferably 4%, of the polysaccharides within the HS-GAG mixture; (c) the weight-average molecular weight of all of the polysaccharides within the HS-GAG mixture is in the range of 4,000 Da to 7,000 Da, and preferably in the range of 5,000 Da to 6,000 Da; and (d) the anticoagulant N,2,3,6-HS product comprises a sulfate to carboxyl group ratio in the range of 2.0:1 to 2.2:1. In a further embodiment, the HS-GAG mixture can comprise a substantially equivalent composition, weight-average molecular weight, and/or anticoagulant activity relative to danaparoid.

In another aspect of the invention, any of the N,2,3,6-HS product compositions produced by any of the methods described herein can be further modified to form a secondary low-molecular-weight heparin sulfate (LMW-HS) product composition upon depolymerizing and/or modifying polysaccharides within the N,2,3,6-HS product composition. Processes for depolymerizing heparin compositions, including unfractionated heparin compositions and API heparin compositions, are well known in the art, and in some embodiments, any such process can be applied to N,2,3,6-HS product compositions synthesized by any of the methods described herein. Non-limiting examples of LMW-HS product compositions produced from synthesized N,2,3,6-HS product compositions using such processes, are provided in further detail, below.

In various embodiments, LMW-HS product compositions synthesized from any of the N,2,3,6-HS products described herein can have either an equivalent or modified anticoagulant activity relative to the unmodified N,2,3,6-HS product. In various embodiments, a secondary LMW-HS product composition can have a substantially equivalent anticoagulant activity relative to any low molecular weight heparin (LMWH) composition known in the art. In various embodiments, LMW-HS product compositions produced by any of the methods described herein can have a ratio of anti-Xa to anti-IIa activity ranging from at least 0.5:1, up to at least 100:1, including as non-limiting examples, a ratio from at least 1.5:1, and up to at least 10:1, or a ratio from at least 20:1, and up to at least 100:1.

In various embodiments, an N,2,3,6-HS product produced by any method described above can be referred to as an "unfractionated" N,2,3,6-HS product, relative to an LMW-HS product that is produced from the N,2,3,6-HS product.

Generally, methods of the present invention for synthesizing an LMW-HS product can comprise the following steps: (a) synthesizing an N,2,3,6-HS product according to any of the methods described herein; (b) providing one or more depolymerization agents; and (c) treating the N,2,3,6-HS product with the one or more depolymerization agents for a time sufficient to depolymerize at least a portion of the polysaccharides within the N,2,3,6-HS product, thereby forming the LMW-HS product. In various embodiments, the weight-average molecular weight of the LMW-HS product is at least 2,000 Da, and up to 12,000 Da, and is preferably in the range of 3,000 Da to 8,000 Da.

In various embodiments, the one or more depolymerization agents can be formed by, and/or be comprised of, one or more reaction components within one or more reaction mixtures, that can be combined with an unfractionated N,2,3,6-HS product to chemically and/or enzymatically depolymerize the N,2,3,6-HS product and form the LMW-HS product. In various embodiments, the selection of the depolymerization agent can determine which chemical or enzymatic depolymerization process occurs, as well as the chemical structure and/or anticoagulant activity of the LMW-HS product that is formed as a result of the depolymerization. Such depolymerization processes can include, but are not limited to: chemical and/or enzymatic β-elimination reactions; deamination reactions; and oxidation reactions, including combinations thereof. In various embodiments, an unfractionated N,2,3,6-HS product can be treated with any combination of depolymerization agents in order to form an LMW-HS product.

In various embodiments, the amount of time that an unfractionated N,2,3,6-HS product is treated with the one or more depolymerization agents can be controlled to form an LMW-HS product with a desired molecular weight, chemical structure, and/or anticoagulant activity. According to the present invention, with respect to the same depolymerization agent, the amount of time that an unfractionated N,2,3,6-HS product is treated with the depolymerization agent can be varied to form LMW-HS products with similar chemical structures, but different molecular weights and anticoagulant activities relative to each other.

In one-non-limiting example, an enzymatic β-elimination reaction can be performed on the unfractionated N,2,3,6-HS product to form an enzymatically-depolymerized LMW-HS product. In various embodiments, the depolymerization agent can comprise a carbon-oxygen lyase reaction mixture comprising at least one carbon-oxygen lyase enzyme, preferably at least one carbon-oxygen lyase enzyme comprising an amino acid sequence selected from the group consisting of SEQ ID NO: 30, SEQ ID NO: 31, and SEQ ID NO: 32. In various embodiments, the unfractionated N,2,3,6-HS product can be treated with the carbon-oxygen lyase reaction mixture for a time sufficient to catalyze β-eliminative cleavage of the unfractionated N,2,3,6-HS product and form an enzymatically-depolymerized LMW-HS product. In various embodiments, the weight-average molecular weight of the enzymatically-depolymerized LMW-HS product can be in the range of 2,000 Da to 10,000 Da, preferably 5,500 Da to 7,500 Da, and more preferably 6,500 Da. In various embodiments, the enzymatically-depolymerized LMW-HS product can have anticoagulant activity, particularly an anti-Xa activity in a range from at least 70 IU $mg^{-1}$ and up to 120 IU $mg^{-1}$, and a ratio of anti-Xa activity to anti-IIa activity in the range of 1.5:1 to 2.5:1. In various embodiments, the enzymatically-depolymerized LMW-HS product can comprise polysaccharides having a 4,5-unsaturated uronic acid residue at the non-reducing end. In various embodiments, the enzymatically-depolymerized LMW-HS product can comprise a substantially equivalent chemical structure, weight-average molecular weight, and/or anticoagulant activity relative to tinzaparin.

In another non-limiting example, a chemical β-elimination reaction can be performed on the unfractionated N,2,3,6-HS product to form a chemically β-eliminative, LMW-HS product. In various embodiments, the depolymerization agent for a chemical β-elimination reaction can comprise a base, preferably a base selected from the group consisting of sodium hydroxide, a quaternary ammonium hydroxide, and a phosphazene base, including any combination thereof, and the unfractionated N,2,3,6-HS product can be treated with the base for a time sufficient to cause β-eliminative cleavage of the unfractionated N,2,3,6-HS product and form a chemically β-eliminative, LMW-HS product.

In various embodiments, the step of treating the unfractionated N,2,3,6-HS product with the depolymerization agent can comprise the following sub-steps: (i) reacting the unfractionated N,2,3,6-HS product with a benzethonium salt, preferably benzethonium chloride, to form a benzethonium HS salt; and (ii) combining the benzethonium HS salt with a reaction mixture comprising the base for a time sufficient to form the chemically β-eliminative, LMW-HS product. In various embodiments, the weight-average molecular weight of the chemically β-eliminative, LMW-HS product can be at least 2,000 Da, up to 10,000 Da, and preferably in the range of 2,000 Da to 6,000 Da. In various embodiments, the chemically β-eliminative, LMW-HS product can comprise polysaccharides having a 4,5-unsaturated uronic acid residue at the non-reducing end. According to the present invention, and useful in combination with any one or more of the above aspects and embodiments, the chemically β-eliminative, LMW-HS product can have anticoagulant activity, particularly an anti-Xa activity in a range from 80 IU $mg^{-1}$ up to 160 IU $mg^{-1}$, an anti-IIa activity in a range from 2 IU mg$^{-1}$ up to 40 IU mg$^{-1}$, and/or a ratio of anti-Xa activity to anti-IIa activity in the range of 3.0:1 to 100:1.

In various embodiments, once the benzethonium HS salt is formed, it can be subsequently treated with a base for a time sufficient to form the chemically β-eliminative, LMW-HS product. In various embodiments, the base can be a quaternary ammonium hydroxide, preferably benzyl trimethylammonium hydroxide (Triton® B). In various embodiments, the weight-average molecular weight of the chemically β-eliminative, LMW-HS product can be in the range of 3,000 Da to 4,200 Da, and preferably 3,600 Da. In various embodiments, the anti-Xa activity of the chemically 3-eliminative, LMW-HS product can be in a range from at least 80 IU mg$^{-1}$ and up to 120 IU mg$^{-1}$, the anti-IIa activity can be in a range from at least 5 IU mg$^{-1}$ and up to 20 IU mg$^{-1}$, and/or the ratio of anti-Xa activity to anti-IIa activity of the chemically β-eliminative, LMW-HS product can be in the range of 8.0:1 to 10.0:1. In various embodiments, LMW-HS product can comprise a substantially equivalent chemical structure, weight-average molecular weight, and/or anticoagulant activity relative to bemiparin.

In various embodiments, the benzethonium HS salt can instead be further modified prior to reacting with the base. In one non-limiting example, the benzethonium HS salt can be converted to a benzyl ester form of HS upon reacting with a benzyl halide, particularly benzyl chloride. In various embodiments, the conversion to the benzyl ester can take place within a chlorinated solvent, including but not limited to methylene chloride and chloroform.

In various embodiments, once the benzyl ester HS is formed, it can be subsequently reacted with a base to initiate depolymerization. In various embodiments, the base can be sodium hydroxide. In various embodiments, the chemically β-eliminative, LMW-HS product can comprise polysaccharides having a 1,6-anhydromannose or 1,6-anhydroglucosamine residue at the reducing end in addition to the 4,5-unsaturated uronic acid residue at the non-reducing end. In various embodiments, the weight-average molecular weight of the chemically β-eliminative, LMW-HS product can be in the range of 3,800 Da to 5,000 Da, preferably 4,500 Da. In various embodiments, the anti-Xa activity of the chemically β-eliminative, LMW-HS product can be in a range from at least 90 IU mg$^{-1}$ and up to 125 IU mg$^{-1}$, the anti-IIa activity can be in a range from at least 20 IU mg$^{-1}$ and up to 35 IU mg$^{-1}$, and/or the ratio of anti-Xa activity to anti-IIa activity of the chemically β-eliminative, LMW-HS product can be in the range of 3.3:1 to 5.3:1. In various embodiments, the chemically β-eliminative, LMW-HS product can comprise a substantially equivalent chemical structure, weight-average molecular weight, and/or anticoagulant activity relative to enoxaparin.

In various embodiments, the benzyl ester HS can instead be transalified in the presence of a benzethonium salt, preferably benzethonium chloride, in order to form a benzethonium benzyl ester HS, which can then subsequently de-polymerized using a base. In various embodiments, the base is a phosphazene base, preferably 2-tert-butylimino-2-diethylamino-1,3-dimethylperhydro-1,2,3-diaza-phosphorine (BEMP). After depolymerization is complete, the remaining benzyl esters within the chemically β-eliminative, LMW-HS product can be saponified and removed. In various embodiments, the weight-average molecular weight of the chemically β-eliminative, LMW-HS product can be in the range of 2,000 Da to 3,000 Da, and is preferably 2,400 Da. In various embodiments, the anti-Xa activity of the chemically β-eliminative, LMW-HS product can less than or equal to 160 IU mg$^{-1}$, and/or the ratio of anti-Xa activity to anti-IIa activity can be at least 20:1, up to 100:1, and preferably 80:1. In various embodiments, the chemically β-eliminative, LMW-HS product can comprise a substantially equivalent chemical structure, weight-average molecular weight, and/or anticoagulant activity relative to semuloparin.

In various embodiments, unfractionated N,2,3,6-HS products can optionally be depolymerized by both an enzymatic and a chemical β-elimination reaction. For example, an enzymatically-depolymerized LMW-HS product can subsequently be subjected to a chemical β-elimination reaction by reacting with a base. In another example, a chemically β-eliminative, LMW-HS product can subsequently be subjected to an enzymatic β-elimination reaction by reacting one or more carbon-oxygen lyase enzymes.

In another non-limiting example, deamination reaction can be performed on the unfractionated N,2,3,6-HS product to form a deaminated LMW-HS product. In various embodiments, the depolymerization agent can comprise a deamination reaction mixture comprising a deamination agent, preferably a deamination agent selected from the group consisting of isoamyl nitrate and nitrous acid, for a time sufficient to cause deaminative cleavage of the unfractionated N,2,3,6-HS product, thereby forming a deaminated LMW-HS product.

In various embodiments, the deamination agent can be nitrous acid. In various embodiments, the deamination reaction mixture can comprise stoichiometric quantities of an acid, preferably acetic acid or hydrochloric acid, and an alkali or alkaline earth metal nitrite salt, preferably sodium nitrite, to form nitrous acid in situ. In various embodiments, the deaminated LMW-HS product can comprise polysaccharides having a 2,5-anhydro-D-mannose residue at the reducing end. In various embodiments, the weight-average molecular weight of the deaminated LMW-HS product can be in the range of 2,000 Da to 10,000 Da, preferably in the range of 4,000 Da to 6,000 Da. According to the present invention, and useful in combination with any one or more of the above aspects and embodiments, the deaminated LMW-HS product can have anticoagulant activity, particularly having a ratio of anti-Xa activity to anti-IIa activity in the range of 2.0:1 to 4.5:1.

In one non-limiting example, the weight-average molecular weight of the deaminated LMW-HS product can be in the range of 3,600 Da to 5,500 Da, preferably 4,300 Da. In various embodiments, the anti-Xa activity of the deaminated LMW-HS product can be in a range from at least 95 IU mg-1 and up to not more than 130 IU mg$^{-1}$, and/or and the ratio of anti-Xa activity to anti-IIa activity can be in the range of at least 2.5:1 and up to 4.0:1. In various embodiments, the deaminated LMW-HS product can comprise a substantially equivalent chemical structure, weight-average molecular weight, and/or anticoagulant activity relative to nadroparin.

In another non-limiting example, the weight-average molecular weight of the deaminated LMW-HS product can be in the range of 5,600 Da to 6,400 Da, preferably 6,000 Da. In various embodiments, the anti-Xa activity of the deaminated LMW-HS product can be in a range from at least 110 IU mg$^{-1}$ and up to not more than 210 IU mg$^{-1}$, the anti-IIa activity can be in a range from at least 35 IU mg$^{-1}$ and up to not more than 100 IU mg$^{-1}$, and/or the ratio of anti-Xa activity to anti-IIa activity of the deaminated LMW-HS product can be at least 1.9:1, and up to 3.2:1. In various embodiments, the deaminated LMW-HS product can comprise a substantially equivalent chemical structure, weight-average molecular weight, and/or anticoagulant activity relative to dalteparin.

In another non-limiting example, the weight-average molecular weight of the deaminated LMW-HS product can be in the range of 4,200 Da to 4,600 Da, preferably 4,400 Da, the anti-Xa activity can be in a range from at least 98 IU mg$^{-1}$ and up to 155 IU mg$^{-1}$, and the ratio of anti-Xa activity to anti-IIa activity of the deaminated LMW-HS product can be at least 4.0:1, and up to 4.5:1, preferably 4.2:1. In various embodiments, the deaminated LMW-HS product can comprise a substantially equivalent chemical structure, weight-average molecular weight, and/or anticoagulant activity relative to reviparin.

In another non-limiting example, the deamination agent is isoamyl nitrate, the weight-average molecular weight of the deaminated LMW-HS product can be in the range of 5,000 Da to 5,600 Da, preferably 5,400 Da, the anti-Xa activity can be in a range from at least 80 IU mg$^{-1}$ and up to 120 IU mg$^{-1}$, and the ratio of anti-Xa activity to anti-IIa activity of the deaminated LMW-HS product can be at least 2.0:1, and up to 2.5:1, preferably 2.4:1. In various embodiments, the deaminated LMW-HS product can comprise a substantially equivalent chemical structure, weight-average molecular weight, and/or anticoagulant activity relative to certoparin.

In another non-limiting example, an oxidation reaction can be performed on the unfractionated N,2,3,6-HS product to form an oxidized LMW-HS product. In various embodiments, the depolymerization agent can comprise an oxidation agent, preferably an oxidation agent selected from the group consisting of a peroxide or a superoxide, and more preferably hydrogen peroxide to form an oxidized LMW-HS product. In various embodiments, the step of treating an unfractionated N,2,3,6-HS product with the oxidation agent can comprise the following sub-steps: (i) acidifying the unfractionated N,2,3,6-HS product to form an acidified HS product; (ii) combining the acidified HS product with the oxidation reaction mixture; and (iii) incubating the acidified HS product within the oxidation reaction mixture at a temperature of at least than 50° C. for a time sufficient to form the oxidized LMW-HS product.

In various embodiments, the sub-step of acidifying the unfractionated N,2,3,6-HS product can comprise the addition of a reaction mixture comprising an acid, preferably ascorbic acid, to the HS product to form the acidified HS product. Alternatively, the sub-step of acidifying the unfractionated N,2,3,6-HS product can further comprise the sub-steps of: loading the unfractionated N,2,3,6-HS product into a cation exchange resin, preferably a cation exchange resin suspended within a chromatography column; and eluting the unfractionated N,2,3,6-HS product from the cation exchange resin, forming the acidified HS product. In various embodiments, the pH of the acidified HS product can be at least 3.0, and up to 5.0, and preferably in a range of 3.0 to 3.5.

In various embodiments, the weight-average molecular weight of the oxidized LMW-HS product can be in the range of 2,000 Da to 12,000 Da, preferably in the range of 4,000 Da to 6,000 Da. In various embodiments, the oxidized LMW-HS product can have anticoagulant activity, particularly in which the ratio of anti-Xa activity to anti-IIa activity is in the range of 1.5:1 to 3.0:1.

In one non-limiting example, the weight-average molecular weight of the oxidized LMW-HS product can be in the range of at least 4,000 Da up to 6,000 Da, and is preferably 5,000 Da, the anti-Xa activity of the oxidized LMW-HS product is in a range from at least 95 IU mg$^{-1}$ and up to not more than 110 IU mg$^{-1}$, and the ratio of anti-Xa activity to anti-IIa activity is at least 1.5:1, and up to 3.0:1.

In various embodiments, the oxidized LMW-HS product can comprise a substantially equivalent chemical structure, pH, weight-average molecular weight, and/or anticoagulant activity relative to parnaparin.

In another non-limiting example, the weight-average molecular weight of the oxidized LMW-HS product can be in the range of 5,500 Da to 6,500 Da, preferably 6,000 Da, and the ratio of anti-Xa activity to anti-IIa activity is at least 2.0:1, and up to 2.5:1. In various embodiments, the oxidized LMW-HS product can comprise a substantially equivalent chemical structure, pH, weight-average molecular weight, and/or anticoagulant activity relative to ardeparin.

In various embodiments, LMW-HS products can be formed from N,2,3,6-HS products synthesized by any of the methods of the present invention, wherein the N,2,3,6-HS product has a substantially equivalent molecular weight profile and anticoagulant activity relative to API heparin, namely that: (a) the weight-average molecular weight of the N,2,3,6-HS product is at least 15,000 Da, and up to 19,000 Da; (b) less than or equal to 20% of the polysaccharides within the N,2,3,6-HS product have a molecular weight greater than 24,000 Da; (c) the number of polysaccharide chains within the N,2,3,6-HS product having a molecular weight between 8,000 Da and 16,000 Da is greater than the number of polysaccharide chains having a molecular weight between 16,000 Da and 24,000 Da; (d) the anti-Xa activity of the N,2,3,6-HS product is about 180 IU mg$^{-1}$; (e) the anti-IIa activity of the N,2,3,6-HS product is about 180 IU mg$^{-1}$; and the ratio of anti-Xa activity to anti-IIa activity in the N,2,3,6-HS product is at least 0.9:1, and up to 1.1:1. In various embodiments, LMW-HS products can be formed from N,2,3,6-HS products synthesized by any of the methods of the present invention, wherein the N,2,3,6-HS product is produced from N-deacetylated heparosan compositions having a weight average molecular weight of less than 9,000 Da, non-limiting examples of which are less than 8,000 Da, less than 7,000 Da, less than 6,000 Da, less than 5,000 Da, less than 4,000 Da, less than 3,000 Da, or less than 2,000 Da.

In another aspect of the invention, kits for forming N,2,3,6-HS or LMW-HS products, particularly anticoagulant N,2,3,6-HS or LMW-HS products, according to any of the methods described above, are provided. In various embodiments, the kit can comprise at least one engineered aryl sulfate-dependent sulfotransferase and at least one aryl sulfate compound, preferably PNS or NCS In various embodiments, the kit can comprise an engineered NST, an engineered 2OST, an engineered 6OST, and/or an engineered 3OST, each of which is dependent on reacting with an aryl sulfate compound as a sulfo group donor to catalyze a transfer of the sulfo group to a polysaccharide, preferably a heparosan-based polysaccharide. In various embodiments, the kit can further comprise any of the starting polysaccharides or sulfated polysaccharides described above, including heparosan and/or other HS polysaccharides. In various embodiments, the kit can further comprise an epimerase, preferably an epimerase comprising the amino acid sequence of SEQ ID NO: 29, and more preferably an epimerase comprising amino acid residues 34-617 of SEQ ID NO: 29. In various embodiments, the kit can comprise any of the components and/or reaction mixtures for chemically N-sulfating heparosan-based polysaccharides, particularly N-deacetylated heparosan. In various embodiments, the kit can comprise any of the components and/or reaction mixtures for isolating and purifying heparosan from a host, preferably a bacterial host, and more preferably *E. coli*. In various embodiments, the kit can comprise any of the components and/or reaction mixtures for depolymerizing an N,2,3,6-HS product according to any of the methods described above, in order to form any of the enzymatically-depolymerized, chemically β-eliminative, deaminated, or oxidized LMW-HS products.

According to the present invention, and useful in combination with any one or more of the above aspects and embodiments, any of the non-anticoagulant or anticoagulant HS products, N,2,3,6-HS products, and/or LMW-HS products prepared according to any of the methods described above can be prepared as pharmaceutically-acceptable salts, particularly alkali or alkali earth salts including, but not limited to, sodium, lithium, or calcium salts.

These and other embodiments of the present invention will be apparent to one of ordinary skill in the art from the following detailed description.

DEFINITIONS

Figure 1A:
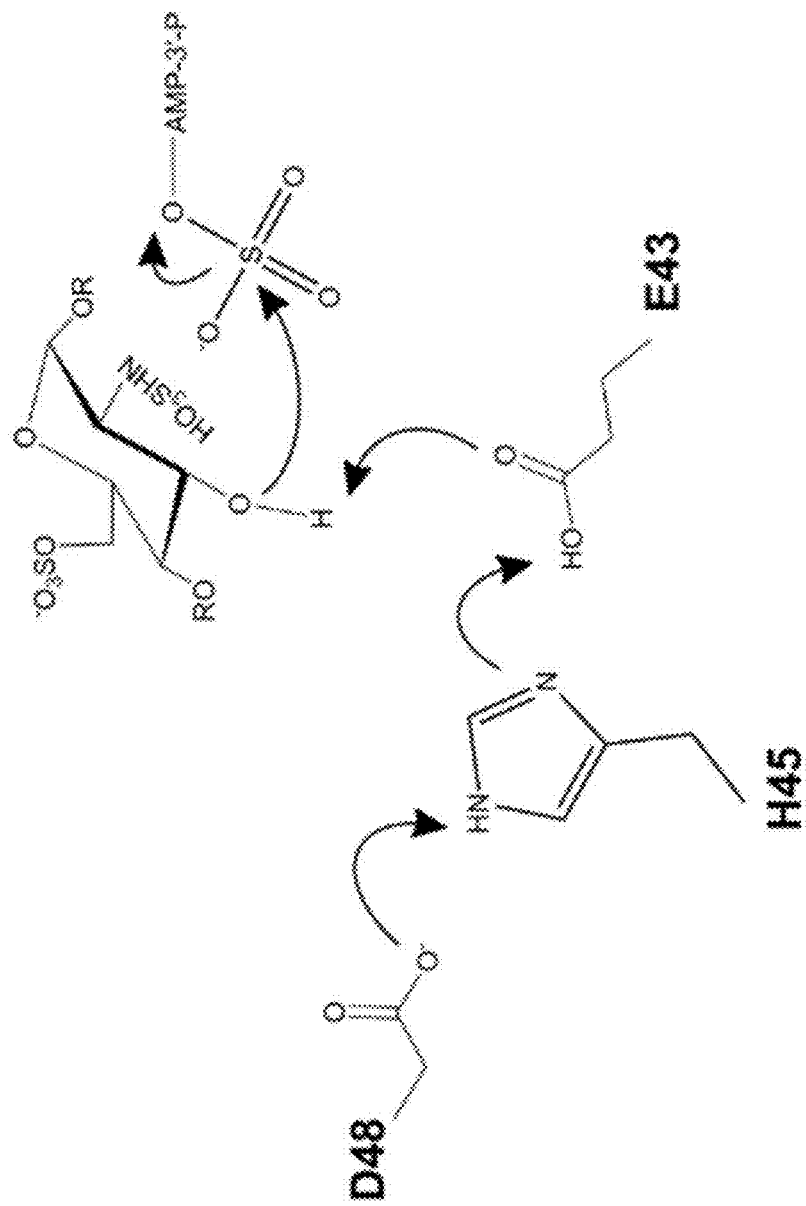
FIGS. 1A-1C show an example reaction mechanism between the human 3OST enzyme, PAPS, and an N-sulfated, 6-O sulfated glucosamine residue within heparan sulfate.

The term, "active site," refers to sites in catalytic proteins, in which catalysis occurs, and can include one or more substrate binding sites. Active sites are of significant utility in the identification of compounds that specifically interact with, and modulate the activity of, a particular polypeptide. The association of natural ligands or substrates with the active sites of their corresponding receptors or enzymes is the basis of many biological mechanisms of action. Similarly, many compounds exert their biological effects through association with the active sites of receptors and enzymes. Such associations may occur with all or any parts of the active site. An understanding of such associations helps lead to the design of engineered active sites within sulfotransferases that are capable of binding to and reacting with aryl sulfate compounds instead of PAPS.

The term, "amino acid," refers to a molecule having the structure wherein a central carbon atom (the alpha-carbon atom) is linked to a hydrogen atom, a carboxylic acid group (the carbon atom of which is referred to herein as a "carboxyl carbon atom"), an amino group (the nitrogen atom of which is referred to herein as an "amino nitrogen atom"), and a side chain group, R. When incorporated into a peptide, polypeptide, or protein, an amino acid loses one or more atoms of its amino and carboxylic groups in the dehydration reaction that links one amino acid to another. As a result, when incorporated into a protein, an amino acid is referred to as an "amino acid residue." In the case of naturally occurring proteins, an amino acid residue's R group differentiates the 20 amino acids from which proteins are synthesized, although one or more amino acid residues in a protein may be derivatized or modified following incorporation into protein in biological systems (e.g., by glycosylation and/or by the formation of cysteine through the oxidation of the thiol side chains of two non-adjacent cysteine amino acid residues, resulting in a disulfide covalent bond that frequently plays an important role in stabilizing the folded conformation of a protein, etc.). Additionally, when an alpha-carbon atom has four different groups (as is the case with the 20 amino acids used by biological systems to synthesize proteins, except for glycine, which has two hydrogen atoms bonded to the carbon atom), two different enantiomeric forms of each amino acid exist, designated D and L. In mammals, only L-amino acids are incorporated into naturally occurring polypeptides. Engineered sulfotransferase enzymes utilized in accordance with methods of the present invention can incorporate one or more D- and L-amino acids, or can be comprised solely of D- or L-amino acid residues.

Non-naturally occurring amino acids can also be incorporated into any of the sulfotransferase enzymes utilized in accordance with the methods of the present invention, particularly engineered sulfotransferase enzymes having aryl sulfate-dependent activity. Examples of such amino acids include, without limitation, alpha-amino isobutyric acid, 4-amino butyric acid, L-amino butyric acid, 6-amino hexanoic acid, 2-amino isobutyric acid, 3-amino propionic acid, ornithine, norleucine, norvaline, hydroxyproline, sarcosine, citrulline, cysteic acid, t-butyl glycine, t-butyl alanine, phenylglycine, cyclohexyl alanine, beta-alanine, fluoro-amino acids, designer amino acids (e.g., beta-methyl amino acids, alpha-methyl amino acids, alpha-methyl amino acids) and amino acid analogs in general.

The term, "and/or," when used in the context of a listing of entities, refers to the entities being present singly or in combination. Thus, for example, the phrase "A, B, C, and/or D" includes A, B, C, and D individually, but also includes any and all combinations and sub-combinations of A, B, C, and D.

The term, "API heparin," refers to the form of heparin that is regulated for administering to patients, and which conforms to the United States Pharmacopeia (USP) reference standard with respect to identity, strength, quality, purity, and potency. Properties defined by the USP monograph for heparin sodium include: a characteristic $^1$H-NMR spectrum; chromatographic purity, particularly with respect to dermatan sulfate and oversulfated chondroitin sulfate; anti-Factor Xa activity; anti-Factor IIa activity; the ratio of anti-factor Xa activity relative to anti-factor IIa activity; the presence or absence of inorganic and inorganic impurities; and a characteristic molecular weight distribution or profile. In particular, the USP Heparin Sodium standard has an anti-Factor Xa activity of not less than 180 IU mg$^{-1}$; an anti-factor IIa activity of not less than 180 IU mg$^{-1}$; a ratio of anti-Factor Xa activity to anti-Factor IIa activity of 0.9-1.1; the amount of polysaccharide chains greater than 24,000 Da is less than 20% of a heparin sample; the amount of polysaccharide chains between 8,000 Da and 16,000 Da being greater than the amount of polysaccharide chains between 16,000 Da and 24,000 Da within the heparin sample; and a weight average molecular weight of the heparin sample in the range of at least 15,000 Da and up to 19,000 Da.

The terms, "aryl sulfate" or "aryl sulfate compound," refer to any compound, functional group, or substituent derived from an aromatic ring in which one or more of the hydrogen atoms directly bonded to the aromatic ring is replaced by a sulfate functional group. Typically, the sulfate functional group is covalently bound to the aromatic moiety of an aryl sulfate compound through a sulfate ester linkage. Exemplary aryl sulfate compounds that can donate a sulfo group to a polysaccharide, particularly a heparosan-based polysaccharide, using any of the engineered sulfotransferases include, but are not limited to, p-nitrophenyl sulfate (PNS), 4-methylumbelliferyl sulfate (MUS), 7-hydroxycoumarin sulfate, phenyl sulfate, 4-acetylphenyl sulfate, indoxyl sulfate, 1-naphthyl sulfate, 2-naphthyl sulfate, and 4-nitrocatechol sulfate (NCS).

The term, "aryl sulfate-dependent sulfotransferase," refers to the collective group of engineered sulfotransferases that possess biological or catalytic activity with aryl sulfate compounds as sulfo donors. Non-limiting examples of aryl sulfate compounds upon which the biological activity of the sulfotransferase can be dependent include PNS and NCS. As described herein, engineered sulfotransferases having biological activity with aryl sulfate compounds as sulfo group donors can possess biological activity with polysaccharides, particularly heparosan-based polysaccharides, as sulfo group acceptors. "Aryl sulfate-dependent sulfotransferase" also includes both nucleic acids and polypeptides encoding for any aryl sulfate-dependent sulfotransferase, including mutants derived from the sequences disclosed herein.

The term, "average molecular weight," with respect to any of the polysaccharide starting materials, intermediates, and/or products used or generated according to any of the methods of the present invention, and unless otherwise indicated, can refer to any accepted measure of determining the molar mass distribution or molar mass average of a mixture of polymers having varying degrees of polymerization, functionalization, and molar mass, including but not limited to "number-average molecular weight," "mass-average molecular weight," "weight-average molecular weight," "Z (centrifugation) average molar mass," or "viscosity average molar mass."

The term, "weight-average molecular weight," refers to a method of reporting the average molecular weight of polysaccharides in a mixture, calculated using the mole fraction distribution of the polysaccharides within the sample, using the equation $$\overline{M}_w = \frac{\sum_i N_i M_i^2}{\sum_i N_i M_i},$$

wherein $N_i$ is the number of polysaccharides of molecular mass $M_i$.

The term, "number-average molecular weight," refers to a method of reporting the average molecular weight of polysaccharides in a mixture, calculated by dividing the total weight of all of the polysaccharides in the sample divided by the number of polysaccharides in a sample, using the equation, $$\overline{M}_N = \frac{\sum_i N_i M_i}{\sum_i N_i},$$

wherein $N_i$ is the number of polysaccharides of molecular mass $M_i$. Accordingly, the weight-average molecular weight, $\overline{M}_w$, is necessarily skewed toward higher values corresponding to polysaccharides within the sample that are larger than other polysaccharides within the same mixture, and will always be larger than the number-average molecular weight, $\overline{M}_n$, except when the sample is monodisperse, and $\overline{M}_w$ equals $\overline{M}_n$. If a particular sample of polysaccharides within the sample has a large dispersion of actual weights, then $\overline{M}_w$ will be much larger than $\overline{M}_n$. Conversely, as the weight dispersion of polysaccharides in a sample narrows, $\overline{M}_w$ approaches $\overline{M}_n$.

The terms, "relative molecular weight" or "relative molar mass" ($M_r$), refers to another method of reporting the average molecular weight of polysaccharides in a mixture as a unitless quantity, most broadly determined by dividing the average mass of the molecule by an atomic mass constant, such as 1 atomic mass unit (amu) or 1 Dalton (Da). With respect to polysaccharides, $M_r$ does not take into account the different chain-lengths, functionalization, and/or weight distribution of the polysaccharides in the sample, and instead simply represents the true average mass of the polysaccharides in the sample in a manner similar to small molecules.

The terms, "biological activity" or "catalytic activity," refer to the ability of an enzyme to catalyze a particular chemical reaction by specific recognition of a particular substrate or substrates to generate a particular product or products. In some embodiments, the engineered enzymes of the present invention possess a biological or catalytic activity that is dependent on binding and reacting with aryl sulfate compounds, particularly PNS, as substrates. Additionally, some engineered enzymes are capable of having promiscuous catalytic activity with one or more alternate aryl sulfate compounds in addition to PNS, including but not limited to MUS, 7-hydroxycoumarin sulfate, phenyl sulfate, 4-acetylphenyl sulfate, indoxyl sulfate, 1-naphthyl sulfate, 2-naphthyl sulfate, and NCS.

The term, "coding sequence," refers to that portion of a nucleic acid, for example, a gene, that encodes an amino acid sequence of a protein.

The term, "codon-optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, it is well known that codon usage by particular organisms is non-random and biased toward particular codon triplets. In some embodiments of the invention, the polynucleotide encoding for an engineered enzyme may be codon optimized for optimal production from the host organism selected for expression.

The terms, "corresponding to," "reference to," or "relative to," when used in the context of the numbering of a given amino acid or polynucleotide sequence, refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence.

The term, "deletion," refers to modification of a polypeptide by removal of one or more amino acids from the reference polypeptide. Deletions can comprise removal of 1 or more amino acids, the net result of which is retaining the catalytic activity of the reference polypeptide. Deletions can be directed to the internal portions and/or terminal portions of a polypeptide. Additionally, deletions can comprise continuous segments or they can be discontinuous.

The term, "disaccharide unit," refers to the smallest repeating backbone unit within many polysaccharides, including linear polysaccharides, in which the smallest repeating unit consists of two sugar residues. With respect to a heparosan-based polysaccharide, the disaccharide unit consists of a hexuronic acid residue and a glucosamine residue, either of which can be functionalized and in which the hexuronic acid residue can either be glucuronic acid or iduronic acid. Each disaccharide unit within the heparosan-based polysaccharide can be described by its backbone structure and by the number and position of sulfo groups that are present. Further, the relative abundance of disaccharide units having the same structure within the same polysaccharide, and/or within the same sample of polysaccharides, can be characterized to determine the amount of sulfation at a particular position as a result of reacting with any of the sulfotransferases described herein.

The terms, "fragment" or "segment," refer to a polypeptide that has an amino- or carboxy-terminal deletion, but where the remaining amino acid sequence is identical to the corresponding positions in a reference sequence. Fragments can be at least 50 amino acids or longer, and up to 70%, 80%, 90%, 95%, 98%, and 99% of a full-length aryl sulfate-dependent or natural sulfotransferase enzyme.

The terms, "functional site" or "functional domain," generally refer to any site in a protein that confers a function on the protein. Representative examples include active sites (i.e., those sites in catalytic proteins where catalysis occurs) and ligand binding sites. Ligand binding sites include, but are not limited to, metal binding sites, co-factor binding sites, antigen binding sites, substrate channels and tunnels, and substrate binding domains. In an enzyme, a ligand binding site that is a substrate binding domain may also be an active site. Functional sites may also be composites of multiple functional sites, wherein the absence of one or more sites comprising the composite results in a loss of function. As a non-limiting example, the active site of a particular sulfotransferase enzyme may include multiple binding sites or clefts, including one site for the sulfo donor and one site for the sulfo acceptor.

The terms, "gene," "gene sequence," and "gene segment," refer to a functional unit of nucleic acid unit encoding for a functional protein, polypeptide, or peptide. As would be understood by those skilled in the art, this functional term includes both genomic sequences and cDNA sequences. The terms, "gene," "gene sequence," and "gene segment," additionally refer to any DNA sequence that is substantially identical to a polynucleotide sequence disclosed herein encoding for engineered enzyme gene product, protein, or polysaccharide, and can comprise any combination of associated control sequence. The terms also refer to RNA, or antisense sequences, complementary to such DNA sequences. As used herein, the term "DNA segment" includes isolated DNA molecules that have been isolated free of recombinant vectors, including but not limited to plasmids, cosmids, phages, and viruses.

The term, "glycosaminoglycan," refers to long, linear polysaccharides consisting of repeating disaccharide units. Examples of glycosaminoglycans (GAGs) include chondroitin, dermatan, heparosan, hyaluronic acid, and keratan. GAGs are generally heterogeneous with respect to mass, length, disaccharide unit structure and functionalization, degree of sulfation.

The term, "heparosan," refers to a particular GAG having repeating $[\beta(1,4)\text{GlcA-}\alpha(1,4)\text{GlcNAc}]_n$ disaccharide units, in which GlcA is glucuronic acid and GlcNAc is N-acetyl glucosamine.

The term, "heparosan-based polysaccharide," refers to polysaccharides having the same backbone structure as heparosan, in which the disaccharide unit contains 1→4 glycosidically-linked hexuronic acid and glucosamine residues. The hexuronic acid residue can either be GlcA, as in heparosan, or iduronic acid (IdoA), and can optionally have a sulfo group at the 2-O position. The glucosamine residue can either be N-acetylated, as in heparosan, N-sulfated, or N-unsubstituted, and can optionally be sulfated at the N-, 3-O, or 6-O position. As used herein, the term "N-unsubstituted," with respect to a glucosamine residue, is equivalent to an "N-deacetylated" glucosamine residue, and refers to an amine functional group that is capable of receiving a sulfo group either chemically, or enzymatically using an NST enzyme. According to the present invention, heparosan-based polysaccharides can be utilized as starting materials, formed as intermediates, acting as sulfo group acceptors and/or synthesized as products according to any of the methods described herein.

The term, "insertion," refers to modifications to the polypeptide by addition of one or more amino acids to the reference polypeptide. Insertions can be in the internal portions of the polypeptide, or to the C- or N-termini of the polypeptide. Insertions can include fusion proteins as is known in the art and described below. The insertions can comprise a continuous segment of amino acids or multiple insertions separated by one or more of the amino acids in the reference polypeptide.

The term, "isolated nucleic acid" as used herein with respect to nucleic acids derived from naturally-occurring sequences, means a ribonucleic or deoxyribonucleic acid which comprises a naturally-occurring nucleotide sequence and which can be manipulated by standard recombinant DNA techniques, but which is not covalently joined to the nucleotide sequences that are immediately contiguous on its 5' and 3' ends in the naturally-occurring genome of the organism from which it is derived. As used herein with respect to synthetic nucleic acids, the term "isolated nucleic acid" means a ribonucleic or deoxyribonucleic acid which comprises a nucleotide sequence which does not occur in nature and which can be manipulated by standard recombinant DNA techniques. An isolated nucleic acid can be manipulated by standard recombinant DNA techniques when it may be used in, for example, amplification by polymerase chain reaction (PCR), in vitro translation, ligation to other nucleic acids (e.g., cloning or expression vectors), restriction from other nucleic acids (e.g., cloning or expression vectors), transformation of cells, hybridization screening assays, or the like.

The term, "low molecular weight heparin" refers to a natural or synthesized heparin composition, generally having a weight average molecular weight less than 12,000 Da, and typically either prepared by depolymerizing unfractionated heparin or API heparin, or by chemically, enzymatically, or chemoenzymatically synthesizing the polysaccharides de novo.

The terms, "naturally occurring" or "natural," refer to forms of an enzyme found in nature. For example, a naturally occurring or natural polypeptide or polynucleotide sequence is a sequence present in an organism that can be isolated from a source in nature and which has not been intentionally modified by human manipulation. A natural polypeptide or polynucleotide sequence can also refer to recombinant proteins or nucleic acids that can be synthesized, amplified, and/or expressed in vitro, and which have the same sequence and biological activity as an enzyme produced in vivo. In contrast to naturally occurring or natural sulfotransferase enzymes, the engineered aryl sulfate-dependent sulfotransferase enzymes utilized in accordance with methods of the present invention have different amino acid and nucleic acid sequences, biological activity with aryl sulfate compounds instead of PAPS as sulfo group donors, and cannot be found in nature.

The term, "oligosaccharide," refers to saccharide polymers containing a small number, typically three to nine, sugar residues within each molecule.

The term, "percent identity," refers to a quantitative measurement of the similarity between two or more nucleic acid or amino acid sequences. As a non-limiting example, the percent identity can be assessed between two or more engineered enzymes of the present invention, two or more naturally occurring enzymes, or between one or more engineered enzymes and one or more naturally occurring enzymes. Percent identity can be assessed relative to two or more full-length sequences, two or more truncated sequences, or a combination of full-length sequences and truncated sequences.

The term, "polysaccharide," refers to polymeric carbohydrate structures formed of repeating units, typically monosaccharide or disaccharide units, joined together by glycosidic bonds, and which can range in structure from a linear chain to a highly-branched three-dimensional structure. Although the term "polysaccharide," as used in the art, can refer to saccharide polymers having more than ten sugar residues per molecule, "polysaccharide" is used within this application to describe saccharide polymers having more than one sugar residue, including saccharide polymers that have three to nine sugar residues that may be defined in the art as an "oligosaccharide." According to the present invention, the term "polysaccharide," is also used to generally describe GAGs and GAG-based compounds, including chondroitin, dermatan, heparosan, hyaluronic acid, and keratan compounds.

The terms, "protein," "gene product," "polypeptide," and "peptide" can be used interchangeably to describe a biomolecule consisting of one or more chains of amino acid residues. In addition, proteins comprising multiple polypeptide subunits (e.g., dimers, trimers or tetramers), as well as other non-proteinaceous catalytic molecules will also be understood to be included within the meaning of "protein" as used herein. Similarly, "protein fragments," i.e., stretches of amino acid residues that comprise fewer than all of the amino acid residues of a protein, are also within the scope of the invention and may be referred to herein as "proteins." Additionally, "protein domains" are also included within the term "protein." A "protein domain" represents a portion of a protein comprised of its own semi-independent folded region having its own characteristic spherical geometry with hydrophobic core and polar exterior.

The term, "recombinant," when used with reference to, for example, a cell, nucleic acid, or polypeptide, refers to a material that has been modified in a manner that would not otherwise exist in nature. Non-limiting examples include, among others, recombinant cells expressing genes that are not found within the native (non-recombinant) form of the cell or express native genes that are otherwise expressed at a different level.

The term, "reference sequence," refers to a disclosed or defined sequence used as a basis for sequence comparison. A reference sequence may be a subset of a larger sequence, for example, a segment of a full-length gene or polypeptide sequence. Generally, a reference sequence refers to at least a portion of a full-length sequence, typically at least 20 amino acids, or the full-length sequence of the nucleic acid or polypeptide.

The term, "saccharide," refers to a carbohydrate, also known as a sugar, which is a broad term for a chemical compound comprised of carbon, hydrogen, and oxygen, wherein the number of hydrogen atoms is essentially twice that of the number of oxygen atoms. Often, the number of repeating units may vary in a saccharide. Thus, disaccharides, oligosaccharides, and polysaccharides are all examples of chains composed of saccharide units that are recognized by the engineered sulfotransferase enzymes of the present invention as sulfo group acceptors.

The term, "substantially equivalent," with respect to polysaccharides utilized as starting materials, formed as intermediates, acting as sulfo group acceptors, and/or synthesized as products according to any of the methods described herein, refers to one or more properties of a polysaccharide sample that are identical to those found in a polysaccharide sample characterized in the prior art. Such properties may include, but are not limited to, chemical structure, sulfation frequency and location, disaccharide unit composition, molecular weight profile, and/or anticoagulant activity. Even if the two polysaccharide samples have additional properties that may be different, such differences do not significantly affect their substantial equivalence. In a non-limiting example, anticoagulant N,2,3,6-HS products synthesized according to methods of the present invention can be substantially equivalent to the United States Pharmacopeia (USP) reference standard (CAS No: 9041-08-1) with respect to chemical structure, molecular weight profile, and/or anticoagulant activity, but can be produced at a different purity than the USP reference standard, which is isolated from natural sources and can contain non-trace amounts of other GAGs in the same sample.

The term, "substantially pure," with respect to protein preparations, refers to a preparation which contains at least 60% (by dry weight) the protein of interest, exclusive of the weight of other intentionally included compounds. Particularly the preparation is at least 75%, more particularly at least 90%, and most particularly at least 99%, by dry weight the protein of interest, exclusive of the weight of other intentionally included compounds. Purity can be measured by any appropriate method, e.g., column chromatography, gel electrophoresis, or high-performance liquid chromatography (HPLC) analysis. If a preparation intentionally includes two or more different proteins of the invention, a "substantially pure" preparation means a preparation in which the total dry weight of the proteins of the invention is at least 60% of the total dry weight, exclusive of the weight of other intentionally included compounds. Particularly, for such preparations containing two or more proteins of the invention, the total weight of the proteins of the invention can be at least 75%, more particularly at least 90%, and most particularly at least 99%, of the total dry weight of the preparation, exclusive of the weight of other intentionally included compounds.

The terms, "sulfo" or "sulfuryl" refer to a functional group, substituent, or moiety having the chemical formula $SO_3H^-$ that can be removed from an aryl sulfate compound and/or be transferred from a donor compound to an acceptor compound. In some embodiments, the engineered sulfotransferases of the present invention catalyze the transfer of sulfo groups from aryl sulfate compounds to a polysaccharide, particularly heparosan and/or heparosan-based polysaccharides.

The term, "sulfotransferase," refers to any enzyme in an in vivo or in vitro process that is used to catalyze the transfer of a sulfo group from a sulfo donor compound to a sulfo acceptor compound. "Sulfotransferase" can be used interchangeably to describe enzymes that catalyze sulfotransfer reactions in vivo or to describe engineered enzymes of the present invention that catalyze sulfotransfer reactions in vitro.

The term, "transformation," refers to any method of introducing exogenous a nucleic acid into a cell including, but not limited to, transformation, transfection, electroporation, microinjection, direct injection of naked nucleic acid, particle-mediated delivery, viral-mediated transduction or any other means of delivering a nucleic acid into a host cell which results in transient or stable expression of said nucleic acid or integration of said nucleic acid into the genome of said host cell or descendant thereof.

The term, "unfractionated heparin," refers to any synthesized or isolated heparin that has not been modified and/or partially depolymerized to form low molecular weight heparin. With respect to naturally-obtained heparin, the term "unfractionated heparin" generally represents the form of the heparin isolated from the animal, typically from porcine or bovine sources, prior to purification to meet USP reference standards. With respect to products synthesized by methods of the present invention, the term "unfractionated heparin" can refer to the N,2,3,6-HS product having polysaccharides comprising the pentasaccharide sequence of Formula I, prior to purification to form API heparin or low-molecular-weight heparin.

DETAILED DESCRIPTION OF THE INVENTION

Figure 1B:
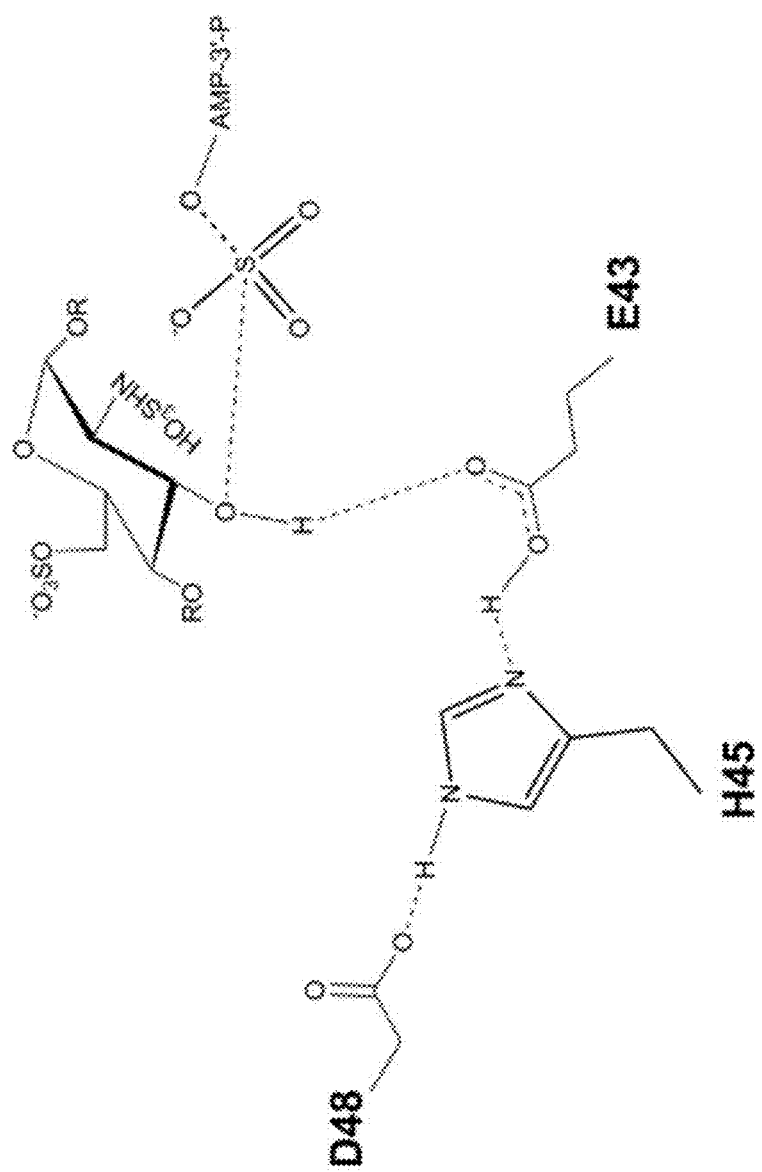
Figure 1C:
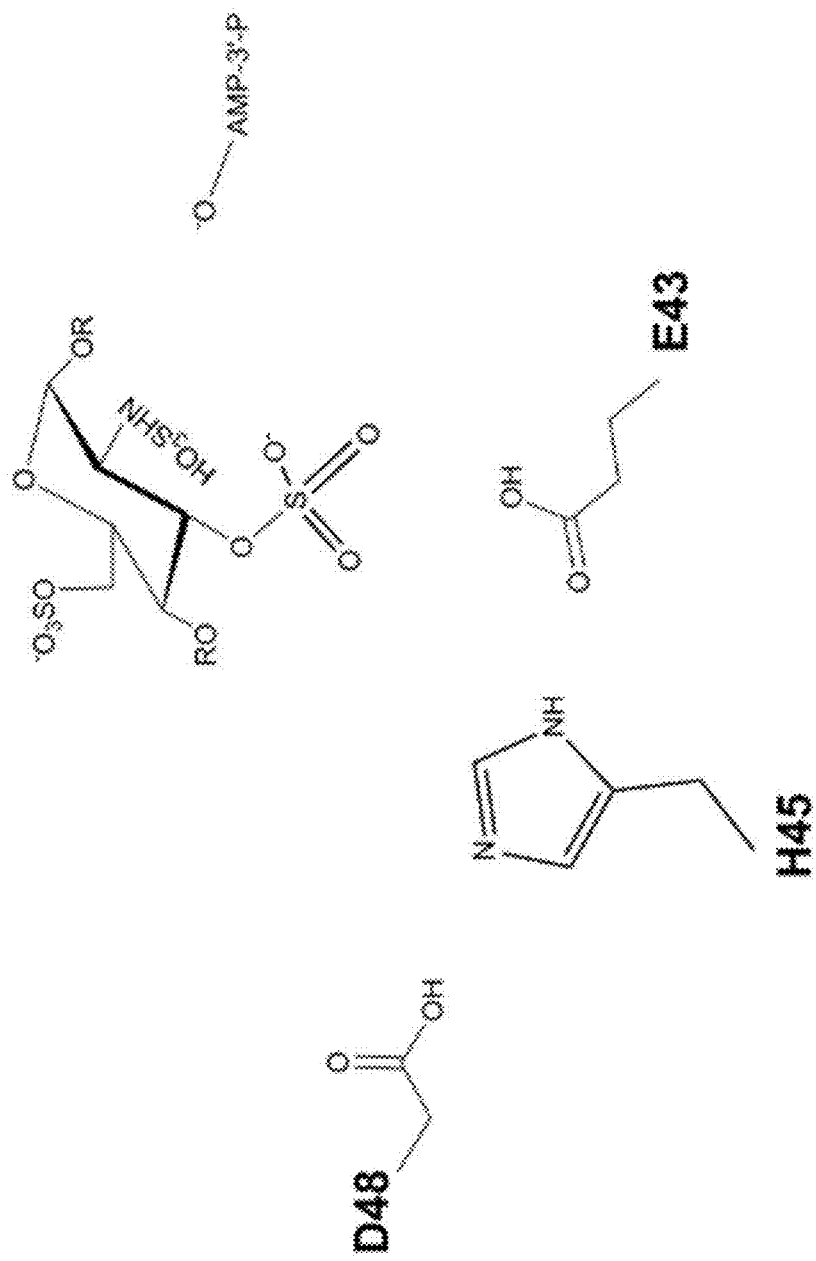

In nature, heparosan is synthesized in the Golgi apparatus as co-polymers of glucuronic acid and N-acetylated glucosamine, before being modified by one or more sulfotransferases to form heparan sulfate (HS) products. Such modifications include N-deacetylation and N-sulfation of glucosamine, $C_5$ epimerization of glucuronic acid to form iduronic acid residues, 2-O-sulfation of iduronic and/or glucuronic acid, as well as 6-O-sulfation and 3-O-sulfation of glucosamine residues. The natural sulfotransferases that catalyze N-sulfation, 2-O-sulfation, 6-O-sulfation and 3-O-sulfation of heparosan and HS polysaccharides in vivo exclusively recognize and bind with PAPS, a nearly ubiquitous sulfo group donor recognized by nearly all sulfotransferases, particularly in eukaryotes. An example of a sulfotransfer reaction mechanism between the human glucosaminyl 3-O sulfotransferase (3OST) enzyme, PAPS, and heparan sulfate is illustrated in FIGS. 1A-1C. In particular, the glutamic acid residue at position 43 abstracts the proton from the 3-O position of the N-sulfoglucosamine residue within the polysaccharide, enabling the nucleophilic attack and removal of the sulfo group from PAPS, whereas His-45 and Asp-48 coordinate to stabilize the transition state of the enzyme before the sulfated polysaccharide product is released from the active site.

However, although PAPS is the exclusive sulfo donor in eukaryotes, it has a short half-life and can readily decompose into adenosine 3',5'-diphosphate, which acts as a competitive inhibitor during sulfotransfer reactions. Animals can efficiently utilize PAPS because they can metabolize adenosine 3',5'-diphosphate to prevent competitive inhibition and also replenish PAPS for each sulfotransfer reaction, as needed. On the other hand, aryl sulfate compounds, which can be utilized as sulfo donors in a limited number of bacterial systems (see Malojcic, G., et al., above), cannot react with any of the known native sulfotransferase enzymes in eukaryotes, including those that are involved in synthesizing HS polysaccharides in vivo. Without being limited by a particular theory, it is believed that the binding pockets for PAPS within the active sites of eukaryotic sulfotransferases either do not have a high enough affinity for aryl sulfate compounds to facilitate binding, and/or that the aryl sulfate compounds are sterically hindered from entering the active site at all.

The present disclosure includes methods and kits for synthesizing sulfated polysaccharides, particularly HS polysaccharides, using sulfotransferase enzymes that are engineered to recognize and bind with aryl sulfate compounds as sulfo group donors. Particularly, the engineered sulfotransferase enzymes are designed to transfer sulfo groups from aryl sulfate compounds to heparosan-based polysaccharides, containing alternating polymers of 1→4 glycosidically-linked hexuronic acid and glucosamine residues, to form HS polysaccharides. In vivo, HS polysaccharides play critical roles in a variety of important biological processes, including assisting viral infection, regulating blood coagulation and embryonic development, suppressing tumor growth, and controlling the eating behavior of test subjects by interacting with specific regulatory proteins. Depending on the role, HS polysaccharides can contain one or more unique patterns or motifs recognized by specific protein(s) involved in the particular biological process. The HS polysaccharide produced by any of the methods or kits described herein can have anticoagulant activity either analogous or identical to naturally-sourced heparin.

It should be understood that while reference is made to exemplary embodiments and specific language is used to describe them, no limitation of the scope of the invention is intended. Further modifications of the methods described herein, as well as additional applications of the principles of those inventions as described, which would occur to one skilled in the relevant art and having possession of this disclosure, are to be considered within the scope of this invention. Furthermore, unless defined otherwise, all technical and scientific terms used herein have the same meaning as commonly understood by one of ordinary skill in the art to which embodiments of this particular invention pertain. The terminology used is for the purpose of describing those embodiments only, and is not intended to be limiting unless specified as such. Headings are provided for convenience only and are not to be construed to limit the invention in any way. Additionally, throughout the specification and claims, a given chemical formula or name shall encompass all optical isomers and stereoisomers, as well as racemic mixtures where such isomers and mixtures exist.

In Vitro Synthesis of Heparan Sulfate Polysaccharides

In an embodiment of the invention, the synthesis of HS polysaccharides can be accomplished by treating a heparosan-based polysaccharide with an aryl sulfate compound and a sulfotransferase enzyme that has been engineered to recognize, bind, and react with aryl sulfate compounds as sulfo group donors. Each of the engineered sulfotransferase enzymes, including their sequences, structures, and biological activities, are described in further detail below. Without being limited by a particular theory, it is believed that sulfotransferase enzymes that recognize polysaccharides as sulfo group acceptors, but also bind and react with aryl sulfate compounds as sulfo donors, have neither been observed in nature nor described previously.

Those skilled in the art will appreciate that the engineered sulfotransferase enzymes utilized in the methods of the present invention have several advantages over in vitro and in vivo reaction mechanisms that are unable to bind and react with aryl sulfate compounds in order to catalyze sulfo transfer. Presently, obtaining large-scale quantities of sulfated polysaccharides, including heparin, requires isolating and purifying them from animal sources, such as pigs and cattle (see Xu, Y., et al., (2011) *Science* 334 (6055): 498-501). However, a worldwide contamination crisis of heparin in 2007 and 2009 shone a spotlight on the fragility of solely relying on obtaining them from animal sources. Consequently, in recent years, there has been a push to develop synthetic routes to synthesizing anticoagulant HS polysaccharides in large enough quantities to compliment or replace animal-sourced products.

In order to synthesize sulfated polysaccharides in vitro, there have historically been two reaction schemes: total chemical synthesis and chemoenzymatic synthesis. While both types of reaction schemes have led to purified products that in some instances are homogeneous, synthetic routes as a whole have been inadequate to produce sulfated polysaccharides, particularly heparin, on an industrial scale. Indeed, the production of such polysaccharides using total chemical synthesis has historically required as many as 60 steps and resulted in very low yields (see Balagurunathan, K., et al., (eds.) (2015) *Glycosaminoglycans: Chemistry and Biology*, Methods in Molecular Biology, vol. 1229, DOI 10.1007/978-1-4939-1714-3_2, © Springer Science+Business Media New York).

Chemoenzymatic synthesis routes, on the other hand, generally utilize far fewer steps and increase the scale of the generated anticoagulant products into multi-milligram amounts (See U.S. Pat. Nos. 8,771,995 and 9,951,149, the disclosures of which are incorporated by reference in its entirety). The improvements in the quantity of obtainable product can be attributed to the ability to combine recombinant natural sulfotransferases and PAPS in a reaction vessel in order to catalyze sulfo group transfer. Yet, chemoenzymatic methods to this point are inadequate for forming heparin on a large scale, because of the natural sulfotransferases' requirement to react with PAPS. PAPS is a highly expensive and unstable molecule that has been an obstacle to the large-scale production of enzymatically sulfated products, including heparin, because the half-life of PAPS at pH 8.0 is only about 20 hours.

Furthermore, product inhibition by adenosine 3',5'-diphosphate, which is a product of the sulfotransfer reaction, has also been a limiting factor to large-scale synthesis of heparin. The highly negative impact of the product inhibition by adenosine 3',5'-diphosphate can be somewhat reduced by employing a PAPS regeneration system (see U.S. Pat. No. 6,255,088, above, and Burkhart, et al. (2000) *J. Org. Chem.* 65: 5565-5574) that converts adenosine 3',5'-diphosphate into PAPS. Despite the PAPS regeneration system, however, the absolute necessity to supply PAPS to initiate the chemical reaction with native sulfotransferases nonetheless creates an insurmountably high-cost barrier to synthesize sulfated products, including heparin, on an industrial, production-grade scale.

In contrast to prior chemoenzymatic syntheses of sulfated polysaccharides that require PAPS as a sulfo donor in order to drive activity, the methods of the present invention obviate the need to use PAPS altogether, because each of the sulfotransferases have been engineered to recognize, bind, and react with aryl sulfate compounds as sulfo donors. As described above, some aryl sulfate compounds, such as PNS or MUS, are cheap, widely-available, and have previously been shown to react with some bacterial sulfotransferases as sulfo group donors (see Malojcic, G., et al., above). However, bacterial sulfotransferases are unsuitable to synthesize heparin or any other sulfated polysaccharide, because bacterial sulfotransferases can only react with other aromatic compounds as substrates, and cannot bind or react with polysaccharides. Consequently, and without being limited by a particular theory, it is believed that the engineered sulfotransferases utilized in methods of the present invention are the only known sulfotransferases that are capable of catalyzing sulfo group transfer from an aryl sulfate compound to a polysaccharide, particularly heparosan-based polysaccharides. Generally, any of the methods described herein for synthesizing sulfated products can be performed using one or more engineered sulfotransferases, and such engineered sulfotransferases can comprise any amino acid sequence so long as its biological activity is dependent on transferring a sulfo group from an aryl sulfate compound to heparosan-based polysaccharide. Non-limiting examples of engineered enzymes, aryl sulfate compounds, and heparosan-based polysaccharides are described in further detail, below.

In nature, heparan sulfate can be sulfated at the 2-O position of any hexuronic acid residue and the N-, 3-O, 6-O position of any glucosamine residue within the polysaccharide. Further, several of the hexuronic acid or glucosamine residues within the same polysaccharide chain can be sulfated at any of the above positions, and can form a characteristic sulfation pattern that can be recognized by one or more enzymes or co-factors within the body. As a non-limiting example, heparin contains polysaccharides having a characteristic pentasaccharide sequence with a specific sulfation pattern that is recognized by antithrombin.

In an embodiment of the invention, methods are provided for chemoenzymatically synthesizing N-, 2-O-, 3-O-, 6-O-sulfated-HS (N,2,3,6-HS) products, particularly heparin. One or more, and preferably all, of the N-, 2-O-, 3-O-, and 6-O sulfation steps can be catalyzed using sulfotransferase enzymes that are engineered to react with aryl sulfate compounds in the absence of PAPS. Each of these enzymes are described in further detail below. By controlling the molecular weight and N-acetyl glucosamine content of heparosan-based polysaccharides utilized as starting materials, an N,2,3,6-HS product composition can be formed that has a comparable molecular weight, sulfation, and anticoagulant activity to the United States Pharmacopeia (USP) reference standard (CAS No: 9041-08-1) for API heparin.

Heparin produced in vitro and in vivo contains heparan sulfate polysaccharides having a consensus pentasaccharide motif, which can only be formed when sulfated in a specific order. Thus, in methods of the present invention in which a heparin product is synthesized, the order of sulfation within the pentasaccharide motif is typically: (1) N-sulfation; (2) 2-O-sulfation; (3) 6-O-sulfation; and (4) 3-O sulfation. However, other portions of the polysaccharide can be sulfated in any order, and other N,2,3,6-HS products can be synthesized by sulfating heparosan-based polysaccharides in any order. Each of the reaction steps utilized to synthesize any N,2,3,6-HS product, including heparin, can optionally be performed in a single pot, or performed in one or more separate steps in which the products are isolated and purified prior to performing the next sulfation step.

In general, and as described above, a vast majority of natural sulfotransferases, including all sulfotransferases known to react with polysaccharides, react with PAPS as a sulfo donor. Consequently, each sulfotransferase enzyme is generally classified by the chemical reaction it catalyzes, particularly the sulfo group acceptor and the subsequently-formed product. With respect to sulfotransferases that react with heparosan-based polysaccharides, the enzymes must further recognize specific structural motifs and sulfation patterns within the polysaccharide chain in order to bind and react. Each of the engineered, aryl sulfate-dependent sulfotransferases, and the sulfo acceptor polysaccharides that they recognize, bind, and react with, are described in further detail below.

Glucosaminyl N-Sulfotransferases

In nature, N-sulfation is typically carried out by N-deacetylase/N-sulfotransferase (NDST) enzymes have dual activity, in which the same enzyme can catalyze the N-deacetylation of N-acetyl glucosamine residues and the N-sulfation of unsubstituted glucosamine residues within heparosan. In particular, N-sulfation is accomplished by the enzymatic transfer of a sulfo group from PAPS to the glucosamine residue. The dual N-deacetylase and N-sulfotransferase activity of NDST is achieved via two separate structural domains-an N-deacetylase domain and an N-sulfotransferase domain. However, the activity of one of the domains is not a pre-requisite for the activity of the other domain, and recombinant single domain proteins comprising either N-deacetylase or N-sulfotransferase activity can be expressed and purified. Thus, in in vitro syntheses of heparan sulfate products, a single-domain, recombinant N-sulfotransferase enzyme is often utilized to carry out the N-sulfation step. Similarly, and in an embodiment of the invention, engineered aryl sulfate-dependent NST enzymes can be expressed and purified to comprise a single, N-sulfotransferase domain, in order to catalyze the N-sulfation of N-deacetylated heparosan in the absence of PAPS.

Naturally-occurring NDST enzymes, which react with PAPS as a sulfo group donor, are members of the EC 2.8.2.8 enzyme class. N-deacetylated portions of heparosan that can react with natural NDST enzymes, recombinant N-sulfotransferase domains of natural NDST enzymes, and the engineered aryl-sulfate dependent NST enzymes described herein can comprise one or more disaccharide units comprising the structure of Formula II, below:

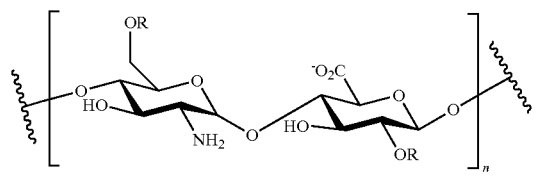

wherein n is an integer and R is selected from the group consisting of a hydrogen atom or a sulfo group. Although the portion of the polysaccharide that reacts with the enzyme comprises the structure of Formula II, other portions of the polysaccharide can be N- or O-substituted. Typically, N-deacetylated heparosan comprising the structure of Formula II can comprise at least four disaccharide units, or eight sugar residues total. Sulfotransfer reactions in which N-deacetylated heparosan is utilized as the sulfo group acceptor are discussed in Sheng, J., et al., (2011) *J. Biol. Chem.* 286 (22):19768-76, as well as Gesteira, T. F., et al., (2013) *PLoS One* 8 (8):e70880, the disclosures of which are incorporated by reference in their entireties.

Upon successfully binding PAPS and N-deacetylated heparosan, NDST enzymes can catalyze transfer of the sulfo group to an unsubstituted glucosamine, forming an N-sulfated heparosan product comprising the structure of Formula II, below:

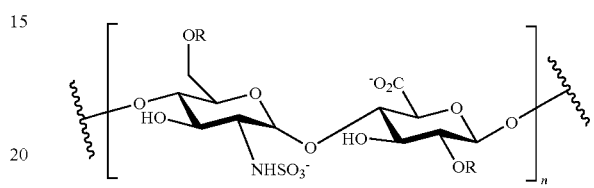

wherein n is an integer and R is selected from the group consisting of a hydrogen atom or a sulfo group. Similarly, when an engineered aryl sulfate-dependent NST enzyme successfully binds with an aryl sulfate compound and N-deacetylated heparosan, N-sulfation is catalyzed to form an N-sulfated heparosan product comprising the structure of Formula III.

Figure 2:
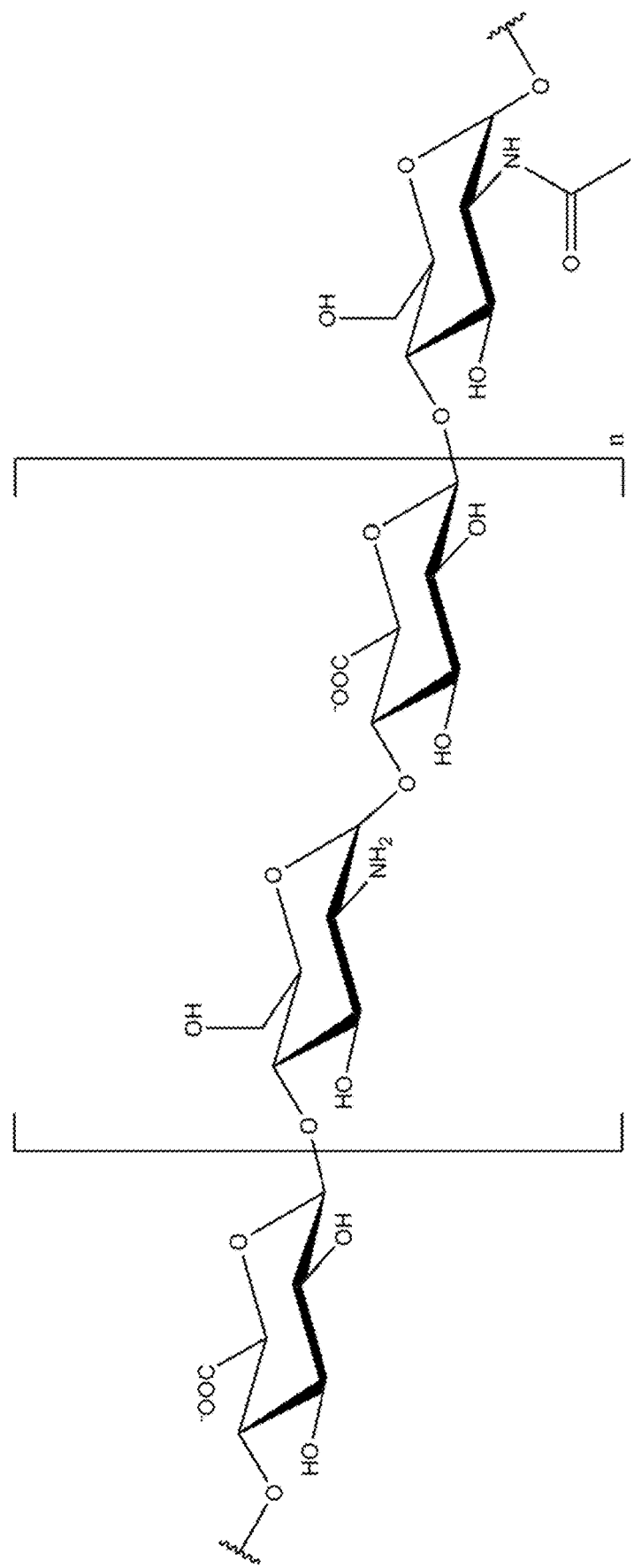
FIG. 2 shows a non-limiting example of an N-deacetylated heparosan polysaccharide capable of reacting as a sulfo group acceptor for both natural NDST enzymes and engineered NST enzymes that can be used in accordance with methods of the present invention.

In another embodiment, each of the repeating disaccharide units within the N-deacetylated heparosan that reacts with any of the natural NDST enzymes or any of the engineered aryl sulfate-dependent NST enzymes comprises the structure of Formula II. In further embodiments, both of the R groups at the 6-O position of the glucosaminyl residues and the 2-O position of the glucuronic acid residues are hydrogen atoms, in all of the disaccharide units. In other embodiments, in some locations within the polysaccharide, at least a portion of the glucosamine residues are still N-acetylated, as shown in FIG. 2, although glucosaminyl residues that are N-acetylated cannot directly participate as sulfo group acceptors. However, the presence of N-acetylated residues within the polysaccharide does not affect the sulfotransferases' binding affinity for non-acetylated residues within the same polysaccharide. In another embodiment, regardless of the structure of the heparosan-based polysaccharide adjacent to portion comprising the structure of Formula II, the N-sulfated polysaccharide product generated by reacting with an engineered NST or natural NDST (or the recombinant N-sulfotransferase domain of NDST) comprises the structure of Formula III.

In another embodiment, when there are multiple dimers comprising the structure of Formula II within the polysaccharide, any unsubstituted glucosamine residue can be N-sulfated. Similarly, the same polysaccharide can be N-sulfated multiple times, including and up to all available unsubstituted glucosaminyl residues that are present within the chain.

In another embodiment, heparosan-based polysaccharides comprising the structure of Formula II can be provided as a homogenous composition. In still other embodiments, sulfo acceptor polysaccharides comprising the structure of Formula II can be comprised within a composition comprising a polydisperse mixture of polysaccharides having variable chain lengths, molecular weights, and monosaccharide composition and functionalization.

In another embodiment, heparosan-based polysaccharides comprising the structure of Formula II and utilized in accordance with methods of the present invention can be obtained and/or modified from commercial sources. In other embodiments, heparosan can be isolated from bacterial or eukaryotic sources and subsequently chemically treated in order to produce an N-deacetylated polysaccharide that comprises the structure of Formula II. Such processes are discussed in detail in the description and examples, below.

The N-sulfotransferase domains of natural NDST enzymes within EC 2.8.2.8 typically comprise approximately 300 to 350 amino acid residues that can vary greatly in their sequence, yet ultimately have the exact same function, namely, to catalyze the N-sulfation of unsubstituted glucosamine residues within N-deacetylated heparosan. Without being limited by a particular theory, it is believed that each of the natural N-sulfotransferase domains can catalyze the same chemical reaction because there are multiple amino acid sequence motifs and secondary structures that are either identical or highly conserved across all species.

Figure 3A:
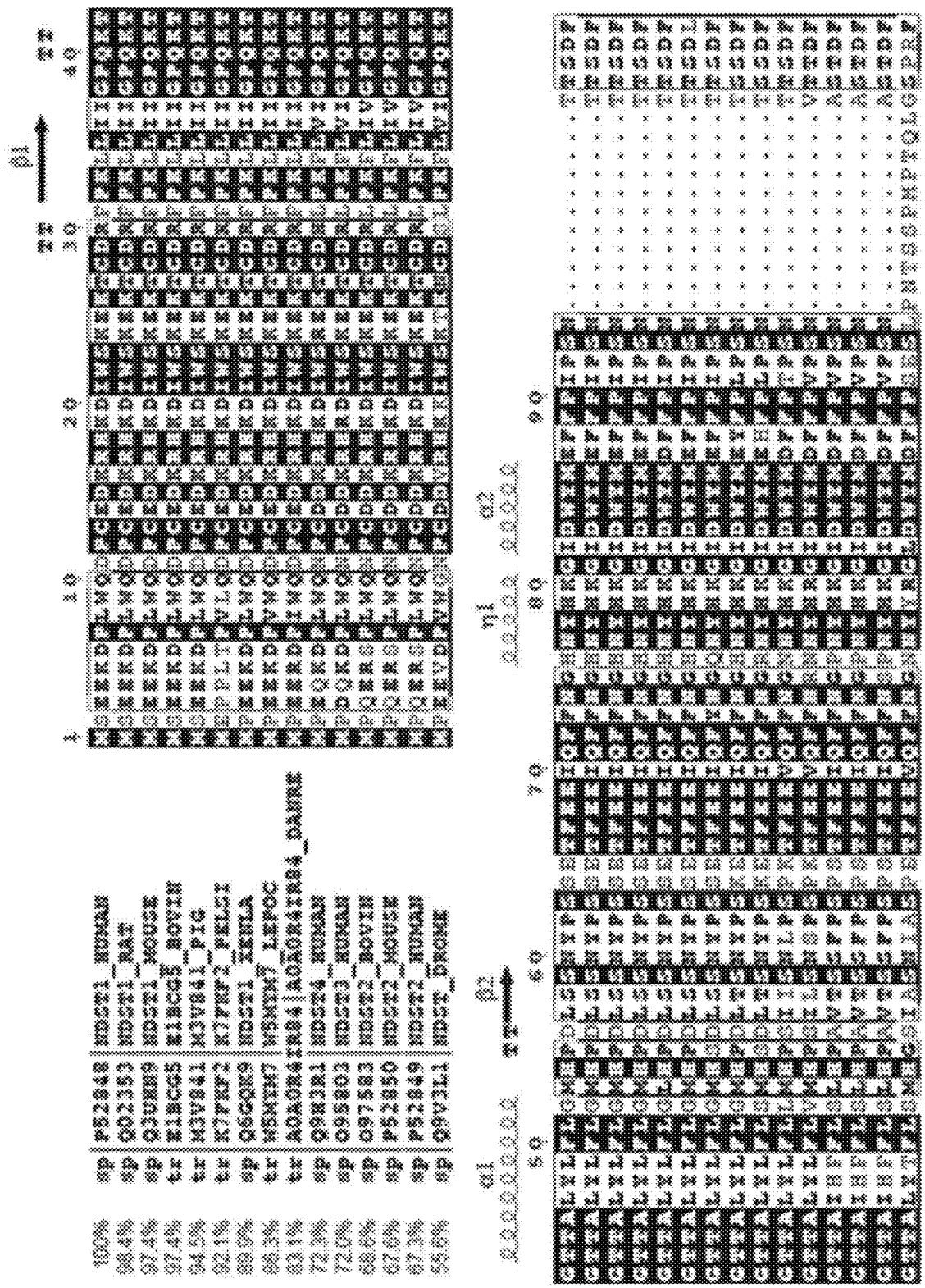
FIGS. 3A-3C show a multiple sequence alignment for the N-sulfotransferase domains of fifteen natural NDST enzymes within enzyme class EC 2.8.2.8, illustrating conserved amino acid sequence motifs that are present regardless of overall sequence identity.
Figure 3B:
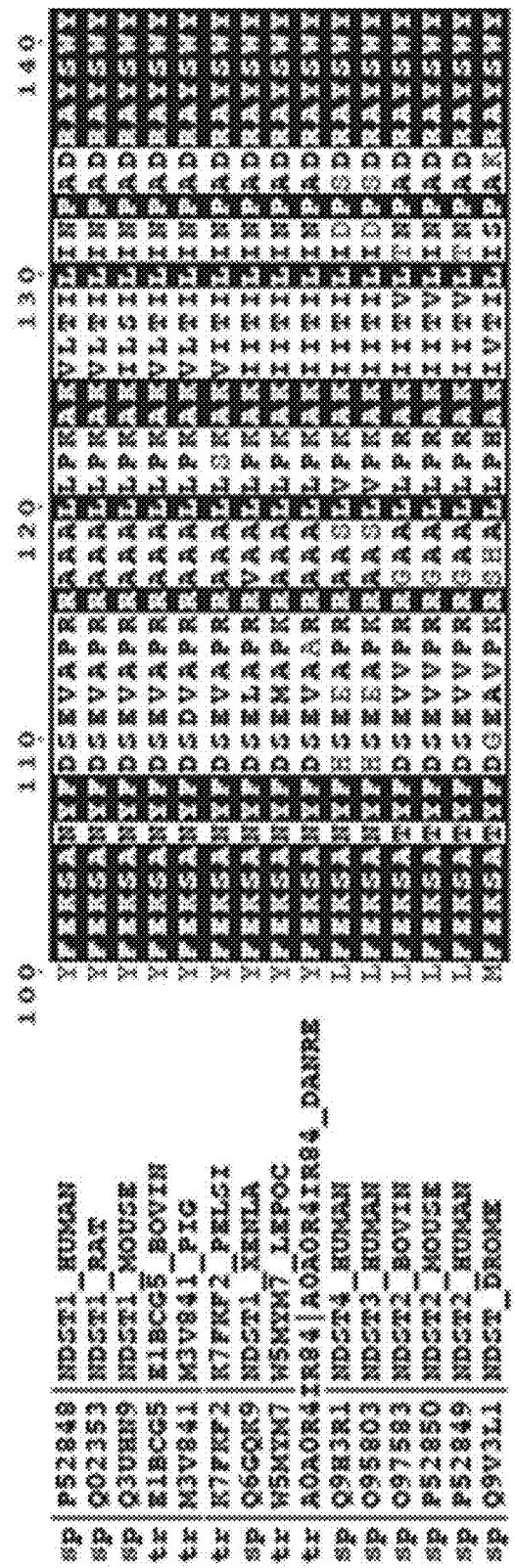
Figure 3B:
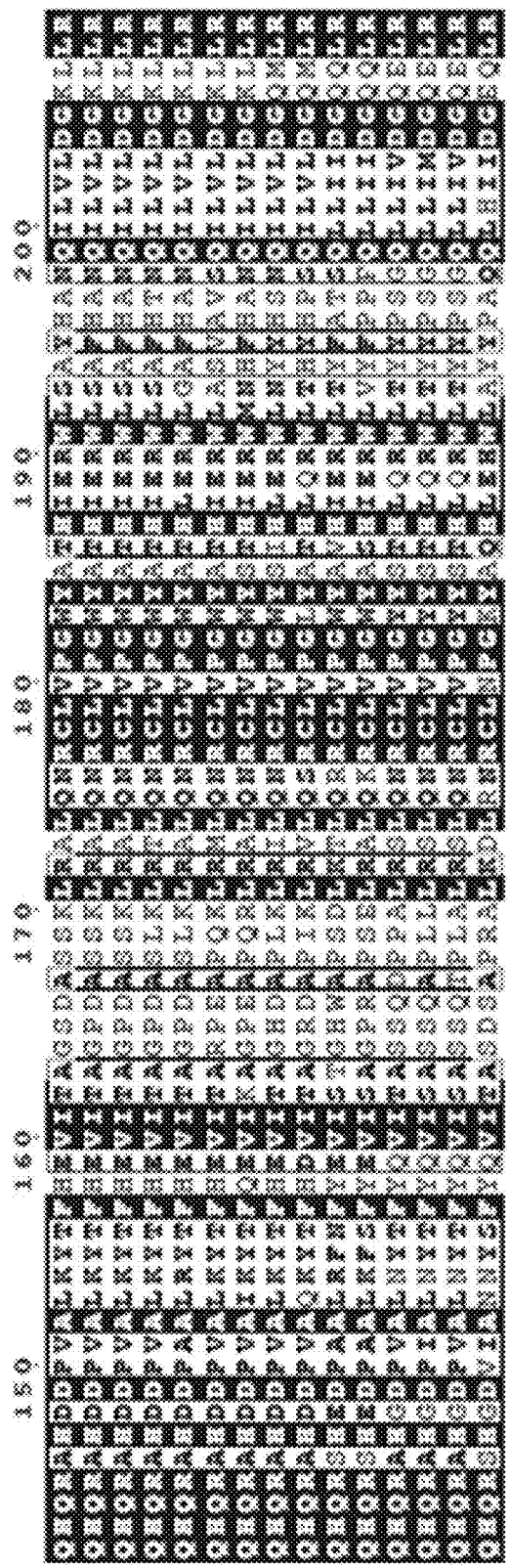
Figure 3C:
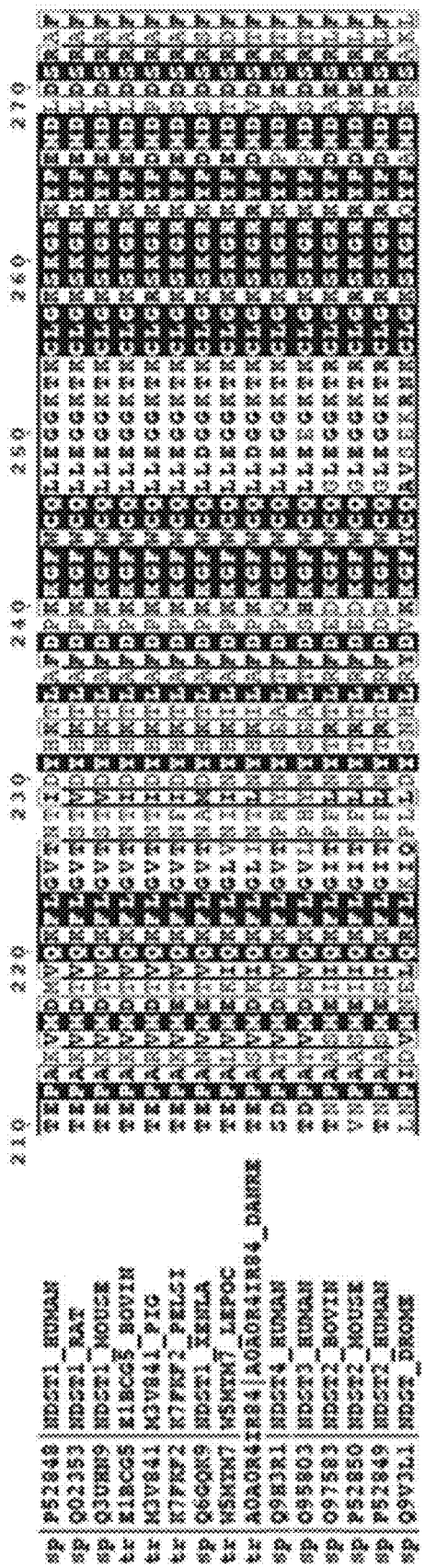

Further, it is believed that several of the conserved amino acid sequence motifs within NDST are directly involved in binding of either PAPS and/or the polysaccharide, or participate in the chemical reaction itself. The identity of conserved amino acid sequence motifs between the NDST enzymes can be demonstrated by comparing the amino acid sequence of the N-sulfotransferase domain of the human NDST1 enzyme, which has a solved crystal structure (PDB code: 1NST) in which amino acid residues within the active site have been identified, with the amino acid sequences of the N-sulfotransferase domains of other natural NDSTs. A multiple sequence alignment of the N-sulfotransferase domains of fifteen enzymes within EC 2.8.2.8, including several eukaryotic organisms and several isoforms of the human NDST, is shown in FIGS. 3A-3C, along with their percent identity relative to the human NDST1 (UniProtKB Accession No. P52848). As illustrated in FIGS. 3A-3C, sequences range from having 98.4% sequence identity with the P52848 reference sequence (entry sp|Q02353|NDST1_RAT) for the rat N-sulfotransferase domain down to 55.6% sequence identity (entry sp|Q9V3L1|NDST_DROME) for the fruit fly N-sulfotransferase domain. Those skilled in the art would appreciate that the multiple sequence alignment was limited to fifteen sequences for clarity, and that there are hundreds of amino acid sequences encoding for the N-sulfotransferase domains of other natural NDST enzymes that have been identified and that have highly conserved active site and/or binding regions as well.

Within FIGS. 3A-3C, amino acids that are depicted in white with a black background at a particular position, are 100% identical across all sequences. Amino acids that are highly conserved, meaning that the amino acids are either identical or chemically or structurally similar, at a particular position are enclosed with a black outline. Within highly conserved regions, consensus amino acids that are present in a majority of the sequences, are in bold. Amino acids at a particular position that are not identical or highly conserved are typically variable. A period within a sequence indicates a gap that has been inserted into the sequence in order to facilitate the sequence alignment with other sequence(s) that have additional residues between highly conserved or identical region. Finally, above each block of sequences are a series of arrows and coils that indicate secondary structure that is conserved across all sequences, based on the identity of the amino acids within the alignment and using the structure of the natural human N-sulfotransferase enzyme as a reference. The β symbol adjacent to an arrow refers to a β-sheet, whereas a coil adjacent to an α symbol or a η symbol refers to a helix secondary structure.

Within the fifteen aligned sequences in FIGS. 3A-3C, there are several conserved amino acid motifs that include one or more amino acids that comprise the active site, based on the crystal structure of the N-sulfotransferase domain of human NDST1. These conserved amino acid sequence motifs, based on the numbering of the amino acid residues within FIGS. 3A-3C include residues 40-46 (Q-K-T-G-T-T-A); residues 66-69 (T-F-E-E); residues 101-105 (F-E-K-S-A); residues 139-143 (S-W-Y-Q-H); and residues 255-262 (C-L-G-K/R-S-K-G-R). In further embodiments, some isoforms of the natural sulfotransferase enzymes within EC 2.8.2.8 that comprise the conserved amino acid sequence motif Q-K-T-G-T-T-A further comprise the expanded conserved amino acid sequence motif, Q-K-T-G-T-T-A-L-Y-L, from residues 40-49.

Figure 4A:
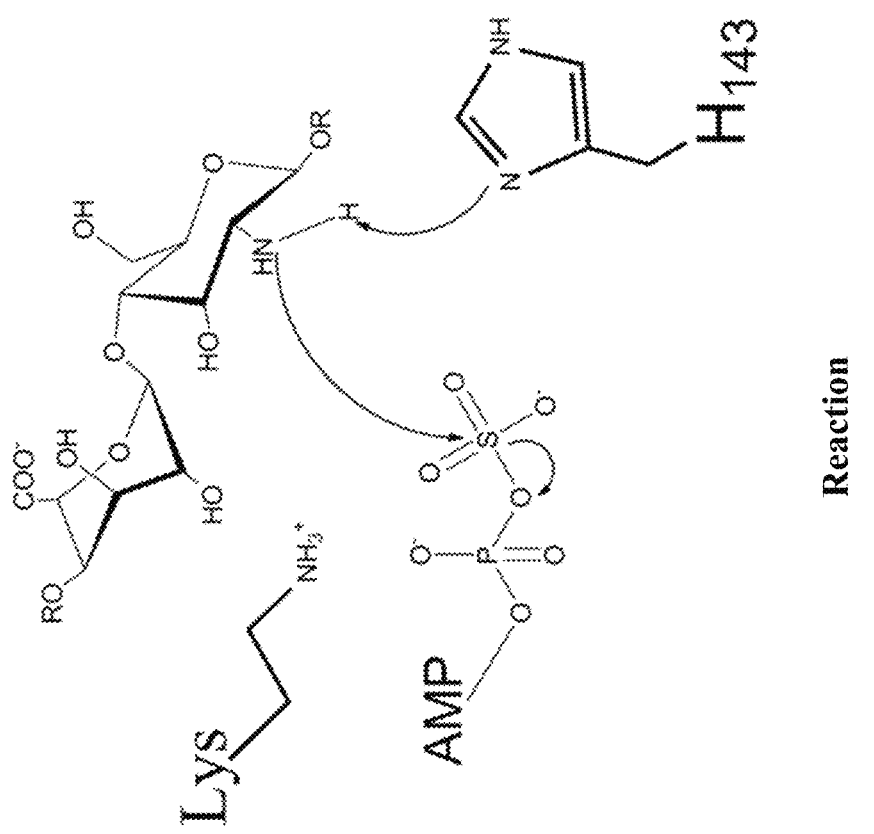
FIGS. 4A-4C show a reaction mechanism between conserved residues within the N-sulfotransferase domain of a natural NDST enzyme, PAPS, and N-deacetylated heparosan.
Figure 4B:
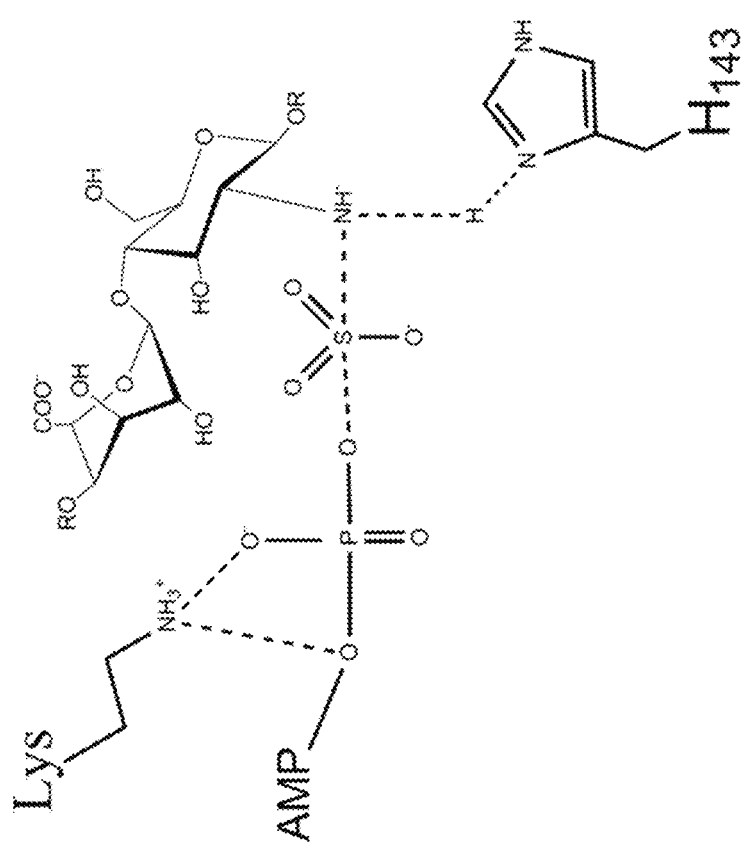
Figure 4C:
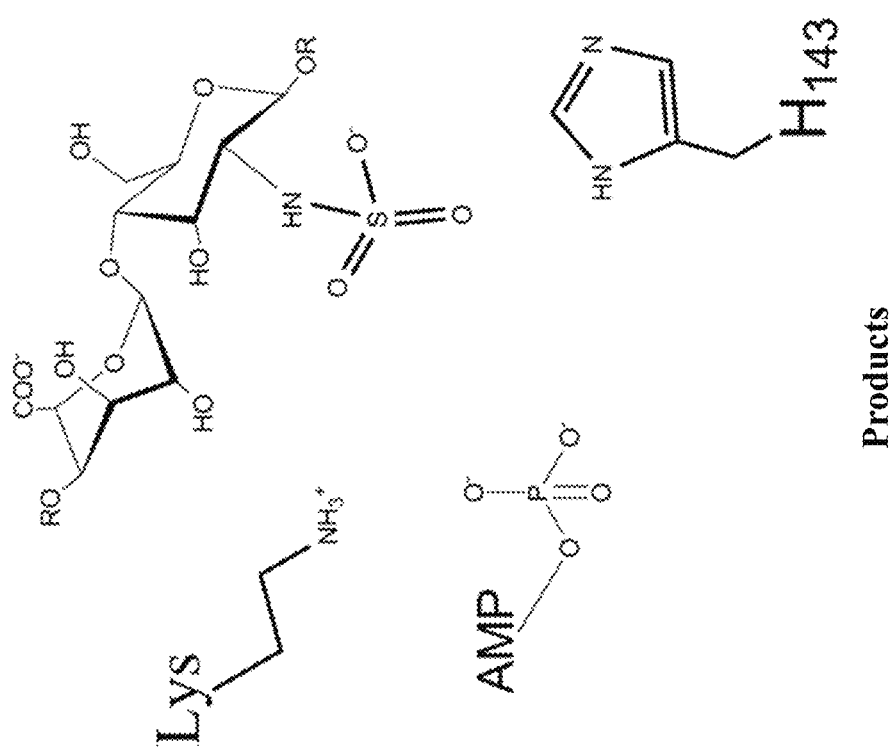

Without being limited by a particular theory, it is believed that these residues either facilitate or participate in the chemical reaction, or enable binding of PAPS or the polysaccharide within the active site. In particular and as illustrated in FIGS. 4A-4C, the histidine residue at position 143 (corresponding to position 716 in the amino acid sequence of the full-length natural sulfotransferase enzyme that also includes an N-deacetylase domain) is in position to abstract one of the two protons within the amine functional group of the unsubstituted glucosaminyl residue within the polysaccharide, enabling the nitrogen atom to initiate the nucleophilic attack of PAPS and remove the sulfuryl group. Additionally, lysine residues at position 41 and 260 are also universally conserved, and are thought to coordinate with the sulfuryl moiety, driving binding of PAPS within the active site as well as stabilizing the transition state during the course of the reaction (see Gesteira, T. F., et al., above, as well as Sueyoshi, T., et al., (1998) *FEBS Letters* 433:211-214, the disclosure of which is incorporated by reference in its entirety).

However, as described above, the natural NDST enzymes are unable to catalyze the transfer of the sulfate group from an aryl sulfate compound to the polysaccharide, because without being limited by a particular theory, it is believed that the binding pocket for PAPS either does not have a high enough affinity for aryl sulfate compounds to facilitate binding and/or that the aryl sulfate compounds are sterically hindered from entering the active site. Consequently, and in another embodiment, the N-sulfotransferase domain of a natural NDST enzyme can be mutated in several locations within its amino acid sequence to enable binding of the aryl sulfate compound within the active site and/or to optimally position the aryl sulfate compound so transfer of the sulfate group to the polysaccharide can occur.

Accordingly, and in another embodiment, engineered NST enzymes that can be utilized in accordance with methods of the present invention can comprise a single N-sulfotransferase domain that is mutated relative to the N-sulfotransferase domain of any NDST enzyme, including enzymes having the amino acid sequences illustrated in FIGS. 3A-3C. In other embodiments, engineered NST enzymes that can be utilized in accordance with methods of the present invention can further comprise an N-deacetylase domain that has an identical or mutated amino acid sequence of the N-deacetylase domain of any natural NDST enzyme.

In another embodiment, mutations engineered into the amino acid sequences of the engineered enzymes facilitate a biological activity in which aryl sulfate compounds can both bind and react with the engineered NST enzymes as sulfo group donors. In further embodiments, the engineered NST enzyme can bind and react with an aryl sulfate compound as a sulfo group donor, while retaining the corresponding natural sulfotransferases' biological activity with heparosan and/or N-deacetylated heparosan as a sulfo group acceptor. Without being limited by a particular theory, it is believed that because of the mutations inserted into the amino acid sequences of the engineered NST enzymes, their sulfotransferase activity may comprise the direct transfer of a sulfuryl group from an aryl sulfate compound to the sulfo acceptor polysaccharide, using a similar mechanism as described in FIGS. 4A-4C above, except that the PAPS is substituted with the aryl sulfate compound. Otherwise, it is believed that the mutations may cause the sulfotransferase activity to comprise a two-step process including the hydrolysis of an aryl sulfate compound and formation of a sulfohistidine intermediate, followed by the nucleophilic attack of the sulfohistidine intermediate by an N-unsubstituted glucosamine within N-deacetylated heparosan to form the N-sulfated product. By either mechanism, engineered NST enzymes have been shown to achieve sulfo transfer from an aryl sulfate compound to a polysaccharide, as described in the examples, below.

In another embodiment, an engineered NST enzyme can comprise one or more mutated amino acid sequence motifs relative to the conserved amino acid sequence motifs described above that are found in the N-sulfotransferase domains of natural NDST enzymes within EC 2.8.2.8, as described above and indicated in the multiple sequence alignment in FIG. 3. In another embodiment, each mutated amino acid sequence motif that is present in the amino acid sequence of the engineered NST enzyme comprises at least one amino acid mutation relative to the corresponding conserved amino acid sequence motif within the N-sulfotransferase domain of a natural NDST. In another embodiment, an engineered NST enzyme comprises one mutated amino acid sequence motif. In another embodiment, an engineered NST enzyme comprises two mutated amino acid sequence motifs. In another embodiment, an engineered NST enzyme comprises three mutated amino acid sequence motifs. In another embodiment, an engineered NST enzyme comprises four mutated amino acid sequence motifs. In another embodiment, an engineered NST enzyme comprises five mutated amino acid sequence motifs. In another embodiment, an engineered NST enzyme that includes at least one mutated amino acid sequence motif relative to an N-sulfotransferase domain of any of the natural NDST enzymes within EC 2.8.2.8 can have an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

Figure 5:
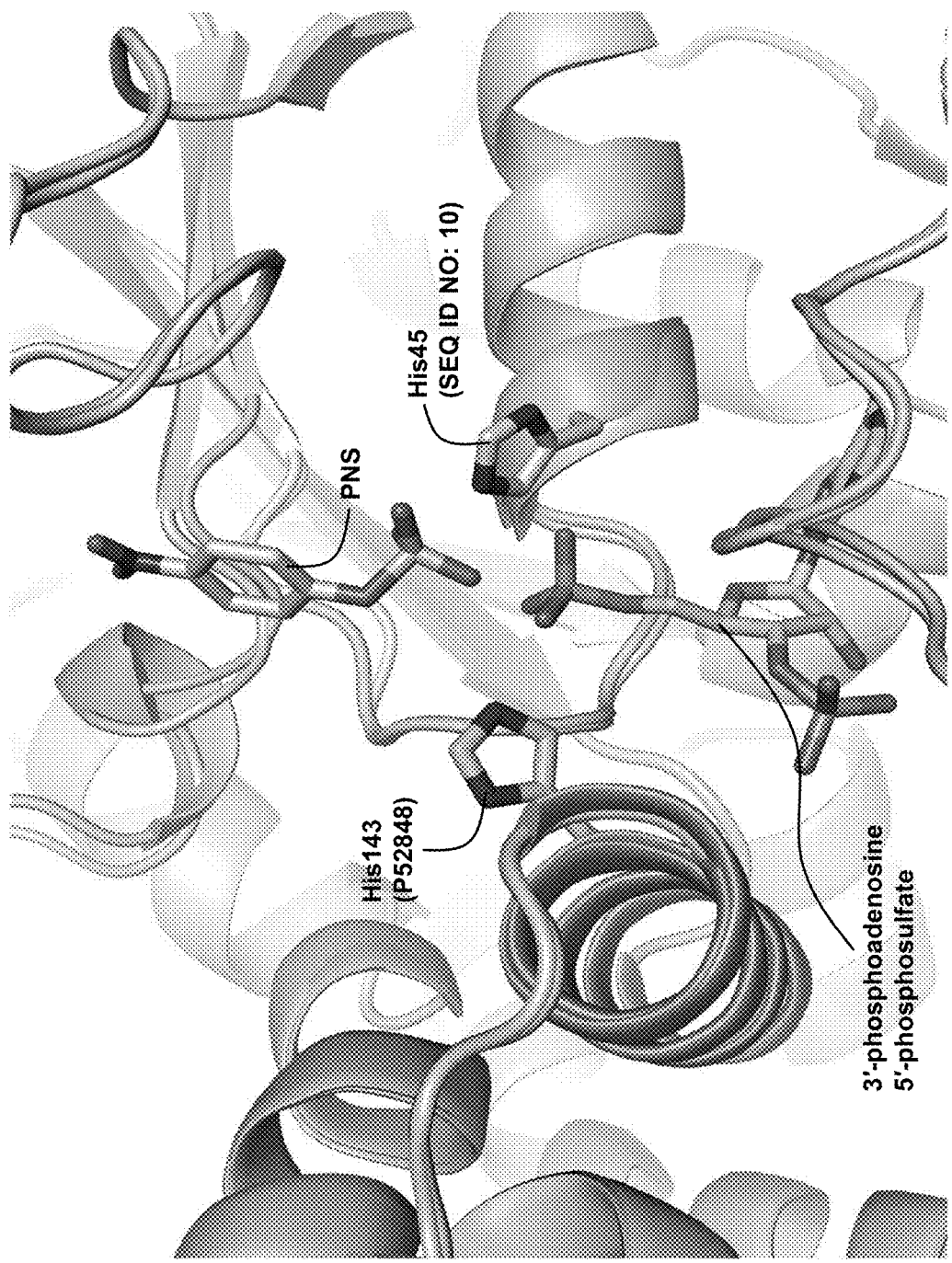
FIG. 5 shows a three-dimensional model of an aryl sulfate compound bound within the active site of a first group of engineered NST enzymes, superimposed over the crystal structure of PAPS bound within the N-sulfotransferase domain of a natural human NDST enzyme.

In another embodiment, upon viewing the crystal structure of the N-sulfotransferase domain of the human NDST1 (PDB code: 1NST) within a 3D molecular visualization system (including, as a non-limiting example, the open-source software, PyMOL), the structure of related sequences, such as those of engineered NST enzymes that contain one or more mutated amino acid sequence motifs relative to the human N-sulfotransferase domain, can be modeled for comparison as illustrated in FIGS. 5-8. In one non-limiting example, FIG. 5 shows a magnified view of the active site of the human N-sulfotransferase domain that is overlaid with an engineered NST enzyme, comprising the amino acid sequence of SEQ ID NO: 10, in which the structure of the engineered enzyme is modelled upon making mutations relative to the human N-sulfotransferase domain amino acid sequence. Adenosine 3',5'-diphosphate, which is the product of a sulfotransfer reaction in which PAPS is the sulfo donor, and which was co-crystallized with the human N-sulfotransferase domain, is also illustrated within the active site. PNS is also modeled into the engineered enzyme active site, using the consensus solutions of molecular dynamics (MD) simulations that designed to calculate the optimized position and orientation of a ligand within an enzyme active site adjacent to the polysaccharide binding site (not shown), if such solutions are possible.

As illustrated in FIG. 5, although there are several mutations within SEQ ID NO: 10, relative to sequence of the human N-sulfotransferase domain (UniProtKB Accession No. P52848) indicated in FIG. 3, the respective protein backbones are in a nearly identical location to one another, enabling a one-to-one comparison of the active sites. Within the structure of the engineered enzyme comprising the sequence of SEQ ID NO: 10, the consensus solutions from MD simulations indicate that the sulfate moiety within PNS is favored to bind adjacent to a histidine residue, His-45, that has been mutated relative to the natural amino acid residue, threonine, which is also universally conserved within EC 2.8.2.8. On the other hand, within the human N-sulfotransferase domain, the adenosine 3',5'-diphosphate is located near to the conserved His-143, described above. Although the sulfo group that would be comprised within the PAPS substrate is not shown, those skilled in the art would appreciate that if PAPS were present, the sulfate group would be oriented in a position immediately adjacent to His-143 and partially overlapping with the sulfate group within PNS. Without being limited by a particular theory, it is believed that the nearly overlapping location of the sulfate groups accounts for the engineered enzyme's ability to facilitate sulfo group transfer by using His-143 as a base to remove the proton from the glucosaminyl residue within the polysaccharide.

Figure 6:
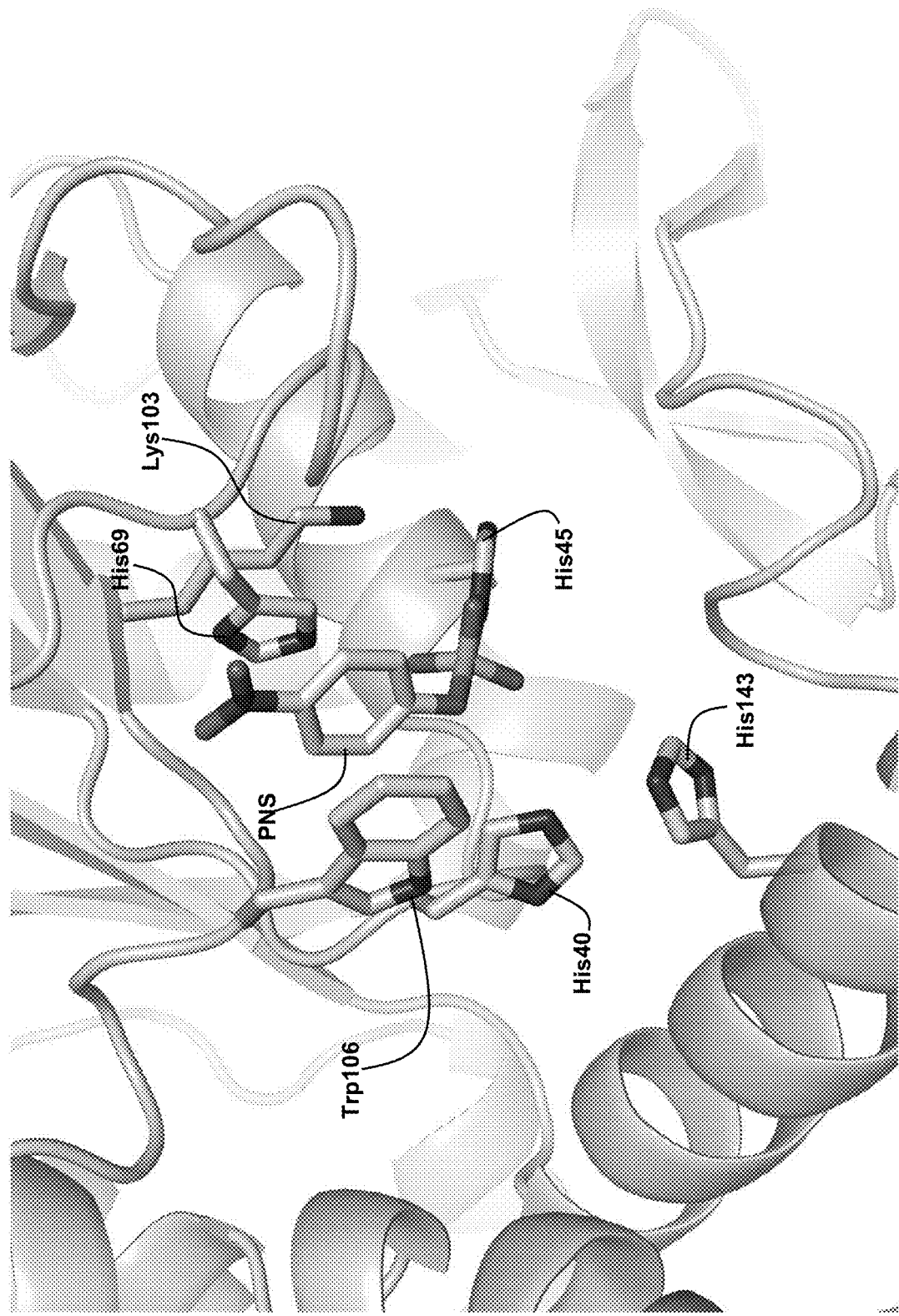
FIG. 6 shows an alternate view of the modelled active site of the engineered NST enzyme shown in FIG. 5, illustrating amino acid mutations present within the active site.

However, even though the sulfate groups can bind in a nearly identical location within the active site, aryl sulfate compounds cannot be utilized with EC 2.8.2.8 enzymes to facilitate sulfo group transfer to a polysaccharide. As described above, the amino acid residues within the active site of the natural enzymes are evolved to have strong binding affinity for PAPS, and likely do not have enough affinity for aryl sulfate compounds to drive binding and subsequently, reactivity. Consequently, other mutations must be present within the engineered enzymes to drive binding of aryl sulfate compounds within the active site. FIG. 6 illustrates other mutations that surround PNS within the engineered enzyme comprising the amino acid sequence of SEQ ID NO: 10, including Trp-106, His-69, and His-40. Trp-106 and His-69 are positioned to provide π-π stacking binding contacts with aromatic moiety within PNS. Additionally, the F2 nitrogen atoms within His-69 and His-40 coordinate with the sulfuryl group directly. Lysine residues retained from the natural enzyme sequence, Lys-41 (not shown, for clarity) and Lys-103 are in position to coordinate with the sulfate group during transfer in order to stabilize the transition state. Of note, the natural amino acid residue, Lys-260, which also coordinates with the sulfate group in PAPS, is mutated to a valine residue within the engineered enzyme sequence. Without being limited by a particular theory, it is believed that His-45, which is necessary for the reaction with PNS, would exhibit charge repulsion with a lysine residue at position 260, and that the mutation to a valine residue retains some steric bulk within the binding site while eliminating the charge repulsion. Lys-103 is nonetheless positioned to coordinate with the sulfuryl group, particularly when the sulfuryl group is associated or bound to His-45, as shown in FIG. 6.

Figure 7:
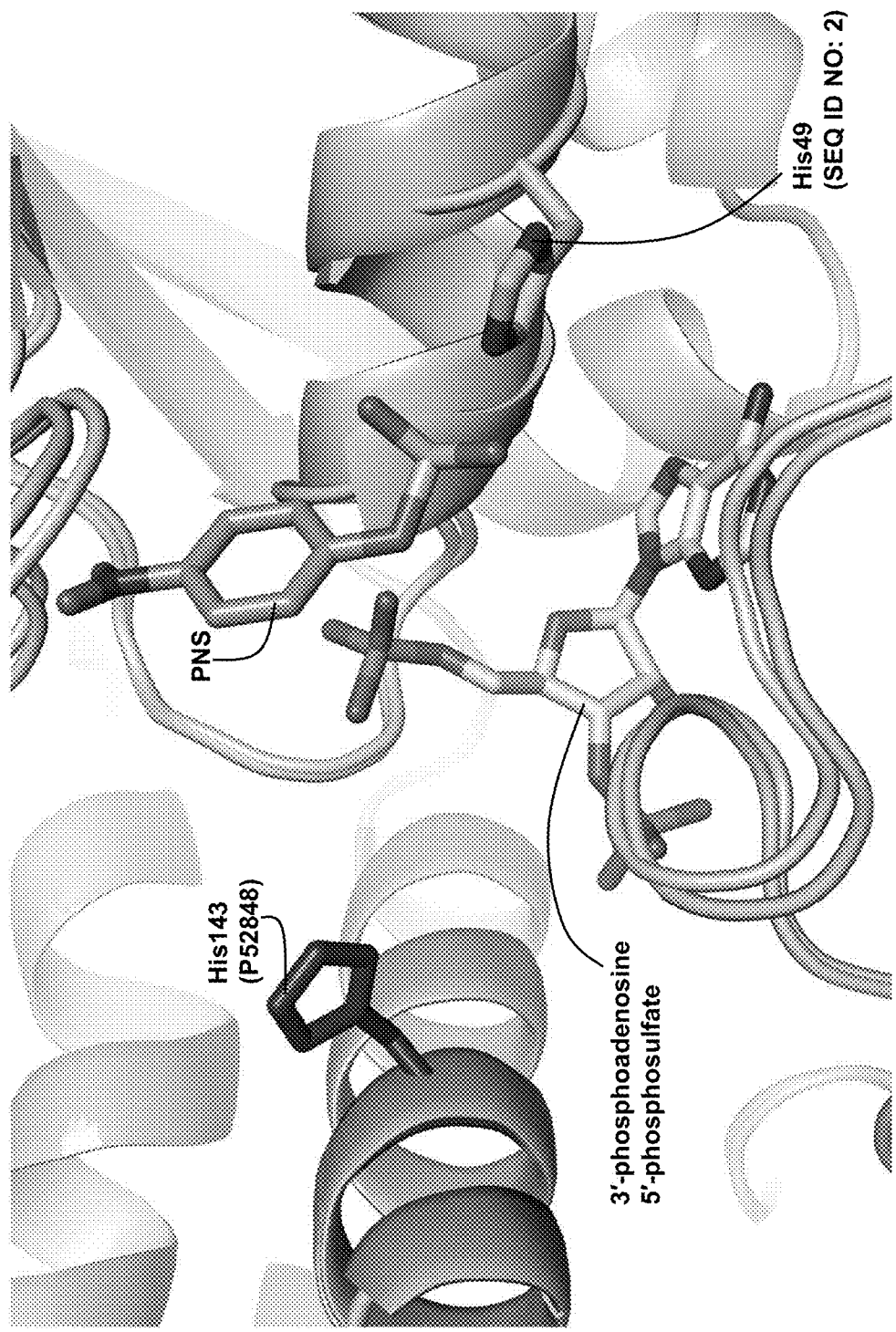
FIG. 7 shows a three-dimensional model of an aryl sulfate compound bound within the active site of a second group of engineered NST enzymes, superimposed over the crystal structure of the N-sulfotransferase domain of a natural human NDST enzyme.
Figure 8:
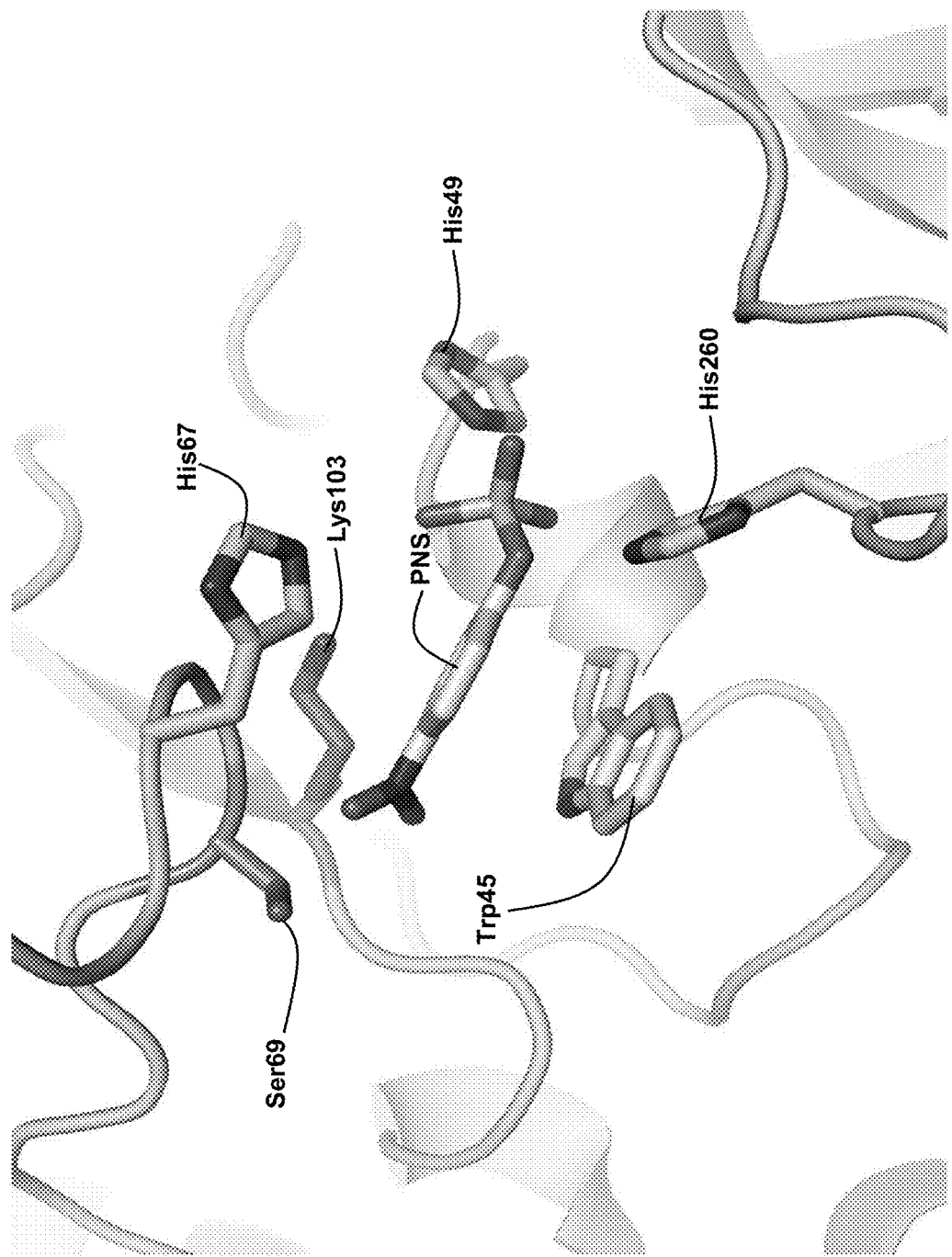
FIG. 8 shows an alternate view of the modelled active site of the engineered NST enzyme shown in FIG. 7, illustrating amino acid mutations present within the active site.

In another non-limiting example, FIG. 7 shows a magnified view of the active site of the human N-sulfotransferase domain (UniProtKB Accession No. P52848) that is overlaid with a different engineered NST enzyme, comprising the amino acid sequence of SEQ ID NO: 2. PNS is modeled into the engineered enzyme active site, as described above. As with the engineered NST having the amino acid sequence SEQ ID NO: 10, the protein backbone of the enzyme having the amino acid sequence SEQ ID NO: 2 also has a nearly identical structure to the N-sulfotransferase domain of the human enzyme. However, the consensus solutions from MD simulations indicate that the sulfate moiety within PNS is favored to bind adjacent to a different histidine mutation (His-49), which is mutated from a natural leucine residue that is conserved in the active site of the N-sulfotransferase domain of several of the natural NDST enzymes. Consequently, mutations within SEQ ID NO: 10 that formed binding contacts with PNS are not necessarily present in SEQ ID NO: 2. As illustrated in FIG. 8 and similar to SEQ ID NO: 10, there are two mutations present within SEQ ID NO: 2 that appear to form π-π stacking binding contacts surrounding the aromatic moiety of PNS, Trp-45 and His-67. Other mutations that comprise side chains that coordinate with PNS include Ser-69 (coordinating with the nitro functional group of PNS) and His-260 (coordinating with the sulfate moiety). Similar to SEQ ID NO: 10, because the natural lysine residue at position 260 is mutated, the natural Lys-103 residue is utilized within SEQ ID NO: 2 to coordinate with the sulfate moiety within PNS.

Those skilled in the art would appreciate that engineered NST enzymes of any other amino acid sequence, including, but not limited to, those described by SEQ ID NO: 4, SEQ ID NO: 6, SEQ ID NO: 8, SEQ ID NO: 12, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40, would likely exhibit a similar structure to the human N-sulfotransferase domain and engineered NST enzymes having the amino acid sequence of SEQ ID NO: 2 and SEQ ID NO: 10. Without being limited by a particular theory, it is also believed that NCS would bind in a similar position as PNS within the active site of any of the engineered NST enzymes, since the structures of the two aryl sulfate compounds are very similar, except that the sulfate group is located ortho on the aromatic ring relative to the nitro group, rather than para to the nitro group.

Further, engineered NST enzymes utilized in accordance with methods of the present invention can include mutated amino acid sequence motifs that include the above-described mutations as well as other mutations that facilitate binding of substrates, the sulfotransfer reaction, or the stability of the enzyme during protein expression. In another embodiment, an engineered NST enzyme can include the mutated amino acid sequence motif, $X_1$-K-T-G-A-W/F-A/L-L-$X_2$-H, mutated from the conserved amino acid sequence Q-K-T-G-T-T-A-L-Y-L within EC 2.8.2.8, wherein $X_1$ is selected from the group consisting of glutamine, serine, and alanine; and $X_2$ is selected from the group consisting of tyrosine, threonine, and histidine. Engineered NST enzymes that include the mutated amino acid sequence motif $X_1$-K-T-G-A-W/F-A/L-L-$X_2$-H include, but are not limited to SEQ ID NO: 2 (described above), as well as SEQ ID NO: 4, SEQ ID NO: 12; SEQ ID NO: 33, SEQ ID NO: 35, SEQ ID NO: 36, and SEQ ID NO: 40. In further embodiments, engineered NST enzymes can further include the mutated amino acid sequence motif, T-$X_3$-$X_4$-S, mutated from the conserved amino acid sequence T-F-E-E, wherein $X_3$ is a mutation relative to the natural sulfotransferase enzymes within EC 2.8.2.8, selected from the group consisting of histidine and glycine; $X_4$ is a mutation relative to the natural sulfotransferase enzymes within EC 2.8.2.8, selected from the group consisting of glycine, histidine, and serine; and wherein at least one of $X_3$ and $X_4$ is a histidine residue. In some even further embodiments, $X_1$ is glutamine, $X_2$ is tyrosine, $X_3$ is histidine, $X_4$ is glycine, and the engineered NST enzyme further comprises the mutated amino acid sequence motif, C-L-G-K/R-S-H-G-R. In other even further embodiments, $X_1$ is serine, $X_2$ is threonine, $X_3$ is glycine, $X_4$ is histidine, and the engineered NST enzyme further comprises the mutated amino acid sequence motif, C-H-G-K/R-R-W-G-R. In sill other even further embodiments, $X_1$ is alanine, $X_2$ is histidine, $X_3$ is histidine, $X_4$ is serine, and the engineered NST enzyme further comprises the mutated amino acid sequence motif, C-A-H-K/R-G-L-G-R.

In another embodiment, engineered NST enzymes can include the mutated amino acid sequence motif, H-$X_5$-T-G-$X_6$-H-A, mutated from the conserved amino acid sequence Q-K-T-G-T-T-A, wherein $X_5$ is selected from the group consisting of lysine and glycine; and $X_6$ is a mutation relative to the natural sulfotransferase enzymes within EC 2.8.2.8, selected from the group consisting of glycine and valine. Engineered NST enzymes that include the mutated amino acid sequence motif H-$X_5$-T-G-$X_6$-H-A include, but are not limited to SEQ ID NO: 10 (described above), as well as SEQ ID NO: 6, SEQ ID NO: 8; SEQ ID NO: 34, SEQ ID NO: 37, SEQ ID NO: 38, and SEQ ID NO: 39. In further embodiments, $X_5$ is glycine and $X_6$ is glycine. In some even further embodiments, the engineered NST enzyme further comprises the mutated amino acid sequence motif, C-G-G-K/R-H-L-G-R. In other even further embodiments, the engineered NST enzyme further comprises the mutated amino acid sequence motif, F-E-H-S-G.

In another embodiment, within any of the engineered NST enzymes that include the mutated amino acid sequence motif, H-$X_5$-T-G-$X_6$-H-A, $X_5$ is selected from the group consisting of lysine and glycine; and $X_6$ is a mutation relative to the natural sulfotransferase enzymes within EC 2.8.2.8, selected from the group consisting of glycine and valine. In further embodiments, $X_5$ is selected to be lysine, $X_6$ is selected to be valine, and the engineered NST enzyme further comprises the mutated amino acid sequence motif, T-G-N-H.

Figure 9:
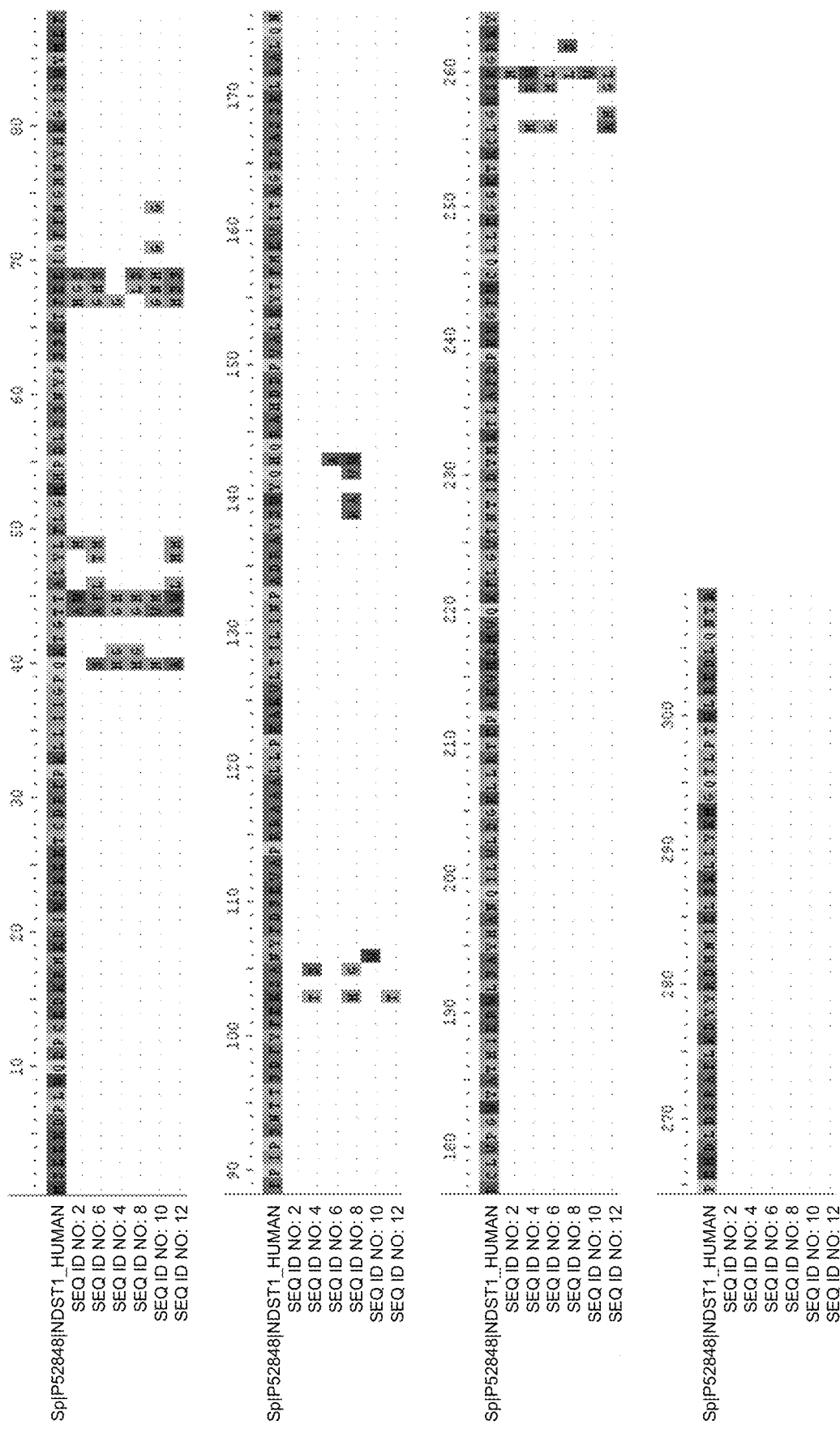
FIG. 9 shows a sequence alignment of polypeptides comprising the amino acid sequences of SEQ ID NO: 2, SEQ ID NO: 4, SEQ ID NO: 6, SEQ ID NO: 8, SEQ ID NO: 10, SEQ ID NO: 12, respectively, depicting the position and identity of amino acid residues differences between each of the illustrated sequences and relative to the human NDST1 enzyme.

Furthermore, the amino acid sequences (SEQ ID NO: 2, SEQ ID NO: 4, SEQ ID NO: 6, SEQ ID NO: 8, SEQ ID NO: 10, SEQ ID NO: 12) of six engineered NST enzymes, which have been experimentally determined to be active with aryl sulfate compounds as sulfo group donors (see Example 2 below) can be compared with the amino acid sequence of the N-sulfotransferase domain of the human NDST1 (entry sp|P52848|NDST1_HUMAN) in a multiple sequence alignment to determine if there are relationships between mutations among each of the enzymes. A period within the amino acid sequence of an engineered enzyme indicates identity at a particular position with the human N-sulfotransferase domain. As shown in FIG. 9, the sequence alignment demonstrates that while over 90% of the amino acid residues within the six sulfotransferase sequences are identical, there are several positions in which multiple amino acids can be chosen. Without being limited by a particular theory, it is believed that these enzymes have a similar relationship with each other as the N-sulfotransferase domains of the natural NDST enzymes that comprise EC 2.8.2.8. As a result, and in another embodiment, engineered NST enzymes comprising an amino acid sequence in which multiple amino acids can be chosen at defined positions are disclosed as SEQ ID NO: 33 and SEQ ID NO: 34. Positions at which the identity of an amino acid can be chosen from a selection of possible residues are denoted in terms "Xaa," "Xn," or "position n," where n refers to the residue position.

In another embodiment, within an engineered NST enzyme comprising the amino acid sequence of SEQ ID NO: 33 or SEQ ID NO: 34, the amino acid residue at position 41 is lysine, the amino acid residue at position 44 is alanine, the amino acid residue at position 45 is an aromatic amino acid residue, preferably tyrosine or phenylalanine, and the amino acid residue at position 49 is histidine. In another embodiment, when the engineered NST enzyme comprises the above residues from positions 41-49, the amino acid residue at position 67 is glycine or histidine, the amino acid residue at position 68 is selected from the group consisting of glycine, histidine, and serine, and the amino acid residue at position 69 is serine.

In another embodiment, within an engineered NST enzyme comprising the amino acid sequence of SEQ ID NO: 33 or SEQ ID NO: 34, the amino acid residue at position 40 is histidine and the amino acid residue at position 45 is histidine. In further embodiments, the amino acid residue at position 41 is glycine and the amino acid residue at position 44 is glycine. In other further embodiments, the amino acid residue at position 41 is lysine and the amino acid residue at position 44 is valine. In even further embodiments, the amino acid residue at position 67 is glycine and the amino acid residue at position 69 is histidine. In still further embodiments, the amino acid residue at position 106 is tryptophan. In even still further embodiments, the amino acid residue at position 260 is valine.

In another embodiment, within an engineered NST enzyme comprising the amino acid sequence of SEQ ID NO: 33 or SEQ ID NO: 34, the amino acid sequence can optionally include one or more mutations at residue positions not specified by an "Xn" or "Xaa," so long as any such mutations do not eliminate the NST and/or aryl sulfate-dependent activity of the enzyme. In another embodiment, such mutations not eliminating aryl sulfate-dependent activity at positions not specified by an "Xn" or "Xaa" can include substitutions, deletions, and/or additions.

Accordingly, in another embodiment, an engineered NST enzyme utilized in accordance with any of the methods of the present invention can comprise an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40. In another embodiment, any of the above enzymes react with an aryl sulfate compound, instead of PAPS, as a sulfo group donor. In further embodiments, the aryl sulfate compound is selected from the group consisting of PNS, MUS, 7-hydroxycoumarin sulfate, phenyl sulfate, 4-acetylphenyl sulfate, indoxyl sulfate, 1-naphthyl sulfate, 2-naphthyl sulfate, and NCS. In some even further embodiments, the aryl sulfate compound is PNS. In other even further embodiments, the aryl sulfate compound is NCS.

Hexuronyl 2-O sulfotransferases

In nature, HS hexuronyl 2-O sulfotransferase (2OST) enzymes recognize, bind, and react with N-sulfated heparosan-based polysaccharides as sulfo group acceptors. As with the natural NDSTs described above, natural 2OSTs transfer the sulfo group to the polysaccharide upon reacting with PAPS as a sulfo group donor. However, natural 2OSTs are members of the EC 2.8.2.-enzyme class. Generally, a majority of the glucosaminyl residues within the heparosan-based polysaccharide are N-sulfated, and the sulfo group is transferred to the 2-O position of a hexuronic acid residue, generally either glucuronic acid or iduronic acid. A first non-limiting example of an N-sulfated heparosan that can bind and react with a natural or engineered 2OST is illustrated by the structure of Formula IV, below:

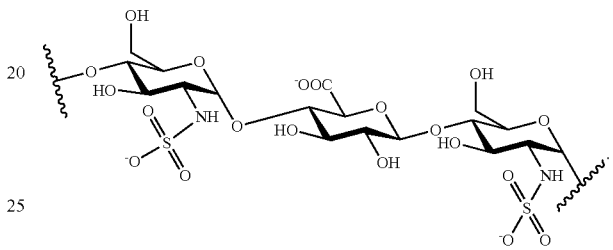

In another non-limiting example, an 2OST enzyme can recognize, bind, and react with heparosan-based polysaccharides having the structure of Formula V, below:

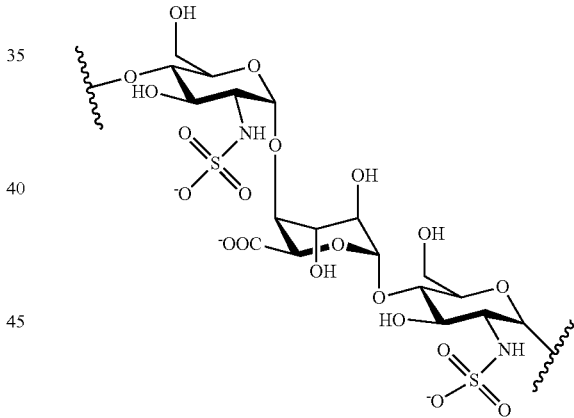

In both instances, the hexuronic acid residue (glucuronic acid in Formula IV, iduronic acid in Formula V) is flanked on either side by N-sulfated glucosamine residues that are otherwise unsubstituted at the 3-O and 6-O positions. Natural 2OST enzymes, and their biological activity with N-sulfated heparosan polysaccharides comprising the structures of Formula IV or Formula V, have been described by Rong, J., et al., (2001) *Biochemistry* 40 (18):5548-5555, the disclosure of which is incorporated by reference in its entirety.

As described above, although the portion of the polysaccharide that reacts with the enzyme comprises the structure of Formula IV or Formula V, other portions can be N- or O-substituted. Similarly, the heparosan-based polysaccharides can comprise both the structure of Formula IV and the structure of Formula V within the same polysaccharide, and either or both of the hexuronyl residues within the structure of Formula IV and Formula V polysaccharide can be sulfated by the same enzyme molecule. Typically, N-sulfated HS polysaccharides comprising the structure of Formula IV and/or Formula V can comprise at least eight monosaccharide residues. In some embodiments, the heparosan-based polysaccharide is only N-sulfated or N-acetylated, and is not 3-O or 6-O sulfated prior to reacting with the 2OST. In another embodiment, engineered 2OSTs that can be utilized in accordance with methods of the present invention have the same biological activity as natural 2OSTs with heparosan-based polysaccharides, particularly those comprising the structure of Formula IV and Formula V, as sulfo acceptors.

The identity of the hexuronic acid residue in N-sulfated heparosan comprising the structure of Formula IV or Formula V can be controlled by the presence of a hexuronyl $C_5$-epimerase, which reversibly inverts the stereochemistry of the $C_5$-carbon. However, once the hexuronyl residue within a polysaccharide comprising the structure of Formula IV or Formula V is 2-O sulfated, epimerization can no longer occur. In eukaryotic systems, the N-sulfated heparosan products of NDST are almost exclusively formed as disaccharide units of N-sulfoglucosamine and glucuronic acid. Consequently, the glucuronic acid residue must be epimerized to an iduronic acid residue to from the structures of Formula V prior to reacting with the 2OST enzyme. However, and without being limited by a particular theory, it is believed that natural 2OST enzymes generally have preference for binding and reacting with heparosan-based polysaccharides comprising the structure of Formula V, and that most N-, 2-O sulfated HS (N,2-HS) polysaccharides produced in vivo generally comprise 2-O sulfated iduronic acid.

Upon successfully binding PAPS and N-sulfated heparosan comprising the structure of Formula IV, natural 2OST enzymes can catalyze transfer of the sulfo group to the 2-O position of the glucuronic acid residue, forming an N,2-HS product comprising the structure of Formula VI, below:

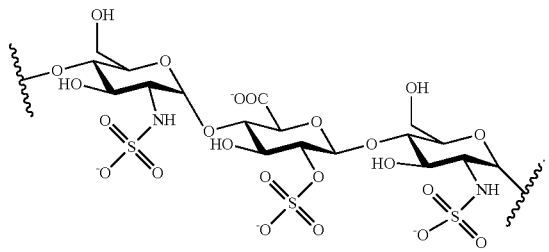

Similarly, engineered 2OST enzymes that successfully bind and react with an aryl sulfate compound and an N-sulfated heparosan comprising the structure of Formula IV can also form an N,2-HS product comprising the structure of Formula VI. Upon successfully binding PAPS and N-sulfated heparosan comprising the structure of Formula V, natural 2OST enzymes can catalyze transfer of the sulfo group to the 2-O position of the iduronic acid residue, forming an N,2-HS product comprising the structure of Formula VII, below:

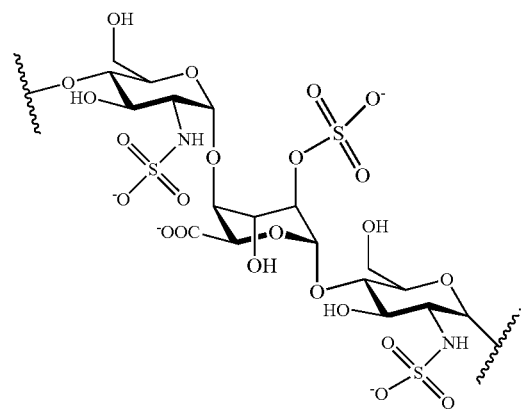

Similarly, engineered 2OST enzymes that successfully bind and react with an aryl sulfate compound and an N-sulfated heparosan comprising the structure of Formula V can also form an N,2-HS product comprising the structure of Formula VII.

Figure 10:
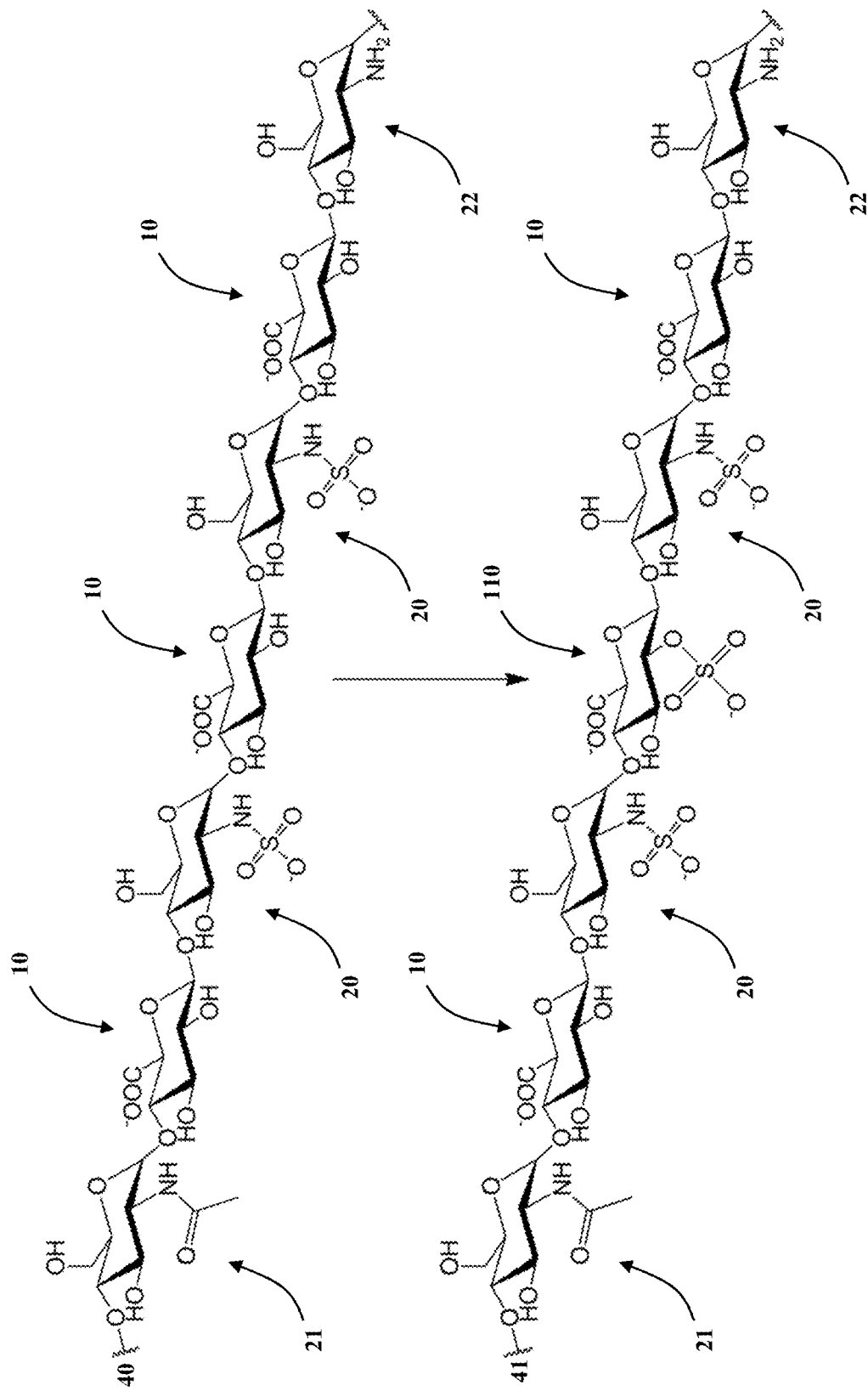
FIG. 10 shows the 2-O sulfation of one non-limiting example of an N-sulfated heparosan polysaccharide, catalyzed by either a natural or engineered 2OST enzyme in accordance with methods of the present invention, wherein the polysaccharide comprises N-sulfated, N-acetylated, and unsubstituted glucosaminyl residues.

In another embodiment, in other locations within the N-sulfated sulfo acceptor polysaccharide, some of the glucosaminyl residues can be N-substituted with a sulfo group, an acetyl group, or a hydrogen, although hexuronyl residues within the polymer must reside between two N-sulfoglucosamine residues, as described above, in order to receive a sulfo group. A non-limiting example of one such polysaccharide is illustrated in FIG. 10. In FIG. 10, hexuronyl residues 10 within polysaccharide 40 are flanked by glucosaminyl residues 20, 21, and 22, that are either N-sulfated, N-acetylated, or unsubstituted, respectively. Upon reacting the polysaccharide with either a natural or engineered 2OST, only the hexuronyl residue 10 flanked by two N-sulfoglucosaminyl residues 20 is sulfated, ultimately forming a sulfated hexuronyl residue 110 within the product polysaccharide 41.

Figure 11:
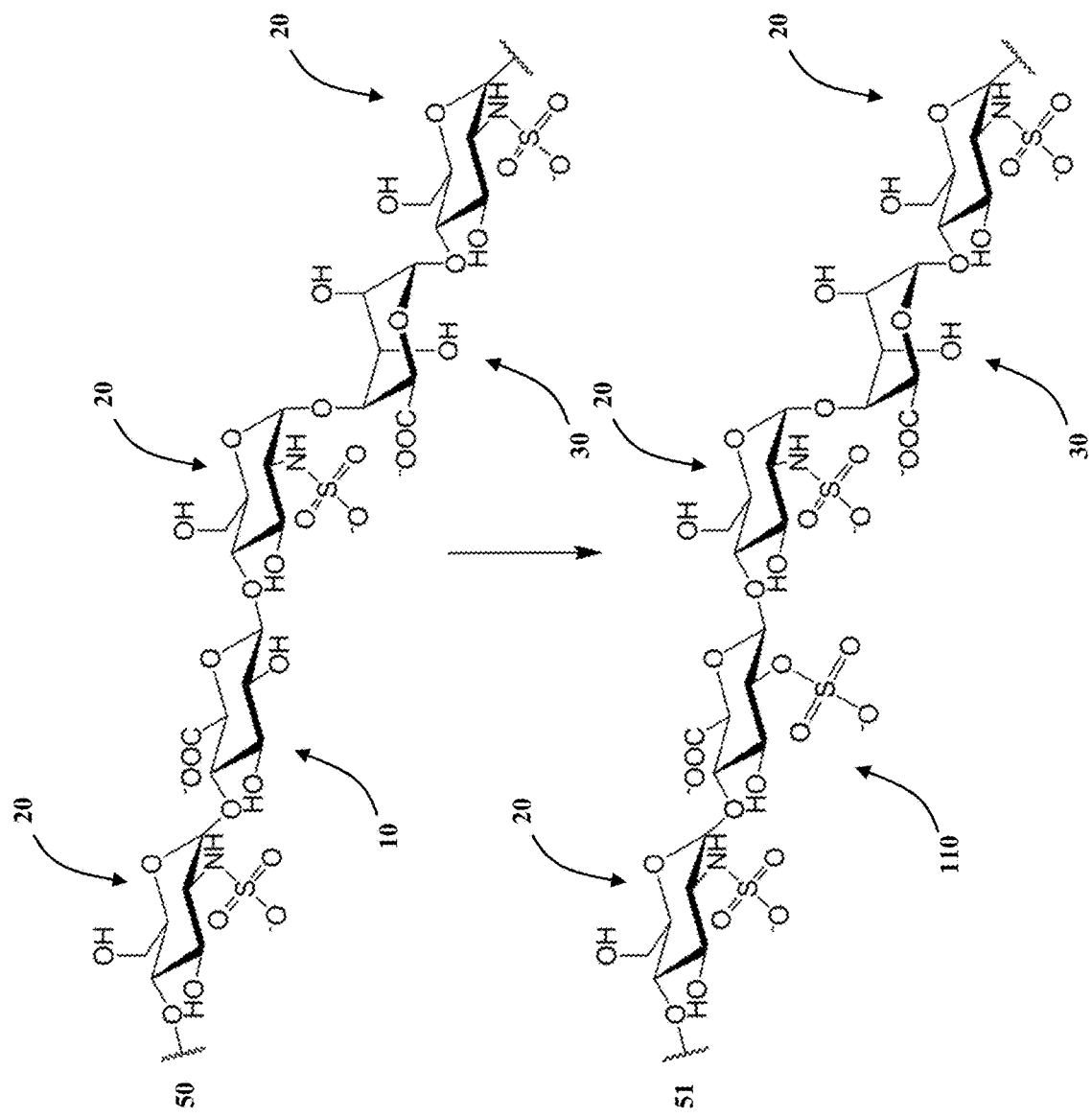
FIG. 11 shows the 2-O sulfation of a glucuronic acid residue within another non-limiting example of an N-sulfated heparosan polysaccharide, catalyzed by either a natural or engineered 2OST enzyme in accordance with methods of the present invention.
Figure 12:
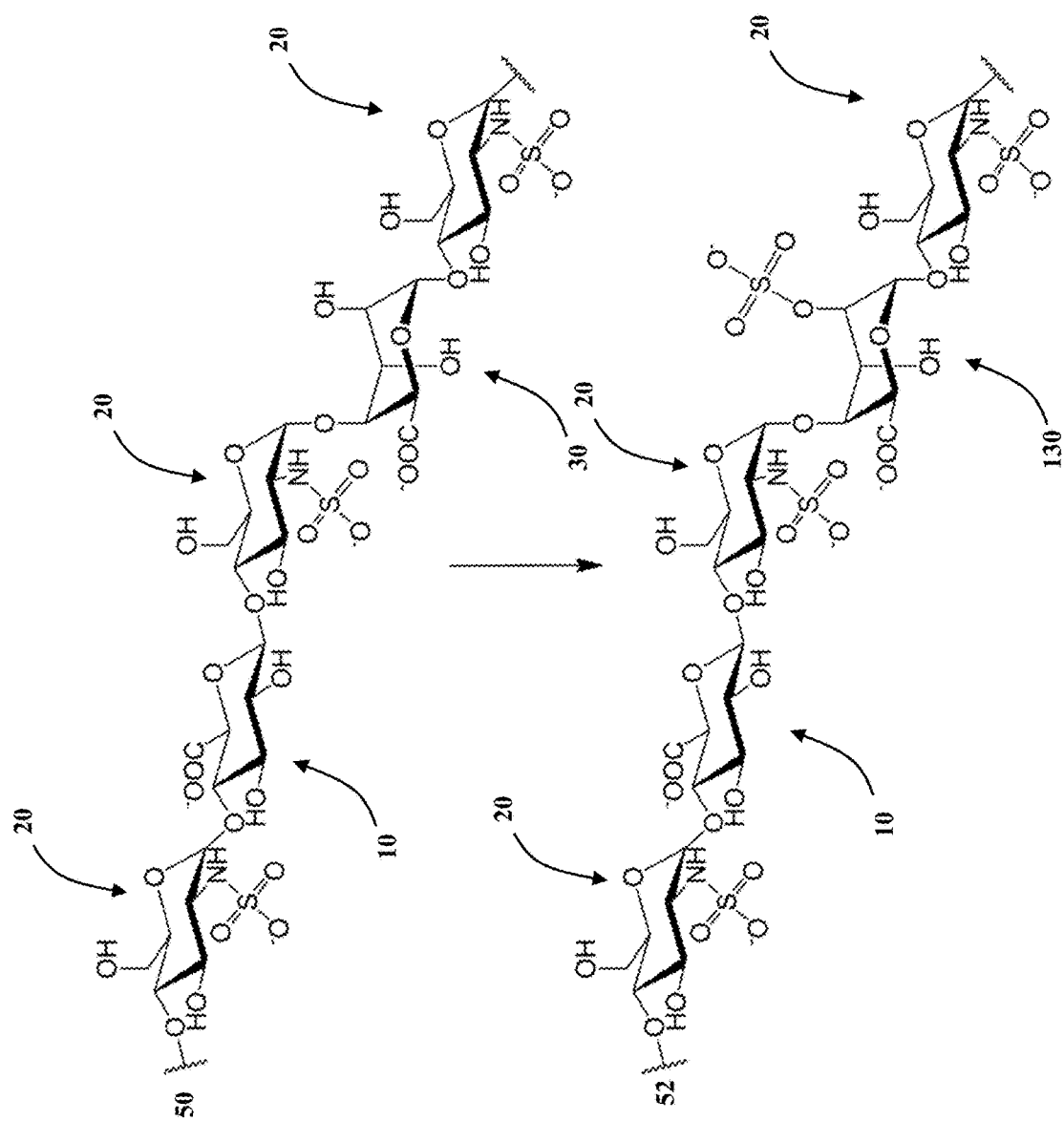
FIG. 12 shows the 2-O sulfation of an iduronic acid residue within the N-sulfated heparosan polysaccharide shown in FIG. 11, catalyzed by either a natural or engineered 2OST enzyme in accordance with methods of the present invention.
Figure 13:
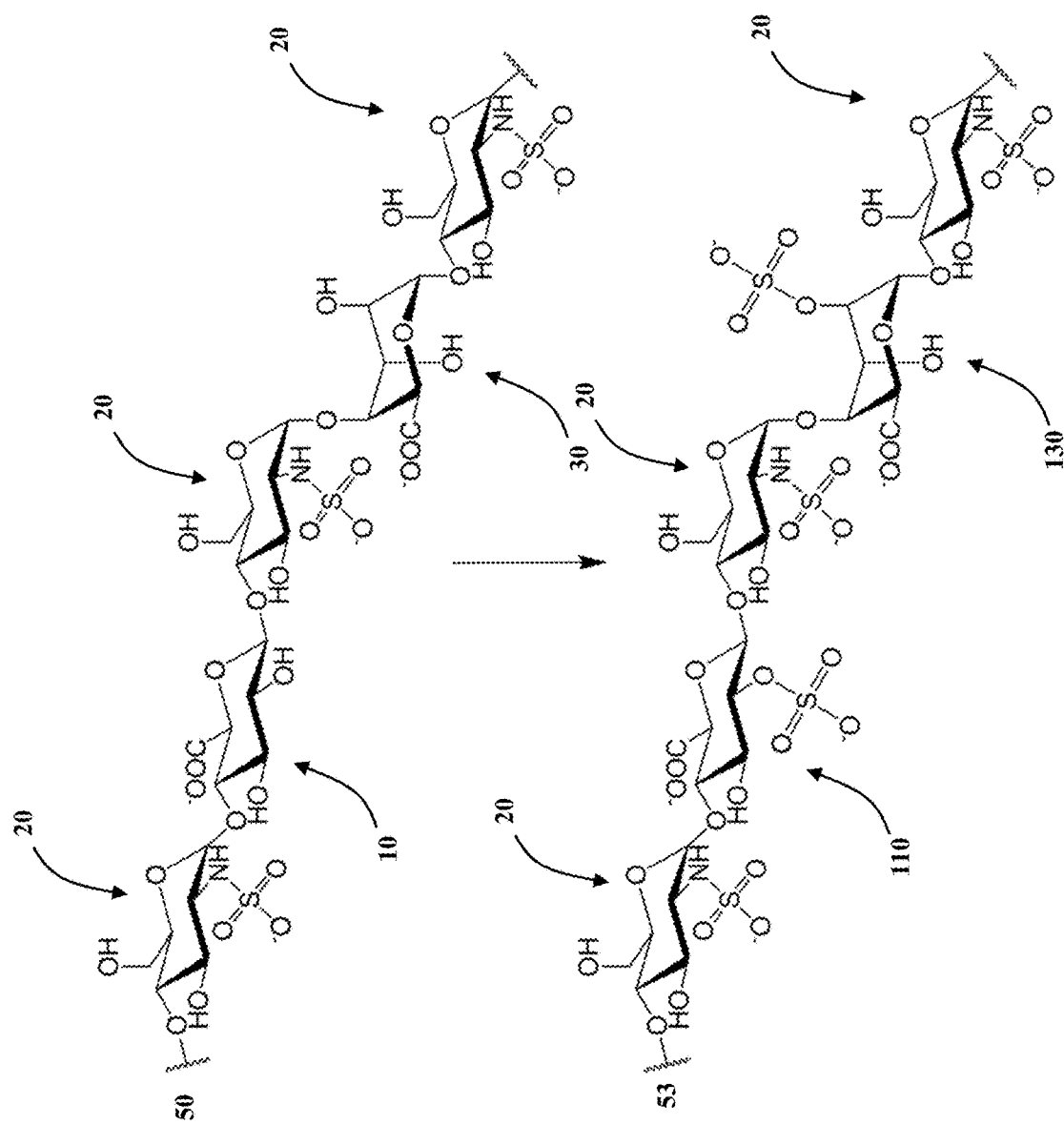
FIG. 13 shows the 2-O sulfation of a glucuronic acid residue and an iduronic acid residue within the N-sulfated heparosan polysaccharide shown in FIG. 11, catalyzed by either a natural or engineered 2OST enzyme in accordance with methods of the present invention.
Figure 14A:
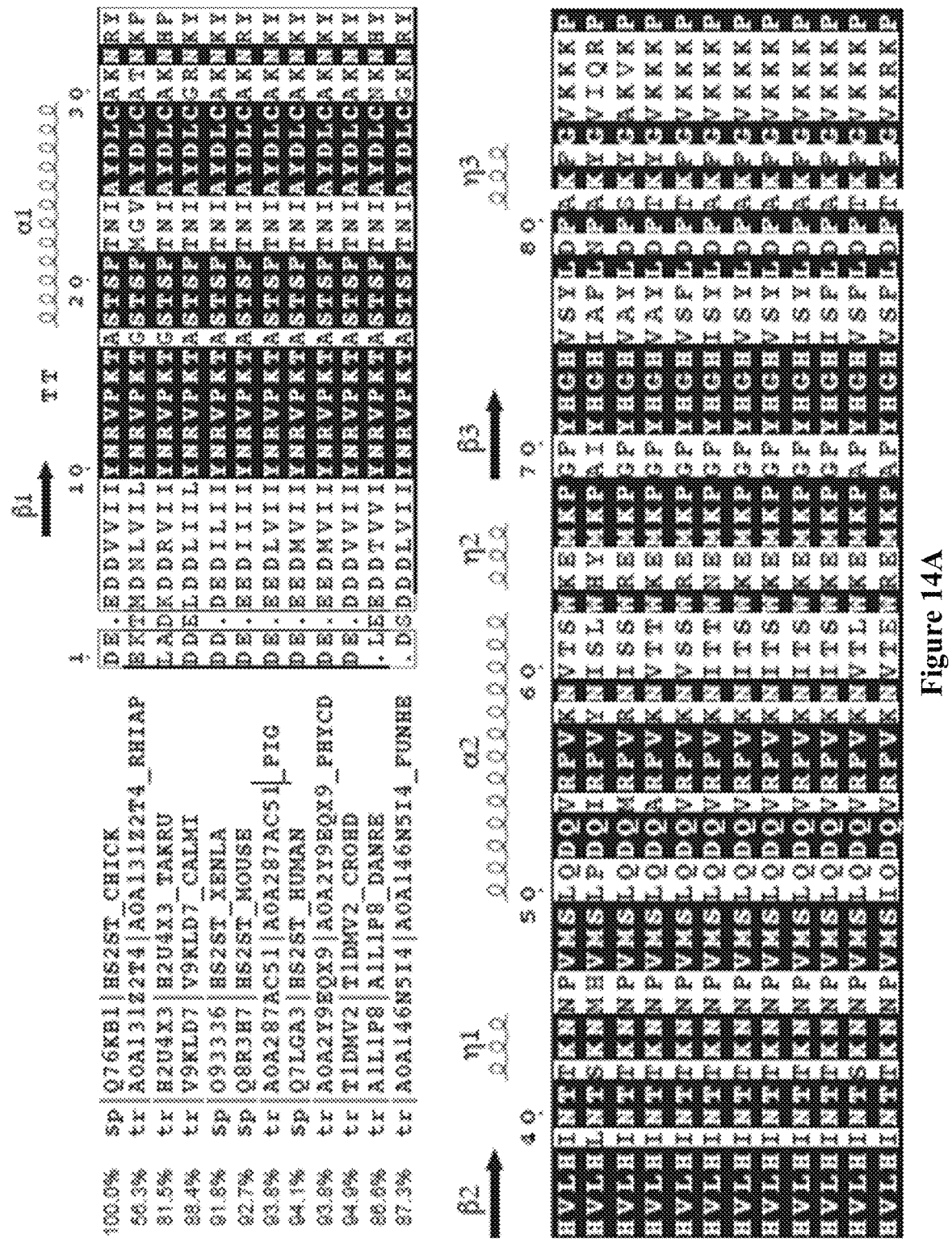
FIGS. 14A-14D show a multiple sequence alignment for twelve natural 2OST enzymes within EC 2.8.2.-, illustrating conserved amino acid sequence motifs that are present regardless of overall sequence identity.
Figure 14B:
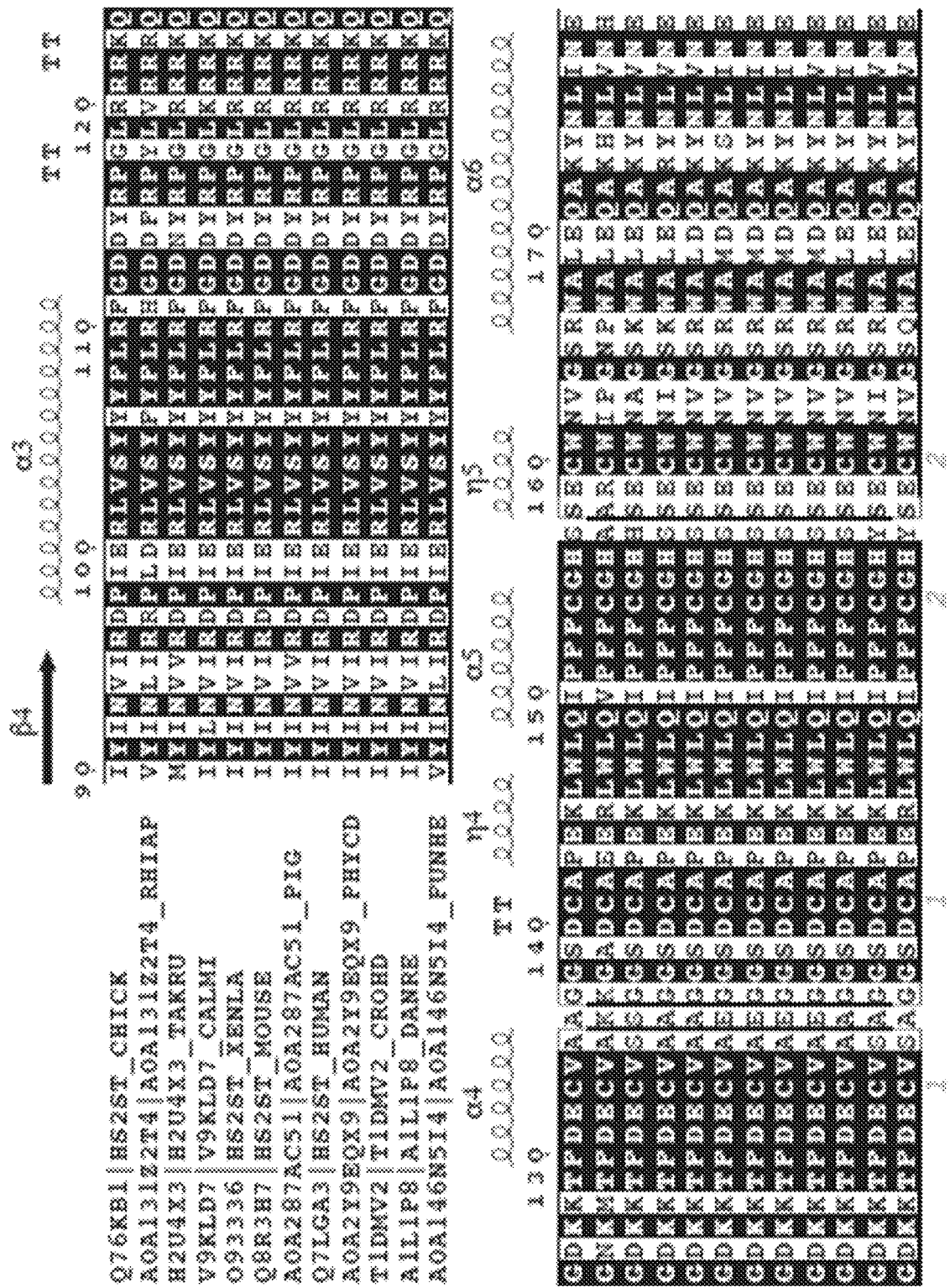
Figure 14C:
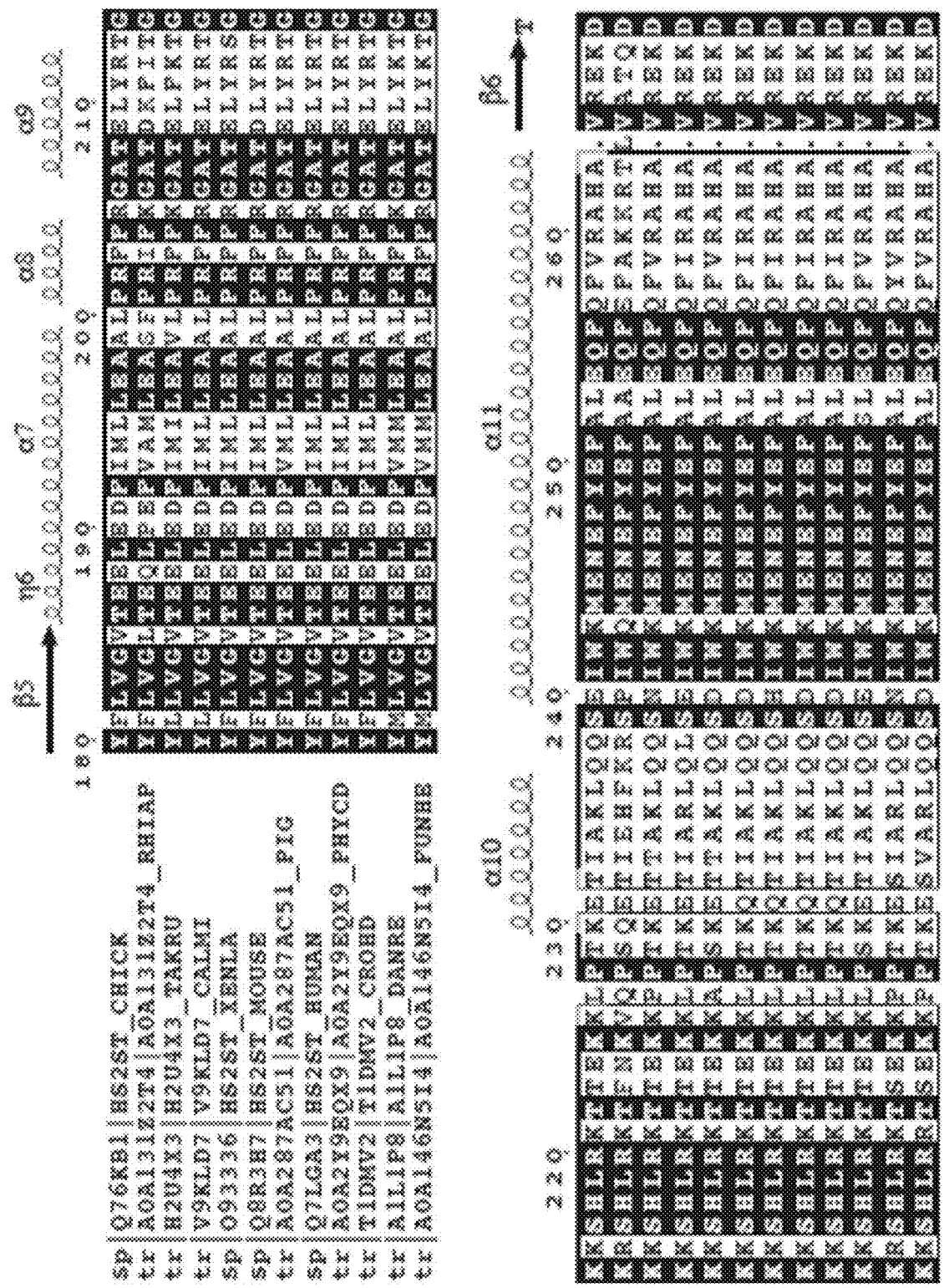
Figure 14D:
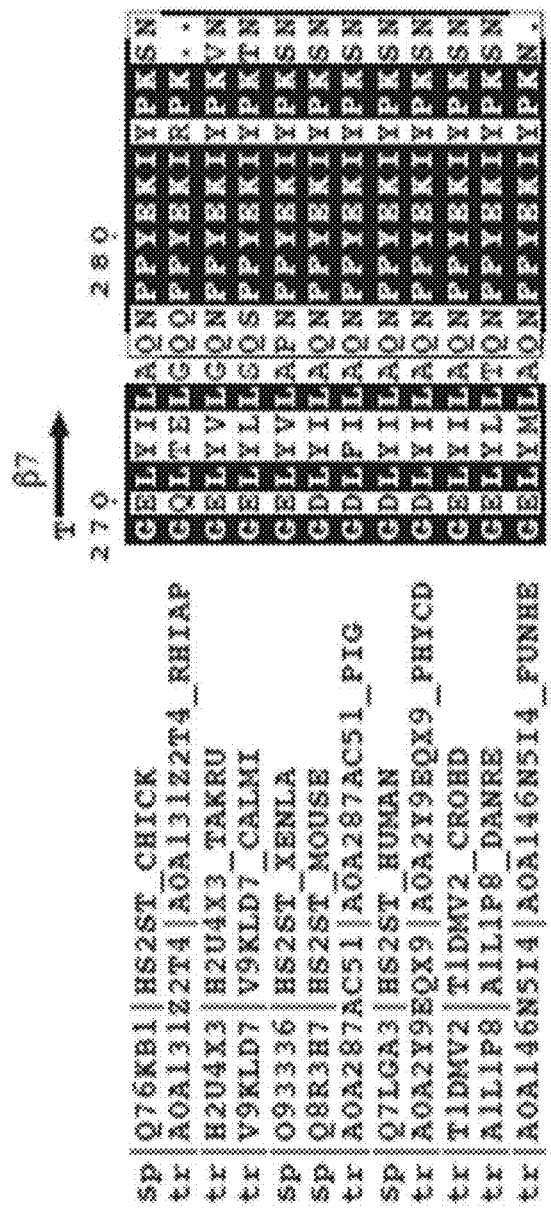

In another non-limiting example, sulfo acceptor polysaccharides comprising the structures of Formula IV and Formula V are illustrated by polysaccharide 50 in FIG. 11, FIG. 12, and FIG. 13. Additional monosaccharide residues required for catalysis are omitted for clarity. In FIG. 11, FIG. 12, and FIG. 13, a hexuronyl residue 10 and an epimerized hexuronyl residue 30 reside between the three N-sulfoglucosaminyl residues 20 within polysaccharide 50. Although hexuronyl residues 10 and 30 are represented in a chair conformation, those skilled in the art can appreciate that such monosaccharide residues within a longer oligo- or polysaccharide chain can adopt several different conformations, including chair, half-chair, boat, skew, and skew boat conformations, and that those additional conformations are omitted for clarity.

Upon reacting polysaccharide 50 with any of the engineered aryl sulfate-dependent 2OST enzymes that can be utilized with methods of the present invention, the enzyme can catalyze sulfo group transfer to hexuronyl residue 10 to form a sulfated hexuronyl residue 110 within product polysaccharide 51 (FIG. 11), to epimerized hexuronyl residue 30 to form a sulfated epimerized hexuronyl residue 130 within product polysaccharide 52 (FIG. 12), or to both hexuronyl residue 10 and epimerized hexuronyl residue 30 to form a sulfated hexuronyl residue 110 and a sulfated epimerized hexuronyl residue 130, respectively, within product polysaccharide 53 (FIG. 13).

In another embodiment, polysaccharides comprising the structure of Formula IV and/or Formula V can be provided as a homogenous composition. In still other embodiments, polysaccharides comprising the structure of Formula IV and/or Formula V can be comprised within a composition comprising a polydisperse mixture of polysaccharides having variable chain lengths, molecular weights, relative abundance of Formula IV and/or Formula V, and overall monosaccharide composition and functionalization.

In some embodiments, polysaccharides comprising the structure of Formula IV and/or Formula V and utilized in accordance with methods of the present invention can be obtained and/or modified from commercial sources. In other embodiments, polysaccharides comprising the structure of Formula IV and/or Formula V can be obtained by enzymatically or chemically N-sulfating polysaccharides isolated and modified from bacterial or eukaryotic sources. In still other embodiments, polysaccharides comprising the structure of Formula IV and/or Formula V can be obtained by isolating and purifying the sulfated polysaccharide products of any of the other engineered aryl sulfate-dependent sulfotransferases utilized in conjunction with methods of the present invention. Each of these processes are discussed in detail in the description and examples, below.

Natural 2OSTs within the EC 2.8.2.-enzyme class generally comprise approximately 325-375 amino acid residues that in some cases vary greatly in their sequence, yet ultimately have the exact same function, namely, to catalyze the transfer of a sulfo group from PAPS to the 2-O position of hexuronyl residues within heparosan-based polysaccharides, particularly those comprising the structure of Formula IV and/or Formula V. Without being limited by a particular theory, it is believed that each of the natural 2OSTs can catalyze the same chemical reaction because there are multiple amino acid sequence motifs and secondary structures that are either identical or highly conserved across all species.

Further, it is believed that several of the conserved amino acid sequence motifs are directly involved in binding of either PAPS and/or the polysaccharide, or participate in the chemical reaction itself. The identity between the natural 2OST enzymes can be demonstrated by comparing the amino acid sequence of enzymes with a known crystal structure (e.g. chicken 2-O sulfotransferase, PDB codes: 3F5F and 4NDZ), in which amino acid residues within the active site have been identified, with the amino acid sequences of other 2OSTs within the EC 2.8.2.-enzyme class. A multiple sequence alignment of twelve enzymes, including the chicken, human, and other 2OST enzymes, is shown in FIGS. 14A-14D, along with percent identity relative to the chicken 2OST reference sequence (UniProtKB Accession No. Q76KB1). As illustrated in FIGS. 14A-14D, sequences range from having 94.9% sequence identity with the Q76KB1 reference sequence (entry tr|T1DMV2|TDMV2_CROHD) for the timber rattlesnake 2OST, down to 56.3% sequence identity (entry tr|A0A131Z2T4|A0A131Z2T4_RHIAP) for the brown ear tick 2OST. The human enzyme (entry sp|Q7LGA3|HS2ST_HUMAN) has 94.1% sequence identity with the Q76KB1 reference sequence. Those skilled in the art would appreciate that the multiple sequence alignment was limited to twelve sequences for clarity, and that there are hundreds of amino acid sequences encoding for natural 2OST enzymes that have been identified and that have highly conserved active site and/or binding regions as well.

Within FIGS. 14A-14D, amino acids that are depicted in white with a black background at a particular position, are 100% identical across all sequences. Amino acids that are highly conserved, meaning that the amino acids are either identical, or chemically or structurally similar, at a particular position are enclosed with a black outline. Within highly conserved regions, consensus amino acids that are present in a majority of the sequences are in bold. Amino acids at a particular position that are not identical or highly conserved are typically variable. A period within a sequence indicates a gap that has been inserted into the sequence in order to facilitate the sequence alignment with other sequence(s) that have additional residues between highly conserved or identical region. Finally, above each block of sequences are a series of arrows and coils that indicate secondary structure that is conserved across all sequences, based on the identity of the amino acids within the alignment and using the structure of the natural chicken 2OST enzyme as a reference. The β symbol adjacent to an arrow refers to a β-sheet, whereas a coil adjacent to an α symbol or a η symbol refers to a helix secondary structure.

Figure 15A:
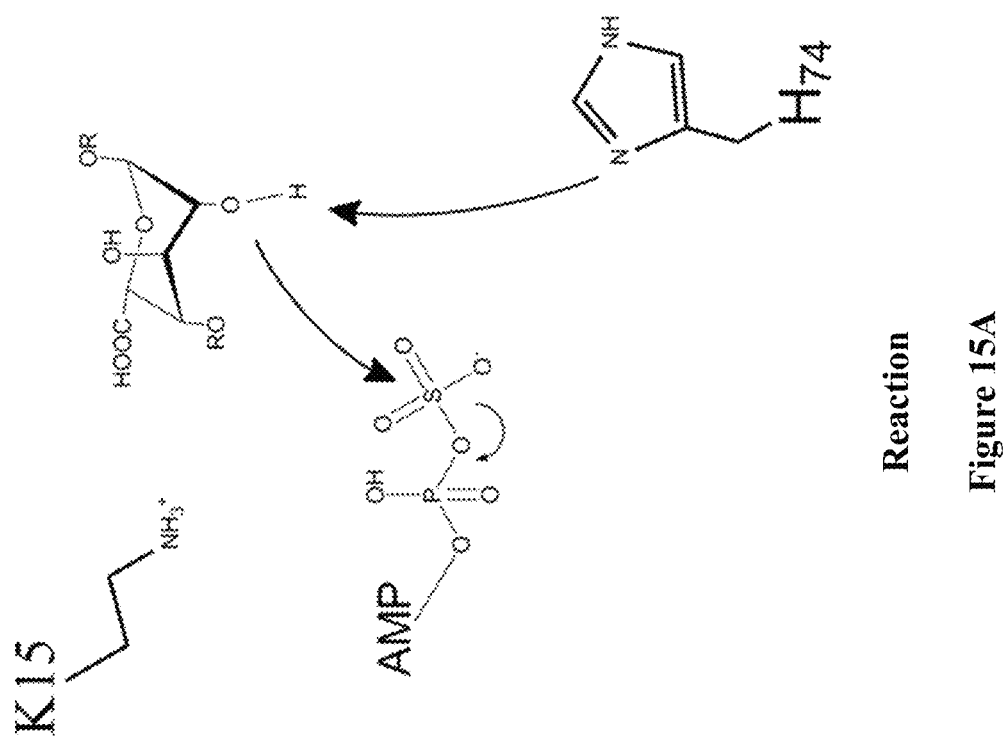
FIGS. 15A-15C show a reaction mechanism between conserved residues within a natural 2OST enzyme, PAPS, and a hexuronic acid residue within N-sulfated heparosan.
Figure 15B:
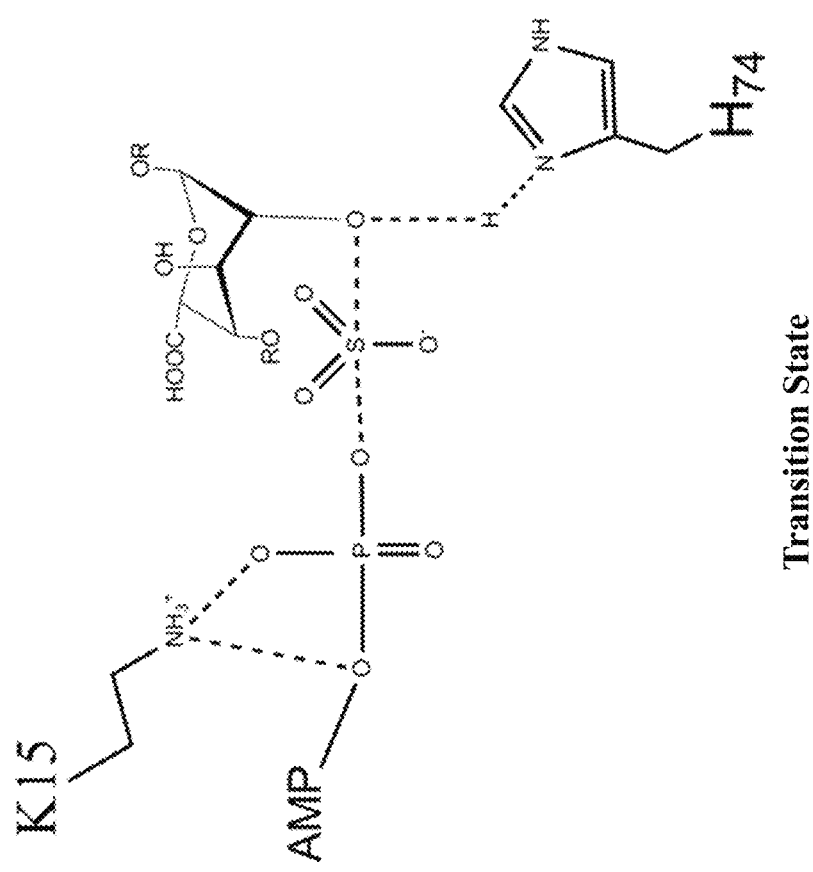
Figure 15C:
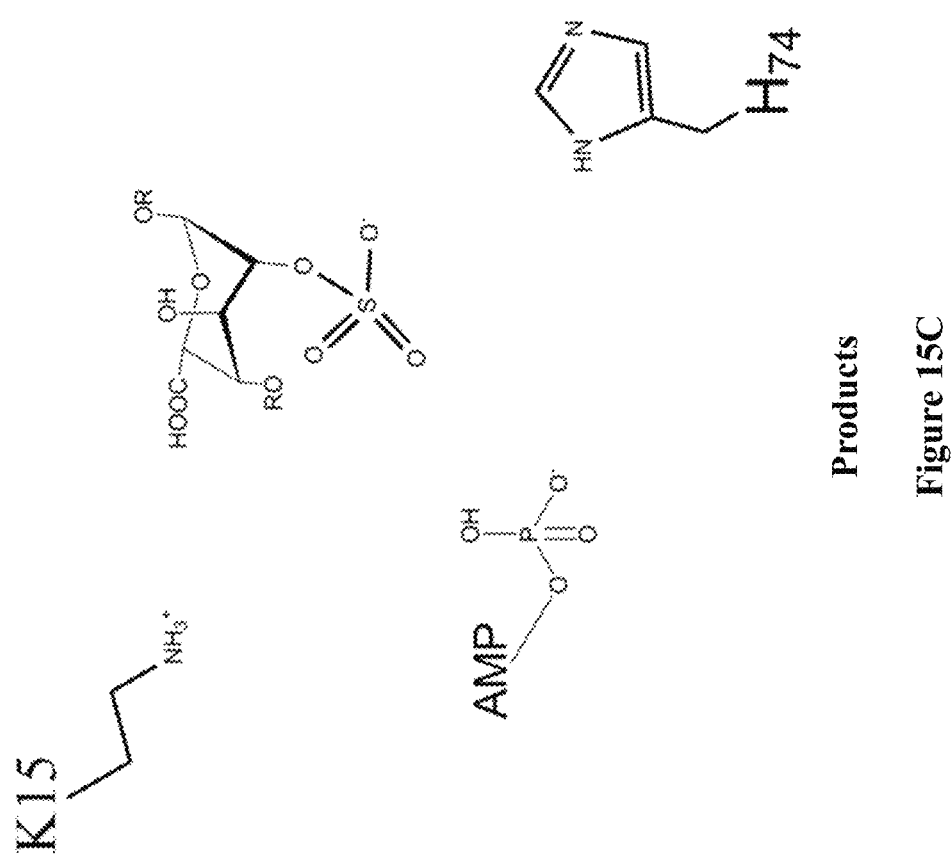

Within the twelve aligned sequences in FIGS. 14A-14D, there are several conserved amino acid motifs that include one or more amino acids that comprise the active site, based on the crystal structures of the chicken 2OST enzyme described above. Based on the numbering of the amino acid residues within FIGS. 14A-14D, these motifs include residues 12-19 (R-V-P-K-T-A/G-S-T), residues 40-44 (N-T-S/T-K-N), residues 71-74 (Y-H-G-H), residues 108-115 (F-L-R-F/H-G-D-D/N-F/Y), residues 121-125 (R-R-K/R-Q-G), and residues 217-222 (S-H-L-R-K/R-T). Without being limited by a particular theory, it is believed that these residues either facilitate or participate in the chemical reaction, or enable binding of PAPS or the polysaccharide within the active site. In particular and as illustrated in FIGS. 15A-15C, the histidine residue at position 74 abstracts the proton from the 2-O position of the iduronic acid residue within the polysaccharide, enabling nucleophilic attack and removal of the sulfo group from PAPS, whereas the lysine residue at position 15 coordinates with the phosphate moiety of PAPS to stabilize the transition state of the enzyme before the N,2-HS product is released from the active site.

However, as described above, the natural 2OST enzymes are unable to catalyze the transfer of the sulfate group from an aryl sulfate compound to the polysaccharide. As with the NDSTs, it is believed that the binding pocket for PAPS within the active site of the natural sulfotransferase either does not have a high enough affinity for aryl sulfate compounds to facilitate binding and/or that the aryl sulfate compounds are sterically hindered from entering the active site. Consequently, and in another embodiment, a natural 2OST enzyme can be mutated in several locations within its amino acid sequence to enable binding of the aryl sulfate compound within the active site and/or to optimally position the aryl sulfate compound so transfer of the sulfate group to the polysaccharide can occur.

Accordingly, and in another embodiment, engineered 2OST enzymes that can be utilized with methods of the present invention can be mutants of natural 2OST enzymes within EC 2.8.2.-, including enzymes having the amino acid sequences illustrated in FIGS. 14A-14D. In another embodiment, the aryl sulfate-dependent, 2OSTs have been engineered to recognize, bind, and react with aryl sulfate compounds as sulfo group donors, while retaining the natural enzymes' ability to recognize, bind, and react with N-sulfated, heparosan-based polysaccharides, particularly those comprising the structure of Formula IV and/or Formula V, as sulfo group acceptors. Without being limited by a particular theory, it is believed that because of the mutations inserted into the amino acid sequences of the engineered 2OST enzymes, their sulfotransferase activity may comprise the direct transfer of a sulfuryl group from an aryl sulfate compound to the sulfo acceptor polysaccharide, using a similar mechanism as described in FIGS. 15A-15C above, except that the PAPS is substituted with the aryl sulfate compound. Otherwise, it is believed that the mutations may cause the sulfotransferase activity to comprise a two-step process including the hydrolysis of an aryl sulfate compound and formation of a sulfohistidine intermediate, followed by the nucleophilic attack of the sulfohistidine intermediate by the oxygen atom at the 2-O position of a hexuronic acid residue, to form the N,2-HS product. By either mechanism, engineered 2OST enzymes achieve sulfo transfer from an aryl sulfate compound to a polysaccharide, as described in the examples, below.

In another embodiment, an engineered 2OST enzyme can comprise one or more mutated amino acid sequence motifs relative to the conserved amino acid sequence motifs described above that are found in the natural 2OST enzymes within EC 2.8.2.-, as described above and indicated in the multiple sequence alignment in FIGS. 14A-14D. In another embodiment, each mutated amino acid sequence motif that is present in the amino acid sequence of the engineered enzyme comprises at least one amino acid mutation relative to the corresponding conserved amino acid sequence motif within the natural 2OST enzymes. In another embodiment, an engineered 2OST enzyme can comprise one mutated amino acid sequence motif. In another embodiment, an engineered 2OST enzyme can comprise two mutated amino acid sequence motifs. In another embodiment, an engineered 2OST enzyme can comprise three mutated amino acid sequence motifs. In another embodiment, an engineered 2OST enzyme can comprise four mutated amino acid sequence motifs. In another embodiment, an engineered 2OST enzyme can comprise five mutated amino acid sequence motifs. In another embodiment, an engineered 2OST enzyme can comprise six mutated amino acid sequence motifs. In another embodiment, an engineered 2OST enzyme that includes at least one mutated amino acid sequence motif relative to any of the natural 2OST enzymes within EC 2.8.2.-can have an amino acid sequence selected from the group consisting of SEQ ID NO: 14, SEQ ID NO: 16, SEQ ID NO: 41, and SEQ ID NO: 42.

Figure 16:
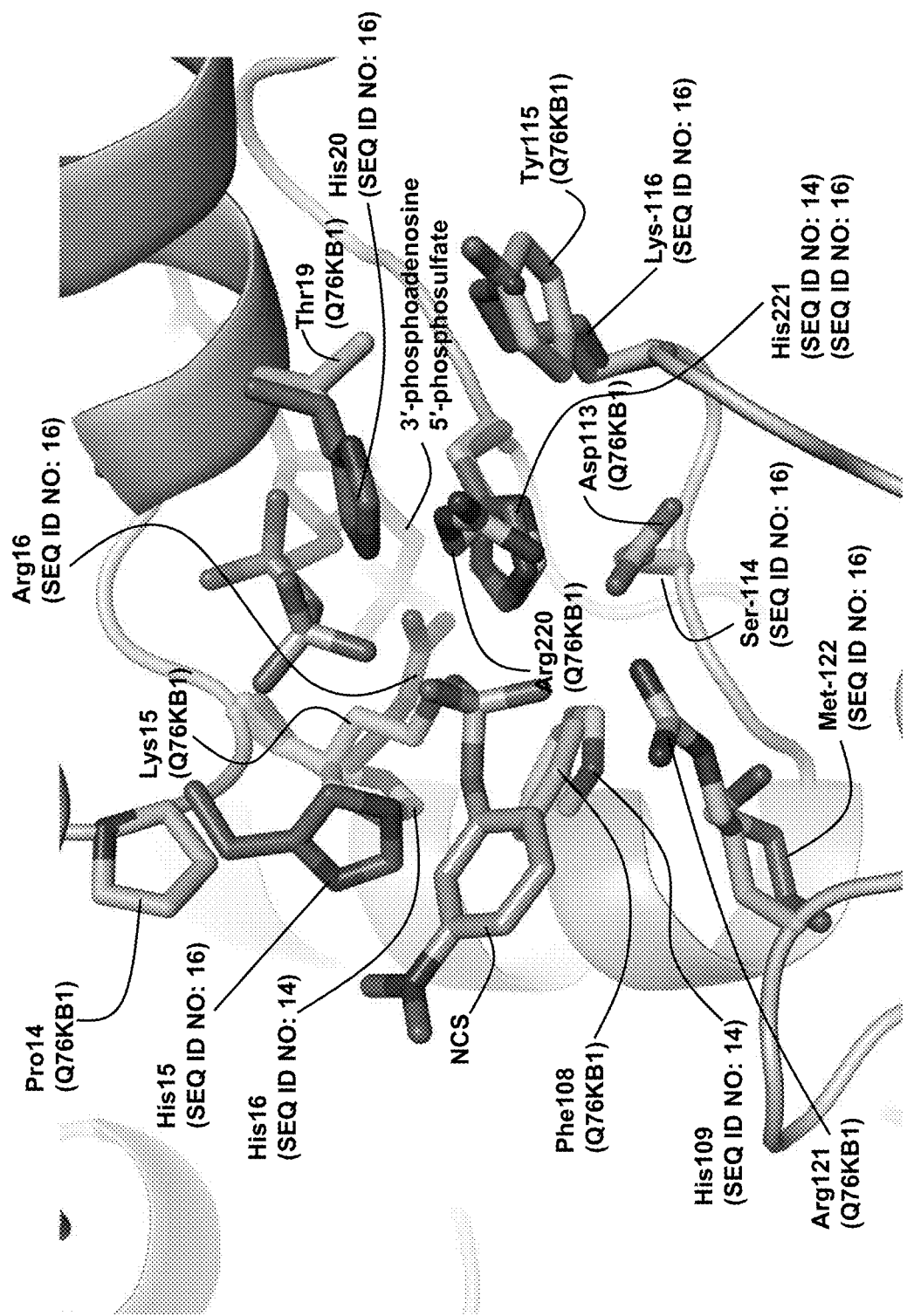
FIG. 16 shows a three-dimensional model of an aryl sulfate compound bound within the active site of an engineered 2OST enzyme, superimposed over the crystal structure of PAPS bound within the active site of the chicken 2OST enzyme.

In another embodiment, upon viewing the crystal structure of the chicken 2OST (PDB code: 3F5F) within a 3D molecular visualization system (including, as a non-limiting example, the open-source software, PyMOL), the structure of related sequences, such as those of engineered 2OST enzymes that contain one or more mutated amino acid sequence motifs relative to the chicken sulfotransferase structure, can be modeled for comparison as illustrated in FIG. 16. FIG. 16 shows a magnified view of the active site of the chicken 2OST enzyme overlaid with two engineered 2OST enzymes, comprising the amino acid sequences of SEQ ID NO: 14 and SEQ ID NO: 16, in which the structure of the engineered enzyme is calculated upon making mutations relative to the chicken 2OST amino acid sequence. Adenosine 3',5'-diphosphate, which is the product of a sulfotransfer reaction in which PAPS is the sulfo donor, and which was co-crystallized with the chicken 2OST, is also illustrated within the active site. The sulfate group that would be present in the natural substrate, PAPS, is modeled onto the 5'-phosphate functional group to illustrate its approximate position within the active site prior to initiating the reaction. NCS is also modeled into the active site of the engineered enzymes, using the consensus solutions of molecular dynamics (MD) simulations that designed to calculate the optimized position and orientation of a ligand within an enzyme active site adjacent to the polysaccharide binding site (not shown), if such solutions are possible. Hydrogen atoms are not shown.

As illustrated in FIG. 16, although there are several mutations made to SEQ ID NO: 14 and SEQ ID NO: 16, relative to the chicken 2OST, the respective protein backbones are in a nearly identical location to one another, enabling a one-to-one comparison of the active sites. When comparing the two active sites, the PAPS is located in the background and adjacent to a lysine residue (position 15 of the Q76KB1 sequence in FIGS. 14A-14D), whereas the convergent solutions from the above MD simulations indicate that NCS binding within the engineered enzymes is favored on the opposite side of the active site. However, binding of NCS would be sterically hindered in the natural enzyme in part by the lysine residue as well as the phenylalanine residue located on the nearby α-helix (position 108 of the Q76KB1 sequence in FIGS. 14A-14D). Without being limited by a particular theory, it is believed that binding of NCS in the active site of the engineered enzyme comprising the amino acid sequence of SEQ ID NO: 14 is facilitated by the mutation of the lysine residue to a histidine residue, which creates additional space within the active site and provides a π-π stacking partner for the aromatic ring within NCS. Also without being limited by a particular theory, it is believed that binding of NCS in the active site of the engineered enzyme comprising the amino acid sequence of SEQ ID NO: 16 is facilitated by the mutation of the lysine to an arginine residue in concert with the adjacent mutation of the proline residue (position 14 of the Q76KB1 sequence in FIGS. 14A-14D) to a histidine residue. The increased number of conformational degrees of freedom of the arginine side chain facilitate entry of the NCS while still being in a position to provide a polar contact to stabilize the transition state during the transfer reaction, whereas the adjacent histidine provides other binding contacts for NCS.

Another mutation of note includes the mutation from an arginine residue (position 220 of the Q76KB1 sequence in FIGS. 14A-14D) to a histidine residue, a mutation that is found at position 221 in both SEQ ID NO: 14 and SEQ ID NO: 16. Without being limited by a particular theory, the mutated histidine residue is in a favorable position to facilitate removal of the sulfate group from NCS. Other illustrated mutations from the chicken 2OST enzyme, particularly mutations present in SEQ ID NO: 16 (His-20, Ser-114, Lys-116, Met-122) may similarly drive binding of NCS within the active site, either by providing a direct binding contact with the sulfate moiety within NCS (His-20), coordinating with other mutated residues (Ser-114 coordinating with His-221), or by increasing the hydrophobic environment near NCS (Met-122).

Those skilled in the art would appreciate that engineered 2OST enzymes of any other amino acid sequence, including, but not limited to, those disclosed by SEQ ID NO: 41 and SEQ ID NO: 42, would likely exhibit a similar structure to the chicken 2OST, as well as engineered 2OSTs having the amino acid sequence of SEQ ID NO: 14 and SEQ ID NO: 16. Without being limited by a particular theory, it is believed that PNS would bind in a similar position as NCS within the active site of any of the engineered 2OST enzymes, since the structures of the two aryl sulfate compounds are very similar, except that the sulfate group is located ortho on the aromatic ring relative to the nitro group in NCS, rather than para to the nitro group in PNS.

Accordingly, in another embodiment, an engineered 2OST enzyme utilized in accordance with any of the methods of the present invention can comprise an amino acid sequence selected from the group consisting of SEQ ID NO: 14, SEQ ID NO: 16, SEQ ID NO: 41, or SEQ ID NO: 42. In another embodiment, any of the above 2OST enzymes react with an aryl sulfate compound, instead of PAPS, as a sulfo group donor. In further embodiments, the aryl sulfate compound is selected from the group consisting of PNS, MUS, 7-hydroxycoumarin sulfate, phenyl sulfate, 4-acetylphenyl sulfate, indoxyl sulfate, 1-naphthyl sulfate, 2-naphthyl sulfate, and NCS. In some even further embodiments, the aryl sulfate compound is PNS. In other even further embodiments, the aryl sulfate compound is NCS.

In another embodiment, within reaction mixtures that comprise any natural or engineered 2OST enzyme, particularly an engineered 2OST enzyme comprising the amino acid sequence of SEQ ID NO: 14, SEQ ID NO: 16, SEQ ID NO: 41, or SEQ ID NO: 42, the reaction mixture can further comprise an hexuronyl $C_5$-epimerase to catalyze formation of an N,2-HS product. In some embodiments, the N,2-HS product can comprise the structure of Formula VI. In other embodiments, the N,2-HS product can comprise the structure of Formula VII. In another embodiment, any isolated or recombinant hexuronyl $C_5$-epimerase can be used. In another embodiment, the hexuronyl $C_5$-epimerase can comprise the amino acid sequence of SEQ ID NO: 29. In another embodiment, the hexuronyl $C_5$-epimerase can comprise residues 34-617 of SEQ ID NO: 29.

Glucosaminyl 6-O Sulfotransferases

In nature, 6OSTs recognize, bind, and react with heparosan-based polysaccharides as sulfo group acceptors. Generally, a majority of the glucosaminyl residues are N-sulfated, but the enzymes can still transfer sulfo groups to the 6-O position of glucosaminyl residues that are N-acetylated. Additionally, either adjacent hexuronic acid residue can be either glucuronic acid or iduronic acid, and can optionally be 2-O sulfated. Generally, the hexuronic acid at the non-reducing end of the glucosamine residue receiving the 6-O sulfo group is 2-O sulfated iduronic acid, and in many instances, the glucosamine residue itself is also N-sulfated. Similar to the NSTs and 2OSTs, naturally-occurring 6OST enzymes transfer the sulfo group to the polysaccharide upon reacting with PAPS as a sulfo group donor. As with natural 2OSTs, natural 6OST enzymes are also members of the EC 2.8.2.-enzyme class. In a non-limiting example, either natural or engineered 6OST enzymes can recognize, bind, and react with heparosan-based polysaccharides comprising the structure of Formula VIII, below:

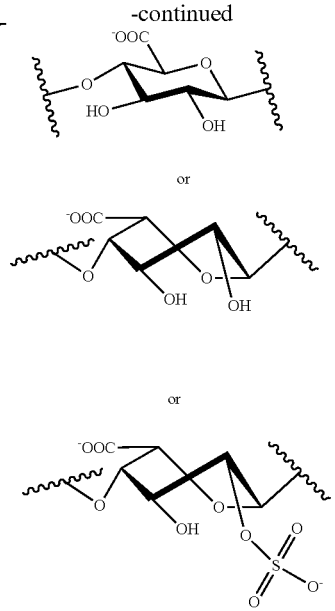

wherein the glucosamine residue receiving the 6-O sulfo group is N-sulfated and is adjacent to a 2-O sulfated iduronic acid residue at its non-reducing end, and X comprises any of the hexuronyl residues depicted in Formula VIII, above. 6OST enzymes within EC 2.8.2.-having biological activity with polysaccharides comprising the structure of Formula VIII have been described by Xu, Y., et al., (2017) *ACS Chem. Biol.* 12 (1):73-82 and Holmborn, K., et al., (2004) *J. Biol. Chem.* 279, (41):42355-42358, the disclosures of which are incorporated by reference in their entireties.

As described above, although the portion of the heparosan-based polysaccharide that reacts with the 6OST enzyme can comprise the structure of Formula VIII, other portions of the polysaccharide can be N- or O-substituted, and can comprise other structural motifs that can also react with the enzyme. Similar to the other enzymes above, 6OST enzymes can transfer a sulfo group to multiple positions within the same polysaccharide molecule, and multiple positions within the same polysaccharide molecule can be 6-O sulfated by the same enzyme molecule. Typically, heparosan-based polysaccharides that can react with 6OST enzymes, including those comprising the structure of Formula VIII, can comprise at least three monosaccharide residues.

Upon successfully binding PAPS and a heparosan-based polysaccharide comprising the structure of Formula VIII, natural 6OST enzymes can catalyze transfer of the sulfo group to the 6-O position of the glucosamine residue, forming an N,2,6-HS product comprising the structure of Formula IX, below:

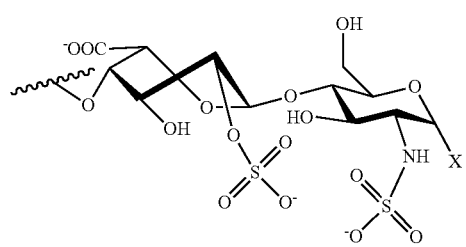

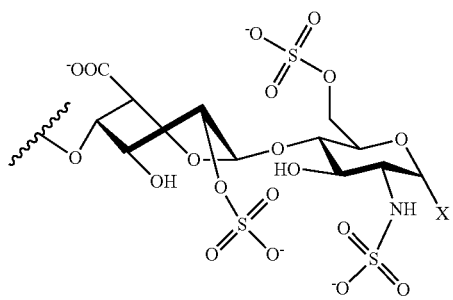

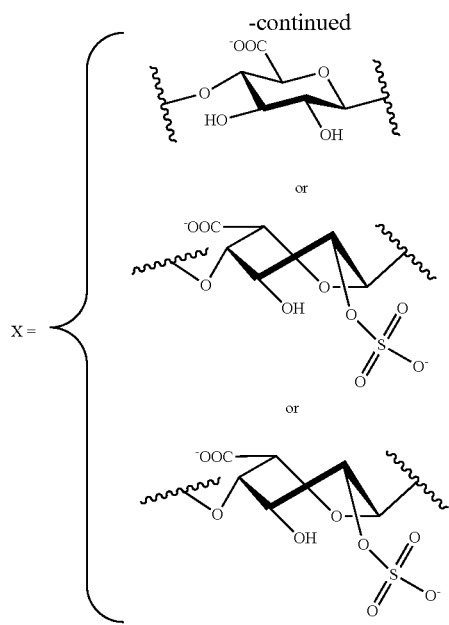

wherein X comprises any of the hexuronyl residues depicted in Formula IX, above. Similarly, an engineered 6OST enzyme that binds and reacts with an aryl sulfate compound and a heparosan-based polysaccharide comprising the structure of Formula VIII can form an N,2,6-HS product comprising the structure of Formula IX.

Figure 17:
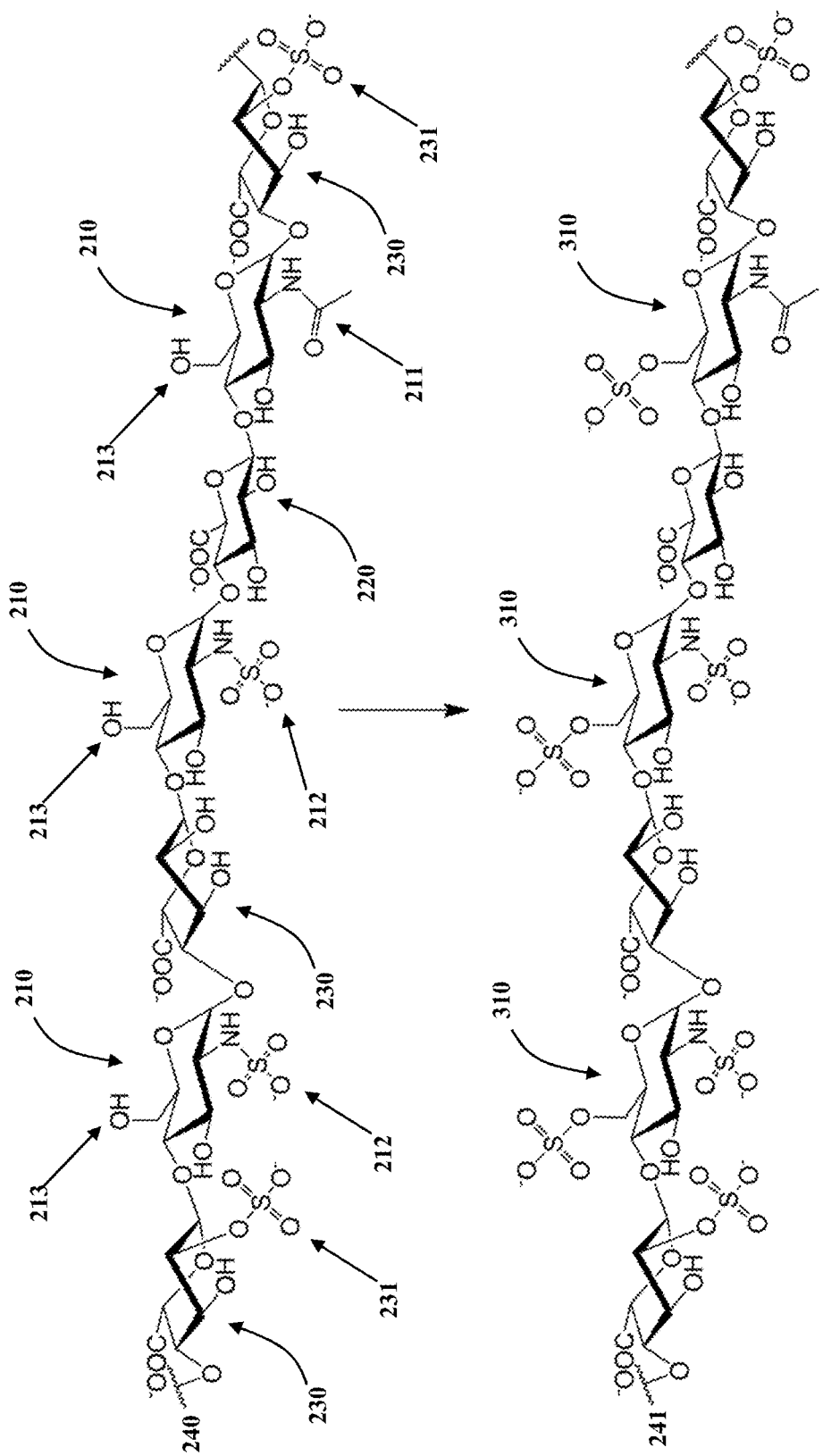
FIG. 17 shows the 6-O sulfation of one non-limiting example of an N-sulfated, 2-O sulfated heparan sulfate polysaccharide, catalyzed by either a natural or engineered 6OST enzyme in accordance with methods of the present invention, wherein multiple glucosamine residues within the polysaccharide are capable of receiving a sulfate group.

A non-limiting example of one such polysaccharide sulfo acceptor that can react with an 6OST enzyme is illustrated in FIG. 17. FIG. 17 shows a heparosan-based polysaccharide 240 that includes three N-substituted glucosamine residues 210 that can be N-substituted with either an acetyl group 211 or a sulfate group 212. Within the polysaccharide 240, N-substituted glucosamine residues 210 that are capable of acting as a sulfo acceptor are flanked by two hexuronyl residues. Hexuronyl residues can include any residue represented by the functional group "X" in Formula VIII, particularly glucuronyl residue 220 and iduronyl residue 230. Either the glucuronyl residue 220 or iduronyl residue 230 can further be substituted by a sulfate group 231 at the 2-O position. Upon reacting the polysaccharide 240 with an 6OST enzyme and a sulfo group donor, the 6-O position 213 of any of the glucosamine residues 210 can be sulfated, ultimately forming 6-O sulfated glucosamine residues 310 within the product polysaccharide 241. In another embodiment, the 6OST enzyme can be an engineered aryl sulfate-dependent enzyme, and the sulfo group donor is an aryl sulfate compound.

In another embodiment, engineered 6OSTs that can be utilized in accordance with methods of the present invention can have the same biological activity with heparosan-based sulfo acceptor polysaccharides as natural 6OSTs, particularly heparosan-based polysaccharides comprising the structure of Formula VIII. In another embodiment, when there are multiple portions of the polysaccharide comprising the structure of Formula VIII within the sulfo acceptor polysaccharide, any glucosamine residue can be sulfated by the engineered 6OST enzyme. Similarly, the same polysaccharide can be sulfated multiple times by the engineered 6OST, including and up to all of the glucosamine residues that are present within the polysaccharide.

In another embodiment, sulfo acceptor polysaccharides that can react with an engineered or natural 6OST, including but not limited to those comprising the structure of Formula VIII, can be provided as a homogenous composition. In still other embodiments, sulfo acceptor polysaccharides that can react with an engineered or natural 6OST can be comprised within a composition comprising a polydisperse mixture of polysaccharides having variable chain lengths, molecular weights, relative abundance of Formula VIII, and overall monosaccharide composition and functionalization.

In another embodiment, N,2-HS polysaccharides, including but not limited to those comprising the structure of Formula VIII, and utilized in accordance with methods of the present invention with either an engineered or natural 6OST enzyme can be obtained and/or modified from commercial sources. In another embodiment, either an engineered or natural 6OST can be utilized in accordance with methods of the present invention can react with N-sulfated heparosan products produced by an NST enzyme in one or more previous steps. In another embodiment, either an engineered or natural 6OST that can be utilized in accordance with methods of the present invention can react with N,2-HS products produced by an NST and/or a 2OST in one or more previous steps. In another embodiment, one or more of the sulfation steps to produce the N,2-HS product was catalyzed by an engineered, aryl sulfate-dependent sulfotransferase. Each of these processes are discussed in detail in the description and examples, below.

Natural 6OST enzymes within the EC 2.8.2.-enzyme class generally comprise between 300 and 700 amino acid residues that can in some cases vary greatly in their sequence, yet ultimately have the exact same function, namely, to catalyze the transfer of a sulfuryl group from PAPS to the 6-O position of glucosamine residues within heparosan-based polysaccharides, particularly those comprising the structure of Formula VIII. Without being limited by a particular theory, it is believed that each of the natural 6OSTs can catalyze the same chemical reaction because there are multiple amino acid sequence motifs and secondary structures that are either identical or highly conserved across all species.

Figure 18A:
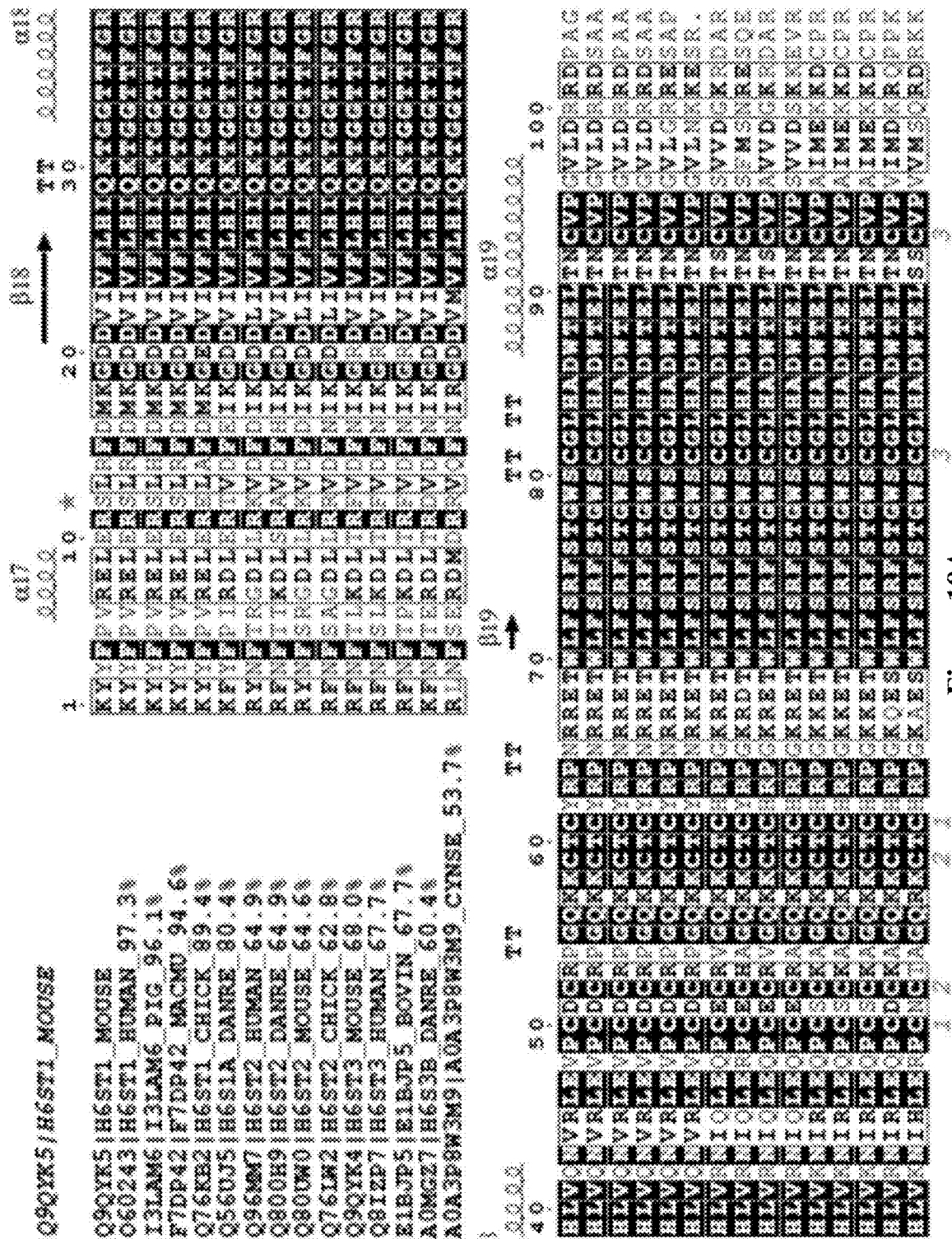
FIGS. 18A-18C show a multiple sequence alignment for fifteen natural 6OST enzymes within EC 2.8.2.-, illustrating conserved amino acid sequence motifs that are present regardless of overall sequence identity.
Figure 18B:
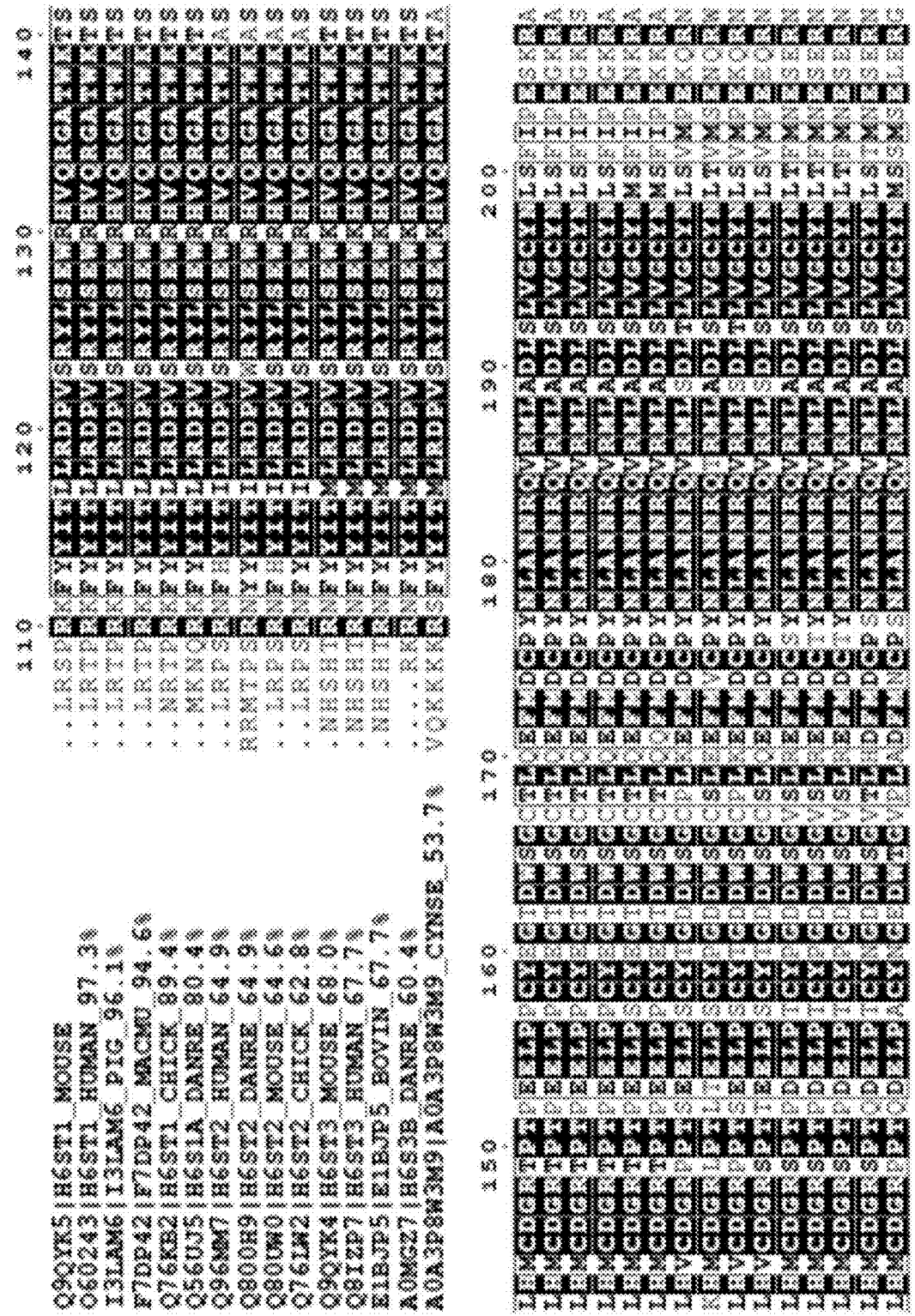
Figure 18C:
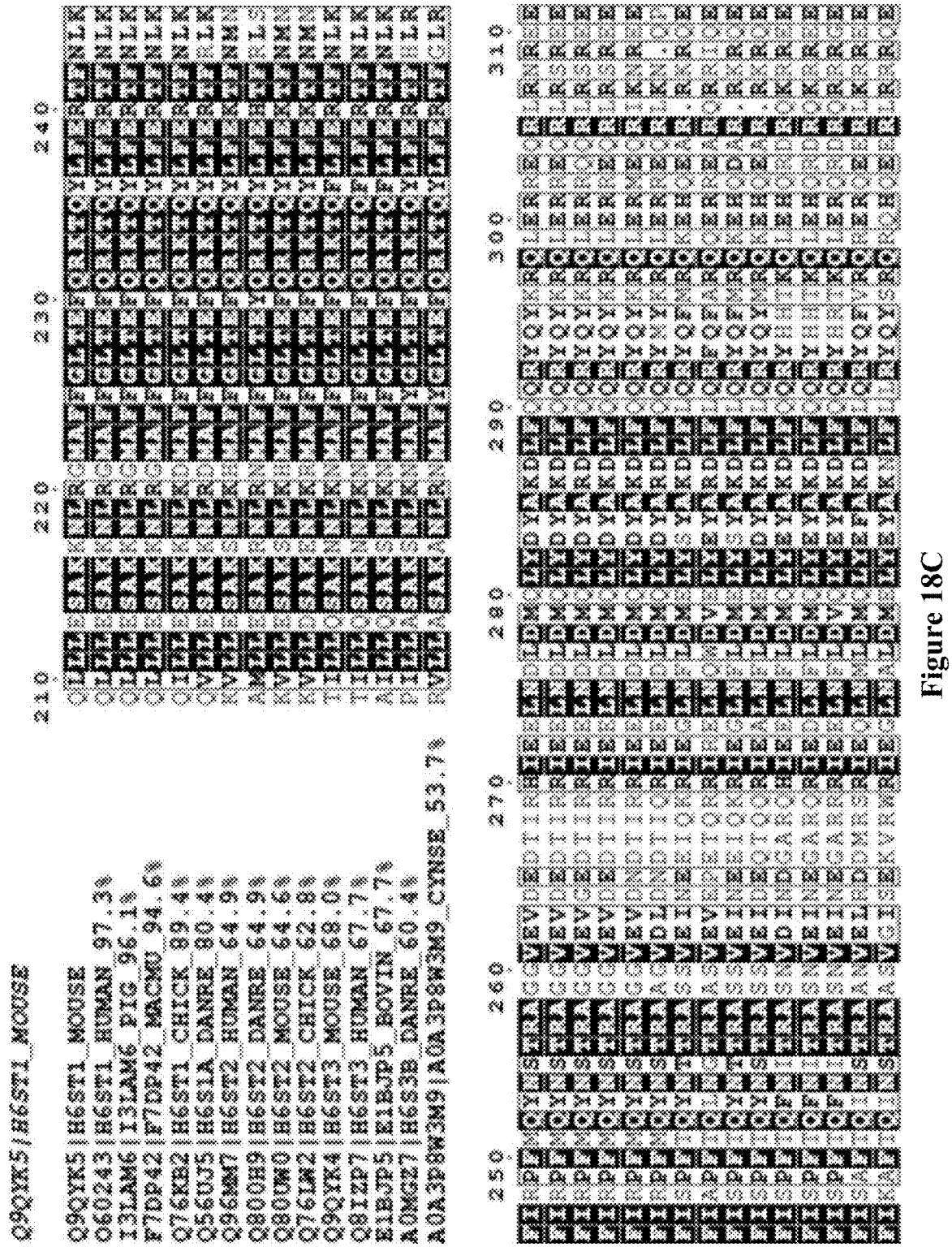

Further, it is believed that several of the conserved amino acid sequence motifs are directly involved in binding of either PAPS and/or the polysaccharide, or participate in the chemical reaction itself. The identity between the natural 6OST enzymes can be demonstrated by comparing the amino acid sequence of an enzyme with a known crystal structure (zebrafish 6OST isoform 3-B, PDB codes 5T03, 5T05 and 5TOA), in which amino acid residues within the active site have been identified, with the amino acid sequences of other natural 6OSTs. A multiple sequence alignment of fifteen enzymes is shown in FIGS. 18A-18C, along with the percent identity of each sequence relative to the mouse 6OST (isoform 1) reference sequence (UniProtKB Accession No. Q9QYK5). As illustrated in FIGS. 18A-18C, sequences range from having 97.3% identity with the Q9QYK5 reference sequence (entry O60243|H6ST1_HUMAN) down to 53.7% identity (entry A0A3P8W3M9|A0A3P8W3M9_CYSNE). For comparison, the zebrafish 6OST isoform 3-B enzyme (entry A0MGZ7|H6S3B_DANRE) has 60.4% sequence identity with the Q9QYK5 reference sequence. Those skilled in the art would appreciate that the multiple sequence alignment was limited to fifteen sequences for clarity, and that there are hundreds of amino acid sequences encoding for natural 6OST enzymes that have been identified and that have highly conserved active site and/or binding regions as well.

Within FIGS. 18A-18C, amino acids that are depicted in white with a black background at a particular position, are 100% identical across all sequences. Amino acids that are highly conserved, meaning that the amino acids are either identical or chemically or structurally similar, at a particular position are enclosed with a black outline. Within highly conserved regions, consensus amino acids that are present in a majority of the sequences, are in bold. Amino acids at a particular position that are not identical or highly conserved are typically variable. A period within a sequence indicates a gap that has been inserted into the sequence in order to facilitate the sequence alignment with other sequence(s) that have additional residues between highly conserved or identical region. Finally, above each block of sequences are a series of arrows and coils that indicate secondary structure that is conserved across all sequences, based on the identity of the amino acids within the alignment and using the structure of the natural mouse 6OST enzymes enzyme as a reference. Theo symbol adjacent to an arrow refers to a β-sheet, whereas a coil adjacent to an α symbol refers to a helix secondary structure. Each of the fifteen aligned sequences in illustrated FIGS. 18A-18C have been truncated relative to their natural full-length sequences to coincide with the engineered enzymes of the present invention, particularly SEQ ID NO: 18, SEQ ID NO: 20, and SEQ ID NO: 22. In particular, the residues illustrated in FIGS. 18A-18C are aligned with residues 67-377 of the Q9QYK5 reference sequence for the mouse 6OST.

Figure 19A:
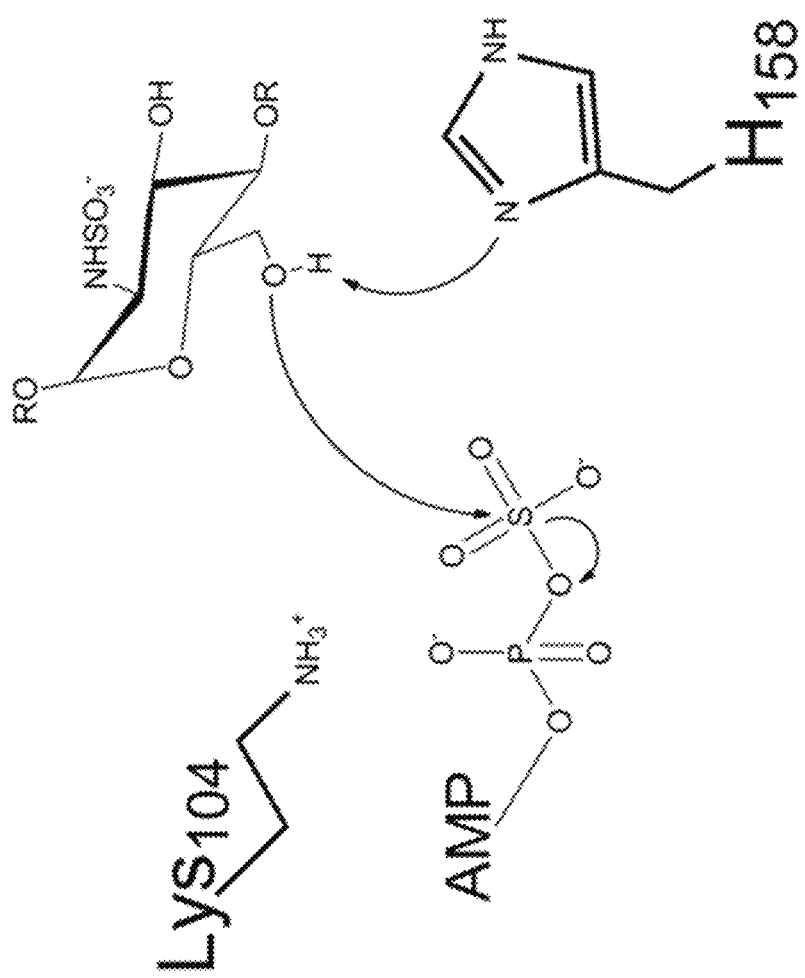
FIGS. 19A-19C show a reaction mechanism between conserved residues within a natural 6OST enzyme, PAPS, and an N-sulfated glucosamine residue within heparan sulfate.
Figure 19B:
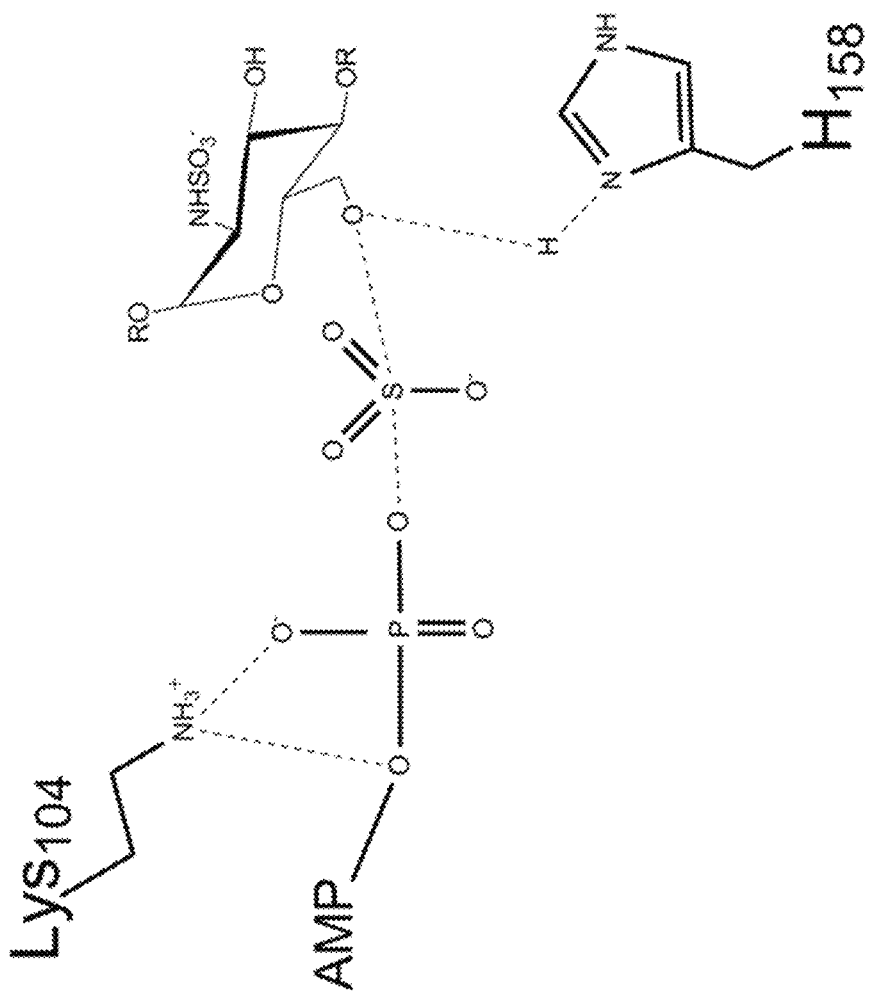
Figure 19C:
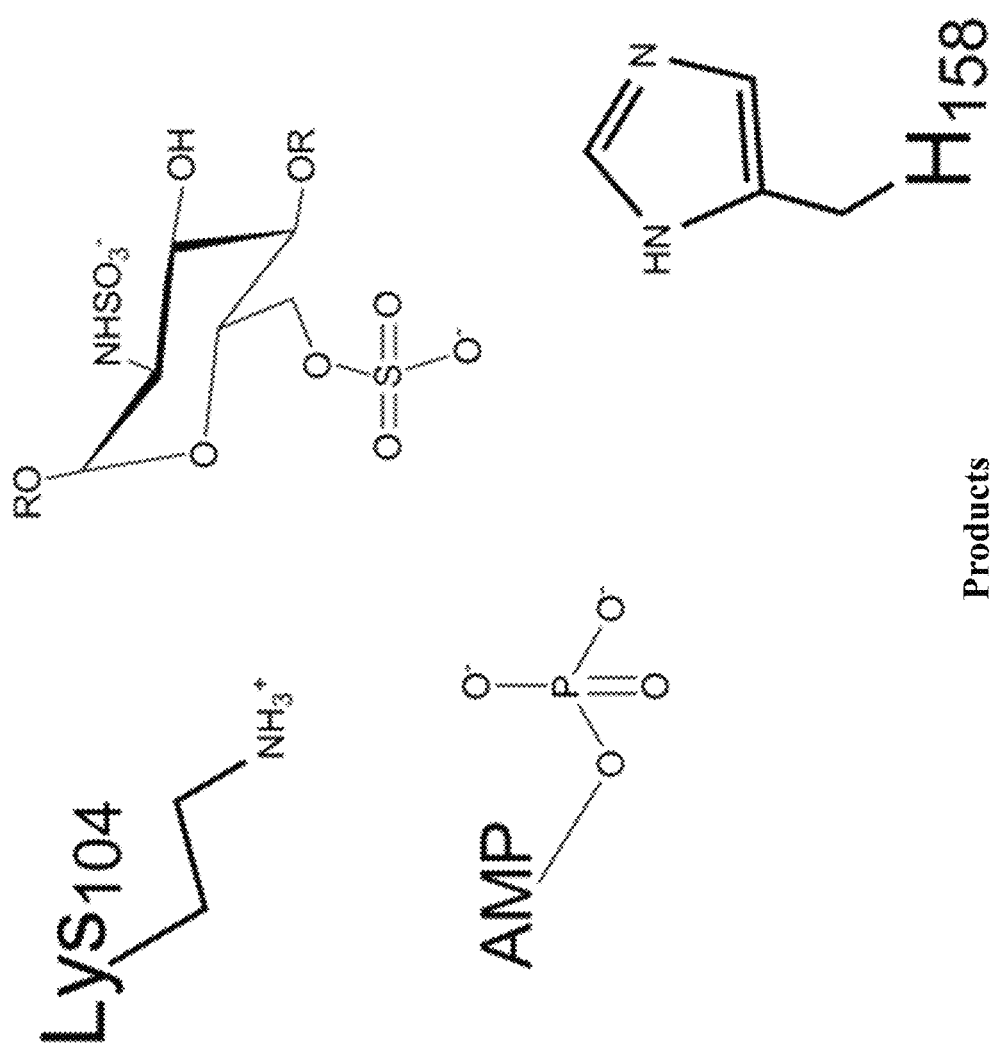

Within the fifteen aligned sequences in FIGS. 18A-18C, there are several conserved amino acid sequence motifs that include one or more amino acids that comprise the active site, based on the crystal structure of the zebrafish 6OST enzyme (entry A0MGZ7|H6S3B_DANRE) described above. Based on the numbering of the amino acid residues within FIGS. 18A-18C, these conserved amino acid sequence motifs include amino acid residues 29 through 34 (Q-K-T-G-G-T); 81 through 86 (C-G-L-H-A-D); 127 through 139 (S-E-W-R/K-H-V-Q-R-G-A-T-W-K); 178 through 184 (N-L-A-N-N-R-Q); and 227 through 231 (L-T-E-F/Y-Q). In particular, and as illustrated in the reaction mechanism in FIGS. 19A-19C, the histidine residue within the C-G-L-H-A-D conserved amino acid sequence motif is in position to abstract the hydrogen atom from the 6' hydroxyl group of an N-sulfoglucosamine residue, enabling the negatively-charged oxygen atom to then initiate the nucleophilic attack of PAPS and remove the sulfate group. Additionally, the universally conserved lysine residue within the Q-K-T-G-G-T conserved amino acid sequence motif coordinates with the 5'-phosphate in PAPS, while the universally conserved histidine and tryptophan residues at positions 131 and 138 coordinate with the N-sulfoglucosamine residue (see Xu, Y., et al., above).

However, as described above, natural 6OST enzymes are unable to catalyze the transfer of the sulfate group from an aryl sulfate compound to a polysaccharide. Without being limited by a particular theory, and as with the NSTs and 2OSTs described above, it is believed that the binding pocket for PAPS within the active site of the natural 6OST either does not have a high enough affinity for aryl sulfate compounds to facilitate binding and/or that the aryl sulfate compounds are sterically hindered from entering the active site. Consequently, and in another embodiment, a natural 6OST enzyme can be mutated in several locations within its amino acid sequence to enable binding of the aryl sulfate compound within the active site and/or to optimally position the aryl sulfate compound so transfer of the sulfate group to the polysaccharide can occur.

Accordingly, and in another embodiment, engineered 6OST enzymes that can be utilized with methods of the present invention can be mutants of natural 6OST enzymes within EC 2.8.2.-, including enzymes having the amino acid sequences illustrated in FIGS. 18A-18C. In another embodiment, the engineered 6OST enzymes have been engineered to recognize, bind, and react with aryl sulfate compounds as sulfo group donors, while retaining the natural enzymes' ability to recognize, bind, and react with any of the HS polysaccharides described above, including but not limited to those comprising the structure of Formula VIII, as sulfo group acceptors. Without being limited by a particular theory, it is believed that because of the mutations inserted into the amino acid sequences of the engineered 6OST enzymes, their sulfotransferase activity may comprise the direct transfer of a sulfuryl group from an aryl sulfate compound to the sulfo acceptor polysaccharide, using a similar mechanism as described in FIGS. 19A-19C, above, except that the PAPS is substituted with the aryl sulfate compound. Otherwise, it is believed that the mutations may cause the sulfotransferase activity to comprise a two-step process including the hydrolysis of an aryl sulfate compound and formation of a sulfohistidine intermediate, followed by the nucleophilic attack of the sulfohistidine intermediate by the oxygen atom at the 6-O position of a glucosamine residue, to form a 6-O sulfated HS product. In another embodiment, the 6-O sulfated HS product of either sulfotransfer mechanism is an N,2,6-HS product.

In another embodiment, an engineered 6OST enzyme can comprise one or more mutated amino acid sequence motifs relative to the conserved amino acid sequence motifs found in natural 6OST enzymes within EC 2.8.2.-, as described above and indicated in the multiple sequence alignment in FIGS. 18A-18C. In another embodiment, each mutated amino acid sequence motif that is present in the amino acid sequence of the engineered enzyme comprises at least one amino acid mutation relative to the corresponding conserved amino acid sequence motif within the natural 6OST enzymes. In another embodiment, an engineered 6OST enzyme can comprise one mutated amino acid sequence motif. In another embodiment, an engineered 6OST enzyme can comprise two mutated amino acid sequence motifs. In another embodiment, an engineered 6OST enzyme can comprise three mutated amino acid sequence motifs. In another embodiment, an engineered 6OST enzyme can comprise four mutated amino acid sequence motifs. In another embodiment, an engineered 6OST enzyme can comprise five mutated amino acid sequence motifs. In another embodiment, an engineered 6OST enzyme that includes at least one mutated amino acid sequence motif relative to any of the natural 6OST enzymes within EC 2.8.2.-can have an amino acid sequence selected from the group consisting of SEQ ID NO: 18, SEQ ID NO: 20, SEQ ID NO: 22, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 59, SEQ ID NO: 60, and SEQ ID NO: 61.

Figure 20:
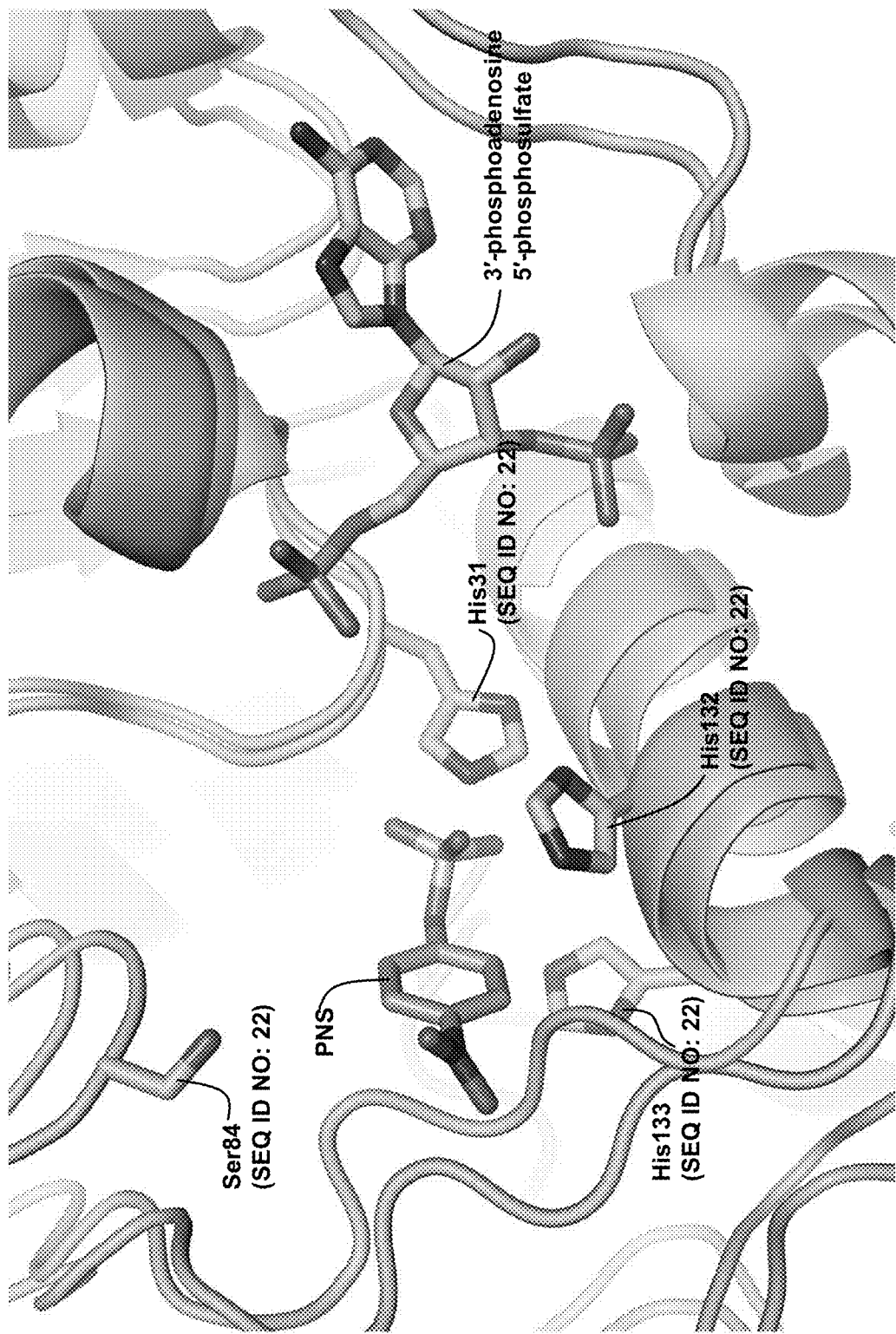
FIG. 20 shows a three-dimensional model of an aryl sulfate compound bound within the active site of an engineered 6OST enzyme, superimposed over the crystal structure of PAPS bound within the zebrafish 6OST3 enzyme.

In another embodiment, upon viewing any of the crystal structures of the zebrafish 6OST (UniProtKB Accession No. A0MGZ7) within a 3D molecular visualization system (including, as a non-limiting example, the open-source software, PyMOL), the structure of related sequences, such as those of engineered 6OST enzymes that contain one or more mutated amino acid sequence motifs relative to any of the zebrafish 6OST structures, can be modeled for comparison as illustrated in FIG. 20. FIG. 20 shows a magnified view of the active site of the zebrafish 6OST enzyme (PDB code: 5T03) with one of the engineered enzymes of the present invention, comprising the amino acid sequence of SEQ ID NO: 22, in which the structure of the engineered 6OST enzyme is calculated upon making mutations relative to the zebrafish 6OST amino acid sequence. Adenosine 3',5'-diphosphate, which is the product of a sulfotransfer reaction in which PAPS is the sulfo donor, and which was co-crystallized with the zebrafish 6OST, is also illustrated within the active site. PNS is also modeled into the active site of the engineered enzymes, using the consensus solutions of molecular dynamics (MD) simulations that designed to calculate the optimized position and orientation of a ligand within an enzyme active site adjacent to the polysaccharide binding site (not shown), if such solutions are possible. Hydrogen atoms are not shown for clarity.

As illustrated in FIG. 20, although there are several mutations made SEQ ID NO: 22, relative to the zebrafish 6OST enzyme, the respective protein backbones are in a nearly identical location to one another, enabling a one-to-one comparison of the active sites. However, when comparing the two active sites, the adenosine 3',5'-diphosphate product is located on the opposite side of the central α-helix as the PNS molecule, as determined by the convergent solutions from the above MD simulations. Without being limited by a particular theory, it is believed that the convergent MD simulation solutions place PNS on the opposite side of the α-helix because there is not enough of an affinity toward PNS in the same or similar position as PAPS within the zebrafish enzyme. As described by Xu, Y., et al., above, the conserved histidine at position 158 of the full-length amino acid sequence is the catalytic histidine that abstracts the proton from the 6' hydroxyl group of N-sulfoglucosamine, which is then subsequently able to react with PAPS to initiate sulfo group transfer. Yet, despite the apparent differences in the binding pocket for PAPS and PNS, engineered 6OST enzymes comprising the amino acid sequences of SEQ ID NO: 18, SEQ ID NO: 20, and SEQ ID NO: 22 all achieved sulfo transfer from an aryl sulfate compound to the glucosaminyl 6-O position within a heparosan-based polysaccharide, as described in the examples below.

As a result, and without being limited by a particular theory, one or more mutations present within the active site of engineered 6OST enzymes may assist binding of the sulfate moiety of the aryl sulfate compound in a position in which it can be transferred to the sulfo acceptor HS polysaccharide. As illustrated in FIG. 20, the engineered enzyme has the amino acid sequence SEQ ID NO: 22, and the aryl sulfate compound is PNS. However, a sulfo acceptor HS polysaccharide is not illustrated. In a non-limiting example, the histidine residue engineered into position 31 of SEQ ID NO: 22 may be in position to facilitate removal of the sulfate group from PNS using a ping-pong mechanism, as described in Malojcic, et al, above. Additionally, the histidine residue engineered into position 133 of SEQ ID NO: 22 may further coordinate with the sulfate moiety along with the conserved histidine at position 132 of SEQ ID NO: 22 (corresponding to positions 131-132 in each of the sequences in FIGS. 18A-18C). Mutation to G-A-N at positions 137-139 of SEQ ID NO: 22 (corresponding to the conserved A-T-W motif at positions 136-138 of the sequences in FIGS. 18A-18C) removes steric bulk that may prevent binding of PNS in a position where the sulfate can be abstracted by the engineered histidine at position 31 of SEQ ID NO: 22. The mutations to G-A-N within the loop containing A-T-W also appears to cause the loop to move away from PNS, which may further assist PNS to reach its binding pocket. Finally, a serine residue engineered into position 84 of SEQ ID NO: 22, immediately adjacent to a native histidine corresponding to His-158 in the full-length zebrafish 6OST, described above, may create an additional hydrogen-binding contact to assist the engineered enzyme in retaining the zebrafish enzyme's natural activity with the sulfo acceptor polysaccharide.

Those skilled in the art would appreciate that engineered 6OST enzymes of any other amino acid sequence, including, but not limited to, those disclosed by SEQ ID NO: 18, SEQ ID NO: 20, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 59, SEQ ID NO: 60, and SEQ ID NO: 61, would exhibit similar structural motifs, particularly within the active site. Without being limited by a particular theory, it is believed that NCS would bind in a similar position as PNS within the active site of any of the engineered enzymes, since the structures of the two aryl sulfate compounds are very similar, except that the sulfate group is located ortho on the aromatic ring relative to the nitro group, rather than para to the nitro group.

In another embodiment, engineered 6OST enzymes that can be utilized in accordance with methods of the present invention can comprise one or more mutated amino acid sequence motifs, which can be determined in-part by comparing conserved amino acid sequence motifs indicated in the multiple sequence alignment of FIGS. 18A-18C with the known structure(s) of natural enzymes and/or modeled engineered enzymes, including but not limited to, as a non-limiting example, enzymes illustrated in FIG. 20. In another embodiment, mutated amino acid sequence motifs that can be comprised within an engineered 6OST enzyme can be selected from the group consisting of (a) G-H-T-G-G-T; (b) C-G-$X_1$-$X_2$-A-D, wherein $X_1$ is selected from the group consisting of threonine and serine, and $X_2$ is selected from the group consisting of asparagine, arginine, and histidine; (c) $X_3$-$X_4$-W-R-H-$X_5$-Q-R-G-G-$X_6$-N-K, wherein $X_3$ is selected from the group consisting of serine and glycine, $X_4$ is selected from the group consisting of glycine and histidine, $X_5$ is selected from the group consisting of histidine and threonine, and $X_6$ is selected from the group consisting of alanine and threonine; and (d) N-L-$X_7$-N-N-R-Q, wherein $X_7$ is selected from the group consisting of alanine and glycine; including any combination thereof. Each of the mutated amino acid sequence motifs corresponds with a conserved amino acid motif indicated in FIGS. 18A-18C above: sequence motif (a) corresponds to the conserved amino acid sequence motif, Q-K-T-G-G-T; mutated amino acid sequence motif (b) corresponds to the conserved amino acid sequence motif, C-G-L-H-A-D; mutated amino acid sequence motif (c) corresponds to the conserved amino acid sequence motif, S-E-W-(R/K)-H-V-Q-R-G-A-T-W-K; and mutated amino acid sequence motif (d) corresponds to the conserved amino acid sequence motif, N-L-A-N-N-R-Q. In another embodiment, engineered 6OST enzymes comprising at least one mutated amino acid sequence motif described above can be selected from the group consisting of: SEQ ID NO: 18, SEQ ID NO: 20, SEQ ID NO: 22, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 59, SEQ ID NO: 60, and SEQ ID NO: 61.

In another embodiment and in one non-limiting example, engineered 6OST enzymes can comprise the mutated amino acid sequence motifs (b) and (c) within the same amino acid sequence. Engineered enzymes comprising the mutated amino acid sequence motifs (b) and (c) include, but are not limited to, enzymes comprising the amino acid sequences of SEQ ID NO: 18, SEQ ID NO: 20, SEQ ID NO: 22, SEQ ID NO: 43, SEQ ID NO: 44, SEQ ID NO: 45, SEQ ID NO: 46, SEQ ID NO: 47, SEQ ID NO: 48, SEQ ID NO: 49, and SEQ ID NO: 50. In another embodiment, each of the engineered 6OST enzymes comprising the mutated amino acid sequence motifs (b) and (c) have a similar active site as SEQ ID NO: 22, as illustrated in FIG. 20. Without being limited to another theory, it is believed that several of the mutations comprised within mutated amino acid sequence motifs (b) and (c) have one or more functions during sulfotransferase activity, including not limited to: increasing the affinity of aryl sulfate compounds to the active site by reducing the size of the binding pocket, increasing the hydrophobicity of the pocket, removing or creating polar or hydrogen bonding contacts, and/or creating $\pi$-$\pi$ interactions with the aromatic moieties of the aryl sulfate compounds; stabilizing the transition state of the enzyme during the chemical reaction; and/or participating in the chemical reaction itself.

In another embodiment, within engineered 6OST enzymes that comprise the mutated amino acid sequence motifs (b) and (c), $X_4$ is glycine and $X_5$ is histidine. In other embodiments, $X_4$ is histidine and $X_5$ is threonine.

In another embodiment, within engineered 6OST enzymes comprising the mutated amino acid sequence motifs (b) and (c), $X_3$ is serine, $X_6$ is alanine, and $X_7$ is glycine. In other embodiments, $X_3$ is glycine, $X_6$ is threonine, and $X_7$ is alanine.

Figure 21:
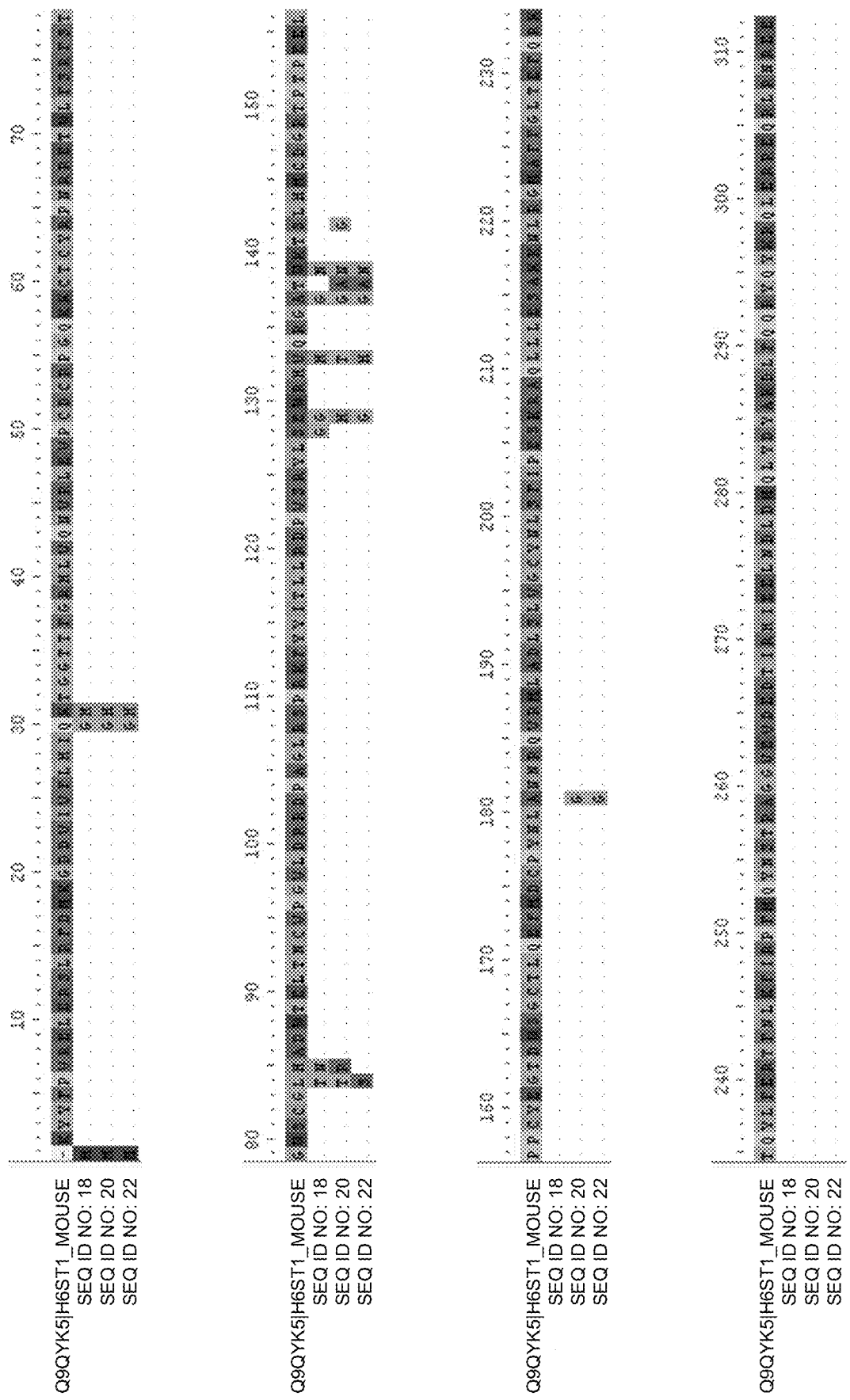
FIG. 21 shows a sequence alignment of polypeptides comprising the amino acid sequences of SEQ ID NO: 18, SEQ ID NO: 20, and SEQ ID NO: 22, respectively, depicting the position and identity of amino acid residues differences between each of the illustrated sequences and relative to the mouse 6OST1 enzyme.

Furthermore, the amino acid sequences (SEQ ID NO: 18, SEQ ID NO: 20, SEQ ID NO: 22) of three engineered 6OST enzymes, which have been experimentally determined to be active with aryl sulfate compounds as sulfo group donors (see Example 4 below) can be compared with the amino acid sequence of the mouse 6OST enzyme (entry Q9QYK5|H6ST1_MOUSE) in a multiple sequence alignment to determine if there are relationships between mutations among each of the enzymes. A period within the amino acid sequence of an engineered enzyme indicates identity at a particular position with the mouse 6OST enzyme. As shown in FIG. 21, the sequence alignment demonstrates that while over 90% of the amino acid residues within the three sulfotransferase sequences are identical, there are several positions in which multiple amino acids can be chosen. Without being limited by a particular theory, these enzymes have a similar relationship with each other as the 6OST enzymes that comprise EC 2.8.2.-. As a result, and in another embodiment, engineered 6OST enzymes comprising an amino acid sequence in which multiple amino acids can be chosen at defined positions are disclosed as SEQ ID NO: 43 and SEQ ID NO: 44. Positions at which the identity of an amino acid can be chosen from a selection of possible residues are denoted in terms "Xaa," "Xn," or "position n," where n refers to the residue position.

In another embodiment, within SEQ ID NO: 43, residues having the designation, "Xaa," illustrate known instances in which there is a lack of identity at a particular position within the amino acid sequences of SEQ ID NO: 18, SEQ ID NO: 20, and SEQ ID NO: 22. In another embodiment, the amino acid sequence, SEQ ID NO: 44, also illustrates known instances in which there is a lack of identity at a particular position within the amino acid sequences of SEQ ID NO: 18, SEQ ID NO: 20, and SEQ ID NO: 22, but SEQ ID NO: 44 further comprises N-terminal residues 1-66, and C-terminal residues 378-411, of several full-length 6OST enzymes within EC 2.8.2.-, including, as non-limiting examples, the mouse, human, and pig 6OST enzymes. In contrast, amino acid residues in SEQ ID NO: 18, SEQ ID NO: 20, SEQ ID NO: 22, and SEQ ID NO: 43 correspond with residues 67-377 of several full-length 6OST enzymes within EC 2.8.2.-, including, as non-limiting examples, the mouse, human, and pig 6OST enzymes. To facilitate protein expression, an N-terminal methionine residue was added to each SEQ ID NO: 18, SEQ ID NO: 20, SEQ ID NO: 22, and SEQ ID NO: 43 amino acid sequence, relative to residues 67-377 of the mouse, human, and pig 6OST enzymes.

In another embodiment, any selection can be made for an Xaa residue, defined by the amino acid sequence SEQ ID NO: 43 or SEQ ID NO: 44, so long as the resulting enzyme maintains its 6OST activity upon reacting with an aryl sulfate compound as a sulfo group donor.

In another embodiment, within an engineered 6OST enzyme comprising the amino acid sequence of SEQ ID NO: 43, the amino acid residue at position 129 is glycine and the amino acid residue at position 133 is histidine. In another embodiment, within an engineered 6OST enzyme comprising the amino acid sequence of SEQ ID NO: 43, the amino acid residue at position 129 is histidine and the amino acid residue at position 133 is threonine. In another embodiment, within an engineered 6OST enzyme comprising the amino acid sequence of SEQ ID NO: 44, the amino acid residue at position 194 is glycine and the amino acid residue at position 198 is histidine. In another embodiment, within an engineered 6OST enzyme comprising the amino acid sequence of SEQ ID NO: 44, the amino acid residue at position 194 is histidine and the amino acid residue at position 198 is threonine.

In another embodiment, within an engineered 6OST enzyme comprising the amino acid sequence of SEQ ID NO: 43, the amino acid residue at position 128 is serine, the amino acid residue at position 138 is alanine, and the amino acid residue at position 181 is glycine. In another embodiment, within an engineered 6OST enzyme comprising the amino acid sequence of SEQ ID NO: 43, the amino acid residue at position 128 is glycine, the amino acid residue at position 138 is threonine, and the amino acid residue at position 181 is alanine. In another embodiment, within an engineered 6OST enzyme comprising the amino acid sequence of SEQ ID NO: 44, the amino acid residue at position 193 is serine, the amino acid residue at position 203 is alanine, and the amino acid residue at position 246 is glycine. In another embodiment, within an engineered 6OST enzyme comprising the amino acid sequence of SEQ ID NO: 44, the amino acid residue at position 193 is glycine, the amino acid residue at position 203 is threonine, and the amino acid residue at position 246 is alanine.

In another embodiment, within an engineered 6OST enzyme comprising the amino acid sequence of SEQ ID NO: 43 or SEQ ID NO: 44, the amino acid sequence can optionally include one or more mutations at residue positions not specified by an "Xn" or "Xaa," so long as any such mutations do not eliminate the 6OST and/or aryl sulfate-dependent activity of the enzyme. In another embodiment, such mutations not eliminating aryl sulfate-dependent activity at positions not specified by an "Xn" or "Xaa" can include substitutions, deletions, and/or additions.

Accordingly, in another embodiment, an engineered 6OST enzyme utilized in accordance with any of the methods of the present invention can comprise an amino acid sequence selected from the group consisting of SEQ ID NO: 18, SEQ ID NO: 20, SEQ ID NO: 22, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 59, SEQ ID NO: 60, and SEQ ID NO: 61. In another embodiment, any of the above engineered 6OST enzymes react with an aryl sulfate compound, instead of PAPS, as a sulfo group donor. In further embodiments, the aryl sulfate compound is selected from the group consisting of PNS, MUS, 7-hydroxycoumarin sulfate, phenyl sulfate, 4-acetylphenyl sulfate, indoxyl sulfate, 1-naphthyl sulfate, 2-naphthyl sulfate, and NCS. In some even further embodiments, the aryl sulfate compound is PNS. In other even further embodiments, the aryl sulfate compound is NCS.

Glucosaminyl 3-O Sulfotransferases

In nature, 3OSTs generally recognize, bind, and react with N,2-HS polysaccharides and N,2,6-HS polysaccharides as sulfo group acceptors. Generally, the glucosamine residue that receives the sulfo group at the 3-O position is N-sulfated, and is optionally also 6-O sulfated. Additionally, either adjacent hexuronic acid residue can be either glucuronic acid or iduronic acid, and can optionally be 2-O sulfated. In some embodiments, the hexuronic acid residue on the non-reducing end of the glucosamine residue is unsulfated glucuronic acid, while the hexuronic acid residue on the reducing end of the glucosamine residue is 2-O sulfated iduronic acid. Similar to each of the natural sulfotransferases described above, naturally-occurring 3OSTs transfer the sulfo group to the polysaccharide upon reacting with PAPS as a sulfo group donor. Natural 3OST enzymes that utilize PAPS as the sulfo group donor are members of the EC 2.8.2.23 enzyme class. In a non-limiting example, both natural 3OST enzymes and engineered aryl sulfate-dependent 3OST enzymes can recognize, bind, and react with N,2,6-HS polysaccharides comprising the structure of Formula X, below:

wherein the central glucosamine residue is N-sulfated and is adjacent to an unsubstituted glucuronic acid residue at its non-reducing end and a 2-O sulfated iduronic acid residue at its reducing end, X can optionally be a sulfate group or an acetyl group, and Y can optionally be a sulfate group or a hydroxyl group.

As described above, although the portion of the polysaccharide that reacts with the enzyme comprises the structure of Formula X, other portions of the polysaccharide can be N- or O-substituted, and can comprise other structural motifs that can also react with the enzyme. Similar to the other enzymes above, 3OST enzymes can transfer a sulfo group to multiple positions within the same polysaccharide molecule, and multiple positions within the same polysaccharide molecule can be 3-O sulfated by the same enzyme molecule. Typically, HS polysaccharides that can react with 3OSTs as sulfo group acceptors typically comprise at least five monosaccharide residues, as shown in Formula X. In another embodiment, polysaccharides comprising the structure of Formula X and can react with 3OSTs as sulfo group acceptors can comprise at least 32 monosaccharide residues.

Upon successfully binding PAPS and an N,2,6-HS polysaccharide comprising the structure of Formula X, natural 3OST enzymes can catalyze transfer of the sulfo group to the 3-O position of the central glucosamine residue, forming an N,2,3,6-HS product comprising the structure of Formula I, below:

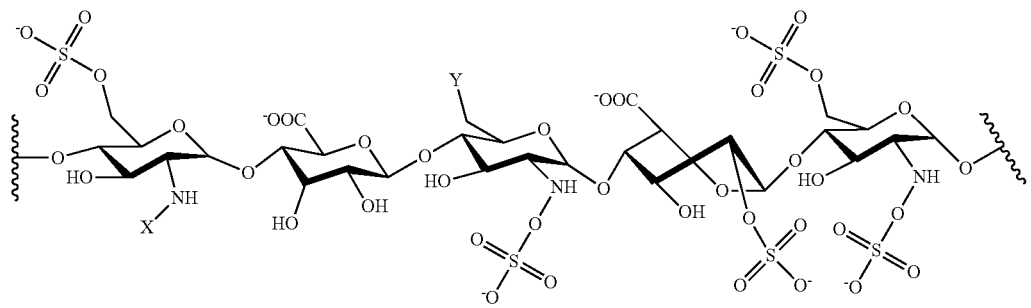

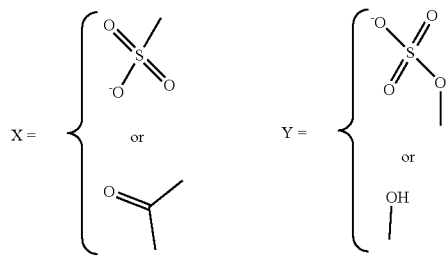

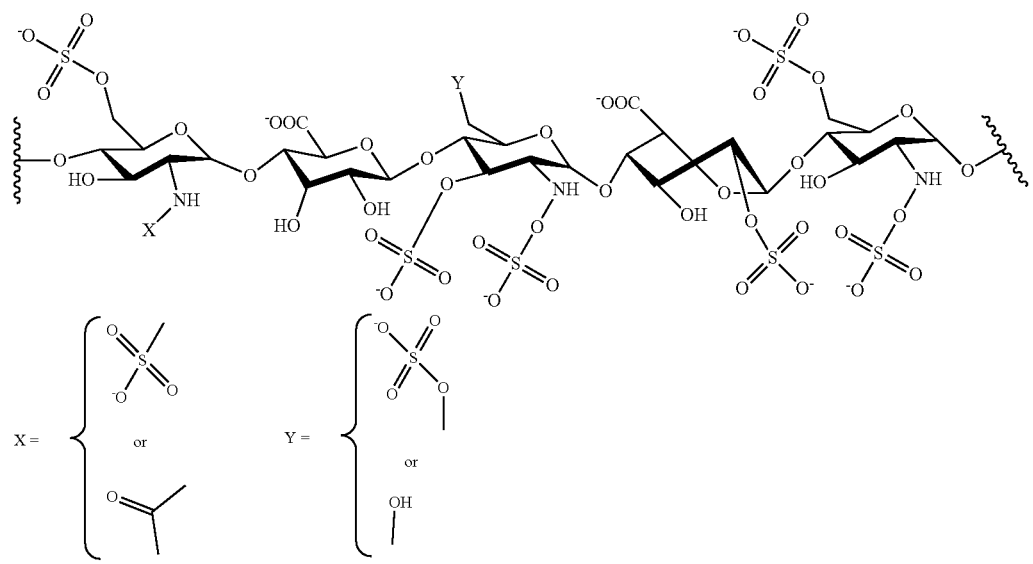

wherein X is either a sulfo group or an acetate group and Y is either a sulfo group or a hydroxyl group. Similarly, engineered 3OST enzymes that react with an aryl sulfate compound and an N,2,6-HS polysaccharide comprising the structure of Formula X can also form an N,2,3,6-HS product comprising the structure of Formula L. In further embodiments, the functional group X in the N,2,3,6-HS product is a sulfate group. In other further embodiments, the functional group Y in the N,2,3,6-HS product is a sulfate group. In another embodiment, in some locations within the polymer, at least a portion of the glucosamine residues are N-acetylated. Natural 3OST enzymes within EC 2.8.2.23, which have biological activity with N,2,6-HS polysaccharides comprising the structure of Formula X as sulfo group acceptors and form N,2,3,6-HS products comprising the structure of Formula I, have been described by Xu, D., et al., (2008)*Nat. Chem. Biol.* 4(3): 200-202 and Edavettal, S.C., et al., (2004) *J. Biol. Chem.* 24(11): 25789-25797, the disclosures of which are incorporated by reference in their entireties.

Figure 22:
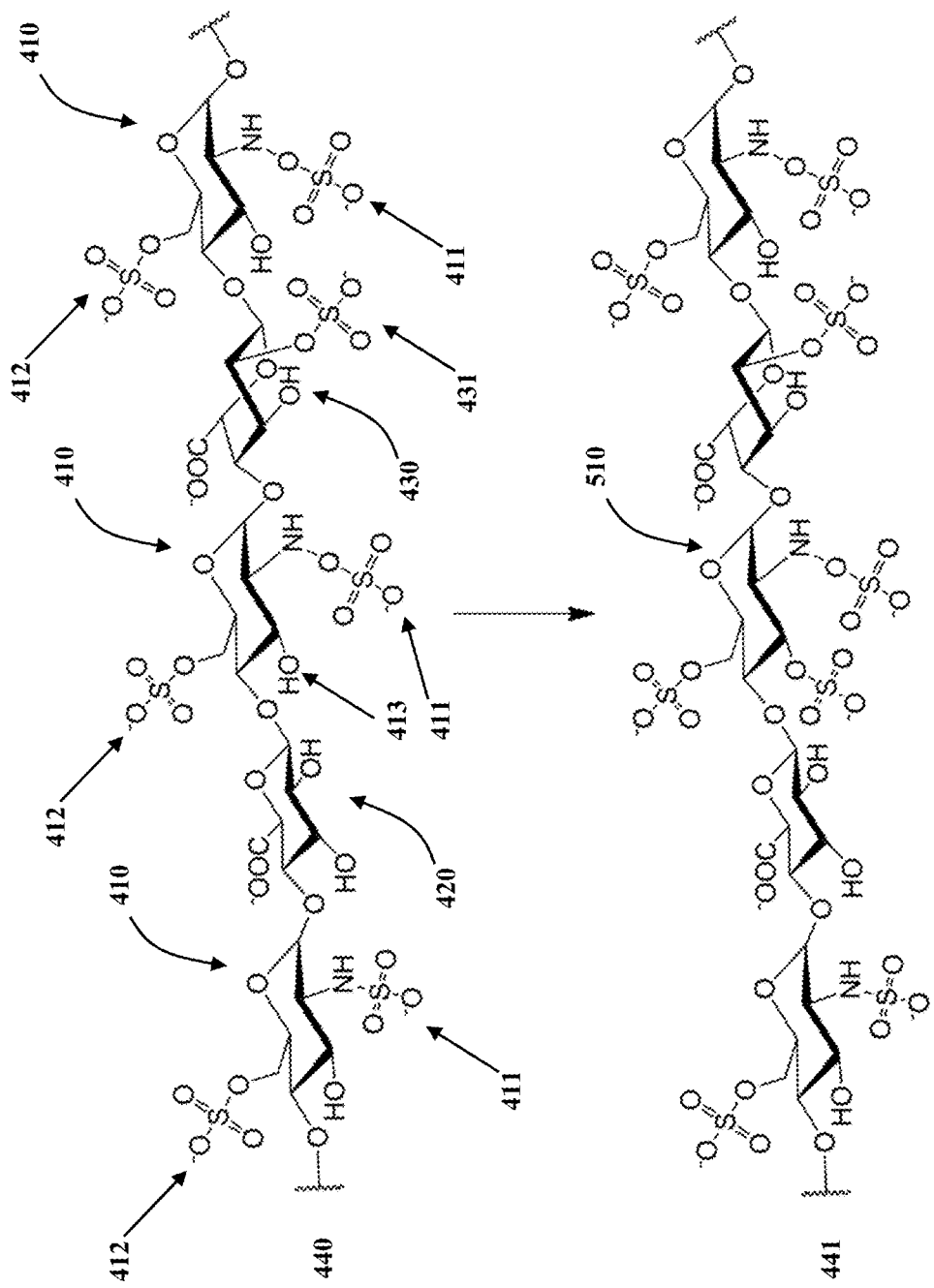
FIG. 22 shows the 3-O sulfation of one non-limiting example of an N-sulfated, 2-O sulfated, 6-O sulfated heparan sulfate polysaccharide, catalyzed by either a natural or engineered 3OST enzyme in accordance with methods of the present invention.

A non-limiting example of one such N,2,6-HS sulfo group acceptor for 3OST enzymes is illustrated in FIG. 22. FIG. 22 shows a polysaccharide 440 that includes three glucosamine residues 410 comprising an N-sulfo group 411 at each N-position and an O-sulfo group 412 at each 6-O position. Within the polysaccharide 440, glucosamine residues 410 that are capable of acting as a sulfo acceptor must be flanked by two hexuronic acid residues. Hexuronic acid residues can include any residue represented by the functional group "X" in Formula X, and are shown in FIG. 22 as glucuronic acid residue 420 and iduronic acid residue 430. Either hexuronic acid residue can further be substituted by a sulfo group 431 at the 2-O position. Upon reacting the polysaccharide 440 with an 3OST enzyme and a sulfo group donor, the 3-O position 413 of any of the glucosaminyl residues 410 can be sulfated. As shown in FIG. 22, the central glucosamine residue 410 receives a sulfo group, ultimately forming a 3-O sulfated glucosaminyl residue 510 within the sulfated product polysaccharide 441. Also as shown, sulfated product polysaccharide 441 comprises the structure of Formula I.

In another embodiment, engineered 3OSTs that can be utilized in accordance with methods of the present invention can have the same biological activity with heparosan-based sulfo acceptor polysaccharides as natural 3OSTs, particularly heparosan-based polysaccharides comprising the structure of Formula X. In another embodiment, when there are multiple portions of the polysaccharide comprising the structure of Formula X within the sulfo acceptor polysaccharide, any N-sulfated glucosamine residue can be 3-O sulfated by the engineered 3OST enzyme. Similarly, the same polysaccharide can be sulfated multiple times by the engineered 3OST, including and up to all of the N-sulfated glucosamine residues that are present within the polysaccharide. In another embodiment, a heparin mixture, either isolated from an animal source or synthesized according to any of the methods described herein, can also be utilized as a sulfo group acceptor and further 3-O sulfated upon reacting with an engineered 3OST enzyme and an aryl sulfate compound, to form an "over-sulfated" heparin mixture.

In another embodiment, sulfo acceptor polysaccharides that can react with an engineered or natural 3OST, including but not limited to those comprising the structure of Formula X, can be provided as a homogenous composition. In still other embodiments, sulfo acceptor polysaccharides that can react with an engineered or natural 3OST can be comprised within a composition comprising a polydisperse mixture of polysaccharides having variable chain lengths, molecular weights, relative abundance of Formula X, and overall monosaccharide composition and functionalization.

In another embodiment, N,2-HS and N,2,6-HS polysaccharides, including but not limited to those comprising the structure of Formula X, and utilized in accordance with methods of the present invention with either an engineered or natural 6OST enzyme, can be obtained and/or modified from commercial sources. In another embodiment, either an engineered or natural 6OST can be utilized in accordance with methods of the present invention can react with N,2-HS products produced by an NST and/or a 2OST in one or more previous steps. In another embodiment, either an engineered or natural 6OST can be utilized in accordance with methods of the present invention can react with N,2,6-HS products produced by an NST, a 2OST, and/or a 6OST in one or more previous steps. In another embodiment, one or more of the sulfation steps to produce the N,2-HS or N,2,6-HS product was catalyzed by an engineered, aryl sulfate-dependent sulfotransferase. In another embodiment, all of the sulfation steps to produce the N,2-HS or N,2,6-HS product was catalyzed by an engineered, aryl sulfate-dependent sulfotransferase. Each of these processes are discussed in detail in the description and examples, below.

Natural 3OST enzymes within the EC 2.8.2.23 enzyme class generally comprise approximately 300 to 325 amino acid residues that can in some cases vary greatly in their sequence, yet ultimately have the exact same function, namely, to catalyze the transfer of a sulfuryl group from PAPS to the 3-O position of N-sulfoglucosamine residues within N,2-HS or N,2,6-HS polysaccharides, particularly those comprising the structure of Formula X. Without being limited by a particular theory, it is believed that each of the natural 3OSTs can catalyze the same chemical reaction because there are multiple amino acid sequence motifs and secondary structures that are either identical or highly conserved across all species.

Figure 23A:
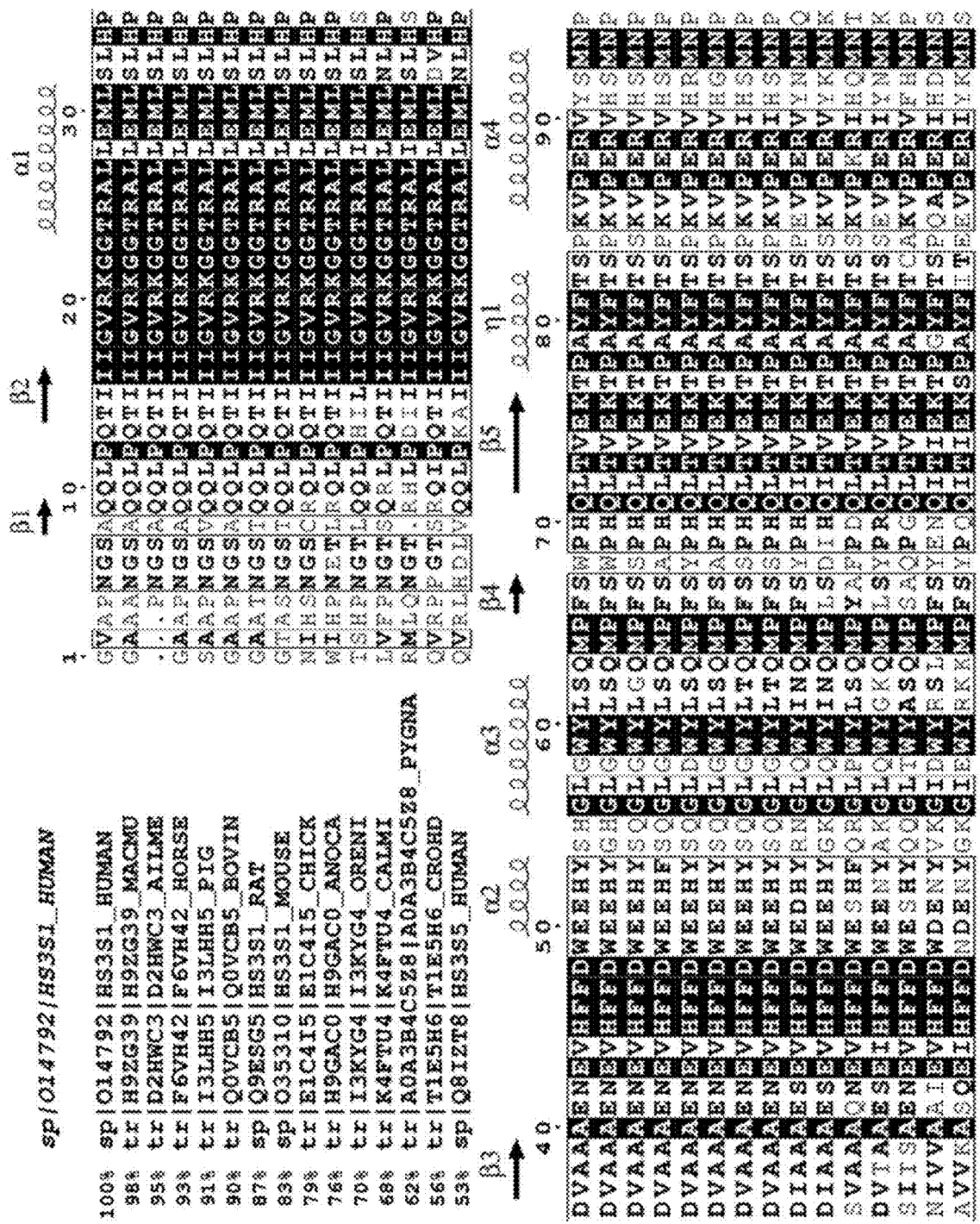
FIGS. 23A-23C show a multiple sequence alignment for fifteen natural 3OST enzymes within EC 2.8.2.23, illustrating conserved amino acid sequence motifs that are present regardless of overall sequence identity.
Figure 23B:
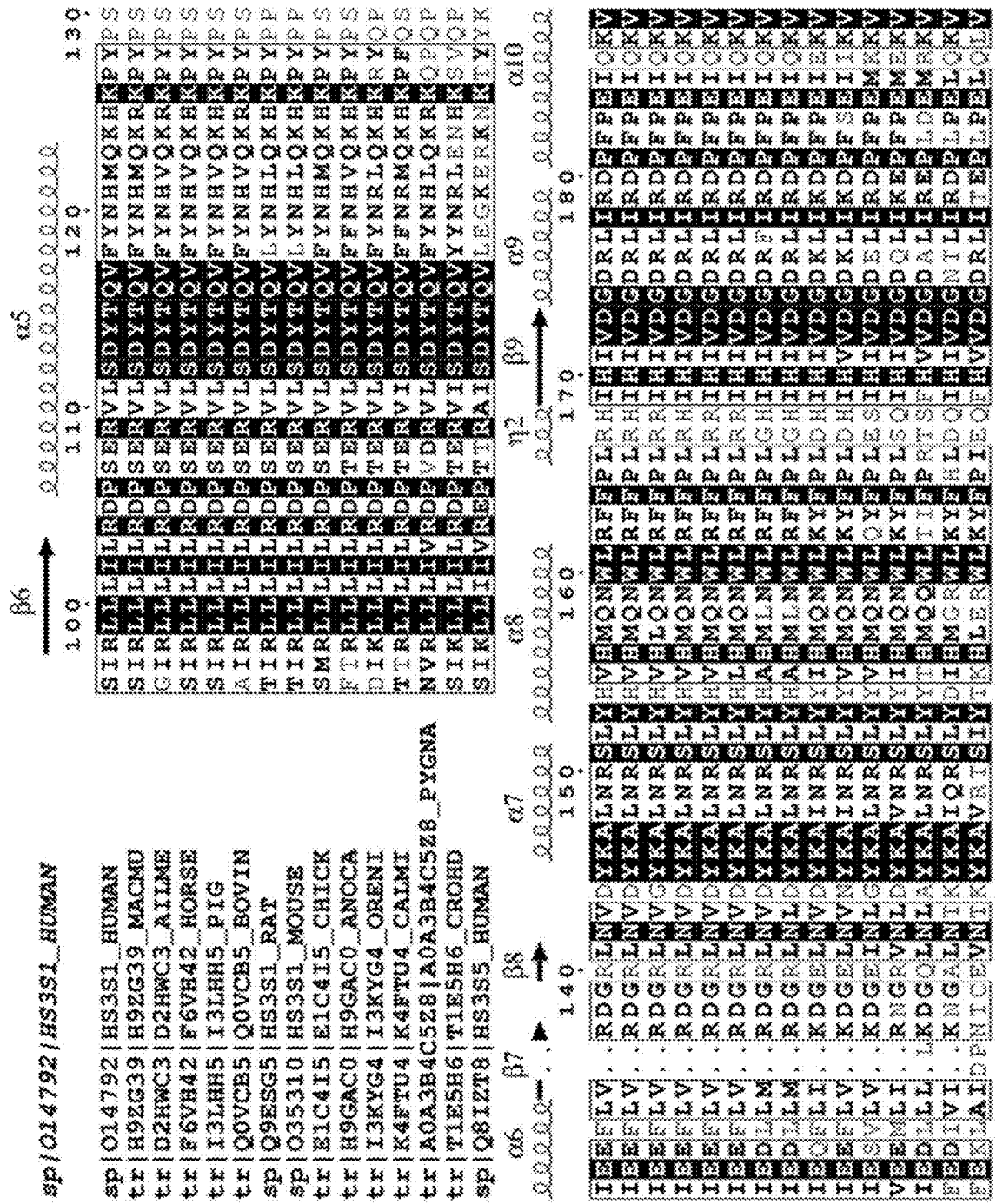
Figure 23C:
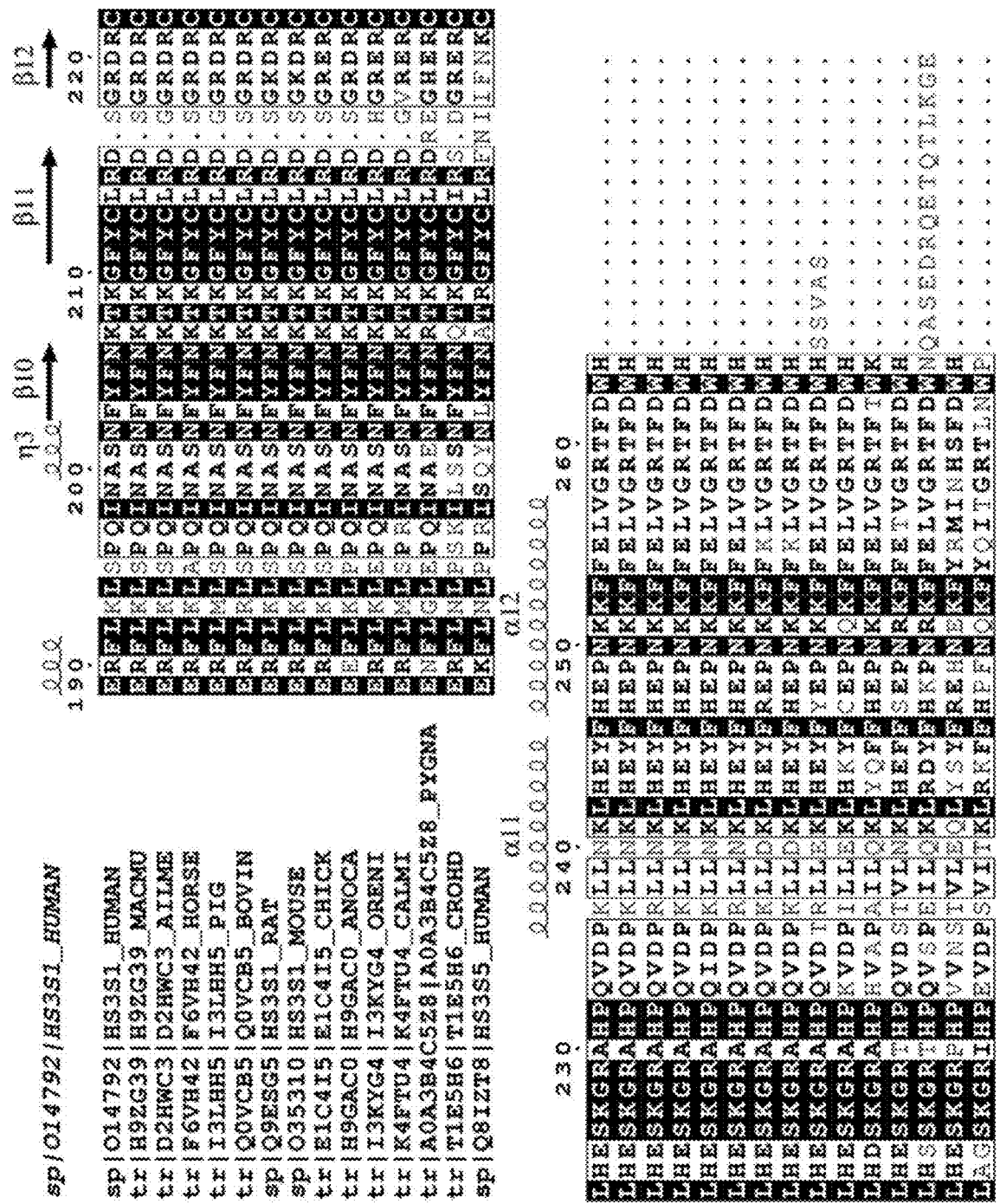
Figure 24:
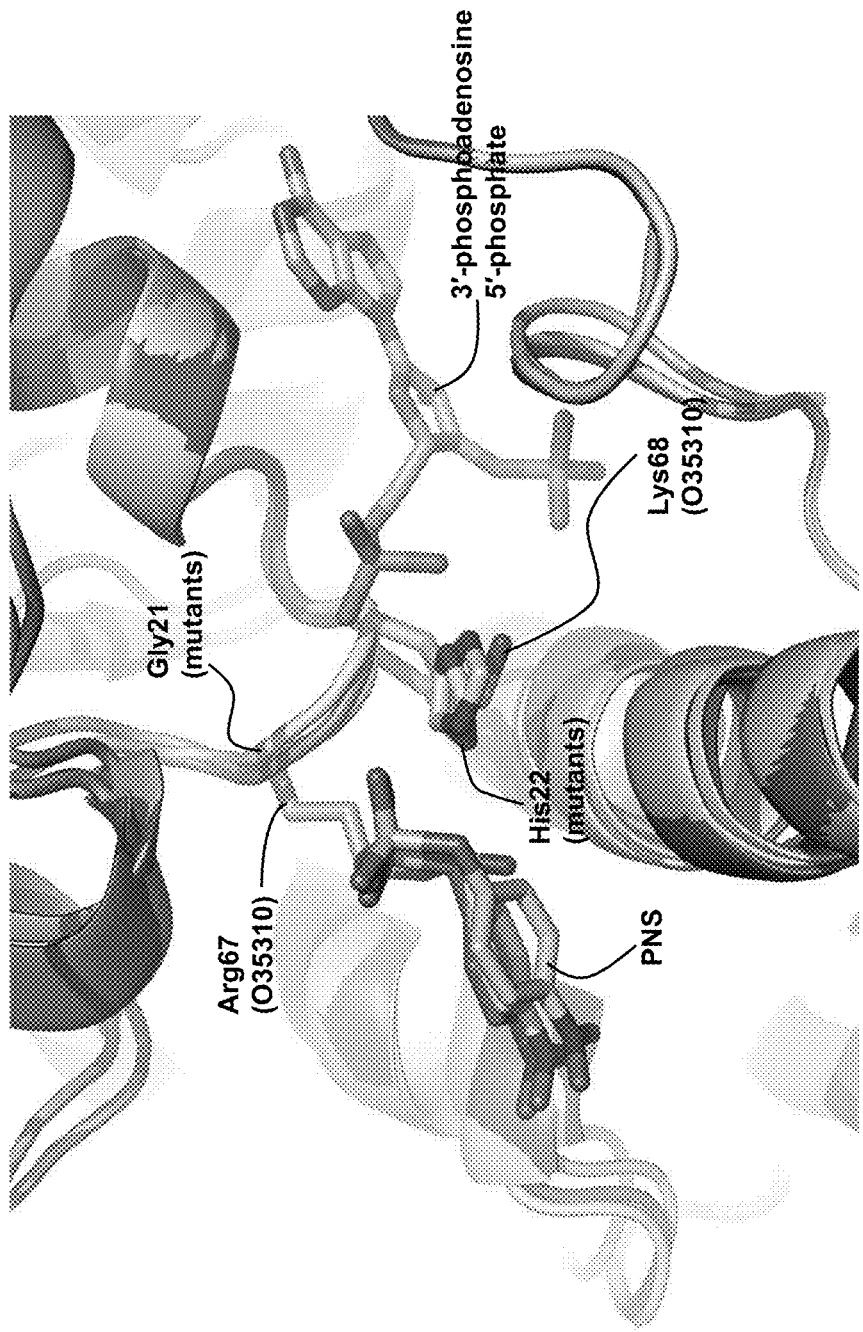
FIG. 24 shows a three-dimensional model of an aryl sulfate compound bound within the active sites of three superimposed engineered 3OST enzymes, which themselves are superimposed over the crystal structure of PAPS bound within the mouse 3OST1 enzyme.

Further, it is believed that several of the conserved amino acid sequence motifs are directly involved in binding of either PAPS and/or the polysaccharide, or participate in the chemical reaction itself. The identity between the natural 3OST enzymes can be demonstrated by comparing the amino acid sequence of a particular enzyme with 3OST enzymes that have known crystal structures in which amino acid residues within the active site have been identified, including the mouse (PDB code: 3UAN) and human (PDB code: 1ZRH) 3OST1 enzymes, which have nearly identical active sites and overall structures even though they have only an 83% sequence identity with one another. A multiple sequence alignment of fifteen enzymes within EC 2.8.2.23, including the mouse and human enzymes, is shown in FIGS. 23A-23C, along with the percent identity of each sequence relative to a human 3OST reference sequence (UniProtKB Accession No. O14792). As illustrated in FIGS. 23A-23C, sequences range from having 98% identity with the O14792 reference sequence (entry tr|H9ZG39|H9ZG39_MACMU) for the rhesus monkey 3OST, down to 53% identity (entry sp|Q8IZT8|HS3S5_HUMAN) for human 3OST5. Those skilled in the art would appreciate that the multiple sequence alignment was limited to fifteen sequences for clarity, and that there are hundreds of amino acid sequences encoding for natural 3OST enzymes that have been identified and that have highly conserved active site and/or binding regions as well.

Within FIGS. 23A-23C, amino acids that are depicted in white with a black background at a particular position, are 100% identical across all sequences. Amino acids that are highly conserved, meaning that the amino acids are either identical or chemically or structurally similar, at a particular position are enclosed with a black outline. Within highly conserved regions, consensus amino acids that are present in a majority of the sequences, are in bold. Amino acids at a particular position that are not identical or highly conserved are typically variable. A period within a sequence indicates a gap that has been inserted into the sequence in order to facilitate the sequence alignment with other sequence(s) that have additional residues between highly conserved or identical region. Finally, above each block of sequences are a series of arrows and coils that indicate secondary structure that is conserved across all sequences, based on the identity of the amino acids within the alignment and using the structure of the natural human sulfotransferase enzyme as a reference. The β symbol adjacent to an arrow refers to a β-sheet, whereas a coil adjacent to an α symbol or a η symbol refers to a helix secondary structure.

Within the fifteen aligned sequences in FIGS. 23A-23C, there are several conserved amino acid sequence motifs that include one or more amino acids that comprise the active site, based on the crystal structures of the mouse (entry sp|O35310|HS3S1_MOUSE) and human 3OST1 (entry sp|O14792|HS3S1_HUMAN) enzymes described above. Based on the numbering of the amino acid residues within FIGS. 23A-23C, these motifs include residues 16-27 (including G-V-R-K-G-G from residues 18-23), residues 43-48 (E-V/I-H-F-F-D), residues 78-81 (P-A/G-Y-F), residues 112-117 (including S-D-Y-T-Q-V), and residues 145-147 (Y-K-A). It is believed that these residues either facilitate or participate in the chemical reaction, or enable binding of PAPS or the polysaccharide within the active site. In particular, within residues 43-48, as described above and as illustrated in FIG. 1, the glutamic acid residue at position 43 abstracts the proton from the 3-O position of the N-sulfoglucosamine residue within the polysaccharide, enabling the nucleophilic attack and removal of the sulfo group from PAPS, whereas His-45 and Asp-48 coordinate to stabilize the transition state of the enzyme before the sulfurylated polysaccharide product is released from the active site.

However, as described above, the natural 3OST enzymes are unable to catalyze the transfer of the sulfate group from an aryl sulfate compound to a polysaccharide. Without being limited by a particular theory, and as with the NSTs, 2OSTs, and the 6OSTs described above, it is believed that the binding pocket for PAPS within the active site of the natural sulfotransferase either does not have a high enough affinity for aryl sulfate compounds to facilitate binding and/or that the aryl sulfate compounds are sterically hindered from entering the active site. Consequently, and in another embodiment, a natural 3OST enzyme can be mutated in several locations within its amino acid sequence to enable binding of the aryl sulfate compound within the active site and/or to optimally position the aryl sulfate compound so transfer of the sulfate group to the polysaccharide can occur.

Accordingly, and in another embodiment, engineered 3OST enzymes that can be utilized with methods of the present invention can be mutants of natural 3OST enzymes within EC 2.8.2.23, including enzymes having the amino acid sequences illustrated in FIGS. 23A-23C. In another embodiment, the engineered 3OST enzymes have been engineered to recognize, bind, and react with aryl sulfate compounds as sulfo group donors, while retaining the natural enzymes' ability to recognize, bind, and react with any of the HS polysaccharides described above, including but not limited to those comprising the structure of Formula X, as sulfo group acceptors. Without being limited by a particular theory, it is believed that because of the mutations inserted into the amino acid sequences of the engineered 3OST enzymes, their sulfotransferase activity may comprise the direct transfer of a sulfuryl group from an aryl sulfate compound to the sulfo acceptor polysaccharide, using a similar mechanism as described in FIG. 1, above, except that the PAPS is substituted with the aryl sulfate compound. Otherwise, it is believed that the mutations may cause the sulfotransferase activity to comprise a two-step process including the hydrolysis of an aryl sulfate compound and formation of a sulfohistidine intermediate, followed by the nucleophilic attack of the sulfohistidine intermediate by the oxygen atom at the 3-O position of a glucosamine residue, to form a 3-O sulfated product. In another embodiment, the 3-O sulfated HS product is an N,2,3,6-HS product.

In another embodiment, an engineered 3OST enzyme can comprise one or more mutated amino acid sequence motifs relative to the conserved amino acid sequence motifs found in natural 3OST enzymes within EC 2.8.2.23, as described above and indicated in the multiple sequence alignment in FIGS. 23A-23C. In another embodiment, each mutated amino acid sequence motif that is present in the amino acid sequence of the engineered enzyme comprises at least one amino acid mutation relative to the corresponding conserved amino acid sequence motif within the natural 3OST enzymes. In another embodiment, an engineered 3OST enzyme can comprise one mutated amino acid sequence motif. In another embodiment, an engineered 3OST enzyme can comprise two mutated amino acid sequence motifs. In another embodiment, an engineered 3OST enzyme can comprise three mutated amino acid sequence motifs. In another embodiment, an engineered 3OST enzyme can comprise four mutated amino acid sequence motifs. In another embodiment, an engineered 3OST enzyme can comprise five mutated amino acid sequence motifs. In another embodiment, an engineered 3OST enzyme that includes at least one mutated amino acid sequence motif relative to any of the natural 3OST enzymes within EC 2.8.2.23 can have an amino acid sequence selected from the group consisting of SEQ ID NO: 24, SEQ ID NO: 26, SEQ ID NO: 28, SEQ ID NO: 51, SEQ ID NO: 52, SEQ ID NO: 53, SEQ ID NO: 54, SEQ ID NO: 56, SEQ ID NO: 57, and SEQ ID NO: 58.

In another embodiment, upon viewing the crystal structure of the mouse 3OST1 enzyme within a 3D molecular visualization system (including, as a non-limiting example, the open-source software, PyMOL), the structure of related sequences, such as those of engineered 3OST enzymes that contain one or more mutated amino acid sequence motifs relative to the mouse 3OST1 (UniProtKB Accession No. 035310) structure, can be modeled for comparison as illustrated in FIG. 24. FIG. 24 shows a magnified view of the active site of the mouse 3OST enzyme (PDB code: 3UAN) with three engineered 3OST enzymes, comprising the amino acid sequences of SEQ ID NO: 24, SEQ ID NO: 26, and SEQ ID NO: 28. Adenosine 3',5'-diphosphate, which is the product of a sulfotransfer reaction in which PAPS is the sulfo donor, and which was co-crystallized with the mouse 3OST, is also illustrated within the active site. PNS is also modeled into the active site of the engineered enzymes, using the consensus solutions of molecular dynamics (MD) simulations that designed to calculate the optimized position and orientation of a ligand within an enzyme active site adjacent to the polysaccharide binding site (not shown), if such solutions are possible. Hydrogen atoms are not shown for clarity.

As illustrated in FIG. 24, although there are several mutations made to SEQ ID NO: 24, SEQ ID NO: 26, and SEQ ID NO: 28, relative to the natural mouse sulfotransferase, the respective protein backbones are in a nearly identical location to one another, enabling a one-to-one comparison of the active sites. However, when comparing the two active sites, the adenosine 3',5'-diphosphate product from the natural sulfotransfer reaction is adjacent to the lysine residue, whereas the convergent solutions from the above MD simulations indicate that PNS binding within the engineered enzymes is favored on the opposite side of the active site. Without being limited by a particular theory, it is believed that the convergent MD simulation solutions place PNS on the opposite side of the active site because there is not enough of an affinity toward PNS in the same or similar position as PAPS. Yet, despite the apparent differences in the binding pocket for PAPS and PNS, engineered 3OST enzymes comprising the amino acid sequences of SEQ ID NO: 24, SEQ ID NO: 26, and SEQ ID NO: 28 all achieved sulfo transfer from an aryl sulfate compound to the glucosaminyl 3-O position within an N,2,6-HS, as described in the examples below.

Further, the arginine residue corresponding to position 20 of the mouse 3OST1, and conserved in all of the other 3OST enzymes illustrated in FIGS. 23A-23C, if present in an engineered 3OST enzyme, would block PNS from binding in the position indicated in FIG. 24. Accordingly, and in another embodiment, engineered 3OST enzymes that bind PNS can comprise a mutation of the active site arginine residue to a glycine residue, which removes all steric hindrance for PNS to bind within the binding pocket. As indicated in the amino acid sequences for SEQ ID NO: 24, SEQ ID NO: 26, SEQ ID NO: 28, SEQ ID NO: 51, SEQ ID NO: 52, SEQ ID NO: 53, and SEQ ID NO: 54, the arginine to glycine mutation is at position 21. As indicated in the amino acid sequences for SEQ ID NO: 56, SEQ ID NO: 57, and SEQ ID NO: 58, the arginine to glycine mutation is at position 99.

Similarly, the next amino acid residue in each of the engineered enzymes, corresponding to position 22 in the amino acid sequences SEQ ID NO: 24, SEQ ID NO: 26, SEQ ID NO: 28, SEQ ID NO: 51, SEQ ID NO: 52, SEQ ID NO: 53, SEQ ID NO: 54, is mutated to a histidine residue. Without being limited by a particular theory, it is believed that the mutation to a histidine residue from the conserved lysine residue (corresponding to position 21 in each of the amino acid sequences in FIGS. 23A-23C) facilitates removal of the sulfate group from PNS, using a similar mechanism described by Malojcic, et al., above. As indicated in the amino acid sequences for SEQ ID NO: 56, SEQ ID NO: 57, and SEQ ID NO: 58, the lysine to histidine residue is at position 100.

Those skilled in the art would appreciate that engineered 3OST enzymes of any other amino acid sequence, including, but not limited to, those disclosed by SEQ ID NO: 51, SEQ ID NO: 52, SEQ ID NO: 53, SEQ ID NO: 54, SEQ ID NO: 56, SEQ ID NO: 57, and SEQ ID NO: 58, would exhibit a similar structure would exhibit similar structural motifs as engineered enzymes having the amino acid sequences of SEQ ID NO: 24, SEQ ID NO: 26, and SEQ ID NO: 28, particularly within the active site. Without being limited by a particular theory, it is also believed that NCS would bind in a similar position as PNS within the active site of any of the engineered enzymes, since the structures of the two aryl sulfate compounds are very similar, except that the sulfate group is located ortho on the aromatic ring relative to the nitro group, rather than para to the nitro group.

In another embodiment, engineered 3OST enzymes that can be utilized in accordance with methods of the present invention can comprise one or more mutated amino acid sequence motifs, which can be determined in-part by comparing conserved amino acid sequence motifs indicated in the multiple sequence alignment of FIGS. 23A-23C with the known structure(s) of natural enzymes and/or modeled engineered enzymes, including but not limited to, as a non-limiting example, enzymes illustrated in FIG. 24. In another embodiment, mutated amino acid sequence motifs that can be comprised within an engineered 3OST enzyme can be selected from the group consisting of (a) G-V-G-H-G-G; (b) H-S-Y-F; (c) S-$X_1$-$X_2$-T-H-$X_3$, wherein $X_1$ is selected from the group consisting of alanine and leucine; $X_2$ is selected from the group consisting of tyrosine and glycine, and $X_3$ is selected from the group consisting of methionine and leucine; and (d) Y-$X_4$-G, wherein $X_4$ is selected from the group consisting of valine and threonine; including any combination thereof. Each of the mutated amino acid sequence motifs corresponds with a conserved amino acid motif indicated in FIGS. 23A-23C above: the mutated amino acid sequence motif G-V-G-H-G-G corresponds to the conserved amino acid sequence motif G-V-R-K-G-G; the mutated amino acid sequence motif H—S-Y-F corresponds to the conserved amino acid sequence motif P-A/G-Y-F; the mutated amino acid sequence motif S-$X_1$-$X_2$-T-H-$X_3$ corresponds to the conserved amino acid sequence motif S-D-Y-T-Q-V; and the mutated amino acid sequence motif Y-$X_4$-G corresponds to the conserved amino acid sequence motif Y-K-A. In another embodiment, an engineered 3OST enzyme comprising each of the mutated amino acid sequence motifs above can be selected from the group consisting of: SEQ ID NO: 24, SEQ ID NO: 26, SEQ ID NO: 28, SEQ ID NO: 51, SEQ ID NO: 52, SEQ ID NO: 53, SEQ ID NO: 54, SEQ ID NO: 56, SEQ ID NO: 57, and SEQ ID NO: 58.

In another embodiment, each of the mutated amino acid sequence motifs can comprise at least one mutation that is made relative to the conserved amino acids found in the natural 3OST enzymes within EC 2.8.2.23. In another embodiment, mutated amino acid sequence motif (a) contains an R-K to G-H mutation, relative to the conserved amino acid sequence motif, G-V-R-K-G-G. In another embodiment, mutated amino acid sequence motif (b) contains a P-A/G to an H-S mutation relative to the conserved amino acid sequence motif, P-A/G-Y-F. In another embodiment, in addition to potential mutations made at the $X_1$, $X_2$, and $X_3$ positions, mutated amino acid sequence motif (c) comprises a Q to H mutation, relative to the conserved amino acid sequence motif, S-D-Y-T-Q-V. In another embodiment, in addition to a mutation at the $X_4$ position, mutated amino acid sequence motif (d) comprises an A to G mutation, relative to the conserved amino acid sequence motif, Y-K-A.

In another embodiment, $X_1$ is alanine, $X_2$ is tyrosine; $X_3$ is methionine, and $X_4$ is valine or threonine. In other embodiments, $X_1$ is leucine, $X_2$ is glycine, $X_3$ is leucine, and $X_4$ is threonine. Without being limited to another theory, it is believed that one or more of the mutations comprised within mutated amino acid sequence motifs (b), (c), and (d) play a role in stabilizing the transition state of the enzyme during the chemical reaction, or in increasing the affinity of aryl sulfate compounds to the active site, including by reducing the size of the binding pocket, increasing the hydrophobicity of the pocket, and/or creating $\pi$-$\pi$ interactions with the aromatic moieties of the aryl sulfate compounds.

Figure 25:
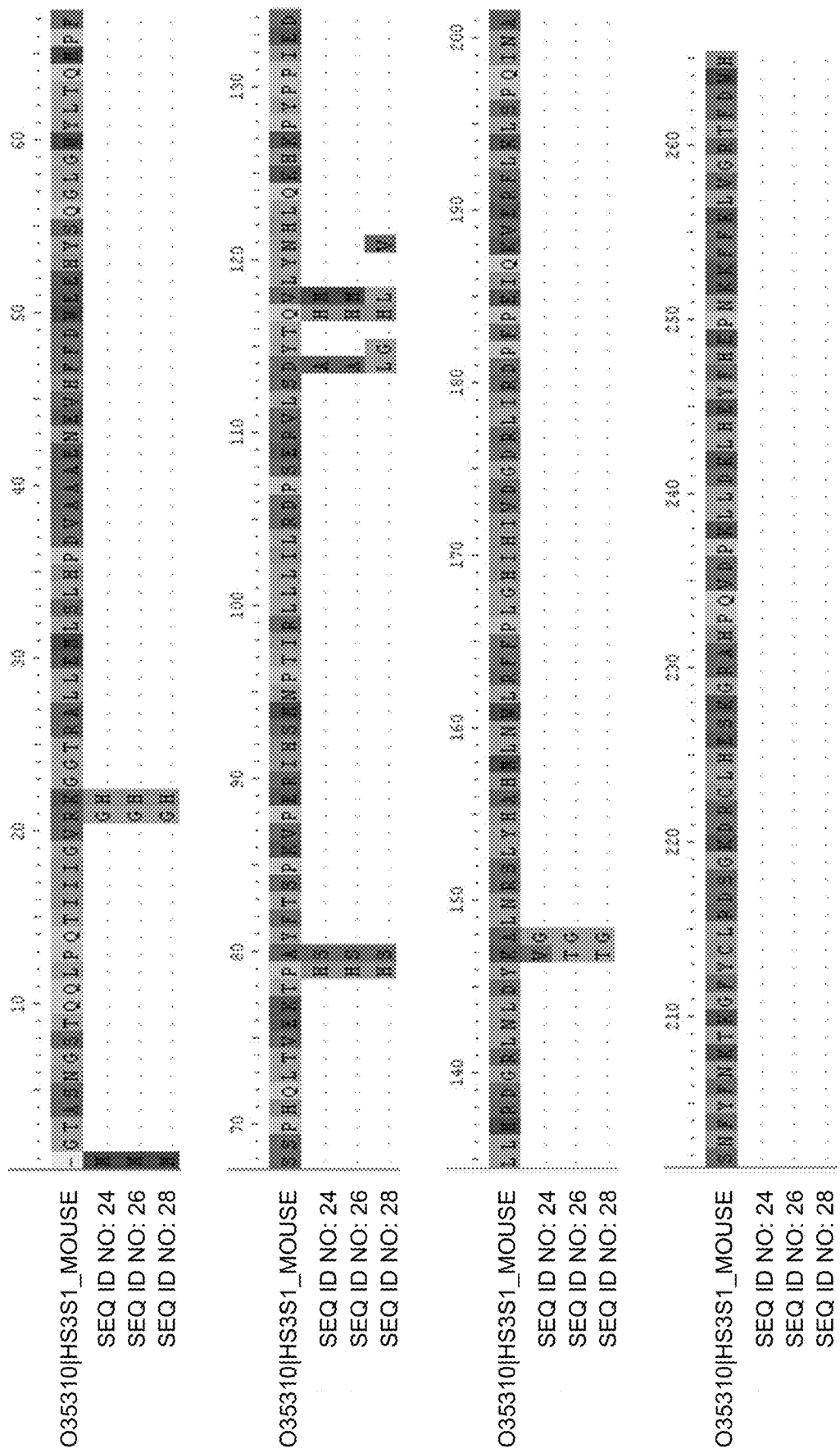
FIG. 25 shows a sequence alignment of polypeptides comprising the amino acid sequences of SEQ ID NO: 24, SEQ ID NO: 26, and SEQ ID NO: 28, respectively, depicting the position and identity of amino acid residues differences between each of the illustrated sequences and relative to the mouse 3OST1 enzyme.

Furthermore, the amino acid sequences (SEQ ID NO: 24, SEQ ID NO: 26, SEQ ID NO: 28) of three engineered 3OST enzymes, which have been experimentally determined to be active with aryl sulfate compounds as sulfo group donors (see Example 5 below) can be compared with the amino acid sequence of the first isoform of the human 3OST enzyme (entry sp|O14792|HS3S1_HUMAN) in a multiple sequence alignment to determine if there are relationships between mutations among each of the enzymes. A period within the amino acid sequence of an engineered enzyme indicates identity at a particular position with the human 3OST enzyme. As shown in FIG. 25, the sequence alignment demonstrates that while over 90% of the amino acid residues within the three sulfotransferase sequences are identical, there are several positions in which multiple amino acids can be chosen. Without being limited by a particular theory, these enzymes have a similar relationship with each other as the 3OST enzymes that comprise EC 2.8.2.23. As a result, and in another embodiment, an engineered 3OST enzyme comprising an amino acid sequence in which multiple amino acids can be chosen at defined positions is disclosed as SEQ ID NO: 51. Positions at which the identity of an amino acid can be chosen from a selection of possible residues are denoted in terms "Xaa," "Xn," or "position n," where n refers to the residue position.

In another embodiment, within an engineered 3OST enzyme comprising the amino acid sequence of SEQ ID NO: 51, the amino acid residue at position 114 is alanine and the amino acid residue at position 118 is methionine. In further embodiments, the amino acid residue at position 147 is selected from the group consisting of valine and threonine.

In another embodiment, within an engineered 3OST enzyme comprising the amino acid sequence of SEQ ID NO: 51, the amino acid residue at position 114 is leucine, the amino acid residue at position 118 is leucine, and the amino acid residue at position 121 is valine. In further embodiments, the amino acid residue at position 115 is glycine. In even further embodiments, the amino acid residue at position 147 is threonine.

In another embodiment, within an engineered 3OST enzyme comprising the amino acid sequence of SEQ ID NO: 51, the amino acid sequence can optionally include one or more mutations at residue positions not specified by an "Xn" or "Xaa," so long as any such mutations do not eliminate the 3OST and/or aryl sulfate-dependent activity of the enzyme. In another embodiment, such mutations not eliminating aryl sulfate-dependent activity at positions not specified by an "Xn" or "Xaa" can include substitutions, deletions, and/or additions.

Accordingly, in another embodiment, an engineered 3OST enzyme utilized in accordance with any of the methods of the present invention can comprise an amino acid sequence selected from the group consisting of SEQ ID NO: 24, SEQ ID NO: 26, SEQ ID NO: 28, SEQ ID NO: 51, SEQ ID NO: 52, SEQ ID NO: 53, SEQ ID NO: 54, SEQ ID NO: 56, SEQ ID NO: 57, and SEQ ID NO: 58. In another embodiment, any of the above engineered 6OST enzymes react with an aryl sulfate compound, instead of PAPS, as a sulfo group donor. In further embodiments, the aryl sulfate compound is selected from the group consisting of PNS, MUS, 7-hydroxycoumarin sulfate, phenyl sulfate, 4-acetylphenyl sulfate, indoxyl sulfate, 1-naphthyl sulfate, 2-naphthyl sulfate, and NCS. In some even further embodiments, the aryl sulfate compound is PNS. In other even further embodiments, the aryl sulfate compound is NCS.

In Vitro Synthesis of Sulfated Polysaccharides

As described above, natural sulfotransferases that recognize, bind, and react with heparosan-based polysaccharides as sulfo group acceptors have the ability to produce a wide range of sulfated polysaccharide products in vivo, including heparin (see Desai, U. R., et al., (1998) *J. Biol. Chem.* 273 (13):7478-7487). The medical use of heparin has been well documented for decades including, but are not limited to, inactivation of Factor IIa (thrombin) and/or Factor Xa, two proteins that are vital in the blood-clotting cascade. In particular, when heparin binds to antithrombin (AT), it causes a conformational change in the enzyme that enables the formation of a ternary complex between the polysaccharide, AT, and either thrombin or Factor Xa (see Li, W., et al., (2004) *Nat. Struct. Mol. Biol.* 11 (9):857-862, the disclosure of which is incorporated by reference in its entirety). In order to bind with AT and induce its conformational change, polysaccharides within the heparin composition must have a specific five-residue AT-recognition sequence, which is identical to the structure of Formula I, described above.

While anticoagulation can be induced by binding antithrombin with an oligosaccharide consisting only of the AT-recognition sequence, there is typically an enhanced inhibition of blood clotting when the polysaccharide comprises more than five sugar residues (see Grey, E., et al., (2008) *Thromb. Haemost.* 99:807-818, the disclosure of which is incorporated by reference in its entirety). As reported by Grey, et al, a secondary binding interaction can be formed between the N,2,3,6-HS polysaccharide and thrombin when the polysaccharide comprises at least thirteen sugar residues on either side of the AT-recognition sequence to act as a "bridge" that facilitates binding to thrombin while also being bound to AT. As a result, heparin polysaccharides typically require a minimum of eighteen sugar residues in order to potentially form the ternary complex between itself, AT, and thrombin. However, and without being limited by a particular theory, it is believed that because the distribution of the AT-recognition sequence within a particular polysaccharide molecule is random, some polysaccharides between eighteen and thirty-one sugar residues can theoretically comprise an AT-recognition sequence toward the center of the molecule that does not have thirteen adjacent sugar residues on either side. Consequently, N,2,3,6-HS polysaccharides typically must comprise at least thirty-two sugar residues to ensure that the thirteen residue "bridge" adjacent to the AT-recognition sequence can be formed, no matter where the AT-recognition sequence is within the molecule.

As described above, the hallmark of nearly all sulfotransferases, whether they are utilized in either in vitro or an in vivo sulfotransfer reaction, is that they universally and exclusively recognize PAPS as the sulfo group donor, as described in U.S. Pat. Nos. 5,541,095, 5,817,487, 5,834,282, 6,861,254, 8,771,995, 9,951,149, and U.S. Pat. Pubs. 2009/0035787, 2013/0296540, and 2016/0122446, the disclosures of which are incorporated by reference in their entireties. These include sulfotransferases in which a polysaccharide is a sulfo group acceptor, particularly HS sulfotransferases that take part in the production of anticoagulant and non-anticoagulant N,2,3,6-HS products. Currently, because PAPS is expensive and unstable in solution, the most convenient and economically feasible method to obtain anticoagulant N,2,3,6-HS polysaccharides in large quantities is to isolate them from animal sources, particularly pigs and cattle, rather than to synthesize them in vitro, even when a coupled, enzymatic PAPS regeneration system (see U.S. Pat. No. 6,255,088, above) is employed. Without being limited by a particular theory, utilizing any of the engineered aryl sulfate-dependent sulfotransferases described above to catalyze one or more of the sulfotransfer reactions in the production of N,2,3,6-HS polysaccharides can reduce the industry's reliance on using PAPS as a sulfo group donor, and if an engineered aryl sulfate-dependent sulfotransferase is utilized in all of the enzymatic sulfotransfer steps, the need to use PAPS can be obviated entirely.

Accordingly, methods for synthesizing an N,2,3,6-HS product can comprise any combination of natural or engineered sulfotransferase enzymes, so long as at least one of the reactions comprises an engineered aryl sulfate-dependent sulfotransferase enzyme and an aryl sulfate compound. In some embodiments, methods for synthesizing an N,2,3,6-HS product can comprise the following steps: (a) providing a starting polysaccharide reaction mixture comprising N-deacetylated heparosan; (b) combining the starting polysaccharide reaction mixture with a reaction mixture comprising a sulfo group donor and a first sulfotransferase enzyme selected from the group consisting of an NST enzyme, a 2OST enzyme, and a 6OST enzyme, to form a first sulfated polysaccharide; (c) combining the first sulfated polysaccharide with a reaction mixture comprising a sulfo group donor and a second sulfotransferase enzyme, wherein the second sulfotransferase enzyme is one of the two enzymes that were not selected in step (b), to form a second sulfated polysaccharide; (d) combining the second sulfated polysaccharide with a reaction mixture comprising a sulfo group donor and a third sulfotransferase enzyme, wherein the third sulfotransferase enzyme is the enzyme that was not selected in step (b) or step (c), to form a third sulfated polysaccharide; and (e) combining the third sulfated polysaccharide with a reaction mixture comprising a sulfo group donor and a 3OST enzyme, to form the N,2,3,6-HS product. Reaction mixtures that do not comprise an engineered sulfotransferase enzyme can comprise PAPS and a natural HS sulfotransferase enzyme that possesses biological activity with PAPS as the sulfo group donor. In another embodiment, the reaction mixture that comprises the 2OST enzyme further comprises a glucuronyl $C_5$-epimerase enzyme.

In another embodiment, when the NST enzyme is an engineered enzyme, the enzyme can comprise an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40. In another embodiment, when the 2OST enzyme is an engineered enzyme, the enzyme can comprise an amino acid sequence selected from the group consisting of SEQ ID NO: 14, SEQ ID NO: 16, SEQ ID NO: 41, and SEQ ID NO: 42. In another embodiment, when the 6OST enzyme is an engineered enzyme, the enzyme can comprise an amino acid sequence selected from the group consisting of SEQ ID NO: 18, SEQ ID NO: 20, SEQ ID NO: 22, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 59, SEQ ID NO: 60, and SEQ ID NO: 61. In another embodiment, when the 3OST enzyme is an engineered enzyme, the enzyme can comprise an amino acid sequence selected from the group consisting of SEQ ID NO: 24, SEQ ID NO: 26, SEQ ID NO: 28, SEQ ID NO: 51, SEQ ID NO: 52, SEQ ID NO: 53, SEQ ID NO: 54, SEQ ID NO: 56, SEQ ID NO: 57, and SEQ ID NO: 58.

In another embodiment, the NST enzyme is the first sulfotransferase enzyme, the 2OST enzyme is the second sulfotransferase enzyme, and the 6OST enzyme is the third sulfotransferase enzyme.

In another embodiment, aryl sulfate compounds used as sulfo group donors can be selected from the group consisting of PNS, MUS, 7-hydroxycoumarin sulfate, phenyl sulfate, 4-acetylphenyl sulfate, indoxyl sulfate, 1-naphthyl sulfate, 2-naphthyl sulfate, and NCS. In even further embodiments, the aryl sulfate compound for an engineered sulfotransferase is PNS. In other even further embodiments, the aryl sulfate compound for an engineered sulfotransferase is NCS.

In another embodiment, the N-deacetylated heparosan within the starting polysaccharide mixture comprises the structure of Formula II. In another embodiment, the third sulfated polysaccharide is an N,2,6-HS product. In another embodiment, the N,2,6-HS product comprises the structure of Formula IX. In another embodiment, the N,2,6-HS product comprises the structure of Formula X. In another embodiment, the N,2,3,6-HS product has anticoagulant activity. In another embodiment, the N,2,3,6-HS product comprises an AT-recognition sequence comprising the structure of Formula I. In another embodiment, the N,2,3,6-HS product comprising an AT-recognition sequence comprises N,2,3,6-HS polysaccharides having at least five sugar residues. In another embodiment, the N,2,3,6-HS product comprising an AT-recognition sequence comprises N,2,3,6-HS polysaccharides having at least eight sugar residues. In another embodiment, the N,2,3,6-HS product comprising an AT-recognition sequence comprises N,2,3,6-HS polysaccharides having at least eighteen sugar residues. In another embodiment, the N,2,3,6-HS product comprising an AT-recognition sequence comprises N,2,3,6-HS polysaccharides having at least thirty-two sugar residues.

In another embodiment, anticoagulant N,2,3,6-HS polysaccharides produced by methods of the present invention can be characterized by the degree of inhibitory activity that they have against Factor Xa and thrombin, termed "anti-Xa" activity and "anti-IIa" activity, respectively. The amount of inhibition induced by anticoagulant polysaccharides is often measured in International Units per milligram (IU mg$^{-1}$) and less often as International Units per milliliter (IU mL$^{-1}$). In either case, an International Unit is an amount approximately equivalent to the quantity required to keep 1-mL of cat's blood fluid for 24 hours at 0° C. Typically, the measurable anti-Xa activity of anticoagulant N,2,3,6-HS polysaccharides is at least about 1 IU mg$^{-1}$, including at least about 50 IU mg$^{-1}$, at least 75 IU mg$^{-1}$, 100 IU mg$^{-1}$, 150 IU mg$^{-1}$, 200 IU mg$^{-1}$, or 500 IU mg$^{-1}$, up to at least about 1,000 IU mg$^{-1}$, and the measurable anti-IIa activity of anticoagulant N,2,3,6-HS polysaccharides is at least about 1 IU mg$^{-1}$, including at least about 10 IU mg$^{-1}$, 25 IU mg$^{-1}$, 50 IU mg$^{-1}$, 100 IU mg$^{-1}$, 150 IU mg$^{-1}$, or 180 IU mg$^{-1}$, up to at least about 200 IU mg$^{-1}$. For anticoagulant N,2,3,6-HS polysaccharides within heparin that are thirty-two sugar residues or longer, and are able to form the tertiary complex with AT and thrombin, the ratio of anti-Xa activity to anti-IIa activity is usually close to 1:1, particularly in a range of 0.9:1 to 1.1:1 (see Keire, D. A., et al., (2011) *Anal. Bioanal. Chem.* 399:581-591, the disclosure of which is incorporated by reference in its entirety). However, as the chain length decreases below thirty-two sugar residues and anticoagulant N,2,3,6-HS polysaccharides are not ensured of interacting with thrombin, the anti-Xa to anti-IIa ratio can increase, up to at least about 10.0:1, up to at least 100:1. Consequently, in another embodiment, the ratio of anti-Xa activity to anti-IIa activity of the N,2,3,6-HS product is at least 0.5:1, including at least 0.75:1, 0.9:1, 1:1, 1.1:1, 1.3:1, 1.5:1, 2.0:1, 3.0:1, 4.0:1, 5.0:1, 6.0:1, 7.0:1, 8.0:1, 9.0:1, 10.0:1, 20:1, 40:1, 60:1, or 80:1, up to at least 100:1. In another embodiment, the ratio of anti-Xa activity to anti-IIa activity of the N,2,3,6-HS product is less than 100:1, including less than 80:1, 60:1. 40:1, 20:1, 10.0:1, 9.0:1, 8.0:1, 7.0:1, 6.0:1, 5.0:1, 4.0:1, 3.0:1, 2.0:1, 1.5:1, 1.3:1, 1.1:1, 0.9:1, or 0.75:1, down to less than 0.5:1. In another embodiment, particularly from about 0.9 to about 1.1. In another embodiment, the ratio of anti-Xa activity to anti-IIa activity of an N,2,3,6-HS product comprising polysaccharides having thirty-two or more sugar residues is in a range from 0.5:1 up to 0.75:1, or 0.9:1, or 1:1, or 1.1:1, or 1.3:1, or 1.5:1, or 2.0:1, or 3.0:1, or 4.0:1, or 5.0:1, or 6.0:1, or 7.0:1, or 8.0:1, or 9.0:1, or 10.0:1. In another embodiment, the ratio of anti-Xa activity to anti-IIa activity of an N,2,3,6-HS product comprising polysaccharides having thirty-two or more sugar residues is in a range from 0.75:1 up to 0.9:1, or 1:1, or 1.1:1, or 1.3:1, or 1.5:1, or 2.0:1, or 3.0:1, or 4.0:1, or 5.0:1, or 6.0:1, or 7.0:1, or 8.0:1, or 9.0:1, or 10.0:1. In another embodiment, the ratio of anti-Xa activity to anti-IIa activity of an N,2,3,6-HS product comprising polysaccharides having thirty-two or more sugar residues is in a range from 0.9:1 up to 1:1, or 1.1:1, or 1.3:1, or 1.5:1, or 2.0:1, or 3.0:1, or 4.0:1, or 5.0:1, or 6.0:1, or 7.0:1, or 8.0:1, or 9.0:1, or 10.0:1. In another embodiment, the ratio of anti-Xa activity to anti-IIa activity of an N,2,3,6-HS product comprising polysaccharides having thirty-two or more sugar residues is in any range listed above between and inclusive of 0.5:1 and 10.0:1. In some preferred embodiments, the ratio of anti-Xa activity to anti-IIa activity of an N,2,3,6-HS product comprising polysaccharides having thirty-two or more sugar residues is in a range from 0.9:1 up to 1:1.

Similarly, all polysaccharide mixtures, including N,2,3,6-HS product mixtures, can be characterized by their weight-average molecular weight ($\overline{M}_w$). Because substantially all of the heparins either isolated from animal sources or synthesized in vitro are obtained as a polydisperse mixture of polysaccharides with different chain lengths and degrees of sulfation, expressing the average molecular weight as a weight average, rather than a number average (i.e. a true arithmetic mean ($\overline{M}_n$), is often the most advantageous because it accounts for the effect larger molecules have on anticoagulation. The $\overline{M}_w$ of a polysaccharide mixture can be measured experimentally using light scattering methods or analytical ultracentrifugation (see Mulloy, B., et al., (2014) *Anal. Bioanal. Chem.* 406:4815-4823, the disclosure of which is incorporated by reference in its entirety). However, determining the $\overline{M}_n$, typically by size exclusion chromatography, can still be useful because the ratio between $\overline{M}_w$ and $\overline{M}_n$ can provide valuable insight into the amount of polydispersity in a particular polysaccharide sample.

In particular, heparin is generally divided into multiple classes based on their average molecular weights, particularly their $\overline{M}_w$. Samples of low-molecular weight heparin (LMWH) typically have an $\overline{M}_w$ of less than 8,000 Da, in which more than 60% of all of the polysaccharide molecules within the sample have an actual molecular weight of less than 8,000 Da (see Linhardt, R. J. and Gunay, N. S., (1999) *Seminars in Thrombosis and Hemostasis* 25 (Suppl. 3):5-16, the disclosure of which is incorporated by reference in its entirety). LMWH is typically prepared by chemically or enzymatically modifying animal-sourced unfractionated heparin or API heparin. Unfractionated heparin typically haa an $\overline{M}_w$ of greater than 8,000 Da. To be approved for use in medical treatments, API heparin has strict molecular weight guidelines that must be met, namely: (1) the proportion of polysaccharides within the composition having a molecular weight over 24,000 Da is not more than 20%; (2) the $\overline{M}_w$ of the composition itself is between 15,000 Da and 19,000 Da; and (3) the ratio of the number of polysaccharides within the composition having a molecular weight between 8,000 Da and 16,000 Da relative to the number of polysaccharides within the composition having a molecular weight between 16,000 Da and 24,000 Da is not less than 1.0:1 (see Mulloy, B., et al., above).

Thus, in another embodiment, the N,2,3,6-HS product that is synthesized according to methods of the present invention can comprise a plurality of N,2,3,6-HS polysaccharides, and can have one or more molecular weight properties that are identical to API heparin. In another embodiment, the N,2,3,6-HS product has an $\overline{M}_w$ of at least 1,000 Da, including at least 2,000 Da, 3,000 Da, 4,000 Da, 5,000 Da, 6,000 Da, 7,000 Da, 8,000 Da, 9,000 Da, 10,000 Da, 11,000 Da, 12,000 Da, 13,000 Da, 14,000 Da, 15,000 Da, 16,000 Da, 17,000 Da, 18,000 Da, 19,000 Da, 20,000 Da, 21,000 Da, 22,000 Da, 23,000 Da, or 24,000 Da, up to at least 50,000 Da. In another embodiment, the N,2,3,6-HS product has an $\overline{M}_w$ of less than 50,000 Da, including less than 24,000 Da, 23,000 Da, 22,000 Da, 21,000 Da, 20,000

Da, 19,000 Da, 18,000 Da, 17,000 Da, 16,000 Da, 15,000 Da, 14,000 Da, 13,000 Da, 12,000 Da, 11,000 Da, 10,000 Da, 9,000 Da, 8,000 Da, 7,000 Da, 6,000 Da, 5,000 Da, 4,000 Da, or 3,000 Da, down to less than 2,000 Da. In another embodiment, the N,2,3,6-HS product has an $\overline{M}_w$ in a range from 1,000 up to 2,000 Da, or 3,000 Da, or 4,000 Da, or 5,000 Da, or 6,000 Da, or 7,000 Da, or 8,000 Da, or 9,000 Da, or 10,000 Da, or 11,000 Da, or 12,000 Da, or 13,000 Da, or 14,000 Da, or 15,000 Da, or 16,000 Da, or 17,000 Da, or 18,000 Da, or 19,000 Da, or 20,000 Da, or 21,000 Da, 22,000 Da, or 23,000 Da, or 24,000 Da. In another embodiment, the N,2,3,6-HS product has an $\overline{M}_w$ in a range from 2,000 Da up to 3,000 Da, or 4,000 Da, or 5,000 Da, or 6,000 Da, or 7,000 Da, or 8,000 Da, or 9,000 Da, or 10,000 Da, or 11,000 Da, or 12,000 Da, or 13,000 Da, or 14,000 Da, or 15,000 Da, or 16,000 Da, or 17,000 Da, or 18,000 Da, or 19,000 Da, or 20,000 Da, or 21,000 Da, 22,000 Da, or 23,000 Da, or 24,000 Da. In another embodiment, the N,2,3,6-HS product is unfractionated after being produced. In another embodiment, the unfractionated N,2,3,6-HS product has an $\overline{M}_w$ in a range from 8,000 Da up to 9,000 Da, or 10,000 Da, or 11,000 Da, or 12,000 Da, or 13,000 Da, or 14,000 Da, or 15,000 Da, or 16,000 Da, or 17,000 Da, or 18,000 Da, or 19,000 Da, or 20,000 Da, or 21,000 Da, 22,000 Da, or 23,000 Da, or 24,000 Da. In another embodiment, the anticoagulant N,2,3,6-HS product is an LMW-HS product. In another embodiment, the anticoagulant LMW-HS product has an $\overline{M}_w$ in a range from 2,000 Da up to 3,000 Da, or 4,000 Da, or 5,000 Da, or 6,000 Da, or 7,000 Da, or 8,000 Da. In another embodiment, the anticoagulant N,2,3,6-HS product has an $\overline{M}_w$ in a range from 15,000 Da up to 16,000 Da, or 17,000 Da, or 18,000 Da, or 19,000 Da. In another embodiment, the N,2,3,6-HS product can have an $\overline{M}_w$ in any range listed above between and inclusive of 1,000 Da and 24,000 Da, and preferably in any range listed above between and inclusive of 15,000 Da and about 19,000 Da.

In another embodiment, less than 50%, including less than 45%, 40%, 35%, 30%, 25%, 20%, 15%, 10%, 5%, 3%, or 2%, down to less than 1% of the N,2,3,6-HS polysaccharides within the N,2,3,6-HS product have a molecular weight greater than 24,000 Da. In some preferred embodiments, less than or equal to 20% of the N,2,3,6-HS polysaccharides within the N,2,3,6-HS product have a molecular weight greater than 24,000 Da. In another embodiment, when less than or equal to 20% of the N,2,3,6-HS polysaccharides within the N,2,3,6-HS product have a molecular weight greater than 24,000 Da, the N,2,3,6-HS product can have an $\overline{M}_w$ in any range listed above between and inclusive of 1,000 Da and 24,000 Da, and preferably in any range listed above between and inclusive of 15,000 Da and about 19,000 Da.

In another embodiment, the relative amount of N,2,3,6-HS polysaccharides having a molecular weight between 8,000 Da and 16,000 Da within an N,2,3,6-HS product can be compared as a ratio with the relative amount of N,2,3,6-HS polysaccharides having a molecular weight between 16,000 Da and 24,000 Da within the same N,2,3,6-HS product. In another embodiment, the ratio of the number of polysaccharides within the composition having a molecular weight between 8,000 Da and 16,000 Da relative to the number of polysaccharides within the composition having a molecular weight between 16,000 Da and 24,000 Da is not less than 0.5:1, including not less than 0.75:1, 0.9:1, 1.0:1, 1.1:1, 1.3:1, or 1.5:1, up to not less than 2.0:1, and preferably not less than 1.0:1. In another embodiment, N,2,3,6-HS products in which the ratio of the number of polysaccharides within the composition having a molecular weight between 8,000 Da and 16,000 Da relative to the number of polysaccharides within the composition having a molecular weight between 16,000 Da and 24,000 Da is not less than 1.0:1 can also have an $\overline{M}_w$ in any range listed above between and inclusive of 1,000 Da and 24,000 Da, and preferably in any range listed above between and inclusive of 15,000 Da and about 19,000 Da, in which less than or equal to 20% of the N,2,3,6-HS polysaccharides within the N,2,3,6-HS product have a molecular weight greater than 24,000 Da.

In another embodiment, N,2,3,6-HS products prepared by any of the methods of the present invention can satisfy any of the benchmark requirements determined by the USP for API heparin, including but not limited to composition, purity, activity, and/or molecular weight. In another embodiment, the anticoagulant N,2,3,6-HS product can possess any of the properties selected from the group consisting of: an anti-IIa activity of not less than 180 IU mg$^{-1}$; an anti-Xa activity of not less than 180 IU mg$^{-1}$; a ratio of anti-Xa to anti-IIa activity in a range of 0.9:1 up to 1.1:1, preferably 1:1; an $\overline{M}_w$ of in a range of 15,000 Da up to 19,000 Da; not more than 20% of the polysaccharides having a molecular weight greater than 24,000 Da; and the ratio of polysaccharides within the composition having a molecular weight between 8,000 Da and 16,000 Da relative to the number of polysaccharides within the composition having a molecular weight between 16,000 Da and 24,000 Da is not less than 1.0:1; including any combination thereof. In another embodiment, anticoagulant N,2,3,6-HS products prepared by any of the methods of the present invention can possess all of the following anticoagulant activity and molecular weight properties: an anti-IIa activity of not less than 180 IU mg$^{-1}$; an anti-Xa activity of not less than 180 IU mg$^{-1}$; a ratio of anti-Xa to anti-IIa activity in a range of 0.9:1 up to 1.1:1, preferably 1:1; an $\overline{M}_w$ of in a range of 15,000 Da up to 19,000 Da; not more than 20% of the polysaccharides having a molecular weight greater than 24,000 Da; and the ratio of polysaccharides within the composition having a molecular weight between 8,000 Da and 16,000 Da relative to the number of polysaccharides within the composition having a molecular weight between 16,000 Da and 24,000 Da is not less than 1.0:1. In another embodiment, anticoagulant N,2,3,6-HS products prepared by any of the methods of the present invention have a substantially equivalent anticoagulant activity and molecular weight properties relative to API heparin (CAS No: 9041-08-1), which is widely commercially-available.

In another embodiment, anticoagulant N,2,3,6-HS products can satisfy benchmark requirements determined by the USP for API heparin with regard to product purity, particularly purity from other sulfated polysaccharides, including but not limited to chondroitin sulfate. In particular, over-sulfated chondroitin sulfate (OSCS) was determined to be the source of contamination within pharmaceutical heparin compositions that caused hundreds of deaths worldwide in 2007 and 2008. In another embodiment, and without being limited by a particular theory, preparations of the N,2,3,6-HS product formed by any of the methods of the present invention can be prepared substantially or completely free from chondroitin sulfate, particularly OSCS, because it is believed that the N-deacetylated heparosan starting material, which can either obtained commercially or after modifying heparosan isolated from bacteria (described in further detail below), itself is free of chondroitin sulfate.

In another embodiment, in order to arrive at N,2,3,6-HS products that meet any of the USP molecular weight benchmarks for API heparin, the molecular weight of any of the polysaccharides utilized as sulfo group acceptors can be controlled. In a non-limiting example, and in another embodiment, the molecular weight properties of the heparosan-based polysaccharides used as starting materials can be controlled by chemically modifying heparosan until a target set of molecular weight properties is reached. As described below, heparosan can be obtained from commercial sources or isolated from bacterial or eukaryotic sources.

In particular, heparosan and other heparosan-based polysaccharides such as heparin are found in several forms of life and have several different functions. In eukaryotes, they operate as sulfo acceptors and/or precursors in the formation of heparan sulfate and heparin. Heparosan and heparosan-based polysaccharides can also be found within bacteria as a capsule that regulates cell entry by metabolites and other exogenous materials. Such bacteria, include, but are not limited to *Pasteurella multocida* and *Escherichia coli* (*E. coli*). In some embodiments, heparosan can be extracted and purified from *E. coli*, particularly K5 strain of *E. coli*, as a polydisperse mixture of polysaccharide molecules having varying molecular weights. Procedures for isolating heparosan from the K5 strain of *E. coli* are discussed and provided in Wang, Z., et al., (2010) *Biotechnol. Bioeng.* 107 (6):964-973, the disclosure of which is incorporated by reference in its entirety; see also DeAngelis, P. L. (2015) *Expert Opinion on Drug Delivery* 12 (3):349-352; Ly, M., et al., (2010) *Anal. Bioanal. Chem.* 399:737-745; and Zhang, C., et al., (2012) *Metabolic Engineering* 14:521-527, the disclosures of which are also incorporated in their entireties. However, because substantially all of the heparosan isolated from bacteria, including *E. coli*, is N-acetylated, it cannot be used directly as a sulfo acceptor for any of the sulfotransferases described herein and utilized in accordance with the methods of the present invention. As a result, heparosan must be at least partially N-deacetylated before it can be utilized as a sulfo group acceptor.

As a result, and in another embodiment, heparosan can be at least partially N-deacetylated by treating it with a base, particularly lithium hydroxide or sodium hydroxide (see Wang, Z., et al., (2011) *Appl. Microbiol. Biotechnol.* 91 (1):91-99, the disclosure of which is incorporated by reference in its entirety; see also PCT publication PCT/US2012/026081, the disclosure of which is incorporated by reference in its entirety). In another embodiment, the base is sodium hydroxide. Depending on the degree of N-deacetylation desired, the concentration of the heparosan, and the concentration of the base, one skilled in the art can determine how long to incubate heparosan with the base according to the procedures described in Wang, et al., (2011), above.

In another embodiment, heparosan can be incubated with a base, preferably sodium hydroxide, until a desired amount of N-acetylated glucosamine residues remains within the N-deacetylated product. In another embodiment, N-acetyl glucosamine residues can comprise less than 60%, including less than 30%, 20%, 18%, 16%, 14%, 12%, or 10%, down to less than 5%, and preferably in a range from 12% and up to 18%, of the glucosamine residues within the N-deacetylated heparosan product. In another embodiment, the N-acetyl glucosamine can comprise about 15% of the glucosamine residues within the N-deacetylated heparosan product.

Additionally, and without being limited by a particular theory, it is believed that in addition to N-deacetylating glucosamine residues, the reaction between heparosan and a base can simultaneously depolymerize the heparosan polysaccharides and reduce their molecular weight, which can in turn reduce the $\overline{M}_W$ of the N-deacetylated heparosan composition. Typically, heparosan polysaccharides isolated from bacteria, including but not limited to *E. coli*, have a molecular weight ranging from about 3,000 Da to about 150,000 Da, and compositions of isolated heparosan can have a $\overline{M}_w$ in the range of about 25,000 Da up to about 50,000 Da (see Ly, M., et al. and Wang, et al., (2011), above). In another embodiment, and independent from its starting $\overline{M}_w$ and overall molecular weight properties, a heparosan composition either obtained from commercial sources or isolated from bacteria, including but not limited to *E. coli*, can be treated with a base, preferably sodium hydroxide, for a time sufficient to reduce the $\overline{M}_w$ of the N-deacetylated heparosan product to a target or desired level. In another embodiment, the depolymerized, N-deacetylated heparosan product has an $M_w$ of at least 1,000 Da, including at least 2,000 Da, 4,000 Da, 6,000 Da, 7,000 Da, 8,000 Da, 8,500 Da, 9,000 Da, 9,500 Da, 10,000 Da, 10,500 Da, 11,000 Da, 11,500 Da, 12,0001 Da, 12,500 Da, 13,000 Da, 13,500 Da, 14,000 Da, 15,000 Da, 16,000 Da, or 18,000 Da, up to at least 20,000 Da. In another embodiment, the depolymerized, N-deacetylated heparosan product has an $\overline{M}_w$ of less than 20,000 Da, including less than 18,000 Da, 16,000 Da, 15,000 Da, 14,000 Da, 13,500 Da, 13,000 Da, 12,500 Da, 12,000 Da, 11,500 Da, 11,000 Da, 10,500 Da, 10,000 Da, 9,500 Da, 9,000 Da, 8,500 Da, 8,000 Da, 7,000 Da, 6,000 Da, or 4,000 Da, down to less than 2,000 Da. In another embodiment, the depolymerized, N-deacetylated heparosan product has an $\overline{M}_w$ in a range from 1,000 up to 2,000 Da, or 4,000 Da, or 6,000 Da, or 7,000 Da, or 8,000 Da, or 8,500 Da, or 9,000 Da, or 9,500 Da, or 10,000 Da, or 10,500 Da, or 11,000 Da, or 11,500 Da, or 12,000 Da, or 12,500 Da, or 13,000 Da, or 13,500 Da, or 14,000 Da, or 15,000 Da, or 16,000 Da, or 18,000 Da, or 20,000 Da. In another embodiment, the anticoagulant N,2,3,6-HS product has an $\overline{M}_w$ in a range from 7,000 Da up to 8,000 Da, or 8,500 Da, or 9,000 Da, or 9,500 Da, or 10,000 Da, or 10,500 Da, or 11,000 Da, or 11,500 Da, or 12,000 Da, or 12,500 Da, or 13,000 Da, or 13,500 Da, or 14,000 Da, or 15,000 Da. In another embodiment, the depolymerized, N-deacetylated heparosan product has an $\overline{M}_w$ in a range from 9,000 Da up to 9,500 Da, or 10,000 Da, or 10,500 Da, or 11,000 Da, or 11,500 Da, or 12,000 Da, or 12,500 Da. In another embodiment, the depolymerized, N-deacetylated heparosan product can have an $\overline{M}_w$ in any range listed above between and inclusive of 1,000 Da and 20,000 Da, and preferably in any range listed above between and inclusive of 9,000 Da and 12,500 Da.

In another embodiment, a heparosan composition can be treated with a base, preferably sodium hydroxide, for a time sufficient to both reduce the $\overline{M}_W$ of the N-deacetylated heparosan product to a target or desired level, and to attain a desired amount of glucosamine residues that remain N-acetylated within the N-deacetylated heparosan product. Methods for providing a starting polysaccharide reaction mixture comprising N-deacetylated heparosan comprise the following sub-steps: (a) providing a precursor polysaccharide composition comprising heparosan; and (b) combining the precursor polysaccharide composition with a reaction mixture comprising a base, preferably lithium hydroxide or sodium hydroxide, for a time sufficient to N-deacetylate at least one of the N-acetylated glucosamine residues within the heparosan, forming the N-deacetylated heparosan composition. In another embodiment, the N-deacetylated heparosan product can have an $\overline{M}_w$ in any range listed above between and inclusive of 1,000 Da and 20,000 Da, simultaneously with having less than 60% of the glucosamine residues within the N-deacetylated heparosan product present as N-acetylglucosamine residues. In another embodiment, the N-deacetylated heparosan product can have an $\overline{M}_w$ in any range listed above between and inclusive of 9,000 Da and 12,500 Da, in which from 12% and up to 18% of the glucosamine residues within the N-deacetylated heparosan product are N-acetylated. The preparation of N-deacetylated heparosan having such molecular weight properties and N-acetyl content is described in detail in Wang, et al., (2011), above. In another embodiment, the time sufficient to react a heparosan with a base, preferably sodium hydroxide, to form an N-deacetylated heparosan product having an $\overline{M}_w$ in a range between 9,000 Da and 12,500 Da, as well as an N-acetyl glucosamine content in a range from 12% and up to 18%, can be at least 1 hour, including at least 2, 4, 6, 8, 10, 12, or 18 hours, and up to at least 24 hours, depending on the molecular weight properties and concentration of the heparosan starting material, and the identity and concentration of the base used to carry out the reaction.

In another embodiment, N-deacetylated heparosan can be combined with an N-sulfation agent within a reaction mixture to form N-sulfated heparosan. As described above, and in another embodiment, the N-sulfation agent can comprise any of the natural or engineered NST enzymes described above. In another embodiment, when the N-sulfation agent is a natural NST, the reaction mixture can also comprise PAPS as a sulfo group donor. In another embodiment, when the N-sulfation agent is an engineered NST, the reaction mixture can also comprise an aryl sulfate compound, preferably PNS or NCS, as a sulfo group donor.

In another embodiment, N-deacetylated heparosan can be chemically N-sulfated, rather than being enzymatically N-sulfated. In another embodiment, the N-sulfation agent is a chemical agent, preferably sulfur trioxide and/or one or more sulfur-trioxide containing compounds or adducts. Chemical N-sulfation of glucosamine residues within polysaccharides using sulfur trioxide is commonly known in the art (see Lloyd, A. G., et al., (1971) *Biochem. Pharmacol.* 20 (3):637-648; Nadkarni, V. D., et al., (1996) *Carbohydrate Research* 290:87-96; Kuberan, B., et al., (2003) *J. Biol. Chem.* 278 (52):52613-52621; Zhang, Z., et al., (2008) *J. Am. Chem. Soc.* 130 (39):12998-13007; and Wang, et al., (2011), above; see also U.S. Pat. No. 6,991,183 and U.S. Pat. Pub. 2008/020789, the disclosures of which are incorporated by reference in their entireties). Sulfur trioxide complexes are generally mild enough bases to enable the selected N-sulfation of polysaccharides without causing depolymerization, unlike sodium hydroxide (see Gilbert, E. E., (1962) *Chem. Rev.* 62 (6):549-589). Non-limiting examples of sulfur trioxide-containing complexes include sulfur dioxide-pyridine, sulfur dioxide-dioxane, sulfur dioxide-trimethylamine, sulfur dioxide-triethylamine, sulfur dioxide-dimethylaniline, sulfur dioxide-thioxane, sulfur dioxide-Bis(2-chloroethyl) ether, sulfur dioxide-2-methylpyridine, sulfur dioxide-quinoline, or sulfur dioxide-dimethylformamide. In another embodiment, the N-sulfation agent comprises a sulfur trioxide-containing adduct selected from the group consisting of a sulfur trioxide-trimethylamine adduct and a sulfur trioxide-pyridine adduct. In another embodiment, the N-sulfation agent comprises a sulfur trioxide-trimethylamine adduct.

In another embodiment, N-sulfation, particularly chemical N-sulfation, can comprise the first sulfation step, with respect to N-deacetylated heparosan. Subsequently, after the N-deacetylated heparosan is either enzymatically or chemically N-sulfated, the N-sulfated heparosan can then be further sulfated using a 2OST, 6OST, and 3OST. In embodiments in which an anticoagulant N,2,3,6-HS product is formed, enzymatic sulfation steps occur in the order of 2-O, 6-O, and 3-O sulfation. As described above, the 3OST enzyme, and preferably all of the sulfotransferase enzymes, are engineered aryl-sulfate dependent sulfotransferase enzymes, and the reactions are performed in the absence of PAPS. In another embodiment, the reaction mixture comprising the 2OST enzyme further comprises a glucuronyl $C_5$-epimerase enzyme, preferably a glucuronyl $C_5$-epimerase enzyme comprising the amino acid sequence of SEQ ID NO: 29, and more preferably a glucuronyl $C_5$-epimerase enzyme comprising the amino acid sequence of residues 34-617 of SEQ ID NO: 29. In another embodiment, the N,2,3,6-HS product comprises anticoagulant activity. In another embodiment, the N,2,3,6-HS product comprises an AT-recognition sequence comprising the structure of Formula I.

In another embodiment, any of the methods for forming an N,2,3,6-HS product described above can be performed sequentially, and each sulfated polysaccharide product can be isolated and purified prior to being treated with another sulfotransferase in a subsequent step. In another embodiment, at least two of the steps can be performed in a single pot, and the sulfated polysaccharide product can be isolated and purified from that pot before being utilized in a subsequent sulfotransfer step. In another embodiment, one non-limiting combination of sulfotransfer reactions that can take place in a single pot includes N-sulfation and 2-O sulfation steps, after which the N,2-HS product is isolated and purified prior to reacting with the 6OST. Without being limited by a particular theory, the N-sulfated HS product can either be utilized a sulfo acceptor for the 2OST enzyme directly and/or the reaction mixture can comprise any of the glucuronyl $C_5$-epimerase enzymes described above to catalyze the conversion between polysaccharides comprising the structure of Formula IV and Formula V. However, and in still further embodiments, the reaction mixtures and enzymes for any combination of sulfotransferase reactions can be combined within a single pot, including reaction mixtures and enzymes for all four sulfation reactions, and at least a 2OST, a 6OST, and a 3OST.

In another embodiment, within any of the methods for forming an N,2,3,6-HS product described above, any of the reaction mixtures comprising an engineered sulfotransferase and an aryl sulfate compound as a sulfo group donor can further comprise one or more reaction components for repopulating the aryl sulfate compound. In another embodiment, the one or more reaction components comprise an aryl sulfotransferase (ASST) enzyme and a secondary aryl sulfate compound. In nature, aryl sulfotransferase enzymes can catalyze the sulfation of aromatic compounds to form an aryl sulfate compound. Typically, the sulfo donor itself is an aryl sulfate compound. The reactivity of ASST enzymes is generally described, for example, in U.S. Pat. Nos. 6,225,088 and 8,771,995, as well as Malojcic, et al., above, the disclosures of which are incorporated by reference in their entireties. Without being limited by a particular theory, it is believed that including an ASST and a secondary aryl sulfate compound within a reaction mixture comprising an engineered sulfotransferase can have the advantage of reducing potential competitive inhibition of the engineered sulfotransferase by the desulfated aromatic product, as well as repopulating the reaction mixture with the sulfo group donor.

In another embodiment, the secondary aryl sulfate compound can be any aryl sulfate compound, including those described above. In another embodiment, the secondary aryl sulfate compound is the same aryl sulfate compound used as the sulfo group donor for the engineered sulfotransferase enzyme. In another embodiment, the secondary aryl sulfate compound is a different aryl sulfate compound than the one used as the sulfo group donor for the engineered sulfotransferase enzyme. As a non-limiting example, and in another embodiment, if the engineered sulfotransferase has biological activity with NCS as a sulfo group donor, then the secondary aryl sulfate compound is PNS. In another non-limiting example, and in another embodiment, if the engineered sulfotransferase has biological activity with PNS as a sulfo group donor, then the secondary aryl sulfate compound is NCS.

In another embodiment, the ASST enzyme utilized in conjunction with any of the above methods to repopulate the sulfo donor aryl sulfate compound can be any bacterial enzyme, either isolated from in vivo sources or generated recombinantly in vitro, which transfers a sulfo group from an aryl sulfate compound to an aromatic compound. In another embodiment, and in one non-limiting example, the ASST is a recombinant ASST from E. coli, preferably from the E. coli strain CFT073 and having the amino acid sequence of SEQ ID NO: 55. In another embodiment, an ASST enzyme, preferably an ASST enzyme comprising the amino acid sequence of SEQ ID NO: 55, when coupled to any of the engineered sulfotransferases described above, can transfer a sulfate group from the secondary aryl sulfate compound to the desulfated aromatic compound formed by the engineered sulfotransferase. Without being limited by a particular theory, it is believed that utilizing the ASST can reduce potential product inhibition by the desulfated aromatic compound, while also regenerating the sulfo group donor for subsequent sulfotransfer reactions to an HS or heparosan-based polysaccharide.

In another embodiment, and also without being limited by a particular theory, it is believed that coupling the engineered sulfotransferase-catalyzed reaction with ASST can provide a further advantage of generating the aryl sulfate sulfo donor directly from a non-sulfated aromatic compound. The reaction mixture for a particular reaction catalyzed by an engineered sulfotransferase can be formulated to combine a non-sulfated aromatic compound with ASST and a secondary aryl sulfate compound either prior to or simultaneously with addition of the engineered sulfotransferase to the reaction mixture. In a non-limiting example, and in another embodiment, a sulfotransfer reaction catalyzed by an engineered sulfotransferase enzyme can be initiated by combining a non-sulfated aromatic compound, an aryl sulfate compound, and an ASST in the same reaction mixture as the engineered sulfotransferase and the polysaccharide sulfo group acceptor. The reaction between the ASST, the aryl sulfate compound, and the non-sulfated aromatic compound can generate the sulfo donor aryl sulfate compound, which can then react with the engineered sulfotransferase enzyme to transfer the sulfate group to the polysaccharide. In another embodiment, the aryl sulfate compound produced by the reaction with the ASST enzyme is a different compound than the aryl sulfate compound that reacts with ASST itself. In a non-limiting example, the non-sulfated aromatic compound is NCS, and the aryl sulfate compound that reacts with the ASST is PNS. As NCS is formed by the reaction between PNS and ASST, the sulfo group can then be transferred from the NCS to the polysaccharide, using the engineered sulfotransferase.

Post-Synthesis Processing of N,2,3,6-HS Products

As described above, API heparin generally adheres to a tightly-regulated set of molecular weight and activity requirements, whereas LMWH generally has an average molecular weight of less than 8,000 Da, in which more than 60% of all of the polysaccharide molecules within the sample have an actual molecular weight of less than 8,000 Da (see Linhardt, R. J. and Gunay, N. S., above). Furthermore, LMWH drugs have their own regulated set of composition, purity, molecular weight and activity requirements in their own right, and are generally prepared from unfractionated heparin or API heparin. Accordingly, and in another embodiment, N,2,3,6-HS products produced by any of the methods described above can be utilized to produce LMW-HS products, using any well-known means in the art. In another embodiment, the N,2,3,6-HS product produced by any of the methods described above and utilized in the synthesis of an LMW-HS product has anticoagulant activity. In another embodiment, the N,2,3,6-HS product produced by any of the methods described above and utilized in the synthesis of an LMW-HS product has molecular weight and/or anticoagulant activity properties that are identical to API heparin. In another embodiment, the LMW-HS product synthesized from an N,2,3,6-HS product produced by any of the methods described above also has anticoagulant activity. Non-limiting exemplary methods for synthesizing LMW-HS products from N,2,3,6-HS products are described in further detail below.

In one non-limiting example, and in another embodiment, N,2,3,6-HS polysaccharides within an N,2,3,6-HS product mixture that have a low molecular weight, particularly a molecular weight less than 15,000 Da, including less than 14,000 Da, 13,000 Da, 12,000 Da, 11,000 Da, 10,000 Da, 9,000 Da, 8,000 Da, 7,000 Da, 6,000 Da, 5,000 Da, 4,000 Da, or 3,000 Da, down to less than 2,000 can be separated from other N,2,3,6-HS polysaccharides within the same mixture. In another embodiment, N,2,3,6-HS polysaccharides within an N,2,3,6-HS product mixture can be separated by electrophoretic mobility using gel electrophoresis. In another embodiment, N,2,3,6-HS polysaccharides within an N,2,3,6-HS product mixture can be separated by size exclusion chromatography. In another embodiment, N,2,3,6-HS polysaccharides within an N,2,3,6-HS product mixture can be separated by precipitation with salts of a divalent cation and a weak anion, including but not limited to barium, calcium, magnesium, strontium, copper, nickel, cadmium, zinc, mercury, beryllium, palladium, platinum, iron, and tin salts. In another embodiment, the polysaccharides can be separated from higher molecular-weight polysaccharides in bulk, by separating all such N,2,3,6-HS polysaccharides under 15,000 Da from those above 15,000 Da, as a non-limiting example. In another embodiment, the polysaccharides can be separated into one or more fractions, such as 10,000 Da to 15,000 Da, 5,000 Da to 10,000 Da, and all N,2,3,6-HS polysaccharides under 5,000 Da, as another non-limiting example.

In another embodiment, N,2,3,6-HS polysaccharide product mixtures having an average molecular weight less than 8,000 Da can be utilized as LMW-HS products directly. In other embodiments, N,2,3,6-HS polysaccharide product mixtures having an average molecular weight less than 8,000 Da can be combined with other glycosaminoglycans (GAGs) to form HS-GAG mixtures. Although an advantage of several of the methods above, particularly methods in which the heparosan starting material is isolated and purified from E. coli, includes the ability to synthesize N,2,3,6-HS products that are free from chondroitin sulfate, dermatan sulfate, and other sulfated GAGs, some highly-purified HS-GAG mixtures that comprise chondroitin sulfate and/or dermatan sulfate have been successfully prescribed to patients in the past because they have beneficial pharmacological properties relative to heparin, even if they don't possess as much anticoagulant activity as heparin. Non-limiting examples of HS-GAG mixtures that have been prescribed medically include sulodexide (CAS No: 57821-29-1) and danaparoid (CAS No: 308068-55-5). In another embodiment, HS-GAG mixtures formed between an anticoagulant N,2,3,6-HS products synthesized by any of the methods of the present invention and one or more GAGs can have anticoagulant activity.

Historically, sulodexide has been extracted from pig intestinal mucosa (see U.S. Pat. No. 3,936,351, herein incorporated by reference in its entirety), but sulodexide can also be prepared by combining dermatan sulfate (CAS No: 24967-94-0) with the "fast-moving" heparin fractions that can be separated from heparin using salt precipitation (see Volpi, N., (1993) Carbohydr. Res. 247:263-278), particularly with barium salts. Fast-moving heparin fractions (FM-HS) are deemed "fast-moving" based on their electrophoretic mobility relative to heavier, "slow-moving" heparin (SM-HS) that are also formed upon salt precipitation of heparin, and can be purified away from SM-HS, using ultracentrifugation, as a non-limiting example. Additionally, FM-HS fractions have reduced anticoagulant activity and overall sulfation relative to heparin, and a relative molecular mass, $M_r$, as determined by high performance size exclusion chromatography (HPSEC) of about 8,000 (see Volpi, N., above). However, the mean molecular weight of the FM-HS fraction itself is about 7,000 Da (see Coccheri, S. and Mannello, F., (2014) Drug Design, Development, and Therapy 8:49-65).

Further, the FM-HS fractions that are separated from heparin generally have similar chemical properties to other LMWH compositions, including a longer half-life and increased oral bioavailability relative to API heparin. On the other hand, dermatan sulfate generally has minimal to no anticoagulant activity and an average molecular weight of 25 kDa, but has been shown to inhibit arterial and venous thrombosis, and to provide protection against vascular wall damage and inflammation as well as accelerated wound healing. Without being limited by a particular theory, it is believed that the combination of FM-HS and dermatan sulfate within sulodexide can react in combinatory, and potentially synergistic, fashion. (see Coccheri, S. and Mannello, F., above.)

Thus, in another embodiment, FM-HS fractions are prepared from anticoagulant N,2,3,6-HS products synthesized by any of the methods of the present invention, using engineered aryl sulfate-dependent sulfotransferase enzymes. In another embodiment, the N,2,3,6-HS product prepared using the engineered sulfotransferase enzymes can be precipitated with divalent-cationic salt, particularly a barium or calcium salt, using a similar procedure described by Volpi, above. In another embodiment, the N,2,3,6-HS product is substantially equivalent to API heparin. Methods for performing a salt precipitation of API heparin to form and subsequently purify FM-HS are also described in U.S. Pat. Nos. 7,687,479 and 8,609,632, the disclosures of which are herein incorporated by reference in their entireties. In another embodiment, once the resulting FM-HS fraction is purified, it can be combined with dermatan sulfate to form an HS-GAG mixture. In another embodiment, any of the methods of the present invention can be utilized to synthesize FM-HS directly, which can then be combined with dermatan sulfate to form an HS-GAG mixture. In another embodiment, the HS-GAG mixture prepared by either method can comprise one or more properties that are identical to sulodexide, including but not limited to a composition comprising 80% of the FM-HS fraction and 20% of dermatan sulfate (see Lauver, D. A. Lucchesi, B. R., Cardio. DrugRev. 24 (3-4):214-216), an average molecular weight of 7,000 Da, an $M_r$ of about 8,000, and/or a sulfate to carboxyl group ratio in the range of 2.0:1 to 2.2:1.

In contrast to sulodexide, the HS-GAG mixture, danaparoid, has been historically prepared from natural HS isolated from porcine sources, rather than API heparin (see U.S. Pat. No. 5,164,377, herein incorporated by reference in its entirety; see also "Danaparoid Sodium" (2010) European Pharmacopoeia 7.0, 1789-1792). HS polysaccharides, as opposed to heparin, contain disaccharide units that are generally either unsulfated or are N-, 2-O, and/or 6-O sulfated. Without being limited by a particular theory, however, it is believed that disaccharide units comprising 3-O sulfated glucosamine residues are rare within HS, resulting in a dramatically reduced anticoagulant activity relative to heparin. Accordingly, danaparoid also has a reduced activity relative to heparin, generally having an anti-Xa activity of 11-20 IU mg$^{-1}$, an anti-IIa activity of less than 1 IU mg$^{-1}$, and a ratio of anti-Xa activity to anti-IIa activity of not less than 22:1.

Additionally, upon purifying danaparoid according to the procedures in U.S. Pat. No. 5,164,377, the resulting product contains not only HS, but also chondroitin sulfate and dermatan sulfate, that have reduced molecular weights as a result of the addition of a base during the extraction process, similar to the effect of reacting a base with heparosan to reduce the molecular weight. According to the European Pharmacopoeia, the weight-average molecular weight ($\overline{M}_w$) of all of the GAGs within a danaparoid HS-GAG composition suitable to be prescribed to patients is in a range of at least 4,000 Da, up to 7,000 Da, and comprise the following size distribution limits: (a) polysaccharide chains comprising an $M_r$ of less than 2,000 comprise a maximum of 13% (w/w) of the danaparoid mixture; (b) polysaccharide chains comprising an $M_r$ of less than 4,000 comprise a maximum of 39% (w/w) of the danaparoid mixture; (c) polysaccharide chains comprising an $M_r$ between 4,000 and 8,000 comprise a minimum of 50% (w/w) of the danaparoid mixture; (d) polysaccharide chains comprising an $M_r$ of higher than 8,000 comprise a maximum of 19% (w/w) of the danaparoid mixture; and (e) polysaccharide chains comprising an $M_r$ of less than 10,000 comprise a maximum of 11% (w/w) of the danaparoid mixture. With regard to particular composition limits for danaparoid determined by the European Pharmacopoeia, chondroitin sulfate can comprise a maximum of 8.5% (w/w) of the danaparoid mixture, and dermatan sulfate can comprise a range from at least 8.0% (w/w) up to 16.0% (w/w) of the danaparoid mixture. As a non-limiting example, the danaparoid composition Orgaran® comprises about 84% (w/w) HS, about 12% (w/w) dermatan sulfate, and about 4% chondroitin sulfate.

In another embodiment, an HS-GAG mixture comprising an HS product produced by any of the methods of the present invention using engineered aryl sulfate-dependent sulfotransferase enzymes, dermatan sulfate, and chondroitin sulfate can be formed that has similar properties to danaparoid (CAS No: 308068-55-5). In another embodiment, the HS product is an N,2,6-HS product. In another embodiment, the HS product is an N,2,3,6-HS product. In another embodiment, the HS product synthesized directly from the reaction has an $\overline{M}_w$ in a range from at least 4,000 Da, and up to 8,000 Da, preferably in a range from at least 4,000 Da, up to 7,000 Da. In another embodiment, the HS product has an $\overline{M}_w$ larger than 8,000 Da, and is prepared for inclusion in a danaparoid-like HS-GAG mixture by subsequently reacting it with a base, similar to methods described above for depolymerizing heparosan, to reduce its molecular weight. In another embodiment, chondroitin sulfate and dermatan sulfate are reacted with a base to reduce their molecular weight. In another embodiment, a composition comprising an HS product produced by any of the methods of the present invention, chondroitin sulfate, and dermatan sulfate can be filtered using a filtration device. Such filtration devices can include, but are not limited to, centrifugal filter units such as an Amicon© Ultra unit (EMD Millipore), or dialysis membranes, either of which have a desired molecular weight cut-off (MWCO). In another embodiment, the MWCO for either a centrifugal filter unit or dialysis membrane is 5,500 Da. In another embodiment, the $\overline{M}_w$ for all of the GAGs in the danaparoid HS-GAG mixture is in a range from at least 4,000 Da, and up to 8,000 Da, preferably in a range from at least 4,000 Da, and up to 7,000 Da, and more preferably in a range from at least 5,000 Da, and up to 6,000 Da. In another embodiment, GAGs within the danaparoid HS-GAG mixture comprise the following size distribution limits: (a) polysaccharide chains comprising an $M_r$ of less than 2,000 comprise a maximum of 13% (w/w) of the danaparoid HS-GAG mixture; (b) polysaccharide chains comprising an $M_r$ of less than 4,000 comprise a maximum of 39% (w/w) of the danaparoid HS-GAG mixture; (c) polysaccharide chains comprising an $M_r$ between 4,000 and 8,000 comprise a minimum of 50% (w/w) of the danaparoid HS-GAG mixture; (d) polysaccharide chains comprising an $M_r$ of higher than 8,000 comprise a maximum of 19% (w/w) of the danaparoid HS-GAG mixture; and (e) polysaccharide chains comprising an $M_r$ of less than 10,000 comprise a maximum of 11% (w/w) of the danaparoid HS-GAG mixture.

In another embodiment, the danaparoid HS-GAG mixture can comprise a GAG composition that is either similar or identical to danaparoid (CAS No: 308068-55-5). In another embodiment, the composition of the GAGs within the danaparoid HS-GAG mixture comprises at least 8% (w/w), up to 16% (w/w), and preferably 12% (w/w) of dermatan sulfate, and less than 8% (w/w), preferably in a range of at least 3% (w/w), up to 5% (w/w), and more preferably 4% (w/w) of chondroitin sulfate.

In another embodiment, the danaparoid HS-GAG mixture can comprise either a similar or identical anticoagulant activity to danaparoid. In another embodiment, the danaparoid HS-GAG mixture can comprise an anti-Xa activity of 11-20 IU mg$^{-1}$, an anti-IIa activity of less than 1 IU mg$^{-1}$, and/or a ratio of anti-Xa activity to anti-IIa activity of not less than 22:1.

In another embodiment, rather than combining HS products, particularly anticoagulant N,2,3,6-HS products, synthesized according to any of the methods of the present invention to form HS-GAG mixtures, the HS products can instead be further modified by one or more subsequent processes to depolymerize and/or modify the HS product to form an LMW-HS product, as described above. Generally, and in another embodiment, the process for forming an LMW-HS from an anticoagulant N,2,3,6-HS product comprises the following steps: (a) synthesizing an N,2,3,6-HS product according to any of the above methods; (b) providing one or more depolymerization agents; and (c) treating the N,2,3,6-HS product with the one or more depolymerization agents for a time sufficient to depolymerize at least a portion of the N,2,3,6-HS product, thereby forming the LMW-HS product. Without being limited by a particular theory, it is believed that the choice in the depolymerization agent can determine the chemical mechanism for forming the LMW-HS product, as well as the product(s) structure, anticoagulant activity, and pharmacological properties. Known chemical mechanisms for forming an LMW-HS product from pharmaceutical heparin include, but are not limited to: chemical and/or enzymatic β-elimination reactions; deamination reactions; and oxidation reactions, including combinations thereof.

In another embodiment, an N,2,3,6-HS product, synthesized according to any of the methods of the present invention, can be modified by an enzymatic β-elimination reaction to form an enzymatically-depolymerized LMW-HS product. Historically, enzymatically-depolymerized LMW-HS products have been prepared by incubating pharmaceutical heparin with one or more carbon-oxygen lyase enzymes until the LMW-HS product comprises a desired chemical structure, average molecular weight, anticoagulant activity, and degree of sulfation. (see "Tinzaparin Sodium" (2010) *European Pharmacopoeia* 7.0, 3098; see also Linhardt, R. J. and Gunay, N. S., above). As a result of the reaction with the one or more carbon-oxygen lyases, the polysaccharide within the heparin both depolymerize and develop a characteristic chemical structure, illustrated by Formula XI, below.

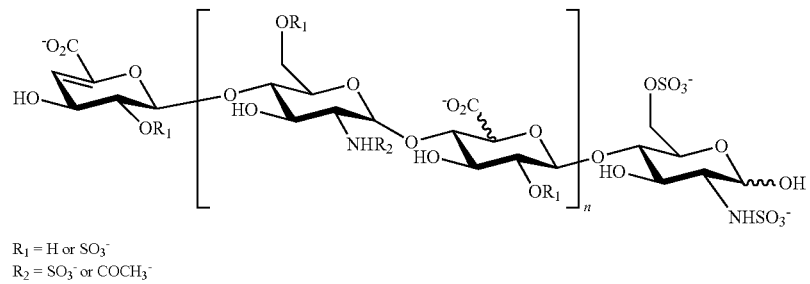

$R_1$ = H or SO$_3^-$
$R_2$ = SO$_3^-$ or COCH$_3^-$

As illustrated above in Formula XI, n can be any integer from 1-25. Instead of a glucuronic acid or uronic acid residue, the sugar residue at the non-reducing end of a majority of the enzymatically-depolymerized LMW-HS polysaccharides within the product is a 2-O-sulfo-4-en-epyranosulfonic acid. Additionally, each glucosamine residue at the reducing end is sulfated at the N- and 6-O positions. Optionally, the 3-O position of a glucosamine residue within one or more of disaccharide units can also be 3-O sulfated. Without being limited by a particular theory, it is believed that at least some of the polysaccharides within the enzymatically-depolymerized LMW-HS product comprises 3-O sulfated glucosamine residues, which ultimately leads to leads to its anticoagulant activity.

Further, much like heparin, enzymatically-depolymerized LMWH products derived from heparin that can be prescribed as anticoagulants must satisfy strict purity and property standards. In particular, one such enzymatically-depolymerized LMWH product, tinzaparin (CAS No: 9041-08-1; ATC code: B01AB10), has a particular set of molecular weight, anticoagulant activity, and sulfation content properties in addition to the chemical structure of Formula XI above, including: an $\overline{M}_w$ in a range from at least 5,500 Da, and up to 7,500 Da, and characteristically 6,500 Da; at least 1.8 and up to 2.5 sulfate groups per disaccharide unit; and an anti-Xa activity of at least 70 IU mg$^{-1}$ and up to 120 IU mg$^{-1}$, and/or a ratio of anti-Xa activity to anti-IIa activity of at least 1.5:1, and up to 2.5:1.

Accordingly, in another embodiment, an N,2,3,6-HS product synthesized according to any of the methods of the present invention described above can subsequently be depolymerized by one or more carbon-oxygen lyases to form an enzymatically-depolymerized LMW-HS product. In another embodiment, the enzymatically-depolymerized LMW-HS product comprises one or more properties that are identical to tinzaparin, including but not limited to chemical structure, molecular weight, anticoagulant activity, and/or sulfation content properties. In another embodiment, the enzymatically-depolymerized LMW-HS product is substantially identical to tinzaparin.

In another embodiment, the enzymatically-depolymerized LMW-HS product can be formed from an N,2,3,6-HS product synthesized according to any of the methods of the present invention described above, according to the following steps: (a) synthesizing an N,2,3,6-HS product according to any of the above methods; (b) providing a reaction mixture comprising at least one carbon-oxygen lyase; and (c) treating the N,2,3,6-HS product with the carbon-oxygen lyase reaction mixture for a time sufficient to depolymerize at least a portion of the N,2,3,6-HS product, thereby forming the enzymatically-depolymerized LMW-HS product. In another embodiment, the enzymatically-depolymerized LMW-HS product comprises the structure of Formula XI. In another embodiment, the N,2,3,6-HS product is an unfractionated N,2,3,6-HS product.

In another embodiment, the at least one carbon-oxygen lyase can be a carbon-oxygen lyase from any species, so long as the enzyme catalyzes β-eliminative cleavage of HS polysaccharides. In another embodiment, the at least one carbon-oxygen lyase can be selected from the group consisting of the carbon-oxygen lyases from *Bacteroides eggerthii* comprising the amino acid sequences of SEQ ID NO: 30, SEQ ID NO: 31, and SEQ ID NO: 32. In another embodiment, the at least one carbon-oxygen lyase can comprise one, two, or all three of the enzymes having the amino acid sequences of SEQ ID NO: 30, SEQ ID NO: 31, and SEQ ID NO: 32, respectively.

In another embodiment, the time sufficient to form the enzymatically-depolymerized LMW-HS product is the time sufficient to cause the product to have a desired average molecular weight. In another embodiment, the $\overline{M}_w$ of the enzymatically-depolymerized LMW-HS product can be in the range of 2,000 Da to 10,000 Da, preferably 5,500 Da to 7,500 Da, and more preferably 6,500 Da. In another embodiment, the enzymatically-depolymerized LMW-HS product can have anticoagulant activity. In another embodiment, the enzymatically-depolymerized LMW-HS product has an anti-Xa activity of at least 70 IU mg$^{-1}$ and up to 120 IU mg$^{-1}$, and/or a ratio of anti-Xa activity to anti-IIa activity of at least 1.5:1, and up to 2.5:1.

In another embodiment, an N,2,3,6-HS product, synthesized according to any of the methods of the present invention, can be modified by a chemical β-elimination reaction to form a chemically β-eliminative, LMW-HS product. Historically, chemically β-eliminative LMWH products have been prepared by treating pharmaceutical heparin or its quaternary ammonium salt with a base. Under these conditions, chemical β-elimination takes place, forming the chemically β-eliminative LMW-HS product that contains a 4,5-unsaturated uronic acid residue at the non-reducing end, a feature observed in enzymatically-depolymerized LWMH polysaccharides comprising the structure of Formula XI (see Linhardt, R. J. and Gunay, N. S., above). Control of the reaction conditions has led to the production of chemically β-eliminative LMWH compositions that have either been approved for clinical use or been administered during clinical trials are which are described in more detail below.

In a first non-limiting example, a chemically β-eliminative LMWH composition that has been prescribed for clinical use is bemiparin (CAS No: 91449-79-5; ATC code: B01AB12) (see e.g. Chapman, T. M. and Goa, K. L., (2003) *Drugs* 63 (21):2357-2377; Sanchez-Ferrer, C. F. (2010) *Drugs* 70 Suppl. 2:19-23; Ciccone, M. M., et al., (2014) *Vascular Pharmacology* 62:32-37). Bemiparin is prepared by alkaline depolymerization of pharmaceutical heparin, particularly by reacting the benzethonium salt of pharmaceutical heparin with a quaternary ammonium hydroxide, such as Triton® B (benzyl trimethylammonium hydroxide), in the presence of methanol (see U.S. Pat. No. 4,981,955 and European Patent EP 0293539, the disclosures of which are incorporated by reference in their entireties). Upon subsequent purification and precipitation, the resulting bemiparin composition comprising the structure of Formula XI has an $\overline{M}_w$ in a range of at least 3,000 Da, up to 4,200 Da, and typically 3,600 Da, and a size distribution such that: less than 35% of the polysaccharide chains have an $M_r$ less than 2,000; a range of at least 50% and up to 75% of the polysaccharide chains have an $M_r$ in a range of at least 2,000 and up to 6,000; and less than 15% of the polysaccharide chains have an $M_r$ greater than 6,000. Additionally, bemiparin compositions can comprise an anti-Xa activity of at least 80 IU mg$^{-1}$ and up to 120 IU mg$^{-1}$, an anti-IIa activity of at least 5 IU mg$^{-1}$ and up to 20 IU mg$^{-1}$, and/or a ratio of anti-Xa activity to anti-IIa activity of at least 8.0:1, and up to 10:1 (see Sanchez-Ferrer, C. F., above).

In another non-limiting example, a chemically β-eliminative LMWH composition that has been administered to patients during clinical trials is semuloparin (CAS No: 9041-08-1). Semuloparin is prepared by reacting the benzyl ester of a pharmaceutical heparin benzethonium salt with the strong phosphazene base, BEMP (2-tert-butylimino-2-diethylamino-1,3-dimethylperhydro-1,2,3-diaza-phosphorine), with subsequent saponification of the benzyl esters and purification (see Viskov, C., et al., (2009) *J. Thromb. Haemost.* 7:1143-1551). Phosphazene bases are among the strongest-known organic bases, by are highly-sterically hindered and non-nucleophilic. As a result, phosphazene bases target the least sterically hindered regions of the heparin for β-elimination, and avoid the AT-recognition sequence that comprises the 3-O sulfated glucosamine residue. The resulting semuloparin product having the structure of Formula XI has an $\overline{M}_w$ in a range of at least 2,000 Da, up to 3,000 Da, and typically 2,400 Da, and the anticoagulant activity of the semuloparin product comprises an anti-Xa activity of about 160 IU mg$^{-1}$, an anti-IIa activity of about 2 IU mg$^{-1}$, and a ratio of anti-Xa activity to anti-IIa activity of about 80:1 (see Viskov, C., above).

In another non-limiting example, a chemically β-eliminative LMWH composition that has been prescribed for clinical use is enoxaparin (CAS No: 679809-58-6; ATC code: B01AB05) (see e.g. Linhardt, R. J. and Gunay, N. S., above). Enoxaparin is prepared similarly to semuloparin in that a benzyl ester form of the pharmaceutical heparin is prepared, before being reacted with a base. The benzyl ester is formed in a chlorinated organic solvent, such as chloroform or methylene chloride, in the presence of a chlorine derivative, such as benzyl chloride, which controls the amount of esterification in the resulting benzyl ester form of the pharmaceutical heparin (about 9-14% efficiency). Once the benzyl ester is formed, it is subsequently treated with a strong, non-sterically hindered base, such as sodium hydroxide, at high temperature (see U.S. Pat. No. 5,389,618 and U.S. Reissue Pat. RE38,743, the disclosures of which are incorporated by reference in their entireties. However, some (about 15% to 25%) polysaccharides within enoxaparin can additionally comprise a terminal 1,6-anhydro sugar residue (either 1,6-anhydromannose or 1,6-anhydroglucosamine) at the reducing end, in addition to the characteristic 4,5-unsaturated uronic acid at the non-reducing end (see Guerrini, M., (2010) *J. Med Chem.* 53:8030-8040). As a result, enoxaparin typically comprises polysaccharides having the characteristic structure illustrated in Formula XII, below, in addition to polysaccharides comprising the structure of Formula XI.

that: at least 12.0%, up to 20.0% percent, and characteristically about 16%, of the polysaccharide chains have an $M_r$ less than 2,000; a range of at least 68.0%, up to 82.0%, and characteristiclay about 74%, of the polysaccharide chains have an $M_r$ in a range of at least 2,000 and up to 8,000; and not more than 18.0% of the polysaccharide chains have an $M_r$ greater than 8,000.

Accordingly, in another embodiment, an N,2,3,6-HS product synthesized according to any of the methods of the present invention described above can subsequently be depolymerized by one or more bases to form a chemically β-eliminative LMW-HS product. In another embodiment, the chemically β-eliminative LMW-HS product comprises one or more properties that are identical to bemiparin, including but not limited to chemical structure, molecular weight, anticoagulant activity, and/or sulfation content properties. In another embodiment, the chemically β-eliminative LMW-HS product is substantially identical to bemiparin. In another embodiment, the chemically β-eliminative LMW-HS product comprises one or more properties that are identical to semuloparin, including but not limited to chemical structure, molecular weight, anticoagulant activity, and/

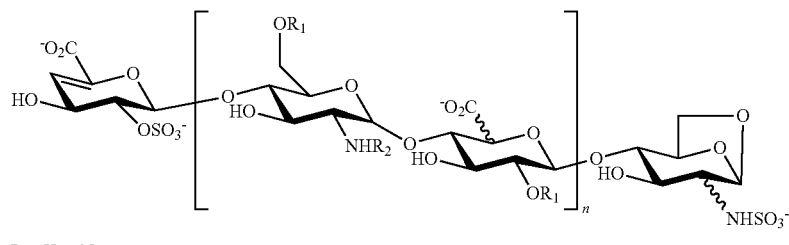

$R_1$ = H or $SO_3^-$
$R_2$ = $SO_3^-$ or $COCH_3^-$

As illustrated above in Formula XII, n can be any integer from 1-21. Instead of a glucuronic acid or uronic acid residue, the sugar residue at the non-reducing end of enoxaparin polysaccharides is 2-O-sulfo-4-enepyranosulfonic acid. Additionally, each glucosamine residue at the reducing end comprises a 1,6-anhydro moiety, and the stereochemistry around the C2 carbon determines whether the residue is a 1,6-anhydromannose or 1,6-anhydroglucosamine residue. Optionally, the 3-O position of a glucosamine residue within one or more of disaccharide units can also be 3-O sulfated. Without being limited by a particular theory, it is believed that at least some of the polysaccharides within enoxaparin comprises 3-O sulfated glucosamine residues, which ultimately leads to its anticoagulant activity.

As a commonly prescribed LMWH drug, compositions of enoxaparin that are administered to patients must satisfy a series of stringent size, activity, and purity requirements established by both the European Pharmacopoeia and the USP. (see "Enoxaparin Sodium" (2010) *European Pharmacopoeia* 7.0, 1920-1921). In addition to comprising the structure of Formula XII above, properties that must be present in order to satisfy the requirements include: an $\overline{M}_w$ in a range from at least 3,800 Da, and up to 5,000 Da, and characteristically 4,500 Da; not less than 1.8 sulfate groups per disaccharide unit; and an anti-Xa activity of at least 90 IU mg$^{-1}$ and up to 125 IU mg$^{-1}$, an anti-IIa activity of at least 20 IU mg$^{-1}$ and up to 35 IU mg$^{-1}$; and/or a ratio of anti-Xa activity to anti-IIa activity of at least 3.3:1, and up to 5.3:1. Further, enoxaparin compositions suitable to be administered to patients comprise a size distribution such or sulfation content properties. In another embodiment, the chemically β-eliminative LMW-HS product is substantially identical to semuloparin. In another embodiment, the chemically β-eliminative LMW-HS product comprises one or more properties that are identical to enoxaparin, including but not limited to chemical structure, molecular weight, anticoagulant activity, and/or sulfation content properties. In another embodiment, the chemically β-eliminative LMW-HS product is substantially identical to enoxaparin.

In another embodiment, the chemically β-eliminative LMW-HS product can be formed from an N,2,3,6-HS product synthesized according to any of the methods of the present invention described above, according to the following steps: (a) synthesizing an N,2,3,6-HS product according to any of the above methods; (b) providing a reaction mixture comprising a base; and (c) treating the N,2,3,6-HS product with the reaction mixture comprising the base for a time sufficient to depolymerize at least a portion of the N,2,3,6-HS product, thereby forming the chemically β-eliminative LMW-HS product.

In another embodiment, the chemically β-eliminative LMW-HS product comprises the structure of Formula XI. In another embodiment, the chemically β-eliminative LMW-HS product comprises the structure of Formula XII. In another embodiment, the N,2,3,6-HS product is an unfractionated N,2,3,6-HS product.

In another embodiment, the base is Triton® B, and the step of treating the N,2,3,6-HS product with the reaction mixture comprising Triton® B further comprises the following sub-steps: (i) reacting the unfractionated N,2,3,6-HS product with a benzethonium salt, preferably benzethonium chloride, to form a benzethonium HS salt; and (ii) combining the benzethonium HS salt with a reaction mixture comprising Triton® B and methanol, to form the chemically β-eliminative LMW-HS product. In another embodiment, the sub-step of preparing the chemically β-eliminative LMW-HS product from the benzethonium HS salt comprises the procedure reported in any of the examples in U.S. Pat. No. 4,981,955, preferably Example 3. In another embodiment, the time sufficient to depolymerize the benzethonium HS salt is the time sufficient to form a chemically β-eliminative LMW-HS product to having an $\overline{M}_w$ in a range of at least 3,000 Da, up to 4,200 Da, and preferably 3,600 Da, and having a size distribution such that: less than 35% of the polysaccharide chains have an $M_r$ less than 2,000; a range of at least 50% and up to 75% of the polysaccharide chains have an $M_r$ in a range of at least 2,000 and up to 6,000; and less than 15% of the polysaccharide chains have an $M_r$ greater than 6,000. In another embodiment, the chemically β-eliminative LMW-HS product comprises the structure of Formula XI. In another embodiment, the chemically β-eliminative LMW-HS product comprises an anti-Xa activity of at least 80 IU mg$^{-1}$ and up to 120 IU mg$^{-1}$, an anti-IIa activity of at least 5 IU mg-1 and up to 20 IU mg$^{-1}$, and/or a ratio of anti-Xa activity to anti-IIa activity of at least 8.0:1, and up to 10:1. In another embodiment, the chemically β-eliminative LMW-HS product is substantially equivalent to bemiparin.

In another embodiment, the base is BEMP, and the step of treating the N,2,3,6-HS product with the reaction mixture comprising BEMP further comprises the following steps: (i) reacting the unfractionated N,2,3,6-HS product with a benzethonium salt, preferably benzethonium chloride, to form a benzethonium HS salt; (ii) esterification of the benzethonium HS salt using benzyl chloride to form a benzyl ester HS; (iii) transalification of the benzyl ester HS with a benzethonium salt, preferably benzethonium chloride, to form a benzethonium benzyl ester HS; (iv) depolymerization of the benzethonium benzyl ester HS with BEMP to form a benzyl ester chemically β-eliminative LMW-HS product; and (v) saponification of the benzyl ester chemically β-eliminative LMW-HS product to form the chemically β-eliminative LMW-HS product, as reported in Viskov, C., et al., above. In another embodiment, the time sufficient to depolymerize the benzethonium benzyl ester HS with BEMP is the time sufficient to form a benzyl ester chemically β-eliminative LMW-HS product such that upon saponification of the benzyl esters, the resulting chemically β-eliminative LMW-HS product has an $\overline{M}_w$ in a range of at least 2,000 Da, up to 3,000 Da, and preferably about 2,400 Da. In another embodiment, the chemically β-eliminative LMW-HS product comprises the structure of Formula XI. In another embodiment, the chemically β-eliminative LMW-HS product comprises an anti-Xa activity of about 160 IU mg$^{-1}$, an anti-IIa activity of about 2 IU mg$^{-1}$, and/or a ratio of anti-Xa activity to anti-IIa activity of at least 80:1, and up to 100:1. In another embodiment, the chemically β-eliminative LMW-HS product is substantially equivalent to semuloparin.

In another embodiment, the base is sodium hydroxide, and the step of treating the N,2,3,6-HS product with the reaction mixture comprising sodium hydroxide further comprises the following sub-steps: (i) reacting the unfractionated N,2,3,6-HS product with a benzethonium salt, preferably benzethonium chloride, to form a benzethonium HS salt; (ii) esterification of the benzethonium HS salt using benzyl chloride in the presence of a chlorinated solvent, preferably methylene chloride or chloroform, to form a benzyl ester HS; and (iii) combining the benzyl ester HS with a reaction mixture comprising sodium hydroxide to form the chemically β-eliminative LMW-HS product. In another embodiment, the benzyl ester HS has a degree of esterification of at least 9%, and up to about 14%. In another embodiment, the reaction between the benzyl ester HS and sodium hydroxide is performed at a temperature selected within the range of at least 50° C., up to 70° C., and preferably within the range of at least 55° C., and up to 65° C. In another embodiment, the benzyl ester HS and chemically β-eliminative LMW-HS product are prepared according to the procedure of Example 3 within U.S. RE38,743. In another embodiment, the time sufficient to depolymerize the benzyl ester HS is the time sufficient to form a chemically β-eliminative LMW-HS product to having an $\overline{M}_w$ in a range of at least 3,800 Da, up to 5,000 Da, and preferably 4,500 Da. In another embodiment, the chemically β-eliminative LMW-HS product comprises a size distribution such that: at least 12.0%, up to 20.0% percent, and preferably about 16%, of the polysaccharide chains have an $M_r$ less than 2,000; a range of at least 68.0%, up to 82.0%, and preferably about 74%, of the polysaccharide chains have an $M_r$ in a range of at least 2,000 and up to 8,000; and not more than 18.0% of the polysaccharide chains have an $M_r$ greater than 8,000. In another embodiment, the chemically β-eliminative LMW-HS product comprises not less than 1.8 sulfate groups per disaccharide unit. In another embodiment, the chemically β-eliminative LMW-HS product comprises an anti-Xa activity of at least 90 IU mg$^{-1}$ and up to 125 IU mg$^{-1}$, an anti-IIa activity of at least 20 IU mg$^{-1}$ and up to 35 IU mg$^{-1}$; and/or a ratio of anti-Xa activity to anti-IIa activity of at least 3.3:1, and up to 5.3:1. In another embodiment, the chemically β-eliminative LMW-HS product is substantially equivalent to enoxaparin.

In another embodiment, an N,2,3,6-HS product, synthesized according to any of the methods of the present invention, can be modified by a deamination reaction to form a deaminated LMW-HS product. Historically, deaminated LMWH products have been prepared by treating pharmaceutical heparin with nitrous acid. Under these conditions, a deaminated LMWH product is formed that contains a 2-O-sulfo-α-L-idopyranosuronic acid residue at the non-reducing end and a 6-O-sulfo-2,5-anhydro-D-mannitol residue at the reducing end (see Linhardt, R. J. and Gunay, N. S., above). Deaminated LMWH products comprising 2-O-sulfo-α-L-idopyranosuronic acid residues at the non-reducing end and 6-O-sulfo-2,5-anhydro-D-mannitol residues at the reducing end generally comprise the structure of Formula XIII, below:

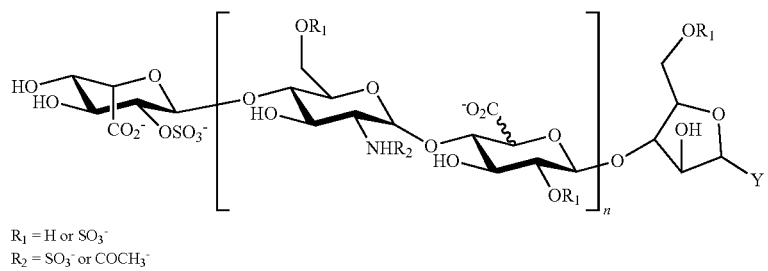

$R_1$ = H or $SO_3^-$
$R_2$ = $SO_3^-$ or $COCH_3^-$

As illustrated above in Formula XIII, n can be any integer from 3-20, and Y can be an aldehyde, hydroxyl, or carboxylic acid functional group. In another embodiment, Y is a hydroxyl group. Optionally, the 3-O position of a glucosamine residue within one or more of disaccharide units can also be 3-O sulfated. Without being limited by a particular theory, it is believed that at least some of the polysaccharides within the deaminated LMWH product comprises 3-O sulfated glucosamine residues, which ultimately leads to its anticoagulant activity.

Non-limiting examples of deaminated LMWH compositions that have been prescribed for clinical use include dalteparin (CAS No: 9041-08-1; ATC code: B01AB04), nadroparin (CAS No: 9005-49-6; ATC code: B01AB06), reviparin (CAS No: 9005-49-6; ATC code: B01AB08) and certoparin (CAS No: 9005-49-6). Generally, each of dalteparin, nadroparin, and reviparin are prepared by depolymerization using nitrous acid, either added directly or formed in situ by the addition of sodium nitrite to an acidic composition. Certoparin is prepared similarly, using a nitrous acid derivative such as isoamyl nitrite (see Linhardt, R. J. and Gunay, N. S., above). Control of the reaction conditions has led to the production of deaminated LMW-HS compositions that have slightly different anticoagulant activities and molecular weight properties relative to each other, and described, for example, in U.S. Pat. Nos. 4,303,651, 4,351, 938, 4,438,261, 4,500,519, 4,686,388, 5,019,649, and 5,599, 801, the disclosures of which are incorporated by reference in their entireties.

In a first non-limiting example, a deaminated LMWH composition that has been prescribed for clinical use is dalteparin (see e.g. Jacobsen, A. F., et al., (2003) *Br J Obstet Gynaecol* 110:139-144; and Guerrini, M., et al., (2007) *Seminars in Thrombosis and Hemostasis* 33 (5):478-487). Dalteparin is typically prepared as a sodium salt by an acid depolymerization of pharmaceutical heparin, particularly by reacting pharmaceutical heparin with nitrous acid (see e.g. U.S. Pat. No. 5,019,649). Upon subsequent purification and precipitation, the resulting dalteparin composition comprising the structure of Formula XIII has an $\overline{M}_w$ in a range of at least 5,600 Da, up to 6,400 Da, and typically 6,000 Da, and a size distribution such that the proportion of polysaccharide chains having an $M_r$ less than 3,000 is not more than 13.0%; and at least 15.0% and up to 25.0% of the chains have an $M_r$ of at least 8,000. Additionally, dalteparin compositions can comprise an anti-Xa activity of at least 110 IU $mg^{-1}$ and not more than 210 IU $mg^{-1}$, an anti-IIa activity of at least 35 IU $mg^{-1}$ and not more than 100 IU $mg^{-1}$, and/or a ratio of anti-Xa activity to anti-IIa activity of at least 1.9:1, and up to 3.2:1 (see "Dalteparin Sodium" (2010) *European Pharmacopoeia* 7.0, 1788-1789).

In another non-limiting example, a deaminated LMWH composition that has been prescribed for clinical use is nadroparin. Nadroparin is commonly prepared as a sodium or calcium salt by an acid depolymerization of pharmaceutical heparin, using sodium nitrite in the presence of hydrochloric acid to maintain a pH of about 2.5 (see e.g. U.S. Pat. Nos. 4,686,388 and 5,599,801) the disclosures of which are incorporated by reference in their entireties). Upon subsequent purification and precipitation, the resulting nadroparin composition comprising the structure of Formula XIII has an $\overline{M}_w$ in a range of at least 3,600 Da, up to 5,000 Da, and typically 4,300 Da, and a size distribution such that the proportion of chains having an $M_r$ less than 2,000 is not more than 15%; and at least 75% and up to 95% of the chains have an $M_r$ in a range of at least 2,000 and up to 8,000, with at least 35% and up to 55% of the chains having an $M_r$ of at least 2,000 and up to 4,000. Additionally, nadroparin compositions can comprise an anti-Xa activity of not less than 95 IU $mg^{-1}$ and not more than 130 IU $mg^{-1}$, and/or a ratio of anti-Xa activity to anti-IIa activity of at least 2.5:1, and up to 4.0:1 (see "Nadroparin Sodium" (2010) *European Pharmacopoeia* 7.0, 1788-1789).

Other non-limiting examples of deaminated LMWH compositions that have been prescribed for clinical use is reviparin and certoparin. Reviparin is prepared similarly to dalteparin and nadroparin, by introducing nitrous acid or forming nitrous acid in situ (see Linhardt, R. J. and Gunay, N. S., above), and the resulting reviparin composition comprising the structure of Formula XIII has an $\overline{M}_w$ in a range of at least 4,200 Da, up to 4,600 Da, and typically 4,400 Da, and a ratio of anti-Xa activity to anti-IIa activity of at least 4.0:1, up to 4.5:1, and typically 4.2:1 (see Grey, et al, above). Certoparin is prepared by reacting heparin with isoamyl nitrite in the presence of acetic or hydrochloric acid (see Ahsan, A., et al., (2000) *Clin. Appl. Thrombosis Hemostasis* 6 (3):169-174). The resulting certoparin composition comprising the structure of Formula XIII has an $\overline{M}_w$ in a range of at least 5,000 Da, up to 5,600 Da, and typically 5,400 Da, and a ratio of anti-Xa activity to anti-IIa activity of at least 2.0:1, up to 2.5:1, and preferably 2.4:1 (see Grey, et al, above).

Accordingly, in another embodiment, an N,2,3,6-HS product synthesized according to any of the methods of the present invention described above can subsequently be depolymerized by nitrous acid, or a nitrous acid derivative such as isoamyl nitrite, to form a deaminated LMW-HS product. In another embodiment, the deaminated LMW-HS product comprises one or more properties that are identical to dalteparin, including but not limited to chemical structure, molecular weight, anticoagulant activity, and/or sulfation content properties. In another embodiment, the deaminated LMW-HS product is substantially identical to dalteparin. In another embodiment, the deaminated LMW-HS product comprises one or more properties that are identical to nadroparin, including but not limited to chemical structure, molecular weight, anticoagulant activity, and/or sulfation content properties. In another embodiment, the deaminated LMW-HS product is substantially identical to nadroparin. In another embodiment, the deaminated LMW-HS product comprises one or more properties that are identical to reviparin, including but not limited to chemical structure, molecular weight, anticoagulant activity, and/or sulfation content properties. In another embodiment, the deaminated LMW-HS product is substantially identical to reviparin. In another embodiment, the deaminated LMW-HS product comprises one or more properties that are identical to certoparin, including but not limited to chemical structure, molecular weight, anticoagulant activity, and/or sulfation content properties. In another embodiment, the deaminated LMW-HS product is substantially identical to certoparin.

In another embodiment, the deaminated LMW-HS product can be formed from an N,2,3,6-HS product synthesized according to any of the methods of the present invention described above, according to the following steps: (a) synthesizing an N,2,3,6-HS product according to any of the above methods; (b) providing a deamination reaction mixture comprising a deamination agent, preferably a deamination agent selected from the group consisting of isoamyl nitrate and nitrous acid; and (c) treating the N,2,3,6-HS product with the deamination reaction mixture for a time sufficient to depolymerize at least a portion of the N,2,3,6-HS product, thereby forming the deaminated LMW-HS product. In another embodiment, the deamination agent is nitrous acid, the deamination reaction mixture can comprise stoichiometric quantities of an acid, preferably acetic acid or hydrochloric acid, and an alkali or alkaline earth metal nitrite salt, preferably sodium nitrite, wherein the nitrous acid is formed within the deamination reaction mixture in situ. In another embodiment, the deamination agent is isoamyl nitrite. In another embodiment, the deaminated LMW-HS product comprises the structure of Formula XIII. In another embodiment, the N,2,3,6-HS product is an unfractionated N,2,3,6-HS product.

In another embodiment, the time sufficient to form the deaminated LMW-HS product is the time sufficient to cause the product to have a desired average molecular weight. In another embodiment, the $\overline{M}_w$ of the deaminated LMW-HS product is in the range of 2,000 Da to 10,000 Da, preferably in the range of 4,000 Da to 6,000 Da. In another embodiment, the $\overline{M}_w$ of the deaminated LMW-HS product is in the range 4,000 Da to 4,500 Da, preferably 4,300 Da. In another embodiment, the $\overline{M}_w$ of the deaminated LMW-HS product is in the range 4,200 Da to 4,600 Da, preferably 4,400 Da. In another embodiment, the $\overline{M}_w$ of the deaminated LMW-HS product is in the range 5,000 Da to 5,600 Da, preferably 5,400 Da. In another embodiment, the $\overline{M}_w$ of the deaminated LMW-HS product is in the range 5,700 Da to 6,300 Da, preferably 6,000 Da.

In another embodiment, the deaminated LMW-HS product can have anticoagulant activity. In another embodiment, the deaminated LMW-HS product has an anti-Xa activity of up to 210 IU mg$^{-1}$.

In another embodiment, the deaminated LMW-HS product has an anti-Xa activity of at least 110 IU mg$^{-1}$ and not more than 210 IU mg$^{-1}$. In another embodiment, the deaminated LMW-HS product has an anti-Xa activity of not less than 95 IU mg$^{-1}$ and not more than 130 IU mg$^{-1}$. In another embodiment, the deaminated LMW-HS product has an anti-IIa activity of at least 35 IU mg$^{-1}$ and not more than 100 IU mg$^{-1}$. In another embodiment, the deaminated LMW-HS product has a ratio of anti-Xa activity to anti-IIa activity of at least 2.0:1, and up to 4.5:1. In another embodiment, the deaminated LMW-HS product has a ratio of anti-Xa activity to anti-IIa activity of at least 3.0:1, and up to 3.6:1. In another embodiment, the deaminated LMW-HS product has a ratio of anti-Xa activity to anti-IIa activity of at least 4.0:1, and up to 4.5:1. In another embodiment, the deaminated LMW-HS product has a ratio of anti-Xa activity to anti-IIa activity of at least 2.0:1, and up to 2.5:1. In another embodiment, the deaminated LMW-HS product has a ratio of anti-Xa activity to anti-IIa activity of at least 2.2:1, and up to 2.7:1.

In another embodiment, an N,2,3,6-HS product, synthesized according to any of the methods of the present invention, can be modified by an oxidation reaction to form an oxidized LMW-HS product. Historically, oxidized LMWH products have been prepared by treating pharmaceutical heparin with an acid, and then reacting the acidified heparin with an oxidizing agent, particularly a peroxide or a superoxide compound such as hydrogen peroxide, at an elevated temperature. Under these conditions, an oxidized LMWH product can be formed that retains the structure of pharmaceutical heparin, particularly comprising the structure of Formula I, but is in the same approximate molecular weight and anticoagulant activity ranges as other LMW-HS compounds.

Control of the reaction conditions has led to the production of oxidized LMWH compositions that have different anticoagulant activities and molecular weight properties relative to each other, and described, for example, in U.S. Pat. Nos. 4,281,108, 4,629,699, and 4,791,195, as well as European Patent EP0101141, the disclosures of which are incorporated by reference in their entireties. In particular, the acidified heparin has been formed by reacting the pharmaceutical heparin with a strong acid, such as hydrochloric acid, or a weak acid, such as ascorbic acid. Acidified heparin has also been formed by binding pharmaceutical heparin to a strong cationic exchange resin. Similarly, the depolymerization conditions can be controlled with respect to the pH and temperature at which the depolymerization takes place, and the oxidizing agent itself.

Non-limiting examples of oxidized LMWH compositions that have been prescribed for clinical use include parnaparin (CAS No: 91449-79-5; ATC code: B01AB05) and ardeparin (CAS No: 9005-49-6). In particular, Parnaparin has been used in the prevention of venous thromboembolism, in the treatment of chronic venous disorders, and in the treatment of venous and arterial thrombosis (see e.g. Camporese, G., et al., (2009) *Vascular Health and Risk Management* 5:819-831). Without being limited by a particular theory, it is believed that parnaparin is produced by forming the acidified heparin using ascorbic acid, and subsequently depolymerizing the acidified heparin under slightly basic conditions in the presence of cupric acetate monohydrate and hydrogen peroxide with incubation at 50° C. (see U.S. Pat. No. 4,791,195, Example 1). Parnaparin that has been administered to patients has an $\overline{M}_w$ in a range of at least 4,000 Da, up to 6,000 Da, and typically 5,000 Da, and a size distribution such that the proportion of polysaccharides having an $M_r$ less than 3,000 is not more than 30% of the composition, and the proportion of polysaccharides having an $M_r$ in a range of at least 3,000 and up to 8,000 is between 50% and 60% of the composition. Additionally, parnaparin compositions can comprise an anti-Xa activity of at least 75 IU mg$^{-1}$ and not more than 110 IU mg$^{-1}$, and/or a ratio of anti-Xa activity to anti-IIa activity of at least 1.5:1, and up to 3.0:1 (see "Parnaparin Sodium" (2010) *European Pharmacopoeia* 7.0, 2672). On the other hand, ardeparin compositions that have been prescribed to patients have generally had an $\overline{M}_w$ in a range of at least 5,500 Da, up to 6,500 Da, and typically 6,000 Da, an anti-Xa activity of 120+/−25 IU mg$^{-1}$, and a ratio of anti-Xa activity to anti-IIa activity of at least 2.0:1, up to 2.5:1, and characteristically 2.3:1.

Accordingly, in another embodiment, an N,2,3,6-HS product synthesized according to any of the methods of the present invention described above can subsequently be depolymerized by an oxidizing agent to form an oxidized LMW-HS product. In another embodiment, the oxidized LMW-HS product comprises one or more properties that are identical to parnaparin, including but not limited to chemical structure, molecular weight, anticoagulant activity, and/or sulfation content properties. In another embodiment, the oxidized LMW-HS product is substantially identical to parnaparin. In another embodiment, the oxidized LMW-HS product comprises one or more properties that are identical to ardeparin, including but not limited to chemical structure, molecular weight, anticoagulant activity, and/or sulfation content properties. In another embodiment, the oxidized LMW-HS product is substantially identical to ardeparin.

In another embodiment, the oxidized LMW-HS product can be formed from an N,2,3,6-HS product synthesized according to any of the methods of the present invention described above, according to the following steps: (a) synthesizing an N,2,3,6-HS product according to any of the above methods; (b) providing an oxidation reaction mixture comprising an oxidation agent, preferably hydrogen peroxide; and (c) treating the N,2,3,6-HS product with the oxidation reaction mixture for a time sufficient to depolymerize at least a portion of the N,2,3,6-HS product, thereby forming the oxidized LMW-HS product. In another embodiment, the step of treating the N,2,3,6-HS product with the oxidation reaction mixture can comprise the following sub-steps: (i) acidifying the N,2,3,6-HS product to form an acidified N,2,3,6-HS product; (ii) combining the acidified HS product with the oxidation reaction mixture; and (c) incubating the acidified HS product within the oxidation reaction mixture at a temperature of at least 50° C. until an oxidized LMW-HS product is formed. In another embodiment, the step of treating the N,2,3,6-HS product with the oxidation reaction mixture can comprise the procedure of Example 1 of U.S. Pat. No. 4,791,195. In another embodiment, the oxidized LMW-HS product comprises the structure of Formula I. In another embodiment, the N,2,3,6-HS product is an unfractionated N,2,3,6-HS product.

In another embodiment, the time sufficient to form the oxidized LMW-HS product is the time sufficient to cause the product to have a desired average molecular weight. In another embodiment, the $\overline{M}_w$ of the oxidized LMW-HS product is in the range of 2,000 Da to 12,000 Da, preferably in the range of 4,000 Da to 6,500 Da. In another embodiment, the $\overline{M}_w$ of the oxidized LMW-HS product is in the range 4,000 Da to 6,000 Da, preferably 5,000 Da. In a further embodiment, the oxidized LMW-HS product comprises a size distribution such that the proportion of polysaccharides having an $M_r$ less than 3,000 is not more than 30% of the composition, and the proportion of polysaccharides having an $M_r$ in a range of at least 3,000 and up to 8,000 is between 50% and 60% of the composition. In another embodiment, the $\overline{M}_w$ of the oxidized LMW-HS product is in the range 5,500 Da to 6,500 Da, preferably 6,000 Da.

In another embodiment, the oxidized LMW-HS product can have anticoagulant activity. In another embodiment, the oxidized LMW-HS product has an anti-Xa activity of at least 75 IU mg$^{-1}$. In another embodiment, the oxidized LMW-HS product has an anti-Xa activity of not more than 110 IU mg$^{-1}$. In another embodiment, the oxidized LMW-HS product has a ratio of anti-Xa activity to anti-IIa activity of at least 1.5:1, and up to 3.0:1. In another embodiment, the oxidized LMW-HS product has a ratio of anti-Xa activity to anti-IIa activity of at least 2.0:1, up to 2.5:1, and preferably 2.3:1.

Those skilled in the art would appreciate that the examples described above of LMW-HS compositions, and methods for forming them from an N,2,3,6-HS product synthesized using one or more engineered aryl sulfate-dependent sulfotransferase enzymes, are non-exhaustive, and that such other examples are excluded for clarity and brevity. Once an N,2,3,6-HS product, particularly an unfractionated N,2,3,6-HS product, is formed according to any of the methods described above, it can be modified and/or depolymerized by any known process to form a secondary product, particularly an LMW-HS product. Such processes include, but are not limited to: fractionation using solvents (French Patent No. 2,440,376, U.S. Pat. No. 4,692,435); fractionation using an anionic resin (French Patent No. 2,453,875); gel filtration; affinity chromatography (U.S. Pat. No. 4,401,758); controlled depolymerization by means of a chemical agent including, but not limited to, nitrous acid (European Patent EP 0014184, European Patent EP 0037319, European Patent EP 0076279, European Patent EP 0623629, French Patent No. 2,503,714, U.S. Pat. No. 4,804,652 and PCT Publication No. WO 81/03276), β-elimination from a heparin ester (European Patent EP 0040144, U.S. Pat. No. 5,389,618), periodate (European Patent EP 0287477), sodium borohydride (European Patent EP 0347588, European Patent EP 0380943), ascorbic acid (U.S. Pat. No. 4,533,549), hydrogen peroxide (U.S. Pat. Nos. 4,629,699, 4,791,195), quaternary ammonium hydroxide from a quaternary ammonium salt of heparin (U.S. Pat. No. 4,981,955), alkali metal hydroxide (European Patent EP 0380943, European Patent EP 0347588), using carbon-oxygen lyase enzymes (European Patent EP 0064452, U.S. Pat. No. 4,396,762, European Patent EP 0244235, European Patent EP 0244236; U.S. Pat. Nos. 4,826,827; 3,766,167), by means of irradiation (European Patent EP 0269981), purification and modification of fast-moving HS fractions (U.S. Pat. Nos. 7,687,479, 8,609,632), and other methods or combinations of methods such as those described in U.S. Pat. Nos. 4,303,651, 4,757,057, U.S. Publication No. 2007/0287683, PCT Publication No. WO 2009/059284 and PCT Publication No. WO 2009/059283, the disclosures of which are incorporated by reference in their entireties.

Preparation of Engineered Aryl Sulfate-Dependent Sulfotransferase Enzymes

In general, the engineered sulfotransferases encoded by the disclosed nucleic acid and amino acid sequences can be expressed and purified using any microbiological technique known in the art, including as described below. The aryl sulfate-dependent sulfotransferase activity of each purified enzyme can be determined spectrophotometrically or fluorescently and/or using mass spectrometry (MS) or nuclear magnetic resonance (NMR) spectroscopy to characterize the starting materials and/or sulfated polysaccharide products. Such methods are described below in the Examples section.

The engineered gene products, proteins and polypeptides utilized in accordance with methods of the present invention can also include analogs that contain insertions, deletions, or mutations relative to the disclosed DNA or peptide sequences, and that also encode for enzymes that catalyze reactions in which aryl sulfate compounds are substrates. In another embodiment, each analog similarly catalyzes sulfotransfer reactions in which aryl sulfate compounds are utilized as sulfo donors. Analogs can be derived from nucleotide or amino acid sequences as disclosed herein, or they can be designed synthetically in silico or de novo using computer modeling techniques. Those skilled in the art will appreciate that other analogs, as yet undisclosed or undiscovered, can be used to design and/or construct different sulfate-dependent sulfotransferase enzymes capable of being utilized in accordance with methods of the present invention. There is no need for a gene product, protein, or polypeptide to comprise all or substantially all of a nucleic acid or amino acid sequence of an engineered sulfotransferase as disclosed herein. Such sequences are herein referred to as "segments." Further, the gene products, proteins, and polypeptides discussed and disclosed herein can also include fusion or recombinant aryl sulfate-dependent sulfotransferases comprising full-length sequences or biologically functional segments of sequences disclosed in the present invention. Methods of preparing such proteins are known in the art.

In addition to the nucleic acid and amino acid sequences disclosed herein, methods of the present invention can be practiced by aryl sulfate-dependent sulfotransferases comprising amino acid sequences that are substantially identical to any of the disclosed amino acid sequences above, or expressed from nucleic acids comprising a nucleotide sequence that is substantially identical to a disclosed nucleotide sequence (SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, or SEQ ID NO: 27). Those skilled in the art can determine appropriate nucleotide sequences that encode for polypeptides having the amino acid sequence of SEQ ID NOs: 33-54 and 56-61, based on the nucleotide sequences above. "Substantially identical" sequences, as used in the art, refer to sequences which differ from a particular reference sequence by one or more deletions, substitutions, or additions, the net effect of which is to retain at least some of the biological activity of the engineered polypeptide encoded by the reference sequence. Namely, the biological activity of the engineered aryl sulfate-dependent sulfotransferases comprises the transfer of a sulfo group from a sulfo donor aryl sulfate compound to a polysaccharide acting as a sulfo group acceptor. In another embodiment, the polysaccharide is a heparosan-based and/or HS polysaccharide. Accordingly, as used to describe the aryl sulfate-dependent enzymes of the present invention, "substantial identity" can refer either to identity with a particular gene product, polypeptide or amino acid sequence of an aryl sulfate-dependent enzyme, or a gene or nucleic acid sequence encoding for an aryl sulfate-dependent enzyme. Such sequences can include mutations of the disclosed sequences or a sequence in which the biological activity is altered, enhanced, or diminished to some degree but retains at least some of the original biological activity of a disclosed reference amino acid sequence or polypeptide encoded by a disclosed reference nucleic acid sequence.

Alternatively, DNA analog sequences are substantially identical to the specific DNA sequences disclosed herein if: (a) the DNA analog sequence is derived from coding regions of the any of the disclosed nucleic acid sequences; or (b) the DNA analog sequence is capable of hybridization of DNA sequences of (a) under stringent conditions and which encode biologically active aryl sulfate-dependent sulfotransferase gene product; or (c) the DNA sequences are degenerate as a result of alternative genetic code to the DNA analog sequences defined in (a) and/or (b). Substantially identical analog proteins will be greater than about 60% identical to the corresponding sequence of the native protein. Sequences having lesser degrees of identity but comparable biological activity, namely, transferring a sulfo group from an aryl sulfate compound to polysaccharides, particularly heparosan-based or HS polysaccharides, are also considered to be substantially identical. In determining the substantial identity of nucleic acid sequences, all subject nucleic acid sequences capable of encoding substantially identical amino acid sequences are considered to be substantially identical to a reference nucleic acid sequence, regardless of differences in codon sequences or amino acid substitutions to create biologically functional equivalents.

At a biological level, identity is just that, i.e. the same amino acid at the same relative position in a given family member of a gene family. Homology and similarity are generally viewed as broader terms. For example, biochemically similar amino acids, for example leucine and isoleucine or glutamic acid/aspartic acid, can be alternatively present at the same position—these are not identical per se, but are biochemically "similar." As disclosed herein, these are referred to as conservative differences or conservative substitutions. This differs from a conservative mutation at the DNA level, which changes the nucleotide sequence without making a change in the encoded amino acid, e.g., TCC to TCA, both of which encode serine.

In some embodiments, the genes and gene products include within their respective sequences a sequence "essentially as that" of a gene encoding for an aryl sulfate-dependent sulfotransferase or its corresponding protein. A sequence essentially as that of a gene encoding for an aryl sulfate-dependent sulfotransferase refers to sequences that are substantially identical or substantially similar to a portion of a disclosed nucleic acid sequence and contains a minority of bases or amino acids (whether DNA or protein) that are not identical to those of a disclosed protein or a gene, or which are not a biologically functional equivalent. Biological functional equivalence is well understood in the art and is further discussed in detail below. Nucleotide sequences are "essentially the same" where they have between about 75% and about 85%, or particularly, between about 86% and about 90%, or more particularly greater than 90%, or even more particularly between about 91% and about 95%, or still more particularly, between about 96% and about 99%, of nucleic acid residues which are identical to the nucleotide sequence of a disclosed gene. Similarly, peptide sequences which have about 80%, or 90%, or particularly from 90-95%, or more particularly greater than 96%, or even more particularly 95-98%, or still more particularly 99% or greater amino acids which are identical or functionally equivalent or biologically functionally equivalent to the amino acids of a disclosed polypeptide sequence will be sequences which are "essentially the same."

Additionally, alternate nucleic acid sequences that include functionally equivalent codons are also encompassed by this invention. Functionally equivalent codons refer to codons that encode the same amino acid, such as the ACG and AGU codons for serine. Thus, substitution of a functionally equivalent codon into any of the nucleotide sequences above encode for biologically functionally equivalent sulfotransferases. Thus, the present invention includes amino acid and nucleic acid sequences comprising such substitutions but which are not set forth herein in their entirety for convenience.

Those skilled in the art would recognize that amino acid and nucleic acid sequences can include additional residues, such as additional N- or C-terminal amino acids or 5' or 3' nucleic acid sequences, and yet still be essentially as set forth in one of the sequences disclosed herein, so long as the sequence retains its biological activity with respect to binding and reacting with aryl sulfate compounds as sulfo donors. The addition of terminal sequences particularly applies to nucleic acid sequences which can, for example, include various non-coding sequences flanking either of the 5' or 3' portions of the coding region or can include various internal sequences, or introns, which are known to occur within genes.

As discussed above, modifications and changes can be made in the sequence of any of the disclosed aryl sulfate-dependent sulfotransferases, including conservative and non-conserved mutations, deletions, and additions while still constituting a molecule having like or otherwise desirable characteristics. For example, certain amino acids can be substituted for other amino acids in a protein structure without appreciable loss of interactive capacity with particular structures or compounds, particularly aryl sulfate compounds and/or sulfo acceptor polysaccharides. This can occur because the ability of a protein to recognize, bind, and react with other structures or compounds within its environment defines that protein's biological functional activity, not the sequence itself. Consequently, certain amino acid sequence substitutions can be made in that protein's sequence to obtain a protein with the equal, enhanced, or diminished properties. One non-limiting example of such amino acid substitutions that can occur without an appreciable loss of interactive activity include substitutions in external domains or surfaces of the protein that do not affect the folding and solubility of the protein. Similarly, amino acids can potentially be added to either terminus of the protein so long as the ability of the protein to fold or to recognize and bind its substrates is not deleteriously affected. One skilled in the art can appreciate that several other methods and/or strategies can be utilized to alter an enzyme's sequence without affecting its activity.

Consequently, mutations, deletions, additions, or other alterations to a parent enzyme's structure or sequence in which the modified enzyme retains the parent enzyme's biological activity can be defined to be biologically functionally equivalent to the parent enzyme. Thus, biologically functional equivalent enzymes, with respect to the engineered aryl sulfate-dependent sulfotransferases, can include any substitution or modification of any of the amino acid sequences disclosed herein, so long as the resultant modified enzyme is dependent on interacting with aryl sulfate compounds, particularly PNS or NCS, to catalyze sulfo transfer to polysaccharides, particularly heparosan-based and/or HS polysaccharides. In particular, such substitutions or modifications can result from conservative mutations in the amino acid sequence in any portion of the protein, as described below, although non-conservative mutations in non-catalytically active regions of the enzyme are also contemplated. Consequently, engineered aryl sulfate-dependent sulfotransferases suitable to practice the methods of the present invention can be expressed from any nucleic acid having a nucleotide sequence that encodes for a biologically functional equivalent enzyme, although such nucleotide sequences are not set forth herein in their entirety for convenience.

Alternatively, recombinant DNA technology can be used to create biologically functionally equivalent proteins or peptides in which changes in the protein structure can be engineered, based on considerations of the properties of the amino acids being exchanged. Rationally-designed changes can be introduced through the application of site-directed mutagenesis techniques, for example, to test whether certain mutations affect positively or negatively affect the enzyme's aryl sulfate-dependent catalytic activity or binding of sulfo donors or acceptors within the enzyme's active site.

Amino acid substitutions, such as those which might be employed in modifying any of the aryl sulfate-dependent sulfotransferases described herein, are generally based on the relative similarity of the amino acid side-chain substituents, for example, their hydrophobicity, hydrophilicity, charge, size, and the like. Those skilled in the art are familiar with the similarities between certain amino acids, such as the size, shape and type of the amino acid side-chain substituents. Non-limiting examples include relationships such as that arginine, lysine and histidine are all positively charged residues; that alanine, glycine and serine are all of similar size; and that phenylalanine, tryptophan and tyrosine all have a generally similar shape. Consequently, the amino acids that comprise the following groups-arginine, lysine and histidine; alanine, glycine and serine; and phenylalanine, tryptophan and tyrosine—are defined herein as biologically functional equivalents to the other amino acids in the same group. Other biologically functionally equivalent changes will be appreciated by those of skill in the art.

In another embodiment, the present invention provides isolated nucleic acids encoding functional fragments of the engineered enzymes of the present invention, or mutants thereof, in which conservative substitutions have been made for particular residues within the amino acid sequence of any of the engineered sulfotransferase enzymes described herein.

Additionally, isolated nucleic acids used to express aryl sulfate-dependent sulfotransferases capable of practicing the methods of the present invention may be joined to other nucleic acid sequences for use in various applications. Thus, for example, the isolated nucleic acids may be ligated into cloning or expression vectors, as are commonly known in the art and as described in the examples below. Additionally, nucleic acids may be joined in-frame to sequences encoding another polypeptide so as to form a fusion protein, as is commonly known in the art. Fusion proteins can comprise a coding region for the aryl sulfate-dependent sulfotransferase that is aligned within the same expression unit with other proteins or peptides having desired functions, such as for solubility, purification, or immunodetection. Thus, in another embodiment, cloning, expression and fusion vectors comprising any of the above-described nucleic acids, that encode for an aryl sulfate-dependent sulfotransferase that can be utilized in with methods of the present invention are also provided.

Furthermore, nucleic acid segments of the present invention, regardless of the length of the coding sequence itself, can be combined with other DNA sequences, such as promoters, enhancers, polyadenylation signals, additional restriction enzyme sites, multiple cloning sites, other coding segments, and the like, such that their overall length can vary considerably. Those skilled in the art would recognize that a nucleic acid fragment of almost any length can be employed, with the total length typically being limited by the ease of preparation and use in the intended recombinant DNA protocol.

In particular, recombinant vectors in which the coding portion of the gene or DNA segment is positioned under the control of a promoter are especially useful. In some embodiments, the coding DNA segment can be associated with promoters isolated from bacterial, viral, eukaryotic, or mammalian cells. Promoters specific to the cell type chosen for expression are often the most effective. The use of promoter and cell type combinations for protein expression is generally known to those of skill in the art of molecular biology (See, e.g., Sambrook et al. (2012) Molecular Cloning: A Laboratory Manual, Fourth Edition, Cold Spring Harbor Laboratory Press, Cold Spring Harbor, N.Y., incorporated by reference in its entirety). The promoters employed can be constitutive or inducible and can be used under the appropriate conditions to direct high-level expression of the introduced DNA segment, such as is advantageous in the large-scale production of recombinant proteins or peptides. Appropriate promoter systems that are often effective for high-level expression include, but are not limited to, the vaccinia virus promoter, the baculovirus promoter, and the Ptac promoter.

Thus, in some embodiments, an expression vector can be utilized that comprises a nucleotide sequence encoding for a biologically-active, aryl sulfate-dependent sulfotransferase suitable for use with methods of the present invention. In one example, an expression vector can comprise any nucleotide sequence that encodes for an aryl sulfate-dependent sulfotransferase gene product. In further embodiments, an expression vector comprises a nucleic acid comprising any of the nucleotide sequences described above, or any nucleotide sequence that encodes for a polypeptide comprising the amino acid sequence of any of the engineered sulfotransferase enzymes described above. In even further embodiments, any nucleic acid sequence encoding for an engineered aryl sulfate-dependent sulfotransferase enzyme of the present invention can be codon-optimized based on the expression host used to produce the enzyme. The preparation of recombinant vectors and codon optimization are well known to those of skill in the art and described in many references, such as, for example, Sambrook et al. (2012) Molecular Cloning: A Laboratory Manual, Fourth Edition, Cold Spring Harbor Laboratory Press, Cold Spring Harbor, N.Y.

Those skilled in the art would recognize that the DNA coding sequences to be expressed, in this case those encoding the aryl sulfate-dependent sulfotransferase gene products, are positioned in a vector adjacent to and under the control of a promoter. As is known in the art, a promoter is a region of a DNA molecule typically within about 100 nucleotide pairs upstream of (i.e., 5' to) the point at which transcription begins (i.e., a transcription start site). That region typically contains several types of DNA sequence elements that are located in similar relative positions in different genes. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter.

One can also desire to incorporate into the transcriptional unit of the vector an appropriate polyadenylation site (e.g., 5'-AATAAA-3'), if one was not contained within the original inserted DNA. Typically, poly-A addition sites are placed about 30 to 2000 nucleotides "downstream" of the coding sequence at a position prior to transcription termination.

Another type of discrete transcription regulatory sequence element is an enhancer. An enhancer imposes specificity of time, location and expression level on a particular coding region or gene. A major function of an enhancer is to increase the level of transcription of a coding sequence in a cell that contains one or more transcription factors that bind to that enhancer. An enhancer can function when located at variable distances from transcription start sites so long as a promoter is present.

Optionally, an expression vector of the invention comprises a polynucleotide operatively linked to an enhancer-promoter. As used herein, the phrase "enhancer-promoter" means a composite unit that contains both enhancer and promoter elements. For example, an expression vector can comprise a polynucleotide operatively linked to an enhancer-promoter that is a eukaryotic promoter and the expression vector further comprises a polyadenylation signal that is positioned 3' of the carboxy-terminal amino acid and within a transcriptional unit of the encoded polypeptide. As used herein, the phrase "operatively linked" means that an enhancer-promoter is connected to a coding sequence in such a way that the transcription of that coding sequence is controlled and regulated by that enhancer-promoter. Techniques for operatively linking an enhancer-promoter to a coding sequence are well known in the art; the precise orientation and location relative to a coding sequence of interest is dependent, inter alia, upon the specific nature of the enhancer-promoter.

An enhancer-promoter used in a vector construct of the present invention can be any enhancer-promoter that drives expression in a cell to be transfected. By employing an enhancer-promoter with well-known properties, the level and pattern of gene product expression can be optimized.

Sulfotransferase enzymes suitable to practice the methods of the present invention can be expressed within cells or cell lines, either prokaryotic or eukaryotic, into which have been introduced the nucleic acids of the present invention so as to cause clonal propagation of those nucleic acids and/or expression of the proteins or peptides encoded thereby. Such cells or cell lines are useful for propagating and producing nucleic acids, as well as for producing the aryl sulfate-dependent sulfotransferases themselves. As used herein, the term "transformed cell" is intended to embrace any cell, or the descendant of any cell, into which has been introduced any of the nucleic acids of the invention, whether by transformation, transfection, transduction, infection, or other means. Methods of producing appropriate vectors, transforming cells with those vectors, and identifying transformants are well known in the art. (See, e.g., Sambrook et al. (2012) Molecular Cloning: A Laboratory Manual, Fourth Edition, Cold Spring Harbor Laboratory Press, Cold Spring Harbor, N.Y.)

Prokaryotic cells useful for producing transformed cells include members of the bacterial genera *Escherichia* (e.g., *E. coli*), *Pseudomonas* (e.g., *P. aeruginosa*), and *Bacillus* (e.g., *B. subtilus, B. stearothermophilus*), as well as many others well known and frequently used in the art. Prokaryotic cells are particularly useful for the production of large quantities of the proteins or peptides (e.g., aryl sulfate-dependent enzymes, fragments of those sequences thereof, or fusion proteins including those sequences). Bacterial cells (e.g., *E. coli*) may be used with a variety of expression vector systems including, for example, plasmids with the T7 RNA polymerase/promoter system, bacteriophage X regulatory sequences, or M13 Phage regulatory elements. Bacterial hosts may also be transformed with fusion protein vectors that create, for example, Protein A, lacZ, trpE, maltose-binding protein (MBP), small ubiquitin-related modifier (SUMO), poly-His tag, or glutathione-S-transferase (GST) fusion proteins. All of these, as well as many other prokaryotic expression systems, are well known in the art and widely available commercially (e.g., pGEX-27 (Amrad, USA) for GST fusions).

In some embodiments of the invention, expression vectors comprising any of the nucleotide sequences described above can also comprise genes or nucleic acid sequences encoding for fusion proteins with any aryl sulfate-dependent sulfotransferase. In further embodiments, expression vectors can additionally include the malE gene, which encodes for the maltose binding protein. Upon inducing protein expression from such expression vectors, the expressed gene product comprises a fusion protein that includes maltose binding protein and any of the aryl sulfate-dependent sulfotransferase enzymes described above. In other further embodiments, an expression vector that includes any of the above nucleic acids that encode for any of the above aryl sulfate-dependent sulfotransferase enzymes can additionally include a gene encoding for a SUMO modifier, such as, in a non-limiting example, SUMO-1.

In other embodiments, expression vectors according to the present invention can additionally include a nucleic acid sequence encoding for a poly-His tag. Upon inducing protein expression from such expression vectors, the expressed gene product comprises a fusion protein that includes the poly-His tag and any of the aryl sulfate-dependent sulfotransferase enzymes described above. In a further embodiment, expression vectors can include both a nucleic acid sequence encoding for a poly-His tag and the malE gene or a SUMO gene, from which a fusion protein can be expressed that includes a poly-His tag, MBP, or SUMO, along with any aryl sulfate-dependent sulfotransferase enzyme.

Eukaryotic cells and cell lines useful for producing transformed cells include mammalian cells (e.g., endothelial cells, mast cells, COS cells, CHO cells, fibroblasts, hybridomas, oocytes, embryonic stem cells), insect cells lines (e.g., *Drosophila* Schneider cells), yeast, and fungi. Non-limiting examples of such cells include, but are not limited to, COS-7 cells, CHO, cells, murine primary cardiac microvascular endothelial cells (CME), murine mast cell line C57.1, human primary endothelial cells of umbilical vein (HU-VEC), F9 embryonal carcinoma cells, rat fat pad endothelial cells (RFPEC), and L cells (e.g., murine LTA tk-cells).

Vectors may be introduced into the recipient or "host" cells by various methods well known in the art including, but not limited to, calcium phosphate transfection, strontium phosphate transfection, DEAE dextran transfection, electroporation, lipofection, microinjection, ballistic insertion on micro-beads, protoplast fusion or, for viral or phage vectors, by infection with the recombinant virus or phage.

In another embodiment, the present invention provides aryl sulfate-dependent sulfotransferase variants in which conservative or non-conservative substitutions have been made for certain residues within any of the engineered sulfotransferase amino acid sequences disclosed above. Conservative or non-conservative substitutions can be made at any point in the amino acid sequence, including residues that surround the active site or are involved in catalysis, provided that the enzyme retains measurable catalytic activity; namely, the transfer of a sulfo group from an aryl sulfate compound to a polysaccharide, particularly a heparosan-based and/or HS polysaccharide. In other embodiments, the aryl sulfate compound is PNS. In still other embodiments, the aryl sulfate compound is NCS.

In another embodiment, the aryl sulfate-dependent sulfotransferase enzymes have at least 50%, including at least 60%, 70%, 80%, 85%, 90% or 95% up to at least 99% amino acid sequence identity to the amino acid sequence of any of the engineered sulfotransferase enzymes disclosed above, including disclosed as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NOs: 33-54 and 56-61, while retaining its catalytic activity of transfer of a sulfo group from an aryl sulfate compound to a polysaccharide, particularly a heparosan-based and/or HS polysaccharide. Such sequences may be routinely produced by those of ordinary skill in the art, and sulfotransferase activity may be tested by routine methods such as those disclosed herein.

Further, and in another embodiment, the amino acid sequence(s) of any of the engineered aryl sulfate-dependent sulfotransferases utilized in accordance with any of the methods described herein can be characterized as a percent identity relative to a natural sulfotransferase that catalyzes the same reaction using PAPS as the sulfo donor, so long as the sulfotransferase has aryl sulfate-dependent activity. For example, and in another embodiment, an engineered aryl sulfate-dependent NST that can be utilized in accordance with any of the methods of the present invention can comprise an amino acid sequence that has at least 50%, including at least 55%, 60%, 65%, 70%, 75%, 80%, 85%, 90%, or 95%, up to at least 97% sequence identity with the amino acid sequence of the N-sulfotransferase domain of any of the natural enzymes within the EC 2.8.2.8 enzyme class, including biological functional fragments thereof. In a further embodiment, the engineered aryl sulfate-dependent NST can comprise at least 50%, including at least 55%, 60%, 65%, 70%, 75%, 80%, 85%, 90%, or 95%, up to at least 97% sequence identity with the amino acid sequence of the N-sulfotransferase domain of the natural human glucosaminyl N-deacetylase/N-sulfotransferase enzyme (entry sp|P52848|NDST_1_HUMAN, in FIG. 3, above).

In another embodiment, an engineered aryl sulfate-dependent 2OST that can be utilized in accordance with any of the methods of the present invention can comprise an amino acid sequence that has at least 50%, including at least 55%, 60%, 65%, 70%, 75%, 80%, 85%, 90%, or 95%, up to at least 97% sequence identity with the amino acid sequence of any of the natural 2OST enzymes within the EC 2.8.2.- enzyme class, including biological functional fragments thereof. In a further embodiment, the engineered aryl sulfate-dependent 2OST can comprise at least 50%, including at least 55%, 60%, 65%, 70%, 75%, 80%, 85%, 90%, or 95%, up to at least 97% sequence identity with the amino acid sequence of the natural chicken 2OST enzyme (entry sp|Q76KB1|HS2ST_CHICK, in FIGS. 14A-14D, above).

In another embodiment, an engineered aryl sulfate-dependent 6OST that can be utilized in accordance with any of the methods of the present invention can comprise an amino acid sequence that has at least 50%, including at least 55%, 60%, 65%, 70%, 75%, 80%, 85%, 90%, or 95%, up to at least 97% sequence identity with the amino acid sequence of any of the natural 6OST enzymes within the EC 2.8.2.- enzyme class, including biological functional fragments thereof. In a further embodiment, the engineered aryl sulfate-dependent 6OST can comprise at least 50%, including at least 55%, 60%, 65%, 70%, 75%, 80%, 85%, 90%, or 95%, up to at least 97% sequence identity with the amino acid sequence of the first isoform of the mouse 6OST (UniProtKB Accession No. Q9QYK5). In a further embodiment, the engineered aryl sulfate-dependent 6OST can comprise at least 50%, including at least 55%, 60%, 65%, 70%, 75%, 80%, 85%, 90%, or 95%, up to at least 97% sequence identity with residues 67-377 of the amino acid sequence of the first isoform of the mouse 6OST (entry Q9QYK5|H6ST1_MOUSE, in FIGS. 18A-18C, above).

In another embodiment, an engineered aryl sulfate-dependent 3OST that can be utilized in accordance with any of the methods of the present invention can comprise an amino acid sequence that has at least 50%, including at least 55%, 60%, 65%, 70%, 75%, 80%, 85%, 90%, or 95%, up to at least 97% sequence identity with the amino acid sequence of any of the natural enzymes within the EC 2.8.2.23 enzyme class, including biological functional fragments thereof. In a further embodiment, the engineered aryl sulfate-dependent 3OST can comprise at least 50%, including at least 55%, 60%, 65%, 70%, 75%, 80%, 85%, 90%, or 95%, up to at least 97% sequence identity with residues 48-311 of the amino acid sequence of the first isoform of the natural human 3OST (UniProtKB Accession No. 014792).

Substantially pure aryl sulfate-dependent sulfotransferases may be joined to other polypeptide sequences for use in various applications. Thus, for example, engineered sulfotransferases may be joined to one or more additional polypeptides so as to form a fusion protein, as is commonly known in the art. The additional polypeptides may be joined to the N-terminus, C-terminus or both termini of the aryl sulfate-dependent sulfotransferase enzyme. Such fusion proteins may be particularly useful if the additional polypeptide sequences are easily identified (e.g., by providing an antigenic determinant), are easily purified (e.g., by providing a ligand for affinity purification), or enhance the solubility of the aryl sulfate-dependent sulfotransferase enzyme in solution.

In another embodiment, substantially pure proteins may comprise only a portion or fragment of the amino acid sequence of a complete aryl sulfate-dependent sulfotransferase. In some instances, it may be preferable to employ a minimal fragment retaining aryl sulfate-dependent sulfotransferase activity, particularly if the minimal fragment enhances the solubility or reactivity of the enzyme. Thus, in some embodiments, methods of the present invention can be practiced using substantially pure aryl sulfate-dependent sulfotransferases of any length, including full-length forms, or minimal functional fragments thereof. Additionally, these proteins may also comprise conservative or non-conservative substitution variants as described above.

In some embodiments, the present invention provides substantially pure preparations of aryl sulfate-dependent sulfotransferases, including those comprising any of the amino acid sequences disclosed above. The engineered sulfotransferases may be substantially purified by any of a variety of methods selected on the basis of the properties revealed by their protein sequences. Typically, the aryl sulfate-dependent sulfotransferases, fusion proteins, or fragments thereof, can be purified from cells transformed or transfected with expression vectors, as described above. Insect, yeast, eukaryotic, or prokaryotic expression systems can be used, and are well known in the art. In the event that the protein or fragment localizes within microsomes derived from the Golgi apparatus, endoplasmic reticulum, or other membrane-containing structures of such cells, the protein may be purified from the appropriate cell fraction. Alternatively, if the protein does not localize within these structures, or aggregates in inclusion bodies within the recombinant cells (e.g., prokaryotic cells), the protein may be purified from whole lysed cells or from solubilized inclusion bodies by standard means.

Purification can be achieved using standard protein purification procedures including, but not limited to, affinity chromatography, gel-filtration chromatography, ion-exchange chromatography, high-performance liquid chromatography (RP-HPLC, ion-exchange HPLC, size-exclusion HPLC), high-performance chromatofocusing chromatography, hydrophobic interaction chromatography, immunoprecipitation, or immunoaffinity purification. Gel electrophoresis (e.g., PAGE, SDS-PAGE) can also be used to isolate a protein or peptide based on its molecular weight, charge properties and hydrophobicity.

An aryl sulfate-dependent sulfotransferase, or a fragment thereof, may also be conveniently purified by creating a fusion protein including the desired sequence fused to another peptide such as an antigenic determinant, a polyhistidine tag (e.g., QIAexpress vectors, QIAGEN Corp., Chatsworth, Calif.), or a larger protein (e.g., GST using the pGEX-27 vector (Amrad, USA), green fluorescent protein using the Green Lantern vector (GlBCO/BRL. Gaithersburg, Md.), maltose binding protein using the pMAL vector (New England Biolabs, Ipswich, Mass.), or a SUMO protein. The fusion protein may be expressed and recovered from prokaryotic or eukaryotic cells and purified by any standard method based upon the fusion vector sequence. For example, the fusion protein may be purified by immunoaffinity or immunoprecipitation with an antibody to the non-aryl sulfate-dependent sulfotransferase portion of the fusion or, in the case of a poly-His tag, by affinity binding to a nickel column. The desired aryl sulfate-dependent sulfotransferase protein or fragment can then be further purified from the fusion protein by enzymatic cleavage of the fusion protein. Methods for preparing and using such fusion constructs for the purification of proteins are well known in the art and numerous kits are now commercially available for this purpose.

Furthermore, in some embodiments, isolated nucleic acids encoding for any aryl sulfate-dependent sulfotransferase may be used to transform host cells. The resulting proteins may then be substantially purified by well-known methods including, but not limited to, those described in the examples below. Alternatively, isolated nucleic acids may be utilized in cell-free in vitro translation systems. Such systems are also well known in the art.

While particular embodiments of the invention have been described, the invention can be further modified within the spirit and scope of this disclosure. Those skilled in the art will recognize, or be able to ascertain using no more than routine experimentation, numerous equivalents to the specific procedures, embodiments, claims, and examples described herein. As such, such equivalents are considered to be within the scope of the invention, and this application is therefore intended to cover any variations, uses or adaptations of the invention using its general principles. Further, the invention is intended to cover such departures from the present disclosure as come within known or customary practice in the art to which this invention pertains and which fall within the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

The contents of all references, patents, and patent applications mentioned in this specification are hereby incorporated by reference, and shall not be construed as an admission that such reference is available as prior art to the present invention. All of the incorporated publications and patent applications in this specification are indicative of the level of ordinary skill in the art to which this invention pertains, and are incorporated to the same extent as if each individual publication or patent application was specifically indicated and individually indicated by reference.

The invention is further illustrated by the following working and prophetic examples, neither of which should be construed as limiting the invention. Additionally, to the extent that section headings are used, they should not be construed as necessarily limiting. Any use of the past tense to describe an example otherwise indicated as constructive or prophetic is not intended to reflect that the constructive or prophetic example has actually been carried out.

EXAMPLES

The following working and prophetic examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. Thus, while the present invention has been described above with particularity, the following examples provide further detail in connection with what are presently deemed to be the most practical and preferred embodiments of the invention.

Example 1: Cloning, Expression, and Purification of the Engineered Aryl Sulfate-Dependent Sulfotransferases A study was conducted in accordance with embodiments of the present disclosure to determine whether genes according to the present invention could be transformed into host cells capable of overexpressing engineered aryl sulfate-dependent sulfotransferases. After expression, each aryl sulfate-dependent enzyme was isolated and purified from the host cell.

Generally, DNA coding for genes of any sequence can be synthesized de novo by methods commonly known in the art, including but not limited to oligonucleotide synthesis and annealing. Alternatively, DNA can be synthesized commercially and purchased from any one of several laboratories that regularly synthesize genes of a given sequence, including but not limited to ThermoFisher Scientific, GenScript, DNA 2.0, or OriGene. Persons skilled in the art would appreciate that there are several companies that provide the same services, and that the list provided above is merely a small sample of them. Genes of interest can be synthesized independently and subsequently inserted into a bacterial or other expression vector using conventional molecular biology techniques, or the genes can be synthesized concurrently with the DNA comprising the expression vector itself. Similar to genes of interest, suitable expression vectors can also be synthesized or obtained commercially. Often, bacterial expression vectors include genes that confer selective antibiotic resistance to the host cell, as well as genes that permit the cell to overproduce the protein of interest in response to the addition of isopropyl β-D-1-thiogalactopyranoside (IPTG). Bacterial production of proteins of interest using IPTG to induce protein expression is widely known in the art.

As described above, expression vectors can also include genes that enable production of fusion proteins that include the desired protein that is co-expressed with an additional, known protein to aid in protein folding and solubility. Non-limiting examples of fusion proteins that are commonly produced and are well-known in the art include fusions with MBP, SUMO, or green fluorescent protein. In particular, MBP fusion proteins facilitate easier purification because MBP possesses high affinity for amylose-based resins used in some affinity chromatography columns, while SUMO fusion proteins can include a poly-histidine tag that enables affinity purification on columns with $Ni^{2+}$-based resins as a stationary phase. Often, fusion proteins between the protein of interest and MBP and/or SUMO can optionally include an amino acid linking sequence that connects the two proteins. Non-limiting examples of commercial expression vectors that can be purchased to produce MBP fusion proteins include the pMAL-c5E™ and pMAL-c5X™ vectors, which can be obtained from New England Biolabs. Similarly, and in another non-limiting example, commercial expression vectors can also be purchased to produce SUMO fusion proteins, such as the pE-SUMOpro AMP vector, available from LifeSensors, Inc. Once the fusion proteins are produced and isolated, proteases can be utilized to cleave the fused protein and any associated linker sequences from the sulfotransferase, if cleavage is necessary for activity.

Additionally, expression vectors can also include DNA coding for a poly-histidine tag that can be synthesized at either the N- or C-terminus of the protein of interest. As with MBP fusions, proteins that include a poly-histidine tag simplify the enzyme purification because the tag has a high affinity for $Ni^2$ resins that are utilized in many purification columns. Additionally, poly-histidine tags can optionally be cleaved after purification if it is necessary for optimal activity of the enzyme. A non-limiting example of an expression vector encoding for a C-terminal poly-histidine tag is the pET21b vector, available from Novagen. Another non-limiting example of an expression vector encoding for a poly-histidine tag is the pE-SUMO vector, which encodes for a poly-histidine tag at the N-terminus of the SUMO protein.

In the present example, double-stranded DNA fragments comprising the nucleotide sequences of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, or SEQ ID NO: 27, encoding for engineered aryl sulfate-dependent sulfotransferases comprising the amino acid sequences of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28, respectively, were synthesized using Integrated DNA Technologies' (IDT) gBlocks® Gene Fragments synthesis service. Polymerase chain reactions (PCR) were initiated to generate copies of each double-stranded DNA fragment, using forward and reverse primers comprising appropriate restriction enzyme recognition sequences to facilitate insertion into an expression vector. Genes encoding for the engineered NST enzymes (SEQ ID NO: 1, SEQ ID NO: 3, SEQ ID NO: 5, SEQ ID NO: 7, SEQ ID NO: 9, SEQ ID NO: 11) and 3OST enzymes (SEQ ID NO: 23, SEQ ID NO: 25, SEQ ID NO: 27) contained NdeI and BamHI restriction enzyme recognition sequences, and were ligated into the pMAL-c5x expression vector using quick ligation kits provided by NEB. Expression vectors were then transformed into competent DH5-α *E. coli* cells.

Single clones were incubated in LB medium with 100 µL/mL ampicillin. Nucleotide sequences of each gene and expression vector within the transformed host cells were confirmed by commercial DNA sequencing (GeneWiz).

Protein expression of the glucosaminyl N- and 3-O sulfotransferase enzymes was achieved by first transforming confirmed DNA constructs into competent SHuffle® T7 Express lysY *E. coli* cells. Protein expression of the glucosaminyl N- and 3-O sulfotransferase enzymes has also been achieved by transforming confirmed DNA constructs into competent BL21 (DE3) *E. coli* cells. From either construct, resultant colonies were used to inoculate 250 mL cultures in LB medium, which were allowed to shake and incubate at 32° C. until an optical density at 600 nM (OD 600) of approximately 0.4 to 0.6 was observed. Expression was induced by the addition of 100 µM IPTG to each culture at 18° C.

Upon incubation at 18° C. overnight, expressed cells were harvested by centrifuging at 3,620 g and resuspending the pellet in 10 mL of resuspension buffer (25 mM Tris-HCl, pH 7.5; 0.15 M NaCl; 0.2 mg/mL lysozyme; 10 µg/ml DNase I; 5 mM MgCl$_2$; and 0.1% (w/v) Triton-X 100). Resuspended cells were lysed upon sonication on ice for three pulses of 10 seconds each, and subsequently passed through a 0.45-µm syringe filter. The resulting supernatant was loaded into a 5-mL spin column (G-biosciences) comprising Dextrin Sepharose® resin (GE Biosciences) suspended in a binding buffer comprising 25 mM Tris-HCl, pH 7.5 and 0.15 M NaCl. Enzymes of interest were eluted from the column upon adding an elution buffer comprising 25 mM Tris-HCl, pH 7.5; 0.15 M NaCl; and 40 mM maltose.

On the other hand, genes encoding for the engineered 2OST (SEQ ID NO: 13, SEQ ID NO: 15) and 6OST enzymes (SEQ ID NO: 17, SEQ ID NO: 19, SEQ ID NO: 21) contained BsaI and XbaI restriction enzyme recognition sequences, and were ligated into the pE-SUMO vector (LifeSensors, Inc.). Expression vectors were then transformed into competent BL21-DE3 *E. coli* cells. Single clones were incubated in Terrific Broth with 100 µL/mL ampicillin. Nucleotide sequences of each gene and expression vector within the transformed host cells were confirmed by commercial DNA sequencing (GeneWiz).

Protein expression of the engineered 2OSTs and 6OSTs was achieved by inoculating 500 mL cultures in Terrific Broth with ampicillin and allowing the cultures to incubate with shaking at 35° C. until an OD 600 of approximately 0.6-0.8 was reached. Protein expression was induced by the addition of 0.2 mM IPTG at 18° C. Cultures were then allowed to incubate at 18° C. overnight, and were subsequently lysed and filtered using an identical procedure to the glucosaminyl N- and 3-O sulfotransferase enzymes above. The 2OST and 6OST enzymes were subsequently purified in a 5-mL spin column (G-biosciences) comprising HisPur Ni-NTA resin (Thermofisher) suspended in a binding buffer comprising 25 mM Tris-HCl, pH 7.5, 0.15 M NaCl, 5 mM MgCl$_2$, and 30 mM imidazole. Enzymes of interest were eluted from the column upon adding an elution buffer comprising 25 mM Tris-HCl, pH 7.5, 0.15 M NaCl, 5 mM MgCl$_2$, and 300 mM imidazole.

Example 2: Mass Spectrometric Characterization of the N-Sulfated Polysaccharide Products of Engineered Aryl Sulfate-Dependent NST Enzymes A study was conducted in accordance with embodiments of the present disclosure to confirm NST activity of enzymes comprising the amino acid sequence of SEQ ID NO: 2, SEQ ID NO: 4, SEQ ID NO: 6, SEQ ID NO: 8, SEQ ID NO: 10, or SEQ ID NO: 12 by detecting the presence of N-sulfated polysaccharide products formed as a result of their sulfotransfer reaction, using mass spectrometry (MS). Each engineered enzyme was purified according to the procedure of Example 1. Sulfotransferase activity was monitored in 100 µL reactions containing 50 µM of enzyme. To each purified protein solution, 20 mg of an aryl sulfate compound (either PNS or NCS) was dissolved in 2 mL of reaction buffer (50 mM MES pH 7.0, 2 mM CaCl$_2$)), added to the protein solution, and incubated at 37° C. for 10 min. 2.5 mL of 2 mg/mL solution of N-deacetylated heparosan was added to protein/donor solution and incubated overnight at 37° C. The N-deacetylated heparosan was synthesized according to the protocol described in Balagurunathan, K. et al (eds.) (2015), *Glycosaminoglycans: Chemistry and Biology*, Methods in Molecular Biology, vol. 1229, DOI 10.1007/978-1-4939-1714-3_2, ©Springer Science+Business Media, New York, pp. 11-19 (section 3.1). To purify the N-sulfated product, the incubated reaction mixture was centrifuged the following day at 5,000×g for 10 min. The filter was washed once with 2 mL water, and centrifuged again. The filtrate was added to a 1K MWCO Dialysis membrane, dialyzed for 2 days in Milli-Q water, with water changes at 1 h, 2 h, 8 h, 16 h, 32 h, and then lyophilized.

The lyophilized N-sulfated products from each reaction were subsequently digested with a mixture of three carbon-oxygen lyases comprising the amino acid sequences of SEQ ID NO: 30, SEQ ID NO: 31, and SEQ ID NO: 32, which catalyze the β-eliminative cleavage of heparosan-based polysaccharides. Such lyases are available from New England Biolabs, among other chemical and biological commercial entities. 1 µL of each lyase was incubated with 50 µg of the lyophilized sulfated polysaccharide product and the provided digestion buffer, and incubated over 24 hours according to the packaged instructions provided by New England Biolabs with each lyase. After digestion, the lyase enzymes were inactivated by heating to 100° C. for 5 minutes. Samples were centrifuged at 14,000 rpm for 30 minutes before introduction to a strong anion exchange, high performance liquid chromatography (SAX) analysis. SAX analysis was performed on a Dionex Ultimate 3000 LC system interface. Separation was carried out on a 4.6×250 mm Waters Spherisorb analytical column with 5.0 µm particle size at 45° C. Mobile phase solution A was 2.5 mM sodium phosphate, pH 3.5, while mobile phase solution B was 2.5 mM sodium phosphate, pH 3.5, and 1.2 M Sodium perchlorate. After each sample was loaded onto the column, mobile phase solutions were applied to the column at a ratio of 98% mobile phase solution A and 2% mobile phase solution B for five minutes at a flow rate of 1.4 mL/min. After five minutes, a linear gradient of increasing mobile phase solution B was applied until the ratio of mobile phase solution A to mobile phase solution B was 50:50.

Using the SAX analysis, it was determined that all six of the tested enzymes were active as sulfotransferases. However, each of the sulfotransferases were not necessarily active with both PNS and NCS. Enzymes having the amino acid sequences of SEQ ID NO: 2, SEQ ID NO: 4, and SEQ ID NO: 10 had activity with NCS only, and the enzyme having the amino acid sequence of SEQ ID NO: 12 had activity with PNS only. Enzymes having the amino acid sequences of SEQ ID NO: 6 and SEQ ID NO: 8 had activity with both aryl sulfate compounds.

Figure 26:
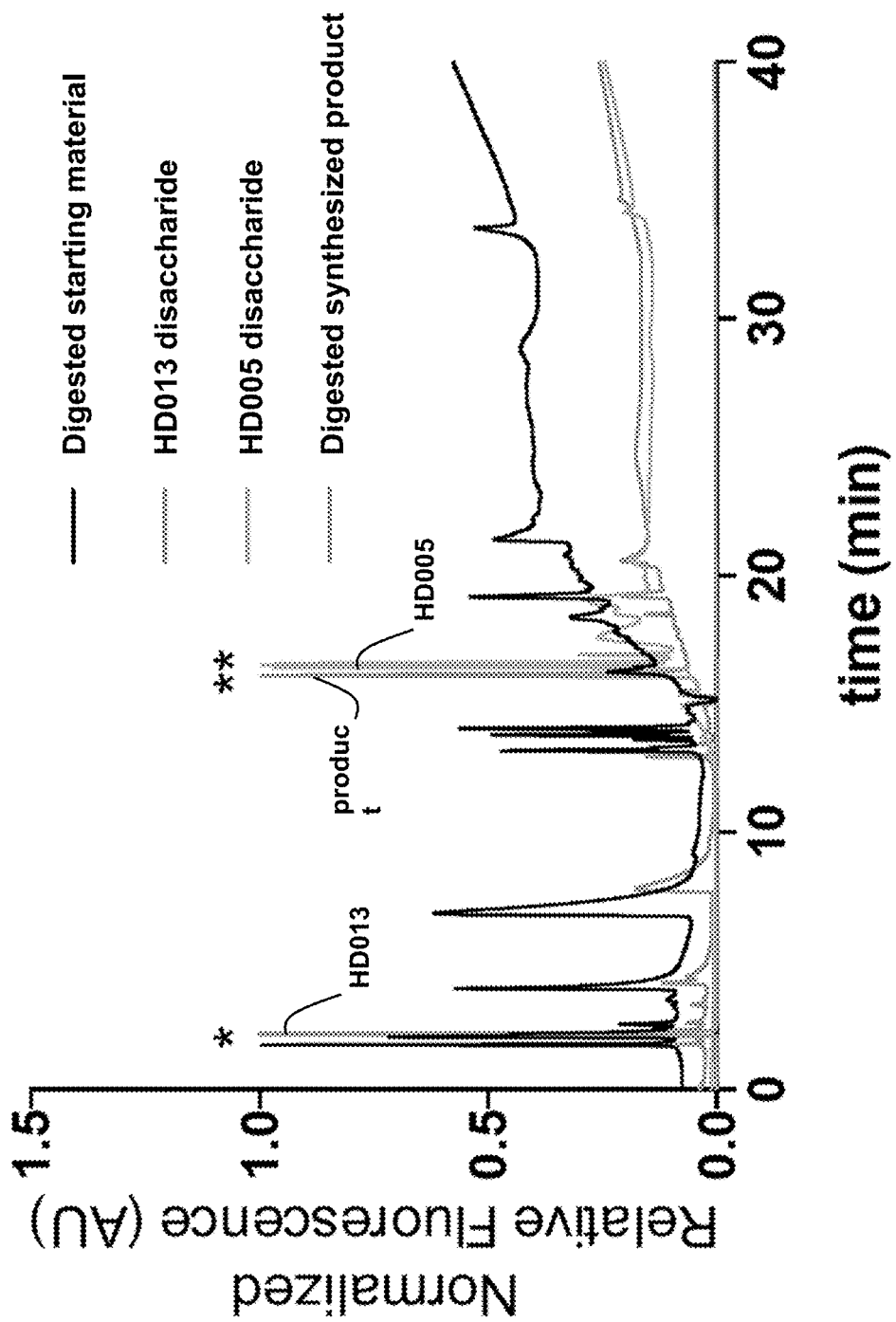
FIG. 26 shows a series of overlaid SAX-HPLC chromatograms of digested N-sulfated heparosan products synthesized using an engineered NST enzyme, compared to commercial standards.

Representative chromatograms from SAX analysis illustrating the presence of N-sulfated products produced as a result of the reaction are shown in FIG. 26. Both the starting material and product were digested with the lyases having the amino acid sequence of SEQ ID NO: 30, SEQ ID NO: 31, and SEQ ID NO: 32 according the digestion procedure described above. Two disaccharide standards (HD005 and HD013) that are commercially available from Iduron, Ltd were also analyzed using SAX. The HD013 disaccharide comprises an unsubstituted glucosamine residue and a reduced hexuronic acid. The HD005 disaccharide is the same as HD013 except that the glucosamine residue is N-sulfated. All of the overlaid chromatograms are normalized so the most prominent peak in each chromatogram is assigned a normalized relative fluorescence value of 1.0.

As shown in FIG. 26, the most prominent peak for HD013 disaccharide (illustrated with a * symbol) elutes almost immediately, whereas the most prominent peak for the HD005 disaccharide (illustrated with a ** symbol) elutes after approximately 17 minutes. This is expected under SAX conditions because positively-charged species (like HD013) typically do not bind to the column, whereas negatively-charged species (like HD005) do bind to the column. The N-deacetylated heparosan, which is similarly non-sulfated, most prominently elutes at a nearly identical time as HD013. Similarly, the lyophilized sample produced during the reaction shows a peak at a nearly identical time as HD005, indicating that the sample likely contains an N-sulfated product. Other peaks within each of the chromatograms, particularly within the synthesized starting materials and products, indicate a lack of sample purity based on the use of spin-filtration columns as the sole basis of purifying the polysaccharides in each instance. Those skilled in the art would appreciate that there are several other separations techniques that can be utilized if a more purified product is desired. Additionally, the drifting upward of the baseline of the fluorescent signal in the chromatograms is a known phenomenon when increasing amounts of salt are introduced onto the column via the mobile phase.

Example 3: Mass Spectrometric Characterization of the 2-O Sulfated Polysaccharide Products of Engineered Aryl Sulfate-Dependent 2OST Enzymes A study was conducted in accordance with embodiments of the present disclosure to confirm 2OST activity of enzymes comprising the amino acid sequence of SEQ ID NO: 14 or SEQ ID NO: 16 by detecting the presence of 2-O sulfated polysaccharide products formed as a result of their sulfotransfer reaction, using a similar procedure as in Example 2, except that the sulfo acceptor polysaccharide was commercial heparin in which the 2-O sulfate groups had been selectively removed by chemical means (product DSH001/2, available from Galen Laboratory Supplies) and analysis of each of the digested samples containing sulfated products was conducted using mass spectrometry, coupled with SAX-based high performance liquid chromatography (LCMS).

Disaccharides obtained by digesting the 2-O sulfated products using the carbon-oxygen lyases having the amino acid sequence of SEQ ID NO: 30, SEQ ID NO: 31, and SEQ ID NO: 32 and according to the procedure described above in Example 2 were quantified on a Shimadzu LCMS-8050 Triple Quadrupole Liquid Chromatograph Mass Spectrometer. 100 ng of each of the digested samples, diluted in 10 mM ammonium bicarbonate (pH 10). The disaccharides were separated on a Thermo Hypercarb HPLC column (100×2.1 mm, 5 µm). The mobile phase consisted of 10 mM ammonium bicarbonate (pH 10), and the disaccharides were eluted with an acetonitrile gradient of 0% to 20% for 2.5 min, held at 20% for the next 2.5 min, with 2 min of equilibration at 0% before the next injection; the flow rate was 0.2 mL/min, and the total run time was 7.1 min.

Figure 27A:
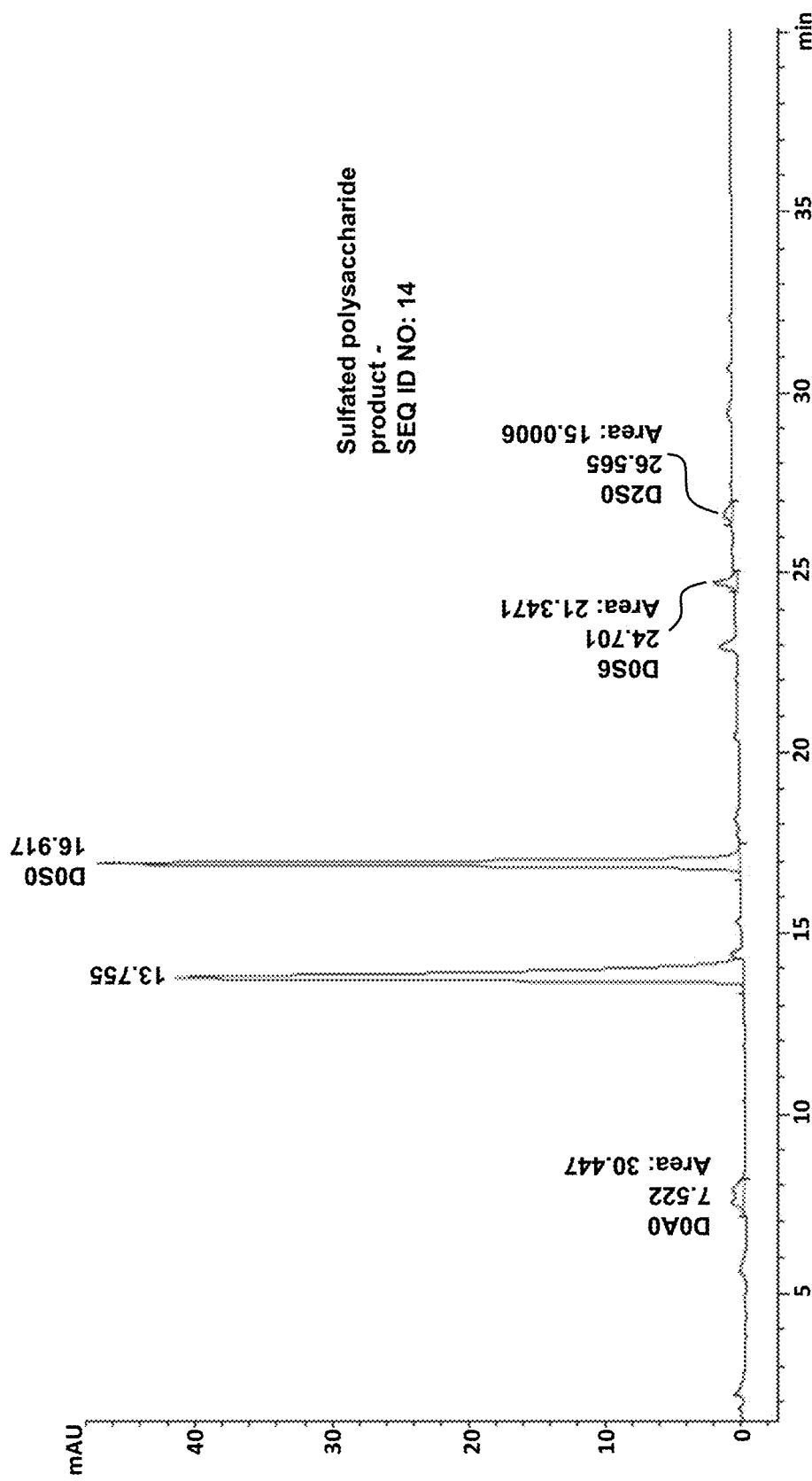
FIGS. 27A-27B show a series of LCMS chromatograms of digested N-, 2-O-sulfated polysaccharide products synthesized using an engineered 2OST having the amino acid sequence SEQ ID NO: 14 or SEQ ID NO: 16, respectively.
Figure 27B:
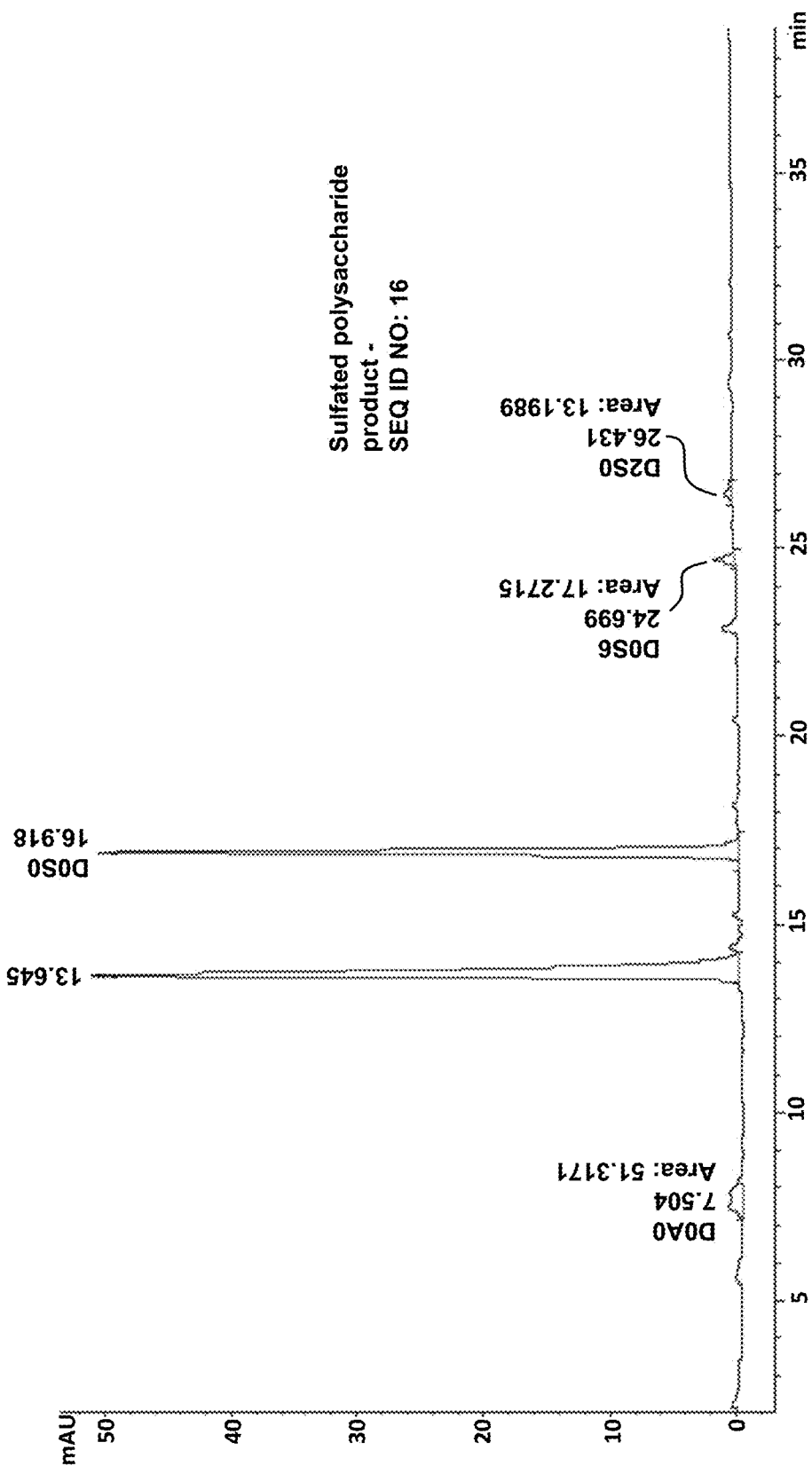

The extracted ion chromatograms from the LCMS are shown in FIGS. 27A and 27B, corresponding to 2-O sulfated products obtained from reactions with engineered enzymes having the amino acid sequences of SEQ ID NO: 14 or SEQ ID NO: 16. Peaks were compared with chromatograms of a series of eight disaccharide standards, as well as a chromatogram from 100 ng of a commercial heparin polysaccharide (CAS code: 9041-08-1, available from Millipore Sigma), which was also digested using the lyase mixture. The eight reference disaccharide standards (D0A0, D0S0, D0A6, D2A0, D0S6, D2S0, D2A6, D2S6) represent disaccharides that are variably sulfated at the N-, 2-O and 6-O positions. In particular, the disaccharide D2S0 represents a disaccharide having a hexuronyl residue sulfated at the 2-O position and an N-sulfated glucosamine residue. The retention time and peak areas from the spectra from all of the disaccharide standards (not shown), the digested commercial sulfated polysaccharide (not shown), and the sulfated polysaccharide products of the engineered enzymes having the amino acid sequence of SEQ ID NO: 14 or SEQ ID NO: 16 are collected in Table 1, below. Since the ionization of each individual disaccharide is different, the present percent in EIC chromatograms may not represent their actual abundance. However, the ionization efficiency is identical for each disaccharide from sample to sample. Therefore, it is believed that comparing the peak area percent of the same saccharides from sample to sample can still be achieved.

TABLE 1

| | | Peak Area % | | |
|---|---|---|---|---|
| Peak No. | Disaccharides | Commercial standard | SEQ ID NO: 14 | SEQ ID NO: 16 |
| 1 | D0A0 | 3.9 | 5.9 | 9.1 |
| 2 | D0S0 | 3.9 | 87.1 | 85.5 |
| 3 | D0A6 | 3.4 | ND | ND |
| 4 | D2A0 | 1.8 | ND | ND |
| 5 | D0S6 | 11.8 | 4.1 | 3.1 |
| 6 | D2S0 | 6.6 | 2.9 | 2.3 |
| 7 | D2A6 | 1.6 | ND | ND |
| 8 | D2S6 | 67.0 | ND | ND |

Sulfotransferase activity of the engineered enzymes was confirmed by the re-sulfation at the 2-O position of hexuronic acid residues within the sulfo acceptor polysaccharide that had previously been desulfated prior to the reaction. This is illustrated by the presence of D2S0 disaccharides within the products isolated from reactions of both engineered enzymes and NCS. Without being limited by a particular theory, it is also believed that the activity of the engineered enzyme is dependent on reacting with a portion of the polysaccharide in which the hexuronic acid residue is adjacent to a glucosamine residue that is N-sulfated, but not 6-O sulfated. This is illustrated by the lack of D2S6 (2-O sulfated hexuronic acid residue and an N,6-sulfated glucosamine residue) and D2A6 (2-O sulfated hexuronic acid residue and a 6-O sulfated N-acetyl glucosamine residue) disaccharides detected within the isolated sulfated polysaccharide product. This is a similar reactivity to wild type 2OSTs within EC 2.8.2.-, which are believed to react with N-sulfated heparosan comprising either the structure of Formula IV or Formula V.

Example 4: Mass Spectrometric Characterization of the 6-O Sulfated Polysaccharide Products of Engineered Aryl Sulfate-Dependent 6OST Enzymes A study was conducted in accordance with embodiments of the present disclosure to confirm 6OST activity of enzymes comprising the amino acid sequence of SEQ ID NO: 18, SEQ ID NO: 20, or SEQ ID NO: 22 by detecting the presence of 6-O sulfated polysaccharide products as a result of their sulfotransfer reaction, using a similar LCMS procedure as in Example 3, except that the sulfo acceptor polysaccharide was prepared by chemically 6-O desulfating commercially available heparin (CAS code: 9041-08-1, available from Millipore Sigma), according to the procedure provided by Kariya, Y., et al., (2000) J. Biol. Chem. 275 (34):25949-25958).

Figure 28A:
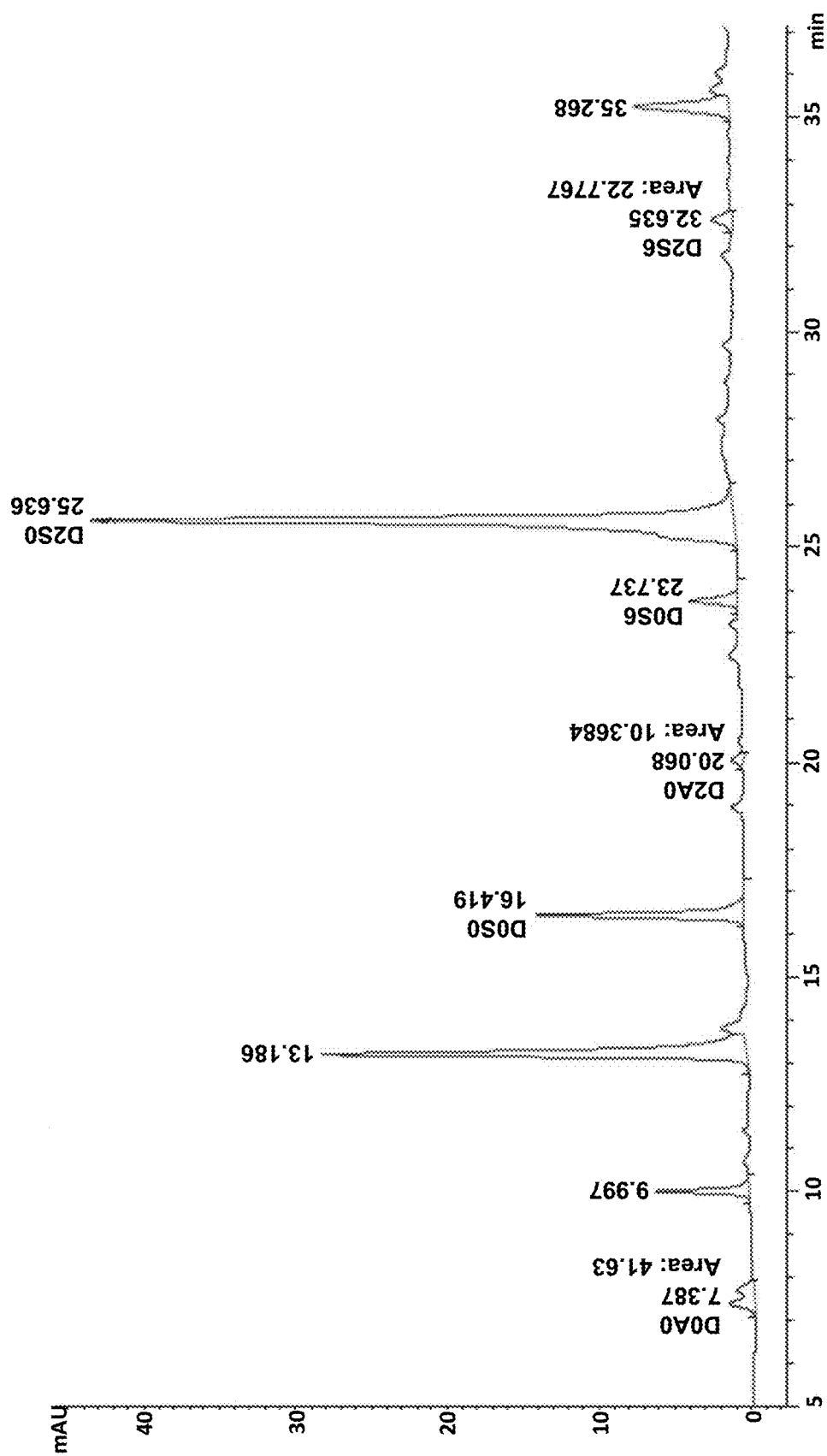
FIGS. 28A-28C shows an LCMS chromatogram of digested N-, 2-O-, 6-O-sulfated polysaccharide products synthesized using an engineered 6OST having the amino acid sequence SEQ ID NO: 18, SEQ ID NO: 20, or SEQ ID NO: 22, respectively.
Figure 28B:
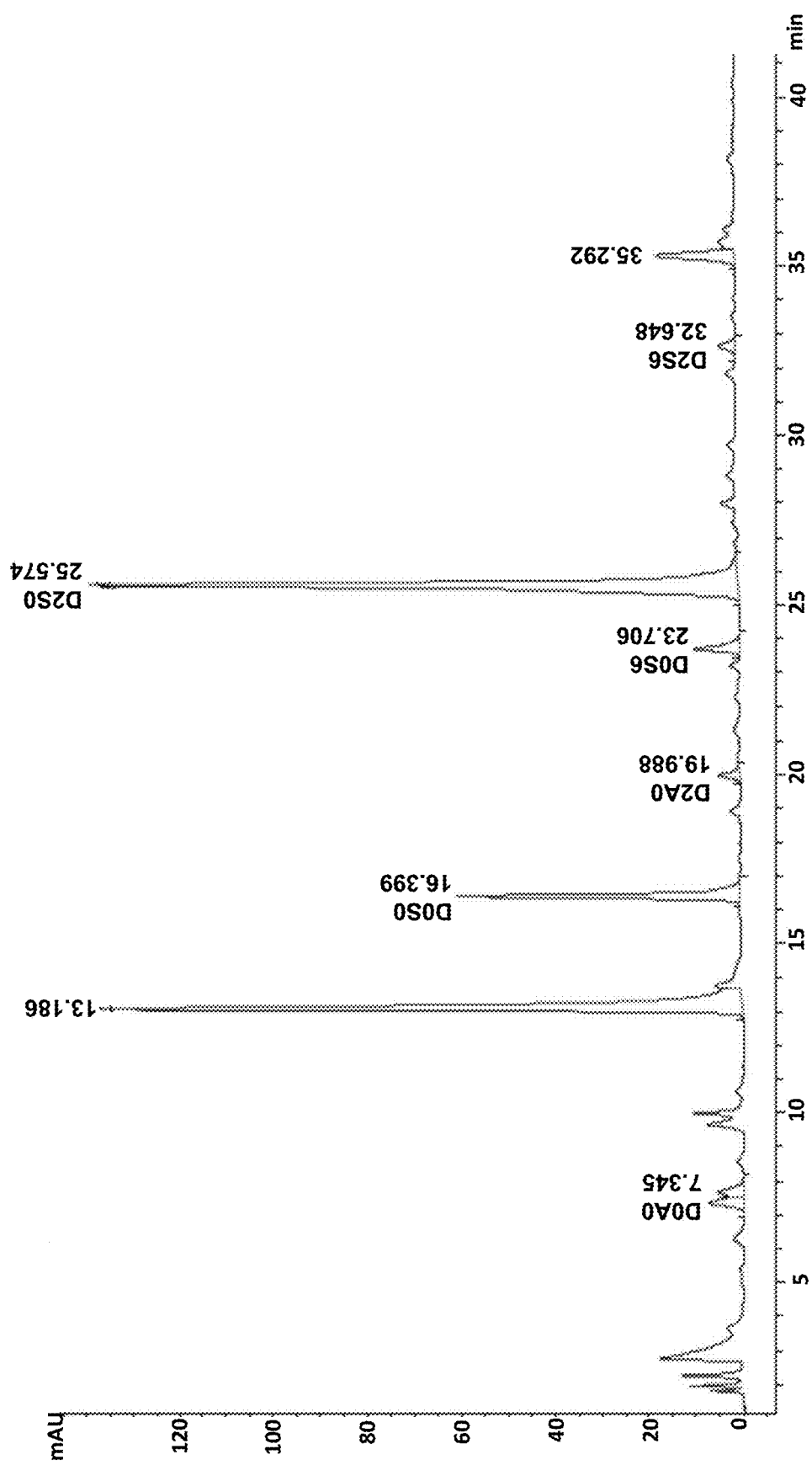
Figure 28C:
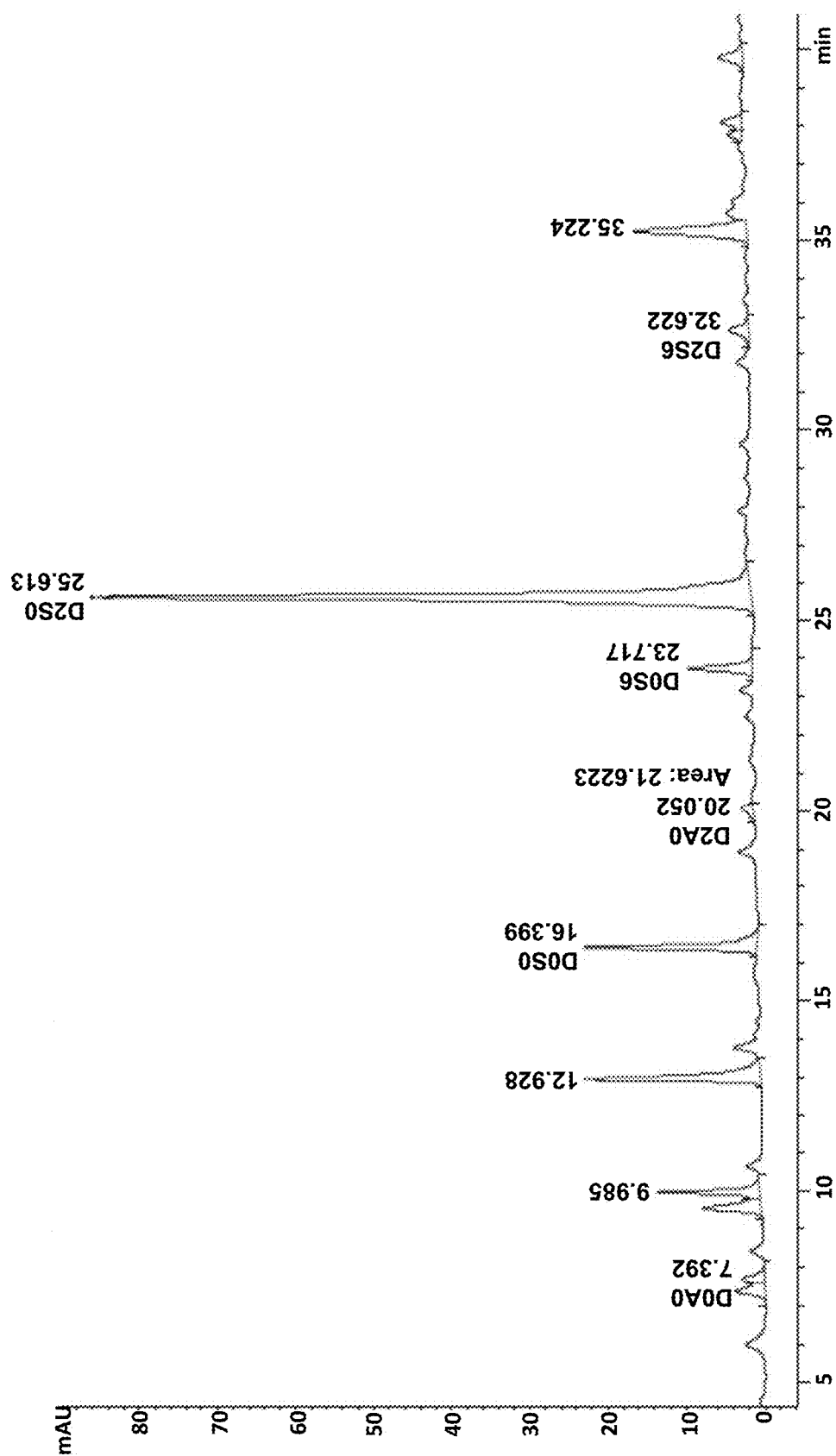

The extracted ion chromatograms corresponding to 6-O sulfated products obtained from reactions with engineered enzymes having the amino acid sequences of SEQ ID NO: 18, SEQ ID NO: 20, or SEQ ID NO: 22 are shown in FIG. 28A, FIG. 28B, and FIG. 28C, respectively. Enzymes having the sequence of SEQ ID NO: 18 and SEQ ID NO: 20 were active when NCS was the sulfo group donor, while the enzyme having the sequence of SEQ ID NO: 22 was active when PNS was the sulfo group donor. Assigned peaks were based on the determined retention times of eight reference disaccharide standards. The eight reference disaccharide standards (D0A0, D0S0, D0A6, D2A0, D0S6, D2S0, D2A6, and D2S6) represent disaccharides that are variably sulfated at the N-, 2-O, and 6-O positions. D0A6, D0S6, D2A6, and D2S6 comprise 6-O sulfated glucosamine residues. S6 indicates an N,6-sulfated glucosamine residue, while A6 indicates a 6-O sulfated N-acetyl glucosamine residue. Each chromatogram indicates two integrable peaks, D0S6 and D2S6, correlating to the synthesis of N,6-sulfated glucosamine residues, adjacent to a hexuronic acid residue that is either non sulfated or sulfated at the 2-O position, respectively. The peak area % of all the labelled disaccharides is in Table 2, below. Since the ionization of each individual disaccharide is different, especially for D0A0 and D2S6, the present percent in EIC chromatograms may not represent their actual abundance. However, the ionization efficiency is identical for each disaccharide from sample to sample. Therefore, it is believed that comparing the peak area percent of the same saccharides from sample to sample can still be achieved.

TABLE 2

| Peak No. | Disaccharides | RT (min) | Peak Area % | | |
|---|---|---|---|---|---|
| | | | SEQ ID NO: 18 | SEQ ID NO: 20 | SEQ ID NO: 22 |
| 1 | D0A0 | 7.7 | 4.6 | 6.0 | 5.4 |
| 2 | D0S0 | 16.4 | 14.2 | 18.4 | 13.0 |
| 3 | D0A6 | ND | ND | ND | ND |
| 4 | D2A0 | 20.0 | 1.1 | 1.8 | 1.3 |
| 5 | D0S6 | 23.7 | 4.0 | 3.7 | 5.6 |
| 6 | D2S0 | 25.6 | 73.5 | 68.4 | 72.4 |
| 7 | D2A6 | ND | ND | ND | ND |
| 8 | D2S6 | 32.7 | 2.5 | 1.7 | 2.3 |

Sulfotransferase activity of the engineered enzymes was confirmed by the re-sulfation at the 6-O position of glucosamine residues that had been desulfated by the procedure according to Kariya, Y., et al, above. This is illustrated by the presence of D0S6 and D2S6 disaccharides within the products isolated from the reactions with each enzyme. Among each of the engineered enzymes, it appears that the 6OST having the amino acid sequence of SEQ ID NO: 22 was the most active, based on comparing the peak area percentages of the D0S6 and D2S6 disaccharides. However, while D0A6 and D2A6 polysaccharides were not observed in any of the 6-O sulfated products produced by the engineered enzymes, without being limited by any particular theory, it is believed that these enzymes may nonetheless be able to transfer a sulfo group to N-acetyl glucosamine residues in different reaction conditions, particularly by increasing the concentration of the enzyme and/or polysaccharide where the presence of N-acetyl glucosamine residues is confirmed prior to the reaction, based on the reactivity of natural natural 6OSTs within EC 2.8.2.-.

Example 5: Mass Spectrometric Characterization of the 3-O Sulfated Polysaccharide Products of Engineered Aryl Sulfate-Dependent 3OST Enzymes A study was conducted in accordance with embodiments of the present disclosure to confirm 3OST activity of enzymes comprising the amino acid sequence of SEQ ID NO: 24, SEQ ID NO: 26, or SEQ ID NO: 28 by detecting the presence of 3-O sulfated polysaccharide products as a result of their sulfotransfer reaction, using a reaction, using a similar LCMS procedure as in Example 3, except that the sulfo acceptor polysaccharide was commercially-available heparin (CAS code: 9041-08-1, available from Millipore Sigma). Even though the unmodified heparin contains ~3.5% (w/w) of 3-O sulfated glucosamine residues, about ~60% of the glucosamine residues are N,6-sulfated and are adjacent to a 2-O sulfated hexuronic acid residue, as in Formula X. Consequently, these N,6-sulfated glucosamine residues can still be 3-O sulfated.

Figure 29A:
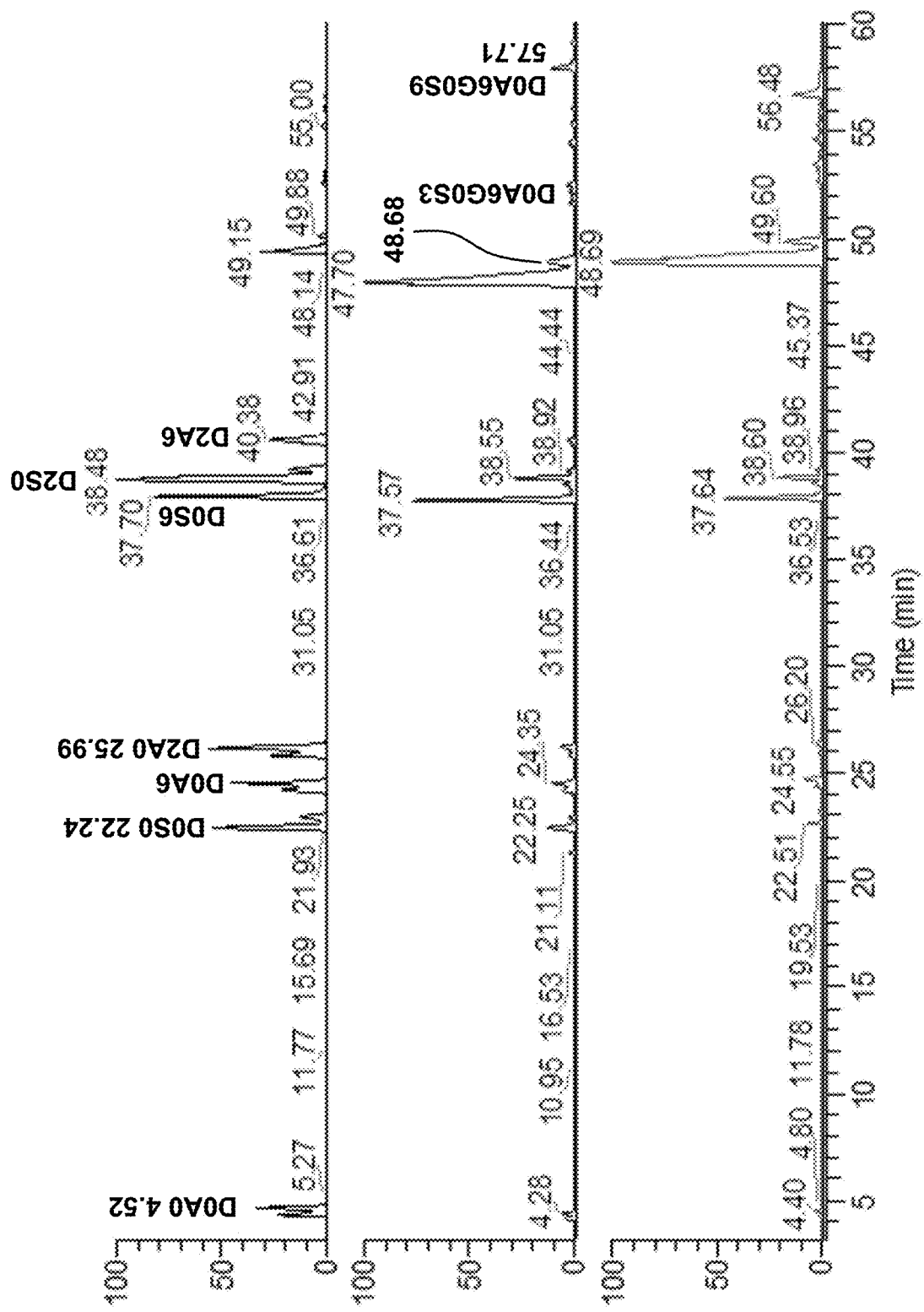
FIGS. 29A-29B show a series of overlaid LCMS chromatograms of digested N-, 2-O-, 6-O-, 3-O-sulfated polysaccharide products synthesized using engineered 3OST enzymes having the amino acid sequence SEQ ID NO: 24, SEQ ID NO: 26, or SEQ ID NO: 28, compared to a series of disaccharide and polysaccharide standards.
Figure 29B:
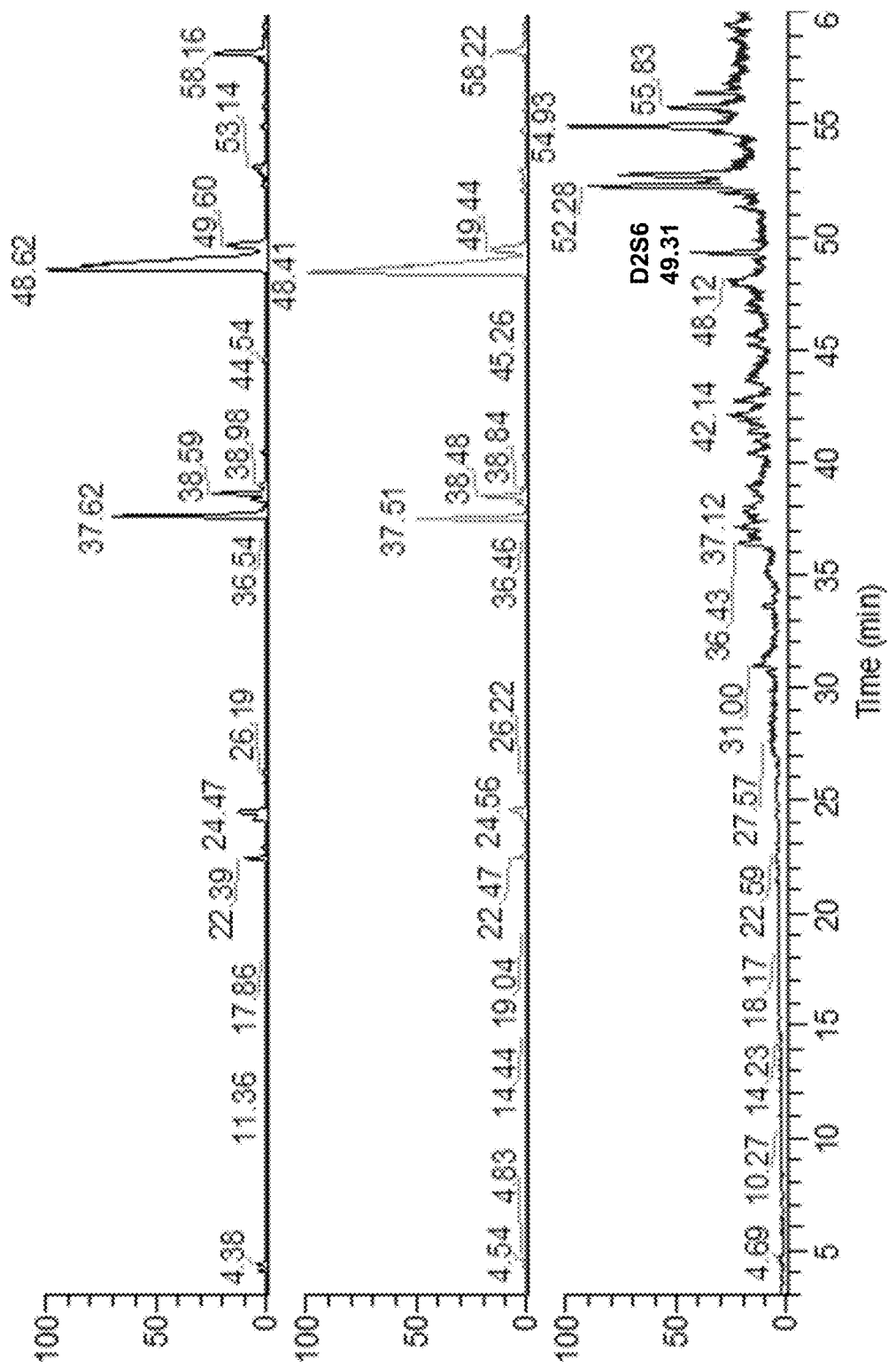

The extracted ion chromatograms are shown in FIG. 29A and FIG. 29B, along with chromatograms of a series of ten reference standards and 100 ng of the commercial polysaccharide, which was also digested using the lyase mixture. The ten reference standards (D0A0, D0S0, D0A6, D2A0, D0S6, D2S0, D2A6, D2S6, D0A6G0S3, and D0A6G0S9) represent di- or tetrasaccharides that are variably sulfated at the N-, 2-O, 3-O, and 6-O positions (black spectrum). For clarity, reference peaks that include 3-O sulfated glucosamine residues (D0A6G0S3) and (D0A6G0S9) are indicated in the digested commercial polysaccharide spectrum, shown in red. Four mass spectra representing the digested sulfated polysaccharide products from reactions with enzymes comprising the amino acid sequence of SEQ ID NO: 24 (PNS, yellow spectrum), SEQ ID NO: 26 (PNS, purple spectrum) (NCS, green spectrum), and SEQ ID NO: 28 (NCS, blue spectrum) are shown below the digested commercial polysaccharide spectrum. The peak area % of all the labelled disaccharides and tetrasaccharides is in Table 3, below. Since the ionization of each individual disaccharide is different, especially for D0A0 and D2S6, the present percent in EIC chromatograms may not represent their actual abundance. However, the ionization efficiency is identical for each disaccharide or tetrasaccharide from sample to sample. Therefore, it is believed that comparing the peak area percent of the same saccharides from sample to sample can still be achieved.

TABLE 3

| peak No. | Disaccharides | RT (min) | Peak Area % | | | |
| --- | --- | --- | --- | --- | --- | --- |
| | | | Commercial standard | SEQ ID NO: 24 | SEQ ID NO: 26 (NCS) | SEQ ID NO: 28 | SEQ ID NO: 26 (PNS) |
| 1 | D0A0 | 4.5 | 1.9 | 0.6 | 0.8 | 1.4 | N.D. |
| 2 | D0S0 | 22.5 | 3.7 | 1.4 | 1.7 | 2.3 | N.D. |
| 3 | D0A6 | 24.6 | 4.2 | 2.8 | 3.1 | 4.5 | N.D. |
| 4 | D2A0 | 26.2 | 2.2 | 0.5 | 0.8 | 0.5 | N.D. |
| 5 | D0S6 | 37.5 | 16.0 | 10.9 | 10.6 | 13.1 | N.D. |
| 6 | D2S0 | 38.5 | 6.5 | 4.9 | 5.4 | 5.4 | N.D. |
| 7 | D2A6 | 40.3 | 1.6 | 0.8 | 0.8 | 0.9 | N.D. |
| 8 | D2S6 | 48.4 | 60.3 | 73.4 | 71.6 | 64.0 | 100.0 |
| 9 | D0A6G0S3 | 52.9 | 0.6 | 0.8 | 0.9 | 1.4 | N.D. |
| 10 | D0A6G0S9 | 58.2 | 3.0 | 4.0 | 4.1 | 6.5 | N.D. |

Sulfotransferase activity of each of the engineered enzymes was confirmed by the increase in the abundance of the D0A6G0S3 (hexuronic acid-6-O-sulfated N-acetyl glucosamine-glucuronic acid-N,3,6-sulfated glucosamine) and D0A6G0S9 (hexuronic acid-6-O-sulfated N-acetyl glucosamine-glucuronic acid-N,3-sulfated glucosamine) tetrasaccharides relative to the commercial heparin sample. However, the total abundance of disaccharides in the SEQ ID NO: 26 PNS sample was much lower than other samples. Subsequent trials included re-running the experiment with 10 times more injection volume, and a re-digestion of the sample with the lyase mixture. Nonetheless, only the D2S6 disaccharide could ever be found, indicating that the abundance of the SEQ ID NO: 26 PNS sulfated polysaccharide sample isolated initially was extremely low, and/or that the polysaccharide resists lyase digestion, causing the product to potentially elute from the column with a retention time longer than one hour.

Nonetheless, NMVR studies (indicated below in Example 6) indicated 3-O sulfotransferase activity with the enzyme comprising the amino acid sequence SEQ ID NO: 26 when PNS is the aryl sulfate compound. Further, the enzyme having the amino acid sequence of SEQ TD NO: 26 was determined to be active as a sulfotransferase when NCS is the aryl sulfate compound. Therefore, it is believed that the observed results for the SEQ TD NO: 26 PNS sulfated polysaccharide sample during the LCMS experiment result from the sample produced for the purpose of the experiment, and not the activity of the enzyme itself. Otherwise, a higher abundance of 3-O sulfation was found in all of the other sulfated polysaccharide products from SEQ ID NO: 24, SEQ ID NO: 26, and SEQ ID NO: 28, relative to the commercial heparin standard.

Example 6: Confirmation of Sulfotransferase Activity of the Engineered 3OSTs Using Nuclear Magnetic Resonance A study was conducted in accordance with embodiments of the present disclosure to confirm the 3-O sulfotransferase activity of the engineered enzymes having the amino acid sequence of SEQ ID NO: 24, SEQ ID NO: 26, and SEQ ID NO: 28, particularly the activity of the enzyme having the amino acid sequence SEQ ID NO: 26 with PNS as the sulfo group donor. Each enzyme was purified according to the procedure of Example 1. To each purified protein solution, 20 mg of an aryl sulfate compound (PNS or NCS) dissolved in 2 mL of reaction buffer (50 mM MES pH 7.0, 2 mM $CaCl_2$)) was added to the protein solution and incubated at 37° C. for 10 min. 2.5 mL of 2 mg/mL solution of the commercial heparin polysaccharide utilized in Example 5 was added to protein/donor solution and incubated overnight at 37° C.

Figure 30:
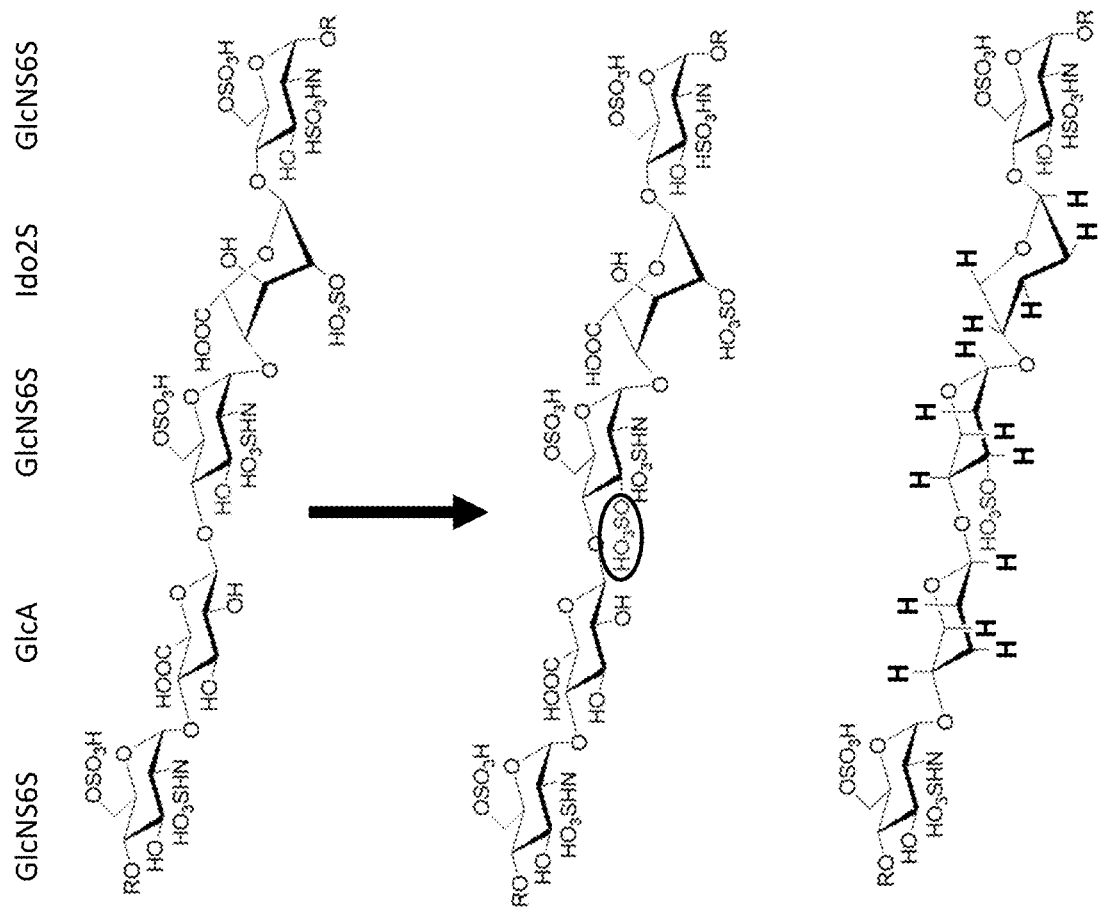
FIG. 30 shows the reaction scheme for deuterium labeling of protons of interest for nuclear magnetic resonance (NMR) studies.

Each reaction was centrifuged at 5,000×g for 10 min, applied to a pre-wetted 30K MWCO Amicon-15 filter and centrifuged at 5,000×g for 10 min. The filter was washed once with 2 mL water, and centrifuged again. The filtrate was added to a 1K MWCO Dialysis membrane, dialyzed for 2 days in Milli-Q water, with water changes at 1 h, 2 h, 8 h, 16 h, 32 h, and then lyophilized. The dry, white powder was resuspended in 400 µL D20, lyophilized to remove exchangeable protons, then resuspended in 600 µL D20 and transferred to NMR tubes (Wilmad, 0.38 mm×7"). To determine if sulfotransfer took place, $^1H$ NMR spectra were obtained on a Bruker 600 MHz NMR, 32 scans, with water suppression. The overall reaction scheme is shown in FIG. 30. Within FIG. 30, the 3-O positions of any of the glucosamine residues can be sulfated by the 3OST enzyme. The sulfated 3-O position is circled in the central polysaccharide. Exchangeable protons having the ability to exhibit resonance upon deuterium exchange are shown in bold, in the bottom polysaccharide. Crude mixture peaks were integrated to literature-referenced spectra for the sulfo acceptor polysaccharide and associated 3-O sulfated product.

Figure 31:
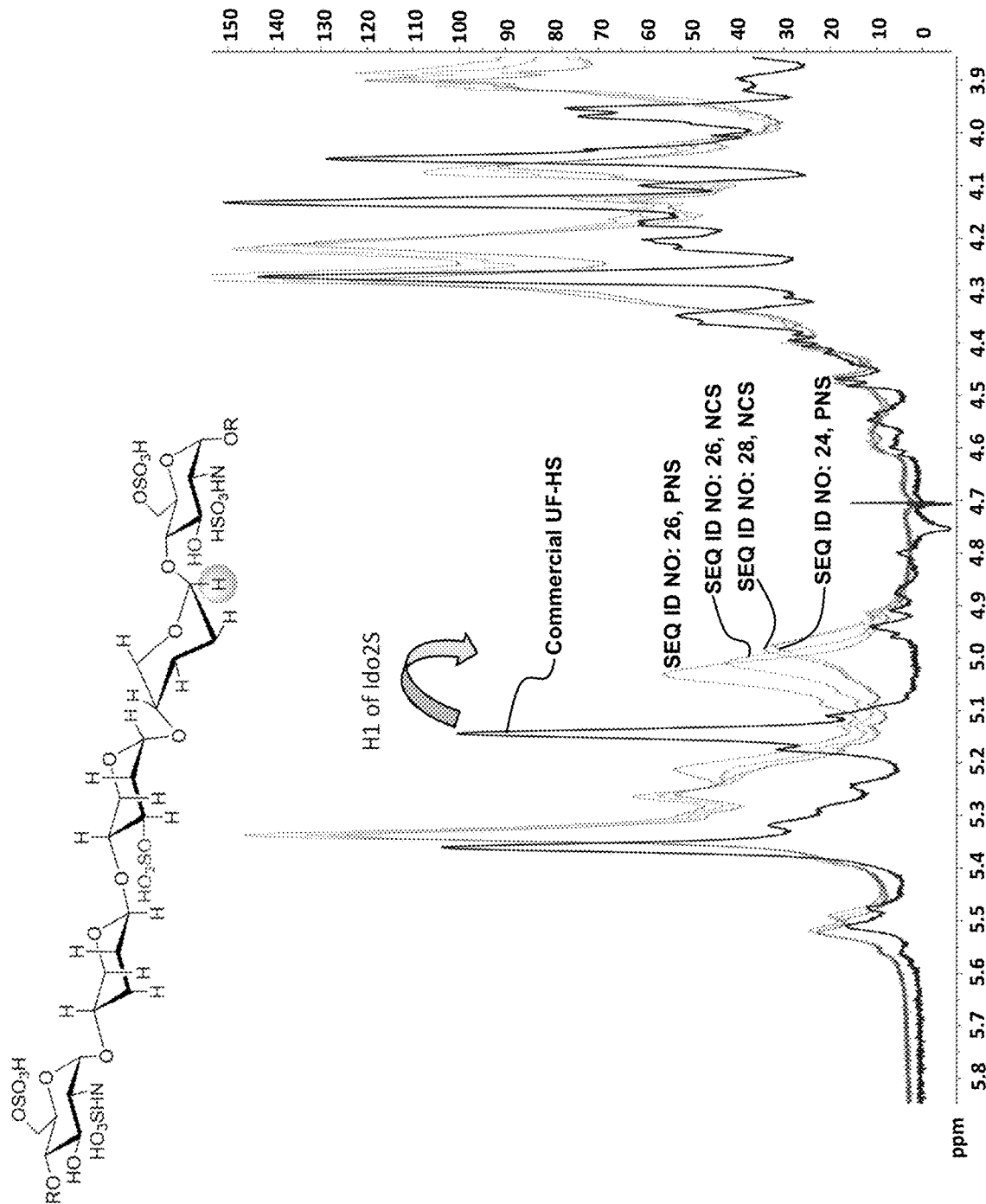
FIG. 31 shows an expanded view of $^1$H-NMR spectra for engineered 3OST enzymes having the amino acid sequence SEQ ID NO: 24, SEQ ID NO: 26, or SEQ ID NO: 28, either with PNS or NCS.

As shown in the overlain spectra in FIG. 31, a sharp peak at 5.15 ppm that correlates to the proton at the C2 carbon of the 2-O sulfated iduronic acid present in the commercial heparin disappears upon reacting with enzymes comprising the amino acid sequence of SEQ ID NO: 24, SEQ ID NO: 26, and SEQ ID NO: 28. The proton of interest is circled in the polysaccharide shown above the spectra. The $^1H$ NMR spectra for a 3-O sulfated product synthesized by enzymes comprising the amino acid sequence of SEQ ID NO: 24, SEQ ID NO: 26, or SEQ ID NO: 28 upon reacting with either PNS and/or NCS are all illustrated. In each of the product spectra, the $IdoA_{2S}$ peak shifts to between approximately 5.0 and 5.05 ppm. A similar transition is shown when incubating the natural human sulfotransferase enzyme with the same polysaccharide substrate and PAPS (data not shown).

Figure 32:
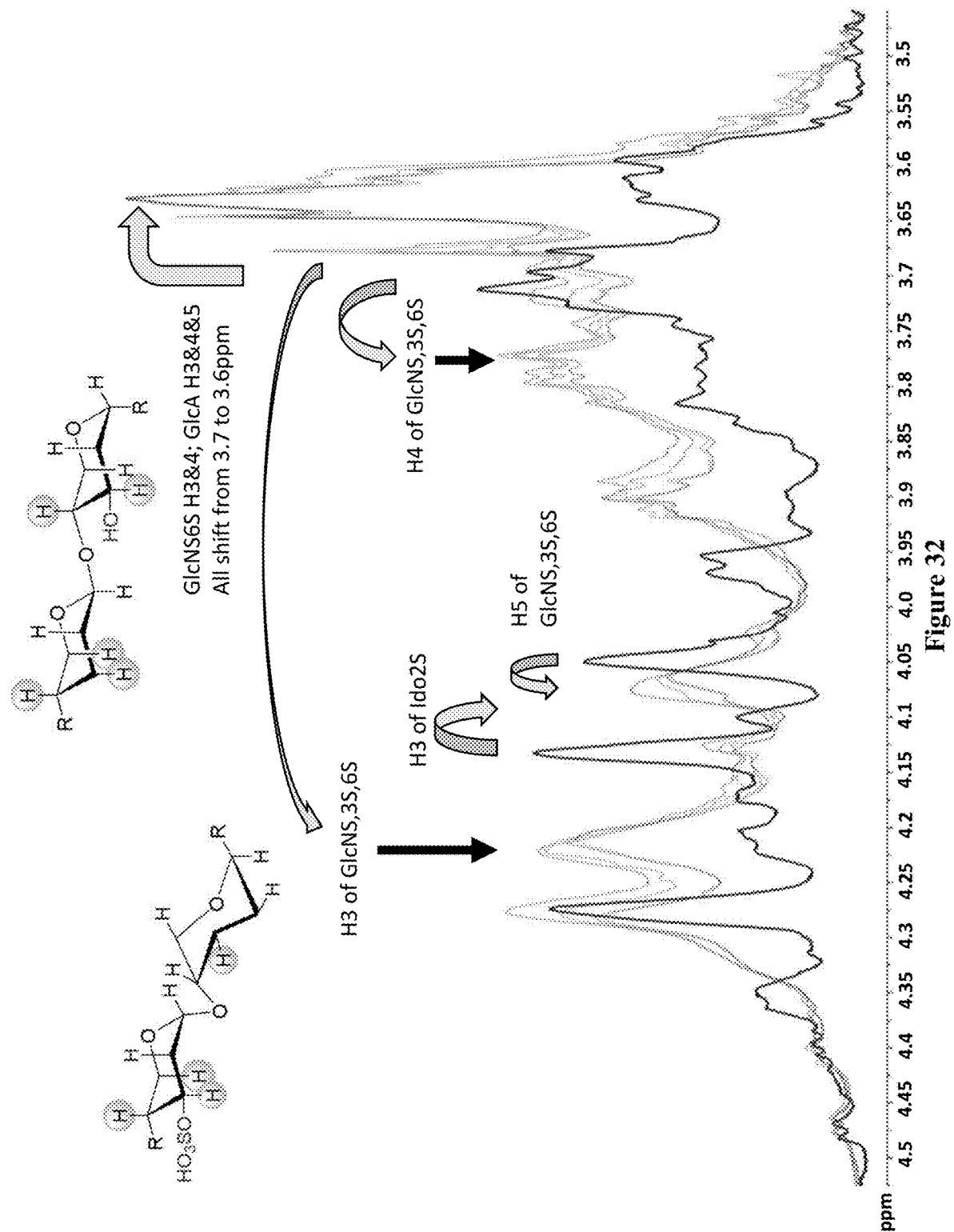
FIG. 32 shows a magnified view of the 3.5 ppm to 4.5 ppm region of the $^1$H-NMR spectra illustrated in FIG. 31.

As shown in FIG. 32, the region between 4.5 and 3.5 shows several peaks that similarly shift in response to the addition of the sulfate group to the 3-O position of a glucosamine residue, all of which correlate to the same shifts observed upon incubating the natural human 3OST enzyme with the same commercial heparin substrate and PAPS. Peaks that shift are indicated in curved arrows, and positions of the peaks from 3-O sulfated polysaccharides produced by enzymes having the amino acid sequence of SEQ ID NO: 24, SEQ ID NO: 26, or SEQ ID NO: 28, are shown with straight arrows. The largest shift occurs for H3 of $Glc_{NS3S6S}$, from 3.7 ppm to 4.2 ppm. This results from being closest to the newly added 3-O sulfate group. Additionally, the H3 proton of $Ido_{2S}$ and H5 of $Glc_{NS3S6S}$ both converge toward a peak at 4.07 ppm, which shows two overlapping peaks. H4 of $Glc_{NS3S6S}$ shifts moderately downfield from the 3.7 ppm region to the 3.8 ppm region, and according to references, many peaks such as H3 & H4 from $Glc_{NS6S}$ and H3, H4, and H5 from GlcA shift from the 3.7 ppm region to the 3.6 ppm region.

Example 7: Chemical Synthesis of N-Sulfated Heparosan

A study was conducted in accordance with embodiments of the present disclosure to chemically synthesize N-sulfated heparosan that can be utilized as sulfo acceptor polysaccharides with any of the engineered aryl sulfate-dependent enzymes, particularly either of the engineered 2OST enzymes. N-deacetylated heparosan was prepared according to the protocol described in Balagurunathan, K. et al., above. Particularly, the heparosan that eluted from the DEAE resin was precipitated overnight in ethanol saturated with sodium acetate, at −30° C., before being resuspended in water and dialyzed within a cellulose dialysis membrane having a 1,000 Da molecular weight cut-off (MWCO).

To N-deacetylate the heparosan, enough sodium hydroxide pellets (~4.0 g) were dissolved to make a 2.5 M solution in a 40 mL aliquot of the dialyzed heparosan in water. The solution was incubated at 55° C. for 16 hours, with shaking at 100 rpm. The sodium hydroxide within the sample was then neutralized with acetic acid until the solution reached a pH of ~7.0, and then dialyzed in water overnight within a 1,000 MWCO dialysis membrane.

Subsequent N-sulfation of the N-deacetylated heparosan was accomplished by adding 100 mg of sodium carbonate and 100 mg of sulfur trioxide-triethylamine complex, and allowing the composition to incubate at 48° C. until all of the solid was dissolved. The pH of the solution was then readjusted to ~9.5, using acetic acid. After incubation at 48° C. overnight with shaking at 100 rpm, an additional 100 mg of sodium carbonate and 100 mg of sulfur trioxide-triethylamine complex was added, before subsequent readjustment of the pH to ~ 9.5 using acetic acid. The solution was incubated at 48° C. for an additional 24 hours. The sulfated polysaccharide solution was neutralized with acetic acid to a pH of ~7.0, and dialyzed in water overnight within a 1,000 MWCO dialysis membrane. The dialyzed N-sulfated heparosan was then lyophilized prior to further use. The N-sulfated heparosan was then further purified by loading it onto a Zenix SEC-100 column and eluting it isocratically with 0.1 M ammonium acetate, pH 9.0.

Figure 33:
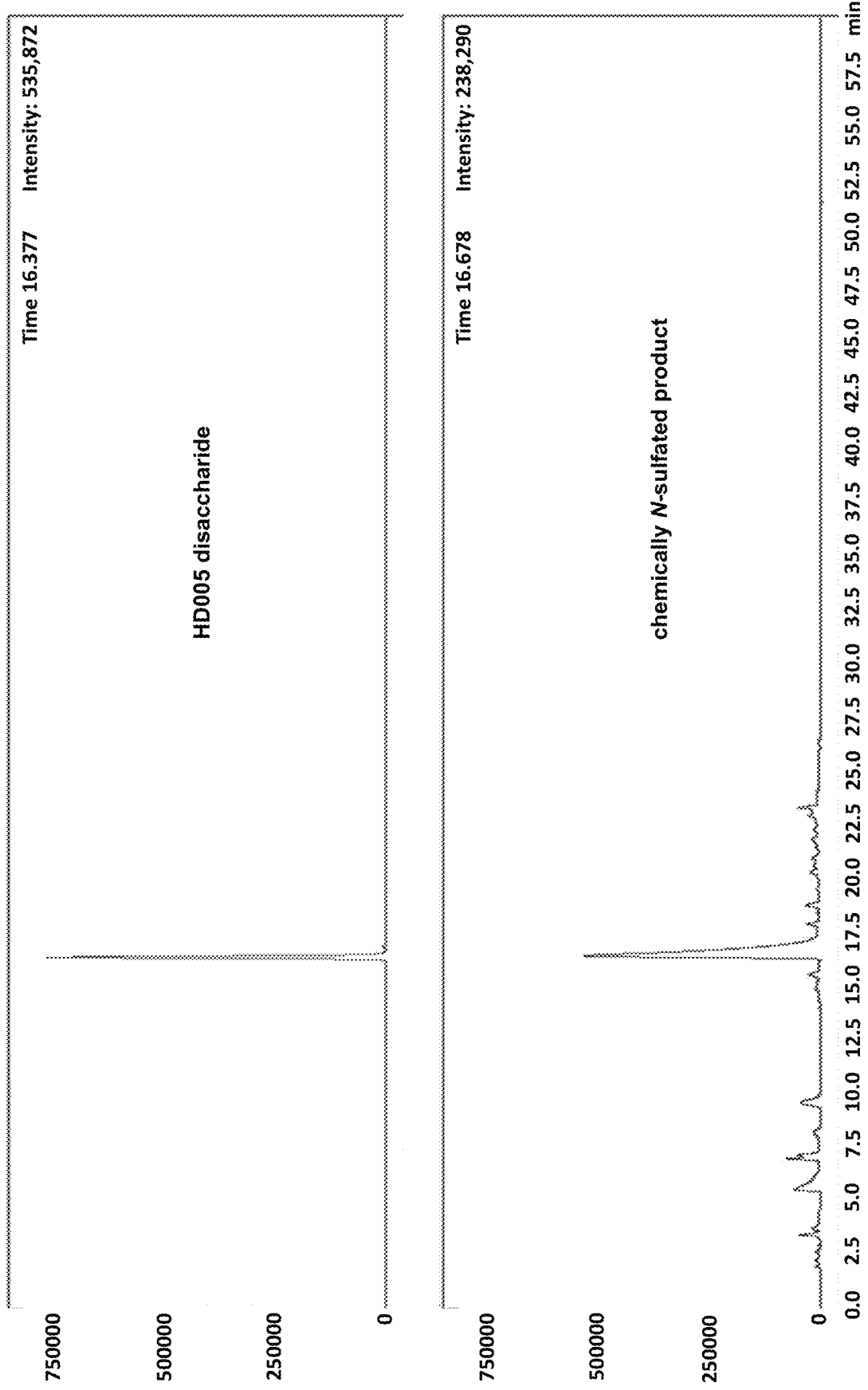
FIG. 33 shows a SAX-HPLC chromatogram of a chemically N-sulfated polysaccharide product, compared to a commercial standard.

The functionalization of the purified heparosan-based polysaccharide was characterized by digesting it with a mixture of three carbon-oxygen lyases comprising the amino acid sequences of SEQ ID NO: 30, SEQ ID NO: 31, and SEQ ID NO: 32, and analyzing the digested samples using SAX, using a similar procedure described above. As a positive control, the commercial HD005 disaccharide of Example 2, containing N-sulfated glucosamine residues, was also analyzed. Representative chromatograms of both samples are shown in FIG. 33. In both chromatograms, a strong peak is present at about 16.5 minutes, indicating that the synthesized sample contains N-sulfated glucosamine residues.

Example 8: Preparation of an N,2-HS Polysaccharide Product

A study was conducted in accordance with embodiments of the present disclosure to synthesize an N,2-HS polysaccharide product using an engineered 2OST, using the N-sulfated heparosan synthesized in Example 7 as the sulfo acceptor. In a conical-bottom centrifuge tube, 80 mM aliquots of NCS were dissolved in 50 mM MES pH 7.0, 2 mM $CaCl_2$). To each solution, 2 mg of the enzyme having the sequence of SEQ ID NO: 14, based on the absorbance of the enzyme sample at 280 nm, was added (about 4 mL). 5 mg of the lyophilized N-sulfated heparosan synthesized in Example 7 was resuspended in 1 mL of water and added to the reaction mixture containing the enzyme and NCS. The entire reaction mixture was then incubated at 34° C. with shaking at 30 rpm, for 48 hours. A second set of reactions were prepared using the same procedure, except that 2 mg of a $C_5$-hexuronyl epimerase comprising the amino acid sequence of SEQ ID NO: 29 was also added to the reaction mixture, prior to incubation.

The sulfated polysaccharide products from both sets of reactions were purified by first precipitating out the proteins from the reaction mixtures by placing the reaction vessels in boiling water for 10 minutes and centrifuging at high speed to form a pellet. The supernatant containing the polysaccharide products was decanted from the pellet and dialyzed in water overnight within a 1,000 MWCO dialysis membrane. The dialyzed products were then lyophilized for future use.

Figure 34:
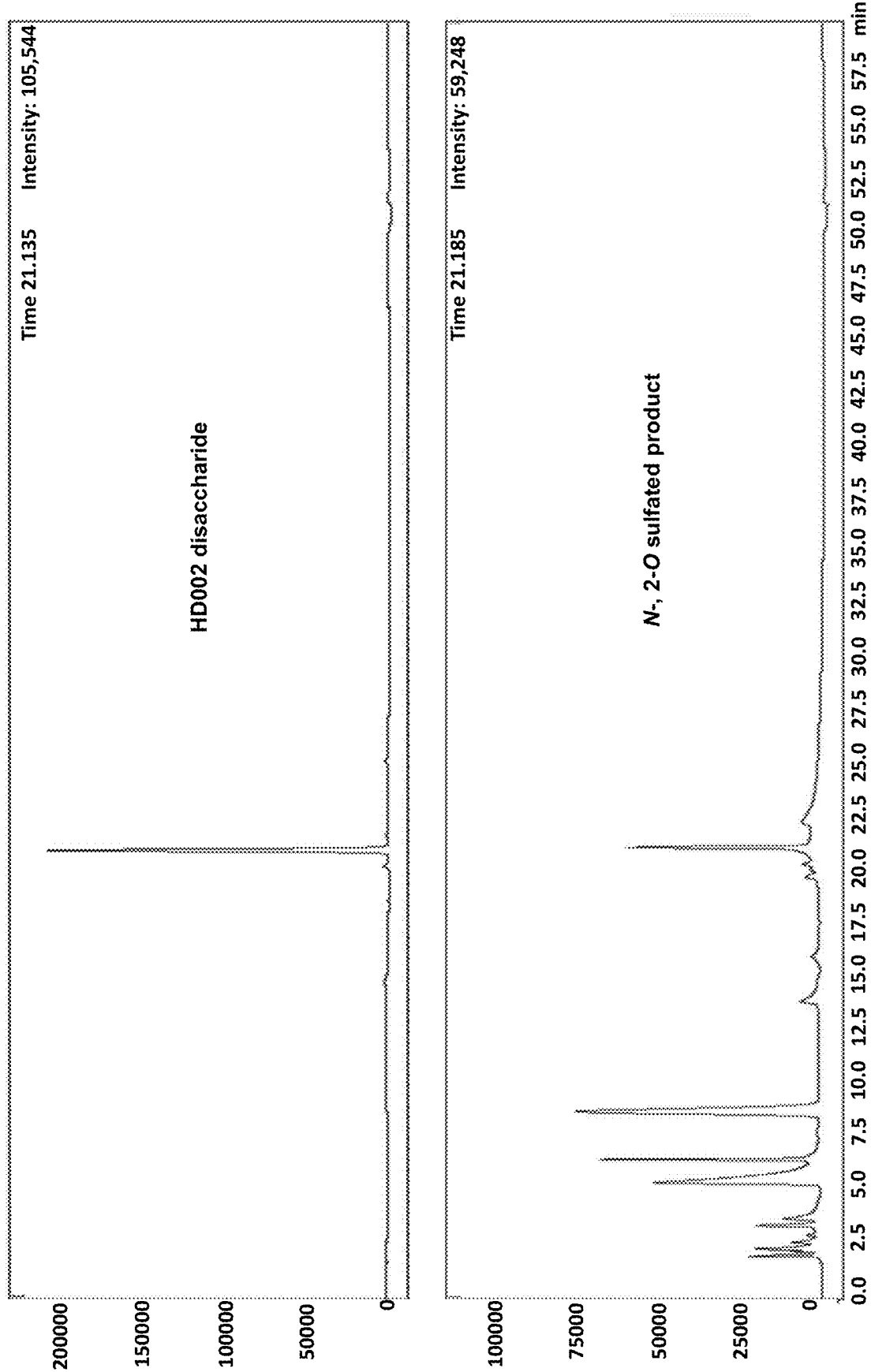
FIG. 34 shows a SAX-HPLC chromatogram of an enzymatically 2-O sulfated polysaccharide product prepared using the chemically N-sulfated polysaccharide product of Example 7 as the sulfo acceptor polysaccharide, compared to a commercial standard.
Figure 35:
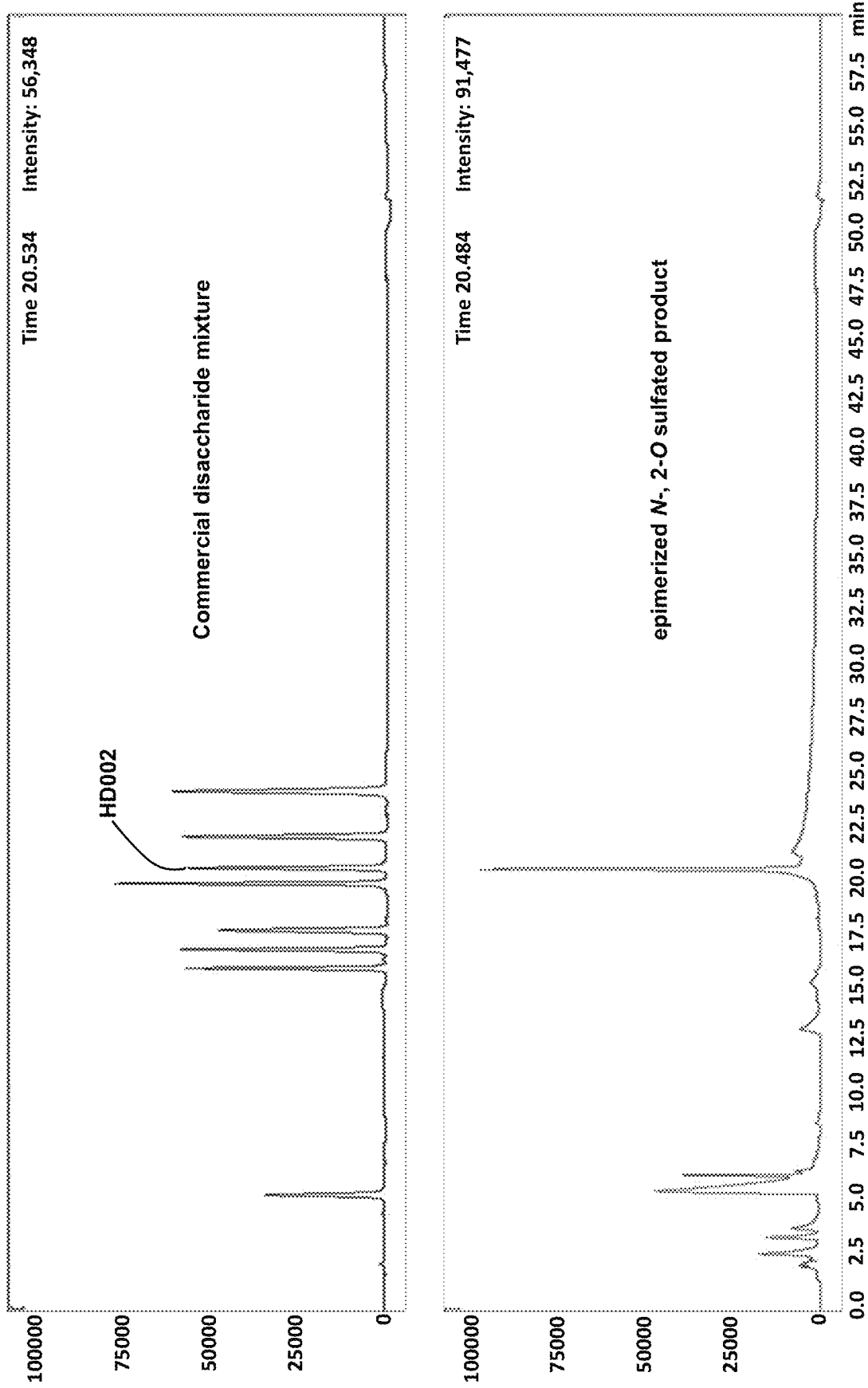
FIG. 35 shows a SAX-HPLC chromatogram of an enzymatically 2-O sulfated polysaccharide product prepared using the chemically N-sulfated polysaccharide product of Example 7 as the sulfo acceptor polysaccharide and with a $C_5$-hexuronyl epimerase included in the reaction mixture, compared to a commercial standard.

To characterize the polysaccharide products, lyophilized samples were resuspended in 400 µL of water, and purified using a Q-Sepharose Fast Flow Column (GE Biosciences). Samples were eluted from the column using a gradient ranging from 0 to 2M NaCl, in 20 mM sodium acetate buffer, pH 5.0. Purified polysaccharides were then digested and analyzed by SAX according to the procedures in Example 2 above, along with a commercial polysaccharide, HD002 (Iduron), which contains disaccharides of 2-O sulfated uronic acid and N-sulfated glucosamine. Representative chromatograms of reactions either without or including the epimerase enzyme are shown in FIG. 34 and FIG. 35, respectively. In FIG. 34, the chromatogram for the HD002 disaccharide has a single, sharp peak at about 21.1 minutes, which correlates to a sharp peak at a nearly identical time in the reaction product, indicating the time that an N,2-HS was formed as a result of the reaction. In FIG. 35, the HD002 disaccharide was provided within a mixture containing other disaccharide standards, with the disaccharide corresponding to HD002 eluting at 20.5 minutes, corresponding with the elution time of the HD002 standard in FIG. 34. The epimerized reaction product has a sharp peak at a nearly identical elution time to the HD002 standard, indicating that an N,2-HS product was formed as a result of the reaction.

Example 9: Preparation of an N,2,6-HS Product

A study was conducted in accordance with embodiments of the present disclosure to synthesize an N,2,6-HS product using the procedure of Example 8, except that the N,2-HS product of Example 8 was used as the sulfo acceptor polysaccharide, and the engineered 6OST having the amino acid sequence of SEQ ID NO: 18 was used as the enzyme.

Figure 36:
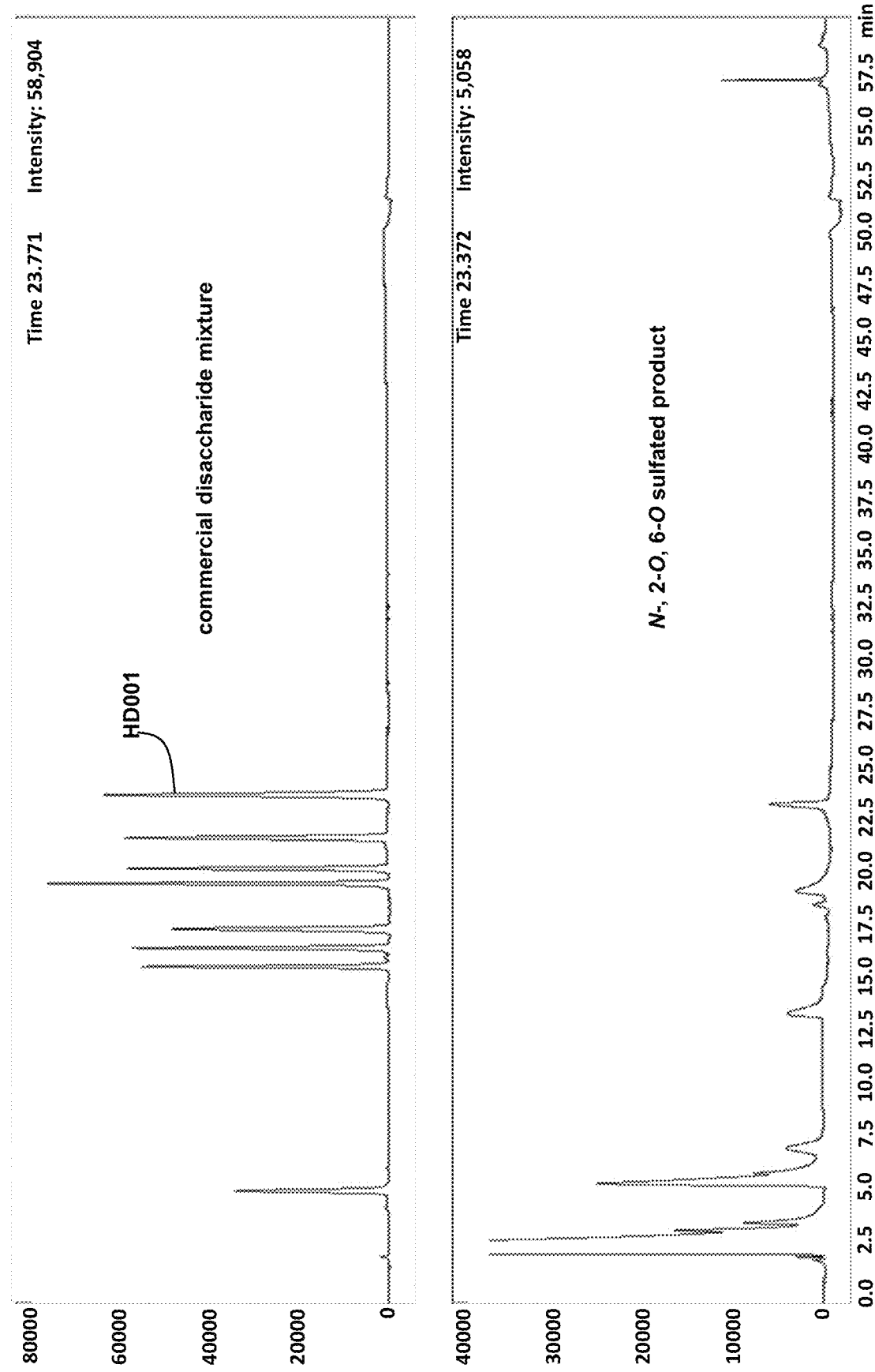
FIG. 36 shows a SAX-HPLC chromatogram of an enzymatically 6-O sulfated polysaccharide product prepared using the sulfated polysaccharide product of Example 8 as the sulfo group acceptor, compared to a commercial standard.

Representative chromatograms of the sulfated polysaccharide product and a mixture of commercial disaccharides are shown in FIG. 36. The chromatogram of the commercial mixture exhibits a peak at about 23.7 minutes and correlates to HD001 (Iduron), which consists of disaccharides of 2-O sulfated uronic acid and N-, 6-O sulfated glucosamine, while the reaction product exhibits a similar peak at 23.4 minutes, indicating that an N,2,6-HS was formed as a result of the reaction. Other peaks present within the N,2,6-HS product include undigested polysaccharide (2.5 min), unsubstituted uronic acid and N-acetylated glucosamine (5.5 min), and unsubstituted uronic acid and N-, 6-O sulfated glucosamine.

Example 10: Preparation of an N,2,3,6-HS Product

A study was conducted in accordance with embodiments of the present disclosure to synthesize a sulfated polysaccharide product comprising N-, 6-O, 3-O sulfated glucosamine and 2-O sulfated hexuronic acid residues, using the procedure of Example 8, except that the chemically synthesized N-, 2-O, 6-O sulfated polysaccharide of Example 9 is used as the sulfo acceptor polysaccharide, and an engineered 3-O sulfotransferase enzyme having the amino acid sequence of SEQ ID NO: 28 is used as the sulfotransferase enzyme.

Sulfated polysaccharide products were digested and analyzed using LCMS to confirm the production of an N,2,3,6-HS product. To facilitate study using LCMS, sulfated polysaccharide products of the SEQ ID NO: 28 sulfotransferase enzyme were isolated and derivatized with aniline tags, according to the procedures described in Lawrence, R., et al., (2008) *J. Biol. Chem.* 283 (48):33674-33684, the disclosure of which is incorporated by reference in its entirety. Briefly, some GAGs, including commercial heparin and other N,2,3,6-HS polysaccharides, can be quantified and compared ratiometrically using LCMS by chemically modifying the sulfated product. Lawrence, R., et al., describes the tagging of the reducing end of lyase-generated disaccharides and tetrasaccharides with [$^{12}C_6$]- and [$^{13}C_6$]-aniline and propionylation of N-unsubstituted glucosamine residues. Isotopic tagging of the disaccharides and tetrasaccharides has no effect on the chromatographic retention times, but can be discriminated using mass spectroscopy.

Sulfated disaccharide and tetrasaccharide products were prepared by anion exchange chromatography, as described in Example 8, and digestion with a mixture of three carbon-oxygen lyases comprising the amino acid sequences of SEQ ID NO: 30, SEQ ID NO: 31, and SEQ ID NO: 32, as described above in Example 7. 1 µmol to 10 nmol of the digested samples were transferred to 1.5-ml microcentrifuge tubes and dried down in a centrifugal evaporator. [$^{12}C_6$]-aniline or [$^{13}C_6$]-aniline (15 µl, 165 µmol) and 15 µl of 1 M NaCNBH$_3$ freshly prepared in dimethyl sulfoxide:acetic acid (7:3, v/v) were added to each sample. Reactions were carried out at 65° C. for 4 h, or alternatively at 37° C. for 16 h, and then dried in a centrifugal evaporator.

Unsubstituted amines were reacted with propionic anhydride. Dried samples were reconstituted in 20 µl of 50% methanol, and 3 µl of propionic anhydride (23.3 µmol) was added. Reactions were carried out at room temperature for 2 h. Acylated samples were subsequently aniline-tagged as described above.

A quadrupole ion trap Liquid Chromatograph Mass Spectrometer with an electrospray ionization source, similar to the Shimadzu LCMS-8050 mass spectrometer described in Example 3, was used for disaccharide analysis. Derivatized and non-derivatized disaccharide residues were separated on a C18 reversed-phase column with the ion pairing agent dibutylamine (DBA). The isocratic steps were: 100% buffer A (8 mm acetic acid, 5 mm DBA) for 10 min, 17% buffer B (70% methanol, 8 mm acetic acid, 5 mm DBA) for 15 min; 32% buffer B for 15 min, 40% buffer B for 15 min, 60% buffer B for 15 min; 100% buffer B for 10 min; and 100% buffer A for 10 min. Generally, mass spectra for samples containing 3-O sulfated product are expected to generate m/z peaks corresponding to tetrasaccharides that are resistant to digestion by the carbon-oxygen lyases, as described above in Example 5. Tetrasaccharides that can be produced include, but are not limited to: 4,5-unsaturated uronic acid-N-acetylated, 6-O sulfated glucosamine-glucuronic acid-N-sulfated, 3-O sulfated glucosamine ($\Delta$U-A$_{NAc6S}$-G-A$_{NS3S}$); 4,5-unsaturated uronic acid-N-acetylated, 6-O sulfated glucosamine-glucuronic acid-N-sulfated, 3-O sulfated, 6-O sulfated glucosamine ($\Delta$U-A$_{NAc6S}$-G-A$_{NS3S6S}$); 4,5-unsaturated uronic acid-N-sulfated, 6-O sulfated glucosamine-glucuronic acid-N-sulfated, 3-O sulfated, 6-O sulfated glucosamine ($\Delta$U-A$_{NS6S}$-G-A$_{NS3S6S}$); 4,5-unsaturated, 2-O sulfated uronic acid-N-sulfoglucosamine-glucuronic acid-N-sulfated, 3-O sulfated, 6-O sulfated glucosamine ($\Delta$U2S-A$_{NS}$-G-A$_{NS3S6S}$); and 4,5-unsaturated, 2-O sulfated uronic acid-N-sulfated, 6-O sulfated glucosamine-glucuronic acid-N-sulfated, 3-O sulfated, 6-O sulfated glucosamine ($\Delta$U2S-A$_{NS6S}$-G-A$_{NS3S6S}$). In particular, LCMS of the digested polysaccharide samples collected from the reaction with the SEQ ID NO: 28 sulfotransferase enzyme generated mass spectra (not shown) with m/z peaks corresponding to the $\Delta$U-A$_{NAc6S}$-G-A$_{NS3S6S}$ (m/z=1036), $\Delta$U-A$_{NS6S}$-G-A$_{NS3S6S}$ (m/z=1074), and $\Delta$U2S-A$_{NS6S}$-G-A$_{NS3S6S}$ (m/z=1154) tetrasaccharides, indicating that the N,2,3,6-HS product was produced by the reaction with the SEQ ID NO: 28 engineered sulfotransferase enzyme.

Example 11: Confirmation of Anticoagulant Activity of the N,2,3,6-HS Product

A study is conducted in accordance with embodiments of the present disclosure to determine whether 3-O sulfated polysaccharide products produced in Example 10 have a binding affinity to antithrombin using a procedure similar to Meneghetti, G., et al. (2017) *Org. Biomol. Chem.* 15:6792-6799). It is expected that melting curves of antithrombin in the presence of the 3-O sulfated polysaccharide products produced in Example 10 will demonstrate a higher melting temperature than antithrombin alone, indicating that the 3-O sulfated polysaccharide product produced in Example 10 comprises the structure of Formula I.

Example 12: Determination of Engineered Aryl Sulfate-Dependent Mutants of Other EC 2.8.2.8 Enzymes A study is conducted in accordance with embodiments of the present disclosure to engineer additional aryl sulfate-dependent NST enzymes. As described above, the aryl sulfate-dependent NST enzymes having the amino acid sequences of SEQ ID NO: 2, SEQ ID NO: 4, SEQ ID NO: 6, SEQ ID NO: 8, SEQ ID NO: 10, and SEQ ID NO: 12 have been engineered to be mutants of the N-sulfotransferase domain of the human glucosaminyl N-deacetylase/N-sulfotransferase enzyme (see entry sp|P52848|NDST_1_HUMAN, in FIG. 3 above), which is a member of enzyme class EC 2.8.2.8. By generating and analyzing a multiple sequence alignment that includes both the amino acid sequences of the N-sulfotransferase domain of one or more of the other glucosaminyl N-deacetylase/N-sulfotransferase enzymes within EC 2.8.2.8 as well as the amino acid sequences of aryl sulfate-dependent NST enzymes having the amino acid sequences of SEQ ID NO: 2, SEQ ID NO: 4, SEQ ID NO: 6, SEQ ID NO: 8, SEQ ID NO: 10, and/or SEQ ID NO: 12, mutations in the amino acid sequences in the engineered NST enzymes can be observed relative to the amino acid sequences of the natural EC 2.8.2.8 enzymes within the same alignment. Upon selecting the amino acid sequence of the N-sulfotransferase domain of a natural 2.8.2.8 enzyme that is not the human glucosaminyl N-deacetylase/N-sulfotransferase enzyme, mutations that are present within the amino acid sequences of SEQ ID NO: 2, SEQ ID NO: 4, SEQ ID NO: 6, SEQ ID NO: 8, SEQ ID NO: 10, and/or SEQ ID NO: 12 can be engineered into the natural sequence in order to form additional mutants that can have aryl sulfate-dependent sulfotransferase activity.

As a non-limiting example, the amino acid sequence encoding for the N-sulfotransferase domain of the pig glucosaminyl N-deacetylase/N-sulfotransferase enzyme (entry tr|M3V841|M3V841_PIG, as illustrated in the sequence alignment in FIG. 3), is aligned with the amino acid sequences of SEQ ID NO: 2, SEQ ID NO: 4, SEQ ID NO: 6, SEQ ID NO: 8, SEQ ID NO: 10, and SEQ ID NO: 12. Amino acid mutations that are present in SEQ ID NO: 2, SEQ ID NO: 4, SEQ ID NO: 6, SEQ ID NO: 8, SEQ ID NO: 10, and SEQ ID NO: 12 are engineered into their equivalent positions within the amino acid sequence of the N-sulfotransferase domain of the pig N-deacetylase/N-sulfotransferase enzyme, in order to generate the mutant amino acid sequences SEQ ID NO: 35, SEQ ID NO: 36, SEQ ID NO: 37, SEQ ID NO: 38, SEQ ID NO: 39, and SEQ ID NO: 40, respectively. Enzymes comprising the amino acid sequences of SEQ ID NO: 35, SEQ ID NO: 36, SEQ ID NO: 37, SEQ ID NO: 38, SEQ ID NO: 39, and SEQ ID NO: 40, respectively, will be utilized in Example 13 and Example 14, below. However, a person skilled in the art would appreciate that the same procedure can be applied to generate mutants of the N-sulfotransferase domain, or the entire enzyme, with respect to any of the other glucosaminyl natural N-deacetylase/N-sulfotransferase enzymes within the EC 2.8.2.8 enzyme class, and that those are omitted for clarity.

Example 13: Expression and Purification of Engineered Aryl Sulfate-Dependent EC 2.8.2.8 Mutants A study is conducted in accordance with embodiments of the present disclosure to determine whether genes encoding for engineered NST enzymes having the amino acid sequences SEQ ID NO: 35, SEQ ID NO: 36, SEQ ID NO: 37, SEQ ID NO: 38, SEQ ID NO: 39, and SEQ ID NO: 40, respectively, can be transformed into host cells, and that enzymes comprising each of those amino acid sequences can be subsequently expressed, isolated, and purified according to the procedure of Example 1, above. Codon-optimized nucleotide sequences are determined that encode for enzymes having the amino acid sequences of SEQ ID NO: 35, SEQ ID NO: 36, SEQ ID NO: 37, SEQ ID NO: 38, SEQ ID NO: 39, and SEQ ID NO: 40, respectively, based on the desired expression host. Upon synthesizing or inserting those genes within a suitable expression vector, it is expected that genes encoding for each of the amino acid sequences SEQ ID NO: 35, SEQ ID NO: 36, SEQ ID NO: 37, SEQ ID NO: 38, SEQ ID NO: 39, and SEQ ID NO: 40, respectively, will be transformed into host cells, and that enzymes containing those sequences will be subsequently expressed, isolated, and purified in a sufficient quantity and purity to determine aryl sulfate-dependent NST activity.

Example 14: Sulfotransferase Activity of EC 2.8.2.8 Mutants

A study is conducted in accordance with embodiments of the present disclosure to determine whether mutant enzymes comprising the sequences of SEQ ID NO: 35, SEQ ID NO: 36, SEQ ID NO: 37, SEQ ID NO: 38, SEQ ID NO: 39, and SEQ ID NO: 40, respectively, are active sulfotransferases, using the procedures of Example 2. It is expected that SAX studies will confirm the presence of N-sulfated polysaccharide products formed as a result of reacting N-deacetylated heparosan and an aryl sulfate compound with each of the engineered enzymes comprising the sequences of SEQ ID NO: 35, SEQ ID NO: 36, SEQ ID NO: 37, SEQ ID NO: 38, SEQ ID NO: 39, or SEQ ID NO: 40, respectively.

Example 15: Determination of Engineered Aryl Sulfate-Dependent Mutants of Other 2OST Enzymes within EC 2.8.2

A study is conducted in accordance with embodiments of the present disclosure to engineer additional aryl sulfate-dependent 2OST enzymes. As described above, the aryl sulfate-dependent 2OST enzymes having the amino acid sequences of SEQ ID NO: 14 and SEQ ID NO: 16 have been engineered to be mutants of the chicken 2OST enzyme (see entry sp|Q76KB1|HS2ST_CHICK, in FIGS. 14A-14D, above), which is a member of enzyme class EC 2.8.2.-. By generating and analyzing a multiple sequence alignment that includes both the amino acid sequences of one or more of the other 2OST enzymes within EC 2.8.2.-, as well as the amino acid sequences of aryl sulfate-dependent 2OST enzymes having the amino acid sequences of SEQ ID NO: 14 and/or SEQ ID NO: 16, mutations in the amino acid sequences in the engineered 2OST enzymes can be observed relative to the amino acid sequences of the natural 2OST enzymes within the same alignment. Upon selecting the amino acid sequence of a natural 2OST enzyme that is not the chicken 2OST enzyme, mutations that are present within the amino acid sequences of SEQ ID NO: 14 and/or SEQ ID NO: 16 can be engineered into the natural sequence in order to form additional mutants that can have aryl sulfate-dependent sulfotransferase activity.

As a non-limiting example, the amino acid sequence encoding for the human 2OST enzyme (entry sp|Q7LGA3|HS2ST_HUMAN, as illustrated in the sequence alignment in FIGS. 14A-14D), is aligned with the amino acid sequences of SEQ ID NO: 14 and SEQ ID NO: 16. Amino acid mutations that are present in SEQ ID NO 14 and SEQ ID NO: 16 are engineered into their equivalent positions within the amino acid sequence of the human 2OST enzyme, in order to generate the mutant amino acid sequences SEQ ID NO: 41 and SEQ ID NO: 42, respectively. Enzymes comprising the amino acid sequences of SEQ ID NO: 41 and SEQ ID NO: 42, respectively, will be utilized in Example 16 and Example 17, below. However, a person skilled in the art would appreciate that the same procedure can be applied to generate aryl sulfate-dependent mutants with respect to any of the other 2OST enzymes within the EC 2.8.2.-enzyme class, and that those are omitted for clarity.

Example 16: Expression and Purification of EC 2.8.2.-Mutants Having 2OST Activity A study is conducted in accordance with embodiments of the present disclosure to determine whether genes encoding for engineered 2OST enzymes having the amino acid sequences SEQ ID NO: 41 and SEQ ID NO: 42, respectively, can be transformed into host cells, and that enzymes comprising each of those amino acid sequences can be subsequently expressed, isolated, and purified according to the procedure of Example 1, above. Codon-optimized nucleotide sequences are determined that encode for enzymes having the amino acid sequences of SEQ ID NO: 41 and SEQ ID NO: 42, respectively, based on the desired expression host. Upon synthesizing or inserting those genes within a suitable expression vector, it is expected that genes encoding for each of the amino acid sequences SEQ ID NO: 41 and SEQ ID NO: 42, respectively, will be transformed into host cells, and that enzymes containing those sequences will be subsequently expressed, isolated, and purified in a sufficient quantity and purity to determine aryl sulfate-dependent 2OST activity.

Example 17: 2OST Activity of EC 2.8.2.-Mutants

A study is conducted in accordance with embodiments of the present disclosure to determine whether mutant enzymes comprising the sequences of SEQ ID NO: 41 and SEQ ID NO: 42, respectively, are active sulfotransferases, using the procedures of Example 3. It is expected that MS studies will confirm the presence of N,2-HS products formed as a result of reacting an N-sulfated heparosan-based polysaccharide and an aryl sulfate compound with each of the engineered enzymes comprising the sequences of SEQ ID NO: 41 and SEQ ID NO: 42, respectively. It is also expected that both enzymes will be active with heparosan-based polysaccharides comprising either or both of Formula IV or Formula V.

Example 18: Determination of Engineered Aryl Sulfate-Dependent Mutants of Other 6OST Enzymes within EC 2.8.2

A study is conducted in accordance with embodiments of the present disclosure to engineer additional aryl sulfate-dependent 6OST enzymes. As described above, the aryl sulfate-dependent 6OST enzymes having the amino acid sequences of SEQ ID NO: 18, SEQ ID NO: 20, and SEQ ID NO: 22 have been engineered to be mutants of isoform 1 of the mouse 6OST enzyme (see entry Q9QYK5|H6ST1_MOUSE, in FIGS. 18A-18C, above), which is a member of enzyme class EC 2.8.2.-. By generating and analyzing a multiple sequence alignment that includes both the amino acid sequences of one or more of the other 6OST enzymes within EC 2.8.2.-, as well as the amino acid sequences of aryl sulfate-dependent 6OST enzymes having the amino acid sequences of SEQ ID NO: 18, SEQ ID NO: 20, and/or SEQ ID NO: 22, mutations in the amino acid sequences in the engineered 6OST enzymes can be observed relative to the amino acid sequences of the natural 6OST enzymes within the same alignment. Upon selecting the amino acid sequence of a natural 6OST enzyme that is not the mouse 6OST enzyme, mutations that are present within the amino acid sequences of SEQ ID NO: 18, SEQ ID NO: 20, and/or SEQ ID NO: 22 can be engineered into the natural sequence in order to form additional mutants that can have aryl sulfate-dependent sulfotransferase activity.

As a non-limiting example, the amino acid sequence encoding for the pig 6OST enzyme (entry I3LAM6|I3LAM6_PIG, as illustrated in the sequence alignment in FIGS. 18A-18C), is aligned with the amino acid sequences of SEQ ID NO: 18, SEQ ID NO: 20, and SEQ ID NO: 22. Amino acid mutations that are present in SEQ ID NO: 18, SEQ ID NO: 20, and SEQ ID NO: 22 are engineered into their equivalent positions within the amino acid sequence of the pig 6OST enzyme, in order to generate mutant amino acid sequences. Generated mutant amino acid sequences corresponding to residues 67-377 of the pig 6OST enzyme, as illustrated in FIGS. 18A-18C, are disclosed as SEQ ID NO: 45, SEQ ID NO: 46, and SEQ ID NO: 47, respectively. Generated mutant amino acid sequences corresponding to the full-length amino acid sequence for the pig 6OST enzyme (not shown in FIGS. 18A-18C) are disclosed as SEQ ID NO: 48, SEQ ID NO: 49, and SEQ ID NO: 50, respectively.

In another non-limiting example, the full-length amino acid sequence encoding for the encoding for isoform 3 of the mouse 6OST enzyme (entry Q9QYK4|H6HS3_MOUSE, a truncated sequence for which is illustrated in the sequence alignment in FIGS. 18A-18C) is aligned with the amino acid sequences of SEQ ID NO: 18, SEQ ID NO: 20, and SEQ ID NO: 22. Amino acid mutations that are present in SEQ ID NO: 18, SEQ ID NO: 20, and SEQ ID NO: 22 are engineered into their equivalent positions within the amino acid sequence of isoform 3 of the mouse 6OST enzyme, in order to generate mutant amino acid sequences. The generated full-length amino acid sequences are disclosed as SEQ ID NO: 59, SEQ ID NO: 60, and SEQ ID NO: 61, respectively. Enzymes comprising the amino acid sequences of SEQ ID NO: 45, SEQ ID NO: 46, SEQ ID NO: 47, SEQ ID NO: 48, SEQ ID NO: 49, SEQ ID NO: 50, SEQ ID NO: 59, SEQ ID NO: 60, and SEQ ID NO: 61, respectively, will be utilized in Example 19 and Example 20, below. However, a person skilled in the art would appreciate that the same procedure can be applied to generate aryl sulfate-dependent mutants with respect to any of the other 6OST enzymes within the EC 2.8.2.-enzyme class, and that those are omitted for clarity.

Example 19: Expression and Purification of EC 2.8.2.-Mutants Having 6OST Activity A study is conducted in accordance with embodiments of the present disclosure to determine whether genes encoding for engineered 6OST enzymes having the amino acid sequences SEQ ID NO: 45, SEQ ID NO: 46, SEQ ID NO: 47, SEQ ID NO: 48, SEQ ID NO: 49, SEQ ID NO: 50, SEQ ID NO: 59, SEQ ID NO: 60, and SEQ ID NO: 61, respectively, can be transformed into host cells, and that enzymes comprising each of those amino acid sequences can be subsequently expressed, isolated, and purified according to the procedure of Example 1, above. Codon-optimized nucleotide sequences are determined that encode for enzymes having the amino acid sequences of SEQ ID NO: 45, SEQ ID NO: 46, SEQ ID NO: 47, SEQ ID NO: 48, SEQ ID NO: 49, SEQ ID NO: 50, SEQ ID NO: 59, SEQ ID NO: 60, and SEQ ID NO: 61, respectively, based on the desired expression host. Upon synthesizing or inserting those genes within a suitable expression vector, it is expected that genes encoding for each of the amino acid sequences SEQ ID NO: 45, SEQ ID NO: 46, SEQ ID NO: 47, SEQ ID NO: 48, SEQ ID NO: 49, SEQ ID NO: 50, SEQ ID NO: 59, SEQ ID NO: 60, and SEQ ID NO: 61, respectively, will be transformed into host cells, and that enzymes containing those sequences will be subsequently expressed, isolated, and purified in a sufficient quantity and purity to determine aryl sulfate-dependent 6OST activity.

Example 20: 6OST Activity of EC 2.8.2.-Mutants

A study is conducted in accordance with embodiments of the present disclosure to determine whether mutant enzymes comprising the sequences of SEQ ID NO: 45, SEQ ID NO: 46, SEQ ID NO: 47, SEQ ID NO: 48, SEQ ID NO: 49, SEQ ID NO: 50, SEQ ID NO: 59, SEQ ID NO: 60, and SEQ ID NO: 61, respectively, are active sulfotransferases, using the procedures of Example 4. It is expected that MS studies will confirm the presence of N,2,6-HS products formed as a result of reacting an N,2-HS polysaccharide and an aryl sulfate compound with each of the engineered enzymes comprising the sequences of SEQ ID NO: 45, SEQ ID NO: 46, SEQ ID NO: 47, SEQ ID NO: 48, SEQ ID NO: 49, SEQ ID NO: 50, SEQ ID NO: 59, SEQ ID NO: 60, and SEQ ID NO: 61, respectively.

Example 21: Determination of Engineered Aryl Sulfate-Dependent Mutants of Other 3OST Enzymes within EC 2.8.2.23

A study is conducted in accordance with embodiments of the present disclosure to engineer additional aryl sulfate-dependent 3OST enzymes. As described above, the aryl sulfate-dependent 3OST enzymes having the amino acid sequences of SEQ ID NO: 24, SEQ ID NO: 26, and SEQ ID NO: 28 have been engineered to be mutants of isoform 1 of the human 3OST enzyme (see entry sp|O14792|HS3S1_HUMAN, in FIGS. 23A-23C, above), which is a member of enzyme class EC 2.8.2.23. By generating and analyzing a multiple sequence alignment that includes both the amino acid sequences of one or more of the other 3OST enzymes within EC 2.8.2.23, as well as the amino acid sequences of aryl sulfate-dependent 3OST enzymes having the amino acid sequences of SEQ ID NO: 24, SEQ ID NO: 26, and/or SEQ ID NO: 28, mutations in the amino acid sequences in the engineered 3OST enzymes can be observed relative to the amino acid sequences of the natural 3OST enzymes within the same alignment. Upon selecting the amino acid sequence of a natural 3OST enzyme that is not the human 3OST enzyme, mutations that are present within the amino acid sequences of SEQ ID NO: 24, SEQ ID NO: 26, and/or SEQ ID NO: 28 can be engineered into the natural sequence in order to form additional mutants that can have aryl sulfate-dependent sulfotransferase activity.

As a non-limiting example, the amino acid sequence encoding for isoform 1 of the pig 3OST enzyme (entry tr|I3LHH5|I3LHH5_PIG, as illustrated in the sequence alignment in FIGS. 23A-23C, is aligned with the amino acid sequences of SEQ ID NO: 24, SEQ ID NO: 26, and SEQ ID NO: 28. Amino acid mutations that are present in SEQ ID NO: 24, SEQ ID NO: 26, and SEQ ID NO: 28 are engineered into their equivalent positions within the amino acid sequence of the pig 3OST enzyme, in order to the generate mutant amino acid sequences SEQ ID NO: 52, SEQ ID NO: 53, and SEQ ID NO: 54, respectively.

In another non-limiting example, the full-length amino acid sequence encoding for the encoding for isoform 5 of the mouse 3OST enzyme (not shown in FIGS. 18A-18C) is aligned with the amino acid sequences of SEQ ID NO: 24, SEQ ID NO: 26, and SEQ ID NO: 28. Amino acid mutations that are present in SEQ ID NO: 24, SEQ ID NO: 26, and SEQ ID NO: 28 are engineered into their equivalent positions within the amino acid sequence of isoform 5 of the mouse 3OST enzyme, in order to generate mutant amino acid sequences. The generated full-length amino acid sequences are disclosed as SEQ ID NO: 56, SEQ ID NO: 57, and SEQ ID NO: 58, respectively.

Enzymes comprising the amino acid sequences of SEQ ID NO: 52, SEQ ID NO: 53, SEQ ID NO: 54, SEQ ID NO: 56, SEQ ID NO: 57, and SEQ ID NO: 58 respectively, will be utilized in Example 22 and Example 23, below. However, a person skilled in the art would appreciate that the same procedure can be applied to generate aryl sulfate-dependent mutants with respect to any of the other 3OST enzymes within the EC 2.8.2.23 enzyme class, and that those are omitted for clarity.

Example 22: Expression and Purification of EC 2.8.2.23 Mutants Having 3OST Activity A study is conducted in accordance with embodiments of the present disclosure to determine whether genes encoding for engineered 3OST enzymes having the amino acid sequences SEQ ID NO: 52, SEQ ID NO: 53, SEQ ID NO: 54, SEQ ID NO: 56, SEQ ID NO: 57, and SEQ ID NO: 58, respectively, can be transformed into host cells, and that enzymes comprising each of those amino acid sequences can be subsequently expressed, isolated, and purified according to the procedure of Example 1, above. Codon-optimized nucleotide sequences are determined that encode for enzymes having the amino acid sequences of SEQ ID NO: 52, SEQ ID NO: 53, SEQ ID NO: 54, SEQ ID NO: 56, SEQ ID NO: 57, and SEQ ID NO: 58, respectively, based on the desired expression host. Upon synthesizing or inserting those genes within a suitable expression vector, it is expected that genes encoding for each of the amino acid sequences SEQ ID NO: 52, SEQ ID NO: 53, SEQ ID NO: 54, SEQ ID NO: 56, SEQ ID NO: 57, and SEQ ID NO: 58, respectively, will be transformed into host cells, and that enzymes containing those sequences will be subsequently expressed, isolated, and purified in a sufficient quantity and purity to determine aryl sulfate-dependent 3OST activity.

Example 23: 3OST Activity of EC 2.8.2.23 Mutants

A study is conducted in accordance with embodiments of the present disclosure to determine whether mutant enzymes comprising the sequences of SEQ ID NO: 52, SEQ ID NO: 53, SEQ ID NO: 54, SEQ ID NO: 56, SEQ ID NO: 57, and SEQ ID NO: 58, respectively, are active sulfotransferases, using the procedures of Example 5 and/or Example 6. It is expected that MS and/or NMR studies will confirm the presence of N,2,3,6-HS products formed as a result of reacting an N,2,6-HS polysaccharide and an aryl sulfate compound with each of the engineered enzymes comprising the sequences of SEQ ID NO: 52, SEQ ID NO: 53, SEQ ID NO: 54, SEQ ID NO: 56, SEQ ID NO: 57, and SEQ ID NO: 58, respectively.

We claim:

1. A method of enzymatically synthesizing an N-, 2-O, 3-O, 6-O sulfated, heparan sulfate (N,2,3,6-HS) product in the absence of 3'-phosphoadenosine 5'-phosphosulfate (PAPS), the method comprising the following steps:
   (a) providing a starting polysaccharide mixture comprising N-sulfated heparosan;
   (b) combining the starting polysaccharide mixture with a first sulfotransferase reaction mixture comprising an engineered hexuronyl 2-O sulfotransferase enzyme (2OST) and a sulfo group donor, the sulfo group donor consisting of an aryl sulfate compound, to form a first product mixture, the first product mixture comprising an N-, 2-O sulfated heparan sulfate (N,2-HS) product;
   (c) combining the first product mixture with a second sulfotransferase reaction mixture comprising an engineered glucosaminyl 6-O sulfotransferase enzyme (6OST) and a sulfa group donor, the sulfo group donor consisting of an aryl sulfate compound, to form a second product mixture, the second product mixture comprising, an N-, 2-O, 6-O sulfated heparan sulfate (N,2,6-HS) product;
d) combining the second product mixture with a third sulfotransferase reaction mixture comprising an engineered glucosaminyl 3-O sulfotransferase enzyme (3OST) and a sulfo group donor, the sulfo group donor consisting of an aryl sulfate compound, to form a third product mixture, the third product mixture comprising N,2,3,6-HS;

wherein the biological activity of each of the engineered 2OST, 6OST, and 3OST enzymes consists of binding and reacting with an aryl sulfate compound to transfer a sulfo group to heparan sulfate in the absence of PAPS.

2. The method according to claim 1, wherein the step of providing the starting polysaccharide reaction mixture comprising N-sulfated heparosan further comprises the steps of:
(i) providing a precursor polysaccharide composition comprising heparosan;
(ii) combining the precursor polysaccharide composition with a reaction mixture, the reaction mixture comprising a base, the base selected from the group consisting of lithium hydroxide and sodium hydroxide, for a time sufficient to N-deacetylate at least one of the N-acetylated glucosamine residues within the heparosan to form a heparosan intermediate composition comprising N-deacetylated heparosan; and
(iii) combining the heparosan intermediate composition with a reaction mixture comprising an N-sulfation agent, thereby forming the starting polysaccharide mixture comprising N-sulfated heparosan.

3. The method according to claim 2, wherein the precursor polysaccharide composition is reacted with the base for a time sufficient to form a heparosan intermediate composition in which at least 12%, and up to 18%, of the glucosamine residues within the heparosan intermediate composition remain N-acetylated.

4. The method according to claim 2, wherein the N-sulfation agent is selected from the group consisting of a sulfur trioxide-trimethylamine adduct, a natural glucosaminyl N-eacetylase/N-sultotransferase (NDST) enzyme from the enzyme class EC 2.8.2,8, and a non-natural glucosaminyl N-sulfotransferase (NST) enzyme, the non-natural NST enzyme comprising an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

5. The method according to claim 2, wherein the step of providing the precursor polysaccharide composition comprising heparosan further comprises a sub-step of isolating heparosan from a bacterial cell culture comprising bacteria selected from the group consisting of the K5 strain of *Escherichia coli* and the BL21 strain of *Escherichia coli*.

6. The method according to claim 1, wherein:
the 2OST enzyme comprises an amino acid sequence selected from the group consisting o SEQ ID NO: 14, SEQ ID NO: 16, SEQ ID NO: 41, and SEQ ID NO: 42;
the 6OST enzyme comprises an amino acid sequence selected from the group consisting of SEQ ID NO: 18, SEQ ID NO: 20, SEQ ID NO: 22, SEQ ID NO: 43, SEQ ID NO: 44, SEQ NO: 45, SEQ ID NO: 46, SEQ ID NO: 47, SEQ ID NO: 48, SEQ ID NO: 49, SEQ ID NO: 50, SEQ ID NO: 59, SEQ ID NO: 60, and SEQ ID NO: 61; and
the 3OST enzyme comprises an amino acid sequence selected from the group consisting of SEQ. ID NO: 24, SEQ ID NO: 26, SEQ ID NO: 28, SEQ ID NO: 51, SEQ ID NO: 52, SEQ ID NO: 53, SEQ ID NO: 54, SEQ ID NO: 56, SEQ ID NO: 57, and SEQ ID NO: 58.

7. The method according to claim 6, wherein the aryl sulfate compounds of steps (b), (c), and (d) are selected from the group consisting of p-nitrophenyl sulfate (PNS) and 4-nitrocatechol sulfate (NCS).

8. The method according to claim 1, wherein the first sulfotransferase reaction mixture further comprises a glucuronyl $C_5$-epimerase enzyme.

9. The method according to claim 1, wherein the N,2O, 3O, 6O-HS product is a heparin product, the heparin product comprising polysaccharides having a sequence motif having the structure of Formula 1, below:

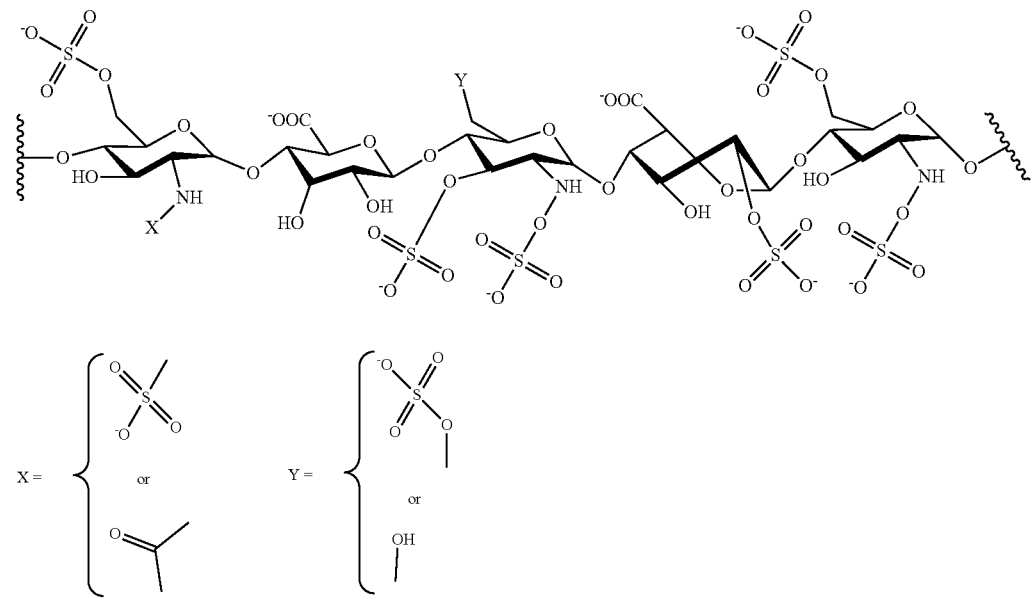

wherein X is either a sulfa group or an acetate group and Y is either a sulfo group or a hydroxyl group.

10. The method according to claim 9, wherein the heparin product is a polydisperse mixture of polysaccharides having a weight average molecular weight, $\overline{M}_w$, of at least 1,000 Da.

11. The method according to claim 10, wherein:
the $\overline{M}_w$ of the heparin product is at least about 15,000 Da, and less than or equal to about 19,000 Da;
not more than 20% of the polysaccharide chains within the heparin product have a molecular weight greater than about 24,000 Da; and
the number of polysaccharide chains having a molecular weight between 8,000 Da and 16,000 Da within the heparin product is greater than the number of polysaccharide chains having a molecular weight between about 16,000 Da and about 24,000 Da.

12. The method according to claim 11, wherein the heparin product has anticoagulant activity.

13. The method according to claim 9, wherein the heparin product is further fractionated to form a low-molecular weight heparin (LMWH) product, the method comprising the following steps:
(i) providing one or more depolymerization agents; and
(ii) treating the heparin product with the one or more depolymerization agents for a time sufficient to depolymerize at least some of the polysaccharides within the heparin product, thereby forming, the LMWH product.

14. The method according to claim 13, wherein the $\overline{M}_w$ of the LMWH product is in a range from at least about 2,000 Da, and up to about 12,000 Da.

15. The method according to claim 13, wherein the depolymerization agent comprises a heparinase reaction mixture comprising at least one heparin lyase enzyme, and the heparin product is treated with the heparinase reaction mixture for a time sufficient to catalyze β-eliminative cleavage of the heparin product and form an enzymatically-depolymerized LMWH product comprising polysaccharide chains having a 4,5-unsaturated uronic acid residue at the non-reducing end.

16. The method according to claim 15, wherein the heparin product is depolymerized for a time sufficient to form an enzymatically-depolymerized LMWH product having the following properties:
a $\overline{M}_w$ in a range from at least 5,500Da and up to 7,500 Da;
an anti-Factor Xa (anti-Xa) activity in a range from at least 70 IU mg$^{-1}$, up to 120 IU mg$^{-1}$; and
a ratio of anti-Xa activity to anti-Factor IIa (anti-IIa) activity in a range from at least 1.5:1 and up to 2.5:1.

17. The method according to claim 15, wherein the enzymatically-depolymerized LMWH product has anticoagulant activity.

18. The method according to claim 13, wherein the depolymerization agent comprises one or more basic compounds, and the heparin product is treated with the one or more basic compounds for a time sufficient to cause β-eliminative cleavage of the heparin product and form a chemically β-eliminative, LMWH product comprising polysaccharide chains having a 4,5-unsaturated uronic acid residue at the non-reducing end.

19. The method according to claim 18, wherein the one or more basic compounds comprises sodium hydroxide, and the heparin product is treated according to the following sub-steps:
(i) reacting the heparin product with a benzethonium halide, to form a heparin benzethonium salt;
(ii) combining the heparin benzethonium salt with a benzyl halide to form a heparin benzyl ester intermediate; and
(iii) combining the heparin benzyl ester intermediate with a reaction mixture comprising sodium hydroxide to depolymerize the heparin benzyl ester intermediate and form the chemically β-eliminative LMWH product.

20. The method according to claim 19, wherein the benzyl ester intermediate is depolymerized for a time sufficient to form a chemically β-eliminative LMWH product having the following properties:
a $\overline{M}_w$ in a range from at least 3,800 Da and up to 5,000 Da;
an anti-Xa activity in a range from at least 90 IU mg$^{-1}$ and up to 125 IU mg$^{-1}$;
an anti-IIa activity in a range from at least 20 IU mg$^{-1}$ and up to 35 1IU mg$^{-1}$;
a ratio of anti-Xa activity to anti-IIa activity in a range from at least 3.3:1 and up to 5.3:1; and
the chemically β-eliminative LMWH product comprises polysaccharide chains having either a 1,6-anhydromannose residue or a 1,6-anhydroglucosamine residue at the reducing end.

21. The method according to claim 18, wherein the chemically β-eliminative LMWH product has anticoagulant activity.

22. The method according to claim 13, wherein the depolymerization agent comprises a deamination reaction mixture comprising a deamination agent selected from the group consisting of isoamyl nitrate and nitrous acid, and the heparin product is treated with the deamination reaction mixture for a time sufficient to form a deaminated LMWH product comprising polysaccharide chains having a 2,5-anhydro-D-mannose residue at the reducing end.

23. The method according to claim 22, wherein the heparin product is treated with nitrous acid for a time sufficient to form a deaminated LMWH product having the following properties:
a $\overline{M}_w$ in a range from at least 5,600 Da and up to 6,000 1Da;
an anti-Xa activity in a range from at least 110 IU mg$^{-1}$ and up to 210 IU mg$^{-1}$;
an anti-IIa activity in a range from at least 35 IU mg$^{-1}$ and up 100 35 IU mg$^{-1}$, and
a ratio of anti-Xa activity to anti-IIa activity in a range from at least 1.9:1 and up to 3.1:1.

24. The method according to claim 22, wherein the deaminated LMWH product has anticoagulant activity.

25. The method according to claim 22, wherein the heparin product is treated with sodium nitrite in the presence of hydrochloric acid, for a time Sufficient to form a deaminated LMWH product having the following properties:
a $\overline{M}_w$ in a range from at least 3,600 Da and up to 5,000 Da;
an anti-Xa activity in a range from at least 95 IU mg$^{-1}$ and up to 130 IU mg$^{-1}$; and
a ratio of anti-Xa activity to anti-IIa activity in a range from at least 2.5:1 and up to 4.0:1.

26. The method according to claim 22, wherein the deaminated LMWH product has a $\overline{M}_w$ in a range from at least 2,000 Da, and up to 10,000 Da.

27. The method according to claim 13, wherein the depolymerization agent comprises an oxidation reaction mixture comprising an oxidation agent, and the heparin product is treated with the oxidation reaction mixture for a time sufficient to cause oxidative cleavage of the heparin product and form an oxidized LMW-HS product.

* * * * *

SEQUENCE LISTING

<160> NUMBER OF SEQ ID NOS: 61

<210> SEQ ID NO 1
<211> LENGTH: 927
<212> TYPE: DNA
<213> ORGANISM: Artificial Sequence
<220> FEATURE:
<223> OTHER INFORMATION: Polynucleotide sequence encoding for engineered
     aryl sulfate-dependent N-sulfotransferase variant 1

<400> SEQUENCE: 1

```
atgagcgaag agaaggaccc tttgtggcag gacccgtgcg aggacaaacg ccacaaagac    60
atttggtcga aggagaaaac ctgtgaccgc ttccctaagt tgcttattat tggtccgcaa   120
aagaccggcg cctgggcgct ttaccatttc ctgggtatgc atcccgatct tagttccaac   180
tacccgtcga gtgaaacaca tggcagtatc caattcttta atggacataa ctaccataag   240
ggcatcgact ggtatatgga atttttcccc attccctcaa ataccacttc tgactttttat   300
ttcgagaaat cagcgaatta ttttgacagt gaggtagcgc ctcgccgcgc agcagcattg   360
ttgcccaaag caaagtgct gactattctt atcaatccag ctgaccgcgc atattcttgg   420
tatcagcacc agcgcgccca cgacgacccg gtggcgctga atacacatt ccatgaagtg   480
attactgctg gaagcgatgc gtcgtctaag ttgcgtgctc tgcagaaccg ctgtttggta   540
cctggctggt atgctacgca cattgaacgt tggctgtccg catatcacgc gaaccagatc   600
ctggttttag atggtaaatt acttcgcacg gagccagcta agtcatgga catggtacaa   660
aagttcctgg gggtaacgaa taccattgat tatcataaga ctttggcttt cgaccccaag   720
aagggattt ggtgccagtt attggagggg ggcaagacga agtgcttagg caaatcgcat   780
gggcgcaagt acccggagat ggatttggac tcacgcgcct ttcttaagga ctactaccgc   840
gaccacaaca ttgaattgag taaattatta tacaaaatgg ggcaaactct tccgacttgg   900
ttgcgtgaag acttgcagaa cacacgc                                       927
```

<210> SEQ ID NO 2
<211> LENGTH: 309
<212> TYPE: PRT
<213> ORGANISM: Artificial Sequence
<220> FEATURE:
<223> OTHER INFORMATION: Amino acid sequence encoding for engineered
     aryl sulfate-dependent N-sulfotransferase variant 1

<400> SEQUENCE: 2

```
Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Gln Lys Thr Gly Ala Trp Ala Leu Tyr
        35                  40                  45

His Phe Leu Gly Met His Pro Asp Leu Ser Ser Asn Tyr Pro Ser Ser
    50                  55                  60

Glu Thr His Gly Ser Ile Gln Phe Phe Asn Gly His Asn Tyr His Lys
65                  70                  75                  80

Gly Ile Asp Trp Tyr Met Glu Phe Phe Pro Ile Pro Ser Asn Thr Thr
                85                  90                  95

Ser Asp Phe Tyr Phe Glu Lys Ser Ala Asn Tyr Phe Asp Ser Glu Val
            100                 105                 110

Ala Pro Arg Arg Ala Ala Ala Leu Leu Pro Lys Ala Lys Val Leu Thr
        115                 120                 125

Ile Leu Ile Asn Pro Ala Asp Arg Ala Tyr Ser Trp Tyr Gln His Gln
    130                 135                 140

Arg Ala His Asp Asp Pro Val Ala Leu Lys Tyr Thr Phe His Glu Val
145                 150                 155                 160
```

```
Ile Thr Ala Gly Ser Asp Ala Ser Ser Lys Leu Arg Ala Leu Gln Asn
                165                 170                 175

Arg Cys Leu Val Pro Gly Trp Tyr Ala Thr His Ile Glu Arg Trp Leu
            180                 185                 190

Ser Ala Tyr His Ala Asn Gln Ile Leu Val Leu Asp Gly Lys Leu Leu
        195                 200                 205

Arg Thr Glu Pro Ala Lys Val Met Asp Met Val Gln Lys Phe Leu Gly
    210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Leu
                245                 250                 255

Gly Lys Ser His Gly Arg Lys Tyr Pro Glu Met Asp Leu Asp Ser Arg
            260                 265                 270

Ala Phe Leu Lys Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Asp
    290                 295                 300

Leu Gln Asn Thr Arg
305
```

<210> SEQ ID NO 3
<211> LENGTH: 927
<212> TYPE: DNA
<213> ORGANISM: Artificial Sequence
<220> FEATURE:
<223> OTHER INFORMATION: Polynucleotide sequence encoding for engineered aryl sulfate-dependent N-sulfotransferase variant 2

<400> SEQUENCE: 3

```
atgagcgaag agaaggaccc tttgtggcag gacccgtgcg aggacaaacg ccataaggac      60
atctggtcga agagaagac ttgtgaccgt tttccaaaat tacttattat cggtccttca     120
aagaccggcg ctttcctttt aacccacttt ttggggatgc atccagacct tagttcaaat     180
taccctccgt ctgagactgg gcattccatt caattcttca acgggcacaa ttatcacaag     240
ggtattgact ggtacatgga attttttccg attccgagca atacaacttc cgattttttac     300
tttgaaacct catccaatta ttttgattcc gaagtcgctc cacgccgcgc cgctgctttg     360
ttgccaaaag ctaaggtttt gactattctg atcaacccgg ctgaccgcgc ctattcatgg     420
taccaacacc agcgtgctca tgatgaccca gtggctttga gtatacgtt ccatgaggtc     480
attacagcgg cagcgacgc aagctccaaa cttcgcgcat tgcaaaaccg ctgccttgtg     540
cccggttggt acgcgacaca cattgaacgc tggctgtccg cttaccacgc caaccaaatt     600
ttagttttag atgggaaatt acttcgtacc gaacctgcca aggtcatgga catggtgcag     660
aaatttttgg gagtcactaa cactatcgac taccacaaaa cattggcatt cgatccaaaa     720
aaggggtttt ggtgccagct tttagaaggg ggcaagacga agtgtcacgg aagcgttgg     780
gggcgtaagt atccagagat ggatcttgat agccgcgctt tcttaaaaga ttattaccgt     840
gaccacaaca ttgagcttag caaactgctt tacaagatgg gtcagacact tccgacatgg     900
ctgcgtgaag acttgcagaa cacacgc                                         927
```

<210> SEQ ID NO 4
<211> LENGTH: 309
<212> TYPE: PRT
<213> ORGANISM: Artificial Sequence
<220> FEATURE:

<223> OTHER INFORMATION: Amino acid sequence encoding for engineered
      aryl sulfate-dependent N-sulfotransferase variant 2

<400> SEQUENCE: 4

```
Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Ser Lys Thr Gly Ala Phe Leu Leu Thr
        35                  40                  45

His Phe Leu Gly Met His Pro Asp Leu Ser Ser Asn Tyr Pro Ser Ser
    50                  55                  60

Glu Thr Gly His Ser Ile Gln Phe Phe Asn Gly His Asn Tyr His Lys
65                  70                  75                  80

Gly Ile Asp Trp Tyr Met Glu Phe Phe Pro Ile Pro Ser Asn Thr Thr
                85                  90                  95

Ser Asp Phe Tyr Phe Glu Thr Ser Ser Asn Tyr Phe Asp Ser Glu Val
            100                 105                 110

Ala Pro Arg Arg Ala Ala Ala Leu Leu Pro Lys Ala Lys Val Leu Thr
        115                 120                 125

Ile Leu Ile Asn Pro Ala Asp Arg Ala Tyr Ser Trp Tyr Gln His Gln
    130                 135                 140

Arg Ala His Asp Asp Pro Val Ala Leu Lys Tyr Thr Phe His Glu Val
145                 150                 155                 160

Ile Thr Ala Gly Ser Asp Ala Ser Ser Lys Leu Arg Ala Leu Gln Asn
                165                 170                 175

Arg Cys Leu Val Pro Gly Trp Tyr Ala Thr His Ile Glu Arg Trp Leu
            180                 185                 190

Ser Ala Tyr His Ala Asn Gln Ile Leu Val Leu Asp Gly Lys Leu Leu
        195                 200                 205

Arg Thr Glu Pro Ala Lys Val Met Asp Met Val Gln Lys Phe Leu Gly
    210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys His
                245                 250                 255

Gly Lys Arg Trp Gly Arg Lys Tyr Pro Glu Met Asp Leu Asp Ser Arg
            260                 265                 270

Ala Phe Leu Lys Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Asp
    290                 295                 300

Leu Gln Asn Thr Arg
305
```

<210> SEQ ID NO 5
<211> LENGTH: 927
<212> TYPE: DNA
<213> ORGANISM: Artificial Sequence
<220> FEATURE:
<223> OTHER INFORMATION: Polynucleotide sequence encoding for engineered
      aryl sulfate-dependent N-sulfotransferase variant 3

<400> SEQUENCE: 5

```
atgagcgaag agaaggaccc tttgtggcag gacccgtgcg aagataagcg tcacaaggac    60
atctggtcaa aagagaaaac ttgcgaccgc tttccgaaat tgttaattat tggaccacat   120
```

```
ggcaccgggg gtcacgcact ttacttattc ttgggaatgc acccagatct gagctccaac    180 tacccccagct ctgaaaccgg cgaagaaatc caattttttca acgggcacaa ttatcataaa    240
ggcattgatt ggtatatgga attcttcccc atcccgtcta atactaccag cgatttctat    300
tttgaaaaaa gtgcgaacta cttcgactcg gaggtggcac cccgtcgtgc tgcggcctta    360
ctgccaaagg ccaaggtttt aaccatcttg attaatccgg ctgaccgtgc ttattcctgg    420
taccaggctc aacgcgcaca tgacgacccc gttgcgctta aatatacatt ccacgaggtc    480
attactgcgg gctctgatgc ttcttcgaaa cttcgtgcgc tgcaaaatcg ttgtttagtg    540
ccgggttggt acgccacgca catcgagcgt tggcttagtg cctaccatgc gaatcaaatc    600
cttgtcttgg atgggaagct tttgcgtact gaaccggcca aggtcatgga catggtccag    660
aagtttctgg gtgttaccaa cactattgat taccataaga ctttagcctt cgatccgaag    720
aaaggcttct ggtgtcaatt acttgagggt ggtaagacca agtgcggagg aaaacatctt    780
gggcgcaaat accccgaaat ggacttagat agccgtgcct ttctgaaaga ttactaccgc    840
gaccataata tcgagcttag caaattattg tacaaaatgg gccaaacctt gccgacgtgg    900
ctgcgtgaag acttgcagaa cacacgc                                         927
```

<210> SEQ ID NO 6
<211> LENGTH: 309
<212> TYPE: PRT
<213> ORGANISM: Artificial Sequence
<220> FEATURE:
<223> OTHER INFORMATION: Amino acid sequence encoding for engineered
      aryl sulfate-dependent N-sulfotransferase variant 3

<400> SEQUENCE: 6

```
Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro His Gly Thr Gly Gly His Ala Leu Tyr
        35                  40                  45

Leu Phe Leu Gly Met His Pro Asp Leu Ser Ser Asn Tyr Pro Ser Ser
    50                  55                  60

Glu Thr Gly Glu Glu Ile Gln Phe Phe Asn Gly His Asn Tyr His Lys
65                  70                  75                  80

Gly Ile Asp Trp Tyr Met Glu Phe Phe Pro Ile Pro Ser Asn Thr Thr
                85                  90                  95

Ser Asp Phe Tyr Phe Glu Lys Ser Ala Asn Tyr Phe Asp Ser Glu Val
            100                 105                 110

Ala Pro Arg Arg Ala Ala Ala Leu Leu Pro Lys Ala Lys Val Leu Thr
        115                 120                 125

Ile Leu Ile Asn Pro Ala Asp Arg Ala Tyr Ser Trp Tyr Gln Ala Gln
    130                 135                 140

Arg Ala His Asp Asp Pro Val Ala Leu Lys Tyr Thr Phe His Glu Val
145                 150                 155                 160

Ile Thr Ala Gly Ser Asp Ala Ser Ser Lys Leu Arg Ala Leu Gln Asn
                165                 170                 175

Arg Cys Leu Val Pro Gly Trp Tyr Ala Thr His Ile Glu Arg Trp Leu
            180                 185                 190

Ser Ala Tyr His Ala Asn Gln Ile Leu Val Leu Asp Gly Lys Leu Leu
        195                 200                 205
```

```
Arg Thr Glu Pro Ala Lys Val Met Asp Met Val Gln Lys Phe Leu Gly
    210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Gly
                245                 250                 255

Gly Lys His Leu Gly Arg Lys Tyr Pro Glu Met Asp Leu Asp Ser Arg
                260                 265                 270

Ala Phe Leu Lys Asp Tyr Tyr Arg Asp His Asn Ile Glu Leu Ser Lys
            275                 280                 285

Leu Leu Tyr Lys Met Gly Gln Thr Leu Pro Thr Trp Leu Arg Glu Asp
        290                 295                 300

Leu Gln Asn Thr Arg
305

<210> SEQ ID NO 7
<211> LENGTH: 927
<212> TYPE: DNA
<213> ORGANISM: Artificial Sequence
<220> FEATURE:
<223> OTHER INFORMATION: Polynucleotide sequence encoding for engineered
      aryl sulfate-dependent N-sulfotransferase variant 4

<400> SEQUENCE: 7
atgagcgaag agaaggaccc tttgtggcag gacccgtgcg aagataagcg ccacaaggac    60
atctggagca aggagaaaac ttgcgaccgc tttccaaagt tgctgattat tgggcctcac   120
ggcacgggcg ccacgcgct gtacctgttt cttggcatgc acccggacct ttccagcaat   180
tatcctagta gtgagacatt tttgagtatc caattttta acggacataa ctatcacaaa   240
ggtatcgatt ggtacatgga attcttccca attccgtcta atacgacatc tgactttat   300 ttcgagcatt cggggaatta ctttgattcc gaggtagccc acgccgtgc cgccgctctt   360 ttgcccaagg cgaaagtctt gactattctt attaatcccg cagaccgtgc ctaccgcgcg   420
tatgtatggc aacgcgcaca cgatgaccca gtcgcattga atatacatt ccatgaggtg   480 attaccgcgg gtagtgacgc ttctagcaag ttacgtgctc ttcagaatcg ctgccttgtc   540
ccaggttggt atgccacaca catcgaacgt tggctgtccg cctaccatgc taatcagatt   600
cttgtgctgg atggtaaatt gttgcgtaca gagcctgcca agttatgga tatggtgcaa   660 aaattttgg gtgttacgaa tactattgat taccataaga cacttgcatt tgacccgaaa   720 aaaggttct ggtgccaatt gttggagggt ggcaagacta agtgcttagg taagagtctt   780
ggttcgaagt accccgaaat ggatttagac tcgcgcgctt tcttgaagga ctattatcgt   840
gaccacaata tcgaactttc taaactttta tataagatgg ccaaacact tcccacgtgg   900 ctgcgtgaag acttgcagaa cacacgc                                        927

<210> SEQ ID NO 8
<211> LENGTH: 309
<212> TYPE: PRT
<213> ORGANISM: Artificial Sequence
<220> FEATURE:
<223> OTHER INFORMATION: Amino acid sequence encoding for engineered
      aryl sulfate-dependent N-sulfotransferase variant 4

<400> SEQUENCE: 8

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
```

```
                        20                  25                  30
Lys Leu Leu Ile Ile Gly Pro His Gly Thr Gly His Ala Leu Tyr
                35                  40                  45
Leu Phe Leu Gly Met His Pro Asp Leu Ser Ser Asn Tyr Pro Ser Ser
 50                  55                  60
Glu Thr Phe Leu Ser Ile Gln Phe Phe Asn Gly His Asn Tyr His Lys
 65                  70                  75                  80
Gly Ile Asp Trp Tyr Met Glu Phe Phe Pro Ile Pro Ser Asn Thr Thr
                 85                  90                  95
Ser Asp Phe Tyr Phe Glu His Ser Gly Asn Tyr Phe Asp Ser Glu Val
                100                 105                 110
Ala Pro Arg Arg Ala Ala Leu Leu Pro Lys Ala Lys Val Leu Thr
            115                 120                 125
Ile Leu Ile Asn Pro Ala Asp Arg Ala Tyr Arg Ala Tyr Val Trp Gln
        130                 135                 140
Arg Ala His Asp Asp Pro Val Ala Leu Lys Tyr Thr Phe His Glu Val
145                 150                 155                 160
Ile Thr Ala Gly Ser Asp Ala Ser Ser Lys Leu Arg Ala Leu Gln Asn
                165                 170                 175
Arg Cys Leu Val Pro Gly Trp Tyr Ala Thr His Ile Glu Arg Trp Leu
            180                 185                 190
Ser Ala Tyr His Ala Asn Gln Ile Leu Val Leu Asp Gly Lys Leu Leu
        195                 200                 205
Arg Thr Glu Pro Ala Lys Val Met Asp Met Val Gln Lys Phe Leu Gly
    210                 215                 220
Val Thr Asn Thr Ile Asp Tyr His Lys Thr Leu Ala Phe Asp Pro Lys
225                 230                 235                 240
Lys Gly Phe Trp Cys Gln Leu Leu Glu Gly Lys Thr Lys Cys Leu
                245                 250                 255
Gly Lys Ser Leu Gly Ser Lys Tyr Pro Glu Met Asp Leu Asp Ser Arg
            260                 265                 270
Ala Phe Leu Lys Asp Tyr Tyr Arg Asp His Asn Ile Glu Leu Ser Lys
        275                 280                 285
Leu Leu Tyr Lys Met Gly Gln Thr Leu Pro Thr Trp Leu Arg Glu Asp
    290                 295                 300
Leu Gln Asn Thr Arg
305

<210> SEQ ID NO 9
<211> LENGTH: 927
<212> TYPE: DNA
<213> ORGANISM: Artificial Sequence
<220> FEATURE:
<223> OTHER INFORMATION: Polynucleotide sequence encoding for engineered
      aryl sulfate-dependent N-sulfotransferase variant 5

<400> SEQUENCE: 9
atgagcgaag agaaggaccc tttgtggcag gacccgtgcg aagataagcg tcataaagac      60
atttggagta agagaagac ttgtgatcgt ttccccaagt tactgatcat cggcccacat     120
aagacaggag tacatgcatt gtacttgttt ttgggaatgc atccggacct gtcttcaaat     180
taccccagtt cagagacagg caatcacatc ggcttcttcg aggacataa ctaccacaaa     240 ggcatcgatt ggtacatgga attctttcct atccctcta atactacctc agattttac     300 ttcgagaaaa gtgcttggta ctttgactcc gaagttgctc ctcgtcgcgc agcagcatta     360
```

```
cttccaaagg cgaaagttct gactattttg atcaaccctg cggatcgcgc ctacagctgg    420
tatcaacacc agcgcgccca cgatgatcct gtcgcattga aatacacctt tcatgaagtt    480
atcaccgctg gctccgatgc gtctagcaaa ttgcgtgcat acagaatcg ttgccttgtg     540 ccaggatggt acgctaccca tattgagcgc tggctgagtg catatcacgc gaatcagatt    600
ctggtgttag atggaaagct gctgcgtact gaaccggcca agtaatgga catggttcaa     660 aagttcctgg gggtgacgaa cacaattgat taccataaga ctcttgcatt tgatcctaag    720
aaaggctttt ggtgtcaact tttagagggg gggaagacca agtgcttagg gaagagcgtg    780
ggacgcaagt accccgaaat ggacttagat agccgtgctt tcttgaagga ttattatcgc    840
gaccacaaca ttgaactttc taaactgtta tacaagatgg ccagacact gccgacctgg      900 ctgcgtgaag acttgcagaa cacacgc                                        927
```

<210> SEQ ID NO 10
<211> LENGTH: 309
<212> TYPE: PRT
<213> ORGANISM: Artificial Sequence
<220> FEATURE:
<223> OTHER INFORMATION: Amino acid sequence encoding for engineered aryl sulfate-dependent N-sulfotransferase variant 5

<400> SEQUENCE: 10

```
Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro His Lys Thr Gly Val His Ala Leu Tyr
        35                  40                  45

Leu Phe Leu Gly Met His Pro Asp Leu Ser Ser Asn Tyr Pro Ser Ser
    50                  55                  60

Glu Thr Gly Asn His Ile Gly Phe Phe Gly Gly His Asn Tyr His Lys
65                  70                  75                  80

Gly Ile Asp Trp Tyr Met Glu Phe Phe Pro Ile Pro Ser Asn Thr Thr
                85                  90                  95

Ser Asp Phe Tyr Phe Glu Lys Ser Ala Trp Tyr Phe Asp Ser Glu Val
            100                 105                 110

Ala Pro Arg Arg Ala Ala Ala Leu Leu Pro Lys Ala Lys Val Leu Thr
        115                 120                 125

Ile Leu Ile Asn Pro Ala Asp Arg Ala Tyr Ser Trp Tyr Gln His Gln
    130                 135                 140

Arg Ala His Asp Asp Pro Val Ala Leu Lys Tyr Thr Phe His Glu Val
145                 150                 155                 160

Ile Thr Ala Gly Ser Asp Ala Ser Ser Lys Leu Arg Ala Leu Gln Asn
                165                 170                 175

Arg Cys Leu Val Pro Gly Trp Tyr Ala Thr His Ile Glu Arg Trp Leu
            180                 185                 190

Ser Ala Tyr His Ala Asn Gln Ile Leu Val Leu Asp Gly Lys Leu Leu
        195                 200                 205

Arg Thr Glu Pro Ala Lys Val Met Asp Met Val Gln Lys Phe Leu Gly
    210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Lys Thr Lys Cys Leu
                245                 250                 255
```

```
Gly Lys Ser Val Gly Arg Lys Tyr Pro Glu Met Asp Leu Asp Ser Arg
            260                 265                 270

Ala Phe Leu Lys Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Asp
    290                 295                 300

Leu Gln Asn Thr Arg
305
```

<210> SEQ ID NO 11
<211> LENGTH: 927
<212> TYPE: DNA
<213> ORGANISM: Artificial Sequence
<220> FEATURE:
<223> OTHER INFORMATION: Polynucleotide sequence encoding for engineered
      aryl sulfate-dependent N-sulfotransferase variant 6

<400> SEQUENCE: 11

```
atgagcgaag agaaggaccc tttgtggcag gacccgtgcg aagataagcg tcacaaggat      60
atttggtcca agaaaagac  ctgcgatcgc tttcccaagc tgttaatcat cggcccggcc     120
aaaacaggcg cctggctttt gcatcatttc ctgggcatgc atcccgactt gtcgagtaac     180
tatccgtcgt ccgaaactca ctcctctatt caattcttca atgggcataa ttatcacaag     240
ggatcgact  ggtacatgga gttctttcca atccctagta atacaaccag tgatttttat     300
tttgagacta gcgctaacta ctttgattca gaggtggcac cgcgtcgtgc ggcggcgctg     360
ttgccgaagg cgaaagtttt aactatcttg atcaatccgg cagatcgtgc gtacagctgg     420
taccaacatc aacgtgctca cgatgacccg gtggccctga atataccttc cacgaggtc      480
attacagccg gaagtgacgc ttccagtaaa ttgcgcgcgt acaaaatcg  ttgtctggtc     540
cctgggtggt acgcaacgca cattgaacgc tggttatcgg cataccacgc aaatcagatc     600
cttgtgcttg acggaaagtt attgcgtact gaaccggcca aggtgatgga tatggtacag     660
aaattccttg gcgtcaccaa tacgatcgac tatcacaaga cgcttgcctt cgaccccaag     720
aaggggtttt ggtgccaact tttagagggt ggtaagacaa agtgtgctca taaggggtta     780
ggccgcaagt accctgaaat ggatctggac tcgcgcgctt ttttgaaaga ctattatcgc     840
gatcacaata ttgagttgag caagttgctg tataaaatgg gacagacact gccgacctgg     900
ctgcgtgaag acttgcagaa cacacgc                                         927
```

<210> SEQ ID NO 12
<211> LENGTH: 309
<212> TYPE: PRT
<213> ORGANISM: Artificial Sequence
<220> FEATURE:
<223> OTHER INFORMATION: Amino acid sequence encoding for engineered
      aryl sulfate-dependent N-sulfotransferase variant 6

<400> SEQUENCE: 12

```
Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Ala Lys Thr Gly Ala Trp Leu Leu His
        35                  40                  45

His Phe Leu Gly Met His Pro Asp Leu Ser Ser Asn Tyr Pro Ser Ser
    50                  55                  60

Glu Thr His Ser Ser Ile Gln Phe Phe Asn Gly His Asn Tyr His Lys
```

```
              65                  70                  75                  80
Gly Ile Asp Trp Tyr Met Glu Phe Phe Pro Ile Pro Ser Asn Thr Thr
                    85                  90                  95

Ser Asp Phe Tyr Phe Glu Thr Ser Ala Asn Tyr Phe Asp Ser Glu Val
                    100                 105                 110

Ala Pro Arg Arg Ala Ala Ala Leu Leu Pro Lys Ala Lys Val Leu Thr
                    115                 120                 125

Ile Leu Ile Asn Pro Ala Asp Arg Ala Tyr Ser Trp Tyr Gln His Gln
    130                 135                 140

Arg Ala His Asp Asp Pro Val Ala Leu Lys Tyr Thr Phe His Glu Val
145                 150                 155                 160

Ile Thr Ala Gly Ser Asp Ala Ser Ser Lys Leu Arg Ala Leu Gln Asn
                    165                 170                 175

Arg Cys Leu Val Pro Gly Trp Tyr Ala Thr His Ile Glu Arg Trp Leu
                    180                 185                 190

Ser Ala Tyr His Ala Asn Gln Ile Leu Val Leu Asp Gly Lys Leu Leu
                    195                 200                 205

Arg Thr Glu Pro Ala Lys Val Met Asp Met Val Gln Lys Phe Leu Gly
    210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Ala
                    245                 250                 255

His Lys Gly Leu Gly Arg Lys Tyr Pro Glu Met Asp Leu Asp Ser Arg
                    260                 265                 270

Ala Phe Leu Lys Asp Tyr Tyr Arg Asp His Asn Ile Glu Leu Ser Lys
                    275                 280                 285

Leu Leu Tyr Lys Met Gly Gln Thr Leu Pro Thr Trp Leu Arg Glu Asp
    290                 295                 300

Leu Gln Asn Thr Arg
305
```

<210> SEQ ID NO 13
<211> LENGTH: 870
<212> TYPE: DNA
<213> ORGANISM: Artificial Sequence
<220> FEATURE:
<223> OTHER INFORMATION: Polynucleotide sequence encoding for engineered
      aryl sulfate-dependent 2-O-sulfotransferase variant 1

<400> SEQUENCE: 13
atggatgagg aggacgatgt ggtgatcatc tacaatcgtg tgccgcacac cgcgagcacg      60
agctttacga acatcgccta cgatctgtgc gcgaaaaatc gctaccacgt gctgcacatc     120
aacaccacca agaacaaccc agtgatgagt ctgcaagatc aagtgcgctt cgtgaagaac     180
gtgacgagct ggaaggagat gaaaccgggc ttctaccacg ccacgtgag ctatctcgat      240
ttcgccaagt tcggcgtgaa gaagaagccg atctacatca acgtgattcg cgatccgatc     300
gagcgtctgg tgagctacta ctaccacctc cgttttggcg atgactatcg tccgggtctg     360
cgccgtcgca agcaaggcga caaaaagacg ttcgacgagt gcgttgcggc cggcggtagt     420
gattgtgccc cagaaaagct gtggctgcag atcccgttct tctgcggtca tagcagcgag     480
tgctggaatg tgggtagccc ctgggcgctg aacaagcca atacaatct gatcaacgag      540
tactttctgg tgggcgtgac ggaggagctg gaggacttta ttatgctgct cgaggcggcg     600
ctgccgcgct ttttcgtgg tgccaccgag ctgtatcgca ccggcaaaaa aagtcacctc     660
```

```
cacaagacca ccgagaagaa gctgccgacg aaagaaacca ttgccaaact gcagcagagc    720
gagatctgga agatggagaa cgaattctac gagttcgcgc tcgagcagtt ccagtttgtt    780
cgtgcccacg ccgtgcgtga aaaggacggc gagctgtaca ttctcgccca gaatttcttc    840
tacgagaaga tctatccaaa aagcaactaa                                     870
```

```
<210> SEQ ID NO 14
<211> LENGTH: 289
<212> TYPE: PRT
<213> ORGANISM: Artificial Sequence
<220> FEATURE:
<223> OTHER INFORMATION: Amino acid sequence encoding for engineered
      aryl sulfate-dependent 2-O-sulfotransferase variant 1

<400> SEQUENCE: 14
```

```
Met Asp Glu Glu Asp Val Val Ile Ile Tyr Asn Arg Val Pro His
1               5                   10                  15

Thr Ala Ser Thr Ser Phe Thr Asn Ile Ala Tyr Asp Leu Cys Ala Lys
            20                  25                  30

Asn Arg Tyr His Val Leu His Ile Asn Thr Thr Lys Asn Asn Pro Val
        35                  40                  45

Met Ser Leu Gln Asp Gln Val Arg Phe Val Lys Asn Val Thr Ser Trp
    50                  55                  60

Lys Glu Met Lys Pro Gly Phe Tyr His Gly His Val Ser Tyr Leu Asp
65                  70                  75                  80

Phe Ala Lys Phe Gly Val Lys Lys Pro Ile Tyr Ile Asn Val Ile
                85                  90                  95

Arg Asp Pro Ile Glu Arg Leu Val Ser Tyr Tyr His Leu Arg Phe
            100                 105                 110

Gly Asp Asp Tyr Arg Pro Gly Leu Arg Arg Arg Lys Gln Gly Asp Lys
        115                 120                 125

Lys Thr Phe Asp Glu Cys Val Ala Ala Gly Gly Ser Asp Cys Ala Pro
    130                 135                 140

Glu Lys Leu Trp Leu Gln Ile Pro Phe Phe Cys Gly His Ser Ser Glu
145                 150                 155                 160

Cys Trp Asn Val Gly Ser Arg Trp Ala Leu Glu Gln Ala Lys Tyr Asn
                165                 170                 175

Leu Ile Asn Glu Tyr Phe Leu Val Gly Val Thr Glu Glu Leu Glu Asp
            180                 185                 190

Phe Ile Met Leu Leu Glu Ala Ala Leu Pro Arg Phe Phe Arg Gly Ala
        195                 200                 205

Thr Glu Leu Tyr Arg Thr Gly Lys Lys Ser His Leu His Lys Thr Thr
    210                 215                 220

Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
                245                 250                 255

Phe Gln Phe Val Arg Ala His Ala Val Arg Glu Lys Asp Gly Glu Leu
            260                 265                 270

Tyr Ile Leu Ala Gln Asn Phe Phe Tyr Glu Lys Ile Tyr Pro Lys Ser
        275                 280                 285

Asn
```

```
<210> SEQ ID NO 15
<211> LENGTH: 870
```

<210> SEQ ID NO 15
<211> LENGTH: 870
<212> TYPE: DNA
<213> ORGANISM: Artificial Sequence
<220> FEATURE:
<223> OTHER INFORMATION: Polynucleotide sequence encoding for engineered aryl sulfate-dependent 2-O-sulfotransferase variant 2

<400> SEQUENCE: 15

```
atggatgagg aggacgatgt ggtgatcatc tacaaccgtg tgcaccgcac ggcgagtcac      60
agtttcacca acatcgcgta tgatctgtgc gcgaagaacc gctaccacgt gctgcatatc     120
aacacgacca aaggcaaccc ggtgatgagt ctgcaagatc aagttcgctt cgtgaagaac     180
gttacgagct ggaaggagat gaaaccgggt ttttaccacg gcccagtgag ctatctcgac     240
ttcgccaagt tcggcgtgaa gaaaaagccg atctacatca tgtgatccg cgacccgatc     300
gaacgtctgg tgagctacta ctactttctg cgcttcggca cgacaagcg tccgggtctg     360
cgcatgcgta acaaggcga agaagacc ttcgacgaat gcgttgccgc cggcggtagt      420
gattgtgccc cagaaaagct gtggctgcag atcccgttct tctgcggtca tagcagcgag     480
tgctggaatg tgggtagccg ctgggcgctg agcaagcca atacaatct gatcaacgaa      540
tactttctcg tgggcgtgac cgaagagctg aagacttca tcatgctgct ggaggccgcg     600
ctgccgcgtt tctttcgtgg tgccaccgaa ctgtatcgta ccggcaaaaa gagccacctc     660
cacaaaacga cggagaagaa gctgccgacg aaggaaacca ttgccaaact gcagcagagc     720
gagatctgga gatggagaa cgaattctac gagtttgcgc tcgagcagtt ccaatttgtg     780
cgcgcccatg ccgtgcgtga aaaggacggc gagctgtaca ttctcgccca gaatttcttc     840
tacgaaaaga tctatccaaa aagcaactaa                                      870
```

<210> SEQ ID NO 16
<211> LENGTH: 289
<212> TYPE: PRT
<213> ORGANISM: Artificial Sequence
<220> FEATURE:
<223> OTHER INFORMATION: Amino acid sequence encoding for engineered aryl sulfate-dependent 2-O-sulfotransferase variant 2

<400> SEQUENCE: 16

```
Met Asp Glu Glu Asp Asp Val Val Ile Ile Tyr Asn Arg Val His Arg
1               5                   10                  15

Thr Ala Ser His Ser Phe Thr Asn Ile Ala Tyr Asp Leu Cys Ala Lys
            20                  25                  30

Asn Arg Tyr His Val Leu His Ile Asn Thr Thr Lys Gly Asn Pro Val
        35                  40                  45

Met Ser Leu Gln Asp Gln Val Arg Phe Val Lys Asn Val Thr Ser Trp
    50                  55                  60

Lys Glu Met Lys Pro Gly Phe Tyr His Gly Pro Val Ser Tyr Leu Asp
65                  70                  75                  80

Phe Ala Lys Phe Gly Val Lys Lys Pro Ile Tyr Ile Asn Val Ile
                85                  90                  95

Arg Asp Pro Ile Glu Arg Leu Val Ser Tyr Tyr Phe Leu Arg Phe
            100                 105                 110

Gly Ser Asp Lys Arg Pro Gly Leu Arg Met Arg Lys Gln Gly Asp Lys
        115                 120                 125

Lys Thr Phe Asp Glu Cys Val Ala Ala Gly Gly Ser Asp Cys Ala Pro
    130                 135                 140

Glu Lys Leu Trp Leu Gln Ile Pro Phe Phe Cys Gly His Ser Ser Glu
145                 150                 155                 160
```

Cys Trp Asn Val Gly Ser Arg Trp Ala Leu Glu Gln Ala Lys Tyr Asn
            165                 170                 175

Leu Ile Asn Glu Tyr Phe Leu Val Gly Val Thr Glu Glu Leu Glu Asp
        180                 185                 190

Phe Ile Met Leu Leu Glu Ala Ala Leu Pro Arg Phe Phe Arg Gly Ala
    195                 200                 205

Thr Glu Leu Tyr Arg Thr Gly Lys Lys Ser His Leu His Lys Thr Thr
210                 215                 220

Glu Lys Lys Leu Pro Thr Lys Glu Thr Ile Ala Lys Leu Gln Gln Ser
225                 230                 235                 240

Glu Ile Trp Lys Met Glu Asn Glu Phe Tyr Glu Phe Ala Leu Glu Gln
            245                 250                 255

Phe Gln Phe Val Arg Ala His Ala Val Arg Glu Lys Asp Gly Glu Leu
        260                 265                 270

Tyr Ile Leu Ala Gln Asn Phe Phe Tyr Glu Lys Ile Tyr Pro Lys Ser
    275                 280                 285

Asn

<210> SEQ ID NO 17
<211> LENGTH: 939
<212> TYPE: DNA
<213> ORGANISM: Artificial Sequence
<220> FEATURE:
<223> OTHER INFORMATION: Polynucleotide sequence encoding for engineered
      aryl sulfate-dependent 6-O-sulfotransferase variant 1

<400> SEQUENCE: 17
atgaagtact attttccggt ccgcgaattg gagcgctcac tgcgttttga tatgaagggt        60
gacgatgtga ttgtattcct tcatattggg catacaggcg ggacgacttt tggacgtcat       120
ttagtccaga acgttcgtct ggaggtaccc tgtgattgcc gcccgggtca aaaaaaatgc       180
acgtgttacc gcccaaatcg ccgtgagacc tggttgttct ctcgcttttc cacaggctgg      240
tcttgcggaa ctaacgccga ctggacagag cttaccaact gtgtcccagg ggtattggac      300
cgccgtgatc cagctgggtt gcgctcgcca cgtaaatttt actatattac cctgctgcgc     360
gatcctgtct cccgctacct gggggggctgg cgccaccatc agcgtggcgg cacaaataaa    420
acatcgttgc acatgtgtga tgggcgcacg ccaacacccg aagagcttcc cccgtgctat    480
gagggaacgg actggagtgg atgtacttta caggaattta tggactgtcc ctacaatttg    540
gcaaacaatc gtcaagtccg catgcttgcg gatcttagtt tggtcggctg ttacaacttg    600
agctttattc ccgaaagtaa gcgcgcacaa cttttattag agagtgccaa gaagaacttg    660
cgtggaatgg cattctttgg attgaccgaa tttcagcgta aaacgcagta tttgtttgaa    720
cgtacattca acctgaaatt tatccgcccg tttatgcagt ataacagtac gcgcgcgggg    780
ggcgtggaag tggacgagga cacgattcgc cacattgagg aattgaatga ccttgatatg    840
caattgtacg actacgccaa agatcttttc cagcaacgtt atcaatacaa gcgccagctt    900
gaacgccgcg agcagcgttt acgcaatcgt gaggaataa                            939

<210> SEQ ID NO 18
<211> LENGTH: 312
<212> TYPE: PRT
<213> ORGANISM: Artificial Sequence
<220> FEATURE:
<223> OTHER INFORMATION: Amino acid sequence encoding for engineered
      aryl sulfate-dependent 6-O-sulfotransferase variant 1

<400> SEQUENCE: 18

| Met | Lys | Tyr | Tyr | Phe | Pro | Val | Arg | Glu | Leu | Glu | Arg | Ser | Leu | Arg | Phe |
| --- | --- | --- | --- | --- | --- | --- | --- | --- | --- | --- | --- | --- | --- | --- | --- |
| 1 | | | | 5 | | | | | 10 | | | | | 15 | |

| Asp | Met | Lys | Gly | Asp | Asp | Val | Ile | Val | Phe | Leu | His | Ile | Gly | His | Thr |
| --- | --- | --- | --- | --- | --- | --- | --- | --- | --- | --- | --- | --- | --- | --- | --- |
| | | | 20 | | | | | 25 | | | | | 30 | | |

| Gly | Gly | Thr | Thr | Phe | Gly | Arg | His | Leu | Val | Gln | Asn | Val | Arg | Leu | Glu |
| --- | --- | --- | --- | --- | --- | --- | --- | --- | --- | --- | --- | --- | --- | --- | --- |
| | | | 35 | | | | | 40 | | | | | 45 | | |

| Val | Pro | Cys | Asp | Cys | Arg | Pro | Gly | Gln | Lys | Lys | Cys | Thr | Cys | Tyr | Arg |
| --- | --- | --- | --- | --- | --- | --- | --- | --- | --- | --- | --- | --- | --- | --- | --- |
| | 50 | | | | | 55 | | | | | 60 | | | | |

| Pro | Asn | Arg | Arg | Glu | Thr | Trp | Leu | Phe | Ser | Arg | Phe | Ser | Thr | Gly | Trp |
| --- | --- | --- | --- | --- | --- | --- | --- | --- | --- | --- | --- | --- | --- | --- | --- |
| 65 | | | | | 70 | | | | | 75 | | | | | 80 |

| Ser | Cys | Gly | Thr | Asn | Ala | Asp | Trp | Thr | Glu | Leu | Thr | Asn | Cys | Val | Pro |
| --- | --- | --- | --- | --- | --- | --- | --- | --- | --- | --- | --- | --- | --- | --- | --- |
| | | | | 85 | | | | | 90 | | | | | 95 | |

| Gly | Val | Leu | Asp | Arg | Arg | Asp | Pro | Ala | Gly | Leu | Arg | Ser | Pro | Arg | Lys |
| --- | --- | --- | --- | --- | --- | --- | --- | --- | --- | --- | --- | --- | --- | --- | --- |
| | | | 100 | | | | | 105 | | | | | 110 | | |

| Phe | Tyr | Tyr | Ile | Thr | Leu | Leu | Arg | Asp | Pro | Val | Ser | Arg | Tyr | Leu | Gly |
| --- | --- | --- | --- | --- | --- | --- | --- | --- | --- | --- | --- | --- | --- | --- | --- |
| | | | 115 | | | | | 120 | | | | | 125 | | |

| Gly | Trp | Arg | His | His | Gln | Arg | Gly | Gly | Thr | Asn | Lys | Thr | Ser | Leu | His |
| --- | --- | --- | --- | --- | --- | --- | --- | --- | --- | --- | --- | --- | --- | --- | --- |
| | 130 | | | | | 135 | | | | | 140 | | | | |

| Met | Cys | Asp | Gly | Arg | Thr | Pro | Thr | Pro | Glu | Glu | Leu | Pro | Pro | Cys | Tyr |
| --- | --- | --- | --- | --- | --- | --- | --- | --- | --- | --- | --- | --- | --- | --- | --- |
| 145 | | | | | 150 | | | | | 155 | | | | | 160 |

| Glu | Gly | Thr | Asp | Trp | Ser | Gly | Cys | Thr | Leu | Gln | Glu | Phe | Met | Asp | Cys |
| --- | --- | --- | --- | --- | --- | --- | --- | --- | --- | --- | --- | --- | --- | --- | --- |
| | | | | 165 | | | | | 170 | | | | | 175 | |

| Pro | Tyr | Asn | Leu | Ala | Asn | Asn | Arg | Gln | Val | Arg | Met | Leu | Ala | Asp | Leu |
| --- | --- | --- | --- | --- | --- | --- | --- | --- | --- | --- | --- | --- | --- | --- | --- |
| | | | 180 | | | | | 185 | | | | | 190 | | |

| Ser | Leu | Val | Gly | Cys | Tyr | Asn | Leu | Ser | Phe | Ile | Pro | Glu | Ser | Lys | Arg |
| --- | --- | --- | --- | --- | --- | --- | --- | --- | --- | --- | --- | --- | --- | --- | --- |
| | | | 195 | | | | | 200 | | | | | 205 | | |

| Ala | Gln | Leu | Leu | Leu | Glu | Ser | Ala | Lys | Lys | Asn | Leu | Arg | Gly | Met | Ala |
| --- | --- | --- | --- | --- | --- | --- | --- | --- | --- | --- | --- | --- | --- | --- | --- |
| | 210 | | | | | 215 | | | | | 220 | | | | |

| Phe | Phe | Gly | Leu | Thr | Glu | Phe | Gln | Arg | Lys | Thr | Gln | Tyr | Leu | Phe | Glu |
| --- | --- | --- | --- | --- | --- | --- | --- | --- | --- | --- | --- | --- | --- | --- | --- |
| 225 | | | | | 230 | | | | | 235 | | | | | 240 |

| Arg | Thr | Phe | Asn | Leu | Lys | Phe | Ile | Arg | Pro | Phe | Met | Gln | Tyr | Asn | Ser |
| --- | --- | --- | --- | --- | --- | --- | --- | --- | --- | --- | --- | --- | --- | --- | --- |
| | | | | 245 | | | | | 250 | | | | | 255 | |

| Thr | Arg | Ala | Gly | Gly | Val | Glu | Val | Asp | Glu | Asp | Thr | Ile | Arg | His | Ile |
| --- | --- | --- | --- | --- | --- | --- | --- | --- | --- | --- | --- | --- | --- | --- | --- |
| | | | 260 | | | | | 265 | | | | | 270 | | |

| Glu | Glu | Leu | Asn | Asp | Leu | Asp | Met | Gln | Leu | Tyr | Asp | Tyr | Ala | Lys | Asp |
| --- | --- | --- | --- | --- | --- | --- | --- | --- | --- | --- | --- | --- | --- | --- | --- |
| | | | 275 | | | | | 280 | | | | | 285 | | |

| Leu | Phe | Gln | Gln | Arg | Tyr | Gln | Tyr | Lys | Arg | Gln | Leu | Glu | Arg | Arg | Glu |
| --- | --- | --- | --- | --- | --- | --- | --- | --- | --- | --- | --- | --- | --- | --- | --- |
| | 290 | | | | | 295 | | | | | 300 | | | | |

| Gln | Arg | Leu | Arg | Asn | Arg | Glu | Glu |
| --- | --- | --- | --- | --- | --- | --- | --- |
| 305 | | | | | 310 | | |

<210> SEQ ID NO 19
<211> LENGTH: 939
<212> TYPE: DNA
<213> ORGANISM: Artificial Sequence
<220> FEATURE:
<223> OTHER INFORMATION: Polynucleotide sequence encoding for engineered
      aryl sulfate-dependent 6-O-sulfotransferase variant 2

<400> SEQUENCE: 19

```
atgaagtact attttccggt ccgcgaattg gagcgctcat tgcgtttcga tatgaagggt      60
gatgatgtca tcgtcttcct tcacattggt cacactggtg gaaccacctt tggacgtcat     120
cttgtgcaaa acgtacgttt agaggtccct tgcgattgtc gtccgggtca aaaaaaatgt     180
acttgctatc gtcctaatcg tcgtgaaacg tggcttttca gtcgttttag tacggggtgg     240
```

```
tcatgcggta cccgcgcaga ctggacggag ttaaccaact gcgtacctgg ggtgttggat    300
cgccgcgatc cggcaggttt acgctcccca cgtaaattct attatattac cctgttacgt    360
gacccagtca gtcgctattt gtctcactgg cgtcacacac aacgtggcgg cgcgaacaag    420
accggactgc acatgtgtga cgggcgtact cctacaccag aggaattacc ccatgctat     480 gagggaactg actggtcggg atgtacactg caggagttca tggactgccc atacaatctg    540 gggataatc gccaagtccg tatgttggcg gatttaagcc ttgtcggatg ctataatttg     600
tcattcattc cagaatcaaa acgcgcgcaa cttcttcttg agtcagccaa gaaaaatttg    660
cgcggaatgg cattttttcgg gttgacgaaa ttttcagcgca aaacacaata tctgttcgag   720
cgcacattca atttaaaatt tattcgtcct ttcatgcaat acaactctac acgtgcagga    780
ggagtcgaag tggacgagga cacaattcgc cacatcgagg aattaaatga tctggatatg    840
cagttgtatg actatgcaaa agatctgttt cagcaacgct atcaatacaa gcgtcagttg    900
gaacgccgcg agcagcgttt acgcaatcgt gaggaataa                            939
```

<210> SEQ ID NO 20
<211> LENGTH: 312
<212> TYPE: PRT
<213> ORGANISM: Artificial Sequence
<220> FEATURE:
<223> OTHER INFORMATION: Amino acid sequence encoding for engineered
      aryl sulfate-dependent 6-O-sulfotransferase variant 2

<400> SEQUENCE: 20

```
Met Lys Tyr Tyr Phe Pro Val Arg Glu Leu Glu Arg Ser Leu Arg Phe
1               5                   10                  15

Asp Met Lys Gly Asp Asp Val Ile Val Phe Leu His Ile Gly His Thr
            20                  25                  30

Gly Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
    50                  55                  60

Pro Asn Arg Arg Glu Thr Trp Leu Phe Ser Arg Phe Ser Thr Gly Trp
65                  70                  75                  80

Ser Cys Gly Thr Arg Ala Asp Trp Thr Glu Leu Thr Asn Cys Val Pro
                85                  90                  95

Gly Val Leu Asp Arg Arg Asp Pro Ala Gly Leu Arg Ser Pro Arg Lys
            100                 105                 110

Phe Tyr Tyr Ile Thr Leu Leu Arg Asp Pro Val Ser Arg Tyr Leu Ser
        115                 120                 125

His Trp Arg His Thr Gln Arg Gly Gly Ala Asn Lys Thr Gly Leu His
    130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Gly Asn Asn Arg Gln Val Arg Met Leu Ala Asp Leu
            180                 185                 190

Ser Leu Val Gly Cys Tyr Asn Leu Ser Phe Ile Pro Glu Ser Lys Arg
        195                 200                 205

Ala Gln Leu Leu Leu Glu Ser Ala Lys Lys Asn Leu Arg Gly Met Ala
    210                 215                 220

Phe Phe Gly Leu Thr Glu Phe Gln Arg Lys Thr Gln Tyr Leu Phe Glu
```

```
                225                 230                 235                 240

Arg Thr Phe Asn Leu Lys Phe Ile Arg Pro Phe Met Gln Tyr Asn Ser
                245                 250                 255

Thr Arg Ala Gly Gly Val Glu Val Asp Glu Asp Thr Ile Arg His Ile
                260                 265                 270

Glu Glu Leu Asn Asp Leu Asp Met Gln Leu Tyr Asp Tyr Ala Lys Asp
                275                 280                 285

Leu Phe Gln Gln Arg Tyr Gln Tyr Lys Arg Gln Leu Glu Arg Arg Glu
            290                 295                 300

Gln Arg Leu Arg Asn Arg Glu Glu
305                 310

<210> SEQ ID NO 21
<211> LENGTH: 939
<212> TYPE: DNA
<213> ORGANISM: Artificial Sequence
<220> FEATURE:
<223> OTHER INFORMATION: Polynucleotide sequence encoding for engineered
      aryl sulfate-dependent 6-O-sulfotransferase variant 3

<400> SEQUENCE: 21
atgaagtact attttccggt ccgcgaattg gagcgctcat tgcgtttcga catgaaagga        60
gacgacgtca ttgtattttt acatattggc cacaccggtg gcacgacttt tggccgtcac       120
ttagtccaaa acgtacgctt agaggtgcct tgcgactgtc gtccagggca aagaaatgc        180 acctgctatc gccccaaccg ccgtgaaaca tggttgttta gtcgctttag taccggttgg       240
agctgtggct ctcatgctga ttggactgaa ctgacgaatt gtgtcccgg agtattggat       300 cgccgtgatc ctgctggttt acgctcacct cgcaaattct attatattac gttacttcgt       360
gatcccgtta gccgttatct tagtgggtgg cgtcaccatc aacgcggagg ggctaataag       420
acgagcctgc acatgtgtga cggacgtacg ccaaccccg aggaactgcc gccctgttac       480
gaggggacgg actggtctgg ctgtacatta caagagttta tggattgccc atataacctg       540
ggtaacaatc gccaagtccg tatgttggcg atctttcgc tggtgggatg ttataattta       600
agttttatcc ggagagcaa gcgtgcacag ttgctgcttg aatcagcgaa gaagaacctt       660
cgcggaatgg cattttcgg tttaacggag tttcaacgta agactcagta ccttttcgag       720
cgtaccttca acttgaaatt tatccgtcc ttcatgcagt acaactccac ccgcgctggt       780
ggagttgaag tcgacgagga taccatccgc cacattgaag aacttaatga cttagatatg       840
caattgtacg actatgctaa ggacttattc cagcaacgtt atcagtacaa acgccaattg       900
gaacgccgcg agcagcgttt acgcaatcgt gaggaataa                              939

<210> SEQ ID NO 22
<211> LENGTH: 312
<212> TYPE: PRT
<213> ORGANISM: Artificial Sequence
<220> FEATURE:
<223> OTHER INFORMATION: Amino acid sequence encoding for engineered
      aryl sulfate-dependent 6-O-sulfotransferase variant 3

<400> SEQUENCE: 22

Met Lys Tyr Tyr Phe Pro Val Arg Glu Leu Glu Arg Ser Leu Arg Phe
1               5                   10                  15

Asp Met Lys Gly Asp Asp Val Ile Val Phe Leu His Ile Gly His Thr
            20                  25                  30

Gly Gly Thr Thr Phe Gly Arg His Leu Val Gln Asn Val Arg Leu Glu
        35                  40                  45
```

Val Pro Cys Asp Cys Arg Pro Gly Gln Lys Lys Cys Thr Cys Tyr Arg
 50                  55                  60

Pro Asn Arg Arg Glu Thr Trp Leu Phe Ser Arg Phe Ser Thr Gly Trp
 65                  70                  75                  80

Ser Cys Gly Ser His Ala Asp Trp Thr Glu Leu Thr Asn Cys Val Pro
                 85                  90                  95

Gly Val Leu Asp Arg Arg Asp Pro Ala Gly Leu Arg Ser Pro Arg Lys
            100                 105                 110

Phe Tyr Tyr Ile Thr Leu Leu Arg Asp Pro Val Ser Arg Tyr Leu Ser
        115                 120                 125

Gly Trp Arg His His Gln Arg Gly Gly Ala Asn Lys Thr Ser Leu His
130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Gly Asn Asn Arg Gln Val Arg Met Leu Ala Asp Leu
            180                 185                 190

Ser Leu Val Gly Cys Tyr Asn Leu Ser Phe Ile Pro Glu Ser Lys Arg
        195                 200                 205

Ala Gln Leu Leu Leu Glu Ser Ala Lys Lys Asn Leu Arg Gly Met Ala
210                 215                 220

Phe Phe Gly Leu Thr Glu Phe Gln Arg Lys Thr Gln Tyr Leu Phe Glu
225                 230                 235                 240

Arg Thr Phe Asn Leu Lys Phe Ile Arg Pro Phe Met Gln Tyr Asn Ser
                245                 250                 255

Thr Arg Ala Gly Gly Val Glu Val Asp Glu Asp Thr Ile Arg His Ile
            260                 265                 270

Glu Glu Leu Asn Asp Leu Asp Met Gln Leu Tyr Asp Tyr Ala Lys Asp
        275                 280                 285

Leu Phe Gln Gln Arg Tyr Gln Tyr Lys Arg Gln Leu Glu Arg Arg Glu
290                 295                 300

Gln Arg Leu Arg Asn Arg Glu Glu
305                 310

<210> SEQ ID NO 23
<211> LENGTH: 795
<212> TYPE: DNA
<213> ORGANISM: Artificial Sequence
<220> FEATURE:
<223> OTHER INFORMATION: Polynucleotide sequence encoding for engineered
      aryl sulfate-dependent 3-O-sulfotransferase variant 1

<400> SEQUENCE: 23
atgggaactg cgtcgaacgg cagtacgcaa caacttccgc agactatcat cattggcgta      60
ggacatggtg gaactcgtgc tctgttggag atgttatcac ttcacccga cgtcgcagcg     120 gctgagaatg aagttcactt tttcgattgg gaagagcatt attcgcaggg gttaggttgg     180
tatcttaccc aaatgccttt ttcgagtccc catcagttaa cagtagagaa gacccattct     240
tactttacat caccaaaagt gcctgagcgc atccattcga tgaatccgac tatccgcctt     300
ttactgatct tacgcgatcc atcagaacgc gttctttcgg catataccca catgctttat     360
aaccatttgc agaaacacaa gccatatccc cctattgagg atttattaat gcgcgatgga     420
cgcttgaacc tggattatgt aggattaaat cgctctcttt atcacgccca tatgttaaac     480

```
tggcttcgct ttttccgct tgggcatatc cacatcgttg atggagaccg tttaattcgt    540
gacccgtttc ctgagatcca gaaggtcgaa cgcttcctga aattaagtcc tcagattaat    600
gcgagcaatt tctatttcaa caagacgaaa ggattctact gcctgcgcga ctccggtaag    660
gatcgctgcc tgcacgagtc aaaagggcgc gcgcaccctc aggtcgaccc aaagctgtta    720
gataaattgc atgagtattt ccacgaacct aataagaagt tcttcaaact tgtcggccgc    780
acatttgatt ggcat                                                    795
```

<210> SEQ ID NO 24
<211> LENGTH: 265
<212> TYPE: PRT
<213> ORGANISM: Artificial Sequence
<220> FEATURE:
<223> OTHER INFORMATION: Amino acid sequence encoding for engineered aryl sulfate-dependent 3-O-sulfotransferase variant 1

<400> SEQUENCE: 24

```
Met Gly Thr Ala Ser Asn Gly Ser Thr Gln Gln Leu Pro Gln Thr Ile
1               5                   10                  15

Ile Ile Gly Val Gly His Gly Gly Thr Arg Ala Leu Leu Glu Met Leu
            20                  25                  30

Ser Leu His Pro Asp Val Ala Ala Glu Asn Glu Val His Phe Phe
        35                  40                  45

Asp Trp Glu Glu His Tyr Ser Gln Gly Leu Gly Trp Tyr Leu Thr Gln
    50                  55                  60

Met Pro Phe Ser Ser Pro His Gln Leu Thr Val Glu Lys Thr His Ser
65                  70                  75                  80

Tyr Phe Thr Ser Pro Lys Val Pro Glu Arg Ile His Ser Met Asn Pro
                85                  90                  95

Thr Ile Arg Leu Leu Leu Ile Leu Arg Asp Pro Ser Glu Arg Val Leu
            100                 105                 110

Ser Ala Tyr Thr His Met Leu Tyr Asn His Leu Gln Lys His Lys Pro
        115                 120                 125

Tyr Pro Pro Ile Glu Asp Leu Leu Met Arg Asp Gly Arg Leu Asn Leu
    130                 135                 140

Asp Tyr Val Gly Leu Asn Arg Ser Leu Tyr His Ala His Met Leu Asn
145                 150                 155                 160

Trp Leu Arg Phe Phe Pro Leu Gly His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
        195                 200                 205

Thr Lys Gly Phe Tyr Cys Leu Arg Asp Ser Gly Lys Asp Arg Cys Leu
    210                 215                 220

His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
                245                 250                 255

Leu Val Gly Arg Thr Phe Asp Trp His
            260                 265
```

<210> SEQ ID NO 25
<211> LENGTH: 795
<212> TYPE: DNA
<213> ORGANISM: Artificial Sequence

```
<220> FEATURE:
<223> OTHER INFORMATION: Polynucleotide sequence encoding for engineered
      aryl sulfate-dependent 3-O-sulfotransferase variant 2

<400> SEQUENCE: 25
atgggaactg cgtcgaacgg cagtacgcaa cagttgccgc agacaatcat tattggcgtc    60
ggacatggcg gaacccgtgc tcttttggaa atgctgagtc tgcaccctga cgtggcagcg   120
gcggagaatg aggttcactt ctttgattgg gaggaacatt attcgcaggg gttgggatgg   180
tatctgacgc aaatgccgtt ctccagtcca caccagttga ccgttgaaaa gacgcatagt   240
tattttacga gtcccaaagt acctgagcgt attcatagta tgaacccgac catccgtctg   300
ttgttgatcc ttcgcgatcc cagcgaacgc gtcttatcag cgtatactca catgctgtac   360
aaccaccttc aaaaacataa gccgtaccct cccatcgagg atcttttaat gcgtgatggt   420
cgtcttaacc ttgattacac aggtttgaac cgcagtttgt atcacgctca catgttgaat   480
tggttgcgct tctttcccct tggtcatatc catattgttg acggggaccg tctgatccgc   540
gacccgttcc cagagattca gaaagtggaa cgtttcctga attatccccc acagatcaac   600
gcgagtaact tctattttaa caagacgaaa ggtttctatt gcttacgtga tagtgggaag   660
gaccgctgcc tgcacgagag caaggacgt gctcatcctc aagttgaccc caagttattg   720
gataaactgc acgagtattt tcacgagcct aataaaaagt tctttaagtt agtcggccgc   780
acatttgatt ggcat                                                    795

<210> SEQ ID NO 26
<211> LENGTH: 265
<212> TYPE: PRT
<213> ORGANISM: Artificial Sequence
<220> FEATURE:
<223> OTHER INFORMATION: Amino acid sequence encoding for engineered
      aryl sulfate-dependent 3-O-sulfotransferase variant 2

<400> SEQUENCE: 26

Met Gly Thr Ala Ser Asn Gly Ser Thr Gln Gln Leu Pro Gln Thr Ile
1               5                   10                  15

Ile Ile Gly Val Gly His Gly Gly Thr Arg Ala Leu Leu Glu Met Leu
            20                  25                  30

Ser Leu His Pro Asp Val Ala Ala Glu Asn Glu Val His Phe Phe
        35                  40                  45

Asp Trp Glu Glu His Tyr Ser Gln Gly Leu Gly Trp Tyr Leu Thr Gln
    50                  55                  60

Met Pro Phe Ser Ser Pro His Gln Leu Thr Val Glu Lys Thr His Ser
65                  70                  75                  80

Tyr Phe Thr Ser Pro Lys Val Pro Glu Arg Ile His Ser Met Asn Pro
                85                  90                  95

Thr Ile Arg Leu Leu Leu Ile Leu Arg Asp Pro Ser Glu Arg Val Leu
            100                 105                 110

Ser Ala Tyr Thr His Met Leu Tyr Asn His Leu Gln Lys His Lys Pro
        115                 120                 125

Tyr Pro Pro Ile Glu Asp Leu Leu Met Arg Asp Gly Arg Leu Asn Leu
    130                 135                 140

Asp Tyr Thr Gly Leu Asn Arg Ser Leu Tyr His Ala His Met Leu Asn
145                 150                 155                 160

Trp Leu Arg Phe Phe Pro Leu Gly His Ile His Ile Val Asp Gly Asp
                165                 170                 175

Arg Leu Ile Arg Asp Pro Phe Pro Glu Ile Gln Lys Val Glu Arg Phe
```

```
                    180                 185                 190
Leu Lys Leu Ser Pro Gln Ile Asn Ala Ser Asn Phe Tyr Phe Asn Lys
            195                 200                 205

Thr Lys Gly Phe Tyr Cys Leu Arg Asp Ser Gly Lys Asp Arg Cys Leu
        210                 215                 220

His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
            245                 250                 255

Leu Val Gly Arg Thr Phe Asp Trp His
            260                 265

<210> SEQ ID NO 27
<211> LENGTH: 795
<212> TYPE: DNA
<213> ORGANISM: Artificial Sequence
<220> FEATURE:
<223> OTHER INFORMATION: Polynucleotide sequence encoding for engineered
      aryl sulfate-dependent 3-O-sulfotransferase variant 3

<400> SEQUENCE: 27
atgggaactg cgtcgaacgg cagtacgcaa caacttccac aaactatcat tattggcgtg      60
ggtcacggtg ggactcgcgc tttacttgaa atgttgagct acatccgga tgttgccgca     120 gctgaaaacg aggtccattt cttgactgg gaggaacact attcccaggg tttggggtgg     180
tatctgacgc agatgccttt ctcgtctcct caccaactta cggttgagaa aactcattca     240
tatttcacgt cccctaaagt accagaacgt atccactcaa tgaacccaac aattcgttta     300
ttgttgattt tgcgcgaccc gtcggaacgt gtgttgtcgt taggtacgca cttgctttac     360
gttcatttgc aaaagcataa accgtatcca ccgattgagg acttttgat gcgtgacgga     420 cgtttgaatt tggactatac gggcctgaat cgctcgctgt atcacgccca catgttgaac     480
tggctgcgct tcttccccct tggtcatatc cacatcgtag atgggaccg tctgatccgt     540 gacccttttcc cggaaatcca gaaagtggag cgtttcctga gttatctcc acaaatcaac     600 gcgagcaatt tttactttaa caagactaaa gggttctact gtttacgtga ttctggcaaa     660
gaccgttgcc ttcatgaaag taaggccgc gctcaccctc aagtcgaccc caaattatta     720
gataagttgc acgagtactt ccatgaacct aataagaagt tcttcaaact tgtcggccgc     780
acatttgatt ggcat                                                     795

<210> SEQ ID NO 28
<211> LENGTH: 265
<212> TYPE: PRT
<213> ORGANISM: Artificial Sequence
<220> FEATURE:
<223> OTHER INFORMATION: Amino acid sequence encoding for engineered
      aryl sulfate-dependent 3-O-sulfotransferase variant 3

<400> SEQUENCE: 28

Met Gly Thr Ala Ser Asn Gly Ser Thr Gln Gln Leu Pro Gln Thr Ile
1               5                   10                  15

Ile Ile Gly Val Gly His Gly Gly Thr Arg Ala Leu Leu Glu Met Leu
            20                  25                  30

Ser Leu His Pro Asp Val Ala Ala Ala Glu Asn Glu Val His Phe Phe
        35                  40                  45

Asp Trp Glu Glu His Tyr Ser Gln Gly Leu Gly Trp Tyr Leu Thr Gln
    50                  55                  60
```

```
Met Pro Phe Ser Ser Pro His Gln Leu Thr Val Glu Lys Thr His Ser
 65                  70                  75                  80

Tyr Phe Thr Ser Pro Lys Val Pro Glu Arg Ile His Ser Met Asn Pro
                 85                  90                  95

Thr Ile Arg Leu Leu Leu Ile Leu Arg Asp Pro Ser Glu Arg Val Leu
            100                 105                 110

Ser Leu Gly Thr His Leu Leu Tyr Val His Leu Gln Lys His Lys Pro
        115                 120                 125

Tyr Pro Pro Ile Glu Asp Leu Leu Met Arg Asp Gly Arg Leu Asn Leu
130                 135                 140

Asp Tyr Thr Gly Leu Asn Arg Ser Leu Tyr His Ala His Met Leu Asn
145                 150                 155                 160

Trp Leu Arg Phe Phe Pro Leu Gly His Ile His Ile Val Asp Gly Asp
                165                 170                 175

Arg Leu Ile Arg Asp Pro Phe Pro Glu Ile Gln Lys Val Glu Arg Phe
                180                 185                 190

Leu Lys Leu Ser Pro Gln Ile Asn Ala Ser Asn Phe Tyr Phe Asn Lys
            195                 200                 205

Thr Lys Gly Phe Tyr Cys Leu Arg Asp Ser Gly Lys Asp Arg Cys Leu
        210                 215                 220

His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
                245                 250                 255

Leu Val Gly Arg Thr Phe Asp Trp His
                260                 265

<210> SEQ ID NO 29
<211> LENGTH: 617
<212> TYPE: PRT
<213> ORGANISM: Homo sapiens

<400> SEQUENCE: 29

Met Arg Cys Leu Ala Ala Arg Val Asn Tyr Lys Thr Leu Ile Ile Ile
1               5                   10                  15

Cys Ala Leu Phe Thr Leu Val Thr Val Leu Leu Trp Asn Lys Cys Ser
                20                  25                  30

Ser Asp Lys Ala Ile Gln Phe Pro Arg Arg Ser Ser Ser Gly Phe Arg
            35                  40                  45

Val Asp Gly Phe Glu Lys Arg Ala Ala Ala Ser Glu Ser Asn Asn Tyr
        50                  55                  60

Met Asn His Val Ala Lys Gln Gln Ser Glu Glu Ala Phe Pro Gln Glu
65                  70                  75                  80

Gln Gln Lys Ala Pro Pro Val Val Gly Gly Phe Asn Ser Asn Val Gly
                85                  90                  95

Ser Lys Val Leu Gly Leu Lys Tyr Glu Glu Ile Asp Cys Leu Ile Asn
            100                 105                 110

Asp Glu His Thr Ile Lys Gly Arg Arg Glu Gly Asn Glu Val Phe Leu
        115                 120                 125

Pro Phe Thr Trp Val Glu Lys Tyr Phe Asp Val Tyr Gly Lys Val Val
130                 135                 140

Gln Tyr Asp Gly Tyr Asp Arg Phe Glu Phe Ser His Ser Tyr Ser Lys
145                 150                 155                 160

Val Tyr Ala Gln Arg Ala Pro Tyr His Pro Asp Gly Val Phe Met Ser
                165                 170                 175
```

```
Phe Glu Gly Tyr Asn Val Glu Val Arg Asp Arg Val Lys Cys Ile Ser
            180                 185                 190

Gly Val Glu Gly Val Pro Leu Ser Thr Gln Trp Gly Pro Gln Gly Tyr
        195                 200                 205

Phe Tyr Pro Ile Gln Ile Ala Gln Tyr Gly Leu Ser His Tyr Ser Lys
    210                 215                 220

Asn Leu Thr Glu Lys Pro Pro His Ile Glu Val Tyr Glu Thr Ala Glu
225                 230                 235                 240

Asp Arg Asp Lys Asn Lys Pro Asn Asp Trp Thr Val Pro Lys Gly Cys
                245                 250                 255

Phe Met Ala Asn Val Ala Asp Lys Ser Arg Phe Thr Asn Val Lys Gln
            260                 265                 270

Phe Ile Ala Pro Glu Thr Ser Glu Gly Val Ser Leu Gln Leu Gly Asn
        275                 280                 285

Thr Lys Asp Phe Ile Ile Ser Phe Asp Leu Lys Phe Leu Thr Asn Gly
    290                 295                 300

Ser Val Ser Val Val Leu Glu Thr Thr Glu Lys Asn Gln Leu Phe Thr
305                 310                 315                 320

Ile His Tyr Val Ser Asn Ala Gln Leu Ile Ala Phe Lys Glu Arg Asp
                325                 330                 335

Ile Tyr Tyr Gly Ile Gly Pro Arg Thr Ser Trp Ser Thr Val Thr Arg
            340                 345                 350

Asp Leu Val Thr Asp Leu Arg Lys Gly Val Gly Leu Ser Asn Thr Lys
        355                 360                 365

Ala Val Lys Pro Thr Lys Ile Met Pro Lys Lys Val Arg Leu Ile
    370                 375                 380

Ala Lys Gly Lys Gly Phe Leu Asp Asn Ile Thr Ile Ser Thr Thr Ala
385                 390                 395                 400

His Met Ala Ala Phe Phe Ala Ala Ser Asp Trp Leu Val Arg Asn Gln
                405                 410                 415

Asp Glu Lys Gly Gly Trp Pro Ile Met Val Thr Arg Lys Leu Gly Glu
            420                 425                 430

Gly Phe Lys Ser Leu Glu Pro Gly Trp Tyr Ser Ala Met Ala Gln Gly
        435                 440                 445

Gln Ala Ile Ser Thr Leu Val Arg Ala Tyr Leu Leu Thr Lys Asp His
    450                 455                 460

Ile Phe Leu Asn Ser Ala Leu Arg Ala Thr Ala Pro Tyr Lys Phe Leu
465                 470                 475                 480

Ser Glu Gln His Gly Val Lys Ala Val Phe Met Asn Lys His Asp Trp
                485                 490                 495

Tyr Glu Glu Tyr Pro Thr Thr Pro Ser Ser Phe Val Leu Asn Gly Phe
            500                 505                 510

Met Tyr Ser Leu Ile Gly Leu Tyr Asp Leu Lys Glu Thr Ala Gly Glu
        515                 520                 525

Lys Leu Gly Lys Glu Ala Arg Ser Leu Tyr Glu Arg Gly Met Glu Ser
    530                 535                 540

Leu Lys Ala Met Leu Pro Leu Tyr Asp Thr Gly Ser Gly Thr Ile Tyr
545                 550                 555                 560

Asp Leu Arg His Phe Met Leu Gly Ile Ala Pro Asn Leu Ala Arg Trp
                565                 570                 575

Asp Tyr His Thr Thr His Ile Asn Gln Leu Gln Leu Leu Ser Thr Ile
            580                 585                 590
```

```
Asp Glu Ser Pro Val Phe Lys Glu Phe Val Lys Arg Trp Lys Ser Tyr
            595                 600                 605

Leu Lys Gly Ser Arg Ala Lys His Asn
    610                 615

<210> SEQ ID NO 30
<211> LENGTH: 394
<212> TYPE: PRT
<213> ORGANISM: Bacteroides eggerthii

<400> SEQUENCE: 30

Met Lys Lys Asn Ile Phe Ile Ile Cys Met Ala Met Ala Ala Gly Cys
1               5                   10                  15

Ile Thr Thr Leu Thr Ala Gln Val Lys Asn Ala Glu Thr Leu Val Pro
            20                  25                  30

Leu Thr Lys Arg Val Asn Val Gln Ala Asp Thr Ala Arg Leu Asp Gln
        35                  40                  45

Ile Ile Asp Gly Cys Trp Val Ala Val Gly Thr Asn Lys Lys His Ala
    50                  55                  60

Ile Gln Arg Asp Phe Thr Arg Leu Phe Ala Gly Lys Pro Ser Tyr Arg
65                  70                  75                  80

Phe Glu Leu Arg Lys Glu Asp Asn Thr Leu Glu Gly Tyr Gly Lys Gly
                85                  90                  95

Glu Thr Lys Gly Arg Ala Glu Phe Ser Tyr Cys Tyr Ala Thr Ser Ala
            100                 105                 110

Asp Phe Lys Gly Leu Pro Ala Asp Ala Tyr Arg Lys Ala Gln Ile Thr
        115                 120                 125

Lys Thr Val Tyr His His Gly Lys Gly Ile Cys Pro Gln Gly Val Ser
    130                 135                 140

Arg Asp Tyr Glu Phe Ser Val Tyr Ile Pro Ser Ala Leu Asp Ser Asn
145                 150                 155                 160

Val Ser Thr Ile Phe Ala Gln Trp His Gly Met Pro Asp Arg Thr Leu
                165                 170                 175

Val Gln Thr Pro Glu Gly Glu Val Lys Lys Leu Thr Val Asp Glu Phe
            180                 185                 190

Leu Glu Leu Asp Lys Thr Thr Ile Phe Lys Lys Asn Thr Gly His Glu
        195                 200                 205

Lys Val Ala Lys Leu Asp Lys Gln Gly Asn Pro Val Lys Asp Lys Lys
    210                 215                 220

Gly Asn Pro Val Tyr Lys Ala Gly Lys Lys Asn Gly Trp Leu Val Glu
225                 230                 235                 240

Gln Gly Gly Tyr Pro Pro Leu Ala Phe Gly Phe Ser Gly Gly Trp Phe
                245                 250                 255

Tyr Ile Lys Ala Asn Ser Asp Arg Arg Trp Leu Thr Asp Lys Thr Asp
            260                 265                 270

Arg Cys Asn Ala Ser Pro Glu Lys Thr Pro Val Met Lys Pro Val Thr
        275                 280                 285

Ser Lys Tyr Lys Ser Ser Thr Ile Ala Tyr Lys Met Pro Phe Ala Asp
    290                 295                 300

Phe Pro Lys Asp Cys Trp Val Thr Phe Arg Val His Ile Asp Trp Thr
305                 310                 315                 320

Thr Tyr Gly Lys Glu Ala Glu Asn Ile Val Lys Pro Gly Lys Leu Asp
                325                 330                 335

Val Gln Met Glu Tyr Thr Asp Lys Lys Lys Thr Val Lys Glu His Ile
            340                 345                 350
```

```
Val Asn Asn Glu Val Ile Gln Ile Gly Arg Asn Asp Asp Gly Tyr
        355                 360                 365

Tyr Phe Lys Phe Gly Ile Tyr Arg Val Gly Asn Ser Thr Val Pro Val
370                 375                 380

Cys Tyr Asn Leu Ala Gly Tyr Lys Glu Glu
385                 390

<210> SEQ ID NO 31
<211> LENGTH: 773
<212> TYPE: PRT
<213> ORGANISM: Bacteroides eggerthii

<400> SEQUENCE: 31

Met Lys Lys Ser Ile Leu Phe Ile Thr Ser Leu Phe Leu Cys Ile Phe
1               5                   10                  15

Cys Leu Lys Ser Asn Ala Gln Gln Ser Arg Thr Glu Val Thr Trp Glu
            20                  25                  30

Lys Met Glu Asp Val Thr Val Pro Ile Pro Gln Val His Pro Arg
        35                  40                  45

Leu Tyr Val Arg Ser Ala Asp Leu Pro Asp Leu Lys Lys Arg Met Asn
50                  55                  60

His Pro His Val Lys Glu Val Leu Ala Thr Leu Asn Lys Leu Gly Lys
65                  70                  75                  80

Asp Arg Thr Pro Glu Glu Ala Lys Val Lys Asp Arg Gly Phe Arg
                85                  90                  95

Tyr Tyr Phe Glu Met Arg Gly Val Thr Ser Arg Val Gln Val Gln Ala
                100                 105                 110

Leu Glu Tyr Leu Val Tyr Gly Asp Lys Lys Gln Ala Arg Arg Ala Ile
            115                 120                 125

Thr Ala Met Leu Asp Thr Leu Gln Asn Val Asn Tyr Gly Thr Gln Gly
130                 135                 140

Asp Leu Ser Arg Ala Ser Gly Val Met Leu Thr Cys Gly Ala Met Val
145                 150                 155                 160

Tyr Asp Trp Cys Tyr Asp Gln Met Lys Glu Ser Glu Lys Lys Ala Tyr
                165                 170                 175

Val Glu Ser Phe Ile Arg Ile Ala Lys Thr Met Glu Cys Gly Tyr Pro
            180                 185                 190

Pro Arg Asn Asn Glu Pro Ile Ala Gly His Ser Ser Glu Trp Met Ile
        195                 200                 205

Leu Arg Asp Met Leu Ser Ala Gly Ile Ala Ile Tyr Asp Glu Tyr Pro
210                 215                 220

Asp Met Tyr Asn Tyr Val Ile Lys Met Met Phe Lys Asp Tyr Leu Pro
225                 230                 235                 240

Val Arg Asn Tyr Ile Tyr Ser Gly His Asn Tyr His Gln Gly Thr Ser
                245                 250                 255

Tyr Val Asn Val Arg Phe Ser Asn Asp Leu Phe Ser Leu Trp Ile Leu
            260                 265                 270

Gln Arg Met Gly Ala Gly Ala Ile Tyr Asn Pro Ala Gln Gln Phe Val
        275                 280                 285

Leu Tyr Asp Phe Leu Tyr Arg Arg Pro Asp Gly Gln Val Met Pro
    290                 295                 300

Ala Gly Asp Thr Asn Pro Ile Arg Lys Asn Thr Pro Ser Tyr Ser Leu
305                 310                 315                 320

Pro Ala Met Leu Ala Ser Ser Phe Tyr Lys Asp Ser Tyr Leu Ala Tyr
```

```
                    325                 330                 335
Glu Tyr Glu Arg Lys Pro Asn Ile Glu Arg His Cys Leu Ile Phe Asp
            340                 345                 350
Ile Leu Trp Arg Asp Leu Asp Leu Lys Ala Lys Ala Pro Asp Asp Leu
            355                 360                 365
Pro Leu Thr Arg Tyr Ser Ser Pro Phe Gly Trp Met Ile Ala Arg
            370                 375             380
Thr Ala Trp Asp Glu Asn Ser Val Ile Ala Glu Met Lys Ile Asn Glu
385                 390                 395                 400
Gln Phe Val Gly Asn His Gln His Leu Asp Gly Gly Ser Phe Gln Leu
                405                 410                 415
Tyr Tyr Lys Gly Pro Leu Ala Ile Asp Ala Gly Ala Tyr Gln Gly Ser
            420                 425                 430
Ser Gly Gly Tyr Asn Ser Pro His Asn Lys Asn Phe Phe Lys Arg Thr
            435                 440                 445
Ile Ala His Asn Ser Leu Leu Val Tyr Asn Pro Asp Glu Lys Phe Ala
            450                 455                 460
Cys Trp Asn Tyr Gly Gly Gly Lys Thr Glu Phe Ala Ala Asn Asp
465                 470                 475                 480
Gly Gly Gln Arg Met Pro Gly Asp Arg Trp Glu Thr Cys Arg Ser Phe
                485                 490                 495
Lys Gln Leu Met Ser Lys Asp Tyr Thr Thr Gly Lys Ala Leu Ala His
            500                 505                 510
Gly Phe Gly Pro Asp Ala Cys Lys Pro Asp Tyr Ser Tyr Leu Lys Gly
            515                 520                 525
Asp Ile Thr Gln Ala Tyr Thr Asp Lys Val Lys Glu Ala Lys Arg Ser
530                 535                 540
Phe Val Phe Leu Asn Leu His Ser Thr Glu Val Pro Gly Ala Leu Ile
545                 550                 555                 560
Val Phe Asp Lys Val Ser Ser Asp Pro Gln Phe Lys Lys Phe Trp
            565                 570                 575
Leu Leu His Ser Ile Glu Glu Pro Val Ile Glu Gly Asp Arg Phe Ile
            580                 585                 590
Ile Arg Arg Thr Lys Asn Gly Asp Thr Gly Met Leu Gln Asn Gln Val
            595                 600                 605
Leu Leu Pro Glu Ala Gly Asn Ala Gln Ile Glu Lys Val Gly Gly Lys
            610                 615                 620
Gly Lys Glu Phe Trp Val Phe Gly Thr Asn Tyr Pro Asn Asp Ala Leu
625                 630                 635                 640
Pro Asn Arg Pro Asp Asp Ala Asn Glu Arg Gly Ala Trp Arg Val Glu
                645                 650                 655
Val Ser Pro Ala Val Pro Ala Ala Glu Asn Tyr Phe Leu Asn Val Ile
            660                 665                 670
Gln Val Ala Asp Asn Thr Cys Lys Arg Met Asn Asp Val Lys Arg Ile
            675                 680                 685
Asp Ala Gly Lys Val Val Gly Val Gln Ile Ala Asp Arg Ile Val Thr
            690                 695                 700
Phe Ser Lys Asn Ser Leu Pro Leu Ser Gly Lys Ile Asp Met Lys Val
705                 710                 715                 720
Asp Gly Asn Thr Ser Met Lys Phe Val Ile Thr Asp Leu Ile Pro Gly
                725                 730                 735
Thr Trp Gln Ile Lys Lys Asp Gly Lys Val Tyr Ile Pro Ala Met Glu
            740                 745                 750
```

Val Arg Ser Asp Asp Gly Ile Leu Ser Phe Glu Gly Thr Ala Gly His
        755                 760                 765

Tyr Glu Phe Leu Arg
        770

<210> SEQ ID NO 32
<211> LENGTH: 666
<212> TYPE: PRT
<213> ORGANISM: Bacteroides eggerthii

<400> SEQUENCE: 32

Met Lys Ile Met Lys Phe Ile Leu Ser Val Phe Leu Leu Thr Ile Ala
1               5                   10                  15

Ile Ile Ala Asp Ala Gln Gln Leu Arg Lys Glu Ala Phe Asp Leu Leu
            20                  25                  30

Asn Leu Asp Tyr Pro Gly Leu Glu Lys Val Lys Thr Ala Cys Ser Arg
        35                  40                  45

Gln Gln Trp Glu Glu Ala Ala Gln Glu Leu Leu Ala Tyr Tyr Arg Asn
    50                  55                  60

Arg Thr Asp Ile Ala His Pro Asp Ile Asp Leu Lys Asn Leu Ala Ile
65                  70                  75                  80

Ser Lys Glu Glu Gln Lys Trp Ala Asp Ala Met Asp His Thr Phe
                85                  90                  95

Phe Val His Lys Gly Tyr Gln Pro Ser Tyr Asn Tyr Gly Lys Asp Ile
            100                 105                 110

Asn Trp Glu Tyr Trp Pro Val Lys Asp Asn Glu Leu Arg Trp Gln Leu
        115                 120                 125

His Arg His Lys Trp Phe Thr Pro Met Gly Lys Ala Tyr Arg Ile Ser
    130                 135                 140

Gly Asp Glu Lys Tyr Ala Lys Glu Trp Ala Phe Gln Tyr Ile Asp Trp
145                 150                 155                 160

Ile Lys Lys Asn Pro Leu Val Lys Met Glu Lys Glu Asn Phe Glu Leu
                165                 170                 175

Val Ser Ala Gly Glu Val Lys Glu Asp Ala Asp Asn Val His Phe Ala
            180                 185                 190

Trp Arg Gln Leu Glu Val Ser Asn Arg Leu Gln Asp Gln Thr Cys Gln
        195                 200                 205

Phe Leu Leu Phe Cys Pro Ala Glu Ala Phe Thr Pro Glu Phe Leu Thr
    210                 215                 220

Glu Phe Leu Val Asn Tyr His Arg His Gly Ala Tyr Leu Phe Lys Asn
225                 230                 235                 240

Tyr Ser Ala Glu Gly Asn His Leu Leu Phe Glu Ala Gln Arg Met Val
                245                 250                 255

Tyr Ala Gly Val Phe Phe Pro Glu Phe Lys Asp Ala Ala Thr Trp Arg
            260                 265                 270

Glu Ser Gly Ile Asn Ile Leu Asn Arg Glu Ile Lys Lys Gln Val Tyr
        275                 280                 285

Asp Asp Gly Gly Gln Tyr Glu Leu Asp Pro His Tyr His Leu Ala Ala
    290                 295                 300

Ile Asn Ile Phe Cys Lys Ala Leu Arg Met Ala Asp Cys Asn Gly Phe
305                 310                 315                 320

Arg Asn Glu Phe Pro Ala Glu Tyr Leu Asp Thr Val Lys Lys Met Ile
                325                 330                 335

Glu Phe Tyr Thr Asn Ile Cys Phe Pro Asp Tyr Thr Asn Pro Cys Phe

```
                340                 345                 350
Ser Asp Ala Lys Leu Gly Asp Tyr Lys Ser Glu Leu Ala Asn Tyr Arg
        355                 360                 365

Asp Trp Val Thr Leu Phe Pro Asp Ser Glu Trp Ile Arg Tyr Tyr Ala
        370                 375                 380

Thr Glu Gly Arg Glu Gly Ala Pro Leu Pro Tyr Leu Ser His Gly Ser
385                 390                 395                 400

Leu Ala Ser Gly Phe Phe Thr Phe Arg Ser Gly Trp Lys Lys Asp Ala
                405                 410                 415

Ala Val Val Val Lys Ala Gly Pro Lys Gly Glu Trp His Cys Gln
        420                 425                 430

Pro Asp Asn Gly Thr Phe Glu Phe Trp Phe Asn Gly Lys Asn Leu Phe
        435                 440                 445

Pro Asp Ser Gly Ala Tyr Val Tyr Ala Gly Ser Asp Glu Val Met Lys
        450                 455                 460

Leu Arg Asn Trp Phe Arg Gln Thr Arg Val His Asn Thr Leu Thr Leu
465                 470                 475                 480

Asp Gly Arg Asn Phe Glu Thr Thr Gln Ser Val Thr Lys Leu Trp Gln
                485                 490                 495

Pro Glu Gly Arg Glu Gln Ile Leu Val Thr Glu Asn Pro Ser Tyr Gln
                500                 505                 510

Gly Leu Lys His Arg Arg Thr Val Phe Phe Val Glu Gln Thr Tyr Tyr
                515                 520                 525

Val Ile Val Asp Glu Ala Val Gly Asp Ala Lys Gly Thr Val Asn Leu
        530                 535                 540

Asn Tyr His Phe Cys Glu Gly Thr Val Asn Val Asp Val Lys Lys Asn
545                 550                 555                 560

Met Ala Thr Thr Ala Tyr Ala Gly Pro Ser Asn Val Lys Leu Gln Cys
                565                 570                 575

Phe Pro Glu Lys Lys Ala Ser Leu Lys Lys Glu Glu Gly Trp Arg Ser
                580                 585                 590

Ile Ala Tyr Arg Gln Arg Val Pro Arg Thr Ser Leu Ser Phe Asp Ile
                595                 600                 605

His Lys Asp Asp Ala Glu Ala Val Arg Tyr Ile Thr Val Ile Tyr Pro
        610                 615                 620

Val Lys Asp Ala Ala Ser Tyr Pro Val Leu Lys Ala Lys Phe Leu Asn
625                 630                 635                 640

Lys Asp Phe Asp Glu Lys Gly Val Lys Val Glu Val Ser Val Asn Gly
                645                 650                 655

Val Ala Arg Gln Leu Met Ser Gln Leu Lys
                660                 665

<210> SEQ ID NO 33
<211> LENGTH: 309
<212> TYPE: PRT
<213> ORGANISM: Artificial Sequence
<220> FEATURE:
<223> OTHER INFORMATION: Amino acid sequence encoding for engineered
      aryl sulfate-dependent N-sulfotransferase variant 7
<220> FEATURE:
<221> NAME/KEY: MISC_FEATURE
<222> LOCATION: (40)..(40)
<223> OTHER INFORMATION: Xaa is glutamine, serine, or alanine
<220> FEATURE:
<221> NAME/KEY: MISC_FEATURE
<222> LOCATION: (45)..(45)
<223> OTHER INFORMATION: Xaa is tryptophan or phenylalanine
<220> FEATURE:
```

```
<221> NAME/KEY: MISC_FEATURE
<222> LOCATION: (46)..(46)
<223> OTHER INFORMATION: Xaa is alanine or leucine
<220> FEATURE:
<221> NAME/KEY: MISC_FEATURE
<222> LOCATION: (48)..(48)
<223> OTHER INFORMATION: Xaa is tyrosine, threonine, or histidine
<220> FEATURE:
<221> NAME/KEY: MISC_FEATURE
<222> LOCATION: (67)..(67)
<223> OTHER INFORMATION: Xaa is histidine or glycine
<220> FEATURE:
<221> NAME/KEY: MISC_FEATURE
<222> LOCATION: (68)..(68)
<223> OTHER INFORMATION: Xaa is glycine, histidine, or serine
<220> FEATURE:
<221> NAME/KEY: MISC_FEATURE
<222> LOCATION: (103)..(103)
<223> OTHER INFORMATION: Xaa is lysine or threonine
<220> FEATURE:
<221> NAME/KEY: MISC_FEATURE
<222> LOCATION: (105)..(105)
<223> OTHER INFORMATION: Xaa is alanine or serine
<220> FEATURE:
<221> NAME/KEY: MISC_FEATURE
<222> LOCATION: (256)..(256)
<223> OTHER INFORMATION: Xaa is leucine, histidine, or alanine
<220> FEATURE:
<221> NAME/KEY: MISC_FEATURE
<222> LOCATION: (257)..(257)
<223> OTHER INFORMATION: Xaa is glycine or histidine
<220> FEATURE:
<221> NAME/KEY: MISC_FEATURE
<222> LOCATION: (259)..(259)
<223> OTHER INFORMATION: Xaa is serine, arginine, or glycine
<220> FEATURE:
<221> NAME/KEY: MISC_FEATURE
<222> LOCATION: (260)..(260)
<223> OTHER INFORMATION: Xaa is histidine, tryptophan, or leucine

<400> SEQUENCE: 33

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Xaa Lys Thr Gly Ala Xaa Xaa Leu Xaa
        35                  40                  45

His Phe Leu Gly Met His Pro Asp Leu Ser Ser Asn Tyr Pro Ser Ser
    50                  55                  60

Glu Thr Xaa Xaa Ser Ile Gln Phe Phe Asn Gly His Asn Tyr His Lys
65                  70                  75                  80

Gly Ile Asp Trp Tyr Met Glu Phe Phe Pro Ile Pro Ser Asn Thr Thr
                85                  90                  95

Ser Asp Phe Tyr Phe Glu Xaa Ser Xaa Asn Tyr Phe Asp Ser Glu Val
            100                 105                 110

Ala Pro Arg Arg Ala Ala Ala Leu Leu Pro Lys Ala Lys Val Leu Thr
        115                 120                 125

Ile Leu Ile Asn Pro Ala Asp Arg Ala Tyr Ser Trp Tyr Gln His Gln
    130                 135                 140

Arg Ala His Asp Asp Pro Val Ala Leu Lys Tyr Thr Phe His Glu Val
145                 150                 155                 160

Ile Thr Ala Gly Ser Asp Ala Ser Ser Lys Leu Arg Ala Leu Gln Asn
                165                 170                 175

Arg Cys Leu Val Pro Gly Trp Tyr Ala Thr His Ile Glu Arg Trp Leu
            180                 185                 190

Ser Ala Tyr His Ala Asn Gln Ile Leu Val Leu Asp Gly Lys Leu Leu
```

```
                195                 200                 205
Arg Thr Glu Pro Ala Lys Val Met Asp Met Val Gln Lys Phe Leu Gly
        210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Lys Thr Lys Cys Xaa
                245                 250                 255

Xaa Lys Xaa Xaa Gly Arg Lys Tyr Pro Glu Met Asp Leu Asp Ser Arg
        260                 265                 270

Ala Phe Leu Lys Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Asp
        290                 295                 300

Leu Gln Asn Thr Arg
305

<210> SEQ ID NO 34
<211> LENGTH: 309
<212> TYPE: PRT
<213> ORGANISM: Artificial Sequence
<220> FEATURE:
<223> OTHER INFORMATION: Amino acid sequence encoding for engineered
      aryl sulfate-dependent N-sulfotransferase variant 8
<220> FEATURE:
<221> NAME/KEY: MISC_FEATURE
<222> LOCATION: (41)..(41)
<223> OTHER INFORMATION: Xaa is glycine or lysine
<220> FEATURE:
<221> NAME/KEY: MISC_FEATURE
<222> LOCATION: (44)..(44)
<223> OTHER INFORMATION: Xaa is glycine or valine
<220> FEATURE:
<221> NAME/KEY: MISC_FEATURE
<222> LOCATION: (67)..(67)
<223> OTHER INFORMATION: Xaa is glycine or phenylalanine
<220> FEATURE:
<221> NAME/KEY: MISC_FEATURE
<222> LOCATION: (68)..(68)
<223> OTHER INFORMATION: Xaa is glutamic acid, leucine, or asparagine
<220> FEATURE:
<221> NAME/KEY: MISC_FEATURE
<222> LOCATION: (69)..(69)
<223> OTHER INFORMATION: Xaa is glutamic acid, serine, or histidine
<220> FEATURE:
<221> NAME/KEY: MISC_FEATURE
<222> LOCATION: (71)..(71)
<223> OTHER INFORMATION: Xaa is glutamine or glycine
<220> FEATURE:
<221> NAME/KEY: MISC_FEATURE
<222> LOCATION: (74)..(74)
<223> OTHER INFORMATION: Xaa is asparagine or glycine
<220> FEATURE:
<221> NAME/KEY: MISC_FEATURE
<222> LOCATION: (103)..(103)
<223> OTHER INFORMATION: Xaa is lysine or histidine
<220> FEATURE:
<221> NAME/KEY: MISC_FEATURE
<222> LOCATION: (105)..(105)
<223> OTHER INFORMATION: Xaa is alanine or glycine
<220> FEATURE:
<221> NAME/KEY: MISC_FEATURE
<222> LOCATION: (106)..(106)
<223> OTHER INFORMATION: Xaa is asparagine or tryptophan
<220> FEATURE:
<221> NAME/KEY: MISC_FEATURE
<222> LOCATION: (139)..(139)
<223> OTHER INFORMATION: Xaa is serine or arginine
<220> FEATURE:
<221> NAME/KEY: MISC_FEATURE
<222> LOCATION: (140)..(140)
<223> OTHER INFORMATION: Xaa is tryptophan or alanine
```

```
<220> FEATURE:
<221> NAME/KEY: MISC_FEATURE
<222> LOCATION: (142)..(142)
<223> OTHER INFORMATION: Xaa is glutamine or valine
<220> FEATURE:
<221> NAME/KEY: MISC_FEATURE
<222> LOCATION: (143)..(143)
<223> OTHER INFORMATION: Xaa is histidine, alanine, or tryptophan
<220> FEATURE:
<221> NAME/KEY: MISC_FEATURE
<222> LOCATION: (256)..(256)
<223> OTHER INFORMATION: Xaa is leucine or glycine
<220> FEATURE:
<221> NAME/KEY: MISC_FEATURE
<222> LOCATION: (259)..(259)
<223> OTHER INFORMATION: Xaa is serine or histidine
<220> FEATURE:
<221> NAME/KEY: MISC_FEATURE
<222> LOCATION: (260)..(260)
<223> OTHER INFORMATION: Xaa is leucine or valine
<220> FEATURE:
<221> NAME/KEY: MISC_FEATURE
<222> LOCATION: (262)..(262)
<223> OTHER INFORMATION: Xaa is arginine or serine

<400> SEQUENCE: 34
```

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro His Xaa Thr Gly Xaa His Ala Leu Tyr
        35                  40                  45

Leu Phe Leu Gly Met His Pro Asp Leu Ser Ser Asn Tyr Pro Ser Ser
50                  55                  60

Glu Thr Xaa Xaa Xaa Ile Xaa Phe Phe Xaa Gly His Asn Tyr His Lys
65                  70                  75                  80

Gly Ile Asp Trp Tyr Met Glu Phe Phe Pro Ile Pro Ser Asn Thr Thr
                85                  90                  95

Ser Asp Phe Tyr Phe Glu Xaa Ser Xaa Xaa Tyr Phe Asp Ser Glu Val
            100                 105                 110

Ala Pro Arg Arg Ala Ala Ala Leu Leu Pro Lys Ala Lys Val Leu Thr
        115                 120                 125

Ile Leu Ile Asn Pro Ala Asp Arg Ala Tyr Xaa Xaa Tyr Xaa Xaa Gln
130                 135                 140

Arg Ala His Asp Asp Pro Val Ala Leu Lys Tyr Thr Phe His Glu Val
145                 150                 155                 160

Ile Thr Ala Gly Ser Asp Ala Ser Ser Lys Leu Arg Ala Leu Gln Asn
                165                 170                 175

Arg Cys Leu Val Pro Gly Trp Tyr Ala Thr His Ile Glu Arg Trp Leu
            180                 185                 190

Ser Ala Tyr His Ala Asn Gln Ile Leu Val Leu Asp Gly Lys Leu Leu
        195                 200                 205

Arg Thr Glu Pro Ala Lys Val Met Asp Met Val Gln Lys Phe Leu Gly
210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Lys Thr Lys Cys Xaa
                245                 250                 255

Gly Lys Xaa Xaa Gly Xaa Lys Tyr Pro Glu Met Asp Leu Asp Ser Arg
            260                 265                 270

Ala Phe Leu Lys Asp Tyr Tyr Arg Asp His Asn Ile Glu Leu Ser Lys

```
                275                 280                 285
Leu Leu Tyr Lys Met Gly Gln Thr Leu Pro Thr Trp Leu Arg Glu Asp
    290                 295                 300

Leu Gln Asn Thr Arg
305

<210> SEQ ID NO 35
<211> LENGTH: 309
<212> TYPE: PRT
<213> ORGANISM: Artificial Sequence
<220> FEATURE:
<223> OTHER INFORMATION: Amino acid sequence encoding for engineered
      aryl sulfate-dependent N-sulfotransferase variant 9

<400> SEQUENCE: 35

Met Ser Glu Glu Lys Asp Pro Leu Trp Gln Asp Pro Cys Glu Asp Lys
1               5                  10                  15

Arg His Lys Asp Ile Trp Ser Lys Glu Lys Thr Cys Asp Arg Phe Pro
            20                  25                  30

Lys Leu Leu Ile Ile Gly Pro Gln Lys Thr Gly Ala Trp Ala Leu Tyr
        35                  40                  45

His Phe Leu Gly Leu His Pro Asp Leu Ser Ser Asn Tyr Pro Ser Ser
    50                  55                  60

Glu Thr His Gly Ser Ile Gln Phe Phe Asn Gly His Asn Tyr His Lys
65                  70                  75                  80

Gly Ile Asp Trp Tyr Met Asp Phe Phe Pro Ile Pro Ser Asn Thr Thr
                85                  90                  95

Ser Asp Phe Tyr Phe Glu Lys Ser Ala Asn Tyr Phe Asp Ser Asp Val
            100                 105                 110

Ala Pro Arg Arg Ala Ala Ala Leu Leu Pro Lys Ala Lys Val Leu Thr
        115                 120                 125

Ile Leu Ile Asn Pro Ala Asp Arg Ala Tyr Ser Trp Tyr Gln His Gln
    130                 135                 140

Arg Ala His Asp Asp Pro Ala Ala Leu Arg Tyr Thr Phe His Glu Val
145                 150                 155                 160

Ile Thr Ala Gly Pro Asp Ala Ser Leu Lys Leu Arg Ala Leu Gln Asn
                165                 170                 175

Arg Cys Leu Val Pro Gly Trp Tyr Ala Thr His Leu Glu Arg Trp Leu
            180                 185                 190

Gly Ala Phe His Ala Asn Gln Ile Leu Val Leu Asp Gly Lys Leu Leu
        195                 200                 205

Arg Thr Glu Pro Ala Arg Val Met Asp Thr Val Gln Lys Phe Leu Gly
    210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Leu
                245                 250                 255

Gly Arg Ser His Gly Arg Lys Tyr Pro Asp Met Asp Pro Asp Ser Arg
            260                 265                 270

Ala Phe Leu Arg Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Glu
    290                 295                 300

Leu Gln Asn Thr Arg
305
```

<210> SEQ ID NO 36
<211> LENGTH: 309
<212> TYPE: PRT
<213> ORGANISM: Artificial Sequence
<220> FEATURE:
<223> OTHER INFORMATION: Amino acid sequence encoding for engineered aryl sulfate-dependent N-sulfotransferase variant 10

<400> SEQUENCE: 36

```
Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro Ser Lys Thr Gly Ala Phe Leu Leu Thr
        35                  40                  45

His Phe Leu Gly Leu His Pro Asp Leu Ser Ser Asn Tyr Pro Ser Ser
    50                  55                  60

Glu Thr Gly His Ser Ile Gln Phe Phe Asn Gly His Asn Tyr His Lys
65                  70                  75                  80

Gly Ile Asp Trp Tyr Met Asp Phe Phe Pro Ile Pro Ser Asn Thr Thr
                85                  90                  95

Ser Asp Phe Tyr Phe Glu Thr Ser Ser Asn Tyr Phe Asp Ser Asp Val
            100                 105                 110

Ala Pro Arg Arg Ala Ala Ala Leu Leu Pro Lys Ala Lys Val Leu Thr
        115                 120                 125

Ile Leu Ile Asn Pro Ala Asp Arg Ala Tyr Ser Trp Tyr Gln His Gln
    130                 135                 140

Arg Ala His Asp Asp Pro Ala Ala Leu Arg Tyr Thr Phe His Glu Val
145                 150                 155                 160

Ile Thr Ala Gly Pro Asp Ala Ser Leu Lys Leu Arg Ala Leu Gln Asn
                165                 170                 175

Arg Cys Leu Val Pro Gly Trp Tyr Ala Thr His Leu Glu Arg Trp Leu
            180                 185                 190

Gly Ala Phe His Ala Asn Gln Ile Leu Val Leu Asp Gly Lys Leu Leu
        195                 200                 205

Arg Thr Glu Pro Ala Arg Val Met Asp Thr Val Gln Lys Phe Leu Gly
    210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys His
                245                 250                 255

Gly Arg Arg Trp Gly Arg Lys Tyr Pro Asp Met Asp Pro Asp Ser Arg
            260                 265                 270

Ala Phe Leu Arg Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Glu
    290                 295                 300

Leu Gln Asn Thr Arg
305
```

<210> SEQ ID NO 37
<211> LENGTH: 309
<212> TYPE: PRT
<213> ORGANISM: Artificial Sequence
<220> FEATURE:
<223> OTHER INFORMATION: Amino acid sequence encoding for engineered aryl sulfate-dependent N-sulfotransferase variant 11

<400> SEQUENCE: 37

```
Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30

Lys Leu Leu Ile Ile Gly Pro His Thr Gly His Ala Leu Tyr
        35                  40                  45

Leu Phe Leu Gly Leu His Pro Asp Leu Ser Ser Asn Tyr Pro Ser Ser
50                  55                  60

Glu Thr Gly Glu Glu Ile Gln Phe Phe Asn Gly His Asn Tyr His Lys
65                  70                  75                  80

Gly Ile Asp Trp Tyr Met Asp Phe Phe Pro Ile Pro Ser Asn Thr Thr
                85                  90                  95

Ser Asp Phe Tyr Phe Glu Lys Ser Ala Asn Tyr Phe Asp Ser Asp Val
                100                 105                 110

Ala Pro Arg Arg Ala Ala Ala Leu Leu Pro Lys Ala Lys Val Leu Thr
            115                 120                 125

Ile Leu Ile Asn Pro Ala Asp Arg Ala Tyr Ser Trp Tyr Gln Ala Gln
130                 135                 140

Arg Ala His Asp Asp Pro Ala Ala Leu Arg Tyr Thr Phe His Glu Val
145                 150                 155                 160

Ile Thr Ala Gly Pro Asp Ala Ser Leu Lys Leu Arg Ala Leu Gln Asn
                165                 170                 175

Arg Cys Leu Val Pro Gly Trp Tyr Ala Thr His Leu Glu Arg Trp Leu
            180                 185                 190

Gly Ala Phe His Ala Asn Gln Ile Leu Val Leu Asp Gly Lys Leu Leu
            195                 200                 205

Arg Thr Glu Pro Ala Arg Val Met Asp Thr Val Gln Lys Phe Leu Gly
210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Gly
            245                 250                 255

Gly Arg His Leu Gly Arg Lys Tyr Pro Asp Met Asp Pro Asp Ser Arg
            260                 265                 270

Ala Phe Leu Arg Asp Tyr Tyr Arg Asp His Asn Ile Glu Leu Ser Lys
            275                 280                 285

Leu Leu Tyr Lys Met Gly Gln Thr Leu Pro Thr Trp Leu Arg Glu Glu
        290                 295                 300

Leu Gln Asn Thr Arg
305
```

<210> SEQ ID NO 38
<211> LENGTH: 309
<212> TYPE: PRT
<213> ORGANISM: Artificial Sequence
<220> FEATURE:
<223> OTHER INFORMATION: Amino acid sequence encoding for engineered
      aryl sulfate-dependent N-sulfotransferase variant 12

<400> SEQUENCE: 38

```
Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
            20                  25                  30
```

Lys Leu Leu Ile Ile Gly Pro His Gly Thr Gly His Ala Leu Tyr
            35                  40                  45

Leu Phe Leu Gly Leu His Pro Asp Leu Ser Ser Asn Tyr Pro Ser Ser
 50                  55                  60

Glu Thr Phe Leu Ser Ile Gln Phe Phe Asn Gly His Asn Tyr His Lys
 65                  70                  75                  80

Gly Ile Asp Trp Tyr Met Asp Phe Phe Pro Ile Pro Ser Asn Thr Thr
                85                  90                  95

Ser Asp Phe Tyr Phe Glu His Ser Gly Asn Tyr Phe Asp Ser Asp Val
                100                 105                 110

Ala Pro Arg Arg Ala Ala Ala Leu Leu Pro Lys Ala Lys Val Leu Thr
                115                 120                 125

Ile Leu Ile Asn Pro Ala Asp Arg Ala Tyr Arg Ala Tyr Val Trp Gln
        130                 135                 140

Arg Ala His Asp Asp Pro Ala Ala Leu Arg Tyr Thr Phe His Glu Val
145                 150                 155                 160

Ile Thr Ala Gly Pro Asp Ala Ser Leu Lys Leu Arg Ala Leu Gln Asn
                165                 170                 175

Arg Cys Leu Val Pro Gly Trp Tyr Ala Thr His Leu Glu Arg Trp Leu
                180                 185                 190

Gly Ala Phe His Ala Asn Gln Ile Leu Val Leu Asp Gly Lys Leu Leu
                195                 200                 205

Arg Thr Glu Pro Ala Arg Val Met Asp Thr Val Gln Lys Phe Leu Gly
        210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Leu
                245                 250                 255

Gly Arg Ser Leu Gly Ser Lys Tyr Pro Asp Met Asp Pro Asp Ser Arg
                260                 265                 270

Ala Phe Leu Arg Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Glu
        290                 295                 300

Leu Gln Asn Thr Arg
305

<210> SEQ ID NO 39
<211> LENGTH: 309
<212> TYPE: PRT
<213> ORGANISM: Artificial Sequence
<220> FEATURE:
<223> OTHER INFORMATION: Amino acid sequence encoding for engineered
      aryl sulfate-dependent N-sulfotransferase variant 13

<400> SEQUENCE: 39

Met Ser Glu Glu Lys Asp Pro Leu Trp Gln Asp Pro Cys Glu Asp Lys
 1               5                   10                  15

Arg His Lys Asp Ile Trp Ser Lys Glu Lys Thr Cys Asp Arg Phe Pro
            20                  25                  30

Lys Leu Leu Ile Ile Gly Pro His Lys Thr Gly Val His Ala Leu Tyr
            35                  40                  45

Leu Phe Leu Gly Leu His Pro Asp Leu Ser Ser Asn Tyr Pro Ser Ser
 50                  55                  60

Glu Thr Gly Asn His Ile Gly Phe Phe Gly Gly His Asn Tyr His Lys

```
                65                  70                  75                  80
Gly Ile Asp Trp Tyr Met Asp Phe Phe Pro Ile Pro Ser Asn Thr Thr
                    85                  90                  95

Ser Asp Phe Tyr Phe Glu Lys Ser Ala Trp Tyr Phe Asp Ser Asp Val
                    100                 105                 110

Ala Pro Arg Arg Ala Ala Ala Leu Leu Pro Lys Ala Lys Val Leu Thr
                    115                 120                 125

Ile Leu Ile Asn Pro Ala Asp Arg Ala Tyr Ser Trp Tyr Gln His Gln
    130                 135                 140

Arg Ala His Asp Asp Pro Ala Ala Leu Arg Tyr Thr Phe His Glu Val
145                 150                 155                 160

Ile Thr Ala Gly Pro Asp Ala Ser Leu Lys Leu Arg Ala Leu Gln Asn
                    165                 170                 175

Arg Cys Leu Val Pro Gly Trp Tyr Ala Thr His Leu Glu Arg Trp Leu
                    180                 185                 190

Gly Ala Phe His Ala Asn Gln Ile Leu Val Leu Asp Gly Lys Leu Leu
                    195                 200                 205

Arg Thr Glu Pro Ala Arg Val Met Asp Thr Val Gln Lys Phe Leu Gly
    210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Leu
                    245                 250                 255

Gly Arg Ser Val Gly Arg Lys Tyr Pro Asp Met Asp Pro Asp Ser Arg
                    260                 265                 270

Ala Phe Leu Arg Asp Tyr Tyr Arg Asp His Asn Ile Glu Leu Ser Lys
                    275                 280                 285

Leu Leu Tyr Lys Met Gly Gln Thr Leu Pro Thr Trp Leu Arg Glu Glu
                    290                 295                 300

Leu Gln Asn Thr Arg
305

<210> SEQ ID NO 40
<211> LENGTH: 309
<212> TYPE: PRT
<213> ORGANISM: Artificial Sequence
<220> FEATURE:
<223> OTHER INFORMATION: Amino acid sequence encoding for engineered
      aryl sulfate-dependent N-sulfotransferase variant 14

<400> SEQUENCE: 40

Met Ser Glu Glu Lys Asp Pro Leu Trp Gln Asp Pro Cys Glu Asp Lys
1               5                   10                  15

Arg His Lys Asp Ile Trp Ser Lys Glu Lys Thr Cys Asp Arg Phe Pro
                20                  25                  30

Lys Leu Leu Ile Ile Gly Pro Ala Lys Thr Gly Ala Trp Leu Leu His
            35                  40                  45

His Phe Leu Gly Leu His Pro Asp Leu Ser Ser Asn Tyr Pro Ser Ser
        50                  55                  60

Glu Thr His Ser Ser Ile Gln Phe Phe Asn Gly His Asn Tyr His Lys
65                  70                  75                  80

Gly Ile Asp Trp Tyr Met Asp Phe Phe Pro Ile Pro Ser Asn Thr Thr
                    85                  90                  95

Ser Asp Phe Tyr Phe Glu Thr Ser Ala Asn Tyr Phe Asp Ser Asp Val
                    100                 105                 110
```

```
Ala Pro Arg Arg Ala Ala Ala Leu Leu Pro Lys Ala Lys Val Leu Thr
            115                 120                 125

Ile Leu Ile Asn Pro Ala Asp Arg Ala Tyr Ser Trp Tyr Gln His Gln
    130                 135                 140

Arg Ala His Asp Asp Pro Ala Ala Leu Arg Tyr Thr Phe His Glu Val
145                 150                 155                 160

Ile Thr Ala Gly Pro Asp Ala Ser Leu Lys Leu Arg Ala Leu Gln Asn
                165                 170                 175

Arg Cys Leu Val Pro Gly Trp Tyr Ala Thr His Leu Glu Arg Trp Leu
            180                 185                 190

Gly Ala Phe His Ala Asn Gln Ile Leu Val Leu Asp Gly Lys Leu Leu
        195                 200                 205

Arg Thr Glu Pro Ala Arg Val Met Asp Thr Val Gln Lys Phe Leu Gly
    210                 215                 220

Val Thr Asn Thr Ile Asp Tyr His Lys Thr Leu Ala Phe Asp Pro Lys
225                 230                 235                 240

Lys Gly Phe Trp Cys Gln Leu Leu Glu Gly Gly Lys Thr Lys Cys Ala
                245                 250                 255

His Arg Gly Leu Gly Arg Lys Tyr Pro Asp Met Asp Pro Asp Ser Arg
            260                 265                 270

Ala Phe Leu Arg Asp Tyr Tyr Arg Asp His Asn Ile Glu Leu Ser Lys
        275                 280                 285

Leu Leu Tyr Lys Met Gly Gln Thr Leu Pro Thr Trp Leu Arg Glu Glu
    290                 295                 300

Leu Gln Asn Thr Arg
305

<210> SEQ ID NO 41
<211> LENGTH: 289
<212> TYPE: PRT
<213> ORGANISM: Artificial Sequence
<220> FEATURE:
<223> OTHER INFORMATION: Amino acid sequence encoding for engineered
      aryl sulfate-dependent 2-O-sulfotransferase variant 3

<400> SEQUENCE: 41

Met Asp Glu Glu Asp Met Val Ile Ile Tyr Asn Arg Val Pro His
1               5                   10                  15

Thr Ala Ser Thr Ser Phe Thr Asn Ile Ala Tyr Asp Leu Cys Ala Lys
            20                  25                  30

Asn Lys Tyr His Val Leu His Ile Asn Thr Thr Lys Asn Asn Pro Val
        35                  40                  45

Met Ser Leu Gln Asp Gln Val Arg Phe Val Lys Asn Ile Thr Ser Trp
    50                  55                  60

Lys Glu Met Lys Pro Gly Phe Tyr His Gly His Val Ser Tyr Leu Asp
65                  70                  75                  80

Phe Ala Lys Phe Gly Val Lys Lys Pro Ile Tyr Ile Asn Val Ile
            85                  90                  95

Arg Asp Pro Ile Glu Arg Leu Val Ser Tyr Tyr His Leu Arg Phe
        100                 105                 110

Gly Asp Asp Tyr Arg Pro Gly Leu Arg Arg Lys Gln Gly Asp Lys
    115                 120                 125

Lys Thr Phe Asp Glu Cys Val Ala Glu Gly Gly Ser Asp Cys Ala Pro
    130                 135                 140

Glu Lys Leu Trp Leu Gln Ile Pro Phe Phe Cys Gly His Ser Ser Glu
145                 150                 155                 160
```

```
Cys Trp Asn Val Gly Ser Arg Trp Ala Met Asp Gln Ala Lys Tyr Asn
            165                 170                 175

Leu Ile Asn Glu Tyr Phe Leu Val Gly Val Thr Glu Leu Glu Asp
            180                 185                 190

Phe Ile Met Leu Leu Glu Ala Ala Leu Pro Arg Phe Phe Arg Gly Ala
            195                 200                 205

Thr Glu Leu Tyr Arg Thr Gly Lys Lys Ser His Leu His Lys Thr Thr
            210                 215                 220

Glu Lys Lys Leu Pro Thr Lys Gln Thr Ile Ala Lys Leu Gln Gln Ser
225                 230                 235                 240

Asp Ile Trp Lys Met Glu Asn Glu Phe Tyr Glu Phe Ala Leu Glu Gln
            245                 250                 255

Phe Gln Phe Ile Arg Ala His Ala Val Arg Glu Lys Asp Gly Asp Leu
            260                 265                 270

Tyr Ile Leu Ala Gln Asn Phe Phe Tyr Glu Lys Ile Tyr Pro Lys Ser
            275                 280                 285

Asn

<210> SEQ ID NO 42
<211> LENGTH: 289
<212> TYPE: PRT
<213> ORGANISM: Artificial Sequence
<220> FEATURE:
<223> OTHER INFORMATION: Amino acid sequence encoding for engineered
      aryl sulfate-dependent 2-O-sulfotransferase variant 4

<400> SEQUENCE: 42

Met Asp Glu Glu Asp Met Val Ile Ile Tyr Asn Arg Val His Arg
1               5                   10                  15

Thr Ala Ser His Ser Phe Thr Asn Ile Ala Tyr Asp Leu Cys Ala Lys
            20                  25                  30

Asn Lys Tyr His Val Leu His Ile Asn Thr Thr Lys Gly Asn Pro Val
            35                  40                  45

Met Ser Leu Gln Asp Gln Val Arg Phe Val Lys Asn Ile Thr Ser Trp
50                  55                  60

Lys Glu Met Lys Pro Gly Phe Tyr His Gly Pro Val Ser Tyr Leu Asp
65                  70                  75                  80

Phe Ala Lys Phe Gly Val Lys Lys Lys Pro Ile Tyr Ile Asn Val Ile
            85                  90                  95

Arg Asp Pro Ile Glu Arg Leu Val Ser Tyr Tyr Tyr Phe Leu Arg Phe
            100                 105                 110

Gly Ser Asp Lys Arg Pro Gly Leu Arg Met Arg Lys Gln Gly Asp Lys
            115                 120                 125

Lys Thr Phe Asp Glu Cys Val Ala Glu Gly Gly Ser Asp Cys Ala Pro
            130                 135                 140

Glu Lys Leu Trp Leu Gln Ile Pro Phe Phe Cys Gly His Ser Ser Glu
145                 150                 155                 160

Cys Trp Asn Val Gly Ser Arg Trp Ala Met Asp Gln Ala Lys Tyr Asn
            165                 170                 175

Leu Ile Asn Glu Tyr Phe Leu Val Gly Val Thr Glu Leu Glu Asp
            180                 185                 190

Phe Ile Met Leu Leu Glu Ala Ala Leu Pro Arg Phe Phe Arg Gly Ala
            195                 200                 205

Thr Glu Leu Tyr Arg Thr Gly Lys Lys Ser His Leu His Lys Thr Thr
            210                 215                 220
```

```
Glu Lys Lys Leu Pro Thr Lys Gln Thr Ile Ala Lys Leu Gln Gln Ser
225                 230                 235                 240

Asp Ile Trp Lys Met Glu Asn Glu Phe Tyr Glu Phe Ala Leu Glu Gln
            245                 250                 255

Phe Gln Phe Ile Arg Ala His Ala Val Arg Glu Lys Asp Gly Asp Leu
        260                 265                 270

Tyr Ile Leu Ala Gln Asn Phe Phe Tyr Glu Lys Ile Tyr Pro Lys Ser
    275                 280                 285

Asn

<210> SEQ ID NO 43
<211> LENGTH: 312
<212> TYPE: PRT
<213> ORGANISM: Artificial Sequence
<220> FEATURE:
<223> OTHER INFORMATION: Amino acid sequence encoding for engineered
      aryl sulfate-dependent 6-O-sulfotransferase variant 4
<220> FEATURE:
<221> NAME/KEY: MISC_FEATURE
<222> LOCATION: (84)..(84)
<223> OTHER INFORMATION: Xaa is threonine or serine
<220> FEATURE:
<221> NAME/KEY: MISC_FEATURE
<222> LOCATION: (85)..(85)
<223> OTHER INFORMATION: Xaa is asparagine, arginine, or histidine
<220> FEATURE:
<221> NAME/KEY: MISC_FEATURE
<222> LOCATION: (128)..(128)
<223> OTHER INFORMATION: Xaa is glycine or serine
<220> FEATURE:
<221> NAME/KEY: MISC_FEATURE
<222> LOCATION: (129)..(129)
<223> OTHER INFORMATION: Xaa is glycine or histidine
<220> FEATURE:
<221> NAME/KEY: MISC_FEATURE
<222> LOCATION: (133)..(133)
<223> OTHER INFORMATION: Xaa is histidine or threonine
<220> FEATURE:
<221> NAME/KEY: MISC_FEATURE
<222> LOCATION: (138)..(138)
<223> OTHER INFORMATION: Xaa is alanine or threonine
<220> FEATURE:
<221> NAME/KEY: MISC_FEATURE
<222> LOCATION: (142)..(142)
<223> OTHER INFORMATION: Xaa is glycine or serine
<220> FEATURE:
<221> NAME/KEY: MISC_FEATURE
<222> LOCATION: (181)..(181)
<223> OTHER INFORMATION: Xaa is glycine or alanine

<400> SEQUENCE: 43

Met Lys Tyr Tyr Phe Pro Val Arg Glu Leu Glu Arg Ser Leu Arg Phe
1               5                   10                  15

Asp Met Lys Gly Asp Asp Val Ile Val Phe Leu His Ile Gly His Thr
            20                  25                  30

Gly Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
    50                  55                  60

Pro Asn Arg Arg Glu Thr Trp Leu Phe Ser Arg Phe Ser Thr Gly Trp
65                  70                  75                  80

Ser Cys Gly Xaa Xaa Ala Asp Trp Thr Glu Leu Thr Asn Cys Val Pro
                85                  90                  95

Gly Val Leu Asp Arg Arg Asp Pro Ala Gly Leu Arg Ser Pro Arg Lys
            100                 105                 110
```

```
Phe Tyr Tyr Ile Thr Leu Leu Arg Asp Pro Val Ser Arg Tyr Leu Xaa
            115                 120                 125

Xaa Trp Arg His Xaa Gln Arg Gly Gly Xaa Asn Lys Thr Xaa Leu His
    130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Xaa Asn Asn Arg Gln Val Arg Met Leu Ala Asp Leu
            180                 185                 190

Ser Leu Val Gly Cys Tyr Asn Leu Ser Phe Ile Pro Glu Ser Lys Arg
            195                 200                 205

Ala Gln Leu Leu Leu Glu Ser Ala Lys Lys Asn Leu Arg Gly Met Ala
            210                 215                 220

Phe Phe Gly Leu Thr Glu Phe Gln Arg Lys Thr Gln Tyr Leu Phe Glu
225                 230                 235                 240

Arg Thr Phe Asn Leu Lys Phe Ile Arg Pro Phe Met Gly Tyr Asn Ser
                245                 250                 255

Thr Arg Ala Gly Gly Val Glu Val Asp Glu Asp Thr Ile Arg His Ile
            260                 265                 270

Glu Glu Leu Asn Asp Leu Asp Met Gln Leu Tyr Asp Tyr Ala Lys Asp
            275                 280                 285

Leu Phe Gln Gln Arg Tyr Gln Tyr Lys Arg Gln Leu Glu Arg Glu
            290                 295                 300

Gln Arg Leu Arg Asn Arg Glu Glu
305                 310

<210> SEQ ID NO 44
<211> LENGTH: 411
<212> TYPE: PRT
<213> ORGANISM: Artificial Sequence
<220> FEATURE:
<223> OTHER INFORMATION: Amino acid sequence encoding for engineered
      aryl sulfate-dependent 6-O-sulfotransferase variant 5
<220> FEATURE:
<221> NAME/KEY: MISC_FEATURE
<222> LOCATION: (149)..(149)
<223> OTHER INFORMATION: Xaa is threonine or serine
<220> FEATURE:
<221> NAME/KEY: MISC_FEATURE
<222> LOCATION: (150)..(150)
<223> OTHER INFORMATION: Xaa is asparagine, arginine, or histidine
<220> FEATURE:
<221> NAME/KEY: MISC_FEATURE
<222> LOCATION: (193)..(193)
<223> OTHER INFORMATION: Xaa is glycine or serine
<220> FEATURE:
<221> NAME/KEY: MISC_FEATURE
<222> LOCATION: (194)..(194)
<223> OTHER INFORMATION: Xaa is glycine or histidine
<220> FEATURE:
<221> NAME/KEY: MISC_FEATURE
<222> LOCATION: (198)..(198)
<223> OTHER INFORMATION: Xaa is histidine or threonine
<220> FEATURE:
<221> NAME/KEY: MISC_FEATURE
<222> LOCATION: (203)..(203)
<223> OTHER INFORMATION: Xaa is alanine or threonine
<220> FEATURE:
<221> NAME/KEY: MISC_FEATURE
<222> LOCATION: (207)..(207)
<223> OTHER INFORMATION: Xaa is glycine or serine
<220> FEATURE:
<221> NAME/KEY: MISC_FEATURE
<222> LOCATION: (246)..(246)
<223> OTHER INFORMATION: Xaa is glycine or alanine
```

<400> SEQUENCE: 44

Met Arg Arg Arg Ala Gly Gly Arg Thr Met Val Glu Arg Ala Ser
1               5                   10                  15

Lys Phe Val Leu Val Val Ala Gly Ser Ala Cys Phe Met Leu Ile Leu
            20                  25                  30

Tyr Gln Tyr Ala Gly Pro Gly Leu Ser Leu Gly Ala Pro Gly Gly Arg
                35                  40                  45

Val Pro Pro Asp Asp Leu Asp Leu Phe Pro Thr Pro Asp Pro His Tyr
    50                  55                  60

Glu Lys Lys Tyr Tyr Phe Pro Val Arg Glu Leu Glu Arg Ser Leu Arg
65                  70                  75                  80

Phe Asp Met Lys Gly Asp Asp Val Ile Val Phe Leu His Ile Gly His
                85                  90                  95

Thr Gly Gly Thr Thr Phe Gly Arg His Leu Val Gln Asn Val Arg Leu
                100                 105                 110

Glu Val Pro Cys Asp Cys Arg Pro Gly Gln Lys Lys Cys Thr Cys Tyr
                115                 120                 125

Arg Pro Asn Arg Arg Glu Thr Trp Leu Phe Ser Arg Phe Ser Thr Gly
            130                 135                 140

Trp Ser Cys Gly Xaa Xaa Ala Asp Trp Thr Glu Leu Thr Asn Cys Val
145                 150                 155                 160

Pro Gly Val Leu Asp Arg Arg Asp Pro Ala Gly Leu Arg Ser Pro Arg
                165                 170                 175

Lys Phe Tyr Tyr Ile Thr Leu Leu Arg Asp Pro Val Ser Arg Tyr Leu
                180                 185                 190

Xaa Xaa Trp Arg His Xaa Gln Arg Gly Gly Xaa Asn Lys Thr Xaa Leu
            195                 200                 205

His Met Cys Asp Gly Arg Thr Pro Thr Pro Glu Glu Leu Pro Pro Cys
            210                 215                 220

Tyr Glu Gly Thr Asp Trp Ser Gly Cys Thr Leu Gln Glu Phe Met Asp
225                 230                 235                 240

Cys Pro Tyr Asn Leu Xaa Asn Asn Arg Gln Val Arg Met Leu Ala Asp
                245                 250                 255

Leu Ser Leu Val Gly Cys Tyr Asn Leu Ser Phe Ile Pro Glu Ser Lys
                260                 265                 270

Arg Ala Gln Leu Leu Leu Glu Ser Ala Lys Lys Asn Leu Arg Gly Met
            275                 280                 285

Ala Phe Phe Gly Leu Thr Glu Phe Gln Arg Lys Thr Gln Tyr Leu Phe
            290                 295                 300

Glu Arg Thr Phe Asn Leu Lys Phe Ile Arg Pro Phe Met Gln Tyr Asn
305                 310                 315                 320

Ser Thr Arg Ala Gly Gly Val Glu Val Asp Glu Asp Thr Ile Arg His
                325                 330                 335

Ile Glu Glu Leu Asn Asp Leu Asp Met Gln Leu Tyr Tyr Ala Lys
            340                 345                 350

Asp Leu Phe Gln Gln Arg Tyr Gln Tyr Lys Arg Gln Leu Glu Arg Arg
            355                 360                 365

Glu Gln Arg Leu Arg Asn Arg Glu Glu Arg Leu Leu His Arg Ser Lys
            370                 375                 380

Glu Ala Leu Pro Arg Glu Asp Pro Glu Pro Gly Arg Val Pro Thr
385                 390                 395                 400

Glu Asp Tyr Met Ser His Ile Ile Glu Lys Trp

<210> SEQ ID NO 45
<211> LENGTH: 312
<212> TYPE: PRT
<213> ORGANISM: Artificial Sequence
<220> FEATURE:
<223> OTHER INFORMATION: Amino acid sequence encoding for engineered aryl sulfate-dependent 6-O-sulfotransferase variant 6

<400> SEQUENCE: 45

| | | | | | | | | | | | | | | | |
|---|---|---|---|---|---|---|---|---|---|---|---|---|---|---|---|
| Met | Lys | Tyr | Tyr | Phe | Pro | Val | Arg | Glu | Leu | Glu | Arg | Ser | Leu | His | Phe |
| 1 | | | | 5 | | | | | 10 | | | | | 15 | |
| Asp | Met | Lys | Gly | Asp | Val | Ile | Val | Phe | Leu | His | Ile | Gly | His | Thr | |
| | | | 20 | | | | | 25 | | | | | 30 | | |
| Gly | Gly | Thr | Thr | Phe | Gly | Arg | His | Leu | Val | Gln | Asn | Val | Arg | Leu | Glu |
| | | | 35 | | | | | 40 | | | | | 45 | | |
| Val | Pro | Cys | Asp | Cys | Arg | Pro | Gly | Gln | Lys | Lys | Cys | Thr | Cys | Tyr | Arg |
| | 50 | | | | | 55 | | | | | 60 | | | | |
| Pro | Asn | Arg | Arg | Glu | Thr | Trp | Leu | Phe | Ser | Arg | Phe | Ser | Thr | Gly | Trp |
| 65 | | | | | 70 | | | | | 75 | | | | | 80 |
| Ser | Cys | Gly | Thr | Asn | Ala | Asp | Trp | Thr | Glu | Leu | Thr | Asn | Cys | Val | Pro |
| | | | | 85 | | | | | 90 | | | | | 95 | |
| Gly | Val | Leu | Asp | Arg | Arg | Asp | Pro | Ala | Ala | Leu | Arg | Thr | Pro | Arg | Lys |
| | | | | 100 | | | | | 105 | | | | | 110 | |
| Phe | Tyr | Tyr | Ile | Thr | Leu | Leu | Arg | Asp | Pro | Val | Ser | Arg | Tyr | Leu | Gly |
| | | | 115 | | | | | 120 | | | | | 125 | | |
| Gly | Trp | Arg | His | His | Gln | Arg | Gly | Gly | Thr | Asn | Lys | Thr | Ser | Leu | His |
| | 130 | | | | | 135 | | | | | 140 | | | | |
| Met | Cys | Asp | Gly | Arg | Thr | Pro | Thr | Pro | Glu | Glu | Leu | Pro | Pro | Cys | Tyr |
| 145 | | | | | 150 | | | | | 155 | | | | | 160 |
| Glu | Gly | Thr | Asp | Trp | Ser | Gly | Cys | Thr | Leu | Gln | Glu | Phe | Met | Asp | Cys |
| | | | | 165 | | | | | 170 | | | | | 175 | |
| Pro | Tyr | Asn | Leu | Ala | Asn | Asn | Arg | Gln | Val | Arg | Met | Leu | Ala | Asp | Leu |
| | | | 180 | | | | | 185 | | | | | 190 | | |
| Ser | Leu | Val | Gly | Cys | Tyr | Asn | Leu | Ser | Phe | Ile | Pro | Glu | Gly | Lys | Arg |
| | | | 195 | | | | | 200 | | | | | 205 | | |
| Ser | Gln | Leu | Leu | Leu | Glu | Ser | Ala | Lys | Lys | Asn | Leu | Arg | Gly | Met | Ala |
| | 210 | | | | | 215 | | | | | 220 | | | | |
| Phe | Phe | Gly | Leu | Thr | Glu | Phe | Gln | Arg | Lys | Thr | Gln | Tyr | Leu | Phe | Glu |
| 225 | | | | | 230 | | | | | 235 | | | | | 240 |
| Arg | Thr | Phe | Asn | Leu | Lys | Phe | Ile | Arg | Pro | Phe | Met | Gln | Tyr | Asn | Ser |
| | | | | 245 | | | | | 250 | | | | | 255 | |
| Thr | Arg | Ala | Gly | Gly | Val | Glu | Val | Gly | Glu | Asp | Thr | Ile | Arg | Arg | Ile |
| | | | 260 | | | | | 265 | | | | | 270 | | |
| Glu | Glu | Leu | Asn | Asp | Leu | Asp | Met | Gln | Leu | Tyr | Asp | Tyr | Ala | Arg | Asp |
| | | | | 275 | | | | | 280 | | | | | 285 | |
| Leu | Phe | Gln | Gln | Arg | Tyr | Gln | Tyr | Lys | Arg | Gln | Leu | Glu | Arg | Arg | Gln |
| | | | 290 | | | | | 295 | | | | | 300 | | |
| Gln | Arg | Leu | Arg | Ser | Arg | Glu | Glu | | | | | | | | |
| 305 | | | | | 310 | | | | | | | | | | |

<210> SEQ ID NO 46
<211> LENGTH: 312
<212> TYPE: PRT
<213> ORGANISM: Artificial Sequence
<220> FEATURE:

-continued

<223> OTHER INFORMATION: Amino acid sequence encoding for engineered
     aryl sulfate-dependent 6-O-sulfotransferase variant 7

<400> SEQUENCE: 46

Met Lys Tyr Tyr Phe Pro Val Arg Glu Leu Glu Arg Ser Leu His Phe
1               5                   10                  15

Asp Met Lys Gly Asp Asp Val Ile Val Phe Leu His Ile Gly His Thr
            20                  25                  30

Gly Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
50                  55                  60

Pro Asn Arg Arg Glu Thr Trp Leu Phe Ser Arg Phe Ser Thr Gly Trp
65                  70                  75                  80

Ser Cys Gly Thr Arg Ala Asp Trp Thr Glu Leu Thr Asn Cys Val Pro
                85                  90                  95

Gly Val Leu Asp Arg Arg Asp Pro Ala Ala Leu Arg Thr Pro Arg Lys
            100                 105                 110

Phe Tyr Tyr Ile Thr Leu Leu Arg Asp Pro Val Ser Arg Tyr Leu Ser
        115                 120                 125

His Trp Arg His Thr Gln Arg Gly Gly Ala Asn Lys Thr Gly Leu His
    130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Gly Asn Asn Arg Gln Val Arg Met Leu Ala Asp Leu
            180                 185                 190

Ser Leu Val Gly Cys Tyr Asn Leu Ser Phe Ile Pro Glu Gly Lys Arg
        195                 200                 205

Ser Gln Leu Leu Leu Glu Ser Ala Lys Lys Asn Leu Arg Gly Met Ala
    210                 215                 220

Phe Phe Gly Leu Thr Glu Phe Gln Arg Lys Thr Gln Tyr Leu Phe Glu
225                 230                 235                 240

Arg Thr Phe Asn Leu Lys Phe Ile Arg Pro Phe Met Gln Tyr Asn Ser
                245                 250                 255

Thr Arg Ala Gly Gly Val Glu Val Gly Glu Asp Thr Ile Arg Arg Ile
            260                 265                 270

Glu Glu Leu Asn Asp Leu Asp Met Gln Leu Tyr Asp Tyr Ala Arg Asp
        275                 280                 285

Leu Phe Gln Gln Arg Tyr Gln Tyr Lys Arg Gly Leu Glu Arg Arg Gln
    290                 295                 300

Gln Arg Leu Arg Ser Arg Glu Glu
305                 310

<210> SEQ ID NO 47
<211> LENGTH: 312
<212> TYPE: PRT
<213> ORGANISM: Artificial Sequence
<220> FEATURE:
<223> OTHER INFORMATION: Amino acid sequence encoding for engineered
     aryl sulfate-dependent 6-O-sulfotransferase variant 8

<400> SEQUENCE: 47

Met Lys Tyr Tyr Phe Pro Val Arg Glu Leu Glu Arg Ser Leu His Phe
1               5                   10                  15

```
Asp Met Lys Gly Asp Asp Val Ile Val Phe Leu His Ile Gly His Thr
            20                  25                  30

Gly Gly Thr Thr Phe Gly Arg His Leu Val Gln Asn Val Arg Leu Glu
        35                  40                  45

Val Pro Cys Asp Cys Arg Pro Gly Gln Lys Lys Cys Thr Cys Tyr Arg
 50                  55                  60

Pro Asn Arg Arg Glu Thr Trp Leu Phe Ser Arg Phe Ser Thr Gly Trp
 65                  70                  75                  80

Ser Cys Gly Ser His Ala Asp Trp Thr Glu Leu Thr Asn Cys Val Pro
                85                  90                  95

Gly Val Leu Asp Arg Arg Asp Pro Ala Ala Leu Arg Thr Pro Arg Lys
            100                 105                 110

Phe Tyr Tyr Ile Thr Leu Leu Arg Asp Pro Val Ser Arg Tyr Leu Ser
            115                 120                 125

Gly Trp Arg His His Gln Arg Gly Ala Asn Lys Thr Ser Leu His
            130                 135                 140

Met Cys Asp Gly Arg Thr Pro Thr Pro Glu Glu Leu Pro Pro Cys Tyr
145                 150                 155                 160

Glu Gly Thr Asp Trp Ser Gly Cys Thr Leu Gln Glu Phe Met Asp Cys
                165                 170                 175

Pro Tyr Asn Leu Gly Asn Asn Arg Gln Val Arg Met Leu Ala Asp Leu
            180                 185                 190

Ser Leu Val Gly Cys Tyr Asn Leu Ser Phe Ile Pro Glu Gly Lys Arg
            195                 200                 205

Ser Gln Leu Leu Leu Glu Ser Ala Lys Lys Asn Leu Arg Gly Met Ala
            210                 215                 220

Phe Phe Gly Leu Thr Glu Phe Gln Arg Lys Thr Gln Tyr Leu Phe Glu
225                 230                 235                 240

Arg Thr Phe Asn Leu Lys Phe Ile Arg Pro Phe Met Gln Tyr Asn Ser
            245                 250                 255

Thr Arg Ala Gly Gly Val Glu Val Gly Glu Asp Thr Ile Arg Arg Ile
            260                 265                 270

Glu Glu Leu Asn Asp Leu Asp Met Gln Leu Tyr Asp Tyr Ala Arg Asp
            275                 280                 285

Leu Phe Gln Gln Arg Tyr Gln Tyr Lys Arg Gly Leu Glu Arg Arg Gln
            290                 295                 300

Gln Arg Leu Arg Ser Arg Glu Glu
305                 310

<210> SEQ ID NO 48
<211> LENGTH: 411
<212> TYPE: PRT
<213> ORGANISM: Artificial Sequence
<220> FEATURE:
<223> OTHER INFORMATION: Amino acid sequence encoding for engineered
      aryl sulfate-dependent 6-O-sulfotransferase variant 9

<400> SEQUENCE: 48

Met Arg Arg Arg Arg Ala Gly Ser Arg Thr Met Val Glu Arg Ala Ser
1               5                   10                  15

Lys Phe Val Leu Val Val Ala Gly Ser Ala Cys Phe Met Leu Ile Leu
            20                  25                  30

Tyr Gln Tyr Ala Gly Pro Gly Leu Ser Leu Gly Ala Pro Gly Gly Arg
            35                  40                  45

Ala Pro Pro Asp Asp Leu Asp Leu Phe Pro Thr Pro Asp Pro His Tyr
 50                  55                  60
```

Glu Lys Lys Tyr Tyr Phe Pro Val Arg Glu Leu Arg Ser Leu His
65                  70                  75                  80

Phe Asp Met Lys Gly Asp Asp Val Ile Val Phe Leu His Ile Gly His
                85                  90                  95

Thr Gly Gly Thr Thr Phe Gly Arg His Leu Val Gln Asn Val Arg Leu
            100                 105                 110

Glu Val Pro Cys Asp Cys Arg Pro Gly Gln Lys Lys Cys Thr Cys Tyr
        115                 120                 125

Arg Pro Asn Arg Arg Glu Thr Trp Leu Phe Ser Arg Phe Ser Thr Gly
    130                 135                 140

Trp Ser Cys Gly Thr Asn Ala Asp Trp Thr Glu Leu Thr Asn Cys Val
145                 150                 155                 160

Pro Gly Val Leu Asp Arg Arg Asp Pro Ala Ala Leu Arg Thr Pro Arg
                165                 170                 175

Lys Phe Tyr Tyr Ile Thr Leu Leu Arg Asp Pro Val Ser Arg Tyr Leu
                180                 185                 190

Gly Gly Trp Arg His His Gln Arg Gly Gly Thr Asn Lys Thr Ser Leu
            195                 200                 205

His Met Cys Asp Gly Arg Thr Pro Thr Pro Glu Glu Leu Pro Pro Cys
210                 215                 220

Tyr Glu Gly Thr Asp Trp Ser Gly Cys Thr Leu Gln Glu Phe Met Asp
225                 230                 235                 240

Cys Pro Tyr Asn Leu Ala Asn Asn Arg Gln Val Arg Met Leu Ala Asp
                245                 250                 255

Leu Ser Leu Val Gly Cys Tyr Asn Leu Ser Phe Ile Pro Glu Gly Lys
                260                 265                 270

Arg Ser Gln Leu Leu Leu Glu Ser Ala Lys Lys Asn Leu Arg Gly Met
    275                 280                 285

Ala Phe Phe Gly Leu Thr Glu Phe Gln Arg Lys Thr Gln Tyr Leu Phe
290                 295                 300

Glu Arg Thr Phe Asn Leu Lys Phe Ile Arg Pro Phe Met Gln Tyr Asn
305                 310                 315                 320

Ser Thr Arg Ala Gly Gly Val Glu Val Gly Asp Thr Ile Arg Arg
                325                 330                 335

Ile Glu Glu Leu Asn Asp Leu Asp Met Gln Leu Tyr Asp Tyr Ala Arg
            340                 345                 350

Asp Leu Phe Gln Gln Arg Tyr Gln Tyr Lys Arg Gln Leu Glu Arg Arg
            355                 360                 365

Gln Gln Arg Leu Arg Ser Arg Glu Arg Leu Leu His Arg Ala Lys
    370                 375                 380

Glu Ala Pro Pro Arg Gly Asp Thr Glu Glu Pro Gly Arg Val Pro Thr
385                 390                 395                 400

Glu Asp Tyr Met Ser His Ile Ile Glu Lys Trp
                405                 410

<210> SEQ ID NO 49
<211> LENGTH: 411
<212> TYPE: PRT
<213> ORGANISM: Artificial Sequence
<220> FEATURE:
<223> OTHER INFORMATION: Amino acid sequence encoding for engineered
      aryl sulfate-dependent 6-O-sulfotransferase variant 10

<400> SEQUENCE: 49

Met Arg Arg Arg Arg Ala Gly Ser Arg Thr Met Val Glu Arg Ala Ser

```
1               5                   10                  15
Lys Phe Val Leu Val Ala Gly Ser Ala Cys Phe Met Leu Ile Leu
                20                  25                  30

Tyr Gln Tyr Ala Gly Pro Gly Leu Ser Leu Gly Ala Pro Gly Gly Arg
                35                  40                  45

Ala Pro Pro Asp Asp Leu Asp Leu Phe Pro Thr Pro Asp Pro His Tyr
50                      55                  60

Glu Lys Lys Tyr Tyr Phe Pro Val Arg Glu Leu Glu Arg Ser Leu His
65                  70                  75                  80

Phe Asp Met Lys Gly Asp Asp Val Ile Val Phe Leu His Ile Gly His
                85                  90                  95

Thr Gly Gly Thr Thr Phe Gly Arg His Leu Val Gln Asn Val Arg Leu
                100                 105                 110

Glu Val Pro Cys Asp Cys Arg Pro Gly Gln Lys Lys Cys Thr Cys Tyr
                115                 120                 125

Arg Pro Asn Arg Arg Glu Thr Trp Leu Phe Ser Arg Phe Ser Thr Gly
                130                 135                 140

Trp Ser Cys Gly Thr Arg Ala Asp Trp Thr Glu Leu Thr Asn Cys Val
145                 150                 155                 160

Pro Gly Val Leu Asp Arg Arg Asp Pro Ala Ala Leu Arg Thr Pro Arg
                165                 170                 175

Lys Phe Tyr Tyr Ile Thr Leu Leu Arg Asp Pro Val Ser Arg Tyr Leu
                180                 185                 190

Ser His Trp Arg His Thr Gln Arg Gly Gly Ala Asn Lys Thr Gly Leu
                195                 200                 205

His Met Cys Asp Gly Arg Thr Pro Thr Pro Glu Glu Leu Pro Pro Cys
                210                 215                 220

Tyr Glu Gly Thr Asp Trp Ser Gly Cys Thr Leu Gln Glu Phe Met Asp
225                 230                 235                 240

Cys Pro Tyr Asn Leu Gly Asn Asn Arg Gln Val Arg Met Leu Ala Asp
                245                 250                 255

Leu Ser Leu Val Gly Cys Tyr Asn Leu Ser Phe Ile Pro Glu Gly Lys
                260                 265                 270

Arg Ser Gln Leu Leu Leu Glu Ser Ala Lys Lys Asn Leu Arg Gly Met
                275                 280                 285

Ala Phe Phe Gly Leu Thr Glu Phe Gln Arg Lys Thr Gln Tyr Leu Phe
                290                 295                 300

Glu Arg Thr Phe Asn Leu Lys Phe Ile Arg Pro Phe Met Gln Tyr Asn
305                 310                 315                 320

Ser Thr Arg Ala Gly Gly Val Glu Val Gly Glu Asp Thr Ile Arg Arg
                325                 330                 335

Ile Glu Glu Leu Asn Asp Leu Asp Met Gln Leu Tyr Asp Tyr Ala Arg
                340                 345                 350

Asp Leu Phe Gln Gln Arg Tyr Gln Tyr Lys Arg Gln Leu Glu Arg Arg
                355                 360                 365

Gln Gln Arg Leu Arg Ser Arg Glu Glu Arg Leu Leu His Arg Ala Lys
                370                 375                 380

Glu Ala Pro Pro Arg Gly Asp Thr Glu Glu Pro Gly Arg Val Pro Thr
385                 390                 395                 400

Glu Asp Tyr Met Ser His Ile Ile Glu Lys Trp
                405                 410
```

<210> SEQ ID NO 50

<211> LENGTH: 411
<212> TYPE: PRT
<213> ORGANISM: Artificial Sequence
<220> FEATURE:
<223> OTHER INFORMATION: Amino acid sequence encoding for engineered
      aryl sulfate-dependent 6-O-sulfotransferase variant 11

<400> SEQUENCE: 50

Met Arg Arg Arg Arg Ala Gly Ser Arg Thr Met Val Glu Arg Ala Ser
1               5                   10                  15

Lys Phe Val Leu Val Val Ala Gly Ser Ala Cys Phe Met Leu Ile Leu
            20                  25                  30

Tyr Gln Tyr Ala Gly Pro Gly Leu Ser Leu Gly Ala Pro Gly Gly Arg
        35                  40                  45

Ala Pro Pro Asp Asp Leu Asp Leu Phe Pro Thr Pro Asp Pro His Tyr
50                  55                  60

Glu Lys Lys Tyr Tyr Phe Pro Val Arg Glu Leu Glu Arg Ser Leu His
65                  70                  75                  80

Phe Asp Met Lys Gly Asp Val Ile Val Phe Leu His Ile Gly His
                85                  90                  95

Thr Gly Gly Thr Thr Phe Gly Arg His Leu Val Gln Asn Val Arg Leu
            100                 105                 110

Glu Val Pro Cys Asp Cys Arg Pro Gly Gln Lys Lys Cys Thr Cys Tyr
        115                 120                 125

Arg Pro Asn Arg Arg Glu Thr Trp Leu Phe Ser Arg Phe Ser Thr Gly
    130                 135                 140

Trp Ser Cys Gly Ser His Ala Asp Trp Thr Glu Leu Thr Asn Cys Val
145                 150                 155                 160

Pro Gly Val Leu Asp Arg Arg Asp Pro Ala Ala Leu Arg Thr Pro Arg
                165                 170                 175

Lys Phe Tyr Tyr Ile Thr Leu Leu Arg Asp Pro Val Ser Arg Tyr Leu
            180                 185                 190

Ser Gly Trp Arg His His Gln Arg Gly Gly Ala Asn Lys Thr Ser Leu
        195                 200                 205

His Met Cys Asp Gly Arg Thr Pro Thr Pro Glu Glu Leu Pro Pro Cys
    210                 215                 220

Tyr Glu Gly Thr Asp Trp Ser Gly Cys Thr Leu Gln Glu Phe Met Asp
225                 230                 235                 240

Cys Pro Tyr Asn Leu Gly Asn Asn Arg Gln Val Arg Met Leu Ala Asp
                245                 250                 255

Leu Ser Leu Val Gly Cys Tyr Asn Leu Ser Phe Ile Pro Glu Gly Lys
            260                 265                 270

Arg Ser Gln Leu Leu Leu Glu Ser Ala Lys Lys Asn Leu Arg Gly Met
        275                 280                 285

Ala Phe Phe Gly Leu Thr Glu Phe Gln Arg Lys Thr Gln Tyr Leu Phe
    290                 295                 300

Glu Arg Thr Phe Asn Leu Lys Phe Ile Arg Pro Phe Met Gln Tyr Asn
305                 310                 315                 320

Ser Thr Arg Ala Gly Gly Val Glu Val Gly Glu Asp Thr Ile Arg Arg
                325                 330                 335

Ile Glu Glu Leu Asn Asp Leu Asp Met Gln Leu Tyr Asp Tyr Ala Arg
            340                 345                 350

Asp Leu Phe Gln Gln Arg Tyr Gln Tyr Lys Arg Gln Leu Glu Arg Arg
        355                 360                 365

Gln Gln Arg Leu Arg Ser Arg Glu Glu Arg Leu Leu His Arg Ala Lys

```
                370               375               380
Glu Ala Pro Pro Arg Gly Asp Thr Glu Glu Pro Gly Arg Val Pro Thr
385                 390               395               400

Glu Asp Tyr Met Ser His Ile Ile Glu Lys Trp
                405               410

<210> SEQ ID NO 51
<211> LENGTH: 265
<212> TYPE: PRT
<213> ORGANISM: Artificial Sequence
<220> FEATURE:
<223> OTHER INFORMATION: Amino acid sequence encoding for engineered
      aryl sulfate-dependent 3-O-sulfotransferase variant 4
<220> FEATURE:
<221> NAME/KEY: MISC_FEATURE
<222> LOCATION: (114)..(114)
<223> OTHER INFORMATION: Xaa is alanine or leucine
<220> FEATURE:
<221> NAME/KEY: MISC_FEATURE
<222> LOCATION: (115)..(115)
<223> OTHER INFORMATION: Xaa is tyrosine or glycine
<220> FEATURE:
<221> NAME/KEY: MISC_FEATURE
<222> LOCATION: (118)..(118)
<223> OTHER INFORMATION: Xaa is methionine or leucine
<220> FEATURE:
<221> NAME/KEY: MISC_FEATURE
<222> LOCATION: (121)..(121)
<223> OTHER INFORMATION: Xaa is asparagine or valine
<220> FEATURE:
<221> NAME/KEY: MISC_FEATURE
<222> LOCATION: (147)..(147)
<223> OTHER INFORMATION: Xaa is valine or threonine

<400> SEQUENCE: 51

Met Gly Thr Ala Ser Asn Gly Ser Thr Gln Gln Leu Pro Gln Thr Ile
1               5                   10                  15

Ile Ile Gly Val Gly His Gly Gly Thr Arg Ala Leu Leu Glu Met Leu
                20                  25                  30

Ser Leu His Pro Asp Val Ala Ala Ala Glu Asn Glu Val His Phe Phe
            35                  40                  45

Asp Trp Glu Glu His Tyr Ser Gln Gly Leu Gly Trp Tyr Leu Thr Gln
50                  55                  60

Met Pro Phe Ser Ser Pro His Gln Leu Thr Val Glu Lys Thr His Ser
65                  70                  75                  80

Tyr Phe Thr Ser Pro Lys Val Pro Glu Arg Ile His Ser Met Asn Pro
                85                  90                  95

Thr Ile Arg Leu Leu Leu Ile Leu Arg Asp Pro Ser Glu Arg Val Leu
            100                 105                 110

Ser Xaa Xaa Thr His Xaa Leu Tyr Xaa His Leu Gln Lys His Lys Pro
            115                 120                 125

Tyr Pro Pro Ile Glu Asp Leu Leu Met Arg Asp Gly Arg Leu Asn Leu
130                 135                 140

Asp Tyr Xaa Gly Leu Asn Arg Ser Leu Tyr His Ala His Met Leu Asn
145                 150                 155                 160

Trp Leu Arg Phe Phe Pro Leu Gly His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
        195                 200                 205

Thr Lys Gly Phe Tyr Cys Leu Arg Asp Ser Gly Lys Asp Arg Cys Leu
```

```
                210                 215                 220
His Glu Ser Lys Gly Arg Ala His Pro Gln Val Asp Pro Lys Leu Leu
225                 230                 235                 240

Asp Lys Leu His Glu Tyr Phe His Glu Pro Asn Lys Lys Phe Phe Lys
                245                 250                 255

Leu Val Gly Arg Thr Phe Asp Trp His
            260                 265

<210> SEQ ID NO 52
<211> LENGTH: 265
<212> TYPE: PRT
<213> ORGANISM: Artificial Sequence
<220> FEATURE:
<223> OTHER INFORMATION: Amino acid sequence encoding for engineered
      aryl sulfate-dependent 3-O-sulfotransferase variant 5

<400> SEQUENCE: 52

Met Gly Val Ala Pro Asn Gly Ser Ala Gln Gln Leu Pro Gln Thr Ile
1               5                   10                  15

Ile Ile Gly Val Gly His Gly Thr Arg Ala Leu Leu Glu Met Leu
            20                  25                  30

Ser Leu His Pro Asp Val Ala Ala Ala Glu Asn Glu Val His Phe Phe
        35                  40                  45

Asp Trp Glu Glu His Tyr Ser His Gly Leu Gly Trp Tyr Leu Ser Gln
    50                  55                  60

Met Pro Phe Ser Trp Pro His Gln Leu Thr Val Glu Lys Thr His Ser
65                  70                  75                  80

Tyr Phe Thr Ser Pro Lys Val Pro Glu Arg Val Tyr Ser Met Asn Pro
                85                  90                  95

Ser Ile Arg Leu Leu Leu Ile Leu Arg Asp Pro Ser Glu Arg Val Leu
            100                 105                 110

Ser Leu Gly Thr His Leu Phe Tyr Val His Met Gln Lys His Lys Pro
        115                 120                 125

Tyr Pro Ser Ile Glu Glu Phe Leu Val Arg Asp Gly Arg Leu Asn Val
    130                 135                 140

Asp Tyr Thr Gly Leu Asn Arg Ser Leu Tyr His Val His Met Gln Asn
145                 150                 155                 160

Trp Leu Arg Phe Phe Pro Leu Arg His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
        195                 200                 205

Thr Lys Gly Phe Tyr Cys Leu Arg Asp Ser Gly Arg Asp Arg Cys Leu
    210                 215                 220

His Glu Ser Lys Gly Arg Ala His Pro Gln Val Asp Pro Lys Leu Leu
225                 230                 235                 240

Asn Lys Leu His Glu Tyr Phe His Glu Pro Asn Lys Lys Phe Phe Glu
                245                 250                 255

Leu Val Gly Arg Thr Phe Asp Trp His
            260                 265

<210> SEQ ID NO 53
<211> LENGTH: 265
<212> TYPE: PRT
<213> ORGANISM: Artificial Sequence
<220> FEATURE:
```

<223> OTHER INFORMATION: Amino acid sequence encoding for engineered
      aryl sulfate-dependent 3-O-sulfotransferase variant 6

<400> SEQUENCE: 53

```
Met Gly Val Ala Pro Asn Gly Ser Ala Gln Gln Leu Pro Gln Thr Ile
1               5                   10                  15

Ile Ile Gly Val Gly His Gly Gly Thr Arg Ala Leu Leu Glu Met Leu
            20                  25                  30

Ser Leu His Pro Asp Val Ala Ala Glu Asn Glu Val His Phe Phe
        35                  40                  45

Asp Trp Glu Glu His Tyr Ser His Gly Leu Gly Trp Tyr Leu Ser Gln
    50                  55                  60

Met Pro Phe Ser Trp Pro His Gln Leu Thr Val Glu Lys Thr His Ser
65              70                  75                  80

Tyr Phe Thr Ser Pro Lys Val Pro Glu Arg Val Tyr Ser Met Asn Pro
                85                  90                  95

Ser Ile Arg Leu Leu Leu Ile Leu Arg Asp Pro Ser Glu Arg Val Leu
            100                 105                 110

Ser Ala Tyr Thr His Met Phe Tyr Asn His Met Gln Lys His Lys Pro
        115                 120                 125

Tyr Pro Ser Ile Glu Glu Phe Leu Val Arg Asp Gly Arg Leu Asn Val
    130                 135                 140

Asp Tyr Thr Gly Leu Asn Arg Ser Leu Tyr His Val His Met Gln Asn
145                 150                 155                 160

Trp Leu Arg Phe Phe Pro Leu Arg His Ile His Ile Val Asp Gly Asp
                165                 170                 175

Arg Leu Ile Arg Asp Pro Phe Pro Glu Ile Gln Lys Val Glu Arg Phe
            180                 185                 190

Leu Lys Leu Ser Pro Gln Ile Asn Ala Ser Asn Phe Tyr Phe Asn Lys
        195                 200                 205

Thr Lys Gly Phe Tyr Cys Leu Arg Asp Ser Gly Arg Asp Arg Cys Leu
    210                 215                 220

His Glu Ser Lys Gly Arg Ala His Pro Gln Val Asp Pro Lys Leu Leu
225                 230                 235                 240

Asn Lys Leu His Glu Tyr Phe His Glu Pro Asn Lys Lys Phe Phe Glu
                245                 250                 255

Leu Val Gly Arg Thr Phe Asp Trp His
            260                 265
```

<210> SEQ ID NO 54
<211> LENGTH: 265
<212> TYPE: PRT
<213> ORGANISM: Artificial Sequence
<220> FEATURE:
<223> OTHER INFORMATION: Amino acid sequence encoding for engineered
      aryl sulfate-dependent 3-O-sulfotransferase variant 7

<400> SEQUENCE: 54

```
Met Gly Val Ala Pro Asn Gly Ser Ala Gln Gln Leu Pro Gln Thr Ile
1               5                   10                  15

Ile Ile Gly Val Gly His Gly Gly Thr Arg Ala Leu Leu Glu Met Leu
            20                  25                  30

Ser Leu His Pro Asp Val Ala Ala Ala Glu Asn Glu Val His Phe Phe
        35                  40                  45

Asp Trp Glu Glu His Tyr Ser His Gly Leu Gly Trp Tyr Leu Ser Gln
    50                  55                  60
```

```
Met Pro Phe Ser Trp Pro His Gln Leu Thr Val Glu Lys Thr His Ser
 65                  70                  75                  80

Tyr Phe Thr Ser Pro Lys Val Pro Glu Arg Val Tyr Ser Met Asn Pro
                 85                  90                  95

Ser Ile Arg Leu Leu Leu Ile Leu Arg Asp Pro Ser Glu Arg Val Leu
            100                 105                 110

Ser Leu Gly Thr His Leu Phe Tyr Val His Met Gln Lys His Lys Pro
            115                 120                 125

Tyr Pro Ser Ile Glu Glu Phe Leu Val Arg Asp Gly Arg Leu Asn Val
            130                 135                 140

Asp Tyr Thr Gly Leu Asn Arg Ser Leu Tyr His Val His Met Gln Asn
145                 150                 155                 160

Trp Leu Arg Phe Phe Pro Leu Arg His Ile His Ile Val Asp Gly Asp
                165                 170                 175

Arg Leu Ile Arg Asp Pro Phe Pro Glu Ile Gln Lys Val Glu Arg Phe
                180                 185                 190

Leu Lys Leu Ser Pro Gln Ile Asn Ala Ser Asn Phe Tyr Phe Asn Lys
            195                 200                 205

Thr Lys Gly Phe Tyr Cys Leu Arg Asp Ser Gly Arg Asp Arg Cys Leu
            210                 215                 220

His Glu Ser Lys Gly Arg Ala His Pro Gln Val Asp Pro Lys Leu Leu
225                 230                 235                 240

Asn Lys Leu His Glu Tyr Phe His Glu Pro Asn Lys Lys Phe Phe Glu
                245                 250                 255

Leu Val Gly Arg Thr Phe Asp Trp His
            260                 265

<210> SEQ ID NO 55
<211> LENGTH: 598
<212> TYPE: PRT
<213> ORGANISM: Escherichia coli
<220> FEATURE:
<221> NAME/KEY: misc_feature
<222> LOCATION: (172)..(172)
<223> OTHER INFORMATION: Xaa can be any naturally occurring amino acid

<400> SEQUENCE: 55

Met Phe Asp Lys Tyr Arg Lys Thr Leu Val Ala Gly Thr Val Ala Ile
1               5                   10                  15

Thr Leu Gly Leu Ser Ala Ser Gly Val Met Ala Ala Gly Phe Lys Pro
            20                  25                  30

Ala Pro Pro Ala Gly Gln Leu Gly Ala Val Ile Val Asp Pro Tyr Gly
            35                  40                  45

Asn Ala Pro Leu Thr Ala Leu Val Asp Leu Asp Ser His Val Ile Ser
        50                  55                  60

Asp Val Lys Val Thr Val His Gly Lys Gly Glu Lys Gly Val Glu Ile
65                  70                  75                  80

Ser Tyr Pro Val Gly Gln Glu Ser Leu Lys Thr Tyr Asp Gly Val Pro
                85                  90                  95

Ile Phe Gly Leu Tyr Gln Lys Phe Ala Asn Lys Val Thr Val Glu Trp
            100                 105                 110

Lys Glu Asn Gly Lys Val Met Lys Asp Tyr Val Val His Thr Ser
            115                 120                 125

Ala Ile Val Asn Asn Tyr Met Asp Asn Arg Ser Ile Ser Asp Leu Gln
            130                 135                 140

Gln Thr Lys Val Ile Lys Val Ala Pro Gly Phe Glu Asp Arg Leu Tyr
```

```
                145                 150                 155                 160
Leu Val Asn Thr His Thr Phe Thr Ala Gln Gly Xaa Asp Leu His Trp
                    165                 170                 175

His Gly Glu Lys Asp Lys Asn Ala Gly Ile Leu Asp Ala Gly Pro Ala
                180                 185                 190

Thr Gly Ala Leu Pro Phe Asp Ile Ala Pro Phe Thr Phe Ile Val Asp
                195                 200                 205

Thr Glu Gly Glu Tyr Arg Trp Trp Leu Asp Gln Asp Thr Phe Tyr Asp
            210                 215                 220

Gly Arg Asp Arg Asp Ile Asn Lys Arg Gly Tyr Leu Met Gly Ile Arg
225                 230                 235                 240

Glu Thr Pro Arg Gly Thr Phe Thr Ala Val Gln Gly Gln His Trp Tyr
                    245                 250                 255

Glu Phe Asp Met Met Gly Gln Val Leu Glu Asp His Lys Leu Pro Arg
                260                 265                 270

Gly Phe Ala Asp Ala Thr His Glu Ser Ile Glu Thr Pro Asn Gly Thr
            275                 280                 285

Val Leu Leu Arg Val Gly Lys Ser Asn Tyr Arg Arg Asp Asp Gly Val
    290                 295                 300

His Val Thr Thr Ile Arg Asp His Ile Leu Glu Val Asp Lys Ser Gly
305                 310                 315                 320

Arg Val Val Asp Val Trp Asp Leu Thr Lys Ile Leu Asp Pro Lys Arg
                    325                 330                 335

Asp Ala Leu Leu Gly Ala Leu Asp Ala Gly Ala Val Cys Val Asn Val
                340                 345                 350

Asp Leu Ala His Ala Gly Gln Gln Ala Lys Leu Glu Pro Asp Thr Pro
            355                 360                 365

Phe Gly Asp Ala Leu Gly Val Gly Pro Gly Arg Asn Trp Ala His Val
    370                 375                 380

Asn Ser Ile Ala Tyr Asp Ala Lys Asp Ser Ile Ile Leu Ser Ser
385                 390                 395                 400

Arg His Gln Gly Val Val Lys Ile Gly Arg Asp Lys Gln Val Lys Trp
                    405                 410                 415

Ile Leu Ala Pro Ser Lys Gly Trp Glu Lys Pro Leu Ala Ser Lys Leu
                420                 425                 430

Leu Lys Pro Val Asp Ala Asn Gly Lys Pro Ile Thr Cys Asn Glu Asn
            435                 440                 445

Gly Leu Cys Glu Asn Ser Asp Phe Asp Phe Thr Tyr Thr Gln His Thr
    450                 455                 460

Ala Trp Ile Ser Ser Lys Gly Thr Leu Thr Ile Phe Asp Asn Gly Asp
465                 470                 475                 480

Gly Arg His Leu Glu Gln Pro Ala Leu Pro Thr Met Lys Tyr Ser Arg
                    485                 490                 495

Phe Val Glu Tyr Lys Ile Asp Glu Lys Lys Gly Thr Val Gln Gln Val
                500                 505                 510

Trp Glu Tyr Gly Lys Glu Arg Gly Tyr Asp Phe Tyr Ser Pro Ile Thr
            515                 520                 525

Ser Ile Ile Glu Tyr Gln Ala Asp Arg Asn Thr Met Phe Gly Phe Gly
    530                 535                 540

Gly Ser Ile His Leu Phe Asp Val Gly Gln Pro Thr Val Gly Lys Leu
545                 550                 555                 560

Asn Glu Ile Asp Tyr Lys Thr Lys Glu Val Lys Val Glu Ile Asp Val
                    565                 570                 575
```

Leu Ser Asp Lys Pro Asn Gln Thr His Tyr Arg Ala Leu Leu Val Arg
            580                 585                 590

Pro Gln Gln Met Phe Lys
        595

<210> SEQ ID NO 56
<211> LENGTH: 346
<212> TYPE: PRT
<213> ORGANISM: Artificial Sequence
<220> FEATURE:
<223> OTHER INFORMATION: Amino acid sequence encoding for engineered
      aryl sulfate-dependent 3-O-sulfotransferase variant 8

<400> SEQUENCE: 56

Met Leu Phe Lys Gln Gln Val Trp Leu Arg Gln Lys Leu Leu Val Leu
1               5                   10                  15

Gly Ser Leu Ala Val Gly Ser Leu Leu Tyr Leu Val Ala Arg Val Gly
            20                  25                  30

Ser Leu Asp Arg Leu Gln Pro Ile Cys Pro Val Glu Ser Arg Phe Gly
        35                  40                  45

Gly Ala His Asn Gln Ala Glu Leu Pro Leu Arg Ala Leu Gln Phe Lys
    50                  55                  60

Arg Gly Leu Leu His Glu Phe Arg Lys Gly Asn Ser Ser Lys Glu Gln
65                  70                  75                  80

Val His Leu His Asp Leu Val Gln Gln Leu Pro Lys Ala Ile Ile Ile
                85                  90                  95

Gly Val Gly His Gly Thr Arg Ala Leu Leu Glu Met Leu Asn Leu
            100                 105                 110

His Pro Ala Val Val Lys Ala Ser Gln Glu Ile His Phe Phe Asp Asn
        115                 120                 125

Asp Glu Asn Tyr Ala Lys Gly Ile Glu Trp Tyr Arg Lys Lys Met Pro
    130                 135                 140

Phe Ser Tyr Pro Gln Gln Ile Thr Ile Glu Lys Ser His Ser Tyr Phe
145                 150                 155                 160

Ile Thr Glu Glu Val Pro Glu Arg Ile Tyr Lys Met Asn Ser Ser Ile
                165                 170                 175

Lys Leu Leu Ile Ile Val Arg Glu Pro Thr Thr Arg Ala Ile Ser Ala
            180                 185                 190

Tyr Thr His Met Leu Glu Gly Lys Glu Arg Lys Asn Lys Thr Tyr Tyr
        195                 200                 205

Lys Phe Glu Lys Leu Ala Ile Asp Pro Asn Thr Cys Glu Val Asn Thr
    210                 215                 220

Lys Tyr Val Gly Val Arg Thr Ser Ile Tyr Thr Lys His Leu Glu Arg
225                 230                 235                 240

Trp Leu Lys Tyr Phe Pro Ile Glu Gln Phe His Ile Val Asp Gly Asp
                245                 250                 255

Arg Leu Ile Thr Glu Pro Leu Pro Glu Leu Gln Leu Val Glu Lys Phe
            260                 265                 270

Leu Asn Leu Pro Pro Arg Ile Ser Gln Tyr Asn Leu Tyr Phe Asn Ala
        275                 280                 285

Thr Arg Gly Phe Tyr Cys Leu Arg Phe Asn Ile Ile Phe Asn Lys Cys
    290                 295                 300

Leu Ala Gly Ser Lys Gly Arg Ile His Pro Glu Val Asp Pro Ser Val
305                 310                 315                 320

Ile Thr Lys Leu Arg Lys Phe Phe His Pro Phe Asn Gln Lys Phe Tyr

Gln Ile Thr Gly Arg Thr Leu Asn Trp Pro
               340                 345

<210> SEQ ID NO 57
<211> LENGTH: 346
<212> TYPE: PRT
<213> ORGANISM: Artificial Sequence
<220> FEATURE:
<223> OTHER INFORMATION: Amino acid sequence encoding for engineered
      aryl sulfate-dependent 3-O-sulfotransferase variant 9

<400> SEQUENCE: 57

Met Leu Phe Lys Gln Gln Val Trp Leu Arg Gln Lys Leu Leu Val Leu
1               5                   10                  15

Gly Ser Leu Ala Val Gly Ser Leu Leu Tyr Leu Val Ala Arg Val Gly
            20                  25                  30

Ser Leu Asp Arg Leu Gln Pro Ile Cys Pro Val Glu Ser Arg Phe Gly
        35                  40                  45

Gly Ala His Asn Gln Ala Glu Leu Pro Leu Arg Ala Leu Gln Phe Lys
    50                  55                  60

Arg Gly Leu Leu His Glu Phe Arg Lys Gly Asn Ser Ser Lys Glu Gln
65                  70                  75                  80

Val His Leu His Asp Leu Val Gln Gln Leu Pro Lys Ala Ile Ile Ile
                85                  90                  95

Gly Val Gly His Gly Gly Thr Arg Ala Leu Leu Glu Met Leu Asn Leu
            100                 105                 110

His Pro Ala Val Val Lys Ala Ser Gln Glu Ile His Phe Phe Asp Asn
        115                 120                 125

Asp Glu Asn Tyr Ala Lys Gly Ile Glu Trp Tyr Arg Lys Lys Met Pro
    130                 135                 140

Phe Ser Tyr Pro Gln Gln Ile Thr Ile Glu Lys Ser His Ser Tyr Phe
145                 150                 155                 160

Ile Thr Glu Glu Val Pro Glu Arg Ile Tyr Lys Met Asn Ser Ser Ile
                165                 170                 175

Lys Leu Leu Ile Ile Val Arg Glu Pro Thr Thr Arg Ala Ile Ser Ala
            180                 185                 190

Tyr Thr His Met Leu Glu Gly Lys Glu Arg Lys Asn Lys Thr Tyr Tyr
        195                 200                 205

Lys Phe Glu Lys Leu Ala Ile Asp Pro Asn Thr Cys Glu Val Asn Thr
    210                 215                 220

Lys Tyr Thr Gly Val Arg Thr Ser Ile Tyr Thr Lys His Leu Glu Arg
225                 230                 235                 240

Trp Leu Lys Tyr Phe Pro Ile Glu Gln Phe His Ile Val Asp Gly Asp
                245                 250                 255

Arg Leu Ile Thr Glu Pro Leu Pro Glu Leu Gln Leu Val Glu Lys Phe
            260                 265                 270

Leu Asn Leu Pro Pro Arg Ile Ser Gln Tyr Asn Leu Tyr Phe Asn Ala
        275                 280                 285

Thr Arg Gly Phe Tyr Cys Leu Arg Phe Asn Ile Phe Asn Lys Cys
    290                 295                 300

Leu Ala Gly Ser Lys Gly Arg Ile His Pro Glu Val Asp Pro Ser Val
305                 310                 315                 320

Ile Thr Lys Leu Arg Lys Phe Phe His Pro Asn Gln Lys Phe Tyr
                325                 330                 335

Gln Ile Thr Gly Arg Thr Leu Asn Trp Pro
            340                 345

<210> SEQ ID NO 58
<211> LENGTH: 346
<212> TYPE: PRT
<213> ORGANISM: Artificial Sequence
<220> FEATURE:
<223> OTHER INFORMATION: Amino acid sequence encoding for engineered
      aryl sulfate-dependent 3-O-sulfotransferase variant 10

<400> SEQUENCE: 58

Met Leu Phe Lys Gln Gln Val Trp Leu Arg Gln Lys Leu Leu Val Leu
1               5                   10                  15

Gly Ser Leu Ala Val Gly Ser Leu Leu Tyr Leu Val Ala Arg Val Gly
            20                  25                  30

Ser Leu Asp Arg Leu Gln Pro Ile Cys Pro Val Glu Ser Arg Phe Gly
        35                  40                  45

Gly Ala His Asn Gln Ala Glu Leu Pro Leu Arg Ala Leu Gln Phe Lys
    50                  55                  60

Arg Gly Leu Leu His Glu Phe Arg Lys Gly Asn Ser Ser Lys Glu Gln
65                  70                  75                  80

Val His Leu His Asp Leu Val Gln Gln Leu Pro Lys Ala Ile Ile Ile
                85                  90                  95

Gly Val Gly His Gly Thr Arg Ala Leu Leu Glu Met Leu Asn Leu
            100                 105                 110

His Pro Ala Val Val Lys Ala Ser Gln Glu Ile His Phe Phe Asp Asn
        115                 120                 125

Asp Glu Asn Tyr Ala Lys Gly Ile Glu Trp Tyr Arg Lys Lys Met Pro
    130                 135                 140

Phe Ser Tyr Pro Gln Gln Ile Thr Ile Glu Lys Ser His Ser Tyr Phe
145                 150                 155                 160

Ile Thr Glu Glu Val Pro Glu Arg Ile Tyr Lys Met Asn Ser Ser Ile
                165                 170                 175

Lys Leu Leu Ile Ile Val Arg Glu Pro Thr Thr Arg Ala Ile Ser Leu
            180                 185                 190

Gly Thr His Leu Leu Glu Val Lys Glu Arg Lys Asn Lys Thr Tyr Tyr
        195                 200                 205

Lys Phe Glu Lys Leu Ala Ile Asp Pro Asn Thr Cys Glu Val Asn Thr
    210                 215                 220

Lys Tyr Thr Gly Val Arg Thr Ser Ile Tyr Thr Lys His Leu Glu Arg
225                 230                 235                 240

Trp Leu Lys Tyr Phe Pro Ile Glu Gln Phe His Ile Val Asp Gly Asp
                245                 250                 255

Arg Leu Ile Thr Glu Pro Leu Pro Glu Leu Gln Leu Val Glu Lys Phe
            260                 265                 270

Leu Asn Leu Pro Pro Arg Ile Ser Gln Tyr Asn Leu Tyr Phe Asn Ala
        275                 280                 285

Thr Arg Gly Phe Tyr Cys Leu Arg Phe Asn Ile Ile Phe Asn Lys Cys
    290                 295                 300

Leu Ala Gly Ser Lys Gly Arg Ile His Pro Glu Val Asp Pro Ser Val
305                 310                 315                 320

Ile Thr Lys Leu Arg Lys Phe Phe His Pro Phe Asn Gln Lys Phe Tyr
                325                 330                 335

Gln Ile Thr Gly Arg Thr Leu Asn Trp Pro
            340                 345

<210> SEQ ID NO 59
<211> LENGTH: 470
<212> TYPE: PRT
<213> ORGANISM: Artificial Sequence
<220> FEATURE:
<223> OTHER INFORMATION: Amino acid sequence encoding for engineered aryl sulfate-dependent 6-O-sulfotransferase variant 12

<400> SEQUENCE: 59

```
Met Asp Glu Arg Phe Asn Lys Trp Leu Leu Thr Pro Val Leu Thr Leu
1               5                   10                  15

Leu Phe Val Val Ile Met Tyr Gln Tyr Val Ser Pro Ser Cys Thr Ser
            20                  25                  30

Ser Cys Thr Asn Phe Gly Glu Gln Leu Arg Ser Gly Glu Ala Arg Pro
        35                  40                  45

Pro Ala Val Pro Ser Pro Ala Arg Arg Ala Gln Ala Pro Leu Asp Glu
    50                  55                  60

Trp Glu Arg Arg Pro Gln Leu Pro Pro Pro Arg Gly Pro Pro Glu
65                  70                  75                  80

Gly Ser Arg Gly Val Ala Ala Pro Glu Asp Glu Asp Glu Asp Pro Gly
                85                  90                  95

Asp Pro Glu Glu Glu Glu Glu Glu Glu Glu Pro Asp Pro Glu
            100                 105                 110

Ala Pro Glu Asn Gly Ser Leu Pro Arg Phe Val Pro Arg Phe Asn Phe
        115                 120                 125

Thr Leu Lys Asp Leu Thr Arg Phe Val Asp Phe Asn Ile Lys Gly Arg
130                 135                 140

Asp Val Ile Val Phe Leu His Ile Gly His Thr Gly Gly Thr Thr Phe
145                 150                 155                 160

Gly Arg His Leu Val Lys Asn Ile Arg Leu Glu Gln Pro Cys Ser Cys
                165                 170                 175

Lys Ala Gly Gln Lys Lys Cys Thr Cys His Arg Pro Gly Lys Lys Glu
            180                 185                 190

Thr Trp Leu Phe Ser Arg Phe Ser Thr Gly Trp Ser Cys Gly Thr Asn
        195                 200                 205

Ala Asp Trp Thr Glu Leu Thr Asn Cys Val Pro Ala Ile Met Glu Lys
    210                 215                 220

Lys Asp Cys Pro Arg Asn His Ser His Thr Arg Asn Phe Tyr Tyr Ile
225                 230                 235                 240

Thr Met Leu Arg Asp Pro Val Ser Arg Tyr Leu Gly Gly Trp Lys His
                245                 250                 255

His Gln Arg Gly Gly Thr Asn Lys Thr Ser Leu His Met Cys Asp Gly
            260                 265                 270

Arg Ser Pro Thr Pro Asp Glu Leu Pro Thr Cys Tyr Pro Gly Asp Asp
        275                 280                 285

Trp Ser Gly Val Ser Leu Arg Glu Phe Met Asp Cys Ser Tyr Asn Leu
    290                 295                 300

Ala Asn Asn Arg Gln Val Arg Met Leu Ala Asp Leu Ser Leu Val Gly
305                 310                 315                 320

Cys Tyr Asn Leu Thr Phe Met Asn Glu Ser Arg Asn Thr Ile Leu
                325                 330                 335

Leu Gln Ser Ala Lys Asn Asn Leu Lys Asn Met Ala Phe Phe Gly Leu
            340                 345                 350

Thr Glu Phe Gln Arg Lys Thr Gln Phe Leu Phe Glu Arg Thr Phe Asn
```

-continued

```
                355                 360                 365
Leu Lys Phe Ile Ser Pro Phe Thr Gln Val Asn Ile Thr Arg Ala Ser
    370                 375                 380

Asn Val Asp Ile Asn Asp Gly Ala Arg Gln His Ile Glu Glu Leu Asn
385                 390                 395                 400

Phe Leu Asp Met Gln Leu Tyr Glu Tyr Ala Lys Asp Leu Phe Gln Gln
                405                 410                 415

Arg Tyr His His Thr Lys Gln Leu Glu His Gln Arg Asp Arg Gln Lys
            420                 425                 430

Arg Arg Glu Glu Arg Arg Leu Gln Arg Glu His Arg Ala His Arg Trp
        435                 440                 445

Pro Lys Glu Asp Arg Ala Met Glu Gly Thr Val Thr Glu Asp Tyr Asn
    450                 455                 460

Ser Gln Val Val Arg Trp
465             470

<210> SEQ ID NO 60
<211> LENGTH: 470
<212> TYPE: PRT
<213> ORGANISM: Artificial Sequence
<220> FEATURE:
<223> OTHER INFORMATION: Amino acid sequence encoding for engineered
      aryl sulfate-dependent 6-O-sulfotransferase variant 13

<400> SEQUENCE: 60

Met Asp Glu Arg Phe Asn Lys Trp Leu Leu Thr Pro Val Leu Thr Leu
1               5                   10                  15

Leu Phe Val Val Ile Met Tyr Gln Tyr Val Ser Pro Ser Cys Thr Ser
                20                  25                  30

Ser Cys Thr Asn Phe Gly Glu Gln Leu Arg Ser Gly Glu Ala Arg Pro
            35                  40                  45

Pro Ala Val Pro Ser Pro Ala Arg Arg Ala Gln Ala Pro Leu Asp Glu
        50                  55                  60

Trp Glu Arg Arg Pro Gln Leu Pro Pro Pro Arg Gly Pro Pro Glu
65                  70                  75                  80

Gly Ser Arg Gly Val Ala Ala Pro Glu Asp Glu Asp Glu Asp Pro Gly
                85                  90                  95

Asp Pro Glu Glu Glu Glu Glu Glu Glu Glu Glu Pro Asp Pro Glu
            100                 105                 110

Ala Pro Glu Asn Gly Ser Leu Pro Arg Phe Val Pro Arg Phe Asn Phe
        115                 120                 125

Thr Leu Lys Asp Leu Thr Arg Phe Val Asp Phe Asn Ile Lys Gly Arg
130                 135                 140

Asp Val Ile Val Phe Leu His Ile Gly His Thr Gly Gly Thr Thr Phe
145                 150                 155                 160

Gly Arg His Leu Val Lys Asn Ile Arg Leu Glu Gln Pro Cys Ser Cys
                165                 170                 175

Lys Ala Gly Gln Lys Lys Cys Thr Cys His Arg Pro Gly Lys Lys Glu
            180                 185                 190

Thr Trp Leu Phe Ser Arg Phe Ser Thr Gly Trp Ser Cys Gly Thr Arg
        195                 200                 205

Ala Asp Trp Thr Glu Leu Thr Asn Cys Val Pro Ala Ile Met Glu Lys
    210                 215                 220

Lys Asp Cys Pro Arg Asn His Ser His Thr Arg Asn Phe Tyr Tyr Ile
225                 230                 235                 240
```

-continued

```
Thr Met Leu Arg Asp Pro Val Ser Arg Tyr Leu Ser His Trp Lys His
            245                 250                 255

Thr Gln Arg Gly Gly Ala Asn Lys Thr Gly Leu His Met Cys Asp Gly
        260                 265                 270

Arg Ser Pro Thr Pro Asp Glu Leu Pro Thr Cys Tyr Pro Gly Asp Asp
        275                 280                 285

Trp Ser Gly Val Ser Leu Arg Glu Phe Met Asp Cys Ser Tyr Asn Leu
    290                 295                 300

Gly Asn Asn Arg Gln Val Arg Met Leu Ala Asp Leu Ser Leu Val Gly
305                 310                 315                 320

Cys Tyr Asn Leu Thr Phe Met Asn Glu Ser Glu Arg Asn Thr Ile Leu
                325                 330                 335

Leu Gln Ser Ala Lys Asn Asn Leu Lys Asn Met Ala Phe Phe Gly Leu
            340                 345                 350

Thr Glu Phe Gln Arg Lys Thr Gln Phe Leu Phe Glu Arg Thr Phe Asn
        355                 360                 365

Leu Lys Phe Ile Ser Pro Phe Thr Gln Phe Asn Ile Thr Arg Ala Ser
    370                 375                 380

Asn Val Asp Ile Asn Asp Gly Ala Arg Gln His Ile Glu Glu Leu Asn
385                 390                 395                 400

Phe Leu Asp Met Gln Leu Tyr Glu Tyr Ala Lys Asp Leu Phe Gln Gln
                405                 410                 415

Arg Tyr His His Thr Lys Gln Leu Glu His Gln Arg Asp Arg Gln Lys
            420                 425                 430

Arg Arg Glu Glu Arg Arg Leu Gln Arg Glu His Arg Ala His Arg Trp
        435                 440                 445

Pro Lys Glu Asp Arg Ala Met Glu Gly Thr Val Thr Glu Asp Tyr Asn
    450                 455                 460

Ser Gln Val Val Arg Trp
465                 470

<210> SEQ ID NO 61
<211> LENGTH: 470
<212> TYPE: PRT
<213> ORGANISM: Artificial Sequence
<220> FEATURE:
<223> OTHER INFORMATION: Amino acid sequence encoding for engineered
      aryl sulfate-dependent 6-O-sulfotransferase variant 13

<400> SEQUENCE: 61

Met Asp Glu Arg Phe Asn Lys Trp Leu Leu Thr Pro Val Leu Thr Leu
1               5                   10                  15

Leu Phe Val Val Ile Met Tyr Gln Tyr Val Ser Pro Ser Cys Thr Ser
            20                  25                  30

Ser

```
Thr Leu Lys Asp Leu Thr Arg Phe Val Asp Phe Asn Ile Lys Gly Arg
    130                 135                 140

Asp Val Ile Val Phe Leu His Ile Gly His Thr Gly Gly Thr Thr Phe
145                 150                 155                 160

Gly Arg His Leu Val Lys Asn Ile Arg Leu Glu Gln Pro Cys Ser Cys
                165                 170                 175

Lys Ala Gly Gln Lys Lys Cys Thr Cys His Arg Pro Gly Lys Lys Glu
                180                 185                 190

Thr Trp Leu Phe Ser Arg Phe Ser Thr Gly Trp Ser Cys Gly Ser His
            195                 200                 205

Ala Asp Trp Thr Glu Leu Thr Asn Cys Val Pro Ala Ile Met Glu Lys
            210                 215                 220

Lys Asp Cys Pro Arg Asn His Ser His Thr Arg Asn Phe Tyr Tyr Ile
225                 230                 235                 240

Thr Met Leu Arg Asp Pro Val Ser Arg Tyr Leu Ser Gly Trp Lys His
                245                 250                 255

His Gln Arg Gly Gly Ala Asn Lys Thr Ser Leu His Met Cys Asp Gly
                260                 265                 270

Arg Ser Pro Thr Pro Asp Glu Leu Pro Thr Cys Tyr Pro Gly Asp Asp
            275                 280                 285

Trp Ser Gly Val Ser Leu Arg Glu Phe Met Asp Cys Ser Tyr Asn Leu
        290                 295                 300

Gly Asn Asn Arg Gln Val Arg Met Leu Ala Asp Leu Ser Leu Val Gly
305                 310                 315                 320

Cys Tyr Asn Leu Thr Phe Met Asn Glu Ser Glu Arg Asn Thr Ile Leu
                325                 330                 335

Leu Gln Ser Ala Lys Asn Asn Leu Lys Asn Met Ala Phe Phe Gly Leu
                340                 345                 350

Thr Glu Phe Gln Arg Lys Thr Gln Phe Leu Phe Glu Arg Thr Phe Asn
        355                 360                 365

Leu Lys Phe Ile Ser Pro Phe Thr Gln Phe Asn Ile Thr Arg Ala Ser
    370                 375                 380

Asn Val Asp Ile Asn Asp Gly Ala Arg Gln His Ile Glu Glu Leu Asn
385                 390                 395                 400

Phe Leu Asp Met Gln Leu Tyr Glu Tyr Ala Lys Asp Leu Phe Gln Gln
                405                 410                 415

Arg Tyr His His Thr Lys Gln Leu Glu His Gln Arg Asp Arg Gln Lys
                420                 425                 430

Arg Arg Glu Glu Arg Arg Leu Gln Arg Glu His Arg Ala His Arg Trp
            435                 440                 445

Pro Lys Glu Asp Arg Ala Met Glu Gly Thr Val Thr Glu Asp Tyr Asn
    450                 455                 460

Ser Gln Val Val Arg Trp
465                 470
```